United States Patent
Forbes et al.

(10) Patent No.: US 11,103,538 B2
(45) Date of Patent: Aug. 31, 2021

(54) TARGETING EPIGENETIC REGULATORS USING A BACTERIAL DELIVERY SYSTEM

(71) Applicant: University of Massachusetts, Boston, MA (US)

(72) Inventors: Neil S. Forbes, Amherst, MA (US); Nele Van Dessel, Amherst, MA (US)

(73) Assignee: University of Massachusetts, Boston, MA (US)

( * ) Notice: Subject to any disclaimer, the term of this patent is extended or adjusted under 35 U.S.C. 154(b) by 182 days.

(21) Appl. No.: 15/503,380

(22) PCT Filed: Aug. 12, 2015

(86) PCT No.: PCT/US2015/044831
§ 371 (c)(1),
(2) Date: Feb. 10, 2017

(87) PCT Pub. No.: WO2016/025582
PCT Pub. Date: Feb. 18, 2016

(65) Prior Publication Data
US 2017/0333490 A1    Nov. 23, 2017

Related U.S. Application Data

(60) Provisional application No. 62/036,579, filed on Aug. 12, 2014.

(51) Int. Cl.
| | |
|---|---|
| *A61K 35/74* | (2015.01) |
| *C12N 15/74* | (2006.01) |
| *C12N 15/113* | (2010.01) |
| *C12N 1/36* | (2006.01) |
| *C07K 14/255* | (2006.01) |
| *C12N 15/11* | (2006.01) |
| *A61K 38/00* | (2006.01) |

(52) U.S. Cl.
CPC ............ *A61K 35/74* (2013.01); *C07K 14/255* (2013.01); *C12N 1/36* (2013.01); *C12N 15/111* (2013.01); *C12N 15/1137* (2013.01); *C12N 15/74* (2013.01); *C12Y 301/04* (2013.01); *A61K 38/00* (2013.01); *C12N 2310/531* (2013.01); *C12N 2320/32* (2013.01); *Y02A 50/30* (2018.01)

(58) Field of Classification Search
None
See application file for complete search history.

(56) References Cited

U.S. PATENT DOCUMENTS

| | | |
|---|---|---|
| 2005/0118193 A1 | 6/2005 | Andino-Pavlovsky et al. |
| 2006/0140975 A1 | 6/2006 | Curtiss et al. |
| 2008/0112928 A1 | 5/2008 | Loessner et al. |
| 2009/0208534 A1 | 8/2009 | Xu et al. |
| 2013/0295054 A1 | 11/2013 | Huang et al. |

FOREIGN PATENT DOCUMENTS

| | | |
|---|---|---|
| WO | WO-2013124425 A1 | 8/2013 |
| WO | WO-2016025582 A2 | 2/2016 |
| WO | WO-2016025582 A3 | 2/2016 |

OTHER PUBLICATIONS

Chen et al., Cancer Sci 2009; 100: 2437-2443 (Year: 2009).*
Kong et al., Proc. Nat'l Acad. Sci. 2008, 105(27)9361-9366 (Year: 2008).*
"International Application Serial No. PCT/US2015/044831, International Search Report dated Feb. 2, 2016", 4 pgs.
"International Application Serial No. PCT/US2015/044831, Written Opinion dated Feb. 2, 2016", 11 pgs.
Knuth, et al., "Large-scale identification of essential *Salmonella* genes by trapping lethal Insertions", Mol Microbiol. vol. 51, (Mar. 2004), 1729-1744.
Xu, et al., "Efficacy of intracellular activated promoters for generation of *Salmonella*-based vaccines", Infect Immun vol. 78, (Aug. 23, 2010), 4828-4838.

* cited by examiner

*Primary Examiner* — James D Schultz
(74) *Attorney, Agent, or Firm* — Schwegman Lundberg & Woessner, P.A.

(57) ABSTRACT

One embodiment provides an attenuated *Salmonella* strain comprising a lysis gene or cassette operably linked to an intracellularly induced *Salmonella* promoter. In one embodiment, the promoter is a promoter for one of the genes in *Salmonella* pathogenicity island 2 type III secretion system (SPI2-T3SS) selected from the group SpiC/SsaB, SseF, SseG, SseI, SseJ, SseK1, SseK2, SifA, SifB, PipB, PipB2, SopD2, GogB, SseL, SteC, SspH1, SspH2, or SirP. In one embodiment, a *Salmonella* gene is under the regulation of an inducible promoter, wherein the gene is selected from ftsW, ftsA, ftsZ, murE, mukF, imp, secF, eno, hemH, tmk, dxs, uppS, cdsA, accA, pssA, msbA, tsf, trmD, cca, infB, rpoA, rpoB, rpoC, holA, dnaC, or eng. In one embodiment, the *Salmonella* strain further comprises a plasmid that expresses DNA, shRNA, non-coding RNA and/or a peptide.

20 Claims, 9 Drawing Sheets

Specification includes a Sequence Listing.

9.5 HOURS

EARLY　　　　　　　　LATE

SEQUENCE LISTING

```
<160> NUMBER OF SEQ ID NOS: 93

<210> SEQ ID NO 1
<211> LENGTH: 380
<212> TYPE: DNA
<213> ORGANISM: Salmonella enterica

<400> SEQUENCE: 1
acatgtcaca taaaacacta gcactttagc aataatagtc ggatgataag tttgtctgtt      60
tttcctgagt atcaagccag ctcatactca cgccagcaca ctaaaatcag gagtggcttc     120 tttttagat ctttgcctta gccaggcgca cactcaataa tgatagcagt cagataatat     180
gtaccaggca ttaacctcac gttgttgatg atatatttac ttcgttgaaa aacaataaac     240
attgtatgta ttttattggc gacgaaaaac tgttaaagaa gcgtaattcc atatacacca     300
tttacctgat tactttctt gctaatattt gctaattaat tatttgctaa agcgtgttta     360
ataaagtaag gaggtctaga                                                380

<210> SEQ ID NO 2
<211> LENGTH: 133
```

```
<212> TYPE: PRT
<213> ORGANISM: Salmonella enterica

<400> SEQUENCE: 2

Met Ser Glu Glu Gly Phe Met Leu Ala Val Leu Lys Gly Ile Pro Leu
1               5                   10                  15

Ile Gln Asp Ile Arg Ala Glu Gly Asn Ser Arg Ser Trp Ile Met Thr
            20                  25                  30

Ile Asp Gly His Pro Ala Arg Gly Glu Ile Phe Ser Glu Ala Phe Ser
        35                  40                  45

Ile Ser Leu Phe Leu Asn Asp Leu Glu Ser Leu Pro Lys Pro Cys Leu
    50                  55                  60

Ala Tyr Val Thr Leu Leu Ala Ala His Pro Asp Val His Asp Tyr
65                  70                  75                  80

Ala Ile Gln Leu Thr Ala Asp Gly Gly Trp Leu Asn Gly Tyr Tyr Thr
                85                  90                  95

Thr Ser Ser Ser Glu Leu Ile Ala Ile Glu Ile Glu Lys His Leu
            100                 105                 110

Ala Leu Thr Cys Ile Leu Lys Asn Val Ile Arg Asn His His Lys Leu
        115                 120                 125

Tyr Ser Gly Gly Val
        130

<210> SEQ ID NO 3
<211> LENGTH: 260
<212> TYPE: PRT
<213> ORGANISM: Salmonella enterica

<400> SEQUENCE: 3

Met Lys Ile His Ile Pro Ser Ala Ala Ser Asn Ile Val Asp Gly Asn
1               5                   10                  15

Ser Pro Pro Ser Asp Ile Gln Ala Lys Glu Val Ser Phe Pro Pro Pro
            20                  25                  30

Glu Ile Pro Ala Pro Gly Thr Pro Ala Ala Pro Val Leu Leu Thr Pro
        35                  40                  45

Glu Gln Ile Arg Gln Arg Asp Tyr Ala Ile His Phe Met Gln Tyr
    50                  55                  60

Thr Ile Arg Ala Leu Gly Ala Thr Val Val Phe Gly Leu Ser Val Ala
65                  70                  75                  80

Ala Ala Val Ile Ser Gly Gly Ala Gly Leu Pro Ile Ala Ile Leu Ala
                85                  90                  95

Gly Ala Ala Leu Val Ile Ala Ile Gly Asp Ala Cys Cys Ala Tyr His
            100                 105                 110

Asn Tyr Gln Ser Ile Cys Gln Gln Lys Glu Pro Leu Gln Thr Ala Ser
        115                 120                 125

Asp Ser Val Ala Leu Val Val Ser Ala Leu Ala Leu Lys Cys Gly Ala
    130                 135                 140

Ser Leu Asn Cys Ala Asn Thr Leu Ala Asn Cys Leu Ser Leu Leu Ile
145                 150                 155                 160

Arg Ser Gly Ile Ala Ile Ser Met Leu Val Leu Pro Leu Gln Phe Pro
                165                 170                 175

Leu Pro Ala Ala Glu Asn Ile Ala Ala Ser Leu Asp Met Gly Ser Val
            180                 185                 190

Ile Thr Ser Val Ser Leu Thr Ala Ile Gly Ala Val Leu Asp Tyr Cys
        195                 200                 205
```

```
Leu Ala Arg Pro Ser Gly Asp Asp Gln Glu Asn Ser Val Asp Glu Leu
210                 215                 220

His Ala Asp Pro Ser Val Leu Leu Ala Glu Gln Met Ala Ala Leu Cys
225                 230                 235                 240

Gln Ser Ala Thr Thr Pro Ala Leu Met Asp Ser Ser Asp His Thr Ser
                245                 250                 255

Arg Gly Glu Pro
            260

<210> SEQ ID NO 4
<211> LENGTH: 229
<212> TYPE: PRT
<213> ORGANISM: Salmonella enterica

<400> SEQUENCE: 4

Met Lys Pro Val Ser Pro Asn Ala Gln Val Gly Gly Gln Arg Pro Val
1               5                   10                  15

Asn Ala Pro Glu Glu Ser Pro Pro Cys Pro Ser Leu Pro His Pro Glu
                20                  25                  30

Thr Asn Met Glu Ser Gly Arg Ile Gly Pro Gln Gln Gly Lys Glu Arg
            35                  40                  45

Val Leu Ala Gly Leu Ala Lys Arg Val Ile Glu Cys Phe Pro Lys Glu
50                  55                  60

Ile Phe Ser Trp Gln Thr Val Ile Leu Gly Gly Gln Ile Leu Cys Cys
65                  70                  75                  80

Ser Ala Gly Ile Ala Leu Thr Val Leu Ser Gly Gly Ala Pro Leu
                85                  90                  95

Val Ala Leu Ala Gly Ile Gly Leu Ala Ile Ala Ile Ala Asp Val Ala
                100                 105                 110

Cys Leu Ile Tyr His His Lys His His Leu Pro Met Ala His Asp Ser
            115                 120                 125

Ile Gly Asn Ala Val Phe Tyr Ile Ala Asn Cys Phe Ala Asn Gln Arg
130                 135                 140

Lys Ser Met Ala Ile Ala Lys Ala Val Ser Leu Gly Gly Arg Leu Ala
145                 150                 155                 160

Leu Thr Ala Thr Val Met Thr His Ser Tyr Trp Ser Gly Ser Leu Gly
                165                 170                 175

Leu Gln Pro His Leu Leu Glu Arg Leu Asn Asp Ile Thr Tyr Gly Leu
            180                 185                 190

Met Ser Phe Thr Arg Phe Gly Met Asp Gly Met Ala Met Thr Gly Met
        195                 200                 205

Gln Val Ser Ser Pro Leu Tyr Arg Leu Leu Ala Gln Val Thr Pro Glu
210                 215                 220

Gln Arg Ala Pro Glu
225

<210> SEQ ID NO 5
<211> LENGTH: 322
<212> TYPE: PRT
<213> ORGANISM: Salmonella enterica

<400> SEQUENCE: 5

Met Pro Phe His Ile Gly Ser Gly Cys Leu Pro Ala Ile Ile Ser Asn
1               5                   10                  15

Arg Arg Ile Tyr Arg Ile Ala Trp Ser Asp Thr Pro Pro Glu Met Ser
                20                  25                  30
```

Ser Trp Glu Lys Met Lys Glu Phe Cys Ser Thr His Gln Ala Glu
        35                  40                  45

Ala Leu Glu Cys Ile Trp Thr Ile Cys His Pro Pro Ala Gly Thr Thr
 50                  55                  60

Arg Glu Asp Val Val Ser Arg Phe Glu Leu Leu Arg Thr Leu Ala Tyr
 65                  70                  75                  80

Asp Gly Trp Glu Glu Asn Ile His Ser Gly Leu His Gly Glu Asn Tyr
                     85                  90                  95

Phe Cys Ile Leu Asp Glu Asp Ser Gln Glu Ile Leu Ser Val Thr Leu
                100                 105                 110

Asp Asp Val Gly Asn Tyr Thr Val Asn Cys Gln Gly Tyr Ser Glu Thr
            115                 120                 125

His His Leu Thr Met Ala Thr Glu Pro Gly Val Glu Arg Thr Asp Ile
        130                 135                 140

Thr Tyr Asn Leu Thr Ser Asp Ile Asp Ala Ala Tyr Leu Glu Glu
145                 150                 155                 160

Leu Lys Gln Asn Pro Ile Ile Asn Asn Lys Ile Met Asn Pro Val Gly
                165                 170                 175

Gln Cys Glu Ser Leu Met Thr Pro Val Ser Asn Phe Met Asn Glu Lys
                180                 185                 190

Gly Phe Asp Asn Ile Arg Tyr Arg Gly Ile Phe Ile Trp Asp Lys Pro
            195                 200                 205

Thr Glu Glu Ile Pro Thr Asn His Phe Ala Val Val Gly Asn Lys Glu
        210                 215                 220

Gly Lys Asp Tyr Val Phe Asp Val Ser Ala His Gln Phe Glu Asn Arg
225                 230                 235                 240

Gly Met Ser Asn Leu Asn Gly Pro Leu Ile Leu Ser Ala Asp Glu Trp
                245                 250                 255

Val Cys Lys Tyr Arg Met Ala Thr Arg Arg Lys Leu Ile Tyr Tyr Thr
                260                 265                 270

Asp Phe Ser Asn Ser Ser Ile Ala Ala Asn Ala Tyr Asp Ala Leu Pro
            275                 280                 285

Arg Glu Leu Glu Ser Glu Ser Met Ala Gly Lys Val Phe Val Thr Ser
        290                 295                 300

Pro Arg Trp Phe Asn Thr Phe Lys Lys Gln Lys Tyr Ser Leu Ile Gly
305                 310                 315                 320

Lys Met

<210> SEQ ID NO 6
<211> LENGTH: 408
<212> TYPE: PRT
<213> ORGANISM: Salmonella enterica

<400> SEQUENCE: 6

Met Pro Leu Ser Val Gly Gln Gly Tyr Phe Thr Ser Ser Ile Ser Ser
1               5                   10                  15

Glu Lys Phe Asn Ala Ile Lys Glu Ser Ala Arg Leu Pro Glu Leu Ser
                20                  25                  30

Leu Trp Glu Lys Ile Lys Ala Tyr Phe Phe Thr Thr His His Ala Glu
            35                  40                  45

Ala Leu Glu Cys Ile Phe Asn Leu Tyr His His Gln Glu Leu Asn Leu
        50                  55                  60

Thr Pro Val Gln Val Arg Gly Ala Tyr Ile Lys Leu Arg Ala Leu Ala
 65                  70                  75                  80

```
Ser Gln Gly Cys Lys Glu Gln Phe Ile Ile Glu Ser Gln Glu His Ala
                85                  90                  95

Asp Lys Leu Ile Ile Lys Asp Asp Asn Gly Glu Asn Ile Leu Ser Ile
            100                 105                 110

Glu Val Glu Cys His Pro Glu Ala Phe Gly Leu Ala Lys Glu Ile Asn
        115                 120                 125

Lys Ser His Pro Lys Pro Lys Asn Ile Ser Leu Gly Asp Ile Thr Arg
    130                 135                 140

Leu Val Phe Phe Gly Asp Ser Leu Ser Asp Ser Leu Gly Arg Met Phe
145                 150                 155                 160

Glu Lys Thr His His Ile Leu Pro Ser Tyr Gly Gln Tyr Phe Gly Gly
                165                 170                 175

Arg Phe Thr Asn Gly Phe Thr Trp Thr Glu Phe Leu Ser Ser Pro His
            180                 185                 190

Phe Leu Gly Lys Glu Met Leu Asn Phe Ala Glu Gly Gly Ser Thr Ser
        195                 200                 205

Ala Ser Tyr Ser Cys Phe Asn Cys Ile Gly Asp Phe Val Ser Asn Thr
    210                 215                 220

Asp Arg Gln Val Ala Ser Tyr Thr Pro Ser His Gln Asp Leu Ala Ile
225                 230                 235                 240

Phe Leu Leu Gly Ala Asn Asp Tyr Met Thr Leu His Lys Asp Asn Val
                245                 250                 255

Ile Met Val Val Glu Gln Gln Ile Asp Asp Ile Glu Lys Ile Ile Ser
            260                 265                 270

Gly Gly Val Asn Asn Val Leu Val Met Gly Ile Pro Asp Leu Ser Leu
        275                 280                 285

Thr Pro Tyr Gly Lys His Ser Asp Glu Lys Arg Lys Leu Lys Asp Glu
    290                 295                 300

Ser Ile Ala His Asn Ala Leu Leu Lys Thr Asn Val Glu Glu Leu Lys
305                 310                 315                 320

Glu Lys Tyr Pro Gln His Lys Ile Cys Tyr Tyr Glu Thr Ala Asp Ala
                325                 330                 335

Phe Lys Val Ile Met Glu Ala Ala Ser Asn Ile Gly Tyr Asp Thr Glu
            340                 345                 350

Asn Pro Tyr Thr His His Gly Tyr Val His Val Pro Gly Ala Lys Asp
        355                 360                 365

Pro Gln Leu Asp Ile Cys Pro Gln Tyr Val Phe Asn Asp Leu Val His
    370                 375                 380

Pro Thr Gln Glu Val His His Cys Phe Ala Ile Met Leu Glu Ser Phe
385                 390                 395                 400

Ile Ala His His Tyr Ser Thr Glu
                405

<210> SEQ ID NO 7
<211> LENGTH: 336
<212> TYPE: PRT
<213> ORGANISM: Salmonella enterica

<400> SEQUENCE: 7

Met Ile Pro Pro Leu Asn Arg Tyr Val Pro Ala Leu Ser Lys Asn Glu
1               5                   10                  15

Leu Val Lys Thr Val Thr Asn Arg Asp Ile Gln Phe Thr Ser Phe Asn
            20                  25                  30

Gly Lys Asp Tyr Pro Leu Cys Phe Leu Asp Glu Lys Thr Pro Leu Leu
        35                  40                  45
```

```
Phe Gln Trp Phe Glu Arg Asn Pro Ala Arg Phe Gly Lys Asn Asp Ile
     50                  55                  60

Pro Ile Ile Asn Thr Glu Lys Asn Pro Tyr Leu Asn Asn Ile Ile Lys
 65                  70                  75                  80

Ala Ala Thr Ile Glu Lys Glu Arg Leu Ile Gly Ile Phe Val Asp Gly
                 85                  90                  95

Asp Phe Phe Pro Gly Gln Lys Asp Ala Phe Ser Lys Leu Glu Tyr Asp
            100                 105                 110

Tyr Glu Asn Ile Lys Val Ile Tyr Arg Asn Asp Ile Asp Phe Ser Met
        115                 120                 125

Tyr Asp Lys Lys Leu Ser Glu Ile Tyr Met Glu Asn Ile Ser Lys Gln
    130                 135                 140

Glu Ser Met Pro Glu Glu Lys Arg Asp Cys His Leu Leu Gln Leu Leu
145                 150                 155                 160

Lys Lys Glu Leu Ser Asp Ile Gln Glu Gly Asn Asp Ser Leu Ile Lys
                165                 170                 175

Ser Tyr Leu Leu Asp Lys Gly His Gly Trp Phe Asp Phe Tyr Arg Asn
            180                 185                 190

Met Ala Met Leu Lys Ala Gly Gln Leu Phe Leu Glu Ala Asp Lys Val
        195                 200                 205

Gly Cys Tyr Asp Leu Ser Thr Asn Ser Gly Cys Ile Tyr Leu Asp Ala
    210                 215                 220

Asp Met Ile Ile Thr Glu Lys Leu Gly Gly Ile Tyr Ile Pro Asp Gly
225                 230                 235                 240

Ile Ala Val His Val Glu Arg Ile Asp Gly Arg Ala Ser Met Glu Asn
                245                 250                 255

Gly Ile Ile Ala Val Asp Arg Asn Asn His Pro Ala Leu Leu Ala Gly
            260                 265                 270

Leu Glu Ile Met His Thr Lys Phe Asp Ala Asp Pro Tyr Ser Asp Gly
        275                 280                 285

Val Cys Asn Gly Ile Arg Lys His Phe Asn Tyr Ser Leu Asn Glu Asp
    290                 295                 300

Tyr Asn Ser Phe Cys Asp Phe Ile Glu Phe Lys His Asp Asn Ile Ile
305                 310                 315                 320

Met Asn Thr Ser Gln Phe Thr Gln Ser Ser Trp Ala Arg His Val Gln
                325                 330                 335

<210> SEQ ID NO 8
<211> LENGTH: 348
<212> TYPE: PRT
<213> ORGANISM: Salmonella enterica

<400> SEQUENCE: 8

Met Ala Arg Phe Asn Ala Ala Phe Thr Arg Ile Lys Ile Met Phe Ser
  1               5                  10                  15

Arg Ile Arg Gly Leu Ile Ser Cys Gln Ser Thr Gln Thr Ile Ala
            20                  25                  30

Pro Thr Leu Ser Pro Pro Ser Ser Gly His Val Ser Phe Ala Gly Ile
         35                  40                  45

Asp Tyr Pro Leu Leu Pro Leu Asn His Gln Thr Pro Leu Val Phe Gln
     50                  55                  60

Trp Phe Glu Arg Asn Pro Asp Arg Phe Gly Gln Asn Glu Ile Pro Ile
 65                  70                  75                  80

Ile Asn Thr Gln Lys Asn Pro Tyr Leu Asn Asn Ile Ile Asn Ala Ala
```

```
                85                  90                  95
Ile Ile Glu Lys Glu Arg Ile Ile Gly Ile Phe Val Asp Gly Asp Phe
                100                 105                 110

Ser Lys Gly Gln Arg Lys Ala Leu Gly Lys Leu Glu Gln Asn Tyr Arg
                115                 120                 125

Asn Ile Lys Val Ile Tyr Asn Ser Asp Leu Asn Tyr Ser Met Tyr Asp
                130                 135                 140

Lys Lys Leu Thr Thr Ile Tyr Leu Glu Asn Ile Thr Lys Leu Glu Ala
145                 150                 155                 160

Gln Ser Ala Ser Glu Arg Asp Glu Val Leu Leu Asn Gly Val Lys Lys
                165                 170                 175

Ser Leu Glu Asp Val Leu Lys Asn Asn Pro Glu Thr Leu Ile Ser
                180                 185                 190

Ser His Asn Lys Asp Lys Gly His Leu Trp Phe Asp Phe Tyr Arg Asn
                195                 200                 205

Leu Phe Leu Leu Lys Gly Ser Asp Ala Phe Leu Glu Ala Gly Lys Pro
                210                 215                 220

Gly Cys His His Leu Gln Pro Gly Gly Gly Cys Ile Tyr Leu Asp Ala
225                 230                 235                 240

Asp Met Leu Leu Thr Asp Lys Leu Gly Thr Leu Tyr Leu Pro Asp Gly
                245                 250                 255

Ile Ala Ile His Val Ser Arg Lys Asp Asn His Val Ser Leu Glu Asn
                260                 265                 270

Gly Ile Ile Ala Val Asn Arg Ser Glu His Pro Ala Leu Ile Lys Gly
                275                 280                 285

Leu Glu Ile Met His Ser Lys Pro Tyr Gly Asp Pro Tyr Asn Asp Trp
                290                 295                 300

Leu Ser Lys Gly Leu Arg His Tyr Phe Asp Gly Ser His Ile Gln Asp
305                 310                 315                 320

Tyr Asp Ala Phe Cys Asp Phe Ile Glu Phe Lys His Glu Asn Ile Ile
                325                 330                 335

Met Asn Thr Ser Ser Leu Thr Ala Ser Ser Trp Arg
                340                 345

<210> SEQ ID NO 9
<211> LENGTH: 336
<212> TYPE: PRT
<213> ORGANISM: Salmonella enterica

<400> SEQUENCE: 9

Met Pro Ile Thr Ile Gly Asn Gly Phe Leu Lys Ser Glu Ile Leu Thr
1               5                   10                  15

Asn Ser Pro Arg Asn Thr Lys Glu Ala Trp Trp Lys Val Leu Trp Glu
                20                  25                  30

Lys Ile Lys Asp Phe Phe Ser Thr Gly Lys Ala Lys Ala Asp Arg
                35                  40                  45

Cys Leu His Glu Met Leu Phe Ala Glu Arg Ala Pro Thr Arg Glu Arg
                50                  55                  60

Leu Thr Glu Ile Phe Phe Glu Leu Lys Glu Leu Ala Cys Ala Ser Gln
65                  70                  75                  80

Arg Asp Arg Phe Gln Val His Asn Pro His Glu Asn Asp Ala Thr Ile
                85                  90                  95

Ile Leu Arg Ile Met Asp Gln Asn Glu Glu Asn Glu Leu Leu Arg Ile
                100                 105                 110
```

```
Thr Gln Asn Thr Asp Thr Phe Ser Cys Glu Val Met Gly Asn Leu Tyr
            115                 120                 125

Phe Leu Met Lys Asp Arg Pro Asp Ile Leu Lys Ser His Pro Gln Met
130                 135                 140

Thr Ala Met Ile Lys Arg Arg Tyr Ser Glu Ile Val Asp Tyr Pro Leu
145                 150                 155                 160

Pro Ser Thr Leu Cys Leu Asn Pro Ala Gly Ala Pro Ile Leu Ser Val
                165                 170                 175

Pro Leu Asp Asn Ile Glu Gly Tyr Leu Tyr Thr Glu Leu Arg Lys Gly
            180                 185                 190

His Leu Asp Gly Trp Lys Ala Gln Glu Lys Ala Thr Tyr Leu Ala Ala
        195                 200                 205

Lys Ile Gln Ser Gly Ile Glu Lys Thr Thr Arg Ile Leu His His Ala
    210                 215                 220

Asn Ile Ser Glu Ser Thr Gln Gln Asn Ala Phe Leu Glu Thr Met Ala
225                 230                 235                 240

Met Cys Gly Leu Lys Gln Leu Glu Ile Pro Pro His Thr His Ile
                245                 250                 255

Pro Ile Glu Lys Met Val Lys Glu Val Leu Leu Ala Asp Lys Thr Phe
            260                 265                 270

Gln Ala Phe Leu Val Thr Asp Pro Ser Thr Ser Gln Ser Met Leu Ala
        275                 280                 285

Glu Ile Val Glu Ala Ile Ser Asp Gln Val Phe His Ala Ile Phe Arg
    290                 295                 300

Ile Asp Pro Gln Ala Ile Gln Lys Met Ala Glu Glu Gln Leu Thr Thr
305                 310                 315                 320

Leu His Val Arg Ser Glu Gln Gln Ser Gly Cys Leu Cys Cys Phe Leu
                325                 330                 335

<210> SEQ ID NO 10
<211> LENGTH: 316
<212> TYPE: PRT
<213> ORGANISM: Salmonella enterica

<400> SEQUENCE: 10

Met Pro Ile Thr Ile Gly Arg Gly Phe Leu Lys Ser Glu Met Phe Ser
1               5                   10                  15

Gln Ser Ala Ile Ser Gln Arg Ser Phe Phe Thr Leu Leu Trp Glu Lys
            20                  25                  30

Ile Lys Asp Phe Phe Cys Asp Thr Gln Arg Ser Thr Ala Asp Gln Tyr
        35                  40                  45

Ile Lys Glu Leu Cys Asp Val Ala Ser Pro Pro Asp Ala Gln Arg Leu
50                  55                  60

Phe Asp Leu Phe Cys Lys Leu Tyr Glu Leu Ser Ser Pro Ser Cys Arg
65                  70                  75                  80

Gly Asn Phe His Phe Gln His Tyr Lys Asp Ala Glu Cys Gln Tyr Thr
                85                  90                  95

Asn Leu Cys Ile Lys Asp Gly Glu Asp Ile Pro Leu Cys Ile Met Ile
            100                 105                 110

Arg Gln Asp His Tyr Tyr Glu Ile Met Asn Arg Thr Val Leu Cys
        115                 120                 125

Val Asp Thr Gln Ser Ala His Leu Lys Arg Tyr Ser Asp Ile Asn Ile
    130                 135                 140

Lys Ala Ser Thr Tyr Val Cys Glu Pro Leu Cys Cys Leu Phe Pro Glu
145                 150                 155                 160
```

```
Arg Leu Gln Leu Ser Leu Ser Gly Gly Ile Thr Phe Ser Val Asp Leu
                165                 170                 175

Lys Asn Ile Glu Glu Thr Leu Ile Ala Met Ala Glu Lys Gly Asn Leu
            180                 185                 190

Cys Asp Trp Lys Glu Gln Glu Arg Lys Ala Ala Ile Ser Ser Arg Ile
            195                 200                 205

Asn Leu Gly Ile Ala Gln Ala Gly Val Thr Ala Ile Asp Asp Ala Ile
        210                 215                 220

Lys Asn Lys Ile Ala Ala Lys Val Ile Glu Asn Thr Asn Leu Lys Asn
225                 230                 235                 240

Ala Ala Phe Glu Pro Asn Tyr Ala Gln Ser Ser Val Thr Gln Ile Val
                245                 250                 255

Tyr Ser Cys Leu Phe Lys Asn Glu Ile Leu Met Asn Met Leu Glu Glu
            260                 265                 270

Ser Ser Ser His Gly Leu Leu Cys Leu Asn Glu Leu Thr Glu Tyr Val
            275                 280                 285

Thr Leu Gln Val His Asn Ser Leu Phe Ser Glu Asp Leu Ser Ser Leu
        290                 295                 300

Val Glu Thr Thr Lys Asn Glu Ala His His Gln Ser
305                 310                 315

<210> SEQ ID NO 11
<211> LENGTH: 291
<212> TYPE: PRT
<213> ORGANISM: Salmonella enterica

<400> SEQUENCE: 11

Met Pro Ile Thr Asn Ala Ser Pro Glu Asn Ile Leu Arg Tyr Leu His
1               5                   10                  15

Ala Ala Gly Thr Gly Thr Lys Glu Ala Met Lys Ser Ala Thr Ser Pro
            20                  25                  30

Arg Gly Ile Leu Glu Trp Phe Val Asn Phe Thr Cys Gly Gly Val
        35                  40                  45

Arg Arg Ser Asn Glu Arg Trp Phe Arg Glu Val Ile Gly Lys Leu Thr
50                  55                  60

Thr Ser Leu Leu Tyr Val Asn Lys Asn Ala Phe Phe Asp Gly Asn Lys
65                  70                  75                  80

Ile Phe Leu Glu Asp Val Asn Gly Cys Thr Ile Cys Leu Ser Cys Gly
                85                  90                  95

Ala Ala Ser Glu Asn Thr Asp Pro Met Val Ile Glu Val Asn Lys
            100                 105                 110

Asn Gly Lys Thr Val Thr Asp Lys Val Asp Ser Glu Arg Phe Trp Asn
            115                 120                 125

Val Cys Arg Met Leu Lys Leu Met Ser Lys His Asn Ile Gln Gln Pro
        130                 135                 140

Asp Ser Leu Ile Thr Glu Asp Gly Phe Leu Asn Leu Arg Gly Val Asn
145                 150                 155                 160

Leu Ala His Lys Asp Phe Gln Gly Glu Asp Leu Ser Lys Ile Asp Ala
                165                 170                 175

Ser Asn Ala Asp Phe Arg Glu Thr Thr Leu Ser Asn Val Asn Leu Val
            180                 185                 190

Gly Ala Asn Leu Cys Cys Ala Asn Leu His Ala Val Asn Leu Met Gly
        195                 200                 205

Ser Asn Met Thr Lys Ala Asn Leu Thr His Ala Asp Leu Thr Cys Ala
```

```
            210                 215                 220
Asn Met Ser Gly Val Asn Leu Thr Ala Ala Ile Leu Phe Gly Ser Asp
225                 230                 235                 240

Leu Thr Asp Thr Lys Leu Asn Gly Ala Lys Leu Asp Lys Ile Ala Leu
                245                 250                 255

Thr Leu Ala Lys Ala Leu Thr Gly Ala Asp Leu Thr Gly Ser Gln His
                260                 265                 270

Thr Pro Thr Pro Leu Pro Asp Tyr Asn Asp Arg Thr Leu Phe Pro His
                275                 280                 285

Pro Ile Phe
        290

<210> SEQ ID NO 12
<211> LENGTH: 350
<212> TYPE: PRT
<213> ORGANISM: Salmonella enterica

<400> SEQUENCE: 12

Met Glu Arg Ser Leu Asp Ser Leu Ala Gly Met Ala Lys Ser Ala Phe
1               5                   10                  15

Gly Ala Gly Thr Ser Ala Ala Met Arg Gln Ala Thr Ser Pro Lys Thr
                20                  25                  30

Ile Leu Glu Tyr Ile Ile Asn Phe Phe Thr Cys Gly Gly Ile Arg Arg
            35                  40                  45

Arg Asn Glu Thr Gln Tyr Gln Glu Leu Ile Glu Thr Met Ala Glu Thr
        50                  55                  60

Leu Lys Ser Thr Met Pro Asp Arg Gly Ala Pro Leu Pro Glu Asn Ile
65                  70                  75                  80

Ile Leu Asp Asp Met Asp Gly Cys Arg Val Glu Phe Asn Leu Pro Gly
                85                  90                  95

Glu Asn Asn Glu Ala Gly Gln Val Ile Val Arg Val Ser Lys Gly Asp
                100                 105                 110

His Ser Glu Thr Arg Glu Ile Pro Leu Ala Ser Phe Glu Lys Ile Cys
            115                 120                 125

Arg Ala Leu Leu Phe Arg Cys Glu Phe Ser Leu Pro Gln Asp Ser Val
        130                 135                 140

Ile Leu Thr Ala Gln Gly Gly Met Asn Leu Lys Gly Ala Val Leu Thr
145                 150                 155                 160

Gly Ala Asn Leu Thr Ser Glu Asn Leu Cys Asp Ala Asp Leu Ser Gly
                165                 170                 175

Ala Asn Leu Glu Gly Ala Val Leu Phe Met Ala Asp Cys Glu Gly Ala
                180                 185                 190

Asn Phe Lys Gly Ala Asn Leu Ser Gly Thr Ser Leu Gly Asp Ser Asn
            195                 200                 205

Phe Lys Asn Ala Cys Leu Glu Asp Ser Ile Met Cys Gly Ala Thr Leu
        210                 215                 220

Asp His Ala Asn Leu Thr Gly Ala Asn Leu Gln His Ala Ser Leu Leu
225                 230                 235                 240

Gly Cys Ser Met Ile Glu Cys Asn Cys Ser Gly Ala Asn Met Asp His
                245                 250                 255

Thr Asn Leu Ser Gly Ala Thr Leu Ile Arg Ala Asp Met Ser Gly Ala
                260                 265                 270

Thr Leu Gln Gly Ala Thr Ile Met Ala Ala Ile Met Glu Gly Ala Val
            275                 280                 285
```

```
Leu Thr Arg Ala Asn Leu Arg Lys Ala Ser Phe Ile Ser Thr Asn Leu
    290                 295                 300

Asp Gly Ala Asp Leu Ala Glu Ala Asn Leu Asn Asn Thr Cys Phe Lys
305                 310                 315                 320

Asp Cys Thr Leu Thr Asp Leu Arg Thr Glu Asp Ala Thr Met Ser Thr
                325                 330                 335

Ser Thr Gln Thr Leu Phe Asn Glu Phe Tyr Ser Glu Asn Ile
            340                 345                 350

<210> SEQ ID NO 13
<211> LENGTH: 319
<212> TYPE: PRT
<213> ORGANISM: Salmonella enterica

<400> SEQUENCE: 13

Met Pro Val Thr Leu Ser Phe Gly Asn Arg His Asn Tyr Glu Ile Asn
1               5                   10                  15

His Ser Arg Leu Ala Arg Leu Met Ser Pro Asp Lys Glu Glu Ala Leu
            20                  25                  30

Tyr Met Gly Val Trp Asp Arg Phe Lys Asp Cys Phe Arg Thr His Lys
        35                  40                  45

Lys Gln Glu Val Leu Glu Val Leu Tyr Thr Leu Ile His Gly Cys Glu
    50                  55                  60

Arg Glu Asn Gln Ala Glu Leu Asn Val Asp Ile Thr Gly Met Glu Lys
65                  70                  75                  80

Ile His Ala Phe Thr Gln Leu Lys Glu Tyr Ala Asn Pro Ser Gln Gln
                85                  90                  95

Asp Arg Phe Val Met Arg Phe Asp Met Asn Gln Thr Gln Val Leu Phe
            100                 105                 110

Glu Ile Asp Gly Lys Val Ile Asp Lys Cys Asn Leu His Arg Leu Leu
        115                 120                 125

Asn Val Ser Glu Asn Cys Ile Phe Lys Val Met Glu Glu Asp Glu Glu
    130                 135                 140

Glu Leu Phe Leu Lys Ile Cys Ile Lys Tyr Gly Glu Lys Ile Ser Arg
145                 150                 155                 160

Tyr Pro Glu Leu Leu Glu Gly Phe Ala Asn Lys Leu Lys Asp Ala Val
                165                 170                 175

Asn Glu Asp Asp Asp Val Lys Asp Glu Val Tyr Lys Leu Met Arg Ser
            180                 185                 190

Gly Glu Asp Arg Lys Met Glu Cys Val Glu Trp Asn Gly Thr Leu Thr
        195                 200                 205

Glu Glu Glu Lys Asn Lys Leu Arg Cys Leu Gln Met Gly Ser Phe Asn
    210                 215                 220

Ile Thr Thr Gln Phe Phe Lys Ile Gly Tyr Trp Glu Leu Glu Gly Glu
225                 230                 235                 240

Val Leu Phe Asp Met Val His Pro Thr Leu Ser Tyr Leu Leu Gln Ala
                245                 250                 255

Tyr Lys Pro Ser Leu Ser Ser Asp Leu Ile Glu Thr Asn Thr Met Leu
            260                 265                 270

Phe Ser Asp Val Leu Asn Lys Tyr Asp Tyr Gln Asn Asn Lys
        275                 280                 285

Arg Glu Ile Asp Ala Ile Leu Arg Arg Ile Tyr Arg Ser His Asn Asn
    290                 295                 300

Thr Leu Phe Ile Ser Glu Lys Ser Ser Cys Arg Asn Met Leu Ile
305                 310                 315
```

<210> SEQ ID NO 14
<211> LENGTH: 480
<212> TYPE: PRT
<213> ORGANISM: Salmonella enterica

<400> SEQUENCE: 14

```
Met Gln Tyr Ala Tyr Thr Ser Asn Glu Ala Thr Ser Asn Leu Glu Leu
1               5                   10                  15

Leu Asn Lys Trp Arg Ile Glu Ser Pro Asp Ile Glu Lys Glu Arg
            20                  25                  30

Asn Ser Ile Tyr Asp Lys Ile Ile Glu Ala Asn His Thr Gly Ser Leu
        35                  40                  45

Ser Ile Thr Ala His His Val Thr Ser Ile Pro Val Phe Pro Asp Asn
    50                  55                  60

Leu Ser Glu Leu Asn Leu Ser Ser Cys Tyr Thr Leu Glu Ser Ile Pro
65                  70                  75                  80

Asn Leu Pro Asp Gly Leu Lys Ser Leu Thr Ile Ser Gly Asn Gln Thr
                85                  90                  95

Ile Lys Ile Ser Tyr Phe Pro Asp Ser Leu Glu Ser Leu Ser Ile Asp
            100                 105                 110

Met Gln Ala Tyr Glu Glu Asn Tyr Thr Phe Pro Ala Leu Pro Tyr Gly
        115                 120                 125

Leu Lys Ser Phe Thr Ala Cys Tyr Gly Lys Phe Leu Pro Pro Leu Pro
    130                 135                 140

Pro His Leu Ser Ser Leu Ser Leu Gln Asn Phe Ser Glu Ile Leu Cys
145                 150                 155                 160

Ala Glu Leu Pro Tyr Lys Leu Asp Lys Leu Asp Leu Gln Asn Cys Pro
                165                 170                 175

Phe Leu Pro Leu Met Lys Met Leu Pro Glu Glu Leu Lys Glu Leu Ser
            180                 185                 190

Ile Glu Leu Ile Arg Thr Val Pro Gly Thr Val Ile Asp Asp Ile Leu
        195                 200                 205

Pro Asp Lys Leu Lys Lys Leu Ser Ile Asn Phe Cys Asp Asn Ile Lys
    210                 215                 220

Leu Pro Val Lys Leu Pro Val Asn Leu Lys Ser Ile Asn Leu Ser Ser
225                 230                 235                 240

Arg Thr Pro Ile Ala Trp Glu Ile Pro Thr Cys Asn Leu Pro Ala His
                245                 250                 255

Ile Asp Ile Ser Thr Asp Gly Tyr Val Lys Leu Asn Pro Glu Phe Leu
            260                 265                 270

Thr Arg Ser Asp Ile Thr Phe Ser Asn Lys Pro Ala Gly Asp Val Leu
        275                 280                 285

Ser Phe Gln Pro Gly Asp Val Val Tyr Gly Leu Cys Lys Ala Arg Asp
    290                 295                 300

Arg Val Asn Thr Leu Val Asn Ser Leu Tyr Tyr Phe Ser Lys Lys Asp
305                 310                 315                 320

Ile Ile Ile Gln Asn Thr Leu Thr Asp Ala Val Trp Asp Arg Lys Asn
                325                 330                 335

Arg Ala Val Phe Asn Lys Asp Glu Lys Ile Ala Glu Arg Leu Asn Asp
            340                 345                 350

Val Gln Arg Gly Ile Phe Phe Arg Glu Phe Leu Ser Gln His Lys Lys
        355                 360                 365

Tyr Asn Ile Thr Glu Asp Lys Tyr Ser Asp Leu Ser Asn Glu Glu Cys
```

```
                370             375             380
Trp Ile Lys Thr Ser Lys Ala Gly Leu Glu Phe Gln Thr Arg Leu Arg
385                 390             395                 400

Glu Arg Ser Val Ile Phe Val Ile Asp Asn Leu Val Asp Ala Ile Ser
                405             410                 415

Asp Ile Ala Asn Lys Thr Gly Lys His Gly Asn Ser Ile Thr Ala His
                420             425                 430

Glu Leu Arg Trp Val Tyr Arg Asn Arg His Asp Asp Leu Val Lys Gln
                435             440                 445

Asn Val Lys Phe Phe Leu Asn Gly Glu Ala Ile Ser His Glu Asp Val
                450             455                 460

Phe Ser Leu Val Gly Trp Asp Lys Tyr Lys Pro Lys Asn Arg Asn Arg
465                 470             475                 480

<210> SEQ ID NO 15
<211> LENGTH: 317
<212> TYPE: PRT
<213> ORGANISM: Salmonella enterica

<400> SEQUENCE: 15

Met Ser Asp Glu Ala Leu Thr Leu Leu Phe Ser Ala Val Glu Asn Gly
1               5                   10                  15

Asp Gln Asn Cys Ile Asp Leu Leu Cys Asn Leu Ala Leu Arg Asn Asp
                20                  25                  30

Asp Leu Gly His Arg Val Glu Lys Phe Leu Phe Asp Leu Phe Ser Gly
                35                  40                  45

Lys Arg Thr Gly Ser Ser Asp Ile Asp Lys Lys Ile Asn Gln Ala Cys
50                  55                  60

Leu Val Leu His Gln Ile Ala Asn Asn Asp Ile Thr Lys Asp Asn Thr
65                  70                  75                  80

Glu Trp Lys Lys Leu His Ala Pro Ser Arg Leu Leu Tyr Met Ala Gly
                85                  90                  95

Ser Ala Thr Thr Asp Leu Ser Lys Lys Ile Gly Ile Ala His Lys Ile
                100                 105                 110

Met Gly Asp Gln Phe Ala Gln Thr Asp Gln Gln Val Gly Val Glu
                115                 120                 125

Asn Leu Trp Cys Gly Ala Arg Met Leu Ser Ser Asp Glu Leu Ala Ala
                130                 135                 140

Ala Thr Gln Gly Leu Val Gln Glu Ser Pro Leu Leu Ser Val Asn Tyr
145                 150                 155                 160

Pro Ile Gly Leu Ile His Pro Thr Thr Lys Glu Asn Ile Leu Ser Thr
                165                 170                 175

Gln Leu Leu Glu Lys Ile Ala Gln Ser Gly Leu Ser His Asn Glu Val
                180                 185                 190

Phe Leu Val Asn Thr Gly Asp His Trp Leu Leu Cys Leu Phe Tyr Lys
                195                 200                 205

Leu Ala Glu Lys Ile Lys Cys Leu Ile Phe Asn Thr Tyr Tyr Asp Leu
210                 215                 220

Asn Glu Asn Thr Lys Gln Glu Ile Ile Glu Ala Ala Lys Ile Ala Gly
225                 230                 235                 240

Ile Ser Glu Ser Asp Glu Val Asn Phe Ile Glu Met Asn Leu Gln Asn
                245                 250                 255

Asn Val Pro Asn Gly Cys Gly Leu Phe Cys Tyr His Thr Ile Gln Leu
                260                 265                 270
```

```
Leu Ser Asn Ala Gly Gln Asn Asp Pro Ala Thr Thr Leu Arg Glu Phe
            275                 280                 285

Ala Glu Asn Phe Leu Thr Leu Ser Val Glu Glu Gln Ala Leu Phe Asn
    290                 295                 300

Thr Gln Thr Arg Arg Gln Ile Tyr Glu Tyr Ser Leu Gln
305                 310                 315

<210> SEQ ID NO 16
<211> LENGTH: 457
<212> TYPE: PRT
<213> ORGANISM: Salmonella enterica

<400> SEQUENCE: 16

Met Pro Phe Thr Phe Gln Ile Gly Asn His Ser Cys Gln Ile Ser Glu
1               5                   10                  15

Arg Tyr Leu Arg Asp Ile Ile Asp Asn Lys Arg Glu His Val Phe Ser
            20                  25                  30

Thr Cys Glu Lys Phe Ile Asp Phe Phe Arg Asn Ile Phe Thr Arg Arg
        35                  40                  45

Ser Leu Ile Ser Asp Tyr Arg Glu Ile Tyr Asn Leu Leu Cys Gln Lys
    50                  55                  60

Lys Glu His Pro Asp Ile Lys Gly Pro Phe Ser Pro Gly Pro Phe Ser
65                  70                  75                  80

Lys Arg Asp Glu Asp Cys Thr Arg Trp Arg Pro Leu Leu Gly Tyr Ile
                85                  90                  95

Lys Leu Ile Asp Ala Ser Arg Pro Glu Thr Ile Asp Lys Tyr Thr Val
            100                 105                 110

Glu Val Leu Ala His Gln Glu Asn Met Leu Leu Gln Met Phe Tyr
        115                 120                 125

Asp Gly Val Leu Val Thr Glu Thr Glu Cys Ser Glu Arg Cys Val Asp
    130                 135                 140

Phe Leu Lys Glu Thr Met Phe Asn Tyr Asn Asn Gly Glu Ile Thr Leu
145                 150                 155                 160

Ala Ala Leu Gly Asn Asp Asn Leu Pro Pro Ser Glu Ala Gly Ser Asn
                165                 170                 175

Gly Ile Tyr Glu Ala Phe Glu Gln Arg Leu Ile Asp Phe Leu Thr Thr
            180                 185                 190

Pro Ala Thr Ala Ser Gly Tyr Glu Ser Gly Ala Ile Asp Gln Thr Asp
        195                 200                 205

Ala Ser Gln Pro Ala Ala Ile Glu Ala Phe Ile Asn Ser Pro Glu Phe
    210                 215                 220

Gln Lys Asn Ile Arg Met Arg Asp Ile Glu Lys Asn Lys Ile Gly Ser
225                 230                 235                 240

Gly Ser Tyr Gly Thr Val Tyr Arg Leu His Asp Phe Val Val Lys
                245                 250                 255

Ile Pro Val Asn Glu Arg Gly Ile Lys Val Asp Val Asn Ser Pro Glu
            260                 265                 270

His Arg Asn Cys His Pro Asp Arg Val Ser Lys Tyr Leu Asn Met Ala
        275                 280                 285

Asn Asp Asp Lys Asn Phe Ser Arg Ser Ala Ile Met Asn Ile Asn Gly
    290                 295                 300

Lys Asp Val Thr Val Leu Val Ser Lys Tyr Ile Gln Gly Gln Glu Phe
305                 310                 315                 320

Asp Val Glu Asp Glu Asp Asn Tyr Arg Met Ala Glu Ala Leu Leu Lys
                325                 330                 335
```

```
Ser Arg Gly Val Tyr Met His Asp Ile Asn Ile Leu Gly Asn Ile Leu
        340                 345                 350

Val Lys Glu Gly Val Leu Phe Phe Val Asp Gly Asp Gln Ile Val Leu
        355                 360                 365

Ser Gln Glu Ser Arg Gln Gln Arg Ser Val Ser Leu Ala Thr Arg Gln
370                 375                 380

Leu Glu Glu Gln Ile Lys Ala His His Met Ile Lys Leu Lys Arg Ala
385                 390                 395                 400

Glu Thr Glu Gly Asn Thr Glu Asp Val Glu Tyr Tyr Lys Ser Leu Ile
                405                 410                 415

Thr Asp Leu Asp Ala Leu Ile Gly Glu Glu Gln Thr Pro Ala Pro
                420                 425                 430

Gly Arg Arg Phe Lys Leu Ala Ala Pro Glu Glu Gly Thr Leu Val Ala
                435                 440                 445

Lys Val Leu Lys Asp Glu Leu Lys Lys
        450                 455

<210> SEQ ID NO 17
<211> LENGTH: 700
<212> TYPE: PRT
<213> ORGANISM: Salmonella enterica

<400> SEQUENCE: 17

Met Phe Asn Ile Arg Asn Thr Gln Pro Ser Val Ser Met Gln Ala Ile
1               5                   10                  15

Ala Gly Ala Ala Ala Pro Glu Ala Ser Pro Glu Glu Ile Val Trp Glu
                20                  25                  30

Lys Ile Gln Val Phe Phe Pro Gln Glu Asn Tyr Glu Glu Ala Gln Gln
            35                  40                  45

Cys Leu Ala Glu Leu Cys His Pro Ala Arg Gly Met Leu Pro Asp His
50                  55                  60

Ile Ser Ser Gln Phe Ala Arg Leu Lys Ala Leu Thr Phe Pro Ala Trp
65                  70                  75                  80

Glu Glu Asn Ile Gln Cys Asn Arg Asp Gly Ile Asn Gln Phe Cys Ile
                85                  90                  95

Leu Asp Ala Gly Ser Lys Glu Ile Leu Ser Ile Thr Leu Asp Asp Ala
            100                 105                 110

Gly Asn Tyr Thr Val Asn Cys Gln Gly Tyr Ser Glu Ala His Asp Phe
        115                 120                 125

Ile Met Asp Thr Glu Pro Gly Glu Glu Cys Thr Glu Phe Ala Glu Gly
    130                 135                 140

Ala Ser Gly Thr Ser Leu Arg Pro Ala Thr Thr Val Ser Gln Lys Ala
145                 150                 155                 160

Ala Glu Tyr Asp Ala Val Trp Ser Lys Trp Glu Arg Asp Ala Pro Ala
                165                 170                 175

Gly Glu Ser Pro Gly Arg Ala Ala Val Gln Glu Met Arg Asp Cys
            180                 185                 190

Leu Asn Asn Gly Asn Pro Val Leu Asn Val Gly Ala Ser Gly Leu Thr
        195                 200                 205

Thr Leu Pro Asp Arg Leu Pro His Ile Thr Thr Leu Val Ile Pro
    210                 215                 220

Asp Asn Asn Leu Thr Ser Leu Pro Glu Leu Pro Glu Gly Leu Arg Glu
225                 230                 235                 240

Leu Glu Val Ser Gly Asn Leu Gln Leu Thr Ser Leu Pro Ser Leu Pro
```

```
                245                 250                 255
Gln Gly Leu Gln Lys Leu Trp Ala Tyr Asn Asn Trp Leu Ala Ser Leu
            260                 265                 270

Pro Thr Leu Pro Pro Gly Leu Gly Asp Leu Ala Val Ser Asn Asn Gln
        275                 280                 285

Leu Thr Ser Leu Pro Glu Met Pro Pro Ala Leu Arg Glu Leu Arg Val
290                 295                 300

Ser Gly Asn Asn Leu Thr Ser Leu Pro Ala Leu Pro Ser Gly Leu Gln
305                 310                 315                 320

Lys Leu Trp Ala Tyr Asn Asn Arg Leu Thr Ser Leu Pro Glu Met Ser
                325                 330                 335

Pro Gly Leu Gln Glu Leu Asp Val Ser His Asn Gln Leu Thr Arg Leu
            340                 345                 350

Pro Gln Ser Leu Thr Gly Leu Ser Ser Ala Ala Arg Val Tyr Leu Asp
        355                 360                 365

Gly Asn Pro Leu Ser Val Arg Thr Leu Gln Ala Leu Arg Asp Ile Ile
370                 375                 380

Gly His Ser Gly Ile Arg Ile His Phe Asp Met Ala Gly Pro Ser Val
385                 390                 395                 400

Pro Arg Glu Ala Arg Ala Leu His Leu Ala Val Ala Asp Trp Leu Thr
                405                 410                 415

Ser Ala Arg Glu Gly Glu Ala Ala Gln Ala Asp Arg Trp Gln Ala Phe
            420                 425                 430

Gly Leu Glu Asp Asn Ala Ala Ala Phe Ser Leu Val Leu Asp Arg Leu
        435                 440                 445

Arg Glu Thr Glu Asn Phe Lys Lys Asp Ala Gly Phe Lys Ala Gln Ile
450                 455                 460

Ser Ser Trp Leu Thr Gln Leu Ala Glu Asp Ala Ala Leu Arg Ala Lys
465                 470                 475                 480

Thr Phe Ala Met Ala Thr Glu Ala Thr Ser Thr Cys Glu Asp Arg Val
                485                 490                 495

Thr His Ala Leu His Gln Met Asn Asn Val Gln Leu Val His Asn Ala
            500                 505                 510

Glu Lys Gly Glu Tyr Asp Asn Asn Leu Gln Gly Leu Val Ser Thr Gly
        515                 520                 525

Arg Glu Met Phe Arg Leu Ala Thr Leu Glu Gln Ile Ala Arg Glu Lys
530                 535                 540

Ala Gly Thr Leu Ala Leu Val Asp Asp Val Glu Val Tyr Leu Ala Phe
545                 550                 555                 560

Gln Asn Lys Leu Lys Glu Ser Leu Glu Leu Thr Ser Val Thr Ser Glu
                565                 570                 575

Met Arg Phe Phe Asp Val Ser Gly Val Thr Val Ser Asp Leu Gln Ala
            580                 585                 590

Ala Glu Leu Gln Val Lys Thr Ala Glu Asn Ser Gly Phe Ser Lys Trp
        595                 600                 605

Ile Leu Gln Trp Gly Pro Leu His Ser Val Leu Glu Arg Lys Val Pro
610                 615                 620

Glu Arg Phe Asn Ala Leu Arg Glu Lys Gln Ile Ser Tyr Glu Asp
625                 630                 635                 640

Thr Tyr Arg Lys Leu Tyr Asp Glu Val Leu Lys Ser Ser Gly Leu Val
                645                 650                 655

Asp Asp Thr Asp Ala Glu Arg Thr Ile Gly Val Ser Ala Met Asp Ser
            660                 665                 670
```

```
Ala Lys Lys Glu Phe Leu Asp Gly Leu Arg Ala Leu Val Asp Glu Val
        675                 680                 685

Leu Gly Ser Tyr Leu Thr Ala Arg Trp Arg Leu Asn
    690                 695                 700

<210> SEQ ID NO 18
<211> LENGTH: 788
<212> TYPE: PRT
<213> ORGANISM: Salmonella enterica

<400> SEQUENCE: 18

Met Pro Phe His Ile Gly Ser Gly Cys Leu Pro Ala Thr Ile Ser Asn
1               5                   10                  15

Arg Arg Ile Tyr Arg Ile Ala Trp Ser Asp Thr Pro Pro Glu Met Ser
            20                  25                  30

Ser Trp Glu Lys Met Lys Glu Phe Phe Cys Ser Thr His Gln Thr Glu
        35                  40                  45

Ala Leu Glu Cys Ile Trp Thr Ile Cys His Pro Ala Gly Thr Thr
    50                  55                  60

Arg Glu Asp Val Ile Asn Arg Phe Glu Leu Leu Arg Thr Leu Ala Tyr
65                  70                  75                  80

Ala Gly Trp Glu Glu Ser Ile His Ser Gly Gln His Gly Glu Asn Tyr
                85                  90                  95

Phe Cys Ile Leu Asp Glu Asp Ser Gln Glu Ile Leu Ser Val Thr Leu
            100                 105                 110

Asp Asp Ala Gly Asn Tyr Thr Val Asn Cys Gln Gly Tyr Ser Glu Thr
        115                 120                 125

His Arg Leu Thr Leu Asp Thr Ala Gln Gly Glu Glu Gly Thr Gly His
    130                 135                 140

Ala Glu Gly Ala Ser Gly Thr Phe Arg Thr Ser Phe Leu Pro Ala Thr
145                 150                 155                 160

Thr Ala Pro Gln Thr Pro Ala Glu Tyr Asp Ala Val Trp Ser Ala Trp
                165                 170                 175

Arg Arg Ala Ala Pro Ala Glu Glu Ser Arg Gly Arg Ala Ala Val Val
            180                 185                 190

Gln Lys Met Arg Ala Cys Leu Asn Asn Gly Asn Ala Val Leu Asn Val
        195                 200                 205

Gly Glu Ser Gly Leu Thr Thr Leu Pro Asp Cys Leu Pro Ala His Ile
    210                 215                 220

Thr Thr Leu Val Ile Pro Asp Asn Asn Leu Thr Ser Leu Pro Ala Leu
225                 230                 235                 240

Pro Pro Glu Leu Arg Thr Leu Glu Val Ser Gly Asn Gln Leu Thr Ser
                245                 250                 255

Leu Pro Val Leu Pro Pro Gly Leu Leu Glu Leu Ser Ile Phe Ser Asn
            260                 265                 270

Pro Leu Thr His Leu Pro Ala Leu Pro Ser Gly Leu Cys Lys Leu Trp
        275                 280                 285

Ile Phe Gly Asn Gln Leu Thr Ser Leu Pro Val Leu Pro Pro Gly Leu
    290                 295                 300

Gln Glu Leu Ser Val Ser Asp Asn Gln Leu Ala Ser Leu Pro Ala Leu
305                 310                 315                 320

Pro Ser Glu Leu Cys Lys Leu Trp Ala Tyr Asn Asn Gln Leu Thr Ser
                325                 330                 335

Leu Pro Met Leu Pro Ser Gly Leu Gln Glu Leu Ser Val Ser Asp Asn
```

```
              340             345                 350
    Gln Leu Ala Ser Leu Pro Thr Leu Pro Ser Glu Leu Tyr Lys Leu Trp
                355                 360                 365
    Ala Tyr Asn Asn Arg Leu Thr Ser Leu Pro Ala Leu Pro Ser Gly Leu
                370                 375                 380
    Lys Glu Leu Ile Val Ser Gly Asn Arg Leu Thr Ser Leu Pro Val Leu
    385                 390                 395                 400
    Pro Ser Glu Leu Lys Glu Leu Met Val Ser Gly Asn Arg Leu Thr Ser
                    405                 410                 415
    Leu Pro Met Leu Pro Ser Gly Leu Leu Ser Leu Ser Val Tyr Arg Asn
                420                 425                 430
    Gln Leu Thr Arg Leu Pro Glu Ser Leu Ile His Leu Ser Ser Glu Thr
                435                 440                 445
    Thr Val Asn Leu Glu Gly Asn Pro Leu Ser Glu Arg Thr Leu Gln Ala
                450                 455                 460
    Leu Arg Glu Ile Thr Ser Ala Pro Gly Tyr Ser Gly Pro Ile Ile Arg
    465                 470                 475                 480
    Phe Asp Met Ala Gly Ala Ser Ala Pro Arg Glu Thr Arg Ala Leu His
                    485                 490                 495
    Leu Ala Ala Ala Asp Trp Leu Val Pro Ala Arg Glu Gly Glu Pro Ala
                500                 505                 510
    Pro Ala Asp Arg Trp His Met Phe Gly Gln Glu Asp Asn Ala Asp Ala
                515                 520                 525
    Phe Ser Leu Phe Leu Asp Arg Leu Ser Glu Thr Glu Asn Phe Ile Lys
                530                 535                 540
    Asp Ala Gly Phe Lys Ala Gln Ile Ser Ser Trp Leu Ala Gln Leu Ala
    545                 550                 555                 560
    Glu Asp Glu Ala Leu Arg Ala Asn Thr Phe Ala Met Ala Thr Glu Ala
                    565                 570                 575
    Thr Ser Ser Cys Glu Asp Arg Val Thr Phe Phe Leu His Gln Met Lys
                580                 585                 590
    Asn Val Gln Leu Val His Asn Ala Glu Lys Gly Gln Tyr Asp Asn Asp
                595                 600                 605
    Leu Ala Ala Leu Val Ala Thr Gly Arg Glu Met Phe Arg Leu Gly Lys
    610                 615                 620
    Leu Glu Gln Ile Ala Arg Glu Lys Val Arg Thr Leu Ala Leu Val Asp
    625                 630                 635                 640
    Glu Ile Glu Val Trp Leu Ala Tyr Gln Asn Lys Leu Lys Lys Ser Leu
                    645                 650                 655
    Gly Leu Thr Ser Val Thr Ser Glu Met Arg Phe Phe Asp Val Ser Gly
                660                 665                 670
    Val Thr Val Thr Asp Leu Gln Asp Ala Glu Leu Gln Val Lys Ala Ala
                675                 680                 685
    Glu Lys Ser Glu Phe Arg Glu Trp Ile Leu Gln Trp Gly Pro Leu His
                690                 695                 700
    Arg Val Leu Glu Arg Lys Ala Pro Glu Arg Val Asn Ala Leu Arg Glu
    705                 710                 715                 720
    Lys Gln Ile Ser Asp Tyr Glu Glu Thr Tyr Arg Met Leu Ser Asp Thr
                    725                 730                 735
    Glu Leu Arg Pro Ser Gly Leu Val Gly Asn Thr Asp Ala Glu Arg Thr
                740                 745                 750
    Ile Gly Ala Arg Ala Met Glu Ser Ala Lys Lys Thr Phe Leu Asp Gly
                755                 760                 765
```

```
Leu Arg Pro Leu Val Glu Glu Met Leu Gly Ser Tyr Leu Asn Val Gln
    770                 775                 780

Trp Arg Arg Asn
785

<210> SEQ ID NO 19
<211> LENGTH: 385
<212> TYPE: PRT
<213> ORGANISM: Salmonella enterica

<400> SEQUENCE: 19

Met Met Ala Ser Arg Asp Lys Asp Ala Asp Ser Leu Ile Met Tyr Asp
1               5                   10                  15

Arg Thr Leu Leu Trp Leu Thr Phe Gly Leu Ala Ile Gly Phe Val
            20                  25                  30

Met Val Thr Ser Ala Ser Met Pro Val Gly Gln Arg Leu Ala Asn Asp
            35                  40                  45

Pro Phe Leu Phe Ala Lys Arg Asp Ala Leu Tyr Ile Phe Leu Ala Phe
    50                  55                  60

Cys Leu Ala Met Val Thr Leu Arg Leu Pro Met Thr Phe Trp Gln Lys
65                  70                  75                  80

Tyr Ser Thr Thr Met Leu Ile Ala Ser Ile Ile Met Leu Leu Ile Val
                85                  90                  95

Leu Val Val Gly Ser Ser Val Asn Gly Ala Ser Arg Trp Ile Ala Leu
                100                 105                 110

Gly Pro Leu Arg Ile Gln Pro Ala Glu Phe Thr Lys Leu Ser Leu Phe
            115                 120                 125

Cys Tyr Leu Ala Asn Tyr Leu Val Arg Lys Val Asp Glu Val Arg Asn
    130                 135                 140

Asn Leu Arg Gly Phe Leu Lys Pro Met Gly Val Ile Leu Val Leu Ala
145                 150                 155                 160

Val Leu Leu Leu Ala Gln Pro Asp Leu Gly Thr Val Val Val Leu Phe
                165                 170                 175

Val Thr Thr Leu Ala Met Leu Phe Leu Ala Gly Ala Lys Leu Trp Gln
                180                 185                 190

Phe Ile Ala Ile Ile Gly Met Gly Ile Ser Ala Val Ile Leu Leu Ile
        195                 200                 205

Leu Ala Glu Pro Tyr Arg Ile Arg Arg Val Thr Ser Phe Trp Asn Pro
    210                 215                 220

Trp Glu Asp Pro Phe Gly Ser Gly Tyr Gln Leu Thr Gln Ser Leu Met
225                 230                 235                 240

Ala Phe Gly Arg Gly Glu Ile Trp Gly Gln Gly Leu Gly Asn Ser Val
                245                 250                 255

Gln Lys Leu Glu Tyr Leu Pro Glu Ala His Thr Asp Phe Ile Phe Ala
            260                 265                 270

Ile Ile Gly Glu Glu Leu Gly Tyr Ile Gly Val Val Leu Ala Leu Leu
        275                 280                 285

Met Val Phe Phe Val Ala Phe Arg Ala Met Ser Ile Gly Arg Lys Ala
    290                 295                 300

Leu Glu Ile Asp His Arg Phe Ser Gly Phe Leu Ala Cys Ser Ile Gly
305                 310                 315                 320

Ile Trp Phe Ser Phe Gln Ala Leu Val Asn Val Gly Ala Ala Ala Gly
                325                 330                 335

Met Leu Pro Thr Lys Gly Leu Thr Leu Pro Leu Ile Ser Tyr Gly Gly
```

```
                    340                 345                 350
Ser Ser Leu Leu Ile Met Ser Thr Ala Ile Met Phe Leu Leu Arg Ile
            355                 360                 365

Asp Tyr Glu Thr Arg Leu Glu Lys Ala Gln Ala Phe Thr Arg Gly Ser
            370                 375                 380

Arg
385

<210> SEQ ID NO 20
<211> LENGTH: 420
<212> TYPE: PRT
<213> ORGANISM: Salmonella enterica

<400> SEQUENCE: 20

Met Ile Lys Ala Thr Asp Arg Lys Leu Val Val Gly Leu Glu Ile Gly
1               5                   10                  15

Thr Ala Lys Val Ala Ala Leu Val Gly Glu Val Leu Pro Asp Gly Met
            20                  25                  30

Val Asn Ile Ile Gly Val Gly Ser Cys Pro Ser Arg Gly Met Asp Lys
        35                  40                  45

Gly Gly Val Asn Asp Leu Glu Ser Val Val Lys Cys Val Gln Arg Ala
    50                  55                  60

Ile Asp Gln Ala Glu Leu Met Ala Asp Cys Gln Ile Ser Ser Val Tyr
65                  70                  75                  80

Leu Ala Leu Ser Gly Lys His Ile Ser Cys Gln Asn Glu Ile Gly Met
                85                  90                  95

Val Pro Ile Ser Glu Glu Val Thr Gln Glu Asp Val Glu Asn Val
            100                 105                 110

Val His Thr Ala Lys Ser Val Arg Val Arg Asp Glu His Arg Val Leu
        115                 120                 125

His Val Ile Pro Gln Glu Tyr Ala Ile Asp Tyr Gln Glu Gly Ile Lys
    130                 135                 140

Asn Pro Val Gly Leu Ser Gly Val Arg Met Gln Ala Lys Val His Leu
145                 150                 155                 160

Ile Thr Cys His Asn Asp Met Ala Lys Asn Ile Val Lys Ala Val Glu
                165                 170                 175

Arg Cys Gly Leu Lys Val Asp Gln Leu Ile Phe Ala Gly Leu Ala Ala
            180                 185                 190

Ser Tyr Ser Val Leu Thr Glu Asp Glu Arg Glu Leu Gly Val Cys Val
        195                 200                 205

Val Asp Ile Gly Gly Gly Thr Met Asp Ile Ala Val Tyr Thr Gly Gly
    210                 215                 220

Ala Leu Arg His Thr Lys Val Ile Pro Tyr Ala Gly Asn Val Val Thr
225                 230                 235                 240

Ser Asp Ile Ala Tyr Ala Phe Gly Thr Pro Pro Ser Asp Ala Glu Ala
                245                 250                 255

Ile Lys Val Arg His Gly Cys Ala Leu Gly Ser Ile Val Gly Lys Asp
            260                 265                 270

Glu Ser Val Glu Val Pro Ser Val Gly Gly Arg Pro Pro Arg Ser Leu
        275                 280                 285

Gln Arg Gln Thr Leu Ala Glu Val Ile Glu Pro Arg Tyr Thr Glu Leu
    290                 295                 300

Leu Asn Leu Val Asn Glu Glu Ile Leu Gln Leu Gln Glu Gln Leu Arg
305                 310                 315                 320
```

```
Gln Gln Gly Val Lys His His Leu Ala Ala Gly Ile Val Leu Thr Gly
                325                 330                 335

Gly Ala Ala Gln Ile Glu Gly Leu Ala Ala Cys Ala Gln Arg Val Phe
            340                 345                 350

His Thr Gln Val Arg Ile Gly Ala Pro Leu Asn Ile Thr Gly Leu Thr
        355                 360                 365

Asp Tyr Ala Gln Glu Pro Tyr Tyr Ser Thr Ala Val Gly Leu Leu His
    370                 375                 380

Tyr Gly Lys Glu Ser His Leu Asn Gly Glu Ala Val Glu Lys Arg
385                 390                 395                 400

Val Thr Ala Ser Val Gly Ser Trp Ile Lys Arg Leu Asn Ser Trp Leu
                405                 410                 415

Arg Lys Glu Phe
            420

<210> SEQ ID NO 21
<211> LENGTH: 383
<212> TYPE: PRT
<213> ORGANISM: Salmonella enterica

<400> SEQUENCE: 21

Met Phe Glu Pro Met Glu Leu Thr Asn Asp Ala Val Ile Lys Val Ile
1               5                   10                  15

Gly Val Gly Gly Gly Gly Asn Ala Val Glu His Met Val Arg Glu
                20                  25                  30

Arg Ile Glu Gly Val Glu Phe Phe Ala Val Asn Thr Asp Ala Gln Ala
            35                  40                  45

Leu Arg Lys Thr Ala Val Gly Gln Thr Ile Gln Ile Gly Ser Gly Ile
    50                  55                  60

Thr Lys Gly Leu Gly Ala Gly Ala Asn Pro Glu Val Gly Arg Asn Ala
65                  70                  75                  80

Ala Asp Glu Asp Arg Glu Ala Leu Arg Ala Ala Leu Glu Gly Ala Asp
                85                  90                  95

Met Val Phe Ile Ala Ala Gly Met Gly Gly Gly Thr Gly Thr Gly Ala
            100                 105                 110

Ala Pro Val Val Ala Glu Val Ala Lys Asp Leu Gly Ile Leu Thr Val
        115                 120                 125

Ala Val Val Thr Lys Pro Phe Asn Phe Glu Gly Lys Lys Arg Met Ala
    130                 135                 140

Phe Ala Glu Gln Gly Ile Thr Glu Leu Ser Lys His Val Asp Ser Leu
145                 150                 155                 160

Ile Thr Ile Pro Asn Asp Lys Leu Leu Lys Val Leu Gly Arg Gly Ile
                165                 170                 175

Ser Leu Leu Asp Ala Phe Gly Ala Ala Asn Asp Val Leu Lys Gly Ala
            180                 185                 190

Val Gln Gly Ile Ala Glu Leu Ile Thr Arg Pro Gly Leu Met Asn Val
        195                 200                 205

Asp Phe Ala Asp Val Arg Thr Val Met Ser Glu Met Gly Tyr Ala Met
    210                 215                 220

Met Gly Ser Gly Val Ala Ser Gly Glu Asp Arg Ala Glu Glu Ala
225                 230                 235                 240

Glu Met Ala Ile Ser Ser Pro Leu Leu Glu Asp Ile Asp Leu Ser Gly
                245                 250                 255

Ala Arg Gly Val Leu Val Asn Ile Thr Ala Gly Phe Asp Leu Arg Leu
            260                 265                 270
```

```
Asp Glu Phe Glu Thr Val Gly Asn Thr Ile Arg Ala Phe Ala Ser Asp
            275                 280                 285

Asn Ala Thr Val Val Ile Gly Thr Ser Leu Asp Pro Asp Met Asn Asp
    290                 295                 300

Glu Leu Arg Val Thr Val Ala Thr Gly Ile Gly Met Asp Lys Arg
305                 310                 315                 320

Pro Glu Ile Thr Leu Val Thr Asn Lys Gln Val Gln Gln Pro Val Leu
                325                 330                 335

Asp Arg Tyr Gln Gln His Gly Met Ala Pro Leu Thr Gln Glu Gln Lys
            340                 345                 350

Thr Val Ala Lys Val Val Asn Asp Asn Thr Pro Gln Ala Ala Lys Glu
        355                 360                 365

Pro Asp Tyr Leu Asp Ile Pro Ala Phe Leu Arg Lys Gln Ala Asp
    370                 375                 380
```

<210> SEQ ID NO 22
<211> LENGTH: 495
<212> TYPE: PRT
<213> ORGANISM: Salmonella enterica

<400> SEQUENCE: 22

```
Met Ala Asp Arg Asn Leu Arg Asp Leu Leu Ala Pro Trp Val Ala Gly
1               5                   10                  15

Leu Pro Ala Arg Glu Leu Arg Glu Met Thr Leu Asp Ser Arg Val Ala
            20                  25                  30

Ala Ala Gly Asp Leu Phe Val Ala Val Val Gly His Gln Ala Asp Gly
        35                  40                  45

Arg Arg Tyr Ile Pro Gln Ala Ile Ala Gln Gly Val Ala Ala Ile Ile
    50                  55                  60

Ala Glu Ala Lys Asp Glu Ala Ser Asp Gly Glu Ile Arg Glu Met His
65                  70                  75                  80

Gly Val Pro Val Val Tyr Leu Ser Gln Leu Asn Glu Arg Leu Ser Ala
                85                  90                  95

Leu Ala Gly Arg Phe Tyr His Glu Pro Ser Glu Asn Met Arg Leu Val
            100                 105                 110

Ala Val Thr Gly Thr Asn Gly Lys Thr Thr Thr Thr Gln Leu Leu Ala
        115                 120                 125

Gln Trp Ser Gln Leu Leu Gly Glu Thr Ser Ala Val Met Gly Thr Val
    130                 135                 140

Gly Asn Gly Leu Leu Gly Lys Val Ile Pro Thr Glu Asn Thr Thr Gly
145                 150                 155                 160

Ser Ala Val Asp Val Gln His Val Leu Ala Ser Leu Val Ala Gln Gly
                165                 170                 175

Ala Thr Phe Gly Ala Met Glu Val Ser Ser His Gly Leu Val Gln His
            180                 185                 190

Arg Val Ala Ala Leu Lys Phe Ala Ala Ser Val Phe Thr Asn Leu Ser
        195                 200                 205

Arg Asp His Leu Asp Tyr His Gly Asp Met Ala His Tyr Glu Ala Ala
    210                 215                 220

Lys Trp Met Leu Tyr Ser Thr His His Gly Gln Ala Ile Val Asn
225                 230                 235                 240

Ala Asp Asp Glu Val Gly Arg Arg Trp Leu Ala Ser Leu Pro Asp Ala
                245                 250                 255

Val Ala Val Ser Met Glu Gly His Ile Asn Pro Asn Cys His Gly Arg
```

```
                260                 265                 270
Trp Leu Lys Ala Glu Ala Val Glu Tyr His Asp Arg Gly Ala Thr Ile
        275                 280                 285
Arg Phe Ala Ser Ser Trp Gly Glu Gly Glu Ile Glu Ser Arg Leu Met
        290                 295                 300
Gly Ala Phe Asn Val Ser Asn Leu Leu Leu Ala Leu Ala Thr Leu Leu
305                 310                 315                 320
Ala Leu Gly Tyr Pro Leu Thr Asp Leu Leu Lys Thr Ala Ala Arg Leu
                325                 330                 335
Gln Pro Val Cys Gly Arg Met Glu Val Phe Thr Ala Pro Gly Lys Pro
                340                 345                 350
Thr Val Val Val Asp Tyr Ala His Thr Pro Asp Ala Leu Glu Lys Ala
                355                 360                 365
Leu Gln Ala Ala Arg Leu His Cys Ala Gly Lys Leu Trp Cys Val Phe
                370                 375                 380
Gly Cys Gly Gly Asp Arg Asp Lys Gly Lys Arg Pro Leu Met Gly Ala
385                 390                 395                 400
Ile Ala Glu Glu Phe Ala Asp Ile Val Val Thr Asp Asp Asn Pro
                405                 410                 415
Arg Thr Glu Glu Pro Arg Ala Ile Ile Asn Asp Ile Leu Ala Gly Met
                420                 425                 430
Leu Asp Ala Gly Gln Val Arg Val Met Glu Gly Arg Ala Glu Ala Val
                435                 440                 445
Thr Asn Ala Ile Met Gln Ala Lys Asp Asn Asp Val Val Leu Ile Ala
                450                 455                 460
Gly Lys Gly His Glu Asp Tyr Gln Ile Val Gly Thr Gln Arg Leu Asp
465                 470                 475                 480
Tyr Ser Asp Arg Val Thr Ala Ala Arg Leu Leu Gly Val Ile Ala
                485                 490                 495

<210> SEQ ID NO 23
<211> LENGTH: 440
<212> TYPE: PRT
<213> ORGANISM: Salmonella enterica

<400> SEQUENCE: 23

Met Ser Glu Phe Ser Gln Thr Val Pro Glu Leu Val Ala Trp Ala Arg
1               5                   10                  15
Lys Asn Asp Phe Ser Ile Ser Leu Pro Val Asp Arg Leu Ser Phe Leu
                20                  25                  30
Leu Ala Val Ala Thr Leu Asn Gly Glu Arg Leu Asp Gly Glu Met Ser
            35                  40                  45
Glu Gly Glu Leu Val Asp Ala Phe Arg His Val Ser Asp Ala Phe Glu
        50                  55                  60
Gln Thr Ser Glu Thr Ile Gly Val Arg Ala Asn Asn Ala Ile Asn Asp
65                  70                  75                  80
Met Val Arg Gln Arg Leu Leu Asn Arg Phe Thr Ser Glu Gln Ala Glu
                85                  90                  95
Gly Asn Ala Ile Tyr Arg Leu Thr Pro Leu Gly Ile Gly Ile Thr Asp
                100                 105                 110
Tyr Tyr Ile Arg Gln Arg Glu Phe Ser Thr Leu Arg Leu Ser Met Gln
            115                 120                 125
Leu Ser Ile Val Ala Gly Glu Leu Lys Arg Ala Ala Asp Ala Ala Ala
        130                 135                 140
```

-continued

Glu Gly Gly Asp Glu Phe His Trp His Arg Asn Val Tyr Ala Pro Leu
145                 150                 155                 160

Lys Tyr Ser Val Ala Glu Ile Phe Asp Ser Ile Asp Leu Thr Gln Arg
        165                 170                 175

Ile Met Asp Glu Gln Gln Gln Val Lys Asp Asp Ile Ala Gln Leu
        180                 185                 190

Leu Asn Lys Asp Trp Arg Ala Ala Ile Ser Ser Cys Glu Leu Leu Leu
        195                 200                 205

Ser Glu Thr Ser Gly Thr Leu Arg Glu Leu Gln Asp Thr Leu Glu Ala
        210                 215                 220

Ala Gly Asp Lys Leu Gln Ala Asn Leu Leu Arg Ile Gln Asp Ala Thr
225                 230                 235                 240

Met Thr His Asp Asp Leu His Phe Val Asp Arg Leu Val Phe Asp Leu
                245                 250                 255

Gln Ser Lys Leu Asp Arg Ile Ile Ser Trp Gly Gln Ser Ile Asp
        260                 265                 270

Leu Trp Ile Gly Tyr Asp Arg His Val His Lys Phe Ile Arg Thr Ala
        275                 280                 285

Ile Asp Met Asp Lys Asn Arg Val Phe Ala Gln Arg Leu Arg Gln Ser
290                 295                 300

Val Gln Thr Tyr Phe Asp Asp Pro Trp Ala Leu Thr Tyr Ala Asn Ala
305                 310                 315                 320

Asp Arg Leu Leu Asp Met Arg Asp Glu Met Ala Leu Arg Asp Asp
                325                 330                 335

Glu Val Thr Gly Glu Leu Pro Pro Asp Leu Glu Tyr Glu Glu Phe Asn
        340                 345                 350

Glu Ile Arg Glu Gln Leu Ala Ala Ile Ile Glu Glu Gln Leu Ala Ile
        355                 360                 365

Tyr Lys Thr Arg Gln Thr Pro Leu Asp Leu Gly Leu Val Val Arg Glu
        370                 375                 380

Tyr Leu Ala Gln Tyr Pro Arg Ala Arg His Phe Asp Val Ala Arg Ile
385                 390                 395                 400

Val Ile Asp Gln Ala Val Arg Leu Gly Val Ala Gln Ala Asp Phe Thr
            405                 410                 415

Gly Leu Pro Ala Lys Trp Gln Pro Ile Asn Asp Tyr Gly Ala Lys Val
                420                 425                 430

Gln Ala His Val Ile Asp Lys Tyr
        435                 440

<210> SEQ ID NO 24
<211> LENGTH: 786
<212> TYPE: PRT
<213> ORGANISM: Salmonella enterica

<400> SEQUENCE: 24

Met Lys Lys Arg Ile Pro Thr Leu Leu Ala Thr Met Ile Ala Ser Ala
1               5                   10                  15

Leu Tyr Ser His Gln Gly Leu Ala Ala Asp Leu Ala Ser Gln Cys Met
            20                  25                  30

Leu Gly Val Pro Ser Tyr Asp Arg Pro Leu Val Lys Gly Asp Thr Asn
        35                  40                  45

Asp Leu Pro Val Thr Ile Asn Ala Asp Asn Ala Lys Gly Asn Tyr Pro
    50                  55                  60

Asp Asp Ala Val Phe Thr Gly Asn Val Asp Ile Met Gln Gly Asn Ser
65                  70                  75                  80

-continued

Arg Leu Gln Ala Asp Glu Val Gln Leu His Gln Lys Gln Ala Glu Gly
                85                  90                  95

Gln Pro Glu Pro Val Arg Thr Val Asp Ala Leu Gly Asn Val His Tyr
            100                 105                 110

Asp Asp Asn Gln Val Ile Leu Lys Gly Pro Lys Gly Trp Ala Asn Leu
        115                 120                 125

Asn Thr Lys Asp Thr Asn Val Trp Glu Gly Asp Tyr Gln Met Val Gly
    130                 135                 140

Arg Gln Gly Arg Gly Lys Ala Asp Leu Met Lys Gln Arg Gly Glu Asn
145                 150                 155                 160

Arg Tyr Thr Ile Leu Glu Asn Gly Ser Phe Thr Ser Cys Leu Pro Gly
            165                 170                 175

Ser Asp Thr Trp Ser Val Val Gly Ser Glu Val Ile His Asp Arg Glu
        180                 185                 190

Glu Gln Val Ala Glu Ile Trp Asn Ala Arg Phe Lys Val Gly Pro Val
    195                 200                 205

Pro Ile Phe Tyr Ser Pro Tyr Leu Gln Leu Pro Val Gly Asp Lys Arg
210                 215                 220

Arg Ser Gly Phe Leu Ile Pro Asn Ala Lys Tyr Thr Thr Lys Asn Tyr
225                 230                 235                 240

Phe Glu Phe Tyr Leu Pro Tyr Tyr Trp Asn Ile Ala Pro Asn Met Asp
            245                 250                 255

Ala Thr Ile Thr Pro His Tyr Met His Arg Arg Gly Asn Ile Met Trp
        260                 265                 270

Glu Asn Glu Phe Arg Tyr Leu Thr Gln Ala Gly Glu Gly Val Met Glu
    275                 280                 285

Leu Asp Tyr Leu Pro Ser Asp Lys Val Tyr Glu Asp His Pro Lys
290                 295                 300

Glu Gly Asp Lys His Arg Trp Leu Phe Asn Trp Gln His Ser Gly Val
305                 310                 315                 320

Met Asp Gln Val Trp Arg Phe Asn Val Asp Tyr Thr Lys Val Ser Asp
            325                 330                 335

Ser Ser Tyr Phe Asn Asp Phe Asp Ser Lys Tyr Gly Ser Ser Thr Asp
        340                 345                 350

Gly Tyr Ala Thr Gln Lys Phe Ser Val Gly Tyr Ala Val Gln Asn Phe
    355                 360                 365

Asp Ala Thr Val Ser Thr Lys Gln Phe Gln Val Phe Asn Asp Gln Asn
    370                 375                 380

Thr Ser Ser Tyr Ser Ala Glu Pro Gln Leu Asp Val Asn Tyr Tyr His
385                 390                 395                 400

Asn Asp Leu Gly Pro Phe Asp Thr Arg Ile Tyr Gly Gln Ala Val His
            405                 410                 415

Phe Val Asn Thr Lys Asp Asn Met Pro Glu Ala Thr Arg Val His Leu
        420                 425                 430

Glu Pro Thr Ile Asn Leu Pro Leu Ser Asn Arg Trp Gly Ser Leu Asn
    435                 440                 445

Thr Glu Ala Lys Leu Met Ala Thr His Tyr Gln Gln Thr Asn Leu Asp
450                 455                 460

Ser Tyr Asn Ser Asp Pro Asn Asn Lys Asn Lys Leu Glu Asp Ser Val
465                 470                 475                 480

Asn Arg Val Met Pro Gln Phe Lys Val Asp Gly Lys Leu Ile Phe Glu
            485                 490                 495

```
Arg Asp Met Ala Met Leu Ala Pro Gly Tyr Thr Gln Thr Leu Glu Pro
            500                 505                 510

Arg Val Gln Tyr Leu Tyr Val Pro Tyr Arg Asp Gln Ser Gly Ile Tyr
        515                 520                 525

Asn Tyr Asp Ser Ser Leu Leu Gln Ser Asp Tyr Asn Gly Leu Phe Arg
    530                 535                 540

Asp Arg Thr Tyr Gly Gly Leu Asp Arg Ile Ala Ser Ala Asn Gln Val
545                 550                 555                 560

Thr Thr Gly Val Thr Thr Arg Ile Tyr Asp Ala Ala Val Glu Arg
                565                 570                 575

Phe Asn Val Ser Val Gly Gln Ile Tyr Tyr Phe Thr Glu Ser Arg Thr
            580                 585                 590

Gly Asp Asp Asn Ile Lys Trp Glu Asn Asp Asp Lys Thr Gly Ser Leu
        595                 600                 605

Val Trp Ala Gly Asp Thr Tyr Trp Arg Ile Ser Glu Arg Trp Gly Leu
    610                 615                 620

Arg Ser Gly Val Gln Tyr Asp Thr Arg Leu Asp Ser Val Ala Thr Ser
625                 630                 635                 640

Ser Ser Ser Leu Glu Tyr Arg Arg Asp Gln Asp Arg Leu Val Gln Leu
                645                 650                 655

Asn Tyr Arg Tyr Ala Ser Pro Glu Tyr Ile Gln Ala Thr Leu Pro Ser
            660                 665                 670

Tyr Tyr Ser Thr Ala Glu Gln Tyr Lys Asn Gly Ile Asn Gln Val Gly
        675                 680                 685

Ala Val Ala Ser Trp Pro Ile Ala Asp Arg Trp Ser Ile Val Gly Ala
    690                 695                 700

Tyr Tyr Phe Asp Thr Asn Ser Ser Lys Pro Ala Asp Gln Met Leu Gly
705                 710                 715                 720

Leu Gln Tyr Asn Ser Cys Cys Tyr Ala Ile Arg Val Gly Tyr Glu Arg
                725                 730                 735

Lys Leu Asn Gly Trp Asp Asn Asp Lys Gln His Ala Ile Tyr Asp Asn
            740                 745                 750

Ala Ile Gly Phe Asn Ile Glu Leu Arg Gly Leu Ser Ser Asn Tyr Gly
        755                 760                 765

Leu Gly Thr Gln Glu Met Leu Arg Ser Asn Ile Leu Pro Tyr Gln Ser
    770                 775                 780

Ser Met
785

<210> SEQ ID NO 25
<211> LENGTH: 323
<212> TYPE: PRT
<213> ORGANISM: Salmonella enterica

<400> SEQUENCE: 25

Met Ala Gln Glu Tyr Thr Val Glu Gln Leu Asn His Gly Arg Lys Val
1               5                   10                  15

Tyr Asp Phe Met Arg Trp Asp Phe Trp Ala Phe Gly Ile Ser Gly Leu
            20                  25                  30

Leu Leu Ile Ala Ala Ile Val Ile Met Gly Val Arg Gly Phe Asn Trp
        35                  40                  45

Gly Leu Asp Phe Thr Gly Gly Thr Val Ile Glu Ile Thr Leu Glu Lys
    50                  55                  60

Pro Ala Glu Met Asp Val Met Arg Glu Ala Leu Gln Lys Ala Gly Tyr
65                  70                  75                  80
```

```
Glu Glu Pro Gln Leu Gln Asn Phe Gly Ser Ser His Asp Ile Met Val
                85                  90                  95

Arg Met Pro Pro Thr Glu Gly Glu Thr Gly Gly Gln Val Leu Gly Ser
            100                 105                 110

Lys Val Val Thr Ile Ile Asn Glu Ala Thr Asn Gln Asn Ala Ala Val
        115                 120                 125

Lys Arg Ile Glu Phe Val Gly Pro Ser Val Gly Ala Asp Leu Ala Gln
    130                 135                 140

Thr Gly Ala Met Ala Leu Leu Val Ala Leu Ile Ser Ile Leu Val Tyr
145                 150                 155                 160

Val Gly Phe Arg Phe Glu Trp Arg Leu Ala Ala Gly Val Val Ile Ala
                165                 170                 175

Leu Ala His Asp Val Ile Ile Thr Leu Gly Ile Leu Ser Leu Phe His
            180                 185                 190

Ile Glu Ile Asp Leu Thr Ile Val Ala Ser Leu Met Ser Val Ile Gly
        195                 200                 205

Tyr Ser Leu Asn Asp Ser Ile Val Val Ser Asp Arg Ile Arg Glu Asn
    210                 215                 220

Phe Arg Lys Ile Arg Arg Gly Thr Pro Tyr Glu Ile Phe Asn Val Ser
225                 230                 235                 240

Leu Thr Gln Thr Leu His Arg Thr Leu Ile Thr Ser Gly Thr Thr Leu
                245                 250                 255

Val Val Ile Leu Met Leu Tyr Leu Phe Gly Gly Pro Val Leu Glu Gly
            260                 265                 270

Phe Ser Leu Thr Met Leu Ile Gly Val Ser Ile Gly Thr Ala Ser Ser
        275                 280                 285

Ile Tyr Val Ala Ser Ala Leu Ala Leu Lys Leu Gly Met Lys Arg Glu
    290                 295                 300

His Met Leu Gln Gln Lys Val Glu Lys Glu Gly Ala Asp Gln Pro Ser
305                 310                 315                 320

Ile Leu Pro

<210> SEQ ID NO 26
<211> LENGTH: 432
<212> TYPE: PRT
<213> ORGANISM: Salmonella enterica

<400> SEQUENCE: 26

Met Ser Lys Ile Val Lys Val Ile Gly Arg Glu Ile Ile Asp Ser Arg
1               5                   10                  15

Gly Asn Pro Thr Val Glu Ala Glu Val His Leu Glu Gly Gly Phe Val
            20                  25                  30

Gly Met Ala Ala Ala Pro Ser Gly Ala Ser Thr Gly Ser Arg Glu Ala
        35                  40                  45

Leu Glu Leu Arg Asp Gly Asp Lys Ser Arg Phe Leu Gly Lys Gly Val
    50                  55                  60

Thr Lys Ala Val Gly Ala Val Asn Gly Pro Ile Ala Gln Ala Ile Leu
65                  70                  75                  80

Gly Lys Asp Ala Lys Asp Gln Ala Gly Ile Asp Lys Ile Met Ile Asp
                85                  90                  95

Leu Asp Gly Thr Glu Asn Lys Ser Asn Phe Gly Ala Asn Ala Ile Leu
            100                 105                 110

Ala Val Ser Leu Ala Asn Ala Lys Ala Ala Ala Ala Lys Gly Met
        115                 120                 125
```

```
Pro Leu Tyr Glu His Ile Ala Glu Leu Asn Gly Thr Pro Gly Lys Tyr
    130                 135                 140

Ser Met Pro Val Pro Met Met Asn Ile Ile Asn Gly Gly Glu His Ala
145                 150                 155                 160

Asp Asn Asn Val Asp Ile Gln Glu Phe Met Ile Gln Pro Val Gly Ala
                165                 170                 175

Lys Thr Val Lys Glu Ala Ile Arg Met Gly Ser Glu Val Phe His His
            180                 185                 190

Leu Ala Lys Val Leu Lys Gly Lys Gly Met Asn Thr Ala Val Gly Asp
        195                 200                 205

Glu Gly Gly Tyr Ala Pro Asn Leu Gly Ser Asn Ala Glu Ala Leu Ala
210                 215                 220

Val Ile Ala Glu Ala Val Lys Ala Ala Gly Tyr Glu Leu Gly Lys Asp
225                 230                 235                 240

Ile Thr Leu Ala Met Asp Cys Ala Ala Ser Glu Phe Tyr Lys Asp Gly
                245                 250                 255

Lys Tyr Val Leu Ala Gly Glu Gly Asn Lys Ala Phe Thr Ser Glu Glu
            260                 265                 270

Phe Thr His Phe Leu Glu Glu Leu Thr Lys Gln Tyr Pro Ile Val Ser
        275                 280                 285

Ile Glu Asp Gly Leu Asp Glu Ser Asp Trp Asp Gly Phe Ala Tyr Gln
290                 295                 300

Thr Lys Val Leu Gly Asp Lys Ile Gln Leu Val Gly Asp Asp Leu Phe
305                 310                 315                 320

Val Thr Asn Thr Lys Ile Leu Lys Glu Gly Ile Glu Lys Gly Ile Ala
                325                 330                 335

Asn Ser Ile Leu Ile Lys Phe Asn Gln Ile Gly Ser Leu Thr Glu Thr
            340                 345                 350

Leu Ala Ala Ile Lys Met Ala Lys Asp Ala Gly Tyr Thr Ala Val Ile
        355                 360                 365

Ser His Arg Ser Gly Glu Thr Glu Asp Ala Thr Ile Ala Asp Leu Ala
370                 375                 380

Val Gly Thr Ala Ala Gly Gln Ile Lys Thr Gly Ser Met Ser Arg Ser
385                 390                 395                 400

Asp Arg Val Ala Lys Tyr Asn Gln Leu Ile Arg Ile Glu Glu Ala Leu
                405                 410                 415

Gly Glu Lys Ala Pro Tyr Asn Gly Arg Lys Glu Ile Lys Gly Gln Ala
            420                 425                 430

<210> SEQ ID NO 27
<211> LENGTH: 320
<212> TYPE: PRT
<213> ORGANISM: Salmonella enterica

<400> SEQUENCE: 27

Met Arg Gln Thr Lys Thr Gly Ile Leu Leu Ala Asn Leu Gly Thr Pro
1               5                   10                  15

Asp Ala Pro Thr Pro Glu Ala Val Lys Arg Tyr Leu Lys Gln Phe Leu
                20                  25                  30

Ser Asp Arg Arg Val Val Asp Thr Pro Arg Leu Leu Trp Pro Leu
            35                  40                  45

Leu Arg Gly Val Ile Leu Pro Leu Arg Ser Pro Arg Val Ala Lys Leu
        50                  55                  60

Tyr Gln Ser Ile Trp Met Asp Gly Gly Ser Pro Leu Met Val Tyr Ser
```

```
                65                  70                  75                  80
Arg Glu Gln Gln Gln Ala Leu Ala Ala Arg Leu Pro Asp Thr Pro Val
                85                  90                  95

Ala Leu Gly Met Ser Tyr Gly Ser Pro Ser Leu Glu Ser Ala Val Asp
                100                 105                 110

Glu Leu Leu Ala Ser Asp Val Asp His Ile Val Val Leu Pro Leu Tyr
                115                 120                 125

Pro Gln Tyr Ser Cys Ser Thr Val Gly Ala Val Trp Asp Glu Leu Gly
            130                 135                 140

Arg Ile Leu Ala Arg Lys Arg Ile Pro Gly Ile Ser Phe Ile Arg
145                 150                 155                 160

Asp Tyr Ala Asp Gly Ala Tyr Ile Asp Ala Leu Ala Lys Ser Ala
                165                 170                 175

Arg Glu Ser Phe Ala Arg His Gly Glu Pro Asp Val Leu Leu Leu Ser
                180                 185                 190

Tyr His Gly Ile Pro Gln Arg Tyr Ala Asp Glu Gly Asp Asp Tyr Pro
            195                 200                 205

Gln Arg Cys Arg Asp Thr Thr Arg Glu Leu Val Ser Ala Leu Gly Leu
            210                 215                 220

Pro Pro Glu Lys Val Met Met Thr Phe Gln Ser Arg Phe Gly Arg Glu
225                 230                 235                 240

Pro Trp Leu Thr Pro Tyr Thr Asp Glu Thr Leu Lys Met Leu Gly Glu
                245                 250                 255

Lys Gly Thr Gly His Ile Gln Val Met Cys Pro Gly Phe Ala Ala Asp
                260                 265                 270

Cys Leu Glu Thr Leu Glu Glu Ile Ala Glu Gln Asn Arg Glu Ile Phe
            275                 280                 285

Leu Glu Ala Gly Gly Lys Lys Tyr Ala Tyr Ile Pro Ala Leu Asn Ala
            290                 295                 300

Thr Pro Glu His Ile Asp Met Met Leu Lys Leu Thr Ala Pro Tyr Arg
305                 310                 315                 320

<210> SEQ ID NO 28
<211> LENGTH: 213
<212> TYPE: PRT
<213> ORGANISM: Salmonella enterica

<400> SEQUENCE: 28

Met Gly Ser Asn Tyr Ile Val Ile Glu Gly Leu Glu Gly Ala Gly Lys
1               5                   10                  15

Thr Thr Ala Arg Asp Val Val Val Glu Thr Leu Glu Gln Leu Gly Ile
                20                  25                  30

Arg Asn Met Ile Phe Thr Arg Glu Pro Gly Gly Thr Gln Leu Ala Glu
            35                  40                  45

Lys Leu Arg Ser Leu Val Leu Asp Ile Arg Ser Val Gly Asp Glu Val
        50                  55                  60

Ile Thr Asp Lys Ala Glu Val Leu Met Phe Tyr Ala Ala Arg Val Gln
65                  70                  75                  80

Leu Val Glu Thr Val Ile Lys Pro Ala Leu Ala Gln Gly Val Trp Val
                85                  90                  95

Ile Gly Asp Arg His Asp Leu Ser Thr Gln Ala Tyr Gln Gly Gly Gly
            100                 105                 110

Arg Gly Ile Asp Gln Thr Met Leu Ala Thr Leu Arg Asp Ala Val Leu
            115                 120                 125
```

```
Gly Asp Phe Arg Pro Asp Leu Thr Leu Tyr Leu Asp Val Thr Pro Glu
        130                 135                 140

Val Gly Leu Lys Arg Ala Arg Ala Arg Gly Asp Leu Asp Arg Ile Glu
145                 150                 155                 160

Gln Glu Ser Phe Asp Phe Phe Asn Arg Thr Arg Ala Arg Tyr Leu Glu
                165                 170                 175

Leu Ala Ala Gln Asp Ser Arg Ile Arg Thr Ile Asp Ala Thr Gln Pro
            180                 185                 190

Leu Asp Ala Val Met Arg Asp Ile Arg Ala Thr Val Thr Lys Trp Val
        195                 200                 205

Gln Glu Gln Ala Ala
    210

<210> SEQ ID NO 29
<211> LENGTH: 620
<212> TYPE: PRT
<213> ORGANISM: Salmonella enterica

<400> SEQUENCE: 29

Met Ser Phe Asp Ile Ala Lys Tyr Pro Thr Leu Ala Leu Val Asp Ser
1               5                   10                  15

Thr Gln Glu Leu Arg Leu Leu Pro Lys Glu Ser Leu Pro Lys Leu Cys
            20                  25                  30

Asp Glu Leu Arg Arg Tyr Leu Leu Asp Ser Val Ser Arg Ser Ser Gly
        35                  40                  45

His Phe Ala Ser Gly Leu Gly Thr Val Glu Leu Thr Val Ala Leu His
    50                  55                  60

Tyr Val Tyr Asn Thr Pro Phe Asp Gln Leu Ile Trp Asp Val Gly His
65                  70                  75                  80

Gln Ala Tyr Pro His Lys Ile Leu Thr Gly Arg Arg Asp Lys Ile Gly
                85                  90                  95

Thr Ile Arg Gln Lys Gly Gly Leu His Pro Phe Pro Trp Arg Gly Glu
            100                 105                 110

Ser Glu Tyr Asp Val Leu Ser Val Gly His Ser Ser Thr Ser Ile Ser
        115                 120                 125

Ala Gly Ile Gly Ile Ala Val Ala Ala Glu Lys Glu Gly Lys Asp Arg
    130                 135                 140

Arg Thr Val Cys Val Ile Gly Asp Gly Ala Ile Thr Ala Gly Met Ala
145                 150                 155                 160

Phe Glu Ala Met Asn His Ala Gly Asp Ile Arg Pro Asp Met Leu Val
                165                 170                 175

Ile Leu Asn Asp Asn Glu Met Ser Ile Ser Glu Asn Val Gly Ala Leu
            180                 185                 190

Asn Asn His Leu Ala Gln Leu Leu Ser Gly Lys Leu Tyr Ser Ser Leu
        195                 200                 205

Arg Glu Gly Gly Lys Lys Val Phe Ser Gly Val Pro Pro Ile Lys Glu
    210                 215                 220

Leu Leu Lys Arg Thr Glu Glu His Ile Lys Gly Met Val Val Pro Gly
225                 230                 235                 240

Thr Leu Phe Glu Glu Leu Gly Phe Asn Tyr Ile Gly Pro Val Asp Gly
                245                 250                 255

His Asp Val Met Gly Leu Ile Ser Thr Leu Lys Asn Met Arg Asp Leu
            260                 265                 270

Lys Gly Pro Gln Phe Leu His Ile Met Thr Lys Lys Gly Arg Gly Tyr
        275                 280                 285
```

Glu Pro Ala Glu Lys Asp Pro Ile Thr Phe His Ala Val Pro Lys Phe
            290                 295                 300

Asp Pro Ser Ser Gly Cys Leu Pro Lys Ser Ser Gly Gly Leu Pro Gly
305                 310                 315                 320

Tyr Ser Lys Ile Phe Gly Asp Trp Leu Cys Glu Thr Ala Ala Lys Asp
                325                 330                 335

Ser Lys Leu Met Ala Ile Thr Pro Ala Met Arg Glu Gly Ser Gly Met
            340                 345                 350

Val Glu Phe Ser Arg Lys Phe Pro Asp Arg Tyr Phe Asp Val Ala Ile
        355                 360                 365

Ala Glu Gln His Ala Val Thr Phe Ala Ala Gly Leu Ala Ile Gly Gly
    370                 375                 380

Tyr Lys Pro Val Val Ala Ile Tyr Ser Thr Phe Leu Gln Arg Ala Tyr
385                 390                 395                 400

Asp Gln Val Ile His Asp Val Ala Ile Gln Lys Leu Pro Val Met Phe
                405                 410                 415

Ala Ile Asp Arg Ala Gly Ile Val Gly Ala Asp Gly Gln Thr His Gln
            420                 425                 430

Gly Ala Phe Asp Leu Ser Tyr Leu Arg Cys Ile Pro Asp Met Val Ile
        435                 440                 445

Met Thr Pro Ser Asp Glu Asn Glu Cys Arg Gln Met Leu Phe Thr Gly
    450                 455                 460

Tyr His Tyr Asn Asp Gly Pro Thr Ala Val Arg Tyr Pro Arg Gly Asn
465                 470                 475                 480

Ala Gln Gly Val Ala Leu Thr Pro Leu Glu Lys Leu Pro Ile Gly Lys
                485                 490                 495

Gly Leu Val Lys Arg His Gly Glu Lys Leu Ala Ile Leu Asn Phe Gly
            500                 505                 510

Thr Leu Met Pro Glu Ala Ala Lys Val Ala Glu Ala Leu Asn Ala Thr
        515                 520                 525

Leu Val Asp Met Arg Phe Val Lys Pro Leu Asp Asp Thr Leu Ile Leu
530                 535                 540

Glu Met Ala Ala Gln His Asp Ala Leu Val Thr Leu Glu Glu Asn Ala
545                 550                 555                 560

Ile Met Gly Gly Ala Gly Ser Gly Val Asn Glu Val Leu Met Ala His
                565                 570                 575

Arg Lys Pro Val Pro Val Leu Asn Ile Gly Leu Pro Asp Phe Phe Ile
            580                 585                 590

Pro Gln Gly Thr Gln Glu Glu Ala Arg Ala Glu Leu Gly Leu Asp Ala
        595                 600                 605

Ala Gly Ile Glu Ala Lys Ile Lys Ala Trp Leu Ala
610                 615                 620

<210> SEQ ID NO 30
<211> LENGTH: 252
<212> TYPE: PRT
<213> ORGANISM: Salmonella enterica

<400> SEQUENCE: 30

Met Leu Ser Ala Thr Gln Pro Val Ser Glu Asn Leu Pro Ala His Gly
1               5                   10                  15

Cys Arg His Val Ala Ile Ile Met Asp Gly Asn Gly Arg Trp Ala Lys
            20                  25                  30

Lys Gln Gly Lys Ile Arg Ala Phe Gly His Lys Ala Gly Ala Lys Ser

```
            35                  40                  45
Val Arg Arg Ala Val Ser Phe Ala Ala Asn Asn Gly Ile Asp Ala Leu
 50                  55                  60

Thr Leu Tyr Ala Phe Ser Ser Glu Asn Trp Asn Arg Pro Ala Gln Glu
65                  70                  75                  80

Val Ser Ala Leu Met Glu Leu Phe Val Trp Ala Leu Asp Ser Glu Val
                 85                  90                  95

Lys Ser Leu His Arg His Asn Val Arg Leu Arg Ile Ile Gly Asp Ile
            100                 105                 110

Ser Arg Phe Asn Ser Arg Leu Gln Glu Arg Ile Arg Lys Ser Glu Ala
        115                 120                 125

Leu Thr Ala His Asn Thr Gly Leu Thr Leu Asn Ile Ala Ala Asn Tyr
    130                 135                 140

Gly Gly Arg Trp Asp Ile Val Gln Gly Val Arg Gln Leu Ala Glu Gln
145                 150                 155                 160

Val Gln Ala Gly Val Leu Arg Pro Asp Gln Ile Asp Glu Glu Arg Leu
                165                 170                 175

Gly Gln Gln Ile Cys Met His Glu Leu Ala Pro Val Asp Leu Val Ile
            180                 185                 190

Arg Thr Gly Gly Glu His Arg Ile Ser Asn Phe Leu Leu Trp Gln Ile
        195                 200                 205

Ala Tyr Ala Glu Leu Tyr Phe Thr Asp Val Leu Trp Pro Asp Phe Asp
    210                 215                 220

Glu Gln Asp Phe Glu Gly Ala Leu His Ala Phe Ala Asn Arg Glu Arg
225                 230                 235                 240

Arg Phe Gly Gly Thr Glu Pro Gly Asp Asp Lys Ala
                245                 250

<210> SEQ ID NO 31
<211> LENGTH: 285
<212> TYPE: PRT
<213> ORGANISM: Salmonella enterica

<400> SEQUENCE: 31

Met Leu Lys Tyr Arg Leu Ile Ser Ala Phe Val Leu Ile Pro Ala Val
 1               5                  10                  15

Ile Ala Ala Leu Phe Leu Leu Pro Pro Val Gly Phe Ala Ile Ile Thr
                20                  25                  30

Leu Val Val Cys Met Leu Ala Ala Trp Glu Trp Gly Gln Leu Ser Gly
            35                  40                  45

Phe Ala Ala Arg Ser Gln Arg Val Trp Leu Ala Val Leu Cys Gly Leu
 50                  55                  60

Leu Leu Ala Leu Met Leu Phe Leu Pro Glu Tyr His His Asn Ile
65                  70                  75                  80

Arg Gln Pro Leu Val Glu Met Ser Leu Trp Ala Ser Leu Gly Trp Trp
                85                  90                  95

Val Val Ala Leu Leu Val Leu Phe Tyr Pro Gly Ser Ala Ala Ile
            100                 105                 110

Trp Arg Asn Ser Lys Thr Leu Arg Leu Ile Phe Gly Leu Leu Thr Ile
        115                 120                 125

Val Pro Phe Phe Trp Gly Met Leu Ala Leu Arg Ala Trp His Tyr Asp
    130                 135                 140

Glu Asn His Tyr Ser Gly Ala Ile Trp Leu Leu Tyr Val Met Ile Leu
145                 150                 155                 160
```

Val Trp Gly Ala Asp Ser Gly Ala Tyr Met Phe Gly Lys Leu Phe Gly
              165                 170                 175

Lys His Lys Leu Ala Pro Lys Val Ser Pro Gly Lys Thr Trp Gln Gly
            180                 185                 190

Phe Ile Gly Gly Leu Ala Thr Ala Ala Val Ile Ser Trp Gly Tyr Gly
            195                 200                 205

Met Trp Ala Asn Leu Asn Val Ala Pro Val Ile Leu Leu Ile Cys Ser
            210                 215                 220

Val Val Ala Ala Leu Ala Ser Val Leu Gly Asp Leu Thr Glu Ser Met
225                 230                 235                 240

Phe Lys Arg Glu Ala Gly Ile Lys Asp Ser Gly His Leu Ile Pro Gly
            245                 250                 255

His Gly Gly Ile Leu Asp Arg Ile Asp Ser Leu Thr Ala Ala Val Pro
            260                 265                 270

Val Phe Ala Cys Leu Leu Leu Leu Val Phe Arg Thr Leu
            275                 280                 285

<210> SEQ ID NO 32
<211> LENGTH: 319
<212> TYPE: PRT
<213> ORGANISM: Salmonella enterica

<400> SEQUENCE: 32

Met Ser Leu Asn Phe Leu Asp Phe Glu Gln Pro Ile Ala Glu Leu Glu
1               5                   10                  15

Ala Lys Ile Asp Ser Leu Thr Ala Val Ser Arg Gln Asp Glu Lys Leu
            20                  25                  30

Asp Ile Asn Ile Asp Glu Glu Val His Arg Leu Arg Glu Lys Ser Val
            35                  40                  45

Glu Leu Thr Arg Lys Ile Phe Ala Asp Leu Gly Ala Trp Gln Val Ala
        50                  55                  60

Gln Leu Ala Arg His Pro Gln Arg Pro Tyr Thr Leu Asp Tyr Val Arg
65              70                  75                  80

Leu Ala Phe Asp Glu Phe Asp Glu Leu Ala Gly Asp Arg Ala Tyr Ala
                85                  90                  95

Asp Asp Lys Ala Ile Val Gly Gly Ile Ala Arg Leu Glu Gly Arg Pro
            100                 105                 110

Val Met Ile Ile Gly His Gln Lys Gly Arg Glu Thr Lys Glu Lys Ile
            115                 120                 125

Arg Arg Asn Phe Gly Met Pro Ala Pro Glu Gly Tyr Arg Lys Ala Leu
130                 135                 140

Arg Leu Met Glu Met Ala Glu Arg Phe Asn Met Pro Ile Ile Thr Phe
145                 150                 155                 160

Ile Asp Thr Pro Gly Ala Tyr Pro Gly Val Gly Ala Glu Glu Arg Gly
                165                 170                 175

Gln Ser Glu Ala Ile Ala Arg Asn Leu Arg Glu Met Ser Arg Leu Asn
            180                 185                 190

Val Pro Val Ile Cys Thr Val Ile Gly Glu Gly Gly Ser Gly Gly Ala
            195                 200                 205

Leu Ala Ile Gly Val Gly Asp Lys Val Asn Met Leu Gln Tyr Ser Thr
            210                 215                 220

Tyr Ser Val Ile Ser Pro Glu Gly Cys Ala Ser Ile Leu Trp Lys Ser
225                 230                 235                 240

Ala Asp Lys Ala Pro Leu Ala Ala Glu Ala Met Gly Ile Ile Ala Pro
            245                 250                 255

Arg Leu Lys Glu Leu Lys Leu Ile Asp Ser Ile Ile Pro Glu Pro Leu
                260                 265                 270

Gly Gly Ala His Arg Asn Pro Glu Ala Met Ala Ala Ser Leu Lys Ala
            275                 280                 285

Gln Leu Leu Glu Asp Leu Ala Asp Leu Asp Val Leu Ser Thr Asp Asp
    290                 295                 300

Leu Lys Asn Arg Arg Tyr Gln Arg Leu Met Ser Tyr Gly Tyr Ala
305                 310                 315

<210> SEQ ID NO 33
<211> LENGTH: 451
<212> TYPE: PRT
<213> ORGANISM: Salmonella enterica

<400> SEQUENCE: 33

Met Leu Ser Lys Phe Lys Arg Asn Lys His Gln Gln His Leu Ala Gln
1               5                   10                  15

Leu Pro Lys Ile Ser Gln Ser Val Asp Asp Val Asp Phe Phe Tyr Thr
            20                  25                  30

Pro Ala Thr Phe Arg Glu Thr Leu Leu Glu Lys Ile Ala Ser Ala Thr
        35                  40                  45

Gln Arg Ile Cys Ile Val Ala Leu Tyr Leu Glu Gln Asp Asp Gly Gly
    50                  55                  60

Lys Gly Ile Leu Asp Ala Leu Tyr Ala Ala Lys Arg Gln Arg Pro Glu
65                  70                  75                  80

Leu Asp Val Arg Val Leu Val Asp Trp His Arg Ala Gln Arg Gly Arg
                85                  90                  95

Ile Gly Ala Ala Ala Ser Asn Thr Asn Ala Asp Trp Tyr Cys Arg Leu
            100                 105                 110

Ala Gln Glu Asn Pro Gly Ile Asp Val Pro Val Tyr Gly Val Pro Ile
        115                 120                 125

Asn Thr Arg Glu Ala Leu Gly Val Leu His Phe Lys Gly Phe Ile Ile
    130                 135                 140

Asp Asp Ser Val Leu Tyr Ser Gly Ala Ser Leu Asn Asp Val Tyr Leu
145                 150                 155                 160

His Gln His Asp Lys Tyr Arg Tyr Asp Arg Tyr Gln Leu Ile Arg Asn
                165                 170                 175

Arg Gln Met Ala Asp Ile Met Phe Asp Trp Val Thr Gln Asn Leu Met
            180                 185                 190

Asn Gly Arg Gly Val Asn Arg Leu Asp Asn Thr Gln Arg Pro Lys Ser
        195                 200                 205

Pro Glu Ile Lys Asn Asp Ile Arg Leu Tyr Arg Gln Glu Leu Arg Asp
    210                 215                 220

Ala Ser Tyr His Phe Gln Gly Asp Ala Asn Asp Glu Gln Leu Ser Val
225                 230                 235                 240

Thr Pro Leu Val Gly Leu Gly Lys Ser Ser Leu Leu Asn Lys Thr Ile
                245                 250                 255

Phe His Leu Met Pro Cys Ala Glu His Lys Leu Thr Ile Cys Thr Pro
            260                 265                 270

Tyr Phe Asn Leu Pro Ala Val Leu Val Arg Asn Ile Ile Gln Leu Leu
        275                 280                 285

Arg Asp Gly Lys Lys Val Glu Ile Ile Val Gly Asp Lys Thr Ala Asn
    290                 295                 300

Asp Phe Tyr Ile Pro Glu Asp Glu Pro Phe Lys Ile Ile Gly Ala Leu

```
            305                 310                 315                 320
        Pro Tyr Leu Tyr Glu Ile Asn Leu Arg Arg Phe Leu Ser Arg Leu Gln
                        325                 330                 335

Tyr Tyr Val Asn Thr Asp Gln Leu Val Arg Leu Trp Lys Asp Asp
                        340                 345                 350

Asp Asn Thr Tyr His Leu Lys Gly Met Trp Val Asp Lys Trp Met
                        355                 360                 365

Leu Leu Thr Gly Asn Asn Leu Asn Pro Arg Ala Trp Arg Leu Asp Leu
            370                 375                 380

Glu Asn Ala Ile Leu Ile His Asp Pro Lys Gln Glu Leu Ala Pro Gln
        385                 390                 395                 400

Arg Glu Lys Glu Leu Glu Leu Ile Arg Thr His Thr Thr Ile Val Lys
                        405                 410                 415

His Tyr Arg Asp Leu Gln Ser Ile Ala Asp Tyr Pro Ile Lys Val Arg
                        420                 425                 430

Lys Leu Ile Arg Arg Leu Arg Arg Ile Arg Ile Asp Arg Leu Ile Ser
                        435                 440                 445

Arg Ile Leu
            450

<210> SEQ ID NO 34
<211> LENGTH: 582
<212> TYPE: PRT
<213> ORGANISM: Salmonella enterica

<400> SEQUENCE: 34

Met His Asn Asp Lys Asp Leu Ser Thr Trp Gln Thr Phe Arg Arg Leu
1               5                   10                  15

Trp Pro Thr Ile Ala Pro Phe Lys Ala Gly Leu Ile Val Ala Gly Ile
                20                  25                  30

Ala Leu Ile Leu Asn Ala Ala Ser Asp Thr Phe Met Leu Ser Leu Leu
            35                  40                  45

Lys Pro Leu Leu Asp Asp Gly Phe Gly Lys Thr Asp Arg Ser Val Leu
        50                  55                  60

Leu Trp Met Pro Leu Val Val Ile Gly Leu Met Ile Leu Arg Gly Ile
65                  70                  75                  80

Thr Ser Tyr Ile Ser Ser Tyr Cys Ile Ser Trp Val Ser Gly Lys Val
                85                  90                  95

Val Met Thr Met Arg Arg Arg Leu Phe Gly His Met Met Gly Met Pro
                100                 105                 110

Val Ala Phe Phe Asp Lys Gln Ser Thr Gly Thr Leu Leu Ser Arg Ile
            115                 120                 125

Thr Tyr Asp Ser Glu Gln Val Ala Ser Ser Ser Gly Ala Leu Ile
        130                 135                 140

Thr Val Val Arg Glu Gly Ala Ser Ile Ile Gly Leu Phe Ile Met Met
145                 150                 155                 160

Phe Tyr Tyr Ser Trp Gln Leu Ser Ile Ile Leu Val Val Leu Ala Pro
                165                 170                 175

Ile Val Ser Ile Ala Ile Arg Val Val Ser Lys Arg Phe Arg Ser Ile
            180                 185                 190

Ser Lys Asn Met Gln Asn Thr Met Gly Gln Val Thr Ser Ala Glu
        195                 200                 205

Gln Met Leu Lys Gly His Lys Glu Val Leu Ile Phe Gly Gly Gln Glu
    210                 215                 220
```

-continued

Val Glu Thr Lys Arg Phe Asp Lys Val Ser Asn Lys Met Arg Leu Gln
225                 230                 235                 240

Gly Met Lys Met Val Ser Ala Ser Ser Ile Ser Asp Pro Ile Ile Gln
            245                 250                 255

Leu Ile Ala Ser Leu Ala Leu Ala Phe Val Leu Tyr Ala Ala Ser Phe
        260                 265                 270

Pro Ser Val Met Asp Ser Leu Thr Ala Gly Thr Ile Thr Val Val Phe
    275                 280                 285

Ser Ser Met Ile Ala Leu Met Arg Pro Leu Lys Ser Leu Thr Asn Val
290                 295                 300

Asn Ala Gln Phe Gln Arg Gly Met Ala Ala Cys Gln Thr Leu Phe Ala
305                 310                 315                 320

Ile Leu Asp Ser Glu Gln Glu Lys Asp Glu Gly Lys Arg Val Ile Asp
            325                 330                 335

Arg Ala Thr Gly Asp Leu Glu Phe Arg Asn Val Thr Phe Thr Tyr Pro
            340                 345                 350

Gly Arg Glu Val Pro Ala Leu Arg Asn Ile Asn Leu Lys Ile Pro Ala
        355                 360                 365

Gly Lys Thr Val Ala Leu Val Gly Arg Ser Gly Ser Gly Lys Ser Thr
    370                 375                 380

Ile Ala Ser Leu Ile Thr Arg Phe Tyr Asp Ile Asp Glu Gly His Ile
385                 390                 395                 400

Leu Met Asp Gly His Asp Leu Arg Glu Tyr Thr Leu Ala Ser Leu Arg
            405                 410                 415

Asn Gln Val Ala Leu Val Ser Gln Asn Val His Leu Phe Asn Asp Thr
        420                 425                 430

Val Ala Asn Asn Ile Ala Tyr Ala Arg Thr Glu Glu Tyr Ser Arg Glu
    435                 440                 445

Gln Ile Glu Glu Ala Ala Arg Met Ala Tyr Ala Met Asp Phe Ile Asn
450                 455                 460

Lys Met Asp Asn Gly Leu Asp Thr Ile Ile Gly Glu Asn Gly Val Leu
465                 470                 475                 480

Leu Ser Gly Gly Gln Arg Gln Arg Ile Ala Ile Ala Arg Ala Leu Leu
            485                 490                 495

Arg Asp Ser Pro Ile Leu Ile Leu Asp Glu Ala Thr Ser Ala Leu Asp
        500                 505                 510

Thr Glu Ser Glu Arg Ala Ile Gln Ala Ala Leu Asp Glu Leu Gln Lys
    515                 520                 525

Asn Arg Thr Ser Leu Val Ile Ala His Arg Leu Ser Thr Ile Glu Gln
530                 535                 540

Ala Asp Glu Ile Val Val Val Glu Asp Gly Ile Ile Val Glu Arg Gly
545                 550                 555                 560

Thr His Ser Glu Leu Leu Ala Gln His Gly Val Tyr Ala Gln Leu His
            565                 570                 575

Lys Met Gln Phe Gly Gln
            580

<210> SEQ ID NO 35
<211> LENGTH: 283
<212> TYPE: PRT
<213> ORGANISM: Salmonella enterica

<400> SEQUENCE: 35

Met Ala Glu Ile Thr Ala Ser Leu Val Lys Glu Leu Arg Glu Arg Thr
1               5                   10                  15

Gly Ala Gly Met Met Asp Cys Lys Lys Ala Leu Thr Glu Ala Asn Gly
                20                  25                  30

Asp Ile Glu Leu Ala Ile Glu Asn Met Arg Lys Ser Gly Ala Ile Lys
            35                  40                  45

Ala Ala Lys Lys Ala Gly Asn Val Ala Ala Asp Gly Val Ile Lys Thr
        50                  55                  60

Lys Ile Asp Gly Asn Val Ala Phe Ile Leu Glu Val Asn Cys Gln Thr
65                  70                  75                  80

Asp Phe Val Ala Lys Asp Ala Gly Phe Gln Ala Phe Ala Asp Lys Val
                85                  90                  95

Leu Asp Ala Ala Val Ala Gly Lys Ile Thr Asp Val Glu Val Leu Lys
            100                 105                 110

Ala Gln Phe Glu Glu Arg Val Ala Leu Val Ala Lys Ile Gly Glu
        115                 120                 125

Asn Ile Asn Ile Arg Arg Val Ala Ser Leu Glu Gly Asp Val Leu Gly
130                 135                 140

Ser Tyr Gln His Gly Ala Arg Ile Gly Val Leu Val Ala Ala Lys Gly
145                 150                 155                 160

Ala Asp Glu Glu Leu Val Lys Gln Leu Ala Met His Val Ala Ala Ser
                165                 170                 175

Lys Pro Glu Phe Val Lys Pro Glu Asp Val Ser Ala Asp Val Val Glu
            180                 185                 190

Lys Glu Tyr Gln Val Gln Leu Asp Ile Ala Met Gln Ser Gly Lys Pro
        195                 200                 205

Lys Glu Ile Ala Glu Lys Met Val Glu Gly Arg Met Lys Lys Phe Thr
210                 215                 220

Gly Glu Val Ser Leu Thr Gly Gln Pro Phe Val Met Glu Pro Ser Lys
225                 230                 235                 240

Ser Val Gly Gln Leu Leu Lys Glu His Asn Ala Asp Val Thr Gly Phe
                245                 250                 255

Ile Arg Phe Glu Val Gly Gly Ile Glu Lys Val Glu Thr Asp Phe
            260                 265                 270

Ala Ala Glu Val Ala Ala Met Ser Lys Gln Ser
        275                 280

<210> SEQ ID NO 36
<211> LENGTH: 255
<212> TYPE: PRT
<213> ORGANISM: Salmonella enterica

<400> SEQUENCE: 36

Met Phe Ile Gly Ile Val Ser Leu Phe Pro Glu Met Phe Arg Ala Ile
1               5                   10                  15

Thr Asp Tyr Gly Val Thr Gly Arg Ala Val Lys Lys Gly Leu Leu Asn
            20                  25                  30

Ile Gln Ser Trp Ser Pro Arg Asp Phe Ala His Asp Arg His Arg Thr
        35                  40                  45

Val Asp Asp Arg Pro Tyr Gly Gly Pro Gly Met Leu Met Met Val
    50                  55                  60

Gln Pro Leu Arg Asp Ala Ile His Ala Ala Lys Ala Ala Gly Glu
65                  70                  75                  80

Gly Ala Lys Val Ile Tyr Leu Ser Pro Gln Gly Arg Lys Leu Asp Gln
                85                  90                  95

Ala Gly Val Ser Glu Leu Ala Thr Asn Gln Lys Leu Ile Leu Val Cys

```
            100                 105                 110
Gly Arg Tyr Glu Gly Val Asp Glu Arg Val Ile Gln Thr Glu Ile Asp
            115                 120                 125

Glu Glu Trp Ser Ile Gly Asp Tyr Val Leu Ser Gly Gly Glu Leu Pro
            130                 135                 140

Ala Met Thr Leu Ile Asp Ser Val Ala Arg Phe Ile Pro Gly Val Leu
145                 150                 155                 160

Gly His Glu Ala Ser Ala Ile Glu Asp Ser Phe Ala Asp Gly Leu Leu
            165                 170                 175

Asp Cys Pro His Tyr Thr Arg Pro Glu Val Leu Glu Gly Met Glu Val
            180                 185                 190

Pro Pro Val Leu Leu Ser Gly Asn His Ala Glu Ile Arg Arg Trp Arg
            195                 200                 205

Leu Lys Gln Ser Leu Gly Arg Thr Trp Leu Arg Arg Pro Glu Leu Leu
            210                 215                 220

Glu Asn Leu Ala Leu Thr Glu Glu Gln Ala Arg Leu Leu Ala Glu Phe
225                 230                 235                 240

Lys Thr Glu His Ala Gln Gln Gln His Lys His Asp Gly Met Ala
            245                 250                 255

<210> SEQ ID NO 37
<211> LENGTH: 413
<212> TYPE: PRT
<213> ORGANISM: Salmonella enterica

<400> SEQUENCE: 37

Met Lys Ile Tyr Leu Val Gly Gly Ala Val Arg Asp Ala Leu Leu Gly
1               5                   10                  15

Leu Pro Val Lys Asp Lys Asp Trp Val Val Gly Ala Thr Pro Gln
            20                  25                  30

Glu Met Leu Asp Ala Gly Tyr Gln Gln Val Gly Arg Asp Phe Pro Val
            35                  40                  45

Phe Leu His Pro Gln Thr His Glu Glu Tyr Ala Leu Ala Arg Thr Glu
50                  55                  60

Arg Lys Ser Gly Ser Gly Tyr Thr Gly Phe Thr Cys Tyr Ala Ala Pro
65                  70                  75                  80

Asp Val Thr Leu Glu Ala Asp Leu Gln Arg Arg Asp Leu Thr Ile Asn
            85                  90                  95

Ala Leu Ala Arg Asp Asp Ala Gly Gln Ile Ile Asp Pro Tyr His Gly
            100                 105                 110

Arg Arg Asp Leu Glu Ala Arg Leu Leu Arg His Val Ser Pro Ala Phe
            115                 120                 125

Gly Glu Asp Pro Leu Arg Val Leu Arg Val Ala Arg Phe Ala Ala Arg
            130                 135                 140

Tyr Ala His Leu Ser Phe Arg Ile Ala Asp Glu Thr Leu Ala Leu Met
145                 150                 155                 160

Arg Glu Met Thr Ala Ala Gly Glu Leu Glu His Leu Thr Pro Glu Arg
            165                 170                 175

Val Trp Lys Glu Thr Glu Asn Ala Leu Thr Thr Arg Asn Pro Gln Val
            180                 185                 190

Tyr Phe Gln Val Leu Arg Asp Cys Gly Ala Leu Arg Val Leu Phe Pro
            195                 200                 205

Glu Ile Asp Ala Leu Phe Gly Val Pro Ala Pro Ala Lys Trp His Pro
            210                 215                 220
```

```
Glu Ile Asp Thr Gly Val His Thr Leu Met Thr Leu Ser Met Ala Ala
225                 230                 235                 240

Met Leu Ser Pro Gln Leu Asp Val Arg Phe Ala Thr Leu Cys His Asp
            245                 250                 255

Leu Gly Lys Gly Leu Thr Pro Lys Asn Leu Trp Pro Arg His His Gly
        260                 265                 270

His Gly Pro Ala Gly Val Lys Leu Val Glu Gln Leu Cys Gln Arg Leu
    275                 280                 285

Arg Val Pro Asn Asp Leu Arg Asp Leu Ala Lys Leu Val Ala Glu Tyr
290                 295                 300

His Asp Leu Ile His Thr Phe Pro Ile Leu Gln Pro Lys Thr Ile Val
305                 310                 315                 320

Lys Leu Phe Asp Ala Ile Asp Ala Trp Arg Lys Pro Gln Arg Val Glu
                325                 330                 335

Gln Ile Ala Leu Thr Ser Glu Ala Asp Val Arg Gly Arg Thr Gly Phe
            340                 345                 350

Glu Ala Ser Asp Tyr Pro Gln Gly Arg Trp Leu Arg Glu Ala Trp Gln
        355                 360                 365

Val Ala Gln Ala Val Pro Thr Lys Glu Val Val Glu Ala Gly Phe Lys
    370                 375                 380

Gly Ile Glu Ile Arg Glu Leu Thr Lys Arg Arg Ile Ala Ala Val
385                 390                 395                 400

Ala Asn Trp Lys Glu Lys Arg Cys Pro Asn Pro Ala Ser
                405                 410
```

<210> SEQ ID NO 38
<211> LENGTH: 892
<212> TYPE: PRT
<213> ORGANISM: Salmonella enterica

<400> SEQUENCE: 38

```
Met Thr Asp Val Thr Leu Lys Ala Leu Ala Ala Glu Arg Gln Val Ser
1               5                   10                  15

Val Asp Arg Leu Val Gln Gln Phe Ala Asp Ala Gly Ile Arg Lys Ser
            20                  25                  30

Ala Asp Asp Ser Val Ser Ala Gln Glu Lys Gln Thr Leu Leu Ala His
        35                  40                  45

Leu Asn Arg Glu Ala Val Ser Gly Pro Asp Lys Leu Thr Leu Gln Arg
    50                  55                  60

Lys Thr Arg Ser Thr Leu Asn Ile Pro Gly Thr Gly Gly Lys Ser Lys
65                  70                  75                  80

Ser Val Gln Ile Glu Val Arg Lys Lys Arg Thr Phe Val Lys Arg Asp
                85                  90                  95

Pro Gln Glu Ala Glu Arg Leu Ala Ala Glu Gln Ala Gln Arg Glu
            100                 105                 110

Ala Glu Glu Gln Ala Arg Arg Glu Ala Glu Gln Ala Lys Arg Glu
        115                 120                 125

Ala Gln Gln Lys Ala Glu Arg Glu Ala Ala Glu Gln Ala Lys Arg Glu
    130                 135                 140

Ala Ala Glu Lys Ala Lys Arg Glu Ala Ala Glu Lys Asp Lys Val Ser
145                 150                 155                 160

Asn Gln Gln Thr Asp Asp Met Thr Lys Thr Ala Gln Ala Glu Lys Ala
                165                 170                 175

Arg Arg Glu Asn Glu Ala Ala Glu Leu Lys Arg Lys Ala Glu Glu Glu
            180                 185                 190
```

```
Ala Arg Arg Lys Leu Glu Glu Ala Arg Val Ala Glu Glu Ala
        195                 200                 205

Arg Arg Met Ala Glu Glu Asn Lys Trp Thr Ala Thr Pro Glu Pro Val
    210                 215                 220

Glu Asp Thr Ser Asp Tyr His Val Thr Thr Ser Gln His Ala Arg Gln
225                 230                 235                 240

Ala Glu Asp Glu Asn Asp Arg Glu Val Glu Gly Gly Arg Gly Arg Gly
                245                 250                 255

Arg Asn Ala Lys Ala Ala Arg Pro Ala Lys Lys Gly Lys His Ala Glu
            260                 265                 270

Ser Lys Ala Asp Arg Glu Glu Ala Arg Ala Val Arg Gly Gly Lys
        275                 280                 285

Gly Gly Lys Arg Lys Gly Ser Ser Leu Gln Gln Gly Phe Gln Lys Pro
    290                 295                 300

Ala Gln Ala Val Asn Arg Asp Val Val Ile Gly Glu Thr Ile Thr Val
305                 310                 315                 320

Gly Glu Leu Ala Asn Lys Met Ala Val Lys Gly Ser Gln Val Ile Lys
                325                 330                 335

Ala Met Met Lys Leu Gly Ala Met Ala Thr Ile Asn Val Ile Asp
            340                 345                 350

Gln Glu Thr Ala Gln Leu Val Ala Glu Glu Met Gly His Lys Val Ile
        355                 360                 365

Leu Arg Arg Glu Asn Glu Leu Glu Glu Ala Val Met Ser Asp Arg Asp
    370                 375                 380

Thr Gly Ala Ala Ala Glu Pro Arg Ala Pro Val Thr Ile Met Gly
385                 390                 395                 400

His Val Asp His Gly Lys Thr Ser Leu Leu Asp Tyr Ile Arg Ser Thr
                405                 410                 415

Lys Val Ala Ser Gly Glu Ala Gly Gly Ile Thr Gln His Ile Gly Ala
            420                 425                 430

Tyr His Val Glu Thr Asp Asn Gly Met Ile Thr Phe Leu Asp Thr Pro
        435                 440                 445

Gly His Ala Ala Phe Thr Ser Met Arg Ala Arg Gly Ala Gln Ala Thr
    450                 455                 460

Asp Ile Val Val Leu Val Val Ala Ala Asp Asp Gly Val Met Pro Gln
465                 470                 475                 480

Thr Ile Glu Ala Ile Gln His Ala Lys Ala Ala Gly Val Pro Val Val
                485                 490                 495

Val Ala Val Asn Lys Ile Asp Lys Pro Glu Ala Asp Pro Asp Arg Val
            500                 505                 510

Lys Asn Glu Leu Ser Gln Tyr Gly Ile Leu Pro Glu Glu Trp Gly Gly
        515                 520                 525

Glu Ser Gln Phe Val His Val Ser Ala Lys Ala Gly Thr Gly Ile Asp
    530                 535                 540

Glu Leu Leu Asp Ala Ile Leu Leu Gln Ala Glu Val Leu Glu Leu Lys
545                 550                 555                 560

Ala Val Arg Lys Gly Met Ala Ser Gly Ala Val Ile Glu Ser Phe Leu
                565                 570                 575

Asp Lys Gly Arg Gly Pro Val Ala Thr Val Leu Val Arg Glu Gly Thr
            580                 585                 590

Leu His Lys Gly Asp Ile Val Leu Cys Gly Phe Glu Tyr Gly Arg Val
        595                 600                 605
```

Arg Ala Met Arg Asn Glu Leu Gly Gln Glu Val Leu Glu Ala Gly Pro
610                 615                 620

Ser Ile Pro Val Glu Ile Leu Gly Leu Ser Gly Val Pro Ala Ala Gly
625                 630                 635                 640

Asp Glu Val Thr Val Arg Asp Glu Lys Lys Ala Arg Glu Val Ala
            645                 650                 655

Leu Tyr Arg Gln Gly Lys Phe Arg Glu Val Lys Leu Ala Arg Gln Gln
            660                 665                 670

Lys Ser Lys Leu Glu Asn Met Phe Ala Asn Met Thr Glu Gly Glu Val
            675                 680                 685

His Glu Val Asn Ile Val Leu Lys Ala Asp Val Gln Gly Ser Val Glu
690                 695                 700

Ala Ile Ser Asp Ser Leu Leu Lys Leu Ser Thr Asp Glu Val Lys Val
705                 710                 715                 720

Lys Ile Ile Gly Ser Gly Val Gly Ile Thr Glu Thr Asp Ala Thr
                725                 730                 735

Leu Ala Ala Ala Ser Asn Ala Ile Leu Val Gly Phe Asn Val Arg Ala
            740                 745                 750

Asp Ala Ser Ala Arg Lys Val Ile Glu Ser Glu Ser Leu Asp Leu Arg
            755                 760                 765

Tyr Tyr Ser Val Ile Tyr Asn Leu Ile Asp Glu Val Lys Ala Ala Met
            770                 775                 780

Ser Gly Met Leu Ser Pro Glu Leu Lys Gln Gln Ile Ile Gly Leu Ala
785                 790                 795                 800

Glu Val Arg Asp Val Phe Lys Ser Pro Lys Phe Gly Ala Ile Ala Gly
                805                 810                 815

Cys Met Val Thr Glu Gly Thr Ile Lys Arg His Asn Pro Ile Arg Val
            820                 825                 830

Leu Arg Asp Asn Val Val Ile Tyr Glu Gly Glu Leu Glu Ser Leu Arg
            835                 840                 845

Arg Phe Lys Asp Asp Val Asn Glu Val Arg Asn Gly Met Glu Cys Gly
            850                 855                 860

Ile Gly Val Lys Asn Tyr Asn Asp Val Arg Val Gly Asp Met Ile Glu
865                 870                 875                 880

Val Phe Glu Ile Ile Glu Ile Gln Arg Thr Ile Ala
                885                 890

<210> SEQ ID NO 39
<211> LENGTH: 329
<212> TYPE: PRT
<213> ORGANISM: Salmonella enterica

<400> SEQUENCE: 39

Met Gln Gly Ser Val Thr Glu Phe Leu Lys Pro Arg Leu Val Asp Ile
1               5                   10                  15

Glu Gln Val Ser Ser Thr His Ala Lys Val Thr Leu Glu Pro Leu Glu
            20                  25                  30

Arg Gly Phe Gly His Thr Leu Gly Asn Ala Leu Arg Arg Ile Leu Leu
        35                  40                  45

Ser Ser Met Pro Gly Cys Ala Val Thr Glu Val Glu Ile Asp Gly Val
    50                  55                  60

Leu His Glu Tyr Ser Thr Lys Glu Gly Val Gln Glu Asp Ile Leu Glu
65                  70                  75                  80

Ile Leu Leu Asn Leu Lys Gly Leu Ala Val Arg Val Gln Gly Lys Asp
                85                  90                  95

```
Glu Val Ile Leu Thr Leu Asn Lys Ser Gly Ile Gly Pro Val Thr Ala
                100                 105                 110

Ala Asp Ile Thr His Asp Gly Asp Val Glu Ile Val Lys Pro Gln His
            115                 120                 125

Val Ile Cys His Leu Thr Asp Glu Asn Ala Ser Ile Ser Met Arg Ile
        130                 135                 140

Lys Val Gln Arg Gly Arg Gly Tyr Val Pro Ala Ser Thr Arg Ile His
145                 150                 155                 160

Ser Glu Glu Asp Glu Arg Pro Ile Gly Arg Leu Leu Val Asp Ala Cys
                165                 170                 175

Tyr Ser Pro Val Glu Arg Ile Ala Tyr Asn Val Glu Ala Ala Arg Val
            180                 185                 190

Glu Gln Arg Thr Asp Leu Asp Lys Leu Val Ile Glu Met Glu Thr Asn
        195                 200                 205

Gly Thr Ile Asp Pro Glu Glu Ala Ile Arg Arg Ala Ala Thr Ile Leu
    210                 215                 220

Ala Glu Gln Leu Glu Ala Phe Val Asp Leu Arg Asp Val Arg Gln Pro
225                 230                 235                 240

Glu Val Lys Glu Lys Pro Glu Phe Asp Pro Ile Leu Leu Arg Pro
                245                 250                 255

Val Asp Asp Leu Glu Leu Thr Val Arg Ser Ala Asn Cys Leu Lys Ala
            260                 265                 270

Glu Ala Ile His Tyr Ile Gly Asp Leu Val Gln Arg Thr Glu Val Glu
        275                 280                 285

Leu Leu Lys Thr Pro Asn Leu Gly Lys Lys Ser Leu Thr Glu Ile Lys
    290                 295                 300

Asp Val Leu Ala Ser Arg Gly Leu Ser Leu Gly Met Arg Leu Glu Asn
305                 310                 315                 320

Trp Pro Pro Ala Ser Ile Ala Asp Glu
                325

<210> SEQ ID NO 40
<211> LENGTH: 1342
<212> TYPE: PRT
<213> ORGANISM: Salmonella enterica

<400> SEQUENCE: 40

Met Val Tyr Ser Tyr Thr Glu Lys Lys Arg Ile Arg Lys Asp Phe Gly
1               5                   10                  15

Lys Arg Pro Gln Val Leu Asp Val Pro Tyr Leu Leu Ser Ile Gln Leu
                20                  25                  30

Asp Ser Phe Gln Lys Phe Ile Glu Gln Asp Pro Glu Gly Gln Tyr Gly
            35                  40                  45

Leu Glu Ala Ala Phe Arg Ser Val Phe Pro Ile Gln Ser Tyr Ser Gly
50                  55                  60

Asn Ser Glu Leu Gln Tyr Val Ser Tyr Arg Leu Gly Glu Pro Val Phe
65                  70                  75                  80

Asp Val Gln Glu Cys Gln Ile Arg Gly Val Thr Tyr Ser Ala Pro Leu
                85                  90                  95

Arg Val Lys Leu Arg Leu Val Ile Tyr Glu Arg Glu Ala Pro Glu Gly
                100                 105                 110

Thr Val Lys Asp Ile Lys Glu Gln Glu Val Tyr Met Gly Glu Ile Pro
            115                 120                 125

Leu Met Thr Asp Asn Gly Thr Phe Val Ile Asn Gly Thr Glu Arg Val
```

```
            130                 135                 140
Ile Val Ser Gln Leu His Arg Ser Pro Gly Val Phe Phe Asp Ser Asp
145                 150                 155                 160

Lys Gly Lys Thr His Ser Ser Gly Lys Val Leu Tyr Asn Ala Arg Ile
                165                 170                 175

Ile Pro Tyr Arg Gly Ser Trp Leu Asp Phe Glu Phe Asp Pro Lys Asp
            180                 185                 190

Asn Leu Phe Val Arg Ile Asp Arg Arg Lys Leu Pro Ala Thr Ile
        195                 200                 205

Ile Leu Arg Ala Leu Asn Tyr Thr Thr Glu Gln Ile Leu Asp Leu Phe
    210                 215                 220

Phe Glu Lys Val Val Phe Glu Ile Arg Asp Asn Lys Leu Gln Met Glu
225                 230                 235                 240

Leu Ile Pro Glu Arg Leu Arg Gly Glu Thr Ala Ser Phe Asp Ile Glu
                245                 250                 255

Ala Asn Gly Lys Val Tyr Val Glu Lys Gly Arg Arg Ile Thr Ala Arg
            260                 265                 270

His Ile Arg Gln Leu Glu Lys Asp Asp Ile Lys His Ile Glu Val Pro
        275                 280                 285

Val Glu Tyr Ile Ala Gly Lys Val Val Ser Lys Asp Tyr Val Asp Glu
    290                 295                 300

Ser Thr Gly Glu Leu Ile Cys Ala Ala Asn Met Glu Leu Ser Leu Asp
305                 310                 315                 320

Leu Leu Ala Lys Leu Ser Gln Ser Gly His Lys Arg Ile Glu Thr Leu
                325                 330                 335

Phe Thr Asn Asp Leu Asp His Gly Pro Tyr Ile Ser Glu Thr Val Arg
            340                 345                 350

Val Asp Pro Thr Asn Asp Arg Leu Ser Ala Leu Val Glu Ile Tyr Arg
        355                 360                 365

Met Met Arg Pro Gly Glu Pro Pro Thr Arg Glu Ala Ala Glu Ser Leu
    370                 375                 380

Phe Glu Asn Leu Phe Phe Ser Glu Asp Arg Tyr Asp Leu Ser Ala Val
385                 390                 395                 400

Gly Arg Met Lys Phe Asn Arg Ser Leu Leu Arg Asp Glu Ile Glu Gly
                405                 410                 415

Ser Gly Ile Leu Ser Lys Asp Asp Ile Ile Asp Val Met Lys Lys Leu
            420                 425                 430

Ile Asp Ile Arg Asn Gly Lys Gly Glu Val Asp Asp Ile Asp His Leu
        435                 440                 445

Gly Asn Arg Arg Ile Arg Ser Val Gly Glu Met Ala Glu Asn Gln Phe
    450                 455                 460

Arg Val Gly Leu Val Arg Val Glu Arg Ala Val Lys Glu Arg Leu Ser
465                 470                 475                 480

Leu Gly Asp Leu Asp Thr Leu Met Pro Gln Asp Met Ile Asn Ala Lys
                485                 490                 495

Pro Ile Ser Ala Ala Val Lys Glu Phe Phe Gly Ser Ser Gln Leu Ser
            500                 505                 510

Gln Phe Met Asp Gln Asn Asn Pro Leu Ser Glu Ile Thr His Lys Arg
        515                 520                 525

Arg Ile Ser Ala Leu Gly Pro Gly Gly Leu Thr Arg Glu Arg Ala Gly
    530                 535                 540

Phe Glu Val Arg Asp Val His Pro Thr His Tyr Gly Arg Val Cys Pro
545                 550                 555                 560
```

```
Ile Glu Thr Pro Glu Gly Pro Asn Ile Gly Leu Ile Asn Ser Leu Ser
            565                 570                 575

Val Tyr Ala Gln Thr Asn Glu Tyr Gly Phe Leu Glu Thr Pro Tyr Arg
            580                 585                 590

Arg Val Val Asp Gly Val Val Thr Asp Glu Ile His Tyr Leu Ser Ala
            595                 600                 605

Ile Glu Glu Gly Asn Tyr Val Ile Ala Gln Ala Asn Ser Asn Leu Asp
            610                 615                 620

Asp Gly His Phe Val Glu Asp Leu Val Thr Cys Arg Ser Lys Gly
625                 630                 635                 640

Glu Ser Ser Leu Phe Ser Arg Asp Gln Val Asp Tyr Met Asp Val Ser
            645                 650                 655

Thr Gln Gln Val Val Ser Val Gly Ala Ser Leu Ile Pro Phe Leu Glu
            660                 665                 670

His Asp Asp Ala Asn Arg Ala Leu Met Gly Ala Asn Met Gln Arg Gln
            675                 680                 685

Ala Val Pro Thr Leu Arg Ala Asp Lys Pro Leu Val Gly Thr Gly Met
            690                 695                 700

Glu Arg Ala Val Ala Val Asp Ser Gly Val Thr Ala Val Ala Lys Arg
705                 710                 715                 720

Gly Gly Thr Val Gln Tyr Val Asp Ala Ser Arg Ile Val Ile Lys Val
            725                 730                 735

Asn Glu Asp Glu Met Tyr Pro Gly Glu Ala Gly Ile Asp Ile Tyr Asn
            740                 745                 750

Leu Thr Lys Tyr Thr Arg Ser Asn Gln Asn Thr Cys Ile Asn Gln Met
            755                 760                 765

Pro Cys Val Ser Leu Gly Glu Pro Val Glu Arg Gly Asp Val Leu Ala
            770                 775                 780

Asp Gly Pro Ser Thr Asp Leu Gly Glu Leu Ala Leu Gly Gln Asn Met
785                 790                 795                 800

Arg Val Ala Phe Met Pro Trp Asn Gly Tyr Asn Phe Glu Asp Ser Ile
            805                 810                 815

Leu Val Ser Glu Arg Val Val Gln Glu Asp Arg Phe Thr Thr Ile His
            820                 825                 830

Ile Gln Glu Leu Ala Cys Val Ser Arg Asp Thr Lys Leu Gly Pro Glu
            835                 840                 845

Glu Ile Thr Ala Asp Ile Pro Asn Val Gly Glu Ala Ala Leu Ser Lys
            850                 855                 860

Leu Asp Glu Ser Gly Ile Val Tyr Ile Gly Ala Glu Val Thr Gly Gly
865                 870                 875                 880

Asp Ile Leu Val Gly Lys Val Thr Pro Lys Gly Glu Thr Gln Leu Thr
            885                 890                 895

Pro Glu Glu Lys Leu Leu Arg Ala Ile Phe Gly Glu Lys Ala Ser Asp
            900                 905                 910

Val Lys Asp Ser Ser Leu Arg Val Pro Asn Gly Val Ser Gly Thr Val
            915                 920                 925

Ile Asp Val Gln Val Phe Thr Arg Asp Gly Val Glu Lys Asp Lys Arg
            930                 935                 940

Ala Leu Glu Ile Glu Glu Met Gln Leu Lys Gln Ala Lys Lys Asp Leu
945                 950                 955                 960

Ser Glu Glu Leu Gln Ile Leu Glu Ala Gly Leu Phe Ser Arg Ile Arg
            965                 970                 975
```

```
Ala Val Leu Val Ser Ser Gly Val Glu Ala Glu Lys Leu Asp Lys Leu
            980                 985                 990

Pro Arg Asp Arg Trp Leu Glu Leu Gly Leu Thr Asp Glu Glu Lys Gln
        995                1000                1005

Asn Gln Leu Glu Gln Leu Ala Glu Gln Tyr Asp Glu Leu Lys His Glu
    1010                1015                1020

Phe Glu Lys Lys Leu Glu Ala Lys Arg Arg Lys Ile Thr Gln Gly Asp
1025                1030                1035                1040

Asp Leu Ala Pro Gly Val Leu Lys Ile Val Lys Val Tyr Leu Ala Val
            1045                1050                1055

Lys Arg Arg Ile Gln Pro Gly Asp Lys Met Ala Gly Arg His Gly Asn
            1060                1065                1070

Lys Gly Val Ile Ser Lys Ile Asn Pro Ile Glu Asp Met Pro Tyr Asp
            1075                1080                1085

Glu Asn Gly Thr Pro Val Asp Ile Val Leu Asn Pro Leu Gly Val Pro
            1090                1095                1100

Ser Arg Met Asn Ile Gly Gln Ile Leu Glu Thr His Leu Gly Met Ala
1105                1110                1115                1120

Ala Lys Gly Ile Gly Asp Lys Ile Asn Ala Met Leu Lys Gln Gln Gln
            1125                1130                1135

Glu Val Ala Lys Leu Arg Glu Phe Ile Gln Arg Ala Tyr Asp Leu Gly
            1140                1145                1150

Ala Asp Val Arg Gln Lys Val Asp Leu Ser Thr Phe Ser Asp Asp Glu
            1155                1160                1165

Val Leu Arg Leu Ala Glu Asn Leu Arg Lys Gly Met Pro Ile Ala Thr
    1170                1175                1180

Pro Val Phe Asp Gly Ala Lys Glu Ala Glu Ile Lys Glu Leu Leu Lys
1185                1190                1195                1200

Leu Gly Asp Leu Pro Thr Ser Gly Gln Ile Thr Leu Phe Asp Gly Arg
            1205                1210                1215

Thr Gly Glu Gln Phe Glu Arg Pro Val Thr Val Gly Tyr Met Tyr Met
            1220                1225                1230

Leu Lys Leu Asn His Leu Val Asp Asp Lys Met His Ala Arg Ser Thr
            1235                1240                1245

Gly Ser Tyr Ser Leu Val Thr Gln Gln Pro Leu Gly Gly Lys Ala Gln
    1250                1255                1260

Phe Gly Gly Gln Arg Phe Gly Glu Met Glu Val Trp Ala Leu Glu Ala
1265                1270                1275                1280

Tyr Gly Ala Ala Tyr Thr Leu Gln Glu Met Leu Thr Val Lys Ser Asp
            1285                1290                1295

Asp Val Asn Gly Arg Thr Lys Met Tyr Lys Asn Ile Val Asp Gly Asn
            1300                1305                1310

His Gln Met Glu Pro Gly Met Pro Glu Ser Phe Asn Val Leu Leu Lys
    1315                1320                1325

Glu Ile Arg Ser Leu Gly Ile Asn Ile Glu Leu Glu Asp Glu
    1330                1335                1340

<210> SEQ ID NO 41
<211> LENGTH: 1407
<212> TYPE: PRT
<213> ORGANISM: Salmonella enterica

<400> SEQUENCE: 41

Met Lys Asp Leu Leu Lys Phe Leu Lys Ala Gln Thr Lys Thr Glu Glu
1               5                   10                  15
```

```
Phe Asp Ala Ile Lys Ile Ala Leu Ala Ser Pro Asp Met Ile Arg Ser
            20                  25                  30

Trp Ser Phe Gly Glu Val Lys Lys Pro Glu Thr Ile Asn Tyr Arg Thr
        35                  40                  45

Phe Lys Pro Glu Arg Asp Gly Leu Phe Cys Ala Arg Ile Phe Gly Pro
    50                  55                  60

Val Lys Asp Tyr Glu Cys Leu Cys Gly Lys Tyr Lys Arg Leu Lys His
65                  70                  75                  80

Arg Gly Val Ile Cys Glu Lys Cys Gly Val Glu Val Thr Gln Thr Lys
                85                  90                  95

Val Arg Arg Glu Arg Met Gly His Ile Glu Leu Ala Ser Pro Thr Ala
                100                 105                 110

His Ile Trp Phe Leu Lys Ser Leu Pro Ser Arg Ile Gly Leu Leu Leu
            115                 120                 125

Asp Met Pro Leu Arg Asp Ile Glu Arg Val Leu Tyr Phe Glu Ser Tyr
    130                 135                 140

Val Val Ile Glu Gly Gly Met Thr Asn Leu Glu Arg Gln Gln Ile Leu
145                 150                 155                 160

Thr Glu Glu Gln Tyr Leu Asp Ala Leu Glu Glu Phe Gly Asp Glu Phe
                165                 170                 175

Asp Ala Lys Met Gly Ala Glu Ala Ile Gln Ala Leu Leu Lys Ser Met
            180                 185                 190

Asp Leu Glu Gln Glu Cys Glu Thr Leu Arg Glu Glu Leu Asn Glu Thr
    195                 200                 205

Asn Ser Glu Thr Lys Arg Lys Lys Leu Thr Lys Arg Ile Lys Leu Leu
210                 215                 220

Glu Ala Phe Val Gln Ser Gly Asn Lys Pro Glu Trp Met Ile Leu Thr
225                 230                 235                 240

Val Leu Pro Val Leu Pro Pro Asp Leu Arg Pro Leu Val Pro Leu Asp
                245                 250                 255

Gly Gly Arg Phe Ala Thr Ser Asp Leu Asn Asp Leu Tyr Arg Arg Val
            260                 265                 270

Ile Asn Arg Asn Asn Arg Leu Lys Arg Leu Leu Asp Leu Ala Ala Pro
    275                 280                 285

Asp Ile Ile Val Arg Asn Glu Lys Arg Met Leu Gln Glu Ala Val Asp
290                 295                 300

Ala Leu Leu Asp Asn Gly Arg Arg Gly Arg Ala Ile Thr Gly Ser Asn
305                 310                 315                 320

Lys Arg Pro Leu Lys Ser Leu Ala Asp Met Ile Lys Gly Lys Gln Gly
                325                 330                 335

Arg Phe Arg Gln Asn Leu Leu Gly Lys Arg Val Asp Tyr Ser Gly Arg
            340                 345                 350

Ser Val Ile Thr Val Gly Pro Tyr Leu Arg Leu His Gln Cys Gly Leu
    355                 360                 365

Pro Lys Lys Met Ala Leu Glu Leu Phe Lys Pro Phe Ile Tyr Gly Lys
370                 375                 380

Leu Glu Leu Arg Gly Leu Ala Thr Thr Ile Lys Ala Ala Lys Lys Met
385                 390                 395                 400

Val Glu Arg Glu Glu Ala Val Val Trp Asp Ile Leu Asp Glu Val Ile
                405                 410                 415

Arg Glu His Pro Val Leu Leu Asn Arg Ala Pro Thr Leu His Arg Leu
            420                 425                 430
```

-continued

Gly Ile Gln Ala Phe Glu Pro Val Leu Ile Glu Gly Lys Ala Ile Gln
                435                 440                 445

Leu His Pro Leu Val Cys Ala Ala Tyr Asn Ala Asp Phe Asp Gly Asp
        450                 455                 460

Gln Met Ala Val His Val Pro Leu Thr Leu Glu Ala Gln Leu Glu Ala
465                 470                 475                 480

Arg Ala Leu Met Met Ser Thr Asn Asn Ile Leu Ser Pro Ala Asn Gly
                485                 490                 495

Glu Pro Ile Ile Val Pro Ser Gln Asp Val Val Leu Gly Leu Tyr Tyr
                500                 505                 510

Met Thr Arg Asp Cys Val Asn Ala Lys Gly Glu Gly Met Val Leu Thr
                515                 520                 525

Gly Pro Lys Glu Ala Glu Arg Ile Tyr Arg Ala Gly Leu Ala Ser Leu
        530                 535                 540

His Ala Arg Val Lys Val Arg Ile Thr Glu Tyr Glu Lys Asp Glu Asn
545                 550                 555                 560

Gly Glu Phe Val Ala His Thr Ser Leu Lys Asp Thr Thr Val Gly Arg
                565                 570                 575

Ala Ile Leu Trp Met Ile Val Pro Lys Gly Leu Pro Phe Ser Ile Val
                580                 585                 590

Asn Gln Ala Leu Gly Lys Lys Ala Ile Ser Lys Met Leu Asn Thr Cys
                595                 600                 605

Tyr Arg Ile Leu Gly Leu Lys Pro Thr Val Ile Phe Ala Asp Gln Thr
        610                 615                 620

Met Tyr Thr Gly Phe Ala Tyr Ala Ala Arg Ser Gly Ala Ser Val Gly
625                 630                 635                 640

Ile Asp Asp Met Val Ile Pro Glu Lys Lys His Glu Ile Ile Ser Glu
                645                 650                 655

Ala Glu Ala Glu Val Ala Glu Ile Gln Glu Gln Phe Gln Ser Gly Leu
                660                 665                 670

Val Thr Ala Gly Glu Arg Tyr Asn Lys Val Ile Asp Ile Trp Ala Ala
                675                 680                 685

Ala Asn Asp Arg Val Ser Lys Ala Met Met Asp Asn Leu Gln Thr Glu
        690                 695                 700

Thr Val Ile Asn Arg Asp Gly Gln Glu Glu Gln Gln Val Ser Phe Asn
705                 710                 715                 720

Ser Ile Tyr Met Met Ala Asp Ser Gly Ala Arg Gly Ser Ala Ala Gln
                725                 730                 735

Ile Arg Gln Leu Ala Gly Met Arg Gly Leu Met Ala Lys Pro Asp Gly
        740                 745                 750

Ser Ile Ile Glu Thr Pro Ile Thr Ala Asn Phe Arg Glu Gly Leu Asn
                755                 760                 765

Val Leu Gln Tyr Phe Ile Ser Thr His Gly Ala Arg Lys Gly Leu Ala
        770                 775                 780

Asp Thr Ala Leu Lys Thr Ala Asn Ser Gly Tyr Leu Thr Arg Arg Leu
785                 790                 795                 800

Val Asp Val Ala Gln Asp Leu Val Val Thr Glu Asp Asp Cys Gly Thr
                805                 810                 815

His Glu Gly Ile Leu Met Thr Pro Val Ile Gly Gly Asp Val Lys
                820                 825                 830

Glu Pro Leu Arg Asp Arg Val Leu Gly Arg Val Thr Ala Glu Asp Val
        835                 840                 845

Leu Lys Pro Gly Thr Ala Asp Ile Leu Val Pro Arg Asn Thr Leu Leu

```
              850                 855                 860
His Glu Gln Trp Cys Asp Leu Leu Glu Ala Asn Ser Val Asp Ala Val
865                 870                 875                 880

Lys Val Arg Ser Val Ser Cys Asp Thr Asp Phe Gly Val Cys Ala
                885                 890                 895

His Cys Tyr Gly Arg Asp Leu Ala Arg Gly His Ile Ile Asn Lys Gly
                900                 905                 910

Glu Ala Ile Gly Val Ile Ala Ala Gln Ser Ile Gly Glu Pro Gly Thr
                915                 920                 925

Gln Leu Thr Met Arg Thr Phe His Ile Gly Ala Ala Ser Arg Ala
            930                 935                 940

Ala Ala Glu Ser Ser Ile Gln Val Lys Asn Lys Gly Ser Ile Lys Leu
945                 950                 955                 960

Ser Asn Val Lys Ser Val Asn Ser Ser Gly Lys Leu Val Ile Thr
                965                 970                 975

Ser Arg Asn Thr Glu Leu Lys Leu Ile Asp Glu Phe Gly Arg Thr Lys
                980                 985                 990

Glu Ser Tyr Lys Val Pro Tyr Gly Ala Val Met Ala Lys Gly Asp Gly
                995                1000                1005

Glu Gln Val Ala Gly Gly Glu Thr Val Ala Asn Trp Asp Pro His Thr
            1010                1015                1020

Met Pro Val Ile Thr Glu Val Ser Gly Phe Ile Arg Phe Thr Asp Met
1025                1030                1035                1040

Ile Asp Gly Gln Thr Ile Thr Arg Gln Thr Asp Glu Leu Thr Gly Leu
                1045                1050                1055

Ser Ser Leu Val Val Leu Asp Ser Ala Glu Arg Thr Thr Gly Gly Lys
                1060                1065                1070

Asp Leu Arg Pro Ala Leu Lys Ile Val Asp Ala Gln Gly Asn Asp Val
                1075                1080                1085

Leu Ile Pro Gly Thr Asp Met Pro Ala Gln Tyr Phe Leu Pro Gly Lys
            1090                1095                1100

Ala Ile Val Gln Leu Glu Asp Gly Val Gln Ile Ser Ser Gly Asp Thr
1105                1110                1115                1120

Leu Ala Arg Ile Pro Gln Glu Ser Gly Gly Thr Lys Asp Ile Thr Gly
                1125                1130                1135

Gly Leu Pro Arg Val Ala Asp Leu Phe Glu Ala Arg Arg Pro Lys Glu
            1140                1145                1150

Pro Ala Ile Leu Ala Glu Ile Ala Gly Ile Val Ser Phe Gly Lys Glu
            1155                1160                1165

Thr Lys Gly Lys Arg Arg Leu Val Ile Thr Pro Val Asp Gly Ser Asp
    1170                1175                1180

Pro Tyr Glu Glu Met Ile Pro Lys Trp Arg Gln Leu Asn Val Phe Glu
1185                1190                1195                1200

Gly Glu Arg Val Glu Arg Gly Asp Val Ile Ser Asp Gly Pro Glu Ala
                1205                1210                1215

Pro His Asp Ile Leu Arg Leu Arg Gly Val His Ala Val Thr Arg Tyr
            1220                1225                1230

Ile Val Asn Glu Val Gln Asp Val Tyr Arg Leu Gln Gly Val Lys Ile
            1235                1240                1245

Asn Asp Lys His Ile Glu Val Ile Val Arg Gln Met Leu Arg Lys Ala
    1250                1255                1260

Thr Ile Glu Ser Ala Gly Ser Ser Asp Phe Leu Glu Gly Glu Gln Val
1265                1270                1275                1280
```

```
Glu Tyr Ser Arg Val Lys Ile Ala Asn Arg Glu Leu Glu Ala Asn Gly
            1285                1290                1295

Lys Val Gly Ala Thr Phe Ser Arg Asp Leu Leu Gly Ile Thr Lys Ala
        1300                1305                1310

Ser Leu Ala Thr Glu Ser Phe Ile Ser Ala Ala Ser Phe Gln Glu Thr
        1315                1320                1325

Thr Arg Val Leu Thr Glu Ala Ala Val Ala Gly Lys Arg Asp Glu Leu
    1330                1335                1340

Arg Gly Leu Lys Glu Asn Val Ile Val Gly Arg Leu Ile Pro Ala Gly
1345                1350                1355                1360

Thr Gly Tyr Ala Tyr His Gln Asp Arg Met Arg Arg Ala Ala Gly
            1365                1370                1375

Glu Gln Pro Ala Thr Pro Gln Val Thr Ala Glu Asp Ala Ser Ala Ser
        1380                1385                1390

Leu Ala Glu Leu Leu Asn Ala Gly Leu Gly Gly Ser Asp Asn Glu
            1395                1400                1405

<210> SEQ ID NO 42
<211> LENGTH: 343
<212> TYPE: PRT
<213> ORGANISM: Salmonella enterica

<400> SEQUENCE: 42

Met Ile Arg Leu Tyr Pro Glu Gln Leu Arg Ala Gln Leu Asn Glu Gly
1               5                   10                  15

Leu Arg Ala Ala Tyr Leu Leu Leu Gly Asn Asp Pro Leu Leu Leu Gln
            20                  25                  30

Glu Ser Gln Asp Ala Ile Arg Leu Ala Ala Ala Ser Gln Gly Phe Glu
        35                  40                  45

Glu His His Ala Phe Thr Leu Asp Pro Ser Thr Asp Trp Gly Ser Leu
    50                  55                  60

Phe Ser Leu Cys Gln Ala Met Ser Leu Phe Ala Ser Arg Gln Thr Leu
65                  70                  75                  80

Val Leu Gln Leu Pro Glu Asn Gly Pro Asn Ala Ala Met Asn Glu Gln
                85                  90                  95

Leu Ala Thr Leu Ser Glu Leu Leu His Asp Asp Leu Leu Leu Ile Val
            100                 105                 110

Arg Gly Asn Lys Leu Thr Lys Ala Gln Glu Asn Ala Ala Trp Tyr Thr
        115                 120                 125

Ala Leu Ala Asp Arg Ser Val Gln Val Ser Cys Gln Thr Pro Glu Gln
    130                 135                 140

Ala Gln Leu Pro Arg Trp Val Ala Ala Arg Ala Lys Ala Gln Asn Leu
145                 150                 155                 160

Gln Leu Asp Asp Ala Ala Asn Gln Leu Leu Cys Tyr Cys Tyr Glu Gly
                165                 170                 175

Asn Leu Leu Ala Leu Ala Gln Ala Leu Glu Arg Leu Ser Leu Leu Trp
            180                 185                 190

Pro Asp Gly Lys Leu Thr Leu Pro Arg Val Glu Gln Ala Val Asn Asp
        195                 200                 205

Ala Ala His Phe Thr Pro Phe His Trp Val Asp Ala Leu Leu Met Gly
    210                 215                 220

Lys Ser Lys Arg Ala Leu His Ile Leu Gln Gln Leu Arg Leu Glu Gly
225                 230                 235                 240

Ser Glu Pro Val Ile Leu Leu Arg Thr Leu Gln Arg Glu Leu Leu Leu
```

```
                    245                 250                 255
Leu Val Asn Leu Lys Arg Gln Ser Ala His Thr Pro Leu Arg Ala Leu
            260                 265                 270

Phe Asp Lys His Arg Val Trp Gln Asn Arg Arg Pro Met Ile Gly Asp
            275                 280                 285

Ala Leu Gln Arg Leu His Pro Ala Gln Leu Arg Gln Ala Val Gln Leu
            290                 295                 300

Leu Thr Arg Thr Glu Ile Thr Leu Lys Gln Asp Tyr Gly Gln Ser Val
305                 310                 315                 320

Trp Ala Asp Leu Glu Gly Leu Ser Leu Leu Cys His Lys Ala Leu
            325                 330                 335

Ala Asp Val Phe Ile Asp Gly
            340

<210> SEQ ID NO 43
<211> LENGTH: 245
<212> TYPE: PRT
<213> ORGANISM: Salmonella enterica

<400> SEQUENCE: 43

Met Lys Asn Val Gly Asp Leu Met Gln Arg Leu Gln Lys Met Met Pro
1               5                   10                  15

Ala His Ile Thr Pro Ala Phe Lys Thr Gly Glu Glu Leu Leu Ala Trp
            20                  25                  30

Gln Lys Glu Gln Gly Glu Ile Arg Ala Ala Leu Ala Arg Glu Asn
        35                  40                  45

Arg Ala Met Lys Met Gln Arg Thr Phe Asn Arg Ser Gly Ile Arg Pro
    50                  55                  60

Leu His Gln Asn Cys Ser Phe Asp Asn Tyr Arg Val Glu Cys Asp Gly
65                  70                  75                  80

Gln Met Asn Ala Leu Ser Lys Ala Arg Gln Tyr Val Asp Glu Phe Asp
                85                  90                  95

Gly Asn Ile Ala Ser Phe Val Phe Ser Gly Lys Pro Gly Thr Gly Lys
            100                 105                 110

Asn His Leu Ala Ala Ala Ile Cys Asn Glu Leu Leu Arg Gly Lys
            115                 120                 125

Ser Val Leu Ile Ile Thr Val Ala Asp Ile Met Ser Ala Met Lys Asp
            130                 135                 140

Thr Phe Ser Asn Arg Glu Thr Ser Glu Glu Gln Leu Leu Asn Asp Leu
145                 150                 155                 160

Ser Asn Val Asp Leu Leu Val Ile Asp Glu Ile Gly Val Gln Thr Glu
                165                 170                 175

Ser Arg Tyr Glu Lys Val Ile Ile Asn Gln Ile Val Asp Arg Arg Ser
            180                 185                 190

Ser Ser Lys Arg Pro Thr Gly Met Leu Thr Asn Ser Asn Met Glu Glu
            195                 200                 205

Met Thr Lys Met Leu Gly Glu Arg Val Met Asp Arg Met Arg Leu Gly
            210                 215                 220

Asn Ser Leu Trp Val Asn Phe Thr Trp Asp Ser Tyr Arg Ser Arg Val
225                 230                 235                 240

Thr Gly Lys Glu Tyr
            245

<210> SEQ ID NO 44
<211> LENGTH: 490
```

<212> TYPE: PRT
<213> ORGANISM: Salmonella enterica

<400> SEQUENCE: 44

```
Met Val Pro Val Val Ala Leu Val Gly Arg Pro Asn Val Gly Lys Ser
1               5                   10                  15

Thr Leu Phe Asn Arg Leu Thr Arg Thr Arg Asp Ala Leu Val Ala Asp
            20                  25                  30

Phe Pro Gly Leu Thr Arg Asp Arg Lys Tyr Gly Arg Ala Glu Val Glu
        35                  40                  45

Gly Arg Glu Phe Ile Cys Ile Asp Thr Gly Gly Ile Asp Gly Thr Glu
    50                  55                  60

Asp Gly Val Glu Thr Arg Met Ala Glu Gln Ser Leu Leu Ala Ile Glu
65                  70                  75                  80

Glu Ala Asp Val Val Leu Phe Met Val Asp Ala Arg Ala Gly Leu Met
                85                  90                  95

Pro Ala Asp Glu Ala Ile Ala Lys His Leu Arg Ser Arg Glu Lys Pro
            100                 105                 110

Thr Phe Leu Val Ala Asn Lys Thr Asp Gly Leu Asp Pro Asp Gln Ala
        115                 120                 125

Val Val Asp Phe Tyr Ser Leu Gly Leu Gly Glu Ile Tyr Pro Ile Ala
    130                 135                 140

Ala Ser His Gly Arg Gly Val Leu Ser Leu Leu Glu His Val Leu Leu
145                 150                 155                 160

Pro Trp Met Asp Asp Val Ala Pro Gln Glu Glu Val Asp Glu Asp Ala
                165                 170                 175

Glu Tyr Trp Ala Gln Phe Glu Ala Glu Gln Asn Gly Glu Glu Ala Pro
            180                 185                 190

Glu Asp Asp Phe Asp Pro Gln Ser Leu Pro Ile Lys Leu Ala Ile Val
        195                 200                 205

Gly Arg Pro Asn Val Gly Lys Ser Thr Leu Thr Asn Arg Ile Leu Gly
    210                 215                 220

Glu Glu Arg Val Val Val Tyr Asp Met Pro Gly Thr Thr Arg Asp Ser
225                 230                 235                 240

Ile Tyr Ile Pro Met Glu Arg Asp Gly Arg Glu Tyr Val Leu Ile Asp
                245                 250                 255

Thr Ala Gly Val Arg Lys Arg Gly Lys Ile Thr Asp Ala Val Glu Lys
            260                 265                 270

Phe Ser Val Ile Lys Thr Leu Gln Ala Ile Glu Asp Ala Asn Val Val
        275                 280                 285

Leu Leu Val Ile Asp Ala Arg Glu Gly Ile Ser Asp Gln Asp Leu Ser
    290                 295                 300

Leu Leu Gly Phe Ile Leu Asn Ser Gly Arg Ser Leu Val Ile Val Val
305                 310                 315                 320

Asn Lys Trp Asp Gly Leu Ser Gln Glu Val Lys Glu Gln Val Lys Glu
                325                 330                 335

Thr Leu Asp Phe Arg Leu Gly Phe Ile Asp Phe Ala Arg Val His Phe
            340                 345                 350

Ile Ser Ala Leu His Gly Ser Gly Val Gly Asn Leu Phe Glu Ser Val
        355                 360                 365

Arg Glu Ala Tyr Asp Ser Ser Thr Arg Val Ser Thr Ala Met Leu
    370                 375                 380

Thr Arg Ile Met Thr Met Ala Val Glu Asp His Gln Pro Pro Leu Val
385                 390                 395                 400
```

```
Arg Gly Arg Arg Val Lys Leu Lys Tyr Ala His Ala Gly Gly Tyr Asn
                405                 410                 415

Pro Pro Ile Val Val Ile His Gly Asn Gln Val Lys Asp Leu Pro Asp
            420                 425                 430

Ser Tyr Lys Arg Tyr Leu Met Asn Tyr Phe Arg Lys Ser Leu Glu Val
        435                 440                 445

Met Gly Thr Pro Ile Arg Ile Gln Phe Lys Glu Gly Glu Asn Pro Tyr
    450                 455                 460

Ala Asn Lys Arg Asn Thr Leu Thr Pro Thr Gln Met Arg Lys Arg Lys
465                 470                 475                 480

Arg Leu Met Lys His Ile Lys Lys Ser Lys
                485                 490

<210> SEQ ID NO 45
<211> LENGTH: 199
<212> TYPE: PRT
<213> ORGANISM: Salmonella enterica

<400> SEQUENCE: 45

Met Met Ser Ala Pro Asp Ile Arg His Leu Pro Ser Asp Cys Gly Ile
1               5                   10                  15

Glu Val Ala Phe Ala Gly Arg Ser Asn Ala Gly Lys Ser Ser Ala Leu
            20                  25                  30

Asn Thr Leu Thr Asn Gln Lys Ser Leu Ala Arg Thr Ser Lys Thr Pro
        35                  40                  45

Gly Arg Thr Gln Leu Ile Asn Leu Phe Glu Val Val Asp Gly Lys Arg
    50                  55                  60

Leu Val Asp Leu Pro Gly Tyr Gly Tyr Ala Glu Val Pro Glu Glu Met
65                  70                  75                  80

Lys Arg Lys Trp Gln Arg Ala Leu Gly Glu Tyr Leu Glu Lys Arg Gln
                85                  90                  95

Ser Leu Gln Gly Leu Val Val Leu Met Asp Ile Arg His Pro Leu Lys
            100                 105                 110

Asp Leu Asp Gln Gln Met Ile Gln Trp Ala Val Glu Ser Asn Ile Gln
        115                 120                 125

Val Leu Val Leu Leu Thr Lys Ala Asp Lys Leu Ala Ser Gly Ala Arg
    130                 135                 140

Lys Ala Gln Leu Asn Met Val Arg Glu Ala Val Leu Ala Phe Asn Gly
145                 150                 155                 160

Asp Val Gln Val Glu Ala Phe Ser Ser Leu Lys Lys Gly Val Asp
                165                 170                 175

Lys Leu Arg Gln Lys Leu Asp Ser Trp Phe Ser Glu Leu Ala Pro Val
            180                 185                 190

Glu Glu Ile Gln Asp Gly Glu
        195

<210> SEQ ID NO 46
<211> LENGTH: 2558
<212> TYPE: DNA
<213> ORGANISM: Homo sapiens

<400> SEQUENCE: 46
aaatgggagg gggagacgca agatggcggc agccgcgaac tccggctcta gcctcccgct      60
gttcgactgc ccaacctggt gagtggcggg gcggccaggg ctagagtggc ccggccggag     120
ctagcctggg ctggaagggc ggctcttttt ttacttttct gctgcgagcc gaacggctca     180
```

```
gaaacccggg aatggttgag gaaaaactgt tgctgcacc gggccgggcg acgtgttgaa      240
gaaccgagag cctggagccc aggcccagga actgaagaaa cccggggttg ggggctcaaa    300
ggcgctcact taggcagccc ctttgagcga ttagccagtc gccggagcgc ttcgaggcct    360
tggcccgaac ttacgcccaa ctcttgactg agtgcctggt gctctcgtgg agcatcgcat    420 ctggccccctt cctgtacgtc ccgagcgcgc tcgagccagc cccggcccca accctacctc   480
caagccccgc atccctctgt ggttgctgca tccctcgtgc ggcacttgtc tgtctgccac    540
agagaatacg aggggcaggt aagccccctc ccggtttaca tctggatgta gtcaaaggag   600
acaaactaat tgagaaactg attattgatg agaagaagta ttacttattt gggagaaacc   660
ctgatttgtg tgactttacc attgaccacc agtcttgctc tcgggtccat gctgcacttg   720
tctaccacaa gcatctgaag agagttttcc tgatagatct caacagtaaa cctgacagag   780
ttcaacactg cccacaacaa gcggatttct acccttacca ttgaggaggg aaatctggac   840
attcaaagac caaagaggaa gaggaagaac tcacgggtga cattcagtga ggatgatgag   900
atcatcaacc cagaggatgt ggatccctca gttggtcgat tcaggaacat ggtgcaaact   960
gcagtggtcc cagtcaagaa gaagcgtgtg gagggccctg gctccctggg cctggaggaa  1020
tcagggagca ggcgcatgca gaactttgcc ttcagcggag gactctacgg gggcctgccc  1080
cccacacaca gtgaagcagg ctcccagcca catggcatcc atgggacagc actcatcggt  1140
ggcttgccca tgccataccc aaaccttgcc cctgatgtgg acttgactcc tgttgtgccg  1200
tcagcagtga acatgaaccc tgcaccaaac cctgcagtct ataaccctga agctgtaaat  1260
gaacccaaga agaagaaata tgcaaaagag gcttggccag gcaagaagcc cacaccttcc  1320
ttgctgattt gatattttttg gtcatggaga agggtgggat tgggtgggaa tggggtggaa  1380
gggtgatggg gagctaatga actagggaga aaaactttcc atgtgtgcgg tatcgtcttt  1440
cagaatgtct cctggcatcc taaccatgta atatgacaat tggggggtgg gttgaaatag  1500
cccataaaga cctgtcttca caacacttgc attgtagaga aaggcttctt atatccttt   1560 caatagactg ccctggctct ttcctaggcc ttccactacc tcctttcttt ctcccacttt   1620
ctaggatcat tttatgtaa agtcacatat cccaggccct caggttgaat ccagagctgt   1680
agaggttaca gtagcatcac cagccttggg ggtccagagc ctaatttata ttcactatcc   1740
ttccaagtcc cgggtagcag aagggttgcc atagatctca gtttgatcaa aaagaaggct   1800
tagaattctg cagttaagct gaggtttaaa ctaaaaaatg tttccttggg tcagtggttt   1860
tgaggtccag tagctaggct tttctctttt gtccttcctg ttggaatgaa acatttcga   1920 ttttccttca tctgtgactg gtgccataga cacaggttta tagttttaac ttacagtatt   1980
gtttgaaatt tacctgtttt tcttgtcaaa cctgagcact cctcctgctg aagtttctta   2040
tttaattcca gagtactgtc ctctactcta aggcattact tttaagtgta ttatgaaggc   2100
agttttcaaa ggatatgacc agttgggta attcaaatta aaaggaaaa gatttgtttg   2160 gaagtaactg gtgtctctaa gaggaatttt tagatgtcag tttggaggct ctttccccc    2220 tcaattgaga gctcttgtta ttcagagctc caagactaga cctggctaac aaacatagga   2280
gacaaagtta ggaaacattg atacaagctt tgtacagaga tttgtacatt tgtgtaatag   2340
gccttttcat gctttatgtg tagcttttta cctgtaacct ttattacatt gtaaattaaa   2400
cgtaactttt gtcatttggg tgcaggctgt gaatttgtct ctcagtcact gattgccact   2460
gccatctgga aatgtttgct aaaggcacag tcactgggct tgggaggcaa tgctccatcc   2520
```

```
ccattatatt acaaataaag atgccctaaa tgagtgtg                             2558
```

<210> SEQ ID NO 47
<211> LENGTH: 2723
<212> TYPE: DNA
<213> ORGANISM: Homo sapiens

<400> SEQUENCE: 47

```
ggcggcgctt gattgggctg gggggggccaa ataaaagcga tggcgattgg gctgccgcgt     60
ttggcgctcg gtccggtcgc gtccgacacc cggtgggact cagaaggcag tggagccccg    120
gcggcggcgg cggcggcgcg cggggggcgac gcgcgggaac aacgcgagtc ggcgcgcggg    180
acgaagaata atcatgggcc agactgggaa gaaatctgag aagggaccag tttgttggcg    240
gaagcgtgta aaatcagagt acatgcgact gagacagctc aagaggttca gacgagctga    300
tgaagtaaag agtatgttta gttccaatcg tcagaaaatt ttggaaagaa cggaaatctt    360
aaaccaagaa tggaaacagc gaaggataca gcctgtgcac atcctgactt ctgtgagctc    420
attgcgcggg actaggagt gttcggtgac cagtgacttg gattttccaa cacaagtcat    480
cccattaaag actctgaatg cagttgcttc agtacccata atgtattctt ggtctcccct    540
acagcagaat tttatggtgg aagatgaaac tgttttacat aacattcctt atatgggaga    600
tgaagtttta gatcaggatg gtactttcat tgaagaacta ataaaaaatt atgatgggaa    660
agtacacggg gatagagaat gtgggtttat aaatgatgaa attttgtgg agttggtgaa    720
tgcccttggt caatataatg atgatgacga tgatgatgat ggagacgatc ctgaagaaag    780
agaagaaaag cagaaagatc tggaggatca ccgagatgat aaagaaagcc gcccacctcg    840
gaaatttcct tctgataaaa tttttgaagc catttcctca atgtttccag ataagggcac    900
agcagaagaa ctaaaggaaa aatataaaga actcaccgaa cagcagctcc caggcgcact    960
tcctcctgaa tgtacccca acatagatgg accaaatgct aaatctgttc agagagagca   1020
aagcttacac tcctttcata cgcttttctg taggcgatgt tttaaatatg actgcttcct   1080
acatcgtaag tgcaattatt cttttcatgc aacacccaac acttataagc ggaagaacac   1140
agaaacagct ctagacaaca aaccttgtgg accacagtgt taccagcatt tggagggagc   1200
aaaggagttt gctgctgctc tcaccgctga gcggataaag accccaccaa aacgtccagg   1260
aggccgcaga agaggacggc ttcccaataa cagtagcagg cccagcaccc ccaccattaa   1320
tgtgctggaa tcaaaggata cagacagtga tagggaagca gggactgaaa cggggggaga   1380
gaacaatgat aaagaagaag aagagaagaa agatgaaact tcgagctcct ctgaagcaaa   1440
ttctcggtgt caaacaccaa taaagatgaa gccaaatatt gaacctcctg agaatgtgga   1500
gtggagtggt gctgaagcct caatgtttag agtcctcatt ggcacttact atgacaattt   1560
ctgtgccatt gctaggttaa ttgggaccaa acatgtaga caggtgtatg agtttagagt   1620
caaagaatct agcatcatag ctccagctcc cgctgaggat gtggatactc ctccaaggaa   1680
aaagaagagg aaacaccggt tgtgggctgc acactgcaga aagatacagc tgaaaaagga   1740
cggctcctct aaccatgttt acaactatca accctgtgat catccacggc agccttgtga   1800
cagttcgtgc ccttgtgtga tagcacaaaa tttttgtgaa aagttttgtc aatgtagttc   1860
agagtgtcaa aaccgctttc cgggatgccg ctgcaaagca cagtgcaaca ccaagcagtg   1920
cccgtgctac ctggctgtcc gagagtgtga ccctgacctc tgtcttactt gtggagccgc   1980
tgaccattgg gacagtaaaa atgtgtcctg caagaactgc agtattcagc ggggctccaa   2040
aaagcatcta ttgctggcac catctgacgt ggcaggctgg gggattttta tcaaagatcc   2100
```

```
tgtgcagaaa aatgaattca tctcagaata ctgtggagag attatttctc aagatgaagc   2160
tgacagaaga gggaaagtgt atgataaata catgtgcagc tttctgttca acttgaacaa   2220
tgattttgtg gtggatgcaa cccgcaaggg taacaaaatt cgttttgcaa atcattcggt   2280
aaatccaaac tgctatgcaa aagttatgat ggttaacggt gatcacagga taggtatttt   2340
tgccaagaga gccatccaga ctggcgaaga gctgttttt gattacagat acagccaggc    2400
tgatgccctg aagtatgtcg gcatcgaaag agaaatggaa atcccttgac atctgctacc   2460
tcctcccccc tcctctgaaa cagctgcctt agcttcagga acctcgagta ctgtgggcaa   2520
tttagaaaaa gaacatgcag tttgaaattc tgaatttgca aagtactgta agaataattt   2580
atagtaatga gtttaaaaat caactttta ttgccttctc accagctgca aagtgttttg     2640
taccagtgaa tttttgcaat aatgcagtat ggtacatttt tcaactttga ataaagaata   2700
cttgaacttg tccttgttga atc                                           2723

<210> SEQ ID NO 48
<211> LENGTH: 1488
<212> TYPE: DNA
<213> ORGANISM: Homo sapiens

<400> SEQUENCE: 48
gcggggccgc gggccggggg cggactgggg cgggcggaag gagagccagg ccggaaggag     60
gctgccggag ggcgggaggc aggagcgggc caggagctgc tgggctggag cggcggcgcc    120
gccatgtccg acagcgagaa gctcaacctg gactcgatca tcgggcgcct gctggaagtg    180
cagggctcgc ggcctggcaa gaatgtacag ctgacagaga acgagatccg cggtctgtgc    240
ctgaaatccc gggagatttt tctgagccag cccattcttc tggagctgga ggcacccctc    300
aagatctgcg gtgacataca cggccagtac tacgaccttt gcgactatt tgagtatggc    360 ggtttccctc ccgagagcaa ctacctcttt ctggggact atgtggacag gggcaagcag    420
tccttggaga ccatctgcct gctgctggcc tataagatca agtaccccga gaacttcttc    480
ctgctccgtg ggaaccacga gtgtgccagc atcaaccgca tctatggttt ctacgatgag    540
tgcaagagac gctacaacat caaactgtgg aaaaccttca ctgactgctt caactgcctg    600
cccatcgcgg ccatagtgga cgaaaagatc ttctgctgcc acggaggcct gtccccggac    660
ctgcagtcta tggagcagat tcggcggatc atgcggccca cagatgtgcc tgaccagggc    720
ctgctgtgtg acctgctgtg gtctgaccct gacaaggacg tgcagggctg gggcgagaac    780
gaccgtggcg tctctttac ctttggagcc gaggtggtgg ccaagttcct ccacaagcac    840
gacttggacc tcatctgccg agcacaccag gtggtagaag acggctacga gttctttgcc    900
aagcggcagc tggtgacact tttctcagct cccaactact gtggcgagtt tgacaatgct    960
ggcgccatga tgagtgtgga cgagaccctc atgtgctctt ccagatcct caagcccgcc   1020 gacaagaaca gggggaagta cgggcagttc agtggcctga ccctggagg ccgacccatc   1080 accccaccc gcaattccgc caaagccaag aaatagcccc cgcacaccac cctgtgcccc    1140
agatgatgga ttgattgtac agaaatcatg ctgccatgct ggggggggt caccccgacc    1200 cctcaggccc acctgtcacg gggaacatgg agccttggtg tatttttctt ttctttttt    1260 aatgaatcaa tagcagcgtc cagtcccccca gggctgcttc ctgcctgcac ctgcggtgac   1320
tgtgagcagg atcctggggc cgaggctgca gctcagggca acggcaggcc aggtcgtggg   1380
tctccagccg tgcttggcct cagggctggc agccggatcc tggggcaacc catctggtct   1440
```

| | |
|---|---:|
| cttgaataaa ggtcaaagct ggattctcgc aaaaaaaaaa aaaaaaaa | 1488 |

<210> SEQ ID NO 49
<211> LENGTH: 4786
<212> TYPE: DNA
<213> ORGANISM: Homo sapiens

<400> SEQUENCE: 49

| | |
|---|---:|
| gctgcgtgac gcggcggcgc gcaagggacg tgcggagtga gtggcgctgc gggtggggcc | 60 |
| gtcggcggcg ctggtgagag aacgccgagc cgtcgccgca gcctccgccg ccgagaagcc | 120 |
| cttgttcccg ctgctgggaa ggagagtctg tgccgacaag atggcggacg gggagctgaa | 180 |
| cgtggacagc ctcatcaccc ggctgctgga ggtacgagga tgtcgtccag gaaagattgt | 240 |
| gcagatgact gaagcagaag ttcgaggctt atgtatcaag tctcgggaga tctttctcag | 300 |
| ccagcctatt cttttggaat tggaagcacc gctgaaaatt tgtggagata ttcatggaca | 360 |
| atatacagat ttactgagat tatttgaata tggaggtttc ccaccagaag ccaactatct | 420 |
| tttcttagga gattatgtgg acagaggaaa gcagtctttg gaaaccattt gtttgctatt | 480 |
| ggcttataaa atcaaatatc cagagaactt cttctctta agaggaaacc atgagtgtgc | 540 |
| tagcatcaat cgcatttatg gattctatga tgaatgcaaa cgaagattta atattaaatt | 600 |
| gtggaagacc ttcactgatt gttttaactg tctgcctata gcagccattg tggatgagaa | 660 |
| gatcttctgt tgtcatggag gattgtcacc agacctgcaa tctatggagc agattcggag | 720 |
| aattatgaga cctactgatg tccctgatac aggtttgctc tgtgatttgc tatggtctga | 780 |
| tccagataag gatgtgcaag gctggggaga aaatgatcgt ggtgtttcct ttacttttgg | 840 |
| agctgatgta gtcagtaaat ttctgaatcg tcatgattta gatttgattt gtcgagctca | 900 |
| tcaggtggtg gaagatggat atgaattttt tgctaaacga cagttggtaa ccttatttc | 960 |
| agccccaaat tactgtggcg agtttgataa tgctggtgga atgatgagtg tggatgaaac | 1020 |
| tttgatgtgt tcatttcaga tattgaaacc atctgaaaag aaagctaaat accagtatgg | 1080 |
| tggactgaat tctggacgtc ctgtcactcc acctcgaaca gctaatccgc gaagaaaag | 1140 |
| gtgaagaaag gaattctgta aagaaaccat cagatttgtt aaggacatac ttcataatat | 1200 |
| ataagtgtgc actgtaaaac catccagcca tttgacaccc tttatgatgt cacacccta | 1260 |
| acttaaggag acgggtaaag gatcttaaat ttttttctaa tagaaagatg tgctacactg | 1320 |
| tattgtaata agtatactct gttatagtca acaaagttaa atccaaattc aaaattatcc | 1380 |
| attaaagtta catcttcatg tatcacaatt tttaagttg aaaagcatcc cagttaaact | 1440 |
| agatgtgata gttaaaccag atgaaagcat gatgatccat ctgtgtaatg tggttttagt | 1500 |
| gttgcttggt tgtttaatta ttttgagctt gttttgtttt tgtttgtttt cactagaata | 1560 |
| atggcaaata cttctaattt ttttccctaa acatttttaa aagtgaaata tgggaagagc | 1620 |
| tttacagaca ttcaccaact attattttcc cttgttatc tacttagata tctgtttaat | 1680 |
| cttactaaga aaactttcgc ctcattacat taaaaaggaa ttttagagat tgattgtttt | 1740 |
| aaaaaaaaat acgcacattg tccaatccag tgattttaat catacagttt gactgggcaa | 1800 |
| acttacagc tgatagtgaa tattttgctt tatacaggaa ttgacactga tttggatttg | 1860 |
| tgcactctaa tttttaactt attgatgctc tattgtgcag tagcatttca tttaagataa | 1920 |
| ggctcatata gtattaccca actagttggt aatgtgatta tgtggtacct tggctttagg | 1980 |
| ttttcattcg cacggaacac cttttggcat gcttaacttc ctggtaacac cttcacctgc | 2040 |
| attggttttc ttttctttt ttctttcttt tttttttttt tttttttttt gagttgttgt | 2100 |

```
ttgttttag atccacagta catgagaatc cttttttgac aagccttgga aagctgacac   2160 tgtctcttt  tcctccctct atacgaagga tgtatttaaa tgaatgctgg tcagtgggac   2220 atttgtcaa  ctatgggtat tgggtgctta actgtctaat attgccatgt gaatgttgta   2280
tacgattgta aggcttatgt cactaaagat ttttattctg attttttcat aatcaaaggt   2340
catatgatac tgtatagaca agctttgtag tgaagtatag tagcaataat ttctgtacct   2400
gatcaagttt attgcagcct ttcttttcct atttctttt  tttaagggtt agtattaaca   2460
aatggcaatg agtagaaaag ttaacatgaa gattttagaa ggagagaact tacaggacac   2520
agatttgtga ttctttgact gtgacactat tggatgtgat tctaaaagct tttattgagc   2580
attgtcaaat ttgtaagctt catagggatg gacatcatat ctataatgcc cttctatatg   2640
tgctaccata gatgtgacat ttttgacctt aatatcgtct ttgaaaatgt taaattgaga   2700
aacctgttaa cttacatttt atgaattggc acattgtatt acttactgca agagatattt   2760
cattttcagc acagtgcaaa agttctttaa aatgcatatg tcttttttc  taattccgtt   2820 ttgttttaaa gcacatttta aatgtagttt tctcatttag taaaagttgt ctaattgata   2880
tgaagcctga ctgatttttt ttttccttac agtgagacat ttaagcacac attttattca   2940
catagatact atgtccttga catattgaaa tgattctttt ctgaaagtat tcatgatctg   3000
catatgatgt attaggttag gtcacaaagg ttttatctga ggtgatttaa ataacttcct   3060
gattggagtg tgtaagctga gcgatttcta ataaaatttt agttgtacac ttttagtagt   3120
catagtgaag caggtctaga aaataagcct ttggcaggga aaagggcaa  tgttgattaa   3180 tctcagtatt aaaccacatt aatctgtatc ccattgtctg gcttttgtaa attcatccag   3240
gtcaagacta agtatgttgg ttaataggaa tccttttttt tttttttaaa gactaaatgt   3300
gaaaaaataa tcactactta agctaattaa tattggtcat taaatttaaa ggatggaaat   3360
ttatcatgtt taaaaattat tcaagcactc ttaaaaccac ttaaacagcc tccagtcata   3420
aaaatgtgtt ctttacaaat atttgcttgg caacacgact tgaaataaat aaaactttgt   3480
ttcttaggag aaaatgattc tgtaattcca gtgtcactaa tttatattgt tctttcctct   3540 gattttttc  aggttagtga ttttttttgta tacaatttaa tccaaatgtt atgacattca   3600
gaaatcatga aacacagtag atatctgtta taatgtggtg tatcacatgg attataaagc   3660
aaagttatgg tcgatttcta ttcttgaaag aatcaactac agtgaatcct ttgcatttga   3720
agccttaaca tgcattgctt taattttgcc cagggacaaa ttttaataat cagcaagact   3780
ggtttgtgca aagcgttgag tcatcaggta tttagagcct agccagctac ccagtatcca   3840
tgctgccata tcccttcatt gtaaaaagta cctaaacatt cgtgaaatga ttttttttag   3900
ctgaaaaatg ctggcaagaa gaattttaaa gcttaaaata ggtggtaaat ttgaagtatg   3960
agtgtgttca cgagaaacat aggcttttca aaaaaatttt tattcaaggc aaagcaagga   4020
acatcttgag atatgtctca agaatataaa gatgtattat tttaagccaa ggagctgaaa   4080
tatatctcag tttataaatt caggtatatt cttttttgtct ccatggcaac cataacttt   4140 gaaccaaaaa aaattgtttt tacatctttta tgctgaaaat gtgtttagat taggaatatg   4200
gtcgggctga atttgctgtt gctccctaac caaatccacc tcttgttttc cttgtgagtc   4260
catggctaaa tcaaagctgc ccctgagaag agacttaatc caagcctgat tgtactagtg   4320
gcatcactta gaagtaggct ttccctcttc ctagtagatc tcaatgtttt ataattcctt   4380
aaaacagctg aaaattggga caacatactt tacgcaatga acagtagtta aataggaaat   4440
```

| | | | | |
|---|---|---|---|---|
| aaactagttc | catataagta | tacacctaga | gttttaatta | cctttataat | gtttcttaaa | 4500 |
| agtgaaactt | agatacaatt | gtgattggat | acttagatac | taagtgaaac | ttagtgtaac | 4560 |
| aattttgatc | tgttaaattg | gattttacat | gtacatttga | atgccagaat | ttctaaataa | 4620 |
| atcccctggt | taggaaattt | taaaagtcaa | agcttgtttt | cttcaaccac | taccttctac | 4680 |
| attggttgac | ttagaccgta | agcttttttaa | gtttctcatt | gtaatttacc | ttctcatgca | 4740 |
| gattgctgat | gttttattaa | accttatttt | tacaaaaatg | aaaaaa | | 4786 |

<210> SEQ ID NO 50
<211> LENGTH: 2526
<212> TYPE: DNA
<213> ORGANISM: Homo sapiens

<400> SEQUENCE: 50

| | | | | | | |
|---|---|---|---|---|---|---|
| taaagaagtc | ccggccgggc | cgctgcactc | cccgcgcgca | tccgtgcgcc | gcccgaggct | 60 |
| gtctaaggag | tcggcggcca | ttttgttctt | ctcgtggttc | cagtggggag | agaaggagga | 120 |
| agtagggagc | ggggtggcag | gggggggacc | cgccgcggct | gctgccaccg | ccgccaccac | 180 |
| cgcctctgct | cgtggcgtgg | aaaggaggt | gtgagtcccg | ggcgcgagcc | ggcggcggcg | 240 |
| ccgctgcggg | agggtcggcg | gtgggaaggc | gatggcggat | ttagataaac | tcaacatcga | 300 |
| cagcattatc | caacggctgc | tggaagtgag | agggtccaag | cctggtaaga | atgtccagct | 360 |
| tcaggagaat | gaaatcagag | gactgtgctt | aaagtctcgt | gaaatctttc | tcagtcagcc | 420 |
| tatcctacta | gaacttgaag | caccactcaa | aatatgtggt | gacatccatg | gacaatacta | 480 |
| tgatttgctg | cgactttttg | agtacggtgg | tttcccacca | gaaagcaact | acctgtttct | 540 |
| tgggactat | gtggacaggg | gaaagcagtc | attggagacg | atctgcctct | tactggccta | 600 |
| caaaataaaa | tatcctgaga | attttttct | tctcagaggg | aaccatgaat | gtgccagcat | 660 |
| caacagaatt | tatggatttt | atgatgaatg | taaagaaga | tacaacatta | aactatggaa | 720 |
| aactttcaca | gactgtttta | actgtttacc | gatagcagcc | atcgtggatg | agaagatatt | 780 |
| ctgctgtcat | ggaggtttat | caccagatct | tcaatctatg | gagcagattc | ggcgaattat | 840 |
| gcgaccaact | gatgtaccag | atcaaggtct | tctttgtgat | cttttgtggt | ctgaccccga | 900 |
| taaagatgtc | ttaggctggg | gtgaaaatga | cagaggagtg | tccttcacat | tggtgcaga | 960 |
| agtggttgca | aaatttctcc | ataagcatga | tttggatctt | atatgtagag | cccatcaggt | 1020 |
| ggttgaagat | ggatatgaat | ttttttgcaaa | gaggcagttg | gtcactctgt | tttctgcgcc | 1080 |
| caattattgc | ggagagtttg | acaatgcagg | tgccatgatg | agtgtggatg | aaacactaat | 1140 |
| gtgttctttt | cagattttaa | agcctgcaga | gaaaagaag | ccaaatgcca | cgagacctgt | 1200 |
| aacgcctcca | aggggtatga | tcacaaagca | agcaaagaaa | tagatgtcgt | tttgacactg | 1260 |
| cctagtcggg | acttgtaaca | tagagtatat | aaccttcatt | tttaagactg | taatgtgtac | 1320 |
| tggtcagctt | gctcagatag | atctgtgttt | gtggggccc | ttccttccat | ttttgattta | 1380 |
| gtgaatggca | tttgctggtt | ataacagcaa | atgaaagact | cttcactcca | aaagaaaag | 1440 |
| tgttttgttt | tttaattctc | tgttcctttt | gcaaacaatt | ttaatgatgg | tgttaaagct | 1500 |
| gtacacccca | ggacagttta | tcctgtctga | ggagtaagtg | tacaattgat | ctttttttaat | 1560 |
| tcagtacaac | ccataatcat | gtaaatgctc | attttcttta | ggacataaag | agagccctag | 1620 |
| ggtgctctga | atctgtacat | gttccttgtca | taaaatgcat | actgttgata | caaaccactg | 1680 |
| tgaacatttt | ttatttgaga | attttgtttc | aaagggattg | cttttcctc | tcattgtctt | 1740 |
| gttatgtaca | aactagtttt | tatagctatc | aacattagga | gtaactttca | accttgccag | 1800 |

-continued

| | |
|---|---|
| catcactggt atgatgtata tttaattaaa gcacactttt ccccgaccgt atacttaaaa | 1860 |
| tgacaaagcc attcttttaa atatttgtga ctctttccta aagccaaagt ttctgttgaa | 1920 |
| ttatgttttg acacacccct aagtacaagg tggtatggtt gtatacacat gctgccttct | 1980 |
| tggggattca aaaacaggtt tttgattttg aatagcaatt agtgatatag tgctgtttaa | 2040 |
| gctactaacg ataaaaggta ataacatttt atacaatttc catatagtct attcattaag | 2100 |
| taatcttttt acagttgcat caggcctgaa cccgtccatt cagaaagctt caaattatag | 2160 |
| aaacaatact gttctatacg agtgaccgat tatgctttct ttggcctaca ttctttattc | 2220 |
| tgcggtgaag ttgaggctta taagttaaaa caaaggaact aacttactgt ccaccagttt | 2280 |
| atacagaact cacagtacct atgactttt taaactaaga tctgttaaaa aagaaatctg | 2340 |
| tttcaacaga tgaccgtgta caataccgtg tggtgaaaat gaattcagac ttattaaatg | 2400 |
| atgaacttgt taaatcttct cagtgtctat ttatcagcac aatacacaca ggagaactgt | 2460 |
| tgatggcata ttgaatagat tttcctgaat aaattgctct ggaaaccaca caaaaaaaaa | 2520 |
| aaaaaa | 2526 |

<210> SEQ ID NO 51
<211> LENGTH: 4477
<212> TYPE: DNA
<213> ORGANISM: Homo sapiens

<400> SEQUENCE: 51

| | |
|---|---|
| ggtgagcggc ctccgaagcg gagcggggct ctgaggagac acttttttt tcctccctcc | 60 |
| ttccctcctc tcctcctccc ttcccttccc ctctcctccc ctctctcctc cttcccccct | 120 |
| cggtccgccg gagcctgctg gggcgagcgg ttggtattgc aggcgcttgc tctccggggc | 180 |
| cgcccggcgg gtagctggcg gggggaggag gcaggaaccg cgatggcgcc tcagaagcac | 240 |
| ggcggtgggg gaggggcgg ctcgggccc agcgcgggt ccggggagg cggcttcggg | 300 |
| ggttcggcgg cggtggcggc ggcgacggct tcggcggca atccggcgg cgggagctgt | 360 |
| ggaggggtg gcagttactc ggcctcctcc tcctcctccg cggcggcagc ggcggggct | 420 |
| gcggtgttac cggtgaagaa gccgaaaatg gagcacgtcc aggctgacca cgagcttttc | 480 |
| ctccaggcct ttgagaagcc aacacagatc tatagatttc ttcgaactcg gaatctcata | 540 |
| gcaccaatat ttttgcacag aactcttact tacatgtctc atcgaaactc cagaacaaac | 600 |
| atcaaaagga aacatttaa agttgatgat atgttatcaa agtagagaa atgaaagga | 660 |
| gagcaagaat ctcatagctt gtcagctcat ttgcagctta cgttactgg ttcttccac | 720 |
| aaaaatgata agccatcacc aaactcagaa atgaacaaa attctgttac cctggaagtc | 780 |
| ctgcttgtga aagtttgcca caaaaaaga aaggatgtaa gttgtccaat aaggcaagtt | 840 |
| cccacaggta aaagcaggt gcctttgaat cctgacctca atcaaacaaa acccggaaat | 900 |
| ttcccgtccc ttgcagtttc cagtaatgaa tttgaaccta gtaacagcca tatggtgaag | 960 |
| tcttactcgt tgctatttag agtgactcgt ccaggaagaa gagagtttaa tggaatgatt | 1020 |
| aatggagaaa ccaatgaaaa tattgatgtc aatgaagagc ttccagccag aagaaaacga | 1080 |
| aatcgtgagg atgggaaaa gacatttgtt gcacaaatga cagtatttga taaaacagg | 1140 |
| cgcttacagc ttttagatgg ggaatatgaa gtagccatgc aggaaatgga agaatgtcca | 1200 |
| ataagcaaga aaagagcaac atgggagact attcttgatg ggaagaggct gcctccattc | 1260 |
| gaaacatttt ctcagggacc tacgttgcag ttcactcttc gttggacagg agagaccaat | 1320 |

```
gataaatcta cggctcctat tgccaaacct cttgccacta gaaattcaga gagtctccat    1380
caggaaaaca agcctggttc agttaaacct actcaaacta ttgctgttaa agaatcattg    1440
actacagatc tacaaacaag aaaagaaaag gatactccaa atgaaaaccg acaaaaatta   1500
agaatatttt atcagtttct ctataacaac aatacaaggc aacaaactga agcaagagat   1560
gacctgcatt gcccttggtg tactctgaac tgccgcaaac tttatagttt actcaagcat   1620
cttaaactct gccatagcag atttatcttc aactatgttt atcatccaaa aggtgctagg   1680
atagatgttt ctatcaatga gtgttatgat ggctcctatg caggaaatcc tcaggatatt   1740
catcgccaac ctggatttgc ttttagtcgc aacggaccag ttaagagaac acctatcaca   1800
catattcttg tgtgcaggcc aaaacgaaca aaagcaagca tgtctgaatt tcttgaatct   1860
gaagatgggg aagtagaaca gcaaagaaca tatagtagtg ccacaatcg tctgtatttc    1920
catagtgata cctgcttacc tctccgtcca caagaaatgg aagtagatag tgaagatgaa   1980
aaggatcctg aatggctaag agaaaaaacc attacacaaa ttgaagagtt ttctgatgtt   2040
aatgaaggag agaaagaagt gatgaaactc tggaatctcc atgtcatgaa gcatgggttt   2100
attgctgaca atcaaatgaa tcatgcctgt atgctgtttg tagaaaatta tggacagaaa   2160
ataattaaga agaatttatg tcgaaacttc atgcttcatc tagtcagcat gcatgacttt   2220
aatcttatta gcataatgtc aatagataaa gctgttacca agctccgtga aatgcagcaa   2280
aaattagaaa aggggggaatc tgcttcccct gcaaacgaag aaataactga agaacaaaat   2340
gggacagcaa atggatttag tgaaattaac tcaaagagaa aagctttgga aacagatagt   2400
gtctcagggg tttcaaaaca gagcaaaaaa caaaaactct gaaaagctct aaccccatgt   2460
tatggacaaa cactgaaatt acattttagg gaattcatcc tctaagaatt atgttttgt     2520
ttttaatcat atgttccaaa caggcactgt tagatgaagt aaatgatttc aacaaggata   2580
tttgtatcag ggttctactt cacttcatta tgcagcatta catgtatatc actttttattg  2640
atgtcattaa aacattctgt actttaagca tgaaaagcaa tatttcaaag tattttaaa    2700
ctcaacaaat gtcatcaaat atgttgaatt gatctagaaa ttatttcata tataaatcag   2760
aatttttttg catttatgaa cggctgtttt tctactttgt aattgtgaga cattttcttg   2820
gggagggaaa attggaatgg ttcccttttt tagaaattga agtggtcttc atatgtcaac   2880
tacagaaaag gaaaaaaata gaaattgaag gattttatg aaattatatt gcattactat    2940
ttgcagtcaa actttgatcc ttgtttttga aatcatttgt caattcggaa tgaaaaatta   3000
taatgtaatt ttacattaca taagttcctt ttacaattaa aaaatagcac ttcttcatct   3060
tatgcctgtt tgagaagata ttaaattttc acattgttga cagtgaaatg ctatgttggt   3120
ttataagatt acagaccatt tgttttcatg tggataattt tagtgcattg ctcacccggt   3180
atgttttttt tttttaactt gaacattttg cttgttttgt ttttcttttt taattagata   3240
atcacacgga aaattaagct gttcatatct ttaaattagg attgcaaacc aaggaaagaa   3300
cgcatttgag attttaagat gtcacttata agggggagaag tgttcttaaa aagtcaacca   3360
gaaaactgtt atgccttta tttgtttgca aggatgtctt tgtaatgtgt tcatgaata    3420
gaatatccaa tagagataag ctgacttgaa tcattttgag caattttgcc ctgtgttata   3480
tgtgtttcac gcacatattt gcagttggat tttctccaac agaaagtgga ttcactactg   3540
gcacattaac aagcaccaat aggttttat tccaactccg agcactgtgg ttgagtaaca    3600
tcacctcaat ttttttatat ccttaaagat attgcatttt catattcttt atttataaag   3660
gatcaatgct gctgtaaata caggtatttt taattttaaa atttcattcc accaccatca   3720
```

```
gatgcagttc cctatttgt ttaatgaagg gatatataag ctttctaatg gtgtcttcag    3780
aaatttataa aatgtaaata ctgatttgac tggtctttaa gatgtgttta actgtgaggc    3840
tatttaacga atagtgtgga tgtgatttgt catccagtat taagttctta gtcattgatt    3900
tttgtgttta aaaaaaaata ggaagagggg aaactgcagc tttcattaca gattccttga    3960
ttggtaagct ctccaaatga tgagttctag taaactctga tttttgcctc tggatagtag    4020
atctcgagcg tttatctcgg gctttaattt gctaaagctg tgcacatatg taaaaaaaaa    4080
aaaaaaaaga ttattttagg ggagatgtag gtgtagaatt attgcttatg tcatttctta    4140
agcagttatg ctcttaatgc ttaaaagaag gctagcattg tttgcacaaa aagttggtga    4200
ttcccacccc aaatagtaat aaaattactt ctgttgagta aacttttat gtcatcgtaa    4260 aagctgaaaa aatccctttg tttctattta taaaaaagt gcttttctat atgtaccctt    4320
gataacagat tttgaagaaa tcctgtaaga tgataaagca tttgaatggt acagtagatg    4380
taaaaaaaat tcagtttaaa agaacatttg tttttacatt aaatgtttat ttgaaatcaa    4440
atgattttgt acataaagtt caataatata aaagctg                            4477
```

<210> SEQ ID NO 52
<211> LENGTH: 2460
<212> TYPE: DNA
<213> ORGANISM: Homo sapiens

<400> SEQUENCE: 52

```
cgctttgaaa tccaccctgg gattcggaaa ccgggtagaa aactacctgg ttcagcaaac      60
gagaattcaa acagaggagg ggcttggagg aggcgggttt cgacgaaccc agcgcaagag     120
tacgccacgg cgcctgcgca tccctgacg ggtactttcc attcgccaga tgggggaagc     180 caggggaag caggttactg tttttgcatt tctatcttca aggaagaatt aggttatgaa     240
tagttccgtg aatagtcagg aagcgctgtc ctccaagttc aagattaagg aaacgtggca     300
tgcacagcta aagcaagagg tgacgtcttg tatcttcccc cgtttcctgg acattggtg     360 gtgtagccca ttccacagac tttcgctccc tagcagcggg tcggagatcg aaggaacggg     420
ccaattgcgg ctgaaacgtc tttggaagga ggaaggggggt gagggagcat ccctttgagt     480
ttcgcctctt ctcgaggcgg tggtgggaag ggagacatac ttaatactgc cctcttaatc     540
caacggacct tacatcgtgt agactgccgg gagggcggcg ggaaaagggc aagacgggag     600
ttggggaagg gaaggagcca ggaagccgcg cgggagggcg cgcgcgcgcg ccccttttc     660 agcagtgtgg cggggtcgca cgcacgcccg cctcggcggc tgggcgcgat ttgcgacagt     720 gggggggcg gtggaggtgg cggcggcagc ggcaactttg cggcaagctc gggccgggct     780
tgcttgacgg cggtgtggcg gaggccccgc cccaggcggc aggaacctgg agggaggcgg     840
aggaatatgt ccgagaggga agtgtcgact gcgccggcgg gaacagacat gcctgcggcc     900
aagaagcaga agctgagcag tgacgagaac agcaatccag acctctctgg agacgagaat     960
gatgacgctg tcagtataga aagtggtaca aacactgaac gccctgatac acctacaaac    1020
acgccaaatg cacctggaag gaaagttgg ggaaagggaa aatggaagtc aaagaaatgc    1080
aaatattctt tcaaatgtgt aaatagtctc aaggaagatc ataaccaacc attgtttgga    1140
gttcagttta actggcacag taaagaagga gatccattag tgtttgcaac tgtaggaagc    1200
aacagagtta ccttgtatga atgtcattca caaggagaaa tccggttgtt gcaatcttac    1260
gtggatgctg atgctgatga aaactttttac acttgtgcat ggacctatga tagcaatacg    1320
```

| | | | | |
|---|---|---|---|---|
| agccatcctc | tgctggctgt | agctggatct | agaggcataa | ttaggataat | aaatcctata | 1380 |
| acaatgcagt | gtataaagca | ctatgttggc | catggaaatg | ctatcaatga | gctgaaattc | 1440 |
| catccaagag | atccaaatct | tctcctgtca | gtaagtaaag | atcatgcttt | acgattatgg | 1500 |
| aatatccaga | cggacactct | ggtggcaata | tttggaggcg | tagaagggca | cagagatgaa | 1560 |
| gttctaagtg | ctgattatga | tcttttgggt | gaaaaaataa | tgtcctgtgg | tatggatcat | 1620 |
| tctcttaaac | tttggaggat | caattcaaag | agaatgatga | atgcaattaa | ggaatcttat | 1680 |
| gattataatc | caaataaaac | taacaggcca | tttatttctc | agaaaatcca | ttttcctgat | 1740 |
| ttttctacca | gagacataca | taggaattat | gttgattgtg | tgcgatggtt | aggcgatttg | 1800 |
| atactttcta | gtcttgtga | aaatgccatt | gtgtgctgga | acctggcaa | gatggaagat | 1860 |
| gatatagata | aaattaaacc | cagtgaatct | aatgtgacta | ttcttgggcg | atttgattac | 1920 |
| agccagtgtg | acatttggta | catgaggttt | tctatggatt | tctggcaaaa | gatgcttgca | 1980 |
| ttgggcaatc | aagttggcaa | actttatgtt | tgggatttag | aagtagaaga | tcctcataaa | 2040 |
| gccaaatgta | caacactgac | tcatcataaa | tgtggtgctg | ctattcgaca | aaccagtttt | 2100 |
| agcagggata | gcagcattct | tatagctgtt | tgtgatgatg | ccagtatttg | gcgctgggat | 2160 |
| cgacttcgat | aaaatacttt | tgcctaatca | aaattagagt | gtgtttgttg | tctgtgtaaa | 2220 |
| atagaattaa | tgtatcttgc | tagtaagggc | acgtagagca | tttagagttg | tctttcagca | 2280 |
| ttcaatcagg | ctgagctgaa | tgtagtgatg | tttacattgt | ttacattctt | tgtactgtct | 2340 |
| tcctgctcag | actctactgc | ttttaataaa | aatttatttt | tgtaaagctg | tgtgtttagt | 2400 |
| tactttcatt | gtggtgaaaa | aaagttaaaa | gtaataaaat | tatgccttat | cttttaaaa | 2460 |

<210> SEQ ID NO 53
<211> LENGTH: 4654
<212> TYPE: DNA
<213> ORGANISM: Homo sapiens

<400> SEQUENCE: 53

| | | | | |
|---|---|---|---|---|
| gcgcatgcgt | cctagcagcg | ggacccgcgg | ctcgggatgg | aggctggaca | cctgttctgc | 60 |
| tgttgtgtcc | tgccattctc | ctgaagaaca | gaggcacact | gtaaaaccca | acacttcccc | 120 |
| ttgcattcta | taagattaca | gcaagatgga | aataccaaat | cccccctacct | ccaaatgtat | 180 |
| cacttactgg | aaaagaaaag | tgaaatctga | atacatgcga | cttcgacaac | ttaaacggct | 240 |
| tcaggcaaat | atgggtgcaa | aggctttgta | tgtggcaaat | tttgcaaagg | ttcaagaaaa | 300 |
| aacccagatc | tcaatgaag | aatggaagaa | gcttcgtgtc | caacctgttc | agtcaatgaa | 360 |
| gcctgtgagt | ggacaccctt | ttctcaaaaa | gtgtaccata | gagagcattt | tcccgggatt | 420 |
| tgcaagccaa | catatgttaa | tgaggtcact | gaacacagtt | gcattggttc | ccatcatgta | 480 |
| ttcctggtcc | cctctccaac | agaactttat | ggtagaagat | gagacggttt | tgtgcaatat | 540 |
| tccctacatg | ggagatgaag | tgaaagaaga | agatgagact | tttattgagg | agctgatcaa | 600 |
| taactatgat | gggaaagtcc | atggtgaaga | agagatgatc | cctggatccg | ttctgattag | 660 |
| tgatgctgtt | tttctggagt | tggtcgatgc | cctgaatcag | tactcagatg | aggaggagga | 720 |
| agggcacaat | gacacctcag | atggaaagca | ggatgacagc | aaagaagatc | tgccagtaac | 780 |
| aagaaagaga | aagcgacatg | ctattgaagg | caacaaaaag | agttccaaga | acagttccc | 840 |
| aaatgacatg | atcttcagtg | caattgcctc | aatgttccct | gagaatggtg | tcccagatga | 900 |
| catgaaggag | aggtatcgag | aactaacaga | gatgtcagac | cccaatgcac | ttccccctca | 960 |
| gtgcacaccc | aacatcgatg | gccccaatgc | caagtctgtg | cagcgggagc | aatctctgca | 1020 |

```
ctccttccac acacttttt gccggcgctg cttaaatac gactgcttcc ttcacccttt    1080
tcatgccacc cctaatgtat ataaacgcaa gaataaagaa atcaagattg aaccagaacc    1140
atgtggcaca gactgcttcc tttgctgga aggagcaaag gagtatgcca tgctccacaa    1200
cccccgctcc aagtgctctg gtcgtcgccg gagaaggcac cacatagtca gtgcttcctg    1260
ctccaatgcc tcagcctctg ctgtggctga gactaaagaa ggagacagtg acagggacac    1320
aggcaatgac tgggcctcca gttcttcaga ggctaactct cgctgtcaga ctcccacaaa    1380
acagaaggct agtccagccc cacctcaact ctgcgtagtg gaagcaccct cggagcctgt    1440
ggaatggact ggggctgaag aatctctttt tcgagtcttc catggcacct acttcaacaa    1500
cttctgttca atagccaggc ttctggggac caagacgtgc aagcaggtct ttcagtttgc    1560
agtcaaagaa tcacttatcc tgaagctgcc aacagatgag ctcatgaacc cctcacagaa    1620
gaagaaaaga aagcacagat tgtgggctgc acactgcagg aagattcagc tgaagaaaga    1680
taactcttcc acacaagtgt acaactacca accctgcgac cacccagacc gcccctgtga    1740
cagcacctgc ccctgcatca tgactcagaa tttctgtgag aagttctgcc agtgcaaccc    1800
agactgtcag aatcgtttcc ctggctgtcg ctgtaagacc cagtgcaata ccaagcaatg    1860
tccttgctat ctggcagtgc gagaatgtga ccctgacctg tgtctcacct gtgggcctc    1920
agagcactgg gactgcaagg tggtttcctg taaaaactgc agcatccagc gtggacttaa    1980
gaagcacctg ctgctggccc cctctgatgt ggccggatgg ggcaccttca taaaggagtc    2040
tgtgcagaag aacgaattca tttctgaata ctgtggtgag ctcatctctc aggatgaggc    2100
tgatcgacgc ggaaaggtct atgacaaata catgtccagc ttcctcttca acctcaataa    2160
tgattttgta gtggatgcta ctcggaaagg aaacaaaatt cgatttgcaa atcattcagt    2220
gaatcccaac tgttatgcca aagtggtcat ggtgaatgga gaccatcgga ttgggatctt    2280
tgccaagagg gcaattcaag ctggcgaaga gctcttcttt gattacaggt acagccaagc    2340
tgatgctctc aagtacgtgg ggatcgagag ggagaccgac gtcctttagc cctcccaggc    2400
cccacggcag cacttatggt agcggcactg tcttggcttt cgtgctcaca ccactgctgc    2460
tcgagtctcc tgcactgtgt ctcccacact gagaaacccc caacccact ccctctgtag    2520
tgaggcctct gccatgtcca gagggcacaa aactgtctca atgagagggg agacagaggc    2580
agctagggct tggtctccca ggacagagag ttacagaaat gggagactgt ttctctggcc    2640
tcagaagaag cgagcacagg ctggggtgga tgacttatgc gtgatttcgt gtcggctccc    2700
caggctgtgg cctcaggaat caacttaggc agttcccaac aagcgctagc ctgtaattgt    2760
agctttccac atcaagagtc cttatgttat tgggatgcag gcaaacctct gtggtcctaa    2820
gacctggaga ggacaggcta agtgaagtgt ggtccctgga gcctacaagt ggtctgggtt    2880
agaggcgagc ctggcaggca gcacagactg aactcagagg tagacaggtc accttactac    2940
ctcctccctc gtggcagggc tcaaactgaa agagtgtggg ttctaagtac aggcattcaa    3000
ggctggggga aggaaagcta cgccatcctt ccttagccag agagggagaa ccagccagat    3060
gatagtagtt aaactgctaa gcttgggccc aggaggcttt gagaaagcct tctctgtgta    3120
ctctggagat agatggagaa gtgttttcag attcctggga acagacacca gtgctccagc    3180
tcctccaaag ttctggctta gcagctgcag gcaagcatta tgctgctatt gaagaagcat    3240
tagggggtatg cctggcaggt gtgagcatcc tggctcgctg gatttgtggg tgttttcagg    3300
ccttccattc cccatagagg caaggcccaa tggccagtgt tgcttatcgc ttcagggtag    3360
```

| | | |
|---|---|---|
| gtgggcacag gcttggacta gagaggagaa agattggtgt aatctgcttt cctgtctgta | 3420 | |
| gtgcctgctg tttggaaagg gtgagttaga atatgttcca aggttggtga ggggctaaat | 3480 | |
| tgcacgcgtt taggctggca ccccgtgtgc agggcacact ggcagagggt atctgaagtg | 3540 | |
| ggagaagaag caggtagacc acctgtccca ggctgtggtg ccaccctctc tggcattcat | 3600 | |
| gcagagcaaa gcactttaac catttctttt aaaaggtcta tagattgggg tagagtttgg | 3660 | |
| cctaaggtct ctagggtccc tgcctaaatc ccactcctga gggaggggga agaagagagg | 3720 | |
| gtgggagatt ctcctccagt cctgtctcat ctcctgggag aggcagacga gtgagtttca | 3780 | |
| cacagaagaa tttcatgtga atggggccag caagagctgc cctgtgtcca tggtgggtgt | 3840 | |
| gccgggctgg ctgggaacaa ggagcagtat gttgagtaga aagggtgtgg gcgggtatag | 3900 | |
| attggcctgg gagtgttaca gtagggagca ggcttctccc ttctttctgg gactcagagc | 3960 | |
| cccgcttctt cccactccac ttgttgtccc atgaaggaag aagtggggtt cctcctgacc | 4020 | |
| cagctgcctc ttacggtttg gtatgggaca tgcacacaca ctcacatgct ctcactcacc | 4080 | |
| acactggagg gcacacacgt accccgcacc cagcaactcc tgacagaaag ctcctcccac | 4140 | |
| ccaaatgggc caggcccag catgatcctg aaatctgcat ccgccgtggt ttgtattcat | 4200 | |
| tgtgcatatc agggataccc tcaagctgga ctgtgggttc caaattactc atagaggaga | 4260 | |
| aaaccagaga aagatgaaga ggaggagtta ggtctatttg aaatgccagg ggctcgctgt | 4320 | |
| gaggaatagg tgaaaaaaaa cttttcacca gcctttgaga gactagactg accccaccct | 4380 | |
| tccttcagtg agcagaatca ctgtggtcag tctcctgtcc cagcttcagt tcatgaatac | 4440 | |
| tcctgttcct ccagtttccc atcctttgtc cctgctgtcc cccactttta aagatgggtc | 4500 | |
| tcaacccctc cccaccacgt catgatggat ggggcaaggt ggtggggact aggggagcct | 4560 | |
| ggtatacatg cggcttcatt gccaataaat ttcatgcact ttaaagtcct gtggcttgtg | 4620 | |
| acctcttaat aaagtgttag aatccaaaaa aaaa | 4654 | |

<210> SEQ ID NO 54
<211> LENGTH: 7943
<212> TYPE: DNA
<213> ORGANISM: Homo sapiens

<400> SEQUENCE: 54

| | | |
|---|---|---|
| gctcccattg gctgatgttg gcgcgaaggt gcgcgagtca gccctcgcgc tgggggcgca | 60 | |
| ggaaacaata gaggccgcgc gcacagagcg agctcttgca gcctccccgc ccctcccgca | 120 | |
| acgctcgacc ccaggattcc cccggctcgc ctgcccgcca tggccgacaa ggaagcagcc | 180 | |
| ttcgacgacg cagtggaaga acgagtgatc aacgaggaat acaaaatatg gaaaagaac | 240 | |
| acccctttttc tttatgattt ggtgatgacc catgctctgg agtggcccag cctaactgcc | 300 | |
| cagtggcttc cagatgtaac cagaccagaa gggaaagatt tcagcattca tcgacttgtc | 360 | |
| ctggggacac acacatcgga tgaacaaaac catcttgtta tagccagtgt gcagctccct | 420 | |
| aatgatgatg ctcagtttga tgcgtcacac tacgacagtg agaaggagaa atttggaggt | 480 | |
| tttggttcag ttagtggaaa aattgaaata gaaatcaaga tcaaccatga aggagaagta | 540 | |
| aacagggccc gttatatgcc ccagaaccct tgtatcatcg caacaaagac tccttccagt | 600 | |
| gatgttcttg tttttgacta tacaaaacat ccttctaaac cagatccttc tggagagtgc | 660 | |
| aacccagact tgcgtctccg tggacatcag aaggaaggct atgggctttc ttggaaccca | 720 | |
| aatctcagtg ggcacttact tagtgcttca gatgaccata ccatctgcct gtgggacatc | 780 | |
| agtgccgttc caaaggaggg aaaagtggta gatgcgaaga ccatctttac agggcatacg | 840 | |

-continued

```
gcagtagtag aagatgtttc ctggcatcta ctccatgagt ctctgtttgg gtcagttgct      900
gatgatcaga aacttatgat ttgggatact cgttcaaaca atacttccaa accaagccac      960
tcagttgatg ctcacactgc tgaagtgaac tgcctttctt tcaatcctta tagtgagttc     1020
attcttgcca caggatcagc tgacaagact gttgccttgt gggatctgag aaatctgaaa     1080
cttaagttgc attcctttga gtcacataag gatgaaatat tccaggttca gtggtcacct     1140
cacaatgaga ctattttagc ttccagtggt actgatcgca gactgaatgt ctgggattta     1200
agtaaaattg gagaggaaca atccccagaa gatgcagaag acgggccacc agagttgttg     1260
tttattcatg gtggtcatac tgccaagata tctgatttct cctggaatcc caatgaacct     1320
tgggtgattt gttctgtatc agaagacaat atcatgcaag tgtggcaaat ggcagagaac     1380
atttataatg atgaagaccc tgaaggaagc gtggatccag aaggacaagg gtcctagata     1440
tgtctttact tgttgtgatt ttagactccc ctttttttctt ctcaaccctg agagtgattt     1500
aacactggtt ttgagacaga ctttattcag ctatccctct atataatagg taccaccgat     1560
aatgctatta gcccaaaccg tgggtgtttt ctaaatatta atagggggc ttgattcaac      1620 aaagccacag acttaacgtt gaaattttct tcaggaattt tctagtaacc caggtctaaa     1680
gtagctacag aaaggggaat attatgtgtg attattttttc ttcttatgct atatccccaa    1740 gttttttcaga ctcatttaag taaaggctag agtgagtaag gaatagagcc aaatgaggta    1800
ggtgtctgag ccatgaagta taaatactga aagatgtcac ttttattcag gaaataggg     1860 gagattcaag tcatatagat tcctactcga aaatcttgac acctgacttt ccaggatgca    1920
cattttcata cgtagaccag tttcctcttg gtttcttcag ttaagtcaaa acaacacgtt    1980
cctctttccc catatattca tatattttg ctcgttagtg tatttcttga gctgttttca     2040
tgttgtttat ttcctgtctg tgaaatggtg tttttttttt tgttgttggt tttttttttt    2100
ttttttttaa cttgggacca ccaagttgta aagatgtatg ttttttacctg acagttatac    2160 cacaggtaga ctgtcaagtt gagaagagtg aatcaataac ttgtatttgt tttaaaaatt    2220
aaattaatcc ttgataagag ttgcttttttt ttttttaggag ttagtccttg accactagtt   2280
tgatgccatc tccatttttgg gtgacctgtt tcaccagcag gcctgttact ctccatgact   2340
aactgtgtaa gtgcttaaaa tggaataaat tgcttttcta cataacccca tgctgatggg    2400
ttttatttag tataaaacat ccatcaaaca ccagtctctg gcttctagaa gagtccttca    2460
gatgacagtt gttgtccatg gtctttgact atcaagagca gaattaaatg taatagtccc    2520
agagctgtag aaaagaactt tactccttcc cagggaaagt gaaagacata aaacactgaa    2580
tcagaggtgg cacagattag tctttgataa ggtaacgttt ctttgaagtc tatctgtaga    2640
gaactacatg gacttccaag agtgtcaaag gcagtgtggt agagagaatt taaggcaaga    2700
tttaaatttg gaaaaggtgc ttgaaccttt tctcagaggt tttatttccc cagtatgttt     2760
ttcactgggg cctttactta ggttagaaat aataggcttt gaaggcctct atcaccagat    2820
gcaataacca gataaaattc ctgtttttttc ccaatcgctt agttttttgt tgttgttgtt    2880
ttttaactga gtagatcatt ctgacccaga actactttca tgaggtaaga tctttgggaa    2940
aatctgaata gcgttaacca ttagattcaa atctcaaatg gtttcttttc aagtctagtt    3000
gttttagagt atagtgagaa ataccttgac acaatttttaa gagtaaacta tatgggtcag    3060
catatccttg aacaaaaagt agactttgta aaagtattca tttaaattct aacactcgtg    3120
gcacaaaaga atgaaaattg taaacccatg taatggaaat tggctatctt tttgaccccca   3180
```

```
catgtgcccc tcaaaaatgt ttttggtttg ggtcaacaca aggcaagata cattctttaa    3240
aatactccca gatgtgtcca tacattcatc cttcactcag tgcatatgtg agggttgttg    3300
ctggaagaca ggaggctcat cttcctttc cttggtgcat tgagatcagt atcaacagca    3360
gatgaaatag aatccagcaa agagttgaca tgttctgcct ccggccaact ctagaatctt    3420
tttaagcagg tcagccagta tttgcaactt ccacaggatg aattgcttgc caagtttctg    3480
gcactcttgt ctggttggaa gagtacatcc aaagggtact tagtgatcct ttgctaagaa    3540
gttttttgct gtttccgggt tacagatttg gccatatatt tctaaacagc ccctgtaaag    3600
ttgaaagaaa aagtttataa cagtgaactt ctgaggttta gttactgcag ctttgttga    3660
gaagagattg ttacagtgtg atttatggat gatcagggat gactttcccc tagcaaatat    3720
ttggatgcct cctgtttgtc aaatagaatg aatggtgatg gtgatgggag ggatagttaa    3780
acgttttctc tgctaggtta acttcttaca ggtataatta caatgcctga aattctgtag    3840
tttcatttct ttggattagt cgttgtcttt tccagattgt acacaatctg atcaacacaa    3900
aggtagttag tagatcatta acctcaattg caaggttata atttctcaaa cattaagcat    3960
attatcagtc atgtggattc aaacacagta taagaaaatc ctcaaggctg ggtgtgatgg    4020
cttatgcctg taatcccagc tacttagcag gctgaggcag gagtattgtt tgaacccagg    4080
aggcagagtt gcagtgagcc aagatcgtgc cactactcca gcctgggcaa atagcaaga    4140
cccgaccccc catctctact aaaaagaaat ttaaaaaaat aaaatcctag aaattagaa    4200
aaagcaacaa tagttacttg tgggccaggc gcggtggttc acgcctgtaa tcccagcact    4260
ttgagaggct gaggcacgtg gatcacaagg tcaggagttc aagaccagcc tggccaagat    4320
ggtgaaaccc cgtttctact aaaaatacaa aaactagctg gccgtggtgg catgctcctg    4380
tagtcccagc tactcaggag gctgaggcag gaaaatcact tgaacccagg aggtggaggt    4440
tgcagtgaac tgagaccgtg ccactgcact ccagcctggg tggcagagcg agactgtctc    4500
aaaaaaaaaa gaaagttgtg aatttgatgt aagcttagga aatgaataaa atttataggc    4560
atctgtataa tgtacaactt gacacggact ttctttatc cttagtttct ttcacggact    4620
ctagaacttt tatcagaata tactggtaaa acattggggg agggatcctg agtaggtgat    4680
tggtcagaaa gatgccttca gttttgtcag tgtctaaaag ttaagtctgt ttaggccaag    4740
catggtggct cacacctgaa atcccagcac tctgggaggc cgaggcaagt ggatcacaag    4800
gtcaggagat gagaccatct tagccaacat ggtgaaaccc cgtctctact aaaatacaaa    4860
aaaattagcc aggcgtggtg gtgcgtgcct ataatcccag ctacttggga ggctgaggca    4920
ggggaatcgc ttgaacccgg gaggcagagg tcacgccact gcactccagc ctggcaacag    4980
agcaagactc cgtctcaaaa aaaaaaaaa aaaaaagag taagtctgtg taacatgaac    5040
atctctgctt ccacccaaaa ccacagcctt tgaatattat ataaggaact taatggatag    5100
atatgtttat tatttttgat agcacaactg ctttctctgc tattataagg aaactgaga    5160
atagcaggtg ggtagggtag gatgaggaaa caagatgccc aaagcctaga tgccacagaa    5220
ttcatggtga taatcagggc atattttgag tcctactaga acaaacatt ccaaatgaac    5280
tctgaatgcc tgactcaggc gttttggagg tttgggttat ccccttgtca ttaggcacac    5340
aagggttttt tgttgttttt gttttttggg tttttgtttt gttttgaggc agtctcactc    5400
tgttgtacaa gctggagtgc tgtattgtga tcttgactca ctgcaacctc tgcctcctgg    5460
ttcaagcgat tctcctgcct tggcctcctg agtagctggg attataagtg cctgccacta    5520
tgcccggcta atttttgtat tttagtggag atggagtttt tgccatgttg gccaggctgg    5580
```

```
tcttgaactc ctgactccag gtgatccacc ctcctcagcc tcccaaagtg ctaggattac    5640
aggcgtgagc cacccgtcc ggcctgtttt taaggcatta attagtattg ttaggaaagc    5700
agtaacaatg caaacaccac tcttctcttc acaaagatca ccttgagact gtgtctccat    5760
tccacctgcc tgagaagtgg gagcatcagc ctgttccagg ctcttgggta gtagcatagc    5820
cctttaaaaa gagagagcca ttttccatgt gttttggat aagcacaatt tgaaaatcat    5880
ttcccaaatc ctcttttgt ttttgattct aaggtaaaat tttccctaag ccctcccacc    5940
atcccctcag ccagtattag atgagatttg tatagcagca gaaactgact tataagtaga    6000
gagctcttca gcaagactga gccttagctg ttccatctct ttgttcttct gttgctggag    6060
ttgcacccca tttcttaact gcctctggcg ttcttccatt tcctccagct gttcctgcat    6120
gagatggcca agaacatttc taatgagcca aacaataaaa actcacattg tccactctta    6180
cttataaaac acttttttgt tcattgttta atcttgatag cagtattgag gctggtattt    6240
atatgatagg ttatgaaaca ggttcaaaga agttgtgtct tggaaaaaaa gtgacaatgc    6300
ttttgaaaat gatgacgaaa aaggcatctt gtctgttaac cacagcttgc tttaatagaa    6360
tcctgggagg gtgattggga cttttttagta ttacaacctt agtgtcattg aggaggattt    6420
tggtctagtt agtgggctga gtttcatata cctctccctc catgtgcagg tttgttaaga    6480
taattggtag ttttttaataa tataaaatac ttaagttgaa atacaaaagt gtggcaacaa    6540
ttattaaata ttggctagaa ttctaggaga gttacacaac tagtggaagt ccatgtttag    6600
aaaataaatg gcttgtttaa ggaaaagttt ttgtgtccaa agctccttaa agtcagagag    6660
atttctacct ggtacttaac atcatatgga aattgatgct ttagtgaggg tgttggctat    6720
cctattgcta atttcctgca tcctttttc ttctttattt ttgtatagag acagggtctc    6780
gctatgttgc ccaggctggt cttgttcctg ggctcaagca gtcctcccgc ctcggtctcc    6840
caaagtgctg ggattacagg tgtgagccac tgtgcccagc ttatccttt ttcattacac    6900 aaaaagactg aatttggtta gttctaagtt ggaagataaa gatggtatgc acaggaggcc    6960
cttgggagcc ctcagataac tttctcattc ttccagaatc aggctgggat gcattctgta    7020
aattttccct gcctaggatg tatacctgag gaataaggta aggaagatgt cagcaagtca    7080
gtctctggtt tacctgctag ctggcatgga tccttaagga agcaggaggg agttgggaag    7140
agaggaaggg gtgaagttgg tatcttttaa agcgagagtg attttacctc agattttgaa    7200
gaatactaag gaatccagtt gttggggtac atgctattat tagaaggatc tagataattt    7260
gtcctctgag tcatacttga cattgtacct gtggcacatc aatccgcact gtttgatact    7320
ctggctgaat ctcagctttc accaacattg tcaaggacc ttttttagtg cccagccatg    7380
cctaagagtg tgtcatctga agagggaagc atctgcatac tgctgtcctg attgctcagt    7440
cctcactacc taccagaccc gttggtaagg tacaaaagta catgcttgga aaagcagtct    7500
gcaccaccag tgataagctg tgacagagtg aacagcctc aatgaaatga aggaaggatt    7560
gctacagtgg cattaaggat ggtctcttaa tcctgtgtta accactagat taactttaca    7620
atcaactcaa aatccttcaa aggctttcca ctttctttag tggcattcag acccctcta    7680 gtttgacccc tacctccaac ttgaacctct gttactcttc cgtatgaaca ttttcctcta    7740
gccctggact actagtaccg aagtcactag tcacatagga ctcatttgaa atatgactag    7800
tctcaattga gatgtaatgt aagtgtaaaa tacacagcag atttctaaga cagcacacaa    7860
aatgtaaaat atgtcaaaaa tatttgatac tgattacatg ttgaaatata tgtgttgggt    7920
```
taaataaaat gcattaaagt taa                                         7943

<210> SEQ ID NO 55
<211> LENGTH: 6112
<212> TYPE: DNA
<213> ORGANISM: Homo sapiens

<400> SEQUENCE: 55

```
tggatagcct ctctctcatt ggttagggg cttggaaaaa agagactcgg cgagccctcg    60
ctgtggtgct gccgccgccg ccgccgccgc cgctggagtt gactcttctg ctcgcactgc   120
tgctgcagca caaacgtgac ttccaacatt ttttatttat cttcccttt tcttttccaa    180
gatgtaacta cggatcagac actaaggacc ttcacgtttc gctgatgtag ttttggagg    240
aaaaaggggg gggagtgaag ggcgtcggtt ttttttgtg tgtgtgtgta tgtgtttcgg    300
gggaaatttt ccattatgag tgttttacta aagtgaattt tttttgttt gcttcgttcg    360
tctttggctc ttttttttc cttcccaatt tcggatttat ttcaaggcga atctggcttt    420
ggggaagag gaagaaaagt cggattacaa gatcaaccac caccaacaac aataaaaacc    480
accaggatat ttttttgcaa atttctgacg gctttaaatt catgaagcaa ttgtcccctt    540
ttgcaatcag catttggatc tcagaatgag caaggaaaga cccaagagga atatcattca    600
gaagaaatac gatgacagtg atgggattcc gtggtcagaa gaacgggtgg tacgtaaagt    660
cctttatttg tctctgaagg agttcaagaa ttcccagaag aggcagcatg cggaaggcat    720
tgctgggagc ctgaaaactg tgaatgggct ccttggtaat gaccagtcta agggattagg    780
accagcatca gaacagtcag agaatgaaaa ggacgatgca tcccaagtgt cctccactag    840
caacgatgtt agttcttcag attttgaaga agggccgtcg aggaaaaggc ccaggctgca    900
agcacaaagg aagtttgctc agtctcagcc gaatagtccc agcacaactc cagtaaagat    960
agtggagcca ttgctacccc ctccagctac tcagatatca gacctctcta aaaggaagcc   1020
taagacagaa gatttctta cctttctctg ccttcgaggt tctcctgcgc tgcccaacag   1080
catggtgtat tttggaagct ctcaggatga ggaggaagtc gaggaggaag atgatgagac   1140
agaagacgtc aaaacagcca ccaacaatgc ttcatcttca tgccagtcga cccccaggaa   1200
aggaaaaacc cacaaacatg ttcacaacgg gcatgttttc aatggttcca gcaggtcaac   1260
acgggagaag gaacctgttc aaaaacacaa aagcaaagag gccactcccg caaaggagaa   1320
gcacagcgat caccgggctg acagccgccg ggagcaggct tcagctaacc accccgcagc   1380
ggccccctcc acgggttcct cggccaaggg gcttgctgcc acccatcacc accccctct   1440
gcatcggtcg gctcaggact tacggaaaca ggtttctaag gtaaacggag tcactcgaat   1500
gtcatctctg ggtgcaggtg taaccagtgc caaaaagatg cgcgaggtca gaccttcacc   1560
atccaaaact gtgaagtaca ctgccacggt gacgaagggg gctgtcacat acaccaaagc   1620
caagagagaa ctggtcaagg acaccaaacc caatcaccac aagcccagtt ccgctgtcaa   1680
ccacacaatc tcaggaaaaa ctgaaagtag caatgcaaaa acccgcaaac aggtgctatc   1740
cctcgggggg gcgtccaagt ccactgggcc cgccgtcaat ggcctcaagg tcagtggcag   1800
gttgaaccca aagtcatgca ctaaggaggt gggggggcgg cagctgcggg agggcctgca   1860
gctgcgggag gggctgcgga actccaagag gagactggaa gaggcacacc aggcggagaa   1920
gccgcagtcg ccccccaaga agatgaaagg ggcggctgc cccgccgaag gcctggcaa    1980
gaaggccccg gccgagagag gtctgctgaa cggacacgtg aagaaggaag tgccggagcg   2040
cagtctggag aggaatcggc cgaagcgggc cacggccggg aagagcacgc caggcagaca   2100
```

```
agcacatggc aaggcggaca gcgcctcctg tgaaaatcgt tctacctcgc aaccggagtc    2160
cgtgcacaag ccgcaggact cgggcaaggc cgagaagggc ggcggcaagg ccgggtgggc    2220
ggccatggac gagatccccg tcctcaggcc ctccgccaag gagttccacg atccgctcat    2280
ctacatcgag tcggtccgcg ctcaggtgga aagttcggg atgtgcaggg tgatcccccc     2340
tccggactgg cggcccgagt gcaagctcaa cgatgagatg cggtttgtca cgcagattca    2400
gcacatccac aagctgggcc ggcgctgggc ccccaacgtg cagcggctgg cctgcatcaa    2460
gaagcacctc aaatctcagg gcatcaccat ggacgagctc ccgctcatag ggggctgtga    2520
gctcgacctg gcctgctttt tccggctgat taatgagatg ggcggcatgc agcaagtgac    2580
tgacctcaaa aaatggaaca aactagcaga catgctgcgc atccccagaa ctgcccagga    2640
ccggctggcc aagctgcagg aggcctactg ccagtaccta ctctcctacg actccctgtc    2700
cccagaggag caccggcggc tggagaagga ggtgctgatg agaaggaga tcctggagaa     2760 gcgcaagggg ccgctggaag ccacacaga gaacgaccac cacaagttcc accctctgcc     2820
ccgcttcgag cccaagaatg ggctcatcca cggcgtggcc cccaggaacg gcttccgcag    2880
caagctcaag gaggtgggcc aggcccagtt gaagactggc cggcggcgac tcttcgctca    2940
ggaaaaagaa gtggtcaagg aagaggagga ggacaaaggc gtcctcaatg acttccacaa    3000
gtgcatctat aagggaaggt ctgtttctct aacaactttt tatcgaacag cgaggaatat    3060
catgagcatg tgtttcagca aggagcctgc cccagccgaa atcgagcaag agtactggag    3120
gctagtggaa gagaaggact gccacgtggc agtgcactgc ggcaaggtgg acaccaacac    3180
tcacggcagt ggattcccag taggaaaatc agaaccctt tcgaggcatg gatggaacct     3240
caccgtcctc cccaataaca cagggtccat cctgcgtcac ctcggtgctg tgcctggagt    3300
gactattccc tggctaaata ttggcatggt cttttctacc tcatgctggt ctcgagacca    3360
aaatcacctt ccatacattg actacttaca cactggtgct gactgcattt ggtattgcat    3420
tcctgctgag gaggagaaca agctggaaga tgtggtccac accctgctgc aagccaatgg    3480
caccccaggg ctgcagatgc tggaaagcaa cgtcatgatc tccccggagg tgctgtgcaa    3540 agagggatc aaggtgcaca ggaccgtgca gcagagtggc cagtttgtcg tctgcttccc     3600
gggatccttt gtgtccaaag tgtgctgtgg gtacagcgtg tctgaaaccg tgcactttgc    3660
taccacccag tggacaagta tgggcttga caccgcaaag gaaatgaagc gtcgccatat     3720
agctaagcca ttctccatgg agaagttact ctaccagatt gcacaagcag aagcaaaaaa    3780
agaaaacggt cccactctca gtaccatctc agccctcctg gatgagctca gggatacaga    3840
gctgcggcag cgcaggcagc tgttcgaggc tggcctccac tcctccgcac gctatggcag    3900
ccacgatggc agcagcacgg tggcggacgg gaagaaaaag cctcgaaagt ggctgcagtt    3960
ggagacgtca gagaggaggt gtcagatctg ccagcacctg tgctacctgt ccatggtggt    4020
acaagagaac gaaaacgtcg tgttctgtct ggagtgtgct ctgcgccacg tggagaaaca    4080
gaagtcctgc cgagggctga gttgatgta ccgctacgat gaggaacaga ttatcagtct     4140
ggtcaatcag atctgcggca agtgtctgg taaaaacggc agcattgaga actgtctcag     4200
taaacccaca ccaaaaagag gtccccgcaa gagagcgaca gtggacgtgc cccctcccg    4260 tctgtcagcc tccagttcat ccaaaagtgc ttcgagctca tcatgaagat gccaacgccc    4320
gtggtcgatt tatatatatt ttttgtaat tattatattc tagttggag tacttgctgt       4380 aggattcaag ctgtctttgc actagctcta aagaagattt tcttctggtt ttagagaact    4440
```

```
aattttgttt tagcattaaa ctgttgaact ttttttttgta cttagaaaac ctagatactg    4500
cagtcagatt ttggaaactg ccgtatagtc actgttttaa aaaccccgga ggggctgtat    4560
taatttgtat tgccccatgg ctgacaaaag ccttttttttt tggttttgat ttttttttttt    4620 ttgtaactgt tgggggggaaa aaggcttttt aacccatttt tgaagagggt gaagtttgga    4680
gaacaaattt aaaaaccatc agtcatgtga gcagattttt tagaagggat aggagacaca    4740
cgcgcacaca cacacacaca cgaaacttga aatggctttg ctttggctgt cgtcttctgc    4800
cgtgtgccag atgagcttgt gatctgggaa gccggggcac ccccgttttg tttctctggg    4860
cggttgtggc agctgaaggc ggacgttgtt cctaaccat aggtggaacg aggagacggg    4920
agcgagtggg ctctccacca gcacatcact atgcatctgt tccaggaaag aagaaaagcg    4980
agcgaggaag acgaaaaga ctgcctgcct tggaggggtc acatgaggga gacctgtgcc    5040
tgatttcatt aggaaatcca ttctgttatt ttttggtgct gttggctact ttatcaaaaa    5100
acccttcaat agcatcctta agatttaaaa aaaaaaaaa aaaaaaggaa aaaaaagtga    5160
tggaagccgt aagtgcttct ttgtcatcga cgtgcaatct ttctaacatt ccatctccat    5220
ctcaccgctt cttgtttgac accttcacaa gtcagcatta atctttcttt taaaacttgt    5280
ttcatttatg atcatgtaga gagccactag gaggcctgca gttattttttg aatgtgaaaa    5340 tgcatttgcg ttcatcttgt ctatttttttc tcttcatgtt gtaacaaaaa ggaaaaaaga    5400
aaaaaaaatc ccatcccttt tgtacatatg cctgtaaatt gttttaaata cttgagcctt    5460
tttctcggtg ggggtgggg aggggggtga gaagacaaga tgaagaaaag ccttacattt    5520
cagtttcttc atcggttgga ttggatgctt acagggtttt tcttgtaaca tttataagtg    5580
ctgcttacat cactgaacaa caacaaaaaa ataataatgg agtagctgtt gcccttctcc    5640
ggttgtgtgt acagtatgtg tggaataaaa aagggaaact gttttcacaa gctgttcttt    5700
gtttcataat tggattcatc aatcccgtag ctacccatat tgcactgagc ttgccagtgg    5760
tgactgccag gaacgtccta tgatccactt tgttggttgt tgttcagaa gactgaactg    5820 ttttggaata tttaacaatt acagaaacag tcaagtgttt tccaatgtgg ttgtccggtt    5880
tctatggcct tgctgtgtac tttccctctt tttgacagta aacttctgcc tatggcttac    5940
agtttgacat ttaatttatt agcgctgctc tgcaccccctc ccttgggagg gagacttcat    6000
gtggtttatt gcgagttttt tgtttactttt tcaggtttgt actacaaggt ttaataataa    6060
aaacaaagtt ttttggacat ttgtctgtct tgtggaaaaa aaaaaaaaaa aa           6112
```

<210> SEQ ID NO 56
<211> LENGTH: 3159
<212> TYPE: DNA
<213> ORGANISM: Homo sapiens

<400> SEQUENCE: 56

```
agggcgaacg ggcgagtggc agcgaggcgg ggcgggctga ggccagcgcg gaagtctcgc      60
gaggccgggc ccgagcagag tgtggcggcg gcggcgagat ctgggctcgg gttgaggagt     120
tggtatttgt gtggaaggag gcggaggcgc aggaggaagg gggaagcgga gcgccggccc     180
ggagggcggg aggaggcgcg gccagggcgg gcggttgcgg cgaggcgagg cgaggcgggg     240
agccgagacg agcagcggcc gagcgagcgc gggcgcgggc gcaccgaggc gagggaggcg     300
gggaagcccc gccgccgccg cggcgcccgc cccttccccc gccgcccgcc ccctctcccc     360
ccgcccgctc gccgccttcc tccctctgcc ttccttcccc acggccggcc gcctcctcgc     420
ccgcccgccc gcagccgagg agccgaggcc gccgcggccg tggcggcgga gccctcagcc     480
```

```
atggcctcgg gcgacaccct ctacatcgcc acggacggct cggagatgcc ggccgagatc      540
gtggagctgc acgagatcga ggtggagacc atcccggtgg agaccatcga gaccacagtg      600
gtgggcgagg aggaggagga ggacgacgac gacgaggacg gcggcggtgg cgaccacggc      660
ggcggggcg gccacgggca cgccggccac caccaccacc accatcacca ccaccaccac      720
ccgcccatga tcgctctgca gccgctggtc accgacgacc cgacccaggt gcaccaccac      780
caggaggtga tcctggtgca gacgcgcgag gaggtggtgg cggcgacga ctcggacggg       840
ctgcgcgccg aggacggctt cgaggatcag attctcatcc cggtgcccgc gccggccggc      900
ggcgacgacg actacattga acaaacgctg gtcaccgtgg cggcggccgg caagagcggc      960
ggcggcggct cgtcgtcgtc gggaggcggc cgcgtcaaga agggcggcgg caagaagagc     1020
ggcaagaaga gttacctcag cggcggggcc ggcgcggcgg gcggcggcgg cgccgacccg     1080
ggcaacaaga agtgggagca gaagcaggtg cagatcaaga ccctggaggg cgagttctcg     1140
gtcaccatgt ggtcctcaga tgaaaaaaaa gatattgacc atgagacagt ggttgaagaa     1200
cagatcattg agagaactc acctcctgat tattcagaat atatgacagg aaagaaactt     1260
cctcctggag gaatacctgg cattgacctc tcagatccca acaactggc agaatttgct     1320
agaatgaagc caagaaaaat taaagaagat gatgctccaa gaacaatagc ttgccctcat     1380
aaaggctgca caaagatgtt cagggataac tcggccatga gaaaacatct gcacacccac     1440
ggtcccagag tccacgtctg tgcagaatgt ggcaaagctt ttgttgagag ttcaaaacta     1500
aaacgacacc aactggttca tactggagag aagccctttc agtgcacgtt cgaaggctgt     1560
gggaaacgct tttcactgga cttcaatttg cgcacacatg tgcgaatcca taccggagac     1620
aggccctatg tgtgcccctt cgatggttgt aataagaagt ttgctcagtc aactaacctg     1680
aaatctcaca tcttaacaca tgctaaggcc aaaaacaacc agtgaaaaga agagagaaga     1740
cccttctcga ccacgggaag catcttccag aagtgtgatt gggaataaat atgcctctcc     1800
tttgtatatt atttctagga agaattttaa aaatgaatcc tacacaccta agggacatgt     1860
tttgataaag tagtaaaaat taaaaaaaaa aaactttact aagatgacat tgctaagatg     1920
ctctatcttg ctctgtaatc tcgtttcaaa aacacagtgt ttttgtaaag tgtggtccca     1980
acaggaggac aattcatgaa cttcgcatca aaagacaatt ctttatacaa cagtgctaaa     2040
aatgggactt cttttcacat tcttataaat atgaagctca cctgttgctt acaatttttt     2100
taattttgta ttttccaagt gtgcatattg tacacttttt tggggatatg cttagtaatg     2160
ctacgtgtga ttttttctgga ggttgataac tttgcttgca gtagattttc tttaaaagaa     2220
tgggcagtta catgcatact tcaaaagtat tttcctgtaa aaaaaaaaaa gttatatagg     2280
ttttgtttgc tatcttaatt ttggttgtat tctttgatgt taacacattt tgtataattg     2340
tatcgtatag ctgtattgaa tcatgtagta tcaaatatta gatgtgattt aatagtgtta     2400
atcaatttaa acccattta gtcactttt ttttccaaaa aaatactgcc agatgctgat      2460
gttcagtgta atttctttgc ctgttcagtt acagaaagtg gtgctcagtt gtagaatgta     2520
ttgtaccttt taacacctga tgtgtacatc ccatgtaaca gaaagggcaa caataaaata     2580
gcaatcctaa agcaagaata tggcagaaca agatctgtaa gcacagtctt attttctttt     2640
gttgtccaga atacttataa ttcttgagcc tcccagaaat tggaagctaa ataaagcaac     2700
tcaagtttcc tttattttgc actcaattac agtgattatt gatgaaagcg atgcatggat     2760
attttaatac ttcctacatg tcctgacttc tgaaagagag taggtaacag gcatcccgag     2820
```

| | |
|---|---|
| ttcaggaact acctcagaac accccaggcc aggttggtca taggctgtga ttttagcccc | 2880 |
| cggcaagtgt gagtgaagca tctgtaccac cgcgcaggct gagcgcctgc gcagggtaag | 2940 |
| gtgccacctg gcagtggggc acacagaggg aagaccaggc ctgtccatca gccggctgcc | 3000 |
| ttcagaggca gctccagcag gaccttggct tgtctgacag gaaatgcttg tggtcgttgg | 3060 |
| ttatttggtt tgagagccct tgttcctcca tctagtggag tccttattaa atgctagcaa | 3120 |
| tgtggcaatt gagtgccagt agcttaattt catgtttct | 3159 |

<210> SEQ ID NO 57
<211> LENGTH: 4265
<212> TYPE: DNA
<213> ORGANISM: Homo sapiens

<400> SEQUENCE: 57

| | |
|---|---|
| ggcggtccgg gcgggtgact ggcggcgggc gccgcggtcg ggctggctgc cgggcagcat | 60 |
| ggaggagctg agcagcgtgg gcgagcaggt cttcgccgcc gagtgcatcc tgagcaagcg | 120 |
| gctccgcaag ggcaagctgg agtacctggt caagtggcgc ggctggtcct ccaaacataa | 180 |
| cagctgggag ccggaggaga acatcctgga cccgaggctg ctcctggcct tccagaagaa | 240 |
| ggaacatgag aaggaggtgc agaaccggaa gagaggcaag aggccgagag gccggccaag | 300 |
| gaagctcact gccatgtcct cctgcagccg gcgctccaag ctcaaggaac ccgatgctcc | 360 |
| ctccaaatcc aagtccagca gttcctcctc ttcctccacg tcatcctcct cttcctcaga | 420 |
| tgaagaggat gacagtgact tagatgctaa gaggggtccc cggggccgcg agacccaccc | 480 |
| agtgccgcag aagaaggccc agatcctggt ggccaaaccc gagctgaagg atcccatccg | 540 |
| gaagaagcgg ggacgaaagc ccctgccccc agagcaaaag gcaacccgaa gacccgtgag | 600 |
| cctggccaag gtgctgaaga ccgcccggaa ggatctgggg gcccccggcca gcaagctgcc | 660 |
| ccctccactc agcgcccccg ttgcaggcct ggcagctctg aaggcccacg ccaaggaggc | 720 |
| ctgtggcggc cccagtgcca tggccacccc agagaacctg gccagcctaa tgaagggcat | 780 |
| ggccagtagc cccggccggg gtggcatcag ctggcagagc tccatcgtgc actacatgaa | 840 |
| ccggatgacc cagagccagg cccaggctgc cagcaggttg gcgctgaagg cccaggccac | 900 |
| caacaagtgc ggcctcgggc tggacctgaa ggtgaggacg cagaaagggg agctgggaat | 960 |
| gagccctcca ggaagcaaaa tcccgaaggc ccccagcggt ggggctgtgg agcagaaagt | 1020 |
| ggggaacaca gggggccccc cgcacaccca tggtgccagc agggtgcctg ctgggtgccc | 1080 |
| aggcccccag ccagcaccca cccaggagct gagcctccag gtcttggact tgcagagtgt | 1140 |
| caagaatggc atgcccgggg tgggtctcct tgcccgccac gccaccgcca ccaagggtgt | 1200 |
| cccgccacc aacccagccc ctgggaaggg cactgggagt ggcctcattg gggcagcgg | 1260 |
| ggccaccatg cccaccgaca caagcaaaag tgagaagctg gcttccagag cagtggcgcc | 1320 |
| acccacccct gccagcaaga gggactgtgt caagggcagt gctaccccca gtgggcagga | 1380 |
| gagccgcaca gcccccggag aagcccgcaa ggcggccaca ctgccagaga tgagcgcagg | 1440 |
| tgaggagagt agcagctcgg actccgaccc cgactccgcc tcgccgccca gcactggaca | 1500 |
| gaacccgtca gtgtccgttc agaccagcca ggactggaag cccacccgca gcctcatcga | 1560 |
| gcacgtattt gtcaccgacg tcactgccaa cctcatcacc gtcacagtga aggagtctcc | 1620 |
| caccagcgtg ggcttcttca acctgaggca ttactgaagc cccggcgcca ccagctcgcc | 1680 |
| ggtcttactc cccttccctg cctatggtgt cgcttggcta agtgactccc agcccaagcc | 1740 |
| ccctcaagag tctgggtcgg gggaggagga gtgggtggcc tccttgatgg gcaggcttgg | 1800 |

```
aagggacttc tcccgcaccc cactctgtcc caggacatag ggcagggggc ctcactgcct    1860
tgttggtctc caccttgttc ctacctctgc aggcctcttt gctctcccct cttgcctcag    1920
gaaacccggt ggcacctgtg gctccaggtg actgtcttga acagagcggg cttcttcatg    1980
gctgcgttgt tgctgagttt gaactgctcc tccctggcct gcgtgactga atcacagctt    2040
tggtccctgt cttgcagggg ctgaggtgtc aggaggggac ttctggccca ccttgccttc    2100
agccctggag tgggcagaga gtattgtggg gaggcatggc cagtgggact agtgttccct    2160
ccatctggcc acagcttttg ggagatgggg tgggcagggg tggtcctggc tggcattgcc    2220
tgagccggca gtgatgaagt ggggagcttg cccttgacag gtgggggctg gctgggcct    2280 taatgtgaaa agacagtggc aggcagctgg agtagagcga gcccagcagc cctaaaaggc    2340
tgccttcatg gccatctagc cccagttcag ggcagcatcc atagcccaca agccagcgtg    2400
ggtggggcgg gggtggtccc acagctgggt tccacctgaa gagcctccgt gcctcggagc    2460
aggagaggca ggctatggct gccacccctcc ctcctgcctg tgtcccagtg agaactgacc    2520
tgagtcccct tccaaaccca gacccacctc ctgccccagg cccactgaag catgttccat    2580
ttctaaaaag cccagagttc agtgtgtccc aaggaaaacc caaagtggag gtgctcaggt    2640
ccaggggagt ccagtgggca ggacccttgg caggcaagcc cctcccttca ctcccaggac    2700
ctaccttctg ctagtaaagg actggcttca ttctaattat ggcccacaga ctgccccgga    2760
gacctggagg acagcagtgc tggcacttgg gtgtccatgg gcccgtctgc cggctctgcc    2820
tgtgctgcaa gtgttggccg tgggtccagc caacaactcc ctacgtcctg tgtggggccc    2880
tgcccaagtg gatgaggcat tccttgagga gtatcatttt ccctgacaat ccccatcacc    2940
tttaggggtt ccctgcttgg ctcctttcca gctgaaaaac tagacctgtg ccattgggga    3000
agctggacaa agtctagggg gcccgcctgg tagagggtcc cggaagctg gatctgtcag    3060 cctcggccct gaggcccctg ttaactcaag actgtgagct gcctctaggt ggtcacgtct    3120
gggagctagc ttgtatggct tctgaccagt atcaggattt ctgttctgag agcagcgtgg    3180
gcagcaaggc agggcagccc agaggtggca gcggcaggca atctggtcac taggtctttg    3240
tgatgccaaa aataaaagag ggtggggtgg gtgctttctg ttcctctgat tggatggagt    3300
ccgccagcag gcatgggct acattccagt gcctgactat agggaggcac tcctgattcc    3360
atggagcagc ccggactttg agaatgggct ctggtttgcg gggggcaggc gtaccagact    3420
gcaagacccc ccagtacctc accgtgccaa ataggaagag gtggccttgg tgtagccaaa    3480
tggatctttt taacagtgtg cctttgggga gggacccatg tccatggctt cgttgagggc    3540
catccatatg ccagctgggg gccagcccac agtggccata ttggctgcag caggaatggt    3600
gcccacctcg gcgaattgaa gggctaagag tcccagatag ctaggccaga gctgaaagca    3660
gacagtaagg ggaagagctg ctcccacagg agagggagag attccagctc actgcgcagc    3720 ctggaggag gcgtggatcc tggcacgctg agcctcaggc accagcctcc ctgtgctcga    3780
cagcaaagtc ttgactcctt cctgctgagc actgtgctac cttcactgct ccaaagccag    3840
actaacagct ctccaagccc ttggggtgac tcggcttcca ggagctgttg gagaaatgag    3900
gatgtctgtc cctgtctgcc tgggcaggcc agattcctcc ccagcagccg ggtctctcca    3960
gaccctgatt cggtgccttt ctgtttacca gctacttcaa tcccaaagtt tgaatctgca    4020
gataccttac tccagccac tttgccttct tactgtgttg tgtgttttc ctggtgcttc    4080 aagagcgtgt gcagggcaag tgccgtcact gggaactgca ccagatgctc agacttggtt    4140
```

| | |
|---|---|
| gtcttatgtt taccaataaa taaaagtaga cttttctat ttttatttgc tgctatttgt | 4200 |
| gtgtgtgttt gtgtttgtgt agctaggtat ctggcacttc tgacgatgca ttgttgcttt | 4260 |
| tttcc | 4265 |

<210> SEQ ID NO 58
<211> LENGTH: 2655
<212> TYPE: DNA
<213> ORGANISM: Homo sapiens

<400> SEQUENCE: 58

| | |
|---|---|
| agccggggcg ggcgcgggca gcggcgggcc ggccgggctg tgcggggcga gcggcggcgg | 60 |
| cggcggggc gcttcggccg gggcggcagc tgggcgccgg cgggagctag cagcgtctgc | 120 |
| agccgcgccg gccgccagcg ccccggcgcg ctccggctcg gccatggagc tgccagctgt | 180 |
| tggcgagcac gtcttcgcgg tggagagcat cgagaagaag cggatccgca agggcagagt | 240 |
| ggagtatctg gtgaaatgga gaggctggtc gcccaaatat aacacgtggg aaccggagga | 300 |
| gaacatcctg gaccccaggc tgctgatcgc cttccagaac agggaacggc aggagcagct | 360 |
| gatgggatat cggaagagag ggccgaagcc caaaccgcta gtggtgcagg tgcctacctt | 420 |
| tgcccgtcgt tccaatgtcc tgaccggcct ccaggactcc tccactgaca accgtgccaa | 480 |
| gctggatttg ggcgcgcagg ggaagggcca ggggcatcag tacgagctca acagcaagaa | 540 |
| gcaccaccag taccagccgc acagcaagga gcgggcgggc aagcccccgc cgccgggcaa | 600 |
| gagcggcaag tactactacc agctcaacag caagaagcac caccctacc agcccgaccc | 660 |
| caaaatgtac gacctgcagt accagggcgg ccacaaggag gcgcccagcc ccacctgccc | 720 |
| ggacctgggg gccaagagcc acccgcccga caagtgggcg caaggtgcgg gggccaaagg | 780 |
| ctacctgggg gcggtgaagc ccctggccgg tgcggcgggt gctccaggca aaggctccga | 840 |
| gaagggcccc cccaacggaa tgatgccggc ccccaaagag gctgtgacgg gcaacgggat | 900 |
| tgggggcaag atgaagatag tcaagaacaa gaacaagaac ggacgcatcg tgatcgtgat | 960 |
| gagcaaatac atggagaacg gcatgcaggc ggtgaagatc aagtccggcg aggtggcaga | 1020 |
| ggggggaggct cgctcccca gccacaagaa gcgggcagcc gacgagcgcc accctcctgc | 1080 |
| cgacaggact tttaaaaagg cggcgggcgc agaggagaag aaggtggagg cgccgcccaa | 1140 |
| gaggagggag gaggaggtgt ccggggttag cgatccgcag ccccaggatg ccggctcccg | 1200 |
| caagctgtcc ccgaccaagg aggcctttgg agagcagccc ctgcagctca ccaccaagcc | 1260 |
| cgacctgctt gcctgggacc cggccccgaa cacgcacccg ccctcacacc acccgcaccc | 1320 |
| gcaccccat caccaccacc accaccacca ccaccaccac cacgccgtcg gcctgaatct | 1380 |
| ctcccacgtg cgcaagcgct gcctctccga gacccacggc gagcgcgagc cctgcaagaa | 1440 |
| gcggctgact gcgcgcagca tcagcacccc cacctgcctg gggggcagcc cagccgctga | 1500 |
| gcgcccggcc gacctgccac cagccgccgc cctcccgcag cccgaggtca tcctgctaga | 1560 |
| ctcagacctg gatgaaccca tagacttgcg ctgcgtcaag acgcgcagcg aggccgggga | 1620 |
| gccgcccagc tccctccagg tgaagcccga dacaccggcg tcgcggcgg tggcggtggc | 1680 |
| ggcggcagcg gcaccaccca cgacggcgga aagcctcca gccgaggccc aggacgaacc | 1740 |
| tgcagagtcg ctgagcgagt tcaagccctt ctttgggaat ataattatca ccgacgtcac | 1800 |
| cgcgaactgc ctcaccgtta ctttcaagga gtacgtgacg gtgtagccgg agggcgtcgg | 1860 |
| aaggggaagc gccattcccg cggggggcg gggagctgag cacctgggc ctcgggcgg | 1920 |
| gctcccctct cgccaacccg ccaaccgcga gagacccagg ctggccccca gggtgaggac | 1980 |

```
gcccggagcg gaggtaacca tgttccccct gcggcggctg tcagacctgg gcggaggccc    2040
cttccacgcg gtgccggcgg ggctcgccct ctcctgccct tccccgctgg agatggaccc    2100
ccggaacgga cagggcagct ctgcgcccgg cctcagagtt ctagtattat atttttaaccg   2160 tgctaacttg tcaagtgctg actctactcc cgtttgtacg tggtgttatt attgaaatgt    2220
attgtttgag ctcaaaaggc ccgaccaccc cccttcgggc tgctatatat atatttattt    2280
gtaggtattt atatattgaa atataaaaac ctagatttat ggagtttcct ctagatcatg    2340
ttatattcta tatcagacaa actattttct tttgaccttt cttcccctcc atccagtatt    2400
tcggttgatt tcattttctc ccctctcttc cccttccacg aactgcaata ccagtaacct    2460
tggtatatat tttttgatac tgtacacatg gatgtcttgt ttctatgtgc aaaaaaaaaa    2520
aaaaaaaaaa gtttgttaaa aggctacacg agctctctag aaactgctgc tactagaaat    2580
gtctaaacta taagcttcca actattacct gcttgaatgt aaatattaaa tggagatgtt    2640
gaaggtgcaa aaaaa                                                     2655

<210> SEQ ID NO 59
<211> LENGTH: 6165
<212> TYPE: DNA
<213> ORGANISM: Homo sapiens

<400> SEQUENCE: 59
gtgacggccc gcagctggaa cgcgagcgcg cgccccgccg cgctcccgcc cgccggggcc      60
tgggcgctgc ggcgcgtgcg cgagcggtgc cgcaccggcc gcgggcgcag ggagtattat     120
gggctgtggg tgccgctgag caagatggag ctgtctgcag tgggcgagcg ggtcttcgcg     180
gccgaatcca tcatcaaacg gcggatccga aagggacgca tcgagtacct ggtgaaatgg     240
aaggggtggg cgatcaagta cagcacttgg gagcccgagg agaacatcct ggactcgcgg     300
ctcattgcag ccttcgaaca aaaggagagg gagcgtgagc tgtatgggcc caagaagagg     360
ggacccaaac ccaaaacttt cctcctgaag gcgcgggccc aggccgaggc cctccgcatc     420
agtgatgtgc atttctctgt caagccgagc gccagtgcct cctcgcccaa gctgcactcc     480
agcgcagccg tgcaccggct caagaaggac atccgccgct gccaccgtat gtcccgccgt     540
cccctgcccc gcccggaccc gcaggggggc agccccggac tgcgcccgcc catttcgccc     600
ttctcggaga cggtgcgcat catcaaccgc aaggtgaagc cgcgggagcc caagcggaac     660
cgcatcatcc tgaacctgaa ggtgatcgac aagggcgctg gcggcggggg cgccgggcag     720
ggggccgggg cgctggcccg ccccaaagtc ccctcgcgga accgcgttat aggcaagagc     780
aagaagttca gcgagagcgt cctgcgtaca cagatccgcc acatgaagtt cggcgccttt     840
gcgctgtaca agcctccgcc cgcccccctg gtagccccgt cccccggcaa ggctgaggcc     900
tcagccccgg gcctgggct acttctggcc gccccgccg cccctacga cgcccgcagc     960 tctggctcct ccggctgccc ctcgcctaca ccacagtcct ctgaccccga cgacacgccc    1020
cccaagctcc tccccgagac cgtgagccca tccgccccca gctggcgcga gccggaggtg    1080
ctcgacctgt ccctccctcc cgagtcggca gccaccagca agcgggcacc gcctgaggtc    1140
acagctgctg ccggcccggc acctcccacg gccctgagcc cgccggtgc ctcctccgag    1200 cccgaggctg gggactggcg ccccgagatg tcaccctgct ccaatgtggt cgtcaccgat    1260
gtcaccagca acctcctgac ggtcacaatc aaggaattct gcaaccctga ggatttcgag    1320
aaggtggctg ctgggggtage aggcgccgct gggggcggtg gcagcattgg ggcgagcaag    1380
```

```
tgaggggget  ccaccaagga  gggggggcttg  ggggggccct  cctgcccgaa  gtcatactct   1440
tgctcccacc  ccaccettge  ccccagecct  ctcteectgt  getttgettg  tetcaaatgg   1500
ctcggtgttg  acccagggat  ggggctgggt  agttggggte  ccagaaagcc  ggggggtaggg  1560
gccaccctgg  aatggggcag  gggaagggca  cccccctgc   ccatgcatgg  tagcccactg   1620
ggtggtttct  ggaaagccct  agaaactagg  gttcctctgc  cccttccaca  tcccacctgt   1680
ctctctagct  tgcttcctgc  tctcctgtgc  ggcgtctgat  ttctcggtgc  taacctggca   1740
gctgtggggc  ccttaggagc  cccccaccga  gggtggacac  agtccctttc  cttcctgcag   1800
atgcctaggc  aggaggaggg  cttcctgcct  gtttggcaaa  gtcccaggca  gaggccaagg   1860
atgaggcctg  actcggctcc  tccctccaca  tcagccaggg  catcagaagt  tgggccaggg   1920
cggggtcttc  cctgctcgat  tttggacgag  gcctaagtag  accccctatg  ccctgcccca   1980
gccctggctc  tttcctaacc  ccctcaacgg  tgggaggaac  tggcagaggg  tgcgcctggc   2040
cacagcctcc  ccgcatctaa  aggccccttc  agttcttgac  caaaggtgct  acgagaacct   2100
gccgtggaaa  cttccagttg  tgcgtctgcc  ccactcgctg  tgtttgtccg  tgggttcata   2160
catgcattgg  gtgctaggcc  ccaggctgcc  gggtggcacc  ctttacagtt  cctttgaaca   2220
ggggcattga  aggcctggac  tgcctctcgc  ctcagtaggc  ctggggacca  ggcttgggtc   2280
tggaggtttg  ctgtggaagt  caccaggcct  cccctcctgg  cccaggtgtg  ctgggggcac   2340
cgtgccccc   accccctgc   cctcctcagg  gtggtcagcc  caacctgtcg  gaccttcact   2400
tcacatcatg  gtggggaccg  agatagagag  ggagacccca  ttccaagctc  cctcttcctc   2460
cgggtgtttg  gggaggatgc  tgaagaatcc  attcccgagg  gcctcccggc  ttgtcccagc   2520
ccctcttttg  cttctgacca  cggaggcttt  ctcacagccc  agcctgcctg  aagcaaagga   2580
ggctcccgtg  tcctgggcag  cttctgtttc  cctctgctgc  ctgggagctg  aggcacccgt   2640
gccagtggca  gaggccacag  ccccagcctt  aggccaggcc  ctgggagggc  aggcaggcaa   2700
aggggagacc  agagggtctg  tgttctccag  gagaatgagg  gtgttggtcc  cagaattggg   2760
accggggccc  cgctggccag  ccctgggcca  cttcccgggt  ctccattgtg  cgtgggtggc   2820
gtgttccagg  cgtggctgga  gctggcttcc  tggctgtgct  gccatgggcc  cctccctcag   2880
aagcacgttg  gcaggaggcc  gatcagaacc  ctagcgcctt  tggtcctaag  aatgggaggc   2940
tgccttcctt  cccaatctcc  ctgccagggc  ccacagcgtg  gccctagccc  tcccctcccc   3000
gggatgtaga  acggggaccc  tcgcagggtt  ggggcggggg  ctgatactcc  tcggcccctc   3060
cctaccctgc  cctgtgtgtt  ggcttttgtgg  ccgtccaagt  gccaattggc  ttttcgccca   3120
aataagggct  ggtatttctc  ctctgtcctt  ggaggtgatt  tccccctgac  cccctccccc   3180
aggtgagtga  ccacctgggt  gccagttaca  ggtgtttcca  gagaccatag  aaatgtgttt   3240
tcctgagagt  tcgtgtcatt  cgtgactttt  ttgtaaagaa  gttgtgtttt  cagaggtgat   3300
tttatgacag  gaaagtgaaa  gaattagttt  tgcaaaaaaa  caaaaacaaa  aaagaggaa    3360
aaaaaaaga   aatagaaaaa  aatattgtgg  gattcctatg  ggggggtggc  ggggggagaaa  3420
gagctattta  agaaaaaata  gtaacgcagt  gattgcacag  gtgaggtggc  aatgtcagga   3480
tggggcggag  gcctgggccc  agctggcagg  tccctggca   tcgcaggcac  tgtggagagg   3540
gcctggaccc  agatctccac  acccgtgctt  gctcaaaggg  aaggacaaca  gcgggcccc    3600
gggagctaac  ccaagctgca  ggtcccggca  agctgaggtt  tgggagggtg  ggggttgtca   3660
ctggtgattt  tctccagggg  gctggtgagt  gggcagtttg  gtttcttgcc  cccttctgtt   3720
cctttcccag  ttgttgggcc  atctggtccc  caccaccgcc  accctatggg  ggagacctcc   3780
```

```
ctccccacgg gtcaccctaa agcccacaac ctctctgagc ctccctggcc tgaaagggga    3840
tgcaggcttc aggaggcaag aagctgggcc cctgggggtg gctggggaga gggaatgcat    3900
ttcccttgcc acaggtggtc tgcttctgct ggcctgagct ccaagtggag cagcccgggc    3960
cagccttggt gcatgaagag gcaccaggca caccgccttg aggtgggcag tgcccatggg    4020
ggcccgagtg gatgggaccg agggtgagtg gagcctcctt cctcccctct ctagtacccc    4080
cgcctcccac acacttgcac ggatcggcct cccttgggag atcagcctcc atgggcccct    4140
cgtccaccct tgctgctttc catttgccta attaccaagc agaagttgca atctggtttg    4200
cttttatttt gtatgtgaaa taaccccaa agcccaatct cctcctacgt tcaatattgg    4260
ttggggcatc cgtcatctcc ccttaagtgc gcccctccc cacccaagta tcataggaaa    4320
ccggtgaggt ctggtgtctc tggtttgaga cggtaagttg ggacccatcc ctgtctgggt    4380
gcccactctg acctttagtt tgcccttctg tgaaatgggt gtattgggta gcaagccctc    4440
ttcagaaagc gctgctggtg tcagagcagc tgcccagtac caggtggggg gtcaaggttg    4500
ctggtactgg ggccccagc tgcccacaac ccctctttgt tctcaccctg caagggggtc    4560
aaggtcaaaa tgagcctcat ccttcctatg atctgggaag aggtgatgat caagtcccca    4620
acttcagtgt gaggtggaca gagttggggg gatggcccct ttttgaagag gtgaaaatgg    4680
ttttggagaa cgcagctgc ttcactgggg gaatgcggca gggactgggg cccaggatgc    4740
tttggcctat ggggaaaagc cctttaaaag gcagggccca ggccctggag ccagcacaag    4800
actggcctcg agcccctgag ccaggaggtc ctggaggaga gccaggccgg tgggcccgcc    4860
caaggctgga gggtcagccc caacagggag ctgggttggc caggggctg gactgctacc    4920 agcctctctg gcctatgggg acccaagagg acacatcccc cttttgccca ctcttctgtg    4980 tcatttgtt gttttggttt gtggtggttt ttctttttc ttttgttttt cttttttctt    5040
tctttctttt ttttttttt tttttttttt tttgcacttc gcccacacag gacagtggag    5100
ccccacctgg tcagttccac ttccgggctc ccatgcactt gcccaaggcg gcctctttgg    5160
gacggggatg gtttgaggaa acacttttaa agaaaaaagg aagacattga aaggttttag    5220
tttcttccct atctgcatgt cctctcatat agaaagccca gaattagggg ctagaactcc    5280
aggagagggt ctccccgact catctcttgc tgacggtcac caggatgcag aaatagggag    5340
atggttagtg ggggccaaag atgccccctc ccaggccttc gtggttccct cctccgcccc    5400
ctgcaatctt tggaggagtc agtgcctcac tccagcagtg agtgcctact gtatgcaggt    5460
agtcagccag gcaaagagag actaacggtc tcatggggga accctcttgc gggaggccgg    5520
gtagctggag cgaagcgttc cggctgccct tgctgctggg tggagtggag agggagactt    5580 cttttttgttg gttttaattt aaaaacacaa aggcctaaag aaatacgtat cttataattt    5640
ttttaatttt tgagacgttc atttaatgaa ttgtgcacga atgaattcta tatatataaa    5700
atatacatat atagctctat atttggggag gggcactgtc tctttttttct ctcatttta    5760 aaatgaagtg ttgttgcctt tgtatgtggt tcaaccatcc agctcccagc tggctaaact    5820
ttgcctccag tggtcaaaga tgggaaaaga gtgggttgg caggagatgg aaaacggagg    5880
tgccgcccca gcatgggggg caggtccccc agtccaccct gccctccccc ctgtggagaa    5940
gacgcttagt tgggggtgtg ggtttgggct ccattctgga ttcggcggtt ccgggggagg    6000
ggtgggtctg tgccgattac tctgtcttgt acgtttgttc tgctgctctt caatattgta    6060
tcaacgccag gaaaggggg tgaaaagcct cttttacccc ccaaataaat tgtcacattc    6120
```
cgaagctgag gcctagcccc taggttgggg tgtgtctgtg tcttc                6165

<210> SEQ ID NO 60
<211> LENGTH: 3964
<212> TYPE: DNA
<213> ORGANISM: Homo sapiens

<400> SEQUENCE: 60

```
ccagccccag catcgcgcgc cgcagccgcg gccccgcagc tccgccccg gcccggcccg      60
gccccgggcc cgctcgcccg ccgccccgca tggagctgtc agccatcggc gagcaggtgt    120
tcgccgtgga gagcatccgg aagaagcgcg tgcggaaggg taaagtcgag tatctggtga    180
agtggaaagg atggcccca agtacagca cgtgggagcc agaagagcac atcttggacc      240
cccgcctcgt catggcctac gaggagaagg aggagagaga ccgagcatcg gggtatagga    300
agagaggtcc gaaacccaag cggcttctgc tgcagcggct gtacagcatg gacctgcgga    360
gctcccacaa ggccaagggc aaggagaagc tctgcttctc cctgacgtgc ccactcggca    420
gcgggagccc tgagggggtg gtcaaggcgg ggcacctga gctggtggac aagggccct     480
tggtgcccac cctgccctt ccgctccgca gccccgaaa ggcccacaag tacctgcggc      540
tctcgcgcaa gaagttcccg ccccgcgggc ccaacctgga gagccacagc catcgacggg    600
agctcttcct gcaggagcca ccggcccag acgtcctgca ggcggctggc gagtgggagc    660
ctgctgcgca gccccctgaa gaggaggcag atgccgacct ggccgagggg ccccctccct    720
ggacacctgc gctcccctca agtgaggtga ccgtgaccga catcaccgcc aactccatca    780
ccgtcaccttt ccgcgaggcc caggcagctg agggcttctt ccgagaccgc agtgggaagt   840
tctgaatcac cgttttttact cttcttaaac tgtttcttt tgggcttggg gtgggacttc    900
cagagatagg gatgggttgg gggcggggta attattttat ttaaaaaaat accgagcagc    960
aaaggggag aagatcccac tactctccca ccacctgccc tttctctgag gacgtttac    1020
cacgaggcct caggctgggg atggagagag ttgctctggg agttggggta ccaccccag    1080
ggcaggatgg ggacaggatc acctgcccgg gacaccacca ttatcattct cctctagtga   1140
cgcagcagct ggttctggga gttaaaggag cattggaagg cccaaaccct ctcccttgag   1200
tggccacccc agcctggttg gctggttttc cccttttctc ttgtttcaat tgggtcttta   1260
ccttgaactc tcctctctgg cttgcggtg gctgtggag ctggttttg accaaaagtg     1320
agtggggcgg gaggaaggg caggaggaag ggttgaggtt acttggggcg agtcccttcc     1380
ccttcagaga ggcttctatc cttcccaggg aggaggcgcc gctgagaccc ttctgctgag    1440
agctctgccc tccctcatc acctggcctg tgcagaaacg ctcatgcaca cctggctgca    1500
caggtgtgca cgcattaccc ttcgcgtgta cgttccatg tgcccgtga agcatgtgt      1560
ggctgcagac gtgtccacat gggccttgcg aacctgggtt agaaaccctg gccaggcgaa    1620
cgtggggtga ttcacagcac aaaagacctc accaccacac ctgcactcac cccaccttgc    1680
atgcaccttg ctacctgctt gcggctttca gtggagggca ggggtctggc acaggtgcga    1740
tggcacccca tgctccaggc atacagatgt ggtttctcgg ctgcaccggg ccaggctgcg    1800
ggtgtgcagg cgtctgctaa gttgtgtgat gtatcagcac aggctttgag acgtctggac    1860
cctgtccttc ctcccgtgag gggttcttgt tctttctgac tcaggtgact tttcagccct    1920
tccaattccc ctctttttct gccctcccct ccaactcagc caaccaggt gtgggcagtc     1980
agggagggag ggagtgtccc accacgttct cagggcagcc cttgactcct aagcccttc    2040
ctccttccat tctgcatccc ctccccatcc aacctaaatg ccacagctgg ggctgagctg    2100
```

```
tattcctgtg agggacctc tgccgtgcct ctctgaggtc aggctgtgct gtgtgatggg    2160
caggctttgc cccagcccac ccctggcaag gtgcacttgt tttctggttt gtacaaggtg    2220
tcctgggggc ccgtggcttc cctgccagtg aggagtgact tctccctctc ttccagtcct    2280
gtaggggaga caaaaccaga ttgggggggcc caaggggagc atggaaaagg ccggctcccc    2340
tgtctttcct tggctgtcag agtcagggta acacacacca agagtggagt gcggccagca    2400
agtttgagac ctgcccgccc tcctcgcagc tctgctctgt gtcctcagga agtcacagag    2460
tctactgagg caaggagagg gtgattcttt ccccaaatcc cttcttccct ggttcccaaa    2520
ccaaagacag cctgcagccc tttctgcatg gggtgctctg ttgacaggct tcccagatcc    2580
ctgagtctct ctttccttcc tcctcgatct ttagttgtcc acggtcaatt cagtgcttcc    2640
attgggggac agtcccctcc gggatgacct gattcacctc cagcccaggg aatgaaatct    2700
agaggaatac gtggggtggg tctggacaag gagcggcagg aatcaccacc catctccagc    2760
tgtggagccc tgtggagggg aaggggaagc ttggggttca gaggggactc ttccaggaga    2820
ggggtgccca gcggaggtaa agatgataga gggttgtggg gggtctctag ttgaatgttt    2880
tggcccatga ctttgaaaca tggctggcag cttccagcag aagtcacgct ccccatcccc    2940
caggggacat aggacctttt tcctgcttcc tggtcacttt caaagaacta tttgcgcaat    3000
ctgtgggtct gtggattcac ggggctttct gtgtgggtgc tgcagttgct tttgtctgca    3060
gcagcaggac acatctttcc tcttactcag ccctttatgg cccatgggga actccgtggc    3120
tcagggagag ctgaactcca ggggtgtgac ctgggacggg tgggcctgag gtgcccagct    3180
cagggcagcc aggtggctca tgggctgtag tgagccagct ccctggggga aaaggctgtg    3240
ggccgttagg accatcctcc aggacaggtg acctctatga ggtcacctac ggctgtggcc    3300
gtgcaggcct ccttccagcc cagagtggcc cagtagagca aggcagacag tgacctccac    3360
ccccgcagcc ctcttaaaag gccagtactc ttggggggtgg ggggagggtt tagaaagcat    3420
ttgcccatct gcctttcttt cccccagccc ccacccgctt tgaatgtaga gacccgtggg    3480 cactttttcct tttgtggtgg ggggtgcgga ggaggtaccc ccaccctgg cacagccgcc    3540 tggaatgcag gactgtcact gctgttcggg tgatgacctc gttgccaagc tcctcctgtc    3600
cccttgttct gggggcaggc gctgtgcttc tgtgaggtgg tttagctttt gctttcgaag    3660
tggccagctg cggccaccag gtctcagcac aagagcgctt cctttgcaca gaatgagctt    3720
cgagctttgt tcagactaaa tgaatgtatc tgggaggggt cgggggcacg agttgattcc    3780
aagcacatgc ctttgctgag tgtgtgtgtg ctggagagt cagagtggat gtagagcgcg    3840
gttttatttt tgtactgaca ttggtaagag actgtatagc atctatttat ttagatgatt    3900
tatctggtaa atgaggcaaa aaaattatta aaatacatt aaagatgatt taaaaaaaag    3960
aaaa                                                                 3964

<210> SEQ ID NO 61
<211> LENGTH: 5206
<212> TYPE: DNA
<213> ORGANISM: Homo sapiens

<400> SEQUENCE: 61
cccgccgcgg aggccgagcg agcccccagc ccagcctggc gactggggac cccggcacat      60
gaggtggacg cccccgggga agacttgggt gcacagccag gcgagaaggt cttgagtcag    120
acagagcacc agccttgggg accctggacc actatcatgg agactgagag cgagcagaac    180
```

-continued

```
tccaattcca ccaatgggag ttctagctca gggggcagct ctcggcccca gatagctcaa    240
atgtcacttt atgaacgaca agcagtgcag gctctgcaag cactgcagcg gcagcccaat    300
gcagctcagt atttccacca gttcatgctc cagcagcagc tcagtaatgc ccagctgcat    360
agcctggctg ccgtccagca ggccacaatt gctgccagtc ggcaggccag ctccccaaac    420
accagcacta cacagcagca gactaccacc acccaggcct cgatcaatct ggccaccaca    480
tcggccgccc agctcatcag ccgatcccag agtgtgagct ctcccagtgc taccaccttg    540
acccaatctg tgctactggg aacaccacc tccccacccc tcaaccagtc tcaggcccag    600
atgtatctac ggccacagct gggaaaccta ttgcaggtaa accgaaccct gggtcggaat    660
gtgcctctag cctcccaact catcctgatg cctaatgggg cggtggctgc agtccagcag    720
gaggtgccat ctgctcagtc tcctggagtt catgcagatg cagatcaggt tcagaacttg    780
gcagtaagga atcaacaggc ctcagctcaa ggacctcaga tgcaaggctc cactcagaag    840
gccattcctc caggagcctc ccctgtctct agcctctccc aggcctctag ccaggcccta    900
gcggtggcac aggcttcctc tggggccaca aaccagtccc tcaaccttag tcaagctggt    960
ggaggcagtg ggaatagcat cccagggtcc atgggtccag gtggaggtgg gcaggcacat   1020
ggtggtttgg gtcagttgcc ttcctcagga atgggtggtg ggagctgtcc cagaaagggt   1080
acaggagtgg tgcagccctt gcctgcagcc caaacagtga ctgtgagcca gggcagccag   1140
acagaggcag aaagtgcagc agccaagaag gcagaagcag atgggagtgg ccagcagaat   1200
gtgggcatga acctgacacg gacagccaca cctgcgccca gccagacact tattagctca   1260
gccacctaca cacagatcca gccccattca ctgattcagc aacagcaaca gatccacctc   1320
cagcagaaac aggtggtgat ccagcagcag attgccatcc accaccagca gcagttccag   1380
caccggcagt cccagctcct tcacacagct acacacctcc agttggcgca gcagcagcag   1440
cagcaacaac agcaacagca gcaacagcag cagccgcaag ccaccaccct cactgcccct   1500
cagccaccac aggtcccacc tactcagcag gtcccacctt cccagtccca gcagcaagcc   1560
caaaccctgg tcgttcagcc catgcttcag tcttcaccct tgtctcttcc acctgatgca   1620
gcccctaagc caccaattcc catccaatcc aaaccctg tagcacctat caagccgcct   1680
cagttagggg ccgctaagat gtcagctgcc cagcaaccac caccccatat ccctgtgcaa   1740
gttgtaggca ctcgacagcc aggtacagcc caggcacagg ctttggggtt ggcacagctg   1800
gcagctgctg tacctacttc ccgggggatg ccaggtacag tgcagtctgg tcaggcccat   1860
ttggcctcct cgccaccttc atcccaggct cctggtgcac tgcaggagtg ccctcccaca   1920
ttggcccctg ggatgaccct tgctcctgtg caggggacag cacatgtggt aaagggtggg   1980
gctaccacct cctcacctgt tgtagcccag gtccctgctg ccttctatat gcagtctgtg   2040
cacttgccgg gtaaacccca gacattggct gtcaaacgca aggctgactc tgaggaggag   2100
agagatgatg tctccacatt gggttcaatg cttcctgcca aggcatctcc agtagcagaa   2160
agcccaaaag tcatggacga gaagagcagt cttggagaaa aagctgaatc agtggctaat   2220
gtgaatgcta atactccaag cagtgaacta gtagccttga cccccgcccc ttcagtaccg   2280
cctcctacac tagccatggt gtctagacaa atgggtgact caaaacccc acaggccatc   2340 gtgaagcccc agattctcac ccacatcatt gaaggctttg ttatccagga aggagcagaa   2400 cctttccgg tgggttgttc tcagttactg aaggagtctg agaagccact acagactggc   2460
cttccgacag ggctgactga gaatcagtca ggtggccctt tgggagtgga cagcccatct   2520
gctgagttag ataagaaggc gaatctcctg aagtgcgagt actgtgggaa gtacgccccc   2580
```

```
gcagagcagt tcgtggctc taagaggttc tgctccatga cttgcgctaa gaggtacaat    2640
gtgagctgta gccatcagtt ccggctgaag aggaaaaaaa tgaaagagtt tcaagaagcc    2700
aactatgctc gcgttcgcag gcgtggaccc cgccgcagct cctctgacat tgcccgtgcc    2760
aagattcagg gcaagtgcca ccggggtcaa gaagactcta gccggggttc agataattcc    2820
agttatgatg aagcactctc tccaacatct cctgggcctt tatcagtaag agctgggcat    2880
ggagaacgtg acctggggaa tcccaataca gctccaccta caccggaatt acatggcatc    2940
aaccctgtgt tcctgtccag taatcccagc cgttggagtg tagaggaggt gtacgagttt    3000
attgcttctc tccaaggctg ccaagagatt gcagaggaat tcgctcaca ggagattgat    3060 ggacaggccc ttttattact taaagaagaa catcttatga gtgccatgaa catcaagctg    3120
ggccctgccc tcaagatctg cgccaagata aatgtcctca aggagaccta aggtggccct    3180
cttgcacaaa ccagcctaag gcagacactc tccactgtcc aggttataac ctggtaccag    3240
cagactttgc agggaagaaa gagttgttcc aatcatgtaa ccttctgtag gggattactg    3300
agacagggaa gagaagtgca agaattggtt gctggtgcta catggcggca gctttgacat    3360
tttctctggg ttctacttta tttttaaaa tctttacagt tctcaccatt tcacgtacct    3420
taatccaatc tttataaaag aggcagtcta gagaactagg actgctcagc cttatcctgg    3480
agtggagcat ttagcccagg tcttaattct ccaagaggag gaatacatag tatggtaagg    3540
caaggaactg ggtggaatgt caggttgcct gcccaatggg agaggtaggg tttttctagc    3600
ttgtgtgaca gaagtagcaa aatctggtcc tccccctcc cagtgtagct gtggctcaga    3660
gttttttctt tttgttgtca cttactccct tgtgattgaa tttttttctcc tgcatccatg    3720 gcaggatccc cagccagtat agagacttgg ttggcatctt ctgctgcagg gactaaaagt    3780
atttgactgg ggcacatgtg gctgttgtca ttctttctgc atcccactgt tccctccaa    3840 tttatgttat tttctaccct gtttttcagt tccatctctg ctctgtccta tagctttata    3900
aaaccagagt gtgtggggct gaggtcagga gtataagtac ctgccttagg cactattcct    3960
tatataacaa aaatattaaa tatttttttc ctcagtaaaa ggatgaaaat tggtttcagt    4020
tgtcttactc tattccagtc tttgcccact ttcacacaaa tgacaaggcc aatatgtttt    4080
gtttgttttt taatcattaa gagttttgt acaaaaggtg atggttttt ttcttcattt    4140 taaacacca gggtgtgggg gagggatgca aacaaataac aaaaaagatg cttttgtaac    4200
attattttcc ctgtttagaa agaaaaaat cactccaata gtattgaaaa gtccaaagat    4260
gaaatagttt cattttcttt tcctaaggct tataaaaggc cccctgcctg ttgattccat    4320
ccctcttttg tgtccagtgg agccatgtta ctcttcagtg gcccagggt tcactattaa    4380 agaaagatca gtccaggttt ctgggcacat ggcctaaaca ggaagatgga agcatcagag    4440
gattaaaaac ctttccccac agaaatgtgg gcaagaagac acttccctga gccagcagaa    4500
gggacaggtg cagcagcatt ccacacccag cgcagaggac agcagagccc tcgatgtccc    4560
acttctgctt ccgttccctt tctagaagat tgaaaaaaag gtcaaaacca catgcctgtg    4620
gagaaagtgc gacatgttta gaaatactgg tagggaacca ggagtaagaa aagctttacc    4680 agctttact acaaatggat gaaagacatc aggatcccac caccgcaagg taaagtgact    4740
tcccttttct ggaacccctg tggcacagga gtaccaattt tcctttccaa cgaactggat    4800
ttctggatag gcattttggc tgtatgtgga cagataagac cacagtcctt agcccaatcc    4860
cagctataca gtcaccccaa tttccacaaa tgatgtgatg gtaccgtata atcctgtaat    4920
```

-continued

| | |
|---|---|
| tgggaaattt cacattttc ctgtcctaat ctcagaggtg ggagaagcaa gtctagaaca | 4980 |
| tctccaggct cagactaaac gagagtactt ggactgcaac caagtaatca ctgcaaagta | 5040 |
| gttccaagca gcaagaaata ccagattctc atggaggcta ctatagggta cagaataaca | 5100 |
| acatgaaagc aatcaaccct gtataaataa tgtttcttgg catttttttt ttaattaaag | 5160 |
| aaatccagtg tctcaaaaaa aaaaaaaaa aaaaaaaaa aaaaa | 5206 |

<210> SEQ ID NO 62
<211> LENGTH: 3873
<212> TYPE: DNA
<213> ORGANISM: Homo sapiens

<400> SEQUENCE: 62

| | |
|---|---|
| catctgcctg cccttctgcc atccgagcgc cctgactgcg ccacactgca ggccatggag | 60 |
| aatgagctgc cagtcccaca tacatctagc agtgcctgtg ccaccagcag taccagcggg | 120 |
| gccagtagca gcagtggctg caacaacagc agcagtggtg gaagtggccg ccccaccggg | 180 |
| ccccagattt ctgtgtacag tggtattcca gaccggcaga ccgtgcaggt gatccagcag | 240 |
| gccctgcaca gacagcccag cacggccgct cagtacctgc agcagatgta cgccgcccag | 300 |
| cagcagcacc tcatgctgca gaccgcggcg ctccagcagc agcacctcag cagcgcccag | 360 |
| ctccagagcc tggcagccgt acagcaggca agcctggtat ccaatagaca aggaagcact | 420 |
| tcaggcagca atgtgtctgc gcaggccccg gcccagtcat cttcgatcaa cctggcagcc | 480 |
| tccccagcag cagcccagct cctcaaccgg gcccagagtg tgaactctgc agcagcctca | 540 |
| ggcatcgctc agcaggctgt gctcttgggc aacacgtctt ccccagccct gactgcaagc | 600 |
| caagcacaga tgtatctgag ggcacagatg ctcatcttca cgcccacggc caccgtcgct | 660 |
| actgtgcagc ctgagctcgg cactggctcc ccgccccggc cccccacccc cgcccaggta | 720 |
| cagaacttga ccctccgaac acagcagaca ccagcggcag cagcctcggg ccccaccccc | 780 |
| actcagcctg tcctgcccag cttggccctg aaacccacgc cgggcggtag ccagcctctg | 840 |
| cctacccag cacagagcag aaatactgct caggcttccc ctgcaggtgc caagcctggc | 900 |
| atagctgaca gtgtgatgga gccacacaag aaaggagatg caacagcag tgtgccaggg | 960 |
| agcatggaag gccgggctgg gctcagccgg acggttcctg ctgtggctgc ccaccccctc | 1020 |
| attgcaccag cctatgctca gctgcagcca ccagctcc tcccacagcc atcctcaaag | 1080 |
| cacctgcagc cccaatttgt gatccagcag cagccacagc cacaacagca gcagccgccg | 1140 |
| ccccagcagt cacggcctgt gctccaagct gagcccacc cccagctcgc ctcagtctct | 1200 |
| ccaagcgtgg ccctccagcc cagctcagag gccatgcca tgccactagg cccggttaca | 1260 |
| cccgccctgc cactccagtg tcccactgcc aacctgcaca gcctggcgg cagtcagcag | 1320 |
| tgtcaccctc ccacacctga tactgggcct cagaatggac atcccgaggg cgtgccccac | 1380 |
| accctcaac gcaggttcca gcacacttca gctgtcatct tacaactgca gcctgcttca | 1440 |
| ccaccccagc agtgtgtccc tgatgactgg aaagaagtgg caccagggga gaaaagtgtg | 1500 |
| cctgagacgc ggtctggccc atcaccacat cagcaggcta ttgtcactgc catgcctggt | 1560 |
| ggcctgcctg tacccacgag ccctaacatc cagccgtccc cagctcacga gacagggcag | 1620 |
| ggcattgttc atgcactgac cgacctcagc agccccggca tgacctcagg aacggaaac | 1680 |
| tctgcctcca gcatcgccgg cactgccccc cagaatggtg agaataaacc accacaggcc | 1740 |
| attgtgaaac cccaaatcct gacgcatgtt atcgaagggt tgtgatcca ggagggggcg | 1800 |
| gagcctttcc cggtgggacg ctcgtccctg ctggtgggga atctcaagaa gaagtatgca | 1860 |

```
caggggttcc tgcctgagaa acttccacag caggatcaca ccaccaccac tgactcggag    1920
atggaggagc cctatctgca agaatccaaa gaggagggtg ctcccctcaa actcaagtgt    1980
gagctctgtg gccgggtgga ctttgcctat aagttcaagc gttccaagcg cttctgttcc    2040
atggcttgtg caaagaggta caacgtggga tgcaccaaac gggtgggact tttccactca    2100
gaccggagca agctgcagaa ggcaggagct gcgacccaca accgccgtcg ggccagcaaa    2160
gccagtctgc caccacttac caaggatacc aagaagcagc aacaggcac tgtgccccctt    2220 tcggttactg ctgctttgca gctaacacac agccaggaag actccagccg ttgctcagat    2280
aactcaagct atgaggaacc cttgtcaccc atctcagcca gctcatctac ttcccgccgg    2340
cgacaaggcc agcgggacct ggagctcccc gacatgcata tgcgggacct ggtgggcatg    2400
ggacaccact tcctgccaag tgagcccacc aagtggaatg tagaagacgt ctacgaattc    2460
atccgctctc tgccaggctg ccaggagata gcagaggaat ccgtgccca ggaaatcgac    2520 gggcaagccc tgctgctgct caaggaggac caccctgatga cgccatgaa catcaagctg    2580 gggcccgccc tgaagatcta cgcccgcatc agcatgctca aggactccta gggctggtgg    2640
cagccaggat tctggcccag ggcgcctcct cccgactgag cagagccaga cagacattcc    2700
tgaggggccc agaaatgggg ccggttggag ggcagggct ctccctaggg gcatagctgg    2760
tgaggaggtc tgggcacctc ctccatggct ctcaggggcc tttcatttct gtgggagggg    2820
cagagaggta ggtggcacag aagatggggc tttatgcttg taaatattga tagcactggc    2880
ttcctccaaa gtcccaatac tctagccccg ctctcttccc ctctttctgt cccccatttt    2940 ccaggggta tatggtcagg gctccccaac ctgagttggg ttacttcaag ggcagccagc    3000
aggcctggat ggaggcctag aaagcccttg ccttccttcc tcccacttct ttctccaggc    3060
ctggttaact cttccgttgt cagcttctcc cccttcagcc tgtttctgca gcagccaggg    3120
ttctcccccc tacaccctct gcaggtggag agagagaagc tgggcccagc cgggccgtgc    3180
ctgctggcac agacgcctta cgctgtgtg tatgactgtg tgactgtgtg ggagcctgga    3240
ctgacagata ggccaagggc tactctctgg catctccagg tgttttgtag caaacagcca    3300
cttagtgctt tgtcctggac tccactcagc ctcaggatgg ggaatagcca agaatggcag    3360
cctcagcgca gaggcaaggt cagaaagaga cggcgcttca gagtttcctt tccagacacc    3420
cctccccgca ctgtgaagtt cccctgaccg ccctcctggt tcacaaagag cattaagaaa    3480
gctgcggtgg tctgagcaac atagcccaaa gggctgagcc tcctggcctg cctgcccgcc    3540
caccctggga gtcccagtgg tgaggctcag agaactgcta aggggaaaga acagctggag    3600
tttctgttga tgtgaagaag gcagctcttg gcctcccact cccacacttc tttgcctata    3660
aatcttccta gcagcaattt gagctacctg aggaggagc agggcagaaa gggcgagggc    3720
ctgcctctga cctgccgtgt cctttgcagg aaggaggtag gcacctttct gagcttattc    3780
tattccccac ccacacccccc aggcagggtt ggaaatgaag gacttttttta acctttgttt    3840 tgttttttaa aaataaatct gtaaaatctg tct                                3873
```

<210> SEQ ID NO 63
<211> LENGTH: 12687
<212> TYPE: DNA
<213> ORGANISM: Homo sapiens

<400> SEQUENCE: 63

```
atgcgcagcc catgttagtg atggaggaga gaagatggcg gaagcggaat ttaaggacca     60
```

| | |
|---|---|
| tagtacagct atggatactg aaccaaaccc gggaacatct tctgtgtcaa caacaaccag | 120 |
| cagtaccacc accaccacca tcaccacttc ctcctctcga atgcagcagc cacagatctc | 180 |
| tgtctacagt ggttcagacc gacatgctgt acaggtaatt caacaggcat tgcatcggcc | 240 |
| ccccagctca gctgctcagt accttcagca aatgtatgca gcccaacaac agcacttgat | 300 |
| gctgcatact gcagctcttc agcagcagca tttaagcagc tcccagcttc agagccttgc | 360 |
| tgctgttcag gcaagtttgt ccagtggaag accatctaca tctcccacag gaagtgtcac | 420 |
| acagcagtca agtatgtccc aaacgtctat caacctctcc acttctccta cacctgcaca | 480 |
| gttaataagc cgttcccagg cttccagttc taccagcggc agtattaccc aacagactat | 540 |
| gttactaggg agtacttccc ctaccctaac ggcaagccaa gctcaaatgt atctccgagc | 600 |
| tcaaatgctg attttcacac ccgctaccac tgtggctgct gtacagtctg acattcctgt | 660 |
| tgtctcgtcg tcatcgtcat cttcctgtca gtctgcagct actcaggttc agaatttaac | 720 |
| attacgcagc cagaagttgg gtgtattatc tagctcacag aatggtccac caaaaagcac | 780 |
| tagtcaaact cagtcattga caatttgtca taacaaaaca acagtgacca gttctaaaat | 840 |
| cagccaacga gatccttctc cagaaagtaa taagaaagga gagagcccaa gcctggaatc | 900 |
| acgaagcaca gctgtcaccc ggacatcaag tattcaccag ttaatagcac cagcttcata | 960 |
| ttctccaatt cagcctcatt ctctaataaa acatcagcag attcctcttc attcaccacc | 1020 |
| ttccaaagtt tccatcatc agctgatatt acaacagcag caacagcaaa ttcagccaat | 1080 |
| cacacttcag aattcaactc aagacccacc cccatcccag cactgtatac cactccagaa | 1140 |
| ccatggcctt cctccagctc ccagtaatgc ccagtcacag cattgttcac cgattcagag | 1200 |
| tcatccctct cctttaacag tgtctcctaa tcagtcacag tcagcacagc agtctgtagt | 1260 |
| ggtgtctcct ccaccacctc attcaccaag tcagtctcct actataatta ttcatccaca | 1320 |
| agcacttatt cagccacacc ctcttgtgtc atcagctctc cagccagggc caaatttgca | 1380 |
| gcagtccact gctaatcagg tgcaagctac agcacagttg aatcttccat cccatcttcc | 1440 |
| acttccagct tcccctgttg tacacattgg cccagttcag cagtctgcct tggtatcccc | 1500 |
| aggccagcag attgtctctc catcacacca gcaatattca tccctgcagt cctctccaat | 1560 |
| cccaattgca agtcctccac agatgtcgac atctcctcca gctcagattc caccactgcc | 1620 |
| cttgcagtct atgcagtctt tacaagtgca gcctgaaatt ctgtcccagg gccaggtttt | 1680 |
| ggtgcagaat gctttggtgt cagaagagga acttccagct gcagaagctt tggtccagtt | 1740 |
| gccatttcag actcttcctc ctccacagac tgttgcggta aacctacaag tgcaaccacc | 1800 |
| agcacctgtt gatccaccag tggtttatca ggtagaagat gtgtgtgaag aagaaatgcc | 1860 |
| agaagagtca gatgaatgtg tccggatgga tagaacccca ccaccaccca ctttgtctcc | 1920 |
| agcagctata acagtgggga gaggagaaga tttgacttct gaacatcctt tgttagagca | 1980 |
| agtggaatta cctgctgtgg catcagtcag tgcttcagta attaaatctc catcagatcc | 2040 |
| ctcacatgtt tctgttccac cacctccatt gttacttcca gctgccacca caaggagtaa | 2100 |
| cagtacatct atgcacagta gcattcccag tatagagaac aaacctccac aggctattgt | 2160 |
| taaaccacag atcctaaccc atgttattga aggctttgtg attcaggagg gattggagcc | 2220 |
| atttcctgtg agtcgttcct ctttgctaat agaacagcct gtgaaaaaac ggcctctttt | 2280 |
| ggataatcag gtgataaatt cagtgtgtgt tcagccagag ctacagaata atacaaaaca | 2340 |
| tgcggataat tcatctgaca cagagatgga agacatgatt gctgaagaga cattagaaga | 2400 |
| aatggacagt gagttgctca agtgtgaatt ctgtgggaaa atgggatatg ctaatgaatt | 2460 |

-continued

```
tttgcggtca aaacgattct gcactatgtc atgtgccaaa aggtacaatg ttagctgttc    2520
taaaaatttt gcacttagtc gttggaatcg taagcctgat aatcaaagtc ttgggcatcg    2580
tggccgtcgt ccaagtggcc ctgatggggc agcgagagaa catatcctta ggcagcttcc    2640
aattacttat ccatctgcag aagaagactt ggcttctcat gaagattctg tgccatctgc    2700
tatgacaact cgtctgcgca ggcagagcga gcgggaaaga gaacgtgagc ttcgggatgt    2760
gagaattcgg aaaatgcctg agaacagtga cttgctacca gttgcacaaa cagagccatc    2820
tatatggaca gttgatgatg tctgggcctt catccattct ttgcctggct gccaggatat    2880
cgcagatgaa ttcagagcac aggagattga tggacaggcc cttctcttgc tgaaagaaga    2940
ccatctcatg agtgcaatga atatcaagct aggcccagcc ctgaagatct gtgcacgcat    3000
caactctctg aaggaatctt aacaggaaca tgaagccttg ataaaacagc agttttactt    3060
ttctcacaaa aacttgtaag gtaaaggcct aacttggtct agaatatgac acttattgtg    3120
gtggatagcc aagcacattg ggatctccac atcaaatact gacatttctt ctacaggtat    3180
aataattcat catgcatttt cataattaat aaacattggt aaaattaatt ttacaggtta    3240
catgaaacat tgaaagactt gttacagagg gccatgatat ttttcaaaga aatgtgttat    3300
actagataat ttttttaaag gtgatgttta tcattaatat aaagaatcct tttaaaagta    3360
atttaatgat ttacatttct cctcttttga ttcaattttc ttatacattt tttctaccct    3420
attagttttc taaaggttgt catgagaggt atattatgga ataatttagt agtccagtga    3480
cagaatcgta tgaaatcagt gtacatttta aaaaacatgt cttttagaca tatgctttat    3540
ctataaaaaa ggaattgtgt tctagtatga acaatactga tctggaagtg agaagagtta    3600
gtttctattc caaacttgac caagaatttg gtttgactga gaacgttttc ctctcagttt    3660
ttgtacattt atttagagca gtggttctca gtggaggtca gttttgatcg ccaggggaca    3720
tctggcaatg ttgagacatt ttggttgtca cagcttgggg gtgggttcag gggagggttg    3780
ctactggtgt ctagtagtta gaagccagag atgtttctaa acatcttata atgcacagga    3840
cagcacccct ccactgtaaa gaattattgg ttcaaaaata tcggtactgc caaggttgag    3900
aaactctgat atagaaggag tgataaatat tgttttcacc caaaggaata cttttaaagg    3960
atgaagctta ctaaacatat atgatggaag tattattcag ataacattaa tattctgctg    4020
aataattttt tctagtttaa tcatactaga aaaagaaaaa aaatctacaa attgtcctat    4080
aaaataagga caaacatgca aataatttaa ctctcagaaa gtactaattc attctgatta    4140
tctttcatac ctctgtgctc ctctgcactg acgaagacat aatatgatta tacctatgaa    4200
ctagtgcaca gccttttctg gcaagaaaat agtttgtagc agatacgtgg ttgctctttg    4260 gattttttc tattgttgaa catgctggga ctagctagaa tgcacattcc tacttccttt    4320
accaaacgtt tgcatgcttc ctgcaaagca cttaccaagt gatttctctt gaaccatcgg    4380
atataatttt gtatgtacat gtttgaggaa aaaaatgtaa agcaaaacct tttactgaac    4440
agtgttctat agaattatga cactaaaaca aaattgtttg tggaagccct gaaagcttta    4500
tagtcctgga catcaaaaat tttatttgag atgatgaatg ttttgttttc atctttcctt    4560
atattaccac aattgagata ttttagtaat tgaaggaaca tacacagata tttggcagaa    4620
gtcgagtaag gaggggaaaa aaagagtccg tgagtttcag tcattttcac tgctcttttc    4680
aaaaagattg tgttgagctg gtagaagact aaagatgtca ctgaagacat cacagatact    4740
atatttatct tttggctttg tgtacattag agaatgttga ttatttttat acaaaaatac    4800
```

```
agcgggtaat ttttttaatc tttagatgcc tcttgtttga atgtatgctt tgtggaattc    4860
tttgtgtagt aatgttttaa aaaaagatgt ttactgatag ttacatgtag gattagaata    4920
tgtaatataa tataaggctc atgttccaga cctacgatag cttgtagtct atgttacgta    4980
tttctttata tcacattttt aatcattgga ttaaagtatc aaggaaagct aggtactcta    5040
taatgagttt tcatttatta gcagttaatc atcatgacag aattgtcata tgcttgactt    5100
ttccctcttc ttggaatttc agaacacaaa tacaggctaa gcattagtaa gagatggccc    5160
acagtatgag agagagaggt gcaacggaaa atctcgcctg gaattaaaac ttttcataga    5220
ttatccacgg ttaatacaaa atttattata tggggataga ctgctccagc aataatgatt    5280
acatcctata actgtattac ctatggcctt taaggtatca attttgaact gtgttgtagg    5340
ctctcctttt atttgttctc tttcctaata gcagccattc tgtacttatt gaaagcccct    5400
gtgcctactg ctgtcttaag tattcaggag gggcttacaa gagggttttc tattggagaa    5460
taccgtataa tcttaaatct agtccagatc tctgttgtcc ccactcaaaa catacacaaa    5520
atatgcactt gctttttca agtgagtttt tatttaaaaa tggcttgttt gctatcacat    5580
tggtgcagct gtttctttca agatgagtta atcatcttaa tttcaaagct tcagctatat    5640
ataatggata tatagacaac actgagcatc cacctctctc ctgagcttta aagcagagtt    5700
tcagtatgat ataggtgggg agagtaaatt gttttcatat cctttcatac tactactaat    5760
agttttagga ttttgactgg ggagagataa tgacaaacag aaagggaaca tggaggttct    5820
tcctactttt gctacctaag tttgcatttt ctgacttcct tgcagtgttg cactctttgt    5880
cccattggga taaaaagcat aagtttgaaa ttttgcttta agccttgtgt tcctggggaa    5940
gttaaacaac taagagagct gatttgtaaa aattattttt tatatgacat taatattcat    6000
caagccttgt gtaggcatgt gtaagacaca gctatgcagc tttgagtagt caatatagta    6060
tgagatagag tgttgtccca atcctcctg tcacttttta agtagcatat tatttccctg     6120
atggtcctgt tactttgctg ttgaatgctc taaacagaac tttttaaaag gtgtgtttta    6180
agagcagtca cctaggagta gacaaggtgg aatgggagga gagaaatggt aatgcaaaag    6240
cttgagcatg ggaagagtca gaggaggagg ccatcatcct tgttagctta gcctacttca    6300
acactgagca catttctgca cttttgaagt gaaattcatg ttttacttag aagaaataat    6360
tttctttcat tagggatccc agttgatttt tgtttcctgg tgtatcaaaa tacttagaac    6420
tatgaaacaa gtattattgt gatcatgcct ttgaataatt tttgacgtag cttatcttca    6480
tgtatcaagt ataaaattat aatgagacat ctattcacaa atacaagtct tagattgaat    6540
tgaaatgtgt tatagtgccc tgtctcccac tgacttgttc agttaaatgt cttaaagtac    6600
attatgtaca tcttcaggct tttggtacca caatggcaca agtatggtag ggaggcaata    6660
tagtcttagg ctatatgcct atattaagtg tgtataaaca atttttgaaa gaatacacta    6720
ttatagatgt atgtgagtga tgctgacctg acagccatat ccagtggatg aaactgactg    6780
gacacactgt taaaatgttt taaagatgta ttttcagcca gaacagcctg gttatagttt    6840
gtggttttca ccttggtgga ttgcaggaac acatgcagcc tactggcatt gagcattagc    6900
taatggcatg aaagggcctc atctcactac ctctctaagg cctctagctc caagaaaacc    6960
atgaaaactt cttcttgga gagatctttg tctcagaatc cttagagagg atttcgtatg     7020
ggggctaact ttaggaaggg aggcagctgg ggcaggactt tctgatacct gacagtcatg    7080
ttccagagca acctttgggc agtggaaact ggcgcatcta tgcaaaatga ttgctcaatc    7140
tctatcttgt gtactacata tgtaactagc tgggccctaa ggaaggtttt ctaggggaa     7200
```

```
ggatagggaa gtagaggagg agacaagtag gaggaacaaa gcattctaga cccaagagga   7260
tagaagatat ttaggataga tatggctttc atccatagtt caaaataatg cgttttgtta   7320
gatgccagtt atagcagtaa ataggttata gttttatat gtcaagattt acctgtaatc    7380
agactcattc tttcactctc tatacccact gtctccatgc ttgggagcat ggatattaat   7440
agttccagtg atgtagaagt tagtgatttt tgatttctga aaaggtgag aacctttat     7500 tacagttgga gaatatttgt caaaaattca aaggttgttg taattgagtt gccagaatta   7560
cagagtttcc attttcagat atcacagttg aatcacctct gtagattgtt ataaagagag   7620 gcatttaag atagtatttt atttgctagg ttgtgtctca gtctaagaat tgggaaaaga    7680
agagctatag gtttctcttt cctagtctgg atttcagtaa acacaagcct acctctgctt   7740
ctttggttca cagcagtgtg gatcatgaaa tgaactgttt acccacattc atcaatattg   7800
gtattttaca aatctacttg gagcatttaa tttcatctca aagattgtga tccactttag   7860
ataagcacaa atacagtatt aggaaaagta aatatgcaat cttactaaaa tttcaacttg   7920
ttaagctgta tatcttaaaa gaaattattt ggggctgggc atggtggctc acacctgtaa   7980
tcccagcact ttgggaggct gaggtgggta gatcacctga ggtcaggagt tcgagaccag   8040
cctgaccaat atggtgaaac cctatctcta ctaaaaacac aaaaattagc tgggtgtggt   8100
ggcatgcacc tgtaattcca gctacttggg aggctgagac aggagaattg cttgaaccca   8160
ggtggtggag gttgcagtga gccaagatca caccctgca ctccagcctg ggtgacagag    8220
cgagactcca tctcaaaaaa acaaaacaaa aaattatttg gaagatacg tcctctttta    8280 ttagaagttc ataaaatgta tcatatagtt ttgttcacag tagttatata agctttcttc   8340
aaataaattt aaaattagat taccttcttt ggaaaaagaa tttcctaaat ttttaagaat   8400
tttcaaagtt ttacatatta gttttagaa cctaatccgt tttaaaattg tactatgaga    8460
aagctttttt ttgaaagttg taaagcatta atacaaataa tacaaatata attattacca   8520
tcacattcca gagaatatgg cttttctaa actttcaatt tagaaaacat acattaaggg    8580
agaatctctg ccctccttt cagctctgaa gatcagcttt tctactcaga cacatgcaca    8640 cacccttcc aagtgtcatg tttatgggaa catttgggaa atgttttcca gatgttttat    8700
tttttccctt ttatagtttg ttgacattta attttactta aagatgacaa ttttaatcgg   8760
aaatgttaga ggtacaacat agtgaggttc tagctagctt tatactttg aaaaatattt    8820 ttgtttctac tgctttttac aagtactagt cctctcagtg atactggtgg tgttcagtat   8880
gaatccatag aaagaaaaca aaatttgttg tttaaaaaaa gcagagtaat gaatgaattt   8940
cagttttgaa acaacataa tttgaaaaca ctgttatact aacatggcaa ggtgttaatt    9000
aaatataaga gtaaggtagt aagttctttt agagcacctg tttaaattta ctccagtaat   9060
catcttaagg attgatagtc accatcactt attggcttaa aagttatatt tcatggaata   9120
ttatcagtgt taaatccaag ctttgtggag cttaagtga tggtggtgaa aaagttggtg    9180
tttatgagag agtggtgggg tgtctagtca ttagtgaagt taaacatcaa cctgttttag   9240
aaagaatttt ttagtcttgc ctaaagtaaa ccagaagtgt ctagtgttta aatctttatt   9300
tagaatgctt ctcttaaaag tattttttgt tttgggtagt attaaataat cagtaaataa   9360
tctatttcag tagtaaataa tgaattaaga tgatgatgaa tgaggattaa cacactggtc   9420
tggagactgg ggttttattt cagtgggtta gctgtgtgtg acatgttggg caattactca   9480
gctgttttaa cagcttccag atatgcagta tggtgcctgt actactcaaa agttgatttt   9540
```

```
ggtttaattc atctttaagg tacctcccag ctctaaaact atgattctag gctgtgtaat    9600
ggggttattc ctactttatt ctcttttcct ttttaagggt tcattttata cttaataagc    9660
atccatttct tgggtcacct acagtctttg ttctcctaag gattaaaata gaaaattcat    9720
acataacaag caaatgatga cattttccta aatgctcctt attggttaac cactgaatat    9780
atgaacacat atgaatattg tcattcatgt acttaaattc atttagcaaa ctatttgaac    9840
acttacatgt gcagtgtttg gtgaacatga catgaggaac tagtagtaag taaaatcttc    9900
cccccaaaat tcattgtggc ttaaataaat atgaacataa tcattactac ttaatatact    9960
gagagggaat cttaataaac ttggaactgg gagggaatat ttgtatacat tgggtaaagg   10020
gttaggctag atgacatcta aggggtctga gtgaatcata tcataatttt tataacacat   10080
ttcacatact aaacatcagt tggccccata cctgattaag ttacaaaatt taggagactt   10140
aacattaagg acttacaggt tgagacagcc cgtatttcac aacattattt tgacacttga   10200
ctctattcca gagttgttgc tatacaaggc atgtggcaga acaaaaaaaa agctggtgtt   10260
gatataagag cttttttaccc agtattgaca gtgagcaact ttctttcttt ttttttttt   10320 ttctttttt tttttttgag atgggttcgc tctgttgccc aggctggtgt gcagtggtgc   10380
gatctcagct cactgcaacc tccacctccc gggttgaagc gattgtcttg cctcagcctt   10440
ccaagtagct ggaattacag gtgcccgccg ccacacctgg ctaattttg tatttttagt    10500 agagacgggg cttcaccatg ttggccaggc tagtctcgaa ctcttgacct caagtgatcc   10560
acctgccttg gcctccctaa gtgctgggat tacaggcatg agccaccaca cctgtccgac   10620
agtgtagcaa ctttctaaaa ctgaaaaatc tcaaggaga tcattggaac tgacttgttc    10680 atttatttt tgttttttaaa ttaagaaaga ttacacaaaa taagtgttac tgtactttaa    10740
gctattacaa atatccaact tttaaagata tgtaagaatc agtaatattc tagaaagcac   10800
atatatagta aaagggcatc ctttaaatgt agaacgggta acatgaaac agttccatgc   10860 ttgaattgtt aagtatctag ggggtaaaca ttgaatggga gaatcattta ttgggttaag   10920
gtcccttcct tgtcattctg ggatctgtga atcacattgt aattcctgtt gacaaagctt   10980
tacttgttaa catcagttga tactgacatt ctccataaag atatagaatg aaaatatcta   11040
ttaaaaatag tttatcattg ttttagcttt tttgttttgt ttgttttgag acagagtctc   11100
actgtcaccc aggcttgagt gcagcggtgt gatcttggct caatgcaacc tccacctccc   11160
aggttcaata gattctccca ccttggcctc ccaagtagct gggattactg gcatgcacca   11220
ctatgcctgg ccagtttttt gtatttttag tagagatggg gtttcaccat gttggccagg   11280
ctggactcga actcctgacc tcaagtgatc cgcccacctc agcctcccaa agtgccggga   11340
ttataggcat gagccactgc gcctagcctg ttgcagcttt ttaaagcagg aaaatatcca   11400
tataaactgt tgggttagaa tctatattag aatctttcaa actaattgaa acaggaaga    11460 ctatcatcta gtagccaga taatctgggt ttcaaaaagt tattccatgg tactggttta    11520
aaaaatactt ttcaagtgtt ttaattttta aagtgtaact aattcttcaa atatgttatg   11580
ctgttaaaat atgtattcca taagtacttt ttgtatatgt attcttaaat tttaaaagt    11640 caactgaatg cgcaaagatg atataatttt ggatgtagac atttaaacta gattcccagt   11700
cctctccttc aaaagcttgg tctttgtttt tcctataggg aaaaagtca aataagttc     11760 caaaaactat cctcaaagta gtattgtgct tgtagtaaat gaaggttgga tggatggata   11820
ctgacaatgg tggcaggcat ttcaagccct ttaaattagt acttttgtc gtcttgctta    11880 ttaaaatttt gttaatttta gcaaagacca attgttgtga taaactggtg ttttttggat   11940
```

```
gcttcaagca cacgttaacc aatttttaa  ttccccttt  ggttcctccc attgttctaa    12000
aataggactt tcatattatt aaaacctcaa agatgatcc  acccaggatg aacaaagatc    12060
accaagggga agaaaacat  tttttatctt tacagaaaac atgttaagat tatatataga    12120
tgtattcttt acattggata ttgtattaga gtcctcctta caagaaatga aatagttttt    12180
agcactctta gcattagagt tcctagattg gtgttgatag ctacagtttt aaaatgtata    12240
acctgaaaat gaaggttaat tttgcattgt aagagcacat ttgatctatg taaaaagtgt    12300
ccatttggtg tattttttta aaaagagaa  agcactttca tattaagtag catgtgtatg    12360
aatttagatt ttcatatttg ttgtgtctgt attcagtgaa gtaaattgag catttaaatg    12420
tttgttgatg gcaacattaa ctattaaatt aaagcacctt atactctgct gcttaacttg    12480
cttgtaattg cacctttgtt acctgcacat tttcatatag aatattgttg taacattgct    12540
tcatgtgggt ctggatggaa gattagtggg cctacaggat catttattta tattgtttat    12600
attacaataa tatattgtag atcagttgta agttcatttc tttacaaata aagcctctt    12660
ccatttgact ggaaaaaaaa aaaaaaa                                        12687

<210> SEQ ID NO 64
<211> LENGTH: 3435
<212> TYPE: DNA
<213> ORGANISM: Homo sapiens

<400> SEQUENCE: 64
acagcaacta tgaaataatc gtagtatgag aggcagagat cggggcgaga caatggggat      60
gtgggcgcgg gagccccgtt ccggcttagc agcacctccc agccccgcag aataaaaccg     120
atcgcgcccc ctccgcgcgc gccctccccc gagtgcggag cgggaggagg cggcggcggc     180
cgaggaggag gaggaggagg ccccggagga ggaggcgttg gaggtcgagg cggaggcgga     240
ggaggaggag gccgaggcgc cggaggaggc cgaggcgccg gagcaggagg aggccggccg     300
gaggcggcat gagacgagcg tggcggccgc ggctgctcgg ggccgcgctg gttgcccatt     360
gacagcggcg tctgcagctc gcttcaagat ggccgcttgg ctcgcattca ttttctgctg     420
aacgactttt aactttcatt gtcttttccg cccgcttcga tcgcctcgcg ccggctgctc     480
tttccgggat ttttttatcaa gcagaaatgc atcgaacaac gagaatcaag atcactgagc     540
taaatcccca cctgatgtgt gtgctttgtg gagggtactt cattgatgcc acaaccataa     600
tagaatgtct acattccttc tgtaaaacgt gtattgttcg ttacctggag accagcaagt     660
attgtcctat ttgtgatgtc caagttcaca agaccagacc actactgaat ataaggtcag     720
ataaaactct ccaagatatt gtatacaaat tagttccagg gcttttcaaa aatgaaatga     780
agagaagaag ggattttat  gcagctcatc cttctgctga tgctgccaat ggctctaatg     840
aagatagagg agaggttgca gatgaagata agagaattat aactgatgat gagataataa     900
gcttatccat tgaattcttt gaccagaaca gattggatcg gaaagtaaac aaagacaaag     960
agaaatctaa ggaggaggtg aatgataaaa gatacttacg atgcccagca gcaatgactg    1020
tgatgcactt aagaaagttt ctcagaagta aaatggacat acctaatact ttccagattg    1080
atgtcatgta tgaggaggaa cctttaaagg attattatac actaatggat attgcctaca    1140
tttatacctg gagaaggaat ggtccacttc cattgaaata cagagttcga cctacttgta    1200
aaagaatgaa gatcagtcac cagagagatg gactgacaaa tgctggagaa ctggaaagtg    1260
actctgggag tgacaaggcc aacagcccag caggaggtat tccctccacc tcttcttgtt    1320
```

```
tgcctagccc cagtactcca gtgcagtctc ctcatccaca gtttcctcac atttccagta    1380
ctatgaatgg aaccagcaac agccccagcg gtaaccacca atcttctttt gccaatagac    1440
ctcgaaaatc atcagtaaat gggtcatcag caacttcttc tggttgatac ctgagactgt    1500
taaggaaaaa aattttaaac ccctgattta tatagatatc ttcatgccat tacagctttc    1560
tagatgctaa tacatgtgac tatcgtccaa tttgctttct tttgtagtga cattaaattt    1620
ggctataaaa gatggactac atgtgatact cctatggacg ttaattgaaa agaaagattg    1680
ttgttataaa gaattggttt cttggaaagc aggcaagact ttttctctgt gttaggaaag    1740
atgggaaatg gtttctgtaa ccattgtttg gatttggaag tactctgcag tggacataag    1800
cattgggcca tagtttgtta atctcaacta acgcctacat tacattctcc ttgatcgttc    1860
ttgttattac gctgttttgt gaacctgtag aaaacaagtg cttttatct tgaaattcaa    1920 ccaacggaaa gaatatgcat agaataatgc attctatgta gccatgtcac tgtgaataac    1980
gatttcttgc atatttagcc attttgattc ctgtttgatt tatacttctc tgttgctacg    2040
caaaaccgat caaagaaaag tgaacttcag ttttacaatc tgtatgccta aaagcgggta    2100
ctaccgttta ttttactgac ttgtttaaat gattcgcttt tgtaagaatc agatggcatt    2160
atgcttgttg tacaatgcca tattggtata tgacataaca ggaaacagta ttgtatgata    2220
tatttataaa tgctataaag aaatattgtg tttcatgcat tcagaaatga ttgttaaaat    2280
tctcccaact ggttcgacct ttgcagatac ccataaccta tgttgagcct tgcttaccag    2340
caaagaatat ttttaatgtg gatatctaat tctaaagtct gttccattag aagcaattgg    2400
cacatctttc tatactttat atactttct ccagtaatac atgttactt taaagattgt    2460 tgcagtgaag aaaaaccttt aactgagaaa tatggaaacc gtcttaattt tccattggct    2520
atgatggaat taatattgta tttttaaaaat gcatattgat cactataatt ctaaaacaat    2580
tttttaaata aaccagcagg ttgctaaaag aaggcatttt atctaaagtt attttaatag    2640
gtggtatagc agtaatttta aatttaagag ttgcttttac agttaacaat ggaatatgcc    2700
ttctctgcta tgtctgaaaa tagaagctat ttattatgag cttctacagg tattttaaa    2760 tagagcaagc atgttgaatt taaaatatga ataaccccac ccaacaattt tcagtttatt    2820
ttttgctttg gtcgaacttg gtgtgtgttc atcacccatc agttatttgt gagggtgttt    2880
attctatatg aatattgttt catgtttgta tgggaaaatt gtagctaaac atttcattgt    2940
ccccagtctg caaagaagc acaattctat tgctttgtct tgcttatagt cattaaatca    3000
ttacttttac atatattgct gttacttctg ctttctttaa aaatatagta aaggatgttt    3060
tatgaagtca caagatacat atatttttat tttgacctaa atttgtacag tcccattgta    3120
agtgttgttt ctaattatag atgtaaaatg aaatttcatt tgtaattgga aaaaatccaa    3180
taaaaaggat attcatttag aaaatagcta agatctttaa taaaaatttg atatgaaaag    3240
cacaatgtgc agaagttatg gaaacctat agaggattac aacaggtaaa cgttaaagag    3300
aatacattgc tgacttatag tgatgtggct aagaagtaca tgctttgttg taaaattgct    3360
tgaaagccca ttgaaagatg tatctgttta tttacagtct ttgaagtaaa agttaccaat    3420
gtttgccaat aaaaa                                                    3435
```

<210> SEQ ID NO 65
<211> LENGTH: 2622
<212> TYPE: DNA
<213> ORGANISM: Homo sapiens

<400> SEQUENCE: 65

```
tctccctcc cgccgcccgg gcgagcgaca cggctgcggc ccccctcccc tcccttccct      60
ccctccctcc catccccccc tccccgagac ccaccggacc ccgaacccag atggccgaaa    120
cgggctcccc gtcttaacga tttggcgtct ccctcgacca ccacctcttt gtgcagcagc    180
ccccgggcag accctgttcc gagggcaacg ctccccagtc cccccacccc cgaccccgga    240
atcatgcatc ggactacacg gatcaaaatc acagagctga accccaccct catgtgtgcc    300
ctctgcgggg ggtacttcat cgacgccacc actatcgtgg agtgcctgca ttccttctgc    360
aaaacctgca tcgtgcgcta cctggagacc aacaaatact gccccatgtg tgacgtgcag    420
gtccataaaa cccggccgct gctgagcatc aggtctgaca aaacacttca agacattgtc    480
tacaaattgg tccctgggct ttttaaagat gagatgaaac ggcggcggga tttctatgca    540
gcgtaccccc tgacggaggt ccccaacggc tccaatgagg accgcggcga ggtcttggag    600
caggagaagg gggctctgag tgatgatgag attgtcagcc tctccatcga attctacgaa    660
ggtgccagga accgggacga gaagaagggc cccctggaga tggggatgg ggacaaagag    720 aaaacagggg tgcgcttcct gcgatgccca gcagccatga ccgtcatgca tcttgccaag    780
tttctccgca acaagatgga tgtgcccagc aagtacaagg tggaggttct gtacgaggac    840
gagccactga aggaatacta caccctcatg gacatcgcct acatctaccc ctggcggcgg    900
aacgggcctc tcccctcaa gtaccgtgtc cagccagcct gcaagcggct caccctagcc    960
acggtgccca cccctccga gggcaccaac accagcgggg cgtccgagtg tgagtcagtc   1020
agcgacaagg ctcccagccc tgccaccctg ccagccacct cctcctcct gcccagccca   1080 gccaccccat cccatggctc tcccagttcc catgggcctc cagccaccca ccctacctcc   1140
cccactcccc cttcgacagc cagtggggcc accacagctg ccaacggggg tagcttgaac   1200
tgcctgcaga caccatcctc caccagcagg gggcgcaaga tgactgtcaa cggcgctccc   1260 gtgccccct taacttgagg ccagggaccc tctcccttct tccagccaag cctctccact   1320
ccttccactt tttctgggcc cttttttcca cctcttctac tttccccagc tcttcccacc   1380 ttggggggtgg ggggcgggtt ttataaataa atatatatat atatgtacat aggaaaaacc   1440
aaatatacat acttattttc tatggaccaa ccagattaat ttaaatgcca caggaaacaa   1500
actttatgtg tgtgtgtatg tgtggaaaat ggtgttcatt ttttttgggg ggggtcttgt   1560
gtaatttgct gtttttgggg gtgcctggag atgaactgga tgggccactg gagtctcaat   1620
aaagctctgc accatcctcg ctgtttccca aggcaggtgg tgtgttgggg gccccttcag   1680
acccaaagct ttaggcatga ttccaactgg ctgcatatag gagtcagtta gaatcgtttc   1740
tttctctccc cgtttctctc cccatcttgg ctgctgtcct gcctctgacc agtggccgcc   1800
ccccacgttg ttgaatgtcc agaaattgct aagaacagtg cctttacaa atgcagttta   1860 tccctggttc tgaggagcaa gtgcagggtg gaggtggcac ctgcatcacc tcctcctctt   1920
gcagtggaaa ctttgtgcaa agaatagata gttctgcctc ttttttttt tttcctgtgt   1980 gtgtggcctt tgcatcattt atcttgtgga aaagaagatt caggccctga gaggtctcag   2040
ctcttggagg agggctaagg ctttagcatt gtgaagcgct gcaccccac caaccttacc   2100 ctcaccgggg aaccctcact agcaggactg gtggtggagt ctcacctggg gcctagagtg   2160 gaagtgggggg tgggttaacc tcacacaagc acagatccca gactttgcca gaggcaaaca   2220
gccttccaat tgcccctcca cccccagctg aggcccggtc acctggtcag gacagagcaa   2280
ctgcatctaa aagcacaaga agacagaaac ctgtaagctc tgaccccacc cccacccctt   2340
```

-continued

| | |
|---|---|
| gagaggtcag cggaccacct ccttagggac agaccctggc aggtcgctgc ccaccgagat | 2400 |
| ttcctcaagt gtgcatagat ctgagaggag tcgggagtcg agactcgaga ttccatcata | 2460 |
| gcgtaggtgt gtggggttgg gagcccctg atgggcttgt ctgtgtttgc accttgtcct | 2520 |
| gtgtctgagg tcctgtgact gtaccctcct ttgccctggg acatctgtat ctcttggctt | 2580 |
| tgtaataaat gctgcatact ttctaaaaaa aaaaaaaaaa aa | 2622 |

<210> SEQ ID NO 66
<211> LENGTH: 2248
<212> TYPE: DNA
<213> ORGANISM: Homo sapiens

<400> SEQUENCE: 66

| | |
|---|---|
| cgaactgtga tggcggcggc cgcggtgatg ggcccggcgc agatcctctg tggttgttga | 60 |
| attgtaacaa gagagagaac tctggctgcc tgagagggca tgactctagt cacagcagga | 120 |
| ggggcttgga caggccctgg ttgttggcat gaagtgaagg atgaagagtc atcttctgaa | 180 |
| cagagcattt ctatagcagt gtcacatgtt aatacttcca aggcaggttt gcccgcacag | 240 |
| acggctctcc cttgtgacat atgtggcccc atcttgaaag atattttgca cctggatgaa | 300 |
| caccagggta cacaccatgg actgaaactt cacacatgtg gggcatgtgg agacaattc | 360 |
| tggttcagtg caaaccttca tcagtaccag aagtgttaca gtatagagca cccttaaga | 420 |
| agggataaaa gtgaggcctc aattgtgaag aactgcacag ttagcaaaga acctcatccg | 480 |
| tcagagaagc cctttacgtg taaggaggag cagaaaaact tccaggctac tttgggtggc | 540 |
| tgccaacaaa aggccatcca cagtaagagg aagacacaca ggagcactga gagtggggat | 600 |
| gcatttcatg gtgaacaaat gcattacaag tgcagtgaat gtgggaaagc tttcagccgc | 660 |
| aaagacacac ttgtccagca ccagagaatt catagtggga gaagcctta tgagtgcagc | 720 |
| gaatgtggga aagccttcag ccgcaaagct acacttgtcc agcatcagag aatccatact | 780 |
| ggagaaaggc cttatgaatg cagcgaatgt ggaaaaacct tcagtcgaaa agacaacctt | 840 |
| actcagcaca gagaatccca cactggagaa atgccttata gtgcaatga atgtgggaaa | 900 |
| tattttagcc atcactccaa tctaattgta caccagagag ttcacaatgg agcaaggcct | 960 |
| tataagtgca gtgattgtgg gaaagtcttc agacacaaat ctacacttgt tcagcatgag | 1020 |
| agtattcaca ctggagaaaa tccttatgat tgcagtgatt gtgggaaatc ctttggccac | 1080 |
| aaatacaccc tcattaaaca tcagcgaatt cacactgagt caaagccgtt tgagtgcatt | 1140 |
| gaatgcggga aattctttag tcgaagttct gactatattg caccagagag ggttcacact | 1200 |
| ggtgaaaggc cttttgtgtg cagtaaatgt gggaaagact ttatcagaac ctcccacctt | 1260 |
| gttcgacacc aaagagttca cactggagaa aggccatatg agtgcagtga atgtgggaag | 1320 |
| gcctacagct taagctccca cctcaatcgg caccagaaag ttcacactgc aggcaggctt | 1380 |
| taggagtgct ttgaatacaa caggactcat caatcagatg ttgaatttca tgtatctgaa | 1440 |
| cattgacaca aaggagatac cttatggtgc caggtacgtg ggaaccttct agggatatgt | 1500 |
| tgcactttct gacttgctca ggttttttgc cagagttatg tcactgtcaa tccatgtggc | 1560 |
| cgaaaccatc ttaactctac cagctaagat accccagcat ggggaaggc agggttttgt | 1620 |
| attgtccagt ccctggagaa aatcatgaaa tgcctgagtt cattgggggt cctcattccc | 1680 |
| ttctgtatga caggtatagg tatgggatatg acccattttt agccaagagg gtctgagctg | 1740 |
| tatctgctgg tggcttatac aaaaagttta ctttcttcat ggatattctt ggtctcacat | 1800 |
| acttgtaatc aagttttttcc agcctccaag tcacctggcc tgggaaagta cttgcctcat | 1860 |

| | |
|---|---|
| gttgctctgg tttgtgataa taaaggcttt acagtttaag ccacatttaa tcttggggct | 1920 |
| tcttcttatg gtctggggtg gattgaaaac aggctctgcc aaactgaaga cagcctttgt | 1980 |
| gcggtgcctc caactttgcc tcaaatggga cagtgggttg agggagaaca gttcttagtc | 2040 |
| cagttttgat gttaacttcc atagctgaca aagcttgtta agtaagaatt aagatcttgt | 2100 |
| gtagacctga tttgtctgga ttttagagtt atttgagagc ccatatttca ccttgaggag | 2160 |
| ggtgctgctg ctgtgacagc ctgcagtgtt ttgaaacagc atggattggg tgtcttgttt | 2220 |
| gcagcatgtg tcccatgttc cccaacac | 2248 |

<210> SEQ ID NO 67
<211> LENGTH: 1744
<212> TYPE: DNA
<213> ORGANISM: Homo sapiens

<400> SEQUENCE: 67

| | |
|---|---|
| cagcgcccgg gccatggcgg cggcggtggc gggagctgct gtctgagcag cggttgcgga | 60 |
| ccgagcgaac ttggcccagg agcccgggcc tagggagagg cgcggcggcg gcgggagcgc | 120 |
| gaacggctgg agctggcctt cttcgccttc tcctcggctg tggagccctg gtgggggtc | 180 |
| tgcgcccggt caccatgacg acgccggcga atgcccagaa tgccagcaaa acgtgggaac | 240 |
| tgagtctgta tgagctgcac cggaccccgc aggaagccat aatggatggc acagagattg | 300 |
| ctgtttcccc tcggtcactg cattcagaac tcatgtgccc tatctgcctg acatgctga | 360 |
| agaatacgat gaccaccaag gagtgcctcc acagattctg ctctgactgc attgtcacag | 420 |
| ccctacggag cgggaacaag gagtgtccta cctgccgaaa gaagctggtg tccaagcgat | 480 |
| ccctacggcc agaccccaac tttgatgccc tgatctctaa gatctatcct agccgggagg | 540 |
| aatacgaggc ccatcaagac cgagtgctta tccgcctgag ccgcctgcac aaccagcagg | 600 |
| cattgagctc cagcattgag gaggggctac gcatgcaggc catgcacagg gcccagcgtg | 660 |
| tgaggcggcc gataccaggg tcagatcaga ccacaacgat gagtgggggg aaggagagc | 720 |
| ccggggaggg agaaggggat ggagaagatg tgagctcaga ctccgcccct gactctgccc | 780 |
| caggccctgc tcccaagcga ccccgtggag ggggcgcagg ggggagcagt gtaggacag | 840 |
| ggggaggcgg cactggtggg gtgggtgggg gtgccggttc ggaagactct ggtgaccggg | 900 |
| gagggactct gggaggggga acgctgggcc ccccaagccc tcctgggggc cccagccccc | 960 |
| cagagccagg tggagaaatt gagctcgtgt tccggcccca ccccctgctc gtggagaagg | 1020 |
| gagaatactg ccgacgagg tatgtgaaga caactgggaa tgccacagtg gaccacctct | 1080 |
| ccaagtactt ggccctgcgc attgccctcg agcggaggca acagcaggaa gcagggagc | 1140 |
| caggagggc tggaggggc gcctctgaca ccggaggacc tgatgggtgt ggcggggagg | 1200 |
| gtgggggtgc cggaggaggt gacggtcctg aggagcctgc tttgcccagc ctggagggcg | 1260 |
| tcagtgaaaa gcagtacacc atctacatcg cacctggagg cggggcgttc acgacgttga | 1320 |
| atggctcgct gaccctggag ctggtgaatg agaaattctg gaaggtgtcc cggccactgg | 1380 |
| agctgtgcta tgctcccacc aaggatccaa agtgaccccca ccaggggaca gccagaggaa | 1440 |
| ggggaccatg gggtatccct gtgtcctggt ctatcacccc agcttctttg tcccccagta | 1500 |
| ccccccagccc agccagccaa taagaggaca caaatgagga cacgtggctt ttatacaaag | 1560 |
| tatctatatg agattcttct atattgtaca gagtggggca aaacacgccc ccatctgctg | 1620 |
| cctttttctat tgccctgcaa cgtcccatct atacgaggtg ttggagaagg tgaagaaccc | 1680 |

| | |
|---|---|
| tcccattcac gcccgcctac caacaacaaa cgtgcttttt tcctctttga aacctgcaaa | 1740 |
| aaaa | 1744 |

<210> SEQ ID NO 68
<211> LENGTH: 3551
<212> TYPE: DNA
<213> ORGANISM: Homo sapiens

<400> SEQUENCE: 68

| | |
|---|---|
| gcgcctccgc ccctcgctcg ctcgctcctt cccgccctcc ccgcagcgcc ggccgagccg | 60 |
| gcttcccctc agtctctcat gaatattgag cggcccctgt tgtatttccc gagctccatt | 120 |
| gcggaagctg aggctcgcca tattgtgcgg cggcgccggc gtccgcggca gctgatacca | 180 |
| gagtcttgct ccggccgcgg ccagcggagc cctgggctgg ggcaggagcc gcaatgtctc | 240 |
| aggctgtgca gacaaacgga actcaaccat taagcaaaac atgggaactc agtttatatg | 300 |
| agttacaacg aacacctcag gaggcaataa cagatggctt agaaattgtg gtttcacctc | 360 |
| gaagtctaca cagtgaatta atgtgcccaa tttgtttgga tatgttgaag aacaccatga | 420 |
| ctacaaagga gtgtttacat cgttttgtg cagactgcat catcacagcc cttagaagtg | 480 |
| gcaacaaaga atgtcctacc tgtcggaaaa aactagtttc caaagatca ctaaggccag | 540 |
| acccaaactt tgatgcactc atcagcaaaa tttatccaag tcgtgatgag tatgaagctc | 600 |
| atcaagagag agtattagcc aggatcaaca agcacaataa tcagcaagca ctcagtcaca | 660 |
| gcattgagga aggactgaag atacaggcca tgaacagact gcagcgaggc aagaaacaac | 720 |
| agattgaaaa tggtagtgga gcagaagata atggtgacag ttcacactgc agtaatgcat | 780 |
| ccacacatag caatcaggaa gcaggcccta gtaacaaacg gaccaaaaca tctgatgatt | 840 |
| ctgggctaga gcttgataat aacaatgcag caatggcaat tgatccagta atggatggtg | 900 |
| ctagtgaaat tgaattagta ttcaggcctc atcccacact tatggaaaaa gatgacagtg | 960 |
| cacagacgag atacataaag acttctggta acgccactgt tgatcactta tccaagtatc | 1020 |
| tggctgtgag gttagcttta gaagaacttc gaagcaaagg tgaatcaaac cagatgaacc | 1080 |
| ttgatacagc cagtgagaag cagtatacca tttatatagc aacagccagt ggccagttca | 1140 |
| ctgtattaaa tggctctttt tctttggaat tggtcagtga gaaatactgg aaagtgaaca | 1200 |
| aacccatgga actttattac gcacctacaa aggagcacaa atgagccttt aaaaaccaat | 1260 |
| tctgagactg aacttttta tagcctattt ctttaatatt aaagatgtac tggcattact | 1320 |
| tttatggaca gatcttggat atgttgttca attttctttc tgagccagac tagtttacgc | 1380 |
| tattcaaatc ttttcccctt tatttaagat ttccttttg gaagggactg caattattca | 1440 |
| gtattttttt ctttccttta aaaaaatata tctgaagttt cttgtgtttt ttttttccc | 1500 |
| cacaaagtgt gtttccactt ggagcaccat tttgacccag gaattttca tagtttctgt | 1560 |
| attcttataa gattcagttg gctgtccttt tcctgctccc ctcaaaagat ttttagtcat | 1620 |
| acagaatgtt aaatattatg tattctgact ttttttttcc cccggagtct tgtatattta | 1680 |
| tagttttcta tataaactgt agtatcttca tgaagaccca aggctcaaat ttactgtcct | 1740 |
| taaaaacaat tctcatagga ttattctttt catggtattt tcttccataa tatctcatt | 1800 |
| taaaagaag ttctttatga acttagtgtc cattgtcatg caatgttttt ttttttccat | 1860 |
| tcttttccc tgtaatttg gaatttctgg tcctgggaag aatcaaacaa aatcttaagt | 1920 |
| tctatgagaa cttggttcat tgacatattc tgctgaagaa agaaaaatta aattggtagt | 1980 |
| aaaatatagt cttcaagtat acgtttgaga gtgcttttt ttgtattagt tctgctgtca | 2040 |

```
cttcatttcc tgtattatat gtgatgtttt tccccattaa aataccagag ataatggaga    2100
tattttgcac tttagccttg atgaaaagta caagatatgt tcaaagcttc cctaattttt    2160
ttcttatttg tagccacata agtttcaaga ataacatggc acacagaaca atggaaaaaa    2220
gtttgttttcc attggaaaat tatatcattt gggttgcca catcagttta taaatttggc    2280
gctcttttaa ttacactctg tagaaggtta atagagcttg agccctgctt taatatgtag    2340
tgaaagataa ttctgtagaa aaacgtcagc cagtagggta aagtcattct actgttctta    2400
atttttatat tgaggaacaa tattgggtgt ttgggagcca gaaagctttg ttgacagatc    2460
agaaataaga ttgacttggg tgttatattt catctctctc cagactctag gtatatttcc    2520
aactttatat atcacagtat ttaaaaagac atgtttgcat tgagaaatta accctaaagg    2580
gttttcaata gggtgtagac ctccagtacc tttgtaacta aagtctgtct agtcattgta    2640
aatatttatc tgtcagtttt gacagattgg ggccagcttg atgttttaaa tcttcagccc    2700
ggtatgaaaa cttaaaggta tatattcaat ttttaccat tttatggaaa atatttaaaa    2760
tctgttttta cagggttttt tttttttttt ttttttgta atctgtgcca tgaaatttga    2820
aaaccaccaa aaatcaaggg aacttttata tattcaattc cttttctggt gtaatgttaa    2880
agttgtatag attattaatg catgcccact gaatataacc ctggttttgt gataaaactg    2940
cttagatttt gttgatgaca ttagattagt agttgcatta aataactaaa ttcccattgt    3000
gattaattga aattttgtct ttaagcagag agttatttgt gactataagc tttgtgctta    3060
gagaatgtat gtgttttat ctgtcagtat gggaggatat aaactgcatc attagtgaaa    3120
ttattggttg tgtaatcctt tgtgaaatat aattctaggt atttgatagg gtattgagtg    3180
tattttgtgt gtgtgtggat gtgtgttttg gggtacgggg agaggcgatg ctattggcca    3240
tcactaccaa ccagggtttc aaaaagtatt acctaagtaa tttctttat cactatctca    3300
actgaggaag aaaaggctca ccacaagtgg tgtgaaggct ttgggtactt agttctaaat    3360
tttttatgg taacatatac atagccacat ttacagtttt aaccatttta aggcatgtaa    3420
ttcagtgggg ttaggtacat tcacaatgtt gtgtaatgat caccgctgtc tacttgtaaa    3480
acttttcat cacccaaac agaaactctg tgtgcaatta agtaatgca tttctcttct    3540
tcttaaccccc t    3551
```

<210> SEQ ID NO 69
<211> LENGTH: 2312
<212> TYPE: DNA
<213> ORGANISM: Homo sapiens

<400> SEQUENCE: 69

```
ctccctcccc ccgccgcct cctcctcctg ccgctgccgc tgctttggct gctgcgtcat      60
acgccccaga gccgccggga cggaggggct gggcctgggg acccccggc ctccgcctgc     120
acgcccccc acgcccggac gtgccctctc cgcgcggggg actcgcctag gtctcctacg     180
tctgcccctg cccggctccc ggcggcccca gctgtcaccg gccccccag gatgcaatgg     240
cgcagccccc ccggctgagc cgctctggtg cctcctcact ttgggaccca gcttctcctg     300
ctcccacctc tggccccagg cctcggcttt ggagggtca agatgtgctg ccagatgga      360
ctgatgggct gctatacttg ggtaccatca aaaaggtgga cagtgctagg gaggtgtgtc    420
tggtccagtt tgaggatgat tcgcagtttc tggttctatg gaaagacatt agccctgctg    480
ccctccctgg agaggaactc ctctgttgtg tctgtcgctc tgagactgtg gtccctggga    540
```

```
accggctggt cagctgtgag aagtgtcgcc atgcttatca ccaggactgc catgttccca    600
gggctccagc ccctggagag ggagagggca catcctgggt atgccgccag tgtgtctttg    660
cgatcgccac caagagggga ggtgccctga agaagggccc ctatgcccgg ccatgctgg     720
gtatgaagct ttctctgcca tatggactga aggggctgga ctgggatgct ggacatctga    780
gcaaccgaca gcagagttac tgttactgtg gtggccctgg ggagtggaac ctgaaaatgc    840
tgcagtgccg gagctgcctg cagtggttcc atgaggcctg cacccagtgt ctgagcaagc    900
ccctcctcta tggggacagg ttctatgaat ttgaatgctg tgtgtgtcgc ggggggccctg   960
agaaagtccg gagactacag cttcgctggg tggatgtggc ccatcttgtc ctgtatcacc   1020
tcagtgtttg ctgtaagaag aaatactttg attttgatcg tgagatcctc cccttcactt   1080
ctgagaattg gacagtttg ctcctggggg agctttcaga caccccccaaa ggagaacgtt   1140
cttccaagct cctctctgct cttaacagcc acaaggaccg tttcatttca gggagagaga   1200
ttaagaagag gaaatgtttg tttggtctcc atgctcggat gcctccccct gtggagcccc   1260
ctactggaga tggagcactc accagcttcc cttcagggca gggccctggg ggaggggtct   1320
cacgtcccct ggggaagcgc cggaggccgg agccagagcc cctgaggagg aggcagaagg   1380
ggaaagtgga ggagctgggg ccaccctcag cagtgcgcaa tcagcccgag ccccaggagc   1440
agagggagcg ggctcatctg cagagggcac tgcaggcctc agtgtctcca ccatccccca   1500
gccctaacca gagttaccag ggcagcagcg ctacaactt ccggcccaca gatgcccgct   1560
gcctgcccag cagcccatc cggatgtttg cttccttcca cccttctgcc agcaccgcag   1620
ggacctctgg ggacagtgga cccccagaca ggtcacccct ggaacttcac attggtttcc   1680
ccacagacat ccctaaaagt gccccccact cgatgactgc ctcatcttcc tcagtttcat   1740
ccccatcccc aggtcttcct agacgctcag caccccctc tcccctgtgc cgtagtttgt   1800
ctcctgggac tgggggagga gtccgaggtg gggttggtta cctgtcccga ggggaccctg   1860
tccgggtcct tgctcggaga gtacggcctg atggctctgt gcagtacctg gttgagtggg   1920
gaggaggggg catcttctga acagcctgcc tctgcccagc tccccattca cacacaccgg   1980
cactttcata ccctgacctc tgacctcacc tacagctggg atgtacctgg agagatagg   2040
ggtagttctc cctactgccc aggctggaat ccaagagtgg ggagtgggga agaggccctc   2100
ttctctaccc tccttcatga ttcctgaccc ctcccatcct tcccatttcc tttgatgtta   2160
ttttgttaca gcttttaaa tatttttaa aattatttaa cccctggggg cagagactga   2220
ggagggagga tgataaggga tcccggactc tgtatgattg aaataaagag aaataaacaa   2280
atctagcagc tctgaaaaaa aaaaaaaaaa aa                                 2312
```

<210> SEQ ID NO 70
<211> LENGTH: 4144
<212> TYPE: DNA
<213> ORGANISM: Homo sapiens

<400> SEQUENCE: 70

```
gctgccattc ggcaccggag tcgctccgcg ctcccagaat gcaccggcag tccgcgggaa     60
accaaaatgg cgaggggctg tattgaagtg ggctgtgttt gaggccggtg taagaacgct    120
cattctaccc ccaacccttg tctccaagga cctcggtttg tgcgtgcata tgtgccgggt    180
acccggtggg gcgggtgccc agtaagtgct cggactcgca ggggaagcgc ccacggggac    240
ggattggttg tttttttcctg tatgaagcgg ttggcaccac tgaagtgacc gaatgagaga    300
ctctacaggg gcaggtaatt cactggtcca caagcggtct cctttacgtc gaaaccaaaa    360
```

-continued

```
gaccccaaca tccttgacca agctgtctttt acaggatgga cataaagcca aaaagccagc    420
atgtaaattt gaagagggtc aggatgtcct agctagatgg tcagatggct tgttttatct    480
tggcactatc aaaaagataa acatattgaa acagagctgc ttcatcatat ttgaagacag    540
ttctaaatcc tgggttctct ggaaggacat tcaaacagga gccactggaa gtggggaaat    600
ggtctgtaca atatgtcaag aagagtattc agaagctccc aatgaaatgg ttatatgtga    660
caagtgtggc caaggatatc atcagttgtg tcacacacct catattgatt ccagtgtgat    720
tgattcagat gaaaaatggc tctgtcggca gtgtgttttt gcaacaacaa caaagagggg    780
tggtgcactt aagaaaggac caaatgccaa agcattgcaa gtcatgaagc agacattacc    840
ctatagtgtg gcagaccttg aatgggatgc aggtcataaa accaatgtcc agcagtgtta    900
ctgctattgt ggaggccctg agactggta tttgaagatg ctacagtgct gcaaatgtaa    960
gcagtggttt catgaggctt gtgtgcaatg ccttcaaaag ccaatgctat ttggagacag   1020
attttatacg tttatatgct ctgtctgcag ttctggacca gaatacctca aacgtctacc   1080
attacagtgg gtagatatag cacacctatg cctttacaac ctaagtgtta ttcataagaa   1140
gaaatacttt gattctgaac ttgagcttat gacatacatt aatgaaaact gggatagatt   1200
gcaccctgga gagctggcag acacaccaaa atctgaaaga tatgagcatg ttctggaggc   1260
attaaatgat tacaagacca tgtttatgtc tgggaaagaa ataaagaaga gaagcatttt   1320
gtttgggttg cgaattcgtg ttcctcctgt gccaccaaat gtggctttca aagcagagaa   1380
agaacctgaa ggaacatctc atgaatttaa aattaaaggc agaaaggcat ccaaacctat   1440
atctgattca agggaagtaa gcaatggcat agaaaaaaaa ggaaagaaaa aatctgtagg   1500
tcgtccacct ggcccatata caagaaaaat gattcaaaaa actgctgagc cacttttgga   1560
taaggaatca atttcagaga tcctactttt ggatttacct tgttctatag ggagaactga   1620
gggaactgca cattcatcca atacctcaga tgtggatttc acgggtgctt ccagtgcaaa   1680
agaaactacc tcgtctagca tttccaggca ttatggatta tctgactcca gaaaaagaac   1740
gcgtacagga agatcttggc ctgctgcaat accacatttg cggagaagaa gaggtcgtct   1800
tccaagaaga gcactccaga ctcagaactc agaaattgta aaagatgatg aaggcaaaga   1860
agattatcag tttgatgaac tcaacacaga gattctgaat aacttagcag atcaggagtt   1920
acaactcaat catctaaaga actccattac cagttatttt ggtgctgcag gtagaatagc   1980
atgtggcgaa aaataccgag ttttggcacg tcgggtgaca cttgatggaa aggtgcagta   2040
tcttgtggaa tgggaaggag caactgcatc ctgactgtag gactgaacat tatgttcact   2100
gcactctgat tttctgtagg tacagttcaa agccctaaag gagtctggct tttactatct   2160
ttcttaaaaa aaaaaaaaag tcaaaaaaat tcaaaaaagg ggatgatact agccttaaca   2220
tgtacctgtc aatgttatgg atattgtcat aaaaaggtat cttttaaaaa tcagaacaga   2280
gacttaatttt tttaaatctt aagatttgta gaatgtttct aggataggat attaaaaatg   2340
attgaaaccc atgcatggtg ttagacaatt tttctaatta ttccattgag tcagtttttt   2400
gtgattagtg attatcagag caaacatcat gtagatagca caagtatttg gagaaacgtt   2460
gtttgttttg ttaccaaaat gttggaaaaa tttatttcaa tacctttag atttcataaa   2520
gtgcagtgta tataatgcct actgaaagac tgtaaaatat tgaaattttc tttcaagcaa   2580
agtgtaaaaa aatatattga gcctgtaaat tgctctgtga ctagacttca ttgtcgtctt   2640
aatatattct tgcatgtgca tatatataca cacgtgtata tatatgtgtg tgattatgtg   2700
```

| | |
|---|---|
| acctatgcaa tacaaattat gggaatgggc agctttggag tatatatccc ataattcttt | 2760 |
| tttcaggaat agttgcagta tttacacagc agcatttctt ctcaggcttt tattgggtgc | 2820 |
| tgttgcttgc tatgtatgaa gagaaatgtg tcagacaagt ttagtgtgtt ctgaagaagg | 2880 |
| gtgtgaacaa cagtgttcat gggcttttag aatgcttttc acttttagtc cttgtaactc | 2940 |
| agctgttcag tacctaaaac aaattcaaat aatatgaaca ttatctccta ctagaagtaa | 3000 |
| cgttttcaag ttttcatggc acattatgat tgtaaatgtc tctcattttt aacagtaagt | 3060 |
| ctataggagt cccgtgaaga ttcctgaaat gtctgtagta actgttagtc atgtttgaat | 3120 |
| aagtgtagta tgaacaaagt attttattgc acagggttaa caaacagtat gttgccagct | 3180 |
| gaggctactg ctgttttatt acaacattac ctcttgtttt tataaagtgt accaagattt | 3240 |
| aaattgataa cttatttta cttgtaaaaa aaagtttct tttatcacca gtgttacagt | 3300 |
| tgtcttctgt ttcttttttgt tttgttttat ttgttttcct ttttagccaa agagtgaaca | 3360 |
| gaagattttc ttattttggt ggctattcat tttacttta aaagtgattg gtggatttta | 3420 |
| gactaattat gggggaattt gccaccaaaa taaaaaatat gtaaagtgta gtgattacag | 3480 |
| agtggtaaaa atgtgggtta gtacttattt attccattaa ttgattattt gactgtttat | 3540 |
| aaagaaagtt gctttatttc tttaaacatc ttcaaaagat gatcctttct tgtcacatta | 3600 |
| tagccaaaag aagcagagaa cttcattgtc tgcatttggt tcctggttgg ccaggtataa | 3660 |
| atgagcttta caaaagtgca aattaaaaac tgttacttct gttacctcc accaaaactt | 3720 |
| gattttcccc tagctattaa tttaaggttg cctttcctgc agctgcaata ttttgaataa | 3780 |
| cacacagagt ttgtgttgat ttttgaatgt ttgtttatat ctaggggtaa tgaaaaatgt | 3840 |
| aaatcccgtg tatccttatt cactccacct gtatcatatt atttcatttt ccccaaagtc | 3900 |
| ctttaattct aactgaacac cagcagtatt tttagaaatt tttctttaac atacttggaa | 3960 |
| gatgatttat ccagctgaac tgtctttaga cgtaattatt gtgaatgtct gttttatttt | 4020 |
| ctcatggtgg ttcacatggc tctgatgttc agtttgtatt tttggaattg ctttacttag | 4080 |
| aaattaaaac agaccaacat taaatgtgtg tatttttaa agagctaaaa aaaaaaaaaa | 4140 |
| aaaa | 4144 |

<210> SEQ ID NO 71
<211> LENGTH: 4181
<212> TYPE: DNA
<213> ORGANISM: Homo sapiens

<400> SEQUENCE: 71

| | |
|---|---|
| accagtaagt cgtgtattta gcattcattc atcaaagcct ccggatgcct cctacgtgcc | 60 |
| ctgcactatg ctggtcttgg taatccgtgg tccctatccc agcgcccagt gtcaggggaa | 120 |
| gctgatggag aatcgagctc tggatccagg gactcgggac tcctatggtg ccaccagcca | 180 |
| cctccccaac aaggggggccc tggcgaaggt caagaacaac ttcaaagact tgatgtccaa | 240 |
| actgacggag ggccagtatg tgctgtgccg gtggacagat ggcctgtact acctcgggaa | 300 |
| gatcaagagg gtcagcagct ctaagcaaag ctgcctcgtg actttcgaag ataattccaa | 360 |
| atactgggtc ctatggaagg acatacagca tgccggtgtt ccaggagagg agcccaagtg | 420 |
| caacatctgc ctagggaaga catcagggcc gctgaatgag atcctcatct gcgggaagtg | 480 |
| tggcctgggt taccaccagc agtgccacat cccatagcg ggcagtgctg accagcccct | 540 |
| gctcacacct tggttctgcc gacgctgcat cttcgcactg ctgtgcggaa aaggcggcgc | 600 |
| gctgaagaag ggcgccatcg ccaggacgct gcaggccgtg aagatggtgc tgtcctacca | 660 |

```
gcccgaggag ctcgagtggg actcgcccca tcgcaccaac cagcagcaat gctactgcta    720
ctgcggcggg cccggagaat ggtacctgcg gatgctgcaa tgttaccggt gcaggcagtg    780
gttccacgag gcctgcaccc agtgcctcaa tgagcccatg atgtttggag accggtttta    840
cctgttcttc tgctccgtgt gtaaccaggg cccagagtac atcgagaggc tgcccctgcg    900
atgggtggat gtggttcacc tggccctcta taatctgggg gtacagagca agaagaagta    960
ctttgacttt gaggagattc tggcctttgt caaccaccac tgggagctcc tgcagcttgg   1020
caagctcacc agcaccccag tgacagatcg aggaccacat ctcctcaacg ctctgaacag   1080
ttataaaagc cggttcctct gcggcaagga gatcaagaag aagaagtgca tcttccgcct   1140
gcgcatccgc gtcccaccca acccgccagg gaagctgctg cctgacaaag gactgctgcc   1200
aaatgagaac agcgcctcct ctgagctgcg taagagagga aagagcaagc tggtttgtt    1260
gcctcacgaa ttccagcagc agaaaaggcg agtttataga agaaaaagat caaagttttt   1320
gctggaagat gctattccca gtagtgactt cacctcagcc tggagcacca accaccacct   1380
ggctagcata tttgacttca cgctggatga aattcaaagt ttaaaaagtg ccagctcagg   1440
ccagaccttc ttctcagatg tcgactccac cgacgctgcc agcacctctg gctctgcctc   1500
caccagcctc tcctatgact ccagatggac agtgggcagc cgaaagagga agctggcagc   1560
caaggcatac atgcccctgc gggcaaagcg gtgggcagct gagctggatg gacgctgccc   1620
ctcggacagc agtgcagagg gggcttcagt ccccgagcgg ccagacgaag gcattgacag   1680
ccacacattt gagagcatca gtgaagatga ctcatccctg tcccacctca agtcatctat   1740
caccaactac tttggtgcag ctgggcggtt ggcctgtggg gagaagtacc aggtgttggc   1800
tcggagggtc acacctgagg gcaaggttca gtacctggtg gagtgggaag ggaccacccc   1860
ttactgacta gcccccgggg gtgccagggg tcctgaaaac caaaggagga gcagcagaag   1920
ccataggctc cccagctttc tccaggctgg ggtgggagaa ggaagcagga cagagctgca   1980
agtgcctggc agaatgccct gcctgcctgc ctgccaggcc aaggcctgcg tctctctgct   2040
gtaccagctc tgttccaggg cctcctcagg ctcgttaccc ctgtgcctgt gtctctacac   2100
actccacacc ccctcaaact ctgtttatct gttctctgac cttgtgtccc ctgcgctggg   2160
acccttcctc ctgaggccca ggtctttgtc cccagttgtg tgccttgacc tctctcgccc   2220
cttttctgggt gtgttcgcac atcctgtgtg tgcacagctg tccctccact ggatcccctt   2280
cacacgtgac ccgtggggca gccagtcctc ccagggacta cataacaggc acctttgaga   2340
gagcatggga gaaggtggat aagaggatgc tgctcagtgc ttttctcttc cactttcctg   2400
ccactcccca ctaccctcgg agagaggtgg tgggatggga gagagcccct gtgaaagcct   2460
gtgaggatct gaagagtaaa gggctgggtc tgcctcagaa ggcaccagca ccagggccca   2520
ggtattaagg ctgagagtga aggctgccaa tgtcagcttt ggaggtccca gaagtcttct   2580
gttctctggc tcacccccct cagtcgccat agagctgggc ctggccttgc tggaatggag   2640
gcatccttcc aaacctgggg gacggggggtg ggggtggta gtggtgggag ggaaaccatg   2700
tcttgctaaa cctgtttctg gtgcctccca tccccagacc caccagacac cacacagcag   2760
acaatacaca cccactcgca caagcttcca tccacatgtg ttgtactttc agctctaggc   2820
atgcagacaa ccccacacgg ccacaccacc acatgcccaa gtgtacacac acagagccac   2880
accgtccctc tgggcctgct ggctcctccc ttggcttttcc cttggcccac ttccagggcc   2940
caggtgctgc aactaaatgt gaaagctcag tggccgctcc ttctttcagc ccatcaacca   3000
```

| | |
|---|---|
| gcattggtcc cataggaag cacaggggac tcaccctctt tcatatccct tgccctgccc | 3060 |
| tgaaatggac aatcactttt tgggataggt tgaaatttt aaagagcctg catcatttgg | 3120 |
| ttccctcaaa gggaagccct tgccagtggg ggtttgaaag agaattttg gaaccaacat | 3180 |
| tcaaattctg cctcatctgg agggaaacca aaattgggag ggggaagagg acccctgatg | 3240 |
| ttttgctgct tccagagata ttagaaactg actcacttga ttggaaaatg acaaaagtg | 3300 |
| ccttgacgtg gagggtgggc accagatggg gaccagcctt gccaactgct gctgtggcct | 3360 |
| ccagcttggc tggttttgca ggccgccagc aggaaggcga aggtggtagt acagcaagag | 3420 |
| gcactggcgg ggcagcaggc ctgcaggagc tgttttccca ttgctaggcc tgaccctct | 3480 |
| ctacctgtga gcgttcaggg ggtccctgag atagtttaga tgcccccca tcttagacct | 3540 |
| cagctcccac agtgccttt aagggggacc tcacctcctg tgcacagccc acccactttc | 3600 |
| ctctgcttcc ctggcacagc ccaggcatag acgagctggc gttggaccca gttcttcccc | 3660 |
| cttttcagcc ccacagctgc tgccacaggg gccaactagg gccaggtgga aggggagctg | 3720 |
| agaagccaac ccctagccca ggggtgctgt gggaactggg atccaatttg tagcttcctg | 3780 |
| cctggcttca gagagcccag caaccttcta ggcctgcttt ccagacttct gagatagcct | 3840 |
| gggatgagca atcctgttat agtacatctg gaccttccct acctgggctc tggggaggct | 3900 |
| gtgggcctgg agagggaaaa ggagggaggg ggtgtctgca ccacctggga agatagcaca | 3960 |
| aggcctaatg aggtcaccct gactccccac cccagcatt cattcatacc agataatagc | 4020 |
| tgcattactg ccaactgacc ttataaccct ctgcaccttc aaaaagattc atggttttta | 4080 |
| attgctgctt ttaataacat ttgttaaagt tataattaat gtgtctgatt tatgatttaa | 4140 |
| aacctccctt tgaacaatca aaaaaaaaaa aaaaaaaaa a | 4181 |

<210> SEQ ID NO 72
<211> LENGTH: 5935
<212> TYPE: DNA
<213> ORGANISM: Homo sapiens

<400> SEQUENCE: 72

| | |
|---|---|
| agtggtgttt ggtgcgcgcg ccggggaggt ggtggtgggg gggcgccgcc gccgccaccg | 60 |
| ctgcggggcc gggtctcgcg ctgccgctgc cgccgcctcg cgccgctgag gtgccgcgcg | 120 |
| aggtgggggg aggggagcc gctcgccggg agcggtgtaa atgagcaaag atggatcagg | 180 |
| aaggtggggg agatgggcag aaggccccga gcttccagtg gcggaactac aagctcatcg | 240 |
| tggatcctgc cttggaccct gccctgcgca ggccttctca gaaggtgtac cgctatgatg | 300 |
| gagtccactt cagtgtcaac gactcaaagt atataccagt cgaagacctc caagaccccc | 360 |
| gttgccatgt caggtccaaa aacagagact tttccctccc agtccctaag tttaagctgg | 420 |
| acgagttcta tattggacag attccactga aggaagtgac ttttgcaagg ctgaatgaca | 480 |
| acgtgcggga gaccttcctg aaggatatgt gccgtaagta cggtgaggtg gaagaggtag | 540 |
| agatcctcct tcacccccgt acgcgcaagc acctgggcct ggcccgtgtg ctcttcacca | 600 |
| gcactcgggg cgccaaggaa acggtcaaaa acctccacct tacctccgtc atgggcaaca | 660 |
| tcatccatgc ccagcttgac atcaaaggac aacaacgaat gaaatactat gaactaattg | 720 |
| tcaatggctc ctacacccct cagactgtgc ccactggggg caaggccctg agtgagaagt | 780 |
| tccaaggctc gggtgcagcc actgagacgg ccgaatcccg ccgccgctct tcctctgaca | 840 |
| cagctgccta cccagcaggc accactgcgg tgggcactcc tggcaacggc accccctgct | 900 |
| cccaggacac aagcttctcc agcagccgac aagataccc atcttccttt ggccagttca | 960 |

```
cacctcagtc ctcccaagga accccctaca cgtctcgggg cagcaccccc tactctcagg    1020
actctgccta ctccagcagc accacttcaa cctccttcaa gccccggcgg tcagagaaca    1080
gctaccaaga tgccttttcc cgccgccact tctctgcatc ttcagcctcc acaaccgcct    1140
ccacggccat cgccgccacc actgcagcca ctgcctcatc ctccgcctct tcctcctcat    1200
tgtcctcgtc ctcctcgtca tcctcttcct cctcgtcctc tcagtttcgt agttctgatg    1260
caaactaccc agcgtattat gaaagctgga atcgctacca cgccatact tcctacccac     1320 cacgccgggc cacacgggag gaacccctg gagcccttt tgctgaaaat acagctgagc      1380
gcttcccacc ttcttacacc tcctacctgc ccccgagcc cagccggccc accgaccagg    1440
actaccggcc tcctgcctca gaggctccac ccccggagcc tccagaacct ggtggaggcg    1500
ggggtggagg agggcccagc cctgagagag aagaagttcg acttcccccc cgcccagcct    1560
cccctgcccg ctctggctcc ccagccccgg agaccaccaa tgagagtgtg cccttcgccc    1620
agcacagcag cctggattcc cgcatcgaga tgctgctgaa ggagcagcgc tccaagtttt    1680
ccttcttggc ctctgacaca gaggaggagg aagagaacag cagcatggtc cttggggcca    1740
gagatacagg gagtgaggtg ccttctgggt cagggcatgg gccctgcaca ccccctccgg    1800
ccccagctaa ttttgaggat gtggcaccta cagggagcgg ggagccaggg gctacccggg    1860
agtctcccaa ggcaaatgga cagaaccagg cttctccatg ctcttctgga gacgacatgg    1920
agatctccga cgacgaccgg ggtggctcac cccctccggc cccgacgccc cctcagcagc    1980
ctccgccacc tcccccctccc ccgccgcctc ctcctcccta cctggcgtcc cttcctcttg    2040
gttatcctcc ccaccaacct gcctacctcc tcccacccag acctgatggg ccgccgcccc    2100
ctgagtaccc cccaccctcct ccaccacccc cgcacatcta tgactttgtg aactccttgg    2160
agctcatgga ccgacttggg gctcagtggg gagggatgcc catgtccttc cagatgcaga    2220
cccagatgtt aactcggctc catcagctgc ggcagggcaa gggattgatt gccgcctcag    2280 ctggccccccc cggtggggcc tttggggagg ccttcctccc gtttccaccc ccgcaggagg    2340
cagcctacgg cttgccgtat gctctatatg cacaggggca ggagggcaga ggggcatact    2400
cacgggaggc ctaccacctg cccatgccaa tggcagccga gccccctgccc tcctcctcag    2460 tctcgggaga ggaggcccgg ctgccaccca gggaagaagc agagctggca gagggcaaga    2520
ccctcccgac agcaggcacc gtgggccgtg tgctcgccat gctggtccag gagatgaaga    2580
gcatcatgca gcgagacctc aaccgcaaga tggtggagaa cgtggccttc ggagcctttg    2640
accagtggtg ggagagcaag gaggagaagg ccaagccatt ccagaacgcg gccaagcagc    2700
aagccaagga ggaggataaa gagaagacga agctgaagga gcctggcctg ctgtccctcg    2760
tggactgggc caagagcggg ggcactacgg gcatcgagcc tttcgccttt gggtcagggc    2820 tgagagggggc cctgcggctg ccttcattca aggtaaagcg gaaagagcca tcggaaattt    2880
ccgaggccag tgaggaaaag aggcctcgtc cctccactcc tgctgaggaa gatgaagacg    2940
accctgaaca agagaaggag gctggagagc caggacgtcc ggggaccaag cccccgaagc    3000
gggacgaaga gcgaggcaag acccagggca agcaccgcaa gtcctttgct ctggacagcg    3060
aaggggagga ggcatcccag gagtcctcct cggagaagga tgaggaggat gacgaggaag    3120
atgaggaaga tgaagatcga gaggaagctg tggataccac aaagaaggag acagaggtgt    3180
cggatggcga ggacgaggaa agcgattcgt cttccaaatg ttctctgtat gctgactcag    3240
atggcgaaaa tgacagcaca tcagactccg agagcagcag ctcttccagc tcctcatcct    3300
```

```
cctcctcctc ctcgtcctca tcctcctcgt cctcttcatc ctctgagtcc tcctctgaag    3360
atgaagagga agaggagcgg ccagcagccc ttccctcagc ctccccgccc ccagagaag     3420 tcccagtgcc cacgccagca cctgtggagg tgccagtgcc ggaaagggtt gcaggctccc    3480
cagtcacacc cctgcccgaa caggaggcgt ctccagcaag gcctgcaggc ccacggagg     3540 agtcaccccc cagtgcgcct ctgcgtcccc cagaaccacc tgctgggccc ccggcccctg    3600
ccccacgccc cgatgagcgt ccctcttctc ccatcccccct cctgccccca cccaagaaac   3660
gccggaaaac tgtctccttc tctgccatcg aggtggtgcc agccccggag ccccctccag    3720
ccacaccgcc gcaggccaag tttcccggcc cagcctcccg caaggctccc cggggcgtgg    3780
agcggaccat ccgcaacctg cccctggacc acgcatctct ggtcaagagt tggcccgagg    3840
aggtgtcccg aggaggccgg agccgggctg gaggccgagg ccgcctcacc gaggaagagg    3900
aggctgagcc agggacagag gtggacctgg cggtcctggc cgacctggcc ctgacccctg    3960
cccggcgcgg gctgcctgcc ctgcctgctg ttgaagactc agaggccaca gagacatcgg    4020
acgaggccga gcgccctagg cccctgctca gccacatcct cctggagcac aactatgccc    4080
tggccgtcaa gcccacgccc ctgcgccag ccctgcggcc cccggagcca gtgcccgcac     4140
ccgccgccct cttcagttcc ccagctgatg aggtcctgga ggcccccgag gtggtggtgg    4200
ctgaggcgga ggagcccaag ccgcagcaac tgcagcagca gcgggaggag ggcgaagagg    4260 aggggggagga agaggggggag gaagaggagg aggagtcctc tgacagcagc agcagcagcg   4320
atggggaggg cgccctccgg aggcgcagcc tccgctccca cgcccggcgc cgccgccctc    4380
cgcccccacc cccgccgcca ccgccccgcg cctacgagcc acgcagtgag tttgaacaga    4440
tgaccatcct gtatgacatt tggaactcgg gcctggactc agaggacatg agttacctgc    4500
ggcttacgta cgagcggctg ctgcagcaga caagcggggc tgactggctc aacgacactc    4560
actgggtcca tcacacaatc accaacctga ccaccccaaa acgcaagcgg cggccccagg    4620
atgggccccg ggagcaccag acaggctcag cccgcagcga aggctactac cccatcagca    4680
agaaggagaa ggacaagtac ctggacgtgt gcccagtctc ggcccggcag ctggagggcg    4740
tggacactca ggggacgaac cgcgtgctgt ccgagcgccg gtccgagcag cggcggctgc    4800
tgagcgccat cggtacctcc gccatcatgg acagtgacct gctgaaactc aaccagctca    4860
agttccggaa gaagaagctc cgatttggcc ggagccggat ccacgagtgg ggtctgtttg    4920
ccatggaacc cattgctgct gacgagatgg tcatcgaata cgtgggtcag aacatccgtc    4980
agatggtggc cgacatgcgg gagaagcgct acgtgcagga gggcattggc agcagctacc    5040
tgttccgggt ggaccacgac accatcatcg atgccaccaa gtgtggcaac ctggccagat    5100
tcatcaacca ctgctgcacg cctaactgct acgccaaggt catcaccatc gagtcccaga    5160
agaagatcgt gatctactcc aagcagccca ttggcgtgga cgaggagatc acctacgact    5220
acaagttccc actggaagac aacaagatcc cgtgtctgtg tggcacagag agctgccggg    5280
gctccctaaa ctgaggtggg gcaggatggg tgccacacc cctatttatt ccccctggtg     5340
ccctgagctc ccagcacccc ccagccttta gtgggctcag cagggcccac atgccccat     5400 ctccaagcgt ggggttgggg gcccaagcc cagcgaggga gcctcagtcc ctggaggcag     5460
cttctgcctc tcctgtcacc cctgcccacc accccctgat tgttttttctt tgcggagaag   5520 aagctgtaaa tgttttgtag cagccagcag ctgtttcctg tggaaacctg gggtgccggc    5580
ctgtacagat tctgtcctgg ggggctacac agtcctcttg ctttgtgtta atggggactt    5640 cccccttacgc cctgcgtgta ccccctcccca gtttaggggt ctctggggca gtggccatgt   5700
```

```
tctcccctg ggggggctct gcaccccag tcctggggac tccgtgcctg gaaccctgcc   5760
tcatctgttc ctgccagacc ctgagggtca cccttccacc ctggtgtcac tccccggctc   5820
agccaggcca ggatggcggg gtgggtccct tttgctgggc tggactgtac atatgttaat   5880
agcgcaaacc cgacgccaca tttttataat tgtgattaaa ctttattgta caaaa        5935
```

<210> SEQ ID NO 73
<211> LENGTH: 8195
<212> TYPE: DNA
<213> ORGANISM: Homo sapiens

<400> SEQUENCE: 73

```
aacggcatgg agaacagtca ccccccccac caccaccacc agcagccccc gccgcagccc     60
ggcccttcgg gcgagaggag gaaccaccat tggagaagtt acaagttgat gattgacccg    120
gctctgaaaa aggggcatca taaactgtac cgctacgatg ggcagcattt cagcctggcg    180
atgtccagca accgcccggt ggaaattgtc gaagatcccc gggtcgtcgg gatctggacc    240
aaaaacaagg agctggagct gtcggtgccc aaattcaaga tcgatgagtt ctacgtgggc    300
ccggtgcctc cgaagcaggt gacatttgcc aagctgaatg ataacatccg tgaaaacttc    360
ctgagggaca tgtgcaagaa gtatggggag gtggaggagg tggagatttt gtacaacccc    420
aagaccaaga agcacctggg catcgccaag gtggtctttg ccacggtccg gggagccaag    480
gatgccgttc agcacttgca cagcacttcc gtcatgggac acattatcca cgtggagctg    540
gacaccaaag gggaaacccg aatgcggttc tatgaactgt tggtcactgg ccgatacacc    600
ccccagaccc tcccagtggg cgagctggac gctgtctctc aatcgtgaa tgagaccctg    660 cagctgtcag atgccctgaa cgcctcaag gatggaggcc tgtctgcagg ctgtggctcc    720
ggctcctcct ctgtcacccc caatagcggt gggacaccct tctcccagga cacagcttat    780
tccagctgcc gcctggacac acccaactcc tatggacagg gcaccccgct cacaccgcgc    840
ctgggcaccc ctttctcaca ggactccagc tactccagcc gccagcccac accctcatac    900
ctcttcagcc aggaccctgc agtgaccttc aaggcccggc gccacgagag caagttcacg    960
gacgcctaca accgccgcca cgaacatcat tatgtacaca attctcccgc ggtcactgcg   1020
gtggccgggg ccacagccgc tttccggggt tcctcggacc tcccgttcgg agcagtcggc   1080
ggcactgggg gcagcagcgg tccccgttc aaggctcaac acaggattc agccacattt   1140 gcccacactc caccacccgc ccaagcaacc cctgctcctg gattcaagtc tgctttctct   1200
ccgtatcaga ccccagtggc ccacttccct ccaccccgg aagagcccac cgccacagcc   1260
gcttttgggg cccgcgacag tggggagttc cggagggcac cggcgccccc acccctgcca   1320
cctgctgagc ctctgccaa ggagaagcca ggcacgccac ccgggcccgcc gcccccgac   1380 accaacagca tggagctggg cggccggccc accttcggct ggagtcctga gccctgtgac   1440
agccctggca cgcccacgct ggagtcgtcc cctgcagggc cagagaaacc ccacgacagc   1500
ctggactcgc gcatcgagat gctgctgaag gagcagcgca ccaagctgct cttcctgagg   1560
gagccggact cggacaccga gctgcagatg gagggcagcc ccatctcctc ctcctcctcc   1620
cagctctccc cactggcccc ctttggcacc aactcccagc aggcttccg ggcgcccacg   1680 ccccctcgt cacgcccctc cagcaccggc ctggaggata tcagcccaac cccctccca   1740 gactccgacg aggacgagga gctcgacctg gccttgggc ctcggcctcc acctgagcca   1800
ggccccccgg accctgctgg gcttctgagc cagacagctg aggtggcctt ggacctggtt   1860
```

-continued

| | |
|---|---|
| ggagacagaa ccccgacctc agagaagatg gatgagggcc agcagtcctc aggcgaggac | 1920 |
| atggagatct cggatgacga gatgccctcg gcccccatca ccagcgctga ctgccccaag | 1980 |
| cccatggtgg tgaccccagg agcggcagcc gtggcagccc cttctgtgct agccccaacc | 2040 |
| ctgccgctgc ccccgccacc tggcttcccc ccgctgcccc cccaccacc accacccca | 2100 |
| ccgcagcctg gcttccccat gccccaccg ctgcccccac cgccgccccc accccctcca | 2160 |
| gcccaccctg ctgtgacagt gcccccacca cccttgccag cgccgcctgg agtcccgccc | 2220 |
| ccacccatcc tgccaccact gccccccttt ccgccgggcc tgttccctgt gatgcaggtg | 2280 |
| gacatgagcc acgtgctggg tggccagtgg ggcggcatgc ccatgtcctt ccagatgcaa | 2340 |
| acgcaggtgc tcagccggct gatgacgggc cagggcgcct gcccctaccc gcccttcatg | 2400 |
| gccgctgcgg ccgccgctgc ctcagctggg ctccagtttg tcaacctgcc gccctaccgg | 2460 |
| ggcccctct ccctgagcaa ctccggccca ggccgcgggg agcactggcc accactgccc | 2520 |
| aagtttgacc cgtcagtgcc tccaccaggc tacatgccac gccaggagga cccacacaaa | 2580 |
| gccacggtgg atgcgtcct gctggtggtc tcaaagaac tcaaggccat catgaagcgt | 2640 |
| gacctgaacc gcaagatggt ggaagtggtg gctttccggg cctttgacga gtggtgggac | 2700 |
| aagaaggagc ggatggccaa ggcctcgctg accccggtga agtcgggcga gcacaaggac | 2760 |
| gaggacaggc cgaagcccaa ggaccgcatc gcctcgtgcc tgctggagtc atggggcaag | 2820 |
| ggcgagggcc tgggctacga gggcctgggc ctgggcattg gctgcgtgg ggccattcgc | 2880 |
| ctgccctcct tcaaggtcaa gaggaaggag ccaccagaca ccacctcatc tggcgaccag | 2940 |
| aagcggctgc ggccctcgac ctctgtggat gaggaagatg aagagtccga gcgagagcga | 3000 |
| gaccgggata tggcagacac cccctgtgag ctcgccaagc gggaccccaa gggcgtgggt | 3060 |
| gtgcggcggc ggccggcgcg gcctctggag ctggacagtg gtggggagga ggacgagaag | 3120 |
| gagtcattgt cggaggaaca ggagagcacc gaggaggaag aggaggcgga ggaggaggag | 3180 |
| gaggaggaag atgacgacga tgacgacagt gatgaccggg acgagtctga gaacgatgac | 3240 |
| gaggacacag ccctgtcaga ggcgagtgag aaggacgaag gggactcgga tgaagaggag | 3300 |
| acagtgagca ttgtaacctc caaggccgaa gccacgtcgt ccagtgagag ttccgagtct | 3360 |
| tctgagtttg agtcaagctc cgagtcctcg ccctcatcct cggaggatga ggaggaggta | 3420 |
| gtggccaggg aagaggagga agaagaggag gaggaggaga tggtggccga ggaaagcatg | 3480 |
| gcttctgcag gccctgagga cttgagcag acggggagg aagcggctct ggccccgggg | 3540 |
| gcacctgcag tggactcgtt gggcatgaa gaggaggtgg acatcgagac tgaggctgtg | 3600 |
| gcccctgagg agcggccctc catgctggac gagccccct tgcctgtggg tgttgaagag | 3660 |
| ccagcggact ccagggagcc gcctgaggaa ccaggcctga ccaggaagg gccatgttg | 3720 |
| ctgtctccag agccccctgc caaggaggtg gaggctcgac ccccattgtc ccctgagcga | 3780 |
| gctccagaac atgacctgga agtggagccg agccccccta tgatgctccc cttgccgctg | 3840 |
| caaccaccat tgccgccccc acgaccaccc cggccaccca gccaccgcc ggagcctgag | 3900 |
| accacagatg cctcacaccc atctgtccct ccggagcccc ttgccgagga ccacccccg | 3960 |
| catactccag gcctctgtgg cagcctggcc aagtcgcaga gcacagagac ggtgccagcc | 4020 |
| acaccaggcg gggagccccc gctatcaggg ggcagcagtg gcctgtccct gagctctccg | 4080 |
| caagtgcccg gcagccctt ctcctaccca gcccgtccc ctagcttgag cagtgggggc | 4140 |
| ctccctcgga cacctggccg ggacttcagc ttcacaccca ccttctccga gcccagcggg | 4200 |
| cccttgctcc tgcccgtctg cccactcccc actggccgac gcgatgaacg ctccgggccc | 4260 |

```
ctggcctccc cggtgctcct ggagacgggc ctgcccctcc ctctgccccT tcccctgccc    4320
ttgcccttgg cattgcccgc cgtcttgcgg gcccaggctc gtgcgcccac cccgctgcca    4380
cccctgctgc ccgcccccct ggcctcttgc cctcccccaa tgaagaggaa gccgggccgg    4440
ccccggcgat ccccaccatc tatgctctcc ttggatgggc ccttggtccg accaccagca    4500
ggggccgccc ttggaaggga actcctgctc ctgccgggcc agccacagac cccgtcttc     4560 cccagcaccc atgaccccg  acggtgacc   ctggacttcc ggaacgcggg gatcccagcc    4620
cctccaccac cccttccccc ccagccaccc caccccac    ctcccccacc tgtagagccc    4680
accaagctgc cctttaagga gctagacaac cagtggccct ccgaggccat tcctccgggc    4740
ccccgtgggc gcgatgaggt cactgaggaa tacatggagt tggccaagag ccgggggccg    4800
tggcgccggc cacctaagaa gcgccatgag gacctggtgc cacctgcggg ctcgcccgaa    4860
ctctcgccac cccagcccct cttccggccc cgctcggagt ttgaggagat gaccatcctg    4920
tatgacatct ggaacggtgg catcgatgag gaggacatcc gcttcctgtg tgtcacctac    4980
gagcgactgc tacagcagga caatggcatg gactggctta cgacacgct   ctgggtctac    5040 catccctcca ccagcctctc ttcagctaag aagaagaaac gggacgatgg catccgcgag    5100
cacgtgacgg gctgtgcccg cagtgagggc ttctacacca tcgacaagaa ggacaagctc    5160
agatacctca acagcagccg tgccagcacc gatgagcccc ccgcagacac ccagggcatg    5220
agcatcccag cacagcccca cgcctccacc cgggcaggct cggagcggcg ttcggagcag    5280
cgccgcctgc tgtcctcctt cactggcagc tgtgacagtg acctgctcaa gttcaaccag    5340
ctcaagttcc ggaagaaaaa gctcaagttc tgcaagagcc acattcacga ctggggcttg    5400
ttcgccatgg agcccatcgc ggctgacgag atggtcatcg agtacgtggg ccagaatatc    5460
cgtcaggtga tcgcagacat gcgggagaag cgttatgagg acgagggcat cgggagcagc    5520
tacatgttcc gggtggacca tgacaccatc atcgacgcca ccaagtgcgg caacttcgcg    5580
cgcttcatca accacagctg caacccccaac tgctatgcca aggtgatcac ggtggagtca    5640
cagaagaaga tagtcatcta ctcgaagcag cacattaacg tcaatgagga gattaccctaT   5700 gactataagt tccccatcga ggacgtcaag atccctgcc   tctgtggctc cgagaactgc    5760 cggggggaccc tcaactaggc cccggcacca gactcaaagg atgtcagccg tagccctggg   5820
actcccgagc gtggagcccc tggccccggg gccggccccc ccgcgcccgc cccatttca    5880 ggtgctgtcc tctacccagc ggccattcag ggcctggcgc ccacactac  cccctggagc    5940 ccctggctcc ggcccctccg cgggaaaggg cttctctgtc gttcagccca cgtctctctc    6000
attttaacaa acgcccctTt caggatttct gtttaactcc agcatcagct tctctctctc    6060
cgtctctcct cccctctctc tcttctctgt ctcttctctc tcccaccatc ccctcggcc     6120 tcttcctgtg aatgctgcta cgttgttttg tcttctctat ttttttcctc gttgtgagaa    6180
aagacattta accgttgaaa tgtgaaggtg gaatcagaga ggggcccgc  ggggtctgc     6240 agaggcctca gtgtggctgt gcgtggcccg tgtcctggaa gccacccgga cctggacgca    6300
gggccaggtg ctgtgggaag gatggaggcc cccacggcct tgacctcaga acactacgcc    6360
ctgaaagcgc cctcactgc  ccgtgggcac agtgaggaga ccccacacct tccccaccc     6420 gagctgcagc ctgttccttc cccagaggcc tggggcacca ctgacccggt ggaccctgat    6480
ggagctaagc tgtcccaggc aggggtctcc gctctgggct ttccctgcca cctcacaccc    6540
cagcaccccc taaaccttgg gttcaatgtt tactttctca ttcggatgcc agcaacgcgg    6600
```

```
gagcctctcg gaggccccag tgcaggtgag gggcgctgag aacgcgggca gccactctct    6660
tctgcccttg ccttcgccct gggtgggaca gggctcccaa gggcaggcgg gtccccagt    6720 cccgccatta cggggttgtca gaccgtctgc gtgtggcatt ttttggctta taagcttcac    6780
ccactcaccc caacccaca ccccacatcc ccctgccggc agcccctcaa cctaagaagg    6840
ccagagcata tttattttcg gagggagcag attacttctc ccagagaaag gaaaatcttg    6900
gaaaagattt aaaaacacaa atctaagcct tgacggtttt ttttttccctt ttgacccccct    6960 tcccatctct tcagaattta ttcccatggc ttttttttttt cttgtgcgtg tataaaatca    7020
aaaggaaggg gaaaaaggtt tttgaagttc agaaccaact tctgtatata gaggctgccg    7080
caaaggactt tctcttggga acattgtttc ttgtagaaac atgcgggaag acatttttttg    7140 ctcatttctt tgtacttcca aaaaaaaagg aaaaaaaaga caaaagcaag tcccccccgta    7200 ccccagaaag cagaggaggc gtgtaaataa tttctggaaa gtgactgttg tgacccggag    7260
tcctcatcaa gatgagcgcg ctccatgagg gagctgctcc cacctgcgg acgcaggcgg    7320 ccggagcctc tggtatctca gcttgtgtca agcttgttat catgtaaatt ctgtacaaag    7380
aattgttatt tttctctttt ttgttgttgg tggttttgtt gtgtgttttt tgttgttttt    7440
tttttattcc tttcccccag gccctctcta tttgagactg tgcccgccgg tttcaagatc    7500
aaggaaattg gtggcaacaa gacacagatg gggtacctgg gcacagcggc gaacttctct    7560
tccgtttgcg gttttctgcc taattgtgca actgaggaaa taattttattt ttcacatgag    7620 gaaatgcgta gcttgtagag acggctgatt caagttacat gtacagcctc caaagggctg    7680
tctccattct gtcccttcc cataaaagaa gtggggtgt tcgagaagac cagggaaggg    7740 accctttgcct caccctccc cctggcctca ccttgctccc agccatcgtg cccagtgtta    7800
acctcggctg gccttcacta aggggactag acctccctct ccccaggagc cccagccccca    7860 gagtggtttg caataatcaa gatatgtgtc gagtcatttt tctttcaact ccctcatttt    7920
tcattgaaca aatctctgct tttcaagagt tggggggttttc tgctattttt tgctttctct    7980
cccctcccct gcaaagatga gaaccaatga gttttaggga tgtttgtgcg ggtagactcc    8040
atcatccata tgtaacttgt tttgaagaga agtgtttccg ttgtgtgtct tgatgtaaat    8100
atttgttcat attttttgtga attcaatact atgtaccatt gtattatagt aacttttata    8160
aagcaaacca taaatatact gacttttctt acaga    8195
```

```
<210> SEQ ID NO 74
<211> LENGTH: 2976
<212> TYPE: DNA
<213> ORGANISM: Homo sapiens

<400> SEQUENCE: 74
ggaaagagtg gtggcaggtg aagtcggaga cgacagagga actggtttcc tccgccccgc      60
aaggcacaca gcctgccgac gccccattaa tacatgtgga aggggaaaga gactgaatgg     120
aggaatgaat acaacttgat ccaggtcgtg cttcggaagc ggtcacttta cctgtgaacc     180
tctctgcctg acaaacgggc aatgtacgga atcaaccacc aagatggcgg cgcccgtgaa     240
gaatccgcaa ttaggtcgcc gtcatatgtc gcctaggaac gtacggaatt cgacccacgt     300
acggaatcgg attccaagat gacggcatct atgaggaagt cacgcagtag gtgcagccat     360
gttgcctgta cgtcgaggcc gtacaagcag ccgccgtacg gactctactg acaaggtggc     420
ggcgccctcg ggaaagccac attagagcgc ggccatgttc ccggcgaaca tatggattcg     480
gccaccatac ggatacgata agcaagatgg cggcgcctga ggggtcttgg gggctctagg     540
```

```
ccggccacct actggtttgc agcggagacg acgcatgggg cctgcgcaat aggagtacgc   600
tgcctgggag gcgtgactag aagcggaagt agttgtgggc gcctttgcaa ccgcctggga   660
cgccgccgag tggtctgtgc aggttcgcgg gtcgctggcg ggggtcgtga gggagtgcgc   720
cgggagcgga gatatggagg gagatggttc agacccagag cctccagatg ccggggagga   780
cagcaagtcc gagaatgggg agaatgcgcc catctactgc atctgccgca aaccggacat   840
caactgcttc atgatcgggt gtgacaactg caatgagtgg ttccatgggg actgcatccg   900
gatcactgag aagatggcca aggccatccg ggagtggtac tgtcgggagt gcagagagaa   960
agaccccaag ctagagattc gctatcggca caagaagtca cgggagcggg atggcaatga  1020
gcgggacagc agtgagcccc gggatgaggg tggagggcgc aagaggcctg tccctgatcc  1080
agacctgcag cgccgggcag ggtcaggagc aggggttggg gccatgcttg ctcggggctc  1140
tgcttcgccc cacaaatcct ctccgcagcc cttggtggcc acacccagcc agcatcacca  1200
gcagcagcag cagcagatca aacggtcagc ccgcatgtgt ggtgagtgtg aggcatgtcg  1260
gcgcactgag gactgtggtc actgtgattt ctgtcgggac atgaagaagt tcggggggccc  1320 caacaagatc cggcagaagt gccggctgcg ccagtgccag ctgcgggccc gggaatcgta  1380
caagtacttc ccttcctcgc tctcaccagt gacgccctca gagtccctgc caaggccccg  1440
ccggccactg cccacccaac agcagccaca gccatcacag aagttagggc gcatccgtga  1500
agatgagggg gcagtggcgt catcaacagt caaggagcct cctgaggcta cagccacacc  1560
tgagccactc tcagatgagg acctacctct ggatcctgac ctgtatcagg acttctgtgc  1620
aggggccttt gatgaccatg gcctgccctg gatgagcgac acagaagagt ccccattcct  1680
ggaccccgcg ctgcggaaga gggcagtgaa agtgaagcat gtgaagcgtc gggagaagaa  1740
gtctgagaag aaggtgatgg agaggaagga ggagcgatac aagcggcatc ggcagaagca  1800
gaagcacaag gataaatgga acacccaga gagggctgat gccaaggacc ctgcgtcact  1860
gccccagtgc ctggggcccg gctgtgtgcg ccccgcccag cccagctcca gtattgctc   1920 agatgactgt ggcatgaagc tggcagccaa ccgcatctac gagatcctcc cccagcgcat  1980
ccagcagtgg cagcagagcc cttgcattgc tgaagagcac ggcaagaagc tgctcgaacg  2040
cattcgccga gagcagcaga gtgcccgcac tcgccttcag gaaatggaac gccgattcca  2100
tgagcttgag gccatcattc tacgtgccaa gcagcaggct gtgcgcgagg atgaggagag  2160
caacgagggt gacagtgatg acacagacct gcagatcttc tgtgtttcct gtgggcaccc  2220
catcaaccca cgtgttgcct gcgccacat ggagcgctgc tacgccaagt atgagagcca  2280
gacgtccttt gggtccatgt accccacacg cattgaaggg ccacacgac tcttctgtga  2340 tgtgtataat cctcagagca aaacatactg taagcggctc caggtgctgt gccccgagca  2400
ctcacgggac cccaaagtgc cagctgacga ggtatgcggg tgcccccttg tacgtgatgt  2460
ctttgagctc acgggtgact tctgccgcct gcccaagcgc cagtgcaatc gccattactg  2520
ctgggagaag ctgcggcgtg cggaagtgga cttggagcgc gtgcgtgtgt ggtacaagct  2580
ggacgagctg tttgagcagg agcgcaatgt gcgcacagcc atgacaaacc gcgcgggatt  2640
gctggccctg atgctgcacc agacgatcca gcacgatccc ctcactaccg acctgcgctc  2700
cagtgccgac cgctgagcct cctggcccgg accccttaca ccctgcattc cagatggggg  2760
agccgcccgg tgcccgtgtg tccgttcctc cactcatctg tttctccggt tctccctgtg  2820
cccatccacc ggttgaccgc ccatctgcct ttatcagagg gactgtcccc gtcgacatgt  2880
```

```
tcagtgcctg gtggggctgc ggagtccact catccttgcc tcctctccct gggttttgtt   2940
aataaaattt tgaagaaacc aaggaaaaaa aaaaaa                             2976

<210> SEQ ID NO 75
<211> LENGTH: 2954
<212> TYPE: DNA
<213> ORGANISM: Homo sapiens

<400> SEQUENCE: 75
cacagcaacg cgcgcgagag aagagagtat tctcgcgaga agtccagggg tggccgtgat     60
ggcggcggca ggagcaggac ctggccagga agcgggtgcc gggcctggcc caggagcggt    120
cgcaaatgca acagggcag aagaggggga gatgaagccg gtggcagcgg gagcagccgc    180
tcctcctgga gagggatct ctgctgctcc gacagttgag cccagttccg gggaggctga    240
aggcggggag gcaaacttgg tcgatgtaag cggtggcttg gagacagaat catctaatgg    300
aaaagataca ctagaaggtg ctggggatac atcagaggtg atggatactc aggcgggctc    360
cgtggatgaa gagaatggcc gacagttggg tgaggtagag ctgcaatgtg ggatttgtac    420
aaaatggttc acggctgaca catttggcat agatacctca tcctgtctac ctttcatgac    480
caactacagt tttcattgca acgtctgcca tcacagtggg aatacctatt tcctccggaa    540
gcaagcaaac ttgaaggaaa tgtgccttag tgctttggcc aacctgacat ggcagtcccg    600
aacacaggat gaacatccga agacaatgtt ctccaaagat aaggatatta taccatttat    660
tgataaatac tgggagtgca tgacaaccag acagagacct gggaaaatga cttggccaaa    720
taacattgtt aaaacaatga gtaaagaaag agatgtattc ttggtaaagg aacacccaga    780
tccaggcagt aaagatccag aagaagatta ccccaaattt ggacttttgg atcaggacct    840
tagtaacatt ggtcctgctt atgacaacca aaaacagagc agtgctgtgt ctactagtgg    900
gaattaaaat gggggaattg cagcaggaag cagcggaaaa ggacgaggag ccaagcgcaa    960
acagcaggat ggagggacca cagggaccac caagaaggcc cggagtgacc ctttgttttc   1020
tgctcagcgc cttcccccctc atggctaccc attggaacac ccgtttaaca aagatggcta   1080
tcggtatatt ctagctgagc ctgatccgca cgccccctgac cccgagaagc tggaacttga   1140
ctgctgggca ggaaaaccta ttcctggaga cctctacaga gcctgcttgt atgaacgggt   1200
tttgttagcc ctacatgatc gagctcccca gttaaagatc tcagatgacc ggctgactgt   1260
ggttggagag aagggctact ctatggtgag ggcctctcat ggagtacgga aggtgcctg    1320 gtattttgaa atcactgtgg atgagatgcc accagatacc gctgccagac tgggttggtc   1380
ccagccccta ggaaaccttc aagctccttt aggttatgat aaatttagct attcttggcg   1440
gagcaaaaag ggaaccaagt tccaccagtc cattggcaaa cactactctt ctggctatgg   1500
acagggagac gtcctgggat tttatattaa tcttcctgaa gacacagaga cagccaagtc   1560
attgccagac acatacaaag ataaggcttt gataaaattc aagagttatt tgtattttga   1620
ggaaaaagac tttgtggata aagcagagaa gagcctgaag cagactcccc atagtgagat   1680
aatattttat aaaaatggtg tcaatcaagg tgtgggttac aaagatattt ttgaggggt    1740 ttacttccca gccatctcac tgtacaagag ctgcacggtt tccattaact ttggaccatg   1800
cttcaagtat cctccgaagg atctcactta ccgccctatg agtgacatgg ctggggcgc    1860 cgtggtagag cacaccctgg ctgacgtctt gtatcacgtg gagacagaag tggatgggag   1920
gcgcagtccc ccatgggaac cctgaccagg tccctctttt ctgtcaagga ctttctggga   1980
ataatactgg gggttttgtt tttgtttttg aactgtctca aatgttctcc caaagatgct   2040
```

```
aaaaacacag cctctccttt tagcaagtta aaaggctggg taggactgcg ggagactgcc    2100
tgcctttcac cattttctcc ccacttccag tgactgctct tattttgtgt accataagcc    2160
aacaaccgct gactccagga ttgcataagc cccctgtgaa atcggtgctg tactgcatac    2220
cctgccagct gtgacttgtt atcctactat attttctaag gagtgaataa tattgtccga    2280
gtaactaact tatttaaaag acatttcctt ctgtgggcat tgactgtatc ccacctgttt    2340
tccaaggaaa tggtaacctg tttctgagaa cacctgaaat caatggctat acattccaaa    2400
ccaatctaaa cgctatttcc ttttggtgtg ggtttggttt tgttcatttt gaaatacact    2460
tttgaacact gagatccgta aaactactag atctctggaa gtgtaattgt gaagaaact     2520 tgcttgcagc tttaacaaaa tgagaaactt cccaaataaa acttgttttg aagtttatgt    2580
gacactttgc ttcccttcag attgggtgcc tcttggtgac agtgttcaga atgtaagca     2640 gcacgaggaa gggagctggc actgggagga agagccgggt ttctgagttg tgttttggct    2700
gctttcctat tgctcccatt cttgccaatc agccacccccc tttcctgtga aaatctgcca   2760
ccttgaggag aggaacaaga gtttaaaagg gctaatgatc tccctcccgg tcttcccttg    2820
gaacatggat gttgatatat gtgcgggtgg tttcctgtct tgcttatctt cctttgccct    2880
gagctgatgg ctaaagggca gttttcggac tattaaagac tgaaatgtaa gaatgagcct    2940
tctaggctgg gcgc                                                     2954

<210> SEQ ID NO 76
<211> LENGTH: 800
<212> TYPE: DNA
<213> ORGANISM: Homo sapiens

<400> SEQUENCE: 76
tggcgcggtg cagggctctt aagaacgaac ggcttgggcg cgggtaatca gctcccttc       60 ccccactttc tcacttattc taggtacttg ggactgtcgt agagtttcca gaccccatgt     120
aggcgcccag tcgtggactg tcccactctg ctgctctact gctcgtggtg ctcccgcgcc     180
cagactggta tccggggact gtgacttgca gggtccgcca tggagccaga gcagatgctg     240
gagggacaaa cgcaggttgc agaaaatcct cactctgagt acgtctcac agacaacgtt      300 gagagaatag tagaaaatga gaagattaat gcagaaaagt catcaaagca gaaggtagat     360
ctccagtctt tgccaactcg tgcctacctg gatcagacag ttgtgcctat cttattacag     420
ggacttgctg tgcttgcaaa ggaaagacca ccaaatccca ttgaatttct agcatcttat     480
cttttaaaaa acaaggcaca gtttgaagat cgaaactgac ttaatgggaa gaacagaaaa    540
atttagttgc tactgtagat ttacatgatt aagaggcagc tttaattgcc atgatcattc     600 cctcttttg gatgtataag aaccttccgg acaacagaac ctattctgg aattgcagaa       660 gataacatat ttcccttatt ttgatttaat caccataaac catacctatt taatgagtgt    720
attctgtgca attttttct cagattgtct ttaactttgt ttttaaaatg accttcaaaa      780
taaactgtca aaacaccatt                                                800

<210> SEQ ID NO 77
<211> LENGTH: 4423
<212> TYPE: DNA
<213> ORGANISM: Homo sapiens

<400> SEQUENCE: 77
ggaagccgcg gggccttcta aggccgaaag tcttcggagc ttgcgccagt ctcttcgcgg      60
```

```
cgtccaccac ttagacgcaa gttgctgaag ccggccgggg agaaggtgtt gttgccggag    120
ctgagaccgg gcggccacag tccgcaggga tgaacctcga gttgctggag tcctttgggc    180
agaactatcc agaggaagct gatggaactt tggattgtat cagcatggct ttgacttgca    240
cctttaacag gtggggcaca ctgcttgcag ttggctgtaa tgatggccga attgtcatct    300
gggatttctt gacaagaggc attgctaaaa taattagtgc acacatccat ccagtgtgtt    360
ctttatgctg gagccgagat ggtcataaac tcgtgagtgc ttccactgat aacatagtgt    420
cacagtggga tgttctttca ggcgactgtg accagaggtt tcgattccct tcacccatct    480
taaaagtcca atatcatcca cgagatcaga acaaggttct cgtgtgtccc atgaaatctg    540
ctcctgtcat gttgacccct tcagattcca acatgttgt tctgccggtg gacgatgact    600
ccgatttgaa cgttgtggca tcttttgata ggcgagggga atatatttat acggaaacg    660 caaaaggcaa gattttggtc ctaaaaacag attctcagga tcttgttgct tccttcagag    720
tgacaactgg aacaagcaat accacagcca ttaagtcaat tgagtttgcc cggaagggga    780
gttgcttttt aattaacacg gcagatcgaa taatcagagt ttatgatggc agagaaatct    840
taacatgtgg aagagatgga gagcctgaac ctatgcagaa attgcaggat ttggtgaata    900
ggaccccatg gaagaaatgt tgtttctctg gggatgggga atacatcgtg gcaggttctg    960
cccggcagca tgccctgtac atctgggaga agagcattgg caacctggtg aagattctcc   1020
atgggacgag aggagaactc ctcttggatg tagcttggca tcctgttcga cccatcatag   1080
catccatttc cagtggagtg gtatctatct gggcacagaa tcaagtagaa aactggagtg   1140
catttgcacc agacttcaaa gaattggatg aaaatgtaga atacgaagaa agggaatcag   1200
agtttgatat tgaagatgaa gataagagtg agcctgagca gacaggggct gatgctgcag   1260
aagatgagga agtggatgtc accagcgtgg accctattgc tgccttctgt agcagtgatg   1320
aagagctgga agattcaaag gctctattgt atttacccat tgcccctgag gtagaagacc   1380
cagaagaaaa tccttacggc cccccaccgg atgcagtcca aacctccttg atggatgaag   1440 ggctagttc agagaagaag aggcagtcct cagcagatgg gtcccagcca cctaagaaga   1500
aacccaaaac aaccaatata gaacttcaag gagtaccaaa tgatgaagtc catccactac   1560
tgggtgtgaa gggggatggc aaatccaaga agaagcaagc aggccggcct aaaggatcaa   1620 aagtaaaga gaaagattct ccatttaaac cgaaactcta caaggggac agaggtttac    1680 ctctggaagg atcagcgaag ggtaaagtgc aggcggaact cagccagccc ttgacagcag   1740
gaggagcaat ctcagaactg ttatgaagac cttcgaagtt cttcattctt tctcactttg   1800
ccatcatgtg gcctctggac actgtggtca gtcatttgaa aattgacttt aatttaaaac   1860
aaaggcctgt gcctcccacc caggaggtgg gagggtgaat tttatgttta atgaagaag    1920 tgaattatgg aagaagagta tacgaccttc ccttcccttt caagcataag tccaaataga   1980
ctctcaggaa tgaagatttg tgaagacatc agataggaat tttgactcat ttaaactttg   2040
atgcttagtt atgttgctgg agaaaagata cttatgtttt gctcatctaa cttcattgta   2100
cccagcgtca tttttgacatg tcatttccta tctcccattt gccttcggtc tcaatgcat   2160 gtctttgagt gacttcttat ctgaaatttt gctactggta tcctaggaaa gcttttgttg   2220
gatactctca tttttaaactt ctcctctccc cagatacctc ctatatttcc atattgtgtg   2280
caaaggatgg gcagaaaaga aagtgcttga agatttcaa attttcagaa agggaacaac   2340
gaaggccctc tcttcctctc ataccacgtt ttgctcaaga agctgggctg taacaattca   2400
gggttttccc ttgttttcct ctcattgcat gtttccctcc aatattggtt cattgtcatc   2460
```

```
aatcatggtt tttgaagata gctagtttta tccatctcca gcaaagaatc atcaatagtt    2520
tatattgctt tacctgtgct ggcttccaga gatggaaaca aacccaggtg tctctcaaca    2580
agctactttt ttactggggt gggggaatct atgcaaggag taaagtaaaa ccatccagaa    2640
tcaaagcagc aaccacatag ttcaaatcaa agatcaaggt gaattttttg tatcactgcc    2700
tgtggaaatc tatcctcatc agtcattgca ttttccctg cctatacctg tgctcctttt    2760
tcttactgtg ttttcagtca cttcctttct gtgaaaggtt gcttagcttt ttttttgaca    2820
tttgttgttc tttataaaaa taacagattg gatagatgtg tacatttggt gtttgaaatt    2880
ctctgaaaat cccattagga aaccaggtgt gaaaagggct cagtagcttc tctgagtggc    2940 gttttagct gactggaagt gcttaatctg gatcgtcttt tttttttttt ttttttttc    3000 aatatttaa aaggagaatt taaatactgt gcttactgtg aaatatatca gttggtgagc    3060
cgggcgtggt gggtcacgcc tgtaatccca gcactttggg aggccaaggc gggttgatca    3120
cccgaggtca ggagttcaag accagcctgg ccaacgtggt gaaagcctgt atctattaaa    3180
agacaaaaat tagctgggcg tggtagtaca tgcctgtaat cccagctaca ctggaggctg    3240
agtcaggaga atcacttgaa cgtgggaggc agaggttgca gtgagtggag atcgcaccac    3300
tgccctccag cctaggtgac agaatgagac tctatctcaa aaaaaaaaa aaaatgatat    3360 cagttggtgg atgctcctat aggtagccaa acacattgat tacctgttag attttaggat    3420
agaaatcaaa gtagagcacg tcagcaagag cctctttgtc tcactccatc atttaaaacc    3480
agtatattca gtagttgaag aaaagagctct ccctgagtca gttgcaaaac gtctatattt    3540
ttagatgcca ctactttttt cttaaatatt cattttgaga ctgtcatgag ttagaccagt    3600
ggttgagatt agtagatggc tcactagaca tgtttttgtt ttgcagacat tatatccatt    3660
ccagtcctct gcactgtaca ctgcagcagt gtgcaaacta tgggacttag agggtttctg    3720
ccatctttcc acgtgtgaag tagcttggtt tcctctgcct gtgcatttgg atgtttgtgc    3780
tatgtccacc tcctaaactg gctactgaga aaatcatctt cagccctgtc agattgtctc    3840
tggcagtagc tcctaataat tatttatgtt tttggaattt ttttttcaac ttttaaaaaa    3900
ccttctatcc atttcaattt gaattatttg atttgtacaa tatatgtata ttctcttctt    3960
cctttttgtc atccctgccc tgccacccc aaaattttgt ttttaaaaat attctgggct    4020
gggcatggtg gctcacacct gtaatcccag cacttgggga ggccgaggct ggtggatcat    4080
ctgaggtcag gtgtttgaga ccagcctggt caacatggtg aaaccccgtc tctactaaaa    4140
atacaaaaat tagctgggcg tggtggcggg cacctgtaat cctagctact cgggaggctg    4200
aggcaggaga attgcttgaa tccaggaggc agaggttgca gtgagctgag attgcgccac    4260
tgcactccag cctgggtgac agagcaagac tccatctcaa aaaaaaaaaa aaaaaaaat    4320 ctgtagtttt gtacaagatg agacttagcc ttgggtactt cttgctgaag ctttaatgct    4380
ttgtaaataa aatcggatgt ttattaaaga aaaaaaaaa aaa                       4423
```

<210> SEQ ID NO 78
<211> LENGTH: 3163
<212> TYPE: DNA
<213> ORGANISM: Homo sapiens

<400> SEQUENCE: 78

```
gccgcctggc gcccgcccga gctgccgcct tgtcgagctg agtccgcgct cccgcccagg     60
cggcggccga cgcgacgccc cgagcgcccg gccccgccgc cgcggccccgg cagactgcct   120
```

```
ctgtcaccgg gtccctccac ccttgtctcc tgtgcggcca gcgtcagagc catggcgacg      180
gaggagaaga agcccgagac cgaggccgcc agagcacagc caacccctc gtcatccgcc       240 actcagagca agcctacacc tgtgaagcca aactatgctc taaagttcac ccttgctggc      300
cacaccaaag cagtgtcctc cgtgaaattc agcccgaatg gagagtggct ggcaagttca      360
tctgctgata aacttattaa aatttggggc gcgtatgatg ggaaatttga gaaaaccata      420
tctggtcaca agctgggaat atccgatgta gcctggtcgt cagattctaa ccttcttgtt      480
tctgcctcag atgacaaaac cttgaagata tgggacgtga gctcgggcaa gtgtctgaaa      540
accctgaagg gacacagtaa ttatgtcttt tgctgcaact tcaatcccca gtccaacctt      600
attgtctcag gatcctttga cgaaagcgtg aggatatggg atgtgaaaac agggaagtgc      660
ctcaagactt tgccagctca ctcggatcca gtctcggccg ttcattttaa tcgtgatgga      720
tccttgatag tttcaagtag ctatgatggt ctctgtcgca tctgggacac cgcctcaggc      780
cagtgcctga agacgctcat cgatgacgac aaccccccg tgtcttttgt gaagttctcc       840
ccgaacggca aatacatcct ggccgccacg ctggacaaca ctctgaagct ctgggactac      900 agcaaggga agtgcctgaa gacgtacact ggccacaaga atgagaaata ctgcatattt       960
gccaatttct ctgttactgg tgggaagtgg attgtgtctg gctcagagga taaccttgtt     1020
tacatctgga accttcagac gaaagagatt gtacagaaac tacaaggcca cacagatgtc     1080
gtgatctcaa cagcttgtca cccaacagaa acatcatcg cctctgctgc gctagaaaat     1140
gacaaaacaa ttaaactgtg aagagtgac tgctaagtcc ctttgctcct gcccgcgaga      1200
gactgtcggg aagttgaccc ggattggcaa gaaacagggt gtcttggagg tggtcccca      1260 gatctgcgcc tggggtcag acagggcct gatttgagcc tcctctctga agatgatttg       1320
gccgagcgga aggtgtggac caccggaaag ttcttaaaag ttgctggtga catttcttgc     1380
caattctaac actgtctagg aagagttcc tagtctattg tgttcaaaca gagtcaacaa      1440 aagttttaa ttttttatta cagaagggtg aagttcaatt taacatgcgt tgtgttttt       1500 cagtaaacgt tctgtatctt tttgatattc catgacccag tgcacgctgt ggcctgtcac     1560
cgccaccgtg gccccgccag ctggcctccc ctttggccca cgccggccgc ccccattctc     1620
tgctgcgtag atgccctggc ccagggccct gactcctcca ttcccgccag tagctgttcc     1680
tagtgtattt tcgtctttct ggaaaacagc attgagtggt tgttttctgt gtaaagagcc     1740
gtttgtgtct tgggagtttg tggcccacat gccgatagca cggtcatcgc acatgactct     1800
cccgtttgtc tcagtgtccc tgcaacaagc agcaccgcag actgtaataa aaggtggggt    1860
tttgtgaatg gttgtggcaa gtgcgtcctt gtgaagctcg tctccatgtg gctttcttgg     1920
agaaaggctc ccctggggca agagggtgga aggtttcttt ggacaggagg tgctgaggct     1980
ggctgcacct gctctctgaa gacgccttcc tctctaggtt cattgttcag tgttgctggg    2040
ggcggggaac gggggtgggg aggttcttag ttgcgaagga gccaagctcc tgatggactt     2100
gcgttgggat gtgggggaca cctgtggcat ggtaaggctc cctgagtccc ttactccagg     2160
tcagatgcca gtgggactca tgcgccctat gagggctgca gggccagtgc tgcccctcgg     2220
actcctcgag gggttgggtg ctaagcgcga gcctcgccgt ccctgctgga gccctcgcct     2280
gcctgcccct ctgcctgtgc tcctggcagt gtggcttccc ggtgctcacc tgcacagcag     2340
ttaacagcag aggccgagcg ggagcctctg gggagcgagg ctgaaacctg aacctgccca    2400
tggagacagt tgtggtgagg gttgccacac acagtgaggg cggagcaggg tggctgaggg     2460
cacaggtgcc tgggtctgtc ccacggggca gggctttggg gctgtgatgc tctgggaagc    2520
```

| | | | | |
|---|---|---|---|---|
| cagcttgggt | cctgggtcta | cagagggccc | tggccccgga | gcccagccag ctctgcctct | 2580 |
| ctcagggcct | ggagtcctgg | gggagctcag | ccagctctgc | ctttctcagg gcctggagtc | 2640 |
| ctggatgaat | cctgcaggtt | tttggttgca | ccggcccagg | gaggaagcgg ggggtttgtc | 2700 |
| aggtgggctc | tcctggaggt | cctcgagtgg | caggggtgag | gaggggatta tctgaggcat | 2760 |
| ctggagatgt | atatcctgtg | gtttcccctg | ccctctgtt | tccgatgagg tgtacggatg | 2820 |
| agtgacctgc | actaagaagt | gagttgccac | agtgaaaatg | ggttggtttt tgtcttcgac | 2880 |
| gctcagggtc | tgggcgcctc | gcatttgcag | tctgttgtga | cagacacggg gagctccgcg | 2940 |
| tgccagcctg | tggctgccct | gctgtggggg | tcctggggcc | ggcgaggccc cttcagtctt | 3000 |
| gttctggggg | gacggcccac | tccggggagg | gggtgtgctg | tgctgagcgc tgtatccctg | 3060 |
| aatatagttt | attttttcta | catttgaatt | ctgttgtaga | tttatgtaaa aatacattct | 3120 |
| ttttgaaaat | aaaaattttc | atgtcttcta | atttaaaaaa | aaa | 3163 |

<210> SEQ ID NO 79
<211> LENGTH: 16608
<212> TYPE: DNA
<213> ORGANISM: Homo sapiens

<400> SEQUENCE: 79

| | | | | |
|---|---|---|---|---|
| ctgcttcact | tcacggggcg | aacatggcgc | acagctgtcg | gtggcgcttc cccgcccgac | 60 |
| ccgggaccac | cggggcggc | ggcggcgggg | ggcgccgggg | cctaggggc gccccgcggc | 120 |
| aacgcgtccc | ggccctgctg | cttccccccg | ggccccggt | cggcggtggc ggccccgggg | 180 |
| cgccccctc | cccccggct | gtggcggccg | cggcggcggc | ggcgggaagc agcggggctg | 240 |
| gggttccagg | gggagcggcc | gccgcctcag | cagcctcctc | gtcgtccgcc tcgtcttcgt | 300 |
| cttcgtcatc | gtcctcagcc | tcttcagggc | cggccctgct | ccgggtgggc ccgggcttcg | 360 |
| acgcggcgct | gcaggtctcg | gccgccatcg | gcaccaacct | gcgccggttc cgggccgtgt | 420 |
| ttggggagag | cggcggggga | ggcggcagcg | gagaggatga | gcaattctta ggttttggct | 480 |
| cagatgaaga | agtcagagtg | cgaagtccca | caaggtctcc | ttcagttaaa actagtcctc | 540 |
| gaaaacctcg | tgggagacct | agaagtggct | ctgaccgaaa | ttcagctatc ctctcagatc | 600 |
| catctgtgtt | ttcccctcta | aataaatcag | agaccaaatc | tggagataag atcaagaaga | 660 |
| aagattctaa | aagtatagaa | aagaagagag | gaagacctcc | caccttccct ggagtaaaaa | 720 |
| tcaaaataac | acatggaaag | gacatttcag | agttaccaaa | gggaaacaaa gaagatagcc | 780 |
| tgaaaaaaat | taaaaggaca | ccttctgcta | cgtttcagca | agccacaaag attaaaaaat | 840 |
| taagagcagg | taaactctct | cctctcaagt | ctaagtttaa | gacagggaag cttcaaatag | 900 |
| gaaggaaggg | ggtacaaatt | gtacgacgga | gaggaaggcc | tccatcaaca gaaaggataa | 960 |
| agacccttc | gggtctcctc | attaattctg | aactggaaaa | gccccagaaa gtccggaaag | 1020 |
| acaaggaagg | aacacctcca | cttacaaaag | aagataagac | agttgtcaga caaagccctc | 1080 |
| gaaggattaa | gccagttagg | attattcctt | cttcaaaaag | gacagatgca accattgcta | 1140 |
| agcaactctt | acagagggca | aaaaaggggg | ctcaaaagaa | aattgaaaaa gaagcagctc | 1200 |
| agctgcaggg | aagaaaggtg | aagacacagg | tcaaaaatat | tcgacagttc atcatgcctg | 1260 |
| ttgtcagtgc | tatctcctcg | cggatcatta | agaccccctcg | gcggtttata gaggatgagg | 1320 |
| attatgaccc | tccaattaaa | attgcccgat | tagagtctac | accgaatagt agattcagtg | 1380 |
| ccccgtcctg | tggatcttct | gaaaaatcaa | gtgcagcttc | tcagcactcc tctcaaatgt | 1440 |

```
cttcagactc ctctcgatct agtagcccca gtgttgatac ctccacagac tctcaggctt    1500
ctgaggagat tcaggtactt cctgaggagc ggagcgatac ccctgaagtt catcctccac    1560
tgcccatttc ccagtcccca gaaaatgaga gtaatgatag gagaagcaga aggtattcag    1620
tgtcggagag aagttttgga tctagaacga cgaaaaaatt atcaactcta caaagtgccc    1680
cccagcagca gacctcctcg tctccacctc cacctctgct gactccaccg ccaccactgc    1740
agccagcctc cagtatctct gaccacacac cttggcttat gcctccaaca atccccttag    1800
catcaccatt tttgcctgct tccactgctc ctatgcaagg gaagcgaaaa tctattttgc    1860
gagaaccgac atttaggtgg acttctttaa agcattctag gtcagagcca caatactttt    1920
cctcagcaaa gtatgccaaa gaaggtctta ttcgcaaacc aatatttgat aatttccgac    1980
cccctccact aactcccgag gacgttggct ttgcatctgg tttttctgca tctggtaccg    2040
ctgcttcagc ccgattgttt tcgccactcc attctggaac aaggtttgat atgcacaaaa    2100
ggagccctct tctgagagct ccaagattta ctccaagtga ggctcactct agaatatttg    2160
agtctgtaac cttgcctagt aatcgaactt ctgctgaaac atcttcttca ggagtatcca    2220
atagaaaaag gaaagaaaaa gtgtttagtc ctattcgatc tgaaccaaga tctccttctc    2280
actccatgag gacaagaagt ggaaggctta gtagttctga gctctcacct ctcaccccc    2340
cgtcttctgt ctcttcctcg ttaagcattt ctgttagtcc tcttgccact agtgccttaa    2400
acccaacttt tacttttcct tctcattccc tgactcagtc tggggaatct gcagagaaaa    2460
atcagagacc aaggaagcag actagtgctc cggcagagcc attttcatca agtagtccta    2520
ctcctctctt cccttggttt accccaggct ctcagactga agagggaga aataaagaca    2580
aggcccccga ggagctgtcc aaagatcgag atgctgacaa gagcgtggag aaggacaaga    2640
gtagagagag agaccgggag agagaaaagg agaataagcg ggagtcaagg aaaagagaaa    2700
ggaaaaaggg atcagaaatt cagagtagtt ctgctttgta tcctgtgggt agggtttcca    2760
aagagaaggt tgttggtgaa gatgttgcca cttcatcttc tgccaaaaaa gcaacagggc    2820
ggaagaagtc ttcatcacat gattctggga ctgatattac ttctgtgact cttggggata    2880
caacagctgt caaaaccaaa atacttataa agaaagggag aggaaatctg gaaaaaacca    2940
acttggacct cggcccaact gccccatccc tggagaagga gaaaaccctc tgccttttca    3000
ctccttcatc tagcactgtt aaacattcca cttcctccat aggctccatg ttggctcagg    3060
cagacaagct tccaatgact gacaagaggg ttgccagcct cctaaaaaag gccaaagctc    3120
agctctgcaa gattgagaag agtaagagtc ttaaacaaac cgaccagccc aaagcacagg    3180
gtcaagaaag tgactcatca gagacctctg tgcgaggacc ccggattaaa catgtctgca    3240
gaagagcagc tgttgccctt ggccgaaaac gagctgtgtt tcctgatgac atgcccaccc    3300
tgagtgcctt accatgggaa gaacgagaaa agattttgtc ttccatgggg aatgatgaca    3360
agtcatcaat tgctggctca gaagatgctg aacctcttgc tccacccatc aaaccaatta    3420
aacctgtcac tagaaacaag gcaccccagg aacctccagt aaagaaagga cgtcgatcga    3480
ggcggtgtgg gcagtgtccc ggctgccagg tgcctgagga ctgtggtgtt tgtactaatt    3540
gcttagataa gcccaagttt ggtggtcgca atataaagaa gcagtgctgc aagatgagaa    3600
aatgtcagaa tctacaatgg atgccttcca aagcctacct gcagaagcaa gctaaagctg    3660
tgaaaaagaa agagaaaaag tctaagacca gtgaaaagag agacagcaaa gagagcagtg    3720
ttgtgaagaa cgtggtggac tctagtcaga aacctacccc atcagcaaga gaggatcctg    3780
ccccaaagaa aagcagtagt gagcctcctc cacgaaagcc cgtcgaggaa aagagtgaag    3840
```

```
aagggaatgt ctcggcccct gggcctgaat ccaaacaggc caccactcca gcttccagga    3900
agtcaagcaa gcaggtctcc cagccagcac tggtcatccc gcctcagcca cctactacag    3960
gaccgccaag aaaagaagtt cccaaaacca ctcctagtga gcccaagaaa aagcagcctc    4020
caccaccaga atcaggtcca gagcagagca aacagaaaaa agtggctccc cgcccaagta    4080
tccctgtaaa acaaaaacca aagaaaagg aaaaaccacc tccggtcaat aagcaggaga    4140
atgcaggcac tttgaacatc ctcagcactc tctccaatgg caatagttct aagcaaaaaa    4200
ttccagcaga tggagtccac aggatcagag tggactttaa ggaggattgt gaagcagaaa    4260
atgtgtggga gatgggaggc ttaggaatct tgacttctgt tcctataaca cccagggtgg    4320
tttgctttct ctgtgccagt agtgggcatg tagagtttgt gtattgccaa gtctgttgtg    4380
agcccttcca caagttttgt ttagaggaga acgagcgccc tctggaggac cagctggaaa    4440
attggtgttg tcgtcgttgc aaattctgtc acgtttgtgg aaggcaacat caggctacaa    4500
agcagctgct ggagtgtaat aagtgccgaa acagctatca ccctgagtgc ctgggaccaa    4560
actaccccac caaacccaca agaagaagaa agtctggat ctgtaccaag tgtgttcgct    4620
gtaagagctg tggatccaca actccaggca aagggtggga tgcacagtgg tctcatgatt    4680
tctcactgtg tcatgattgc gccaagctct ttgctaaagg aaacttctgc cctctctgtg    4740
acaaatgtta tgatgatgat gactatgaga gtaagatgat gcaatgtgga aagtgtgatc    4800
gctgggtcca ttccaaatgt gagaatcttt caggtacaga agatgagatg tatgagattc    4860
tatctaatct gccagaaagt gtggcctaca cttgtgtgaa ctgtactgag cggcaccctg    4920
cagagtggcg actggcccct tgaaaaagagc tgcagatttc tctgaagcaa gttctgacag    4980
ctttgttgaa ttctcggact accagccatt tgctacgcta ccggcaggct gccaagcctc    5040
cagacttaaa tcccgagaca gaggagagta taccttcccg cagctccccc gaaggacctg    5100
atccaccagt tcttactgag gtcagcaaac aggatgatca gcagccttta gatctagaag    5160
gagtcaagag gaagatggac caagggaatt acacatctgt gttggagttc agtgatgata    5220
ttgtgaagat cattcaagca gccattaatt cagatggagg acagccagaa attaaaaaag    5280
ccaacagcat ggtcaagtcc ttcttcattc ggcaaatgga acgtgttttt ccatggttca    5340
gtgtcaaaaa gtccaggttt tgggagccaa ataaagtatc aagcaacagt gggatgttac    5400
caaacgcagt gcttccacct tcacttgacc ataattatgc tcagtggcag gagcgagagg    5460
aaaacagcca cactgagcag cctccttta tgaagaaaat cattccagct cccaaaccca    5520
aaggtcctgg agaaccagac tcaccaactc ctctgcatcc tcctacacca ccaattttga    5580
gtactgatag gagtcgagaa gacagtccag agctgaaccc accccaggc atagaagaca    5640 atagacagtg tgcgttatgt ttgacttatg gtgatgacag tgctaatgat gctggtcgtt    5700
tactatatat tggccaaaat gagtggacac atgtaaattg tgctttgtgg tcagcggaag    5760
tgtttgaaga tgatgacgga tcactaaaga atgtgcatat ggctgtgatc agggcaagc    5820 agctgagatg tgaattctgc caaaagccag gagccaccgt gggttgctgt ctcacatcct    5880
gcaccagcaa ctatcacttc atgtgttccc gagccaagaa ctgtgtcttt ctggatgata    5940
aaaaagtata ttgccaacga catcgggatt tgatcaaagg cgaagtggtt cctgagaatg    6000
gatttgaagt tttcagaaga gtgtttgtgg actttgaagg aatcagcttg agaaggaagt    6060
ttctcaatgg cttggaacca gaaaatatcc acatgatgat tgggtctatg acaatcgact    6120
gcttaggaat tctaaatgat ctctccgact gtgaagataa gctctttcct attggatatc    6180
```

```
agtgttccag ggtatactgg agcaccacag atgctcgcaa gcgctgtgta tatacatgca    6240
agatagtgga gtgccgtcct ccagtcgtag agccggatat caacagcact gttgaacatg    6300
atgaaaacag gaccattgcc catagtccaa catcttttac agaaagttca tcaaaagaga    6360
gtcaaaacac agctgaaatt ataagtcctc catcaccaga ccgacctcct cattcacaaa    6420
cctctggctc ctgttattat catgtcatct caaaggtccc caggattcga acacccagtt    6480
attctccaac acagagatcc cctggctgtc gaccgttgcc ttctgcagga agtcctaccc    6540
caaccactca tgaaatagtc acagtaggtg atcctttact ctcctctgga cttcgaagca    6600
ttggctccag gcgtcacagt acctcttcct tatcacccca gcggtccaaa ctccggataa    6660
tgtctccaat gagaactggg aatacttact ctaggaataa tgtttcctca gtctccacca    6720
ccgggaccgc tactgatctt gaatcaagtg ccaaagtagt tgatcatgtc ttagggccac    6780
tgaattcaag tactagttta gggcaaaaca cttccacctc ttcaaatttg caaaggacag    6840
tggttactgt aggcaataaa aacagtcact tggatggatc ttcatcttca gaaatgaagc    6900
agtccagtgc ttcagacttg gtgtccaaga gctcctcttt aaaggagag aagaccaaag    6960 tgctgagttc caagagctca gagggatctg cacataatgt ggcttaccct ggaattccta    7020
aactggcccc acaggttcat aacacaacat ctagagaact gaatgttagt aaaatcggct    7080
cctttgctga accctcttca gtgtcgtttt cttctaaaga ggccctctcc ttcccacacc    7140
tccatttgag agggcaaagg aatgatcgag accaacacac agattctacc caatcagcaa    7200
actcctctcc agatgaagat actgaagtca aaaccttgaa gctatctgga atgagcaaca    7260
gatcatccat tatcaacgaa catatgggat ctagttccag agataggaga cagaaaggga    7320
aaaaatcctg taagaaaact ttcaaagaaa agcattccag taaatctttt ttggaacctg    7380
gtcaggtgac aactggtgag gaaggaaact tgaagccaga gtttatggat gaggttttga    7440
ctcctgagta tatgggccaa cgaccatgta acaatgtttc ttctgataag attggtgata    7500
aaggcctttc tatgccagga gtcccccaaag ctccacccat gcaagtagaa ggatctgcca    7560
aggaattaca ggcaccacgg aaacgcacag tcaaagtgac actgacacct ctaaaaatgg    7620
aaaatgagag tcaatccaaa aatgccctga agaaagtag tcctgcttcc cctttgcaaa    7680
tagagtcaac atctcccaca gaaccaattt cagcctctga aaatccagga gatggtccag    7740
tggcccaacc aagccccaat aatacctcat gccaggattc tcaaagtaac aactatcaga    7800
atcttccagt acaggacaga aacctaatgc ttccagatgg ccccaaacct caggaggatg    7860 gctctttta aaggaggtat ccccgtcgca gtgcccgtgc acgttctaac atgttttttg    7920 ggcttaccc actctatgga gtaagatcct atggtgaaga agacattcca ttctacagca    7980
gctcaactgg gaagaagcga ggcaagagat cagctgaagg acaggtggat ggggccgatg    8040
acttaagcac ttcagatgaa gacgacttat actattacaa cttcactaga acagtgattt    8100
cttcaggtgg agaggaacga ctggcatccc ataatttatt tcgggaggag aacagtgtg    8160 atcttccaaa aatctcacag ttggatggtg ttgatgatgg gacagagagt gatactagtg    8220
tcacagccac aacaaggaaa agcagccaga ttccaaaaag aaatggtaaa gaaaatggaa    8280
cagagaactt aaagattgat agacctgaag atgctgggga gaagaacat gtcactaaga    8340 gttctgttgg ccacaaaaat gagccaaaga tggataactg ccattctgta agcagagtta    8400
aaacacaggg acaagattcc ttggaagctc agctcagctc attggagtca agccgcagag    8460
tccacacaag tacccctcc gacaaaaatt tactggacac ctataatact gagctcctga    8520
aatcagattc agacaataac aacagtgatg actgtgggaa tatcctgcct tcagacatta    8580
```

```
tggactttgt actaaagaat actccatcca tgcaggcttt gggtgagagc ccagagtcat   8640
cttcatcaga actcctgaat cttggtgaag gattgggtct tgacagtaat cgtgaaaaag   8700
acatgggtct ttttgaagta ttttctcagc agctgcctac aacagaacct gtggatagta   8760
gtgtctcttc ctctatctca gcagaggaac agtttgagtt gcctctagag ctaccatctg   8820
atctgtctgt cttgaccacc cggagtccca ctgtccccag ccagaatccc agtagactag   8880
ctgttatctc agactcaggg gagaagagag taaccatcac agaaaaatct gtagcctcct   8940
ctgaaagtga cccagcactg ctgagcccag gagtagatcc aactcctgaa ggccacatga   9000
ctcctgatca ttttatccaa ggacacatgg atgcagacca catctctagc cctccttgtg   9060
gttcagtaga gcaaggtcat ggcaacaatc aggatttaac taggaacagt agcaccctg    9120 gccttcaggt acctgtttcc ccaactgttc ccatccagaa ccagaagtat gtgcccaatt   9180
ctactgatag tcctggcccg tctcagattt ccaatgcagc tgtccagacc actccacccc   9240
acctgaagcc agccactgag aaactcatag ttgttaacca gaacatgcag ccactttatg   9300
ttctccaaac tcttccaaat ggagtgaccc aaaaaatcca attgacctct tctgttagtt   9360
ctacacccag tgtgatggag acaaatactt cagtattggg acccatggga ggtggtctca   9420
cccttaccac aggactaaat ccaagcttgc caacttctca atctttgttc ccttctgcta   9480
gcaaaggatt gctacccatg tctcatcacc agcacttaca ttccttccct gcagctactc   9540
aaagtagttt cccaccaaac atcagcaatc ctccttcagg cctgcttatt ggggttcagc   9600
ctcctccgga tccccaactt ttggtttcag aatccagcca gaggacagac ctcagtacca   9660
cagtagccac tccatcctct ggactcaaga aaagacccat atctcgtcta cagacccgaa   9720
agaataaaaa acttgctccc tctagtaccc cttcaaacat tgccccttct gatgtggttt   9780
ctaatatgac attgattaac ttcacaccct cccagcttcc taatcatcca agtctgttag   9840
atttggggtc acttaatact tcatctcacc gaactgtccc caacatcata aaagatctca   9900
aatctagcat catgtatttt gaaccggcac ccctgttacc acagagtgtg ggaggaactg   9960
ctgccacagc ggcaggcaca tcaacaataa gccaggatac tagccacctc acatcagggt  10020
ctgtgtctgg cttggcatcc agttcctctg tcttgaatgt tgtatccatg caaactacca  10080 caaccctac aagtagtgcg tcagttccag gacacgtcac cttaaccaac ccaaggttgc    10140
ttggtacccc agatattggc tcaataagca atctttaat caaagctagc cagcagagcc     10200
tggggattca ggaccagcct gtggctttac cgccaagttc aggaatgttt ccacaactgg  10260
ggacatcaca gaccccctct actgctgcaa taacagcggc atctagcatc tgtgtgctcc  10320
cctccactca gactacgggc ataacagccg cttcaccttc tggggaagca gacgaacact  10380
atcagcttca gcatgtgaac cagctccttg ccagcaaaac tgggattcat tcttcccagc  10440
gtgatcttga ttctgcttca gggccccagg tatccaactt tacccagacg gtagacgctc  10500
ctaatagcat gggactggag cagaacaagg ctttatcctc agctgtgcaa gccagccca    10560 cctctcctgg gggttctcca tcctctccat cttctggaca gcggtcagca agcccttcag  10620
tgccgggtcc cactaaaccc aaaccaaaaa ccaaacggtt tcagctgcct ctagacaaag  10680
ggaatggcaa gaagcacaaa gtttcccatt tgcggaccac ttcttctgaa gcacacattc  10740
cagaccaaga aacgacatcc ctgacctcag gcacagggac tccaggagca gaggctgagc  10800
agcaggatac agctagcgtg gagcagtcct cccagaagga gtgtgggcaa cctgcagggc  10860
aagtcgctgt tcttccggaa gttcaggtga cccaaaatcc agcaaatgaa caagaaagtg  10920
```

```
cagaacctaa acagtggaa gaagaggaaa gtaatttcag ctccccactg atgctttggc    10980
ttcagcaaga acaaaagcgg aaggaaagca ttactgagaa aaacccaag aaaggacttg    11040
tttttgaaat ttccagtgat gatggctttc agatctgtgc agaaagtatt gaagatgcct    11100
ggaagtcatt gacagataaa gtccaggaag ctcgatcaaa tgcccgccta agcagctct    11160
catttgcagg tgttaacggt ttgaggatgc tggggattct ccatgatgca gttgtgttcc    11220
tcattgagca gctgtctggt gccaagcact gtcgaaatta caaattccgt ttccacaagc    11280
cagaggaggc caatgaaccc cccttgaacc ctcacggctc agccagggct gaagtccacc    11340
tcaggaagtc agcatttgac atgtttaact tcctggcttc taaacatcgt cagcctcctg    11400
aatacaaccc caatgatgaa gaagaggagg aggtacagct gaagtcagct cggagggcaa    11460
ctagcatgga tctgccaatg cccatgcgct tccggcactt aaaaaagact tctaaggagg    11520
cagttggtgt ctacaggtct cccatccatg gccgggtct tttctgtaag agaaacattg    11580
atgcaggtga gatggtgatt gagtatgccg gcaacgtcat ccgctccatc cagactgaca    11640
agcgggaaaa gtattacgac agcaagggca ttggttgcta tatgttccga attgatgact    11700
cagaggtagt ggatgccacc atgcatggaa atgctgcacg cttcatcaat cactcgtgtg    11760
agcctaactg ctattctcgg gtcatcaata ttgatgggca gaagcacatt gtcatctttg    11820
ccatgcgtaa gatctaccga ggagaggaac tcacttacga ctataagttc cccattgagg    11880
atgccagcaa caagctgccc tgcaactgtg gcgccaagaa atgccggaag ttcctaaact    11940
aaagctgctc ttctccccca gtgttggagt gcaaggaggc ggggccatcc aaagcaacgc    12000
tgaaggcctt ttccagcagc tgggagctcc cggattgcgt ggcacagctg aggggcctct    12060
gtgatggctg agctctctta tgtcctatac tcacatcaga catgtgatca tagtcccaga    12120
gacagagttg aggtctcgaa gaaaagatcc atgatcggct ttctcctggg gcccctccaa    12180
ttgtttactg ttagaaagtg ggaatggggt ccctagcaga cttgcctgga aggagcctat    12240
tatagagggt tggttatgtt gggagattgg gcctgaattt ctcccacagaa ataagttgcc    12300
atcctcaggt tggccctttc ccaagcactg taagtgagtg ggtcaggcaa agccccaaat    12360
ggaggggttgg ttagattcct gacagtttgc cagccaggcc ccacctacag cgtctgtcga    12420
acaaacagag gtctggtggt tttccctact atcctcccac tcgagagttc acttctggtt    12480
gggagacagg attcctagca cctccggtgt caaaaggctg tcatgggtt gtgccaatta    12540
attaccaaac attgagcctg caggctttga gtgggagtgt tgccccagg agccttatct    12600
cagccaatta cctttcttga cagtaggagc ggcttccctc tcccattccc tcttcactcc    12660
cttttcttcc tttccctgt cttcatgcca ctgctttccc atgcttcttt cgggttgtag    12720
gggagactga ctgcctgctc aaggacactc cctgctgggc ataggatgtg cctgcaaaaa    12780
gttccctgag cctgtaagca ctccaggtgg ggaagtggac aggagccatt ggtcataacc    12840
agacagaatt tggaaacatt ttcataaagc tccatggaga gttttaaaga aacatatgta    12900
gcatgatttt gtaggagagg aaaaagatta tttaaatagg atttaaatca tgcaacaacg    12960
agagtatcac agccaggatg acccttgggt cccattccta agacatggtt actttatttt    13020
ccccttgtta agacatagga agacttaatt tttaaacggt cagtgtccag ttgaaggcag    13080
aacactaatc agatttcaag gcccacaact tggggactag accaccttat gttgagggaa    13140
ctctgccacc tgcgtgcaac ccacagctaa agtaaattca atgacactac tgccctgatt    13200
actcctagg atgtggtcaa aacagcatca aatgttctt ctcttccttt ccccaagaca    13260
gagtcctgaa cctgttaaat taagtcattg gatttactc tgttctgttt acagtttact    13320
```

```
atttaaggtt ttataaatgt aaatatattt tgtatatttt tctatgagaa gcacttcata    13380
gggagaagca cttatgacaa ggctatttt taaaccgcgg tattatccta atttaaaaga    13440
agatcggttt ttaataattt tttattttca taggatgaag ttagagaaaa tattcagctg    13500
tacacacaaa gtctggtttt tcctgcccaa cttccccctg gaaggtgtac tttttgttgt    13560
ttaatgtgta gcttgtttgt gccctgttga cataaatgtt tcctgggttt gctctttgac    13620
aataaatgga gaaggaaggt cacccaactc cattgggcca ctcccctcct tcccctattg    13680
aagctcctca aaaggctaca gtaatatctt gatacaacag attctcttct ttcccgcctc    13740
tctcctttcc ggcgcaactt ccagagtggt gggagacggc aatctttaca tttccctcat    13800
ctttcttact tcagagttag caaacaacaa gttgaatggc aacttgacat ttttgcatca    13860
ccatctgcct cataggccac tctttccttt ccctctgccc accaagtcct catatctgca    13920
gagaacccat tgatcacctt gtgccctctt ttggggcagc ctgttgaaac tgaagcacag    13980
tctgaccact cacgataaag cagattttc tctgcctctg ccacaaggtt tcagagtagt    14040
gtagtccaag tagagggtgg ggcaccctt tctcgccgca agaagcccat tcctatggaa    14100
gtctagcaaa gcaatacgac tcagcccagc actctctgcc ccaggactca tggctctgct    14160
gtgccttcca tcctgggctc ccttctctcc tgtgacctta agaactttgt ctggtggctt    14220
tgctggaaca ttgtcactgt tttcactgtc atgcagggag cccagcactg tggccaggat    14280
ggcagagact tccttgtcat catggagaag tgccagcagg ggactgggaa aagcactcta    14340
cccagacctc acctcccttc ctccttttgc ccatgaacaa gatgcagtgg ccctagggt    14400
tccactagtg tctgctttcc tttattattg cactgtgtga ggttttttg taaatccttg    14460
tattcctatt ttttttaaag aaaaaaaaaa aaccttaagc tgcatttgtt actgaaatga    14520
ttaatgcact gatgggtcct gaattcacct tgagaaagac ccaaaggcca gtcaggggt    14580
gggggaact cagctaaata gacctagtta ctgccctgct aggccatgct gtactgtgag    14640
cccctcctca ctctctacca accctaaacc ctgaggacag gggaggaacc cacagcttcc    14700
ttctcctgcc agctgcagat ggtttgcctt gcctttccac cccctaattg tcaaccacaa    14760
aaatgagaaa ttcctcttct agctcagcct tgagtccatt gccaaatttt cagcacacct    14820
gccagcaact tgggggaata agcgaaggtt tccctacaag agggaaagaa ggcaaaaacg    14880
gcacagctat ctccaaacac atctgagttc atttcaaaag tgaccaaggg aatctccgca    14940
caaaagtgca gattgaggaa ttgtgatggg tcattcccaa gaatcccca aggggcatcc    15000
caaatccctg aggagtaaca gctgcaaacc tggtcagttc tcagtgagag ccagctcact    15060
tatagctttg ctgctagaac ctgttgtggc tgcatttcct ggtggccagt gacaactgtg    15120
taaccagaat agctgcatgg cgctgaccct ttggccggaa cttggtctct tggctccctc    15180
cttggccacc caccacctct cgcacagccc ctctgttttt acaccaataa caagaattaa    15240
ggggggaagcc ctggcagcta tacgttttca accagactcc tttgccggga cccagcccgc    15300
caccctgctc gcctccgtca aaccccggc caatgcagtg agcaccatgt agctcccttg    15360
atttaaaaaa aataaaaaat aaaaaaaaaa ggaaaaaaaa atacaacaca cacacaaaaa    15420
taaaaaaaat attctaatga atgtatcttt ctaaggact gacgttcaat caaatatctg    15480
aaaatactaa aggtcaaaac cttgtcagat gttaacttct aagttcggtt tgggattttt    15540
tttttttaat agaaatcaag ttgttttgt ttttaaggaa aagcgggtca ttgcaaaggg    15600
ctgggtgtaa ttttatgttt catttccttc attttaaagc aatacaaggt tatggagcag    15660
```

```
atggttttgt gccgaatcat gaatactagt caagtcacac actctggaaa cttgcaactt    15720
tttgtttgtt ttggtttttca aataaatata aatatgatat atataggaac taatatagta    15780
atgcaccatg taacaaagcc tagttcagtc catggctttt aattctctta acactataga    15840
taaggattgt gttacagttg ctagtagcgg caggaagatg tcaggctcac tttcctctga    15900
ttcccgaaat gggggggaacc tctaaccata aaggaatggt agaacagtcc attcctcgga    15960
tcagagaaaa atgcagacat ggtgtcacct ggatttttt ctgcccatga atgttgccag    16020
tcagtacctg tcctccttgt ttctctattt ttggttatga atgttggggt taccacctgc    16080
atttagggga aaattgtgtt ctgtgctttc ctggtatctt gttccgaggt actctagttc    16140
tgtctttcaa ccaagaaaat agaattgtgg tgtttctttt attgaacttt taacagtctc    16200
tttagtaaat acaggtagtt gaataattgt ttcaagagct caacagatga caagcttctt    16260
ttctagaaat aagacatttt ttgacaactt tatcatgtat aacagatctg tttttttcc    16320 ttgtgttctt ccaagcttct ggttagagaa aagagaaaa aaaaaaagg aaaatgtgtc    16380 taaagtccat cagtgttaac tccctgtgac agggatgaag gaaaatactt taatagttca    16440
aaaaataata atgctgaaag ctctctacga aagactgaat gtaaaagtaa aaagtgtaca    16500
tagttgtaaa aaaaggagt ttttaaacat gtttattttc tatgcacttt tttttattta    16560
agtgatagtt taattaataa acatgtcaag tttaaaaaaa aaaaaaaa                 16608

<210> SEQ ID NO 80
<211> LENGTH: 20709
<212> TYPE: DNA
<213> ORGANISM: Homo sapiens

<400> SEQUENCE: 80
agcggaagga tcccgcagcg tgtgcgtaga actgcagagt cacagccttt cctccgagag      60
ggcgggatcc ctccgccgct ccgctccaac acaaaatagg gccgcctctt ctcctttctc     120
cccctctcga gtggggtgcc ccgggcaaaa ggccccccccg gatctagcgc cgaaggcttc     180
acgaatcttc acgaccgctg cccagctctt gggccaggaa atagccccttt cgcaggaacc     240 accctaccgg ccgaacagga ggcggagggg gggaggcgga gcggcgccgc gctgcactac     300
tttcctctcc ggttgcaaat ggctgcctcg ttccccactt tccgctcagt ttcctgaccc     360
cccggtgccg ggagccgggg ttgggccatg caccctctagg ccgcctgcga tcacagtcag     420 ccggggggtcg agggggtgcc accgaccaga gccggccagg ccggggggcgg ggcagctccc     480 gaggccagag gggaagggag gcgagcgcag ggcctggagc ggccggaggg gagcgggcag     540
agggctcgca ccgcccgccc cttccttttc ctcgcctacc tagcctcctc ccttccccgg     600
ggggagcaga aggtgggggg ctcgaagccg ccgagggtga gcgctcgggg tcgagaagcc     660
cggcgctggg tgtgtgtcag gttcagcccc gcggccccgc cggccccgcg tcgccgtagc     720
tcgcgcggcc ccgggcgccg gccggggcgg ggagagggggc tcggcgctcc tgcgagggtc     780
tcacgttcca tccgggccag gcgcgggggcg gcgcggcatt ccttccgggc tgctggggag     840
gcgcctcgac gttccatctg gagagcctcg acgttccgcc cgagcccggc gcgggcggcc     900
ggggcgctgg ccgggcccta ggactgagag gccgcccggc gacgcggatg cggagcctgc     960
tcgcccaaga tcaaagccac cggtgctctc tttgtgtccg ctcgggattc gccgccctgg    1020
ggctgtccat ggaaacctaa actgctggaa cctgaggcag agaaccctc tttggcttct    1080 tgctgttttt ttgtggggggg agggtggcca ctccgacctg gatttaccgt tcttggcccc    1140
cctaagcccc cccgtgcggg gggcggctgt gatcgctctg gcggttggag gtcggggagc    1200
```

```
ggcccgggct ctggccatgt tctcggatga ggatttctgg atcgccctgt gaagaggtct   1260 cccccgagagg gccctgccca gtcggagaga gggatggaca gccagaagct ggctggtgag   1320
gataaagatt cagaaccggc agctgatgga cctgcagctt ctgaggaccc aagtgccact   1380
gagtcagacc tgcccaaccc acatgtggga gaggtctctg tccttagttc tgggagtccc   1440
aggcttcagg agactcctca ggactgcagt ggggtccgg tgcggcgttg tgctctctgt   1500
aactgcgggg agcccagtct acacgggcag cgggagctac ggcgctttga gttgccattt   1560
gattggcccc ggtgtccagt ggtgtcccct gggggagcc cagggcccaa tgaggcagtg   1620
ctgcccagtg aggacctatc acagattggt ttccctgagg ccttacacc tgcccaccta   1680 ggagaacctg gagggtcctg ctgggctcac cattggtgtg ctgcatggtc ggcaggcgta   1740
tgggggcagg agggcccaga actatgtggt gtggacaagg ccatcttctc agggatctca   1800
cagcgctgct cccactgcac caggctcggt gcctccatcc cttgccgctc acctggatgt   1860
ccacggcttt accacttccc ctgcgcgact gccagcggtt ccttcctatc catgaaaaca   1920
ctgcagctgc tatgcccaga gcacagtgag ggggctgcat atctggagga ggctcgctgt   1980
gcagtgtgtg aggggccagg ggagttgtgt gacctgttct tctgtaccag ctgtgggcat   2040
cactatcacg gggcctgcct ggacactgct ctgactgccc gcaaacgtgc tggctggcag   2100
tgccctgaat gcaaagtgtg ccaagcctgc aggaaacctg gaatgactc taagatgttg   2160 gtttgtgaga cgtgtgacaa aggataccat actttctgcc taaaaccacc catggaggaa   2220
ctgcctgctc actcttggaa gtgcaaggcg tgccgggtgt gccgggcctg tggggcgggc   2280
tcagcagaac tgaatcccaa ctcggagtgg tttgagaact actctctctg tcaccgctgt   2340
cacaaagccc agggaggtca gactatccgc tccgttgctg agcagcatac cccggtgtgt   2400
agcagatttt cacccccaga gcctggcgat accccactg acgagcccga tgctctgtac   2460
gttgcatgcc aagggcagcc aaagggtggg cacgtgacct ctatgcaacc caaggaacca   2520
gggcccctgc aatgtgaagc caaaccacta gggaaagcag gggtccaact tgagcccag   2580 ttggaggccc ccctaaacga ggagatgcca ctgctgcccc cacctgagga gtcacccctg   2640
tccccaccac ctgaggaatc acccacgtcc ccaccacctg aggcatcacg cctgtcacca   2700
ccacctgagg aattgcccgc atccccactt cctgaggcat tgcacctgtc ccggccgctg   2760
gaggaatcgc ccctctctcc gccgcctgag gagtctcctc tgtctccccc acctgaatca   2820 tcacctttt ctccactgga ggagtcgccc ttgtctccac cggaagagtc accccatct   2880 cctgcacttg agacgcctct atccccacca cctgaagcat cgcccctgtc ccaccattt   2940 gaagaatctc ctttgtcccc gccacctgag gaattgccca cttccccgcc acctgaagca   3000
tctcgcctgt ctccaccacc tgaggagtca cccatgtccc ctccacctga agagtcaccc   3060
atgtctccac caccggaggc atctcgtctg ttcccaccat ttgaagagtc tcctctgtcc   3120
cctccacctg aggagtctcc cctttccccca ccacctgagg catcacgcct gtccccacca   3180
cctgaggact cgcctatgtc cccaccacct gaagaatcac ctatgtcccc cccacctgag   3240
gtatcgcgcc tatccccct gcctgtggtg tcacgcctgt ctccaccgcc tgaggaatct   3300
cccttgtccc caccgcctga ggagtctccc acgtcccctc cacctgaggc ttcacgcctc   3360
tccccaccac ctgaggactc ccccacatcc ccaccacctg aggactcacc tgcttcccca   3420
ccaccggagg actcgctcat gtccctgccg ctggaggagt caccccctgtt gccactacct   3480 gaggagccgc aactctgccc ccggtccgag gggccgcacc tgtcacccg gcctgaggag   3540
```

```
ccgcacctgt ccccccggcc tgaggagcca cacctatctc cgcaggctga ggagccacac    3600
ctgtccccc agcctgagga gccatgccta tgcgctgtgc ctgaggagcc acacttgtcc     3660
ccccaggctg agggaccaca tctgtcccct cagcctgagg aattgcacct gtcccccag    3720
actgaggagc cgcacctgtc tcctgtgcct gaggagccat gcttgtcccc caacctgag    3780
gaatcacacc tgtccccca gtctgaggag ccatgcctgt ccccccggcc tgaggaatcg    3840
catctgtccc ctgagcttga aagccaccc ctgtcccctc ggcctgaaaa gcccctgag     3900
gagccaggcc aatgccctgc acctgaggag ctgcccttgt ccctccccc tggggaacca    3960
tccttatctc ccttgcttgg agagccagcc tgtctgagc ctggggaacc acctctgtcc    4020
cctctgcccg aggagctgcc gttgtcccca tctggggagc catccttgtc gcctcagctg    4080
atgccaccag atcccttcc tcctccactc tcacccatca tcacagctgc ggccccaccg    4140
gccctgtctc ctttggggga gttagagtac ccctttggtg ccaaagggga cagtgaccct    4200
gagtcaccgt tggctgcccc catcctggag acacccatca gccctccacc agaagctaac    4260
tgcactgacc ctgagcctgt ccccctatg atccttcccc catctccagg ctccccagtg    4320
gggccggctt ctcccatcct gatggagccc cttcctcctc agtgttcgcc actccttcag    4380
cattccctgg ttccccaaaa ctcccctcct tcccagtgct ctcctcctgc cctaccactg    4440
tccgttccct ccccgttgag tcccataggg aaggtagtgg gggtctcaga tgaggctgag    4500
ctgcacgaga tggagactga aaagtttca gaacctgaat gccagccttt ggaacccagt    4560
gccaccagtc ctctccctc cccaatgggg gactttcct gccccgcccc cagccctgcc    4620
ccagccctga tgacttctc tggcctaggg aagacacag cccctctgga tgggattgat    4680
gctccgggtt cacagccaga gcctggacag accctggca gtttggctag tgaacttaaa    4740
ggctcccctg tgctcctgga ccccgaggag ctggccctg tgaccccat ggaggtctac    4800
cccgaatgca agcagacagc agggcagggc tcaccatgtg aagaacagga agagccacgt    4860
gcaccggtgg ccccccacacc acccactctc atcaaatccg acatcgttaa cgagatctct    4920
aatctgagcc agggtgatgc cagtgccagt tttcctggct cagagcccct cctgggctct    4980
ccagacccgg aggggggtgg ctccctgtcc atggagttgg gggtctctac ggatgttagt    5040
ccagcccgag atgagggctc cctacggctc tgtactgact cactgccaga gactgatgac    5100
tcactattgt gcgatgctgg gacagctatc agcggaggca agctgagggg ggagaagggg    5160
cggcggcgca gctccccagc ccgttcccgc atcaaacagg gtcgcagcag cagtttccca    5220
ggaagacgcc ggcctcgtgg aggagcccat ggaggacgtg gtagaggacg ggcccggcta    5280
aagtcaactg cttcttccat tgagactctg gttgctgaca ttgatagctc tcccagtaag    5340
gaggaggagg aagaagatga tgacaccatg cagaataccg tggttctctt ctccaacaca    5400
gacaaatttg tcctaatgca ggacatgtgt gtggtatgtg gcagctttgg ccgggggca    5460
gagggccacc tccttgcctg ttcgcagtgc tctcagtgct atcaccctta ctgtgtcaac    5520
agcaagatca ccaaggtgat gctgctcaag ggctggcgtt gtgtggagtg tattgtgtgt    5580
gaggtgtgtg gccaggcctc cgacccctca cgcctgctgc tctgtgatga ctgtgatatt    5640
agctaccaca catactgcct ggacccccca ctgctcaccg tccccaaggg cggctggaag    5700
tgcaagtggt gtgtgtcctg tatgcagtgt ggggctgctt cccctggctt ccactgtgaa    5760
tggcagaata gttacacaca ctgtgggccc tgtccagcc tggtgacctg ccctatctgt    5820
catgctcctt acgtagaaga ggacctacta atccagtgcc gccactgtga acggtggatg    5880
catgcaggct gtgagagcct cttcacagag gacgatgtgg agcaggcagc cgatgaaggc    5940
```

```
tttgactgtg tctcctgcca gccctacgtg gtaaagcctg tggcgcctgt tgcacctcca    6000
gagctggtgc ccatgaaggt gaaagagcca gagcccagt actttcgctt cgaaggtgtg     6060
tggctgacag aaactggcat ggccttgctg cgtaacctga ccatgtcacc actgcacaag    6120
cggcgccaac ggcgaggacg gcttggcctc caggcgagg caggattgga gggttctgag     6180
ccctcagatg cccttggccc tgatgacaag aaggatgggg acctggacac cgatgagctg    6240
ctcaaggtg aagtggtgt ggagcacatg gagtgcgaaa ttaaactgga gggccccgtc      6300
agccctgatg tggagcctgg caaagaggag accgaggaaa gcaaaaaacg caagcgtaaa    6360
ccatatcggc ctggcattgg tggtttcatg gtgcgacagc ggaaatccca cacacgcacg    6420
aaaaagggc ctgctgcaca ggcggaggtg ttgagtgggg atgggcagcc cgacgaggtg     6480
atacctgctg acctgcctgc agagggcgcc gtggagcaga gcttagctga agggatgag     6540
aagaagaagc aacagcggcg agggcgcaag aagagcaaac tggaggacat gttccctgct    6600
tacttgcagg aagccttctt tgggaaggag ctgctggacc tgagccgtaa ggccctttt     6660
gcagttgggg tgggccggcc aagctttgga ctagggaccc caaaagccaa gggagatgga    6720
ggctcagaaa ggaaggaact ccccacatcg cagaaaggag atgatggtcc agatattgca    6780
gatgaagaat cccgtggcct cgagggcaaa gccgatacac caggacctga ggatgggggc    6840
gtgaaggcat ccccagtgcc cagtgaccct gagaagccag gcaccccagg tgaagggatg    6900
cttagctctg acttagacag gatttccaca gaagaactgc ccaagatgga atccaaggac    6960
ctgcagcagc tcttcaagga tgttctgggc tctgaacgag aacagcatct gggttgtgga    7020
accctggcc tagaaggcag ccgtacgcca ctgcagaggc cctttcttca aggtggactc     7080
cctttgggca atctgccctc cagcagccca atggactcct acccaggcct ctgccagtcc    7140
ccgttcctgg attctaggga gcgcggggc ttctttagcc cggaacccgg tgagcccgac     7200
agccctgga cgggctcagg tggcaccacg ccctccaccc ccacaacccc caccacggag    7260
ggtgagggcg acggactctc ctataaccag cggagtcttc agcgctggga aaggatgag    7320
gagttgggcc agctgtccac catctcacct gtgctctatg ccaacattaa ttttcctaat    7380
ctcaagcaag actacccaga ctggtcaagc cgttgcaaac aaatcatgaa gctctggaga    7440
aaggttccag cagctgacaa agccccctac ctgcaaaagg ccaaagataa ccgggcagct    7500
caccgcatca caaggtgca gaagcaggct gagagccaga tcaacaagca gaccaaggtg    7560
ggcgacatag cccgtaagac tgaccgaccg gccctacatc tccgcattcc cccgcagcca    7620
ggggcactgg gcagcccgcc ccccgctgct gcccccacca ttttcattgg cagccccact    7680
accccccgccg gcttgtctac ctctgcggac gggttcctga agccgccggc gggctcggtg    7740
cctgccctg actcgcctgg tgagctcttc ctcaagctcc cacccaggt gcccgcccaa      7800
gtgccttcgc aggaccccct tggactggcc cctgcctatc ccctggagcc ccgcttcccc    7860
acggcaccgc ccacctatcc cccctatcct agtcctacgg ggcccctgc gcagcccccg     7920
atgctgggcg cctcatctcg tcctgggct ggccagccag gggaattcca cactacccca    7980
cctggcaccc ccagacacca gccctccaca cctgacccat tcctcaaacc ccgctgcccc    8040
tcgctggata cttggctgt gcctgagagc cctgggtag ggggaggcaa agcttccgag      8100
ccctgctct cgcccccacc tttgggggag tcccggaagg cctagaggt gaagaaggaa      8160
gagcttgggg catcctctcc tagctatggg cccccaaacc tgggctttgt tgactcaccc    8220
tcctcaggca cccacctggg tggcctggag ttaaagacac ctgatgtctt caaagccccc    8280
```

```
ctgacccctc gggcatctca ggtagagccc cagagcccgg gcttgggcct aaggccccag    8340
gagccacccc ctgcccaggc tttggcacct tctcctccaa gtcacccaga catctttcgc    8400
cctggctcct acactgaccc atatgctcag cccccattga ctcctcggcc ccaacctccg    8460
cccccctgaga gctgctgtgc tctgcccct cgctcactgc cctccgaccc tttctcccga     8520
gtgcctgcca gtcctcagtc ccagtccagc tcccagtctc cactgacacc ccggcctctg    8580
tctgctgaag cttttttgccc atcaccgtt accctcgct tccagtcccc tgacccttat       8640
tctcgcccac cctcacgccc tcagtcccgt gacccatttg ccccattgca taagccaccc    8700
cgaccccagc cccctgaagt tgcctttaag gctgggtctc tagcccacac ttcgctgggg    8760
gctgggggt tcccagcagc cctgcccgcg gggccagcag gtgagctcca tgccaaggtc     8820
ccaagtgggc agcccccaa ttttgtccgg tccctgggga cgggtgcatt tgtgggcacc      8880
ccctctccca tgcgtttcac tttccctcag gcagtagggg agccttccct aaagccccct    8940
gtccctcagc ctggtctccc gccaccccat gggatcaaca gccatttgg gcccggcccc      9000
accttgggca agcctcaaag cacaaactac acagtagcca cagggaactt ccacccatcg    9060
ggcagccccc tggggcccag cagcgggtcc acaggggaga gctatgggct gtccccacta    9120
cgccctccgt cggttctgcc accacctgca cccgacggat ccctcccta cctgtcccat      9180
ggagcctcac agcgatcagg catcacctct cctgtcgaaa agcgagaaga cccagggact    9240
ggaatgggta gctcttggc gacagctgaa ctcccaggta cccaggaccc aggcatgtcc     9300
ggccttagcc aaacagagct ggagaagcaa cggcagcgcc agcgactacg agagctgctg    9360
attcggcagc agatccagcg caacaccctg cggcaggaga aggaaacagc tgcagcagct    9420
gcaggagcag tggggcctcc aggcagctgg ggtgctgagc ccagcagccc tgcctttgag    9480
cagctgagtc gaggccagac ccccttgct gggacacagg acaagagcag ccttgtgggg     9540
ttgcccccaa gcaagctgag tggccccatc ctggggccag ggtccttccc tagcgatgac    9600
cgactctccc ggccacctcc accagccacg ccttcctcta tggatgtgaa cagccggcaa    9660
ctggtaggag gctcccaagc tttctatcag cgagcaccct atcctgggtc cctgcccta     9720
cagcagcaac agcaacaact gtggcagcaa caacaggcaa cagcagcaac ctccatgcga    9780
tttgccatgt cagctcgctt tccatcaact cctggacctg aacttggccg ccaagcccta    9840
ggttccccgt tggcgggaat ttccaccgt ctgccaggcc ctggtgagcc agtgcctggt     9900
ccagctggtc ctgcccagtt cattgagctg cggcacaatg tacagaaagg actgggacct    9960
gggggcactc cgtttcctgg tcagggccca cctcagagac cccgttttta ccctgtaagt   10020
gaggaccccc accgactggc tcctgaaggg cttcggggcc tggcggtatc aggtcttccc   10080
ccacagaaac cctcagcccc accggcccct gaattgaaca acagtcttca tccaacaccc   10140
cacaccaagg gtcctaccct gccaactggt ttggagctgg tcaaccggcc ccgtcgagc     10200
actgagcttg gccgcccaa tcctctggcc ctggaagctg gaagttgcc ctgtgaggat      10260
cccgagctgg atgacgattt tgatgcccac aaggccctag aggatgatga agagcttgct   10320
cacctgggtc tgggtgtgga tgtggccaag ggtgatgatg aacttggcac cttagaaaac   10380
ctggagacca atgaccccca cttgatgac ctgctcaatg gagacgagtt tgacctgctg     10440
gcatatactg atcctgagct ggacactggg acaagaagg atatcttcaa tgagcacctg    10500
aggctggtag aatcggctaa tgagaaggct gaacggagg ccctgctgcg gggggtggag     10560
ccaggaccct tgggccctga ggagcgccct cccctgctg ctgatgcctc tgaacccgc      10620
ctggcatctg tgctccctga ggtgaagccc aaggtggagg agggtggacg ccacccttct   10680
```

```
ccttgccaat tcaccattgc tacccccaag gtagagcccg cacctgctgc caattccctt    10740
ggcctggggc taaagccagg acagagcatg atgggcagcc gggatacccg gatgggcaca    10800
gggccatttt ctagcagtgg gcacacagct gagaaggcct cctttggggc cacgggagga    10860
ccaccagctc acctgctgac ccccagccca ctgagtggcc caggaggatc ctccctgctg    10920
gaaaagtttg agctcgagag tggggctttg accttgcctg gtggacctgc agcatctggg    10980
gatgagctag acaagatgga gagctcactg gtagccagcg agttacccct gctcattgag    11040
gacctgttgg agcatgagaa gaaggagctg cagaagaagc agcagctttc agcacagttg    11100
cagcctgccc agcagcagca gcaacagcag cagcagcatt ccctactgtc tgcaccaggc    11160
cctgcccagg ccatgtcttt gccacatgag ggctcttctc ccagtttggc tgggtcccaa    11220
cagcagcttt ccctgggtct tgcaggtgcc cgacagccag gtttgcccca gccactgatg    11280
cccacccagc caccagctca tgccctccag caacgcctgg ctccatccat ggctatggtg    11340
tccaatcaag gcatatgct aagtgggcag catggagggc aggcaggctt ggtaccccag    11400
cagagctcac agccagtgct atcacagaag cccatgggca ccatgccacc ttccatgtgc    11460
atgaagccgc agcaattggc aatgcagcag cagctggcaa acagcttctt cccagataca    11520
gacctggaca aatttgctgc agaagatatc attgatccca ttgcaaaggc caagatggtg    11580
gctttgaaag gcatcaagaa agtgatggct cagggcagca ttggggtggc acctggtatg    11640
aacagacagc aagtgtctct gctagcccag aggctctcgg ggggacctag cagtgatctg    11700
cagaaccatg tggcagctgg gagtggccag gagcggagtg ctggtgatcc ctcccagcct    11760
cgtcccaacc cgcccacttt tgctcaggga gtgatcaatg aagctgacca gcggcagtat    11820
gaggagtggc tgttccatac ccagcagctc ctacagatgc agctgaaggt gctagaggag    11880
cagattggtg tacaccgcaa gtcccggaag gctctgtgtg ccaagcagcg cactgccaaa    11940
aaagctggcc gtgagttccc agaagctgat gctgagaagc tcaagctggt tacagagcag    12000
cagagcaaga tccagaaaca actggatcag gtccggaaac agcagaagga gcacactaat    12060
ctcatggcag aatatcggaa caagcagcag caacaacagc agcagcagca gcaacaacag    12120
caacagcact cagctgtgct ggctctcagc ccttcccaga gtccccggct gctcaccaag    12180
ctccctggtc agctgctccc tggccatggg ctgcagccac cacaggggcc tccgggtggg    12240
caagccggag gtcttcgcct gaccctgggg gtatgcac tacctggaca gcctggtggc    12300
cccttcctta atacagctct ggcccaacag cagcaacagc aacattctgg tggggctgga    12360
tccctggctg gcccttcagg gggcttcttc cctggcaacc ttgctcttcg aagcctcgga    12420
cctgattcaa ggcttttaca ggaaaggcag ctgcagctgc agcagcaacg tatgcagctg    12480
gcccagaaac tgcagcagca gcagcagcag caacagcagc agcagcacct tctaggacag    12540
gtggcaatcc agcagcaaca gcagcagggt cctggagtac agacaaacca agctctgggt    12600
cccaagcccc agggccttat gcctcccagc agccaccaag gcctcctggt ccagcagctg    12660
tcccctcaac caccccaggg gccccagggc atgctgggcc ctgcccaggt ggctgtgttg    12720
cagcagcagc accctggagc tttgggcccc caggccctc acagacaggt gcttatgacc    12780
cagtcccggg tgctcagttc cccccagctg gcacagcagg tcagggcct tatgggacac    12840
aggctggtca cagcccagca gcagcagcag caacaacagc accaacagca agggtccatg    12900
gcagggctgt cccatcttca gcagagtctg atgtcacaca gtgggcagcc caaactgagc    12960
gctcagccca tgggctcttt acagcagctt cagcagcagc agcagctgca acagcaacag    13020
```

-continued

```
caacttcagc agcagcagca gcagcagcta caacagcaac agcaacttca gcagcaacag    13080
cttcaacagc agcaacagca gcagcagctt caacaacagc agcagcaaca gcttcaacag    13140
cagcaacagc agctacaaca gcaacagcaa caacaacagc agcagtttca acagcagcag    13200
caacagcagc agatgggcct tttaaaccag agtcgaactt tactgtctcc tcagcaacaa    13260
cagcagcagc aagtggcact tggccctggc atgccagcaa agcctcttca cactttct     13320 agccctggag ccctgggtcc aaccctcctc ctgacgggca aggaacaaaa caccgtagac    13380
ccagccgttt cttcagaggc cactgagggg ccctctacac atcagggagg gccgttagca    13440
ataggaacta cccctgagtc aatggccact gaaccaggag aggtaaagcc ctcactctct    13500
ggggactcac aactcctgct tgtccaaccc cagccccagc ctcagcccag ctctctgcag    13560
ctgcagccac ctctgaggct tccaggacaa cagcagcagc aagttagcct gctccacaca    13620
gcaggtggag gaagccatgg gcagctaggc agtggatcat cttctgaggc ctcatctgtg    13680
ccccacctgc tggctcagcc ctctgttttc ttaggggatc agcctgggtc catgacccag    13740
aaccttctgg gcccccaaca gcccatgcta gagcggccca tgcaaaataa tacagggcca    13800
caacctccca aaccaggacc tgtcctccag tctgggcagg gtctgcctgg ggttggaatc    13860
atgcctacgg tgggtcagct tcgagcacag ctccaaggag tcctggccaa aaacccacag    13920
ctgcggcact taagtcctca gcagcagcag cagctacagg cactcctcat gcagcggcag    13980
ctgcagcaga gtcaggcagt acgccagacc ccacccctacc aggagcctgg gacccagacc    14040
tctcccctcc agggcctcct gggctgccaa cctcaacttg ggggcttccc tggaccacag    14100
acaggccccc tccaggagct aggggcaggg cctcgacctc agggcccacc ccggctcccc    14160
gccccaccag gagccttatc tacaggacca gtccttggcc ctgtccatcc cacacctcca    14220
ccatccagcc ctcaagagcc aaagagacct tcacaattac cttcccccag ctcccagctt    14280
cccactgagg cccagctccc tcccacccat ccagggaccc ccaaacctca ggggccaacc    14340
ttggagccgc ctcctgggag ggtctcacct gctgctgccc agcttgcaga taccttgttt    14400
agcaagggtc tgggaccttg ggatccccca gacaacctag cagaaaccca gaagccagag    14460
cagagcagcc tggtacctgg gcatctggac caggtgaatg gacaggtggt gcctgaggca    14520
tcccaactca gcatcaagca ggaacctcgg gaagagccat gtgccctggg agcccagtca    14580
gtgaagaggg aggccaatgg ggagccaata ggggcaccag gaaccagcaa ccacctcctg    14640
ctggcaggcc ctcgctcaga agctgggcat ctgctcttgc agaagctact ccgggcaaag    14700
aatgtgcaac tcagcactgg gcggggggtcc gagggggctgc gagctgagat caacgggcac    14760
attgacagca agctggctgg gctggagcag aaactacagg gtaccccag caacaaggag    14820 gatgcagcag caaggaagcc tttgacaccg aagcccaagc gggtacagaa ggcaagcgac    14880
aggttggtga gctcccgaaa gaagctgcgg aaggaggacg gggtcagggc cagcgaggcc    14940
ttgctgaaac agctgaaaca ggagctgtcc ctgctgcccc taacggagcc tgctatcacc    15000
gccaatttta gcctctttgc ccccttggc agtggctgcc cagtcaatgg gcagagccag    15060 ctgaggggg cctttggaag tggggcgctg cccactggcc ctgactacta ttcccagctg    15120
cttaccaaga ataacctgag taacccgccg acaccaccct cgtcgctgcc cccaccccca    15180
cccccatcgg tgcagcagaa gatggtgaat ggcgtcaccc catctgaaga gctgggggag    15240 cacccccaagg atgctgcctc tgcccgggat agtgaaaggg cactgaggga tacttcagag    15300
gtgaagagtc tagacctgct ggctgccttg cctacacccc ctcacaatca gactgaggat    15360
gtcaggatgg agagtgatga ggatagcgat tctcctgaca gcattgtgcc agcttcatcc    15420
```

```
cctgagagca tcttggggga ggaggcccct cgtttccctc atctgggctc aggccggtgg    15480
gagcaagagg accgggccct ctcccctgtc atcccctca ttcctcgggc cagcatccca    15540
gtcttcccag ataccaaacc ttatggggcc cttggcctgg aggtccctgg aaagctgcct    15600
gtcacaactt gggaaaaggg caaggaagtt gaggtgtcag tcatgctcac agtctctgct    15660
gctgcagcca agaacctgaa tggcgtgatg gtggcagtgg cggagctgct gagcatgaag    15720
atccccaact cctatgaggt gctgttccca gagagcccg cccgggcagg cactgagcca    15780 aagaagggg aagctgaggg tcctggtggg aaggaaaagg gtctggaagg caagagccca    15840
gacactggcc ctgattggct gaagcagttt gatgcagtgt tgcctggcta taccctgaag    15900
agccaactag acatcttgag cctcctgaaa caggagagcc ccgccccaga gccacccact    15960
cagcacagct atacctacaa tgtctccaat ctggatgtgc gacagctctc ggccccacct    16020
cctgaagaac cctccccgcc cccttccccc ttggcacctt ctcctgccag tccccctact    16080
gagcccttgg ttgaacttcc caccgaaccc ttggctgagc cacccgtccc ctcacctctg    16140
ccactggcct catcccctga atcagcccga cccaagcccc gtgcccggcc ccctgaagaa    16200
ggtgaagatt cccgtcctcc tcgcctcaag aaatggaaag gagtgcgctg gaagcggctt    16260
cggctgctgc tgaccatcca aagggcagt gggcggcagg aggatgagcg ggaagtggca    16320
gagtttatgg agcagcttgg cacagccttg cgacctgaca aggtaccgcg agacatgcgt    16380
cgctgctgtt tctgtcatga ggagggtgac ggggccactg atgggcctgc ccgtctgctg    16440
aacctggacc tggacctgtg ggtgcacctc aactgtgccc tttggtccac ggaggtgtat    16500
gagacccagg gcggggcact gatgaatgtg gaggttgccc tgcaccgagg actgctaacc    16560
aagtgctccc tgtgccagcg aactggtgcc accagcagct gcaatcgcat gcgttgcccc    16620
aatgtctacc attttgcttg tgccatccgt gccaagtgca tgttcttcaa ggacaagacc    16680
atgctgtgtc caatgcataa gatcaagggg ccctgtgagc aagagctgag ctcttttgct    16740
gtcttccggc gggtctacat tgagcgggac gaggtgaagc aaatcgctag catcattcag    16800 cgggagaac ggctgcacat gttccgtgtg ggggccttg tgttccacgc catcggacag    16860
ctgctgcctc accagatggc tgactttcat agtgccactg ccctctatcc cgtgggctac    16920
gaggccacgc gcatctattg gagcctccgc accaacaatc gtcgctgctg ctatcgctgt    16980
tctattggtg agaacaacgg gcggccggag tttgtaatca aagtcatcga gcagggcctg    17040
gaggacctgg tcttcactga cgcctctccc caggccgtgt ggaatcgcat cattgagcct    17100
gtggctgcca tgagaaaaga ggctgacatg ctgcgactct tccctgagta tctgaagggc    17160
gaggagctct ttgggctgac ggtgcatgcc gtgcttcgca tagctgaatc actgcccggg    17220
gtggagagct gtcaaaacta tttattccgc tatgggcgcc accccttat ggagctgcca    17280 ctcatgatca accccactgg ctgtgcccga tcagagccta aaatcctcac acactacaaa    17340 cggcccccata ccctgaacag caccagcatg tctaaggcat atcagagcac cttcacaggc    17400
gagaccaaca ccccctacag caagcagttt gtgcactcca agtcatctca gtaccggcgg    17460
ctgcgcaccg aatggaagaa caacgtgtac ctggctcgct cccgtatcca gggcctgggg    17520
ctctatgcag ccaaggacct agaaaagcac acaatggtta tcgagtacat tggcaccatc    17580
attcggaacg aggtggccaa ccggcgggag aaaatctacg aagagcagaa tcgaggcatc    17640
tacatgttcc gaataaacaa tgaacatgtg attgatgcta cgttgaccgg cggccctgcc    17700
aggtacatta accattcctg tgcccctaac tgtgtggccg aagtcgtgac atttgacaaa    17760
```

```
gaggacaaaa tcatcatcat ctccagccgg cgaatcccca aaggagagga gctaacctat    17820
gactatcagt ttgattttga ggacgatcag cacaagatcc cctgccactg tggagcctgg    17880
aattgtcgga aatggatgaa ctaagaagct ttgaggctac caggcagggg agtccccta    17940 cccacaacct cttccctgaa agggatgagg gggaagagag gtagcagcca gagccaggac    18000
ccagggttgg ggctgccggc tgacccggag cccctggagc aggaggctgg ggcagagggc    18060
cctaggccaa gcccacccctg gcaccaggg acaatcctct tccccaccac cggccctcag    18120
gctggcatct ctgccccag ctccaggagg ggccagacag aagcagccat tgggcatctc    18180
aggtttgagg gggatatggg ccgggaacta cccagaagca tctggaggc agcagggtgg    18240 gggaagagga tgtgtggccg ggcctcacag ccctgctgct cccactgacc tctccggccc    18300
aactcacggc tgcaaagaga cttgactaag cttgacaatc ccaaaggccg ggtcccacac    18360
ctggccctgc ctgccgggtc ctgcccccac cctcaccccc atccccctcc ctcttgatct    18420
gtctctgttt ccctctttc ctctgtgttt ctgtctctct atgggttgtg tttccttgtt    18480
ttccactctg acaaatgcaa catgaacggg aaagaggcgc ccagctgcct aggagggcaa    18540
gctgggcaag ccgggcaagg agaccccgca cccacaccta cctcatttaa gtgttggatt    18600
ttttgctgtt ttgaaatgtg agaccctctc caagcccct actgcccaa ccctctccc    18660 cacctcactg ccctcttctg agtgggtgga agggggtag gaggaggaag aaaaacaaca    18720
acaaaaaatc catctttgtt tttaattatg ggcatgggat ggtggttgag gcaaatgatg    18780
atgaagattg gggatgactg gcccctagtt gctctaggac ttccttctcc atctggacat    18840
gggggcagga gggagctaaa cctaggacca ggatatctcc ctcctgtttt cccaacctca    18900
tcatgagcct gtttgccctc cagcccctgg acgggttggg tgggggtag ggtgagggct    18960 atccctgagt ggcatgccca tacctagtga ggcagggtgt ggcccggagc tcccactttc    19020
cctcagtcac caaactgctg ctggtctggt gggaaggggt ggtgatgtgg gggtggggga    19080
gcttagtgtc agcgcgggga gggtgggggg tatttatcta tttatacatg ggattgtaca    19140
tagtcttgtg gggcatgggg gagccggctg gaggtgagaa ccctcccctc tccccccacc    19200
ccccggggag agcaaatgta aaactactaa ttttgtgct ttatatattc tatataaata    19260
tatctatttt cttttacaa aaccagttta taaatggtag ggggtgtgg ggcggacaca    19320 tggagctccc cttgtggggg ggccccctcc attacccgac ctaccgccct tttcctcacc    19380
ccccacccca ctccccaccc cctggctgtg actgctgtaa gatgggggta tagaggctgg    19440
gcaattccca ccccctgttg tatagttgga ctatgttata acgcacaaaa gagagctgac    19500
cccaggggga gccagagggt gatgggttcc ttgcctccct ttccttcccc tttctgccca    19560
agcttgtgct gcagttgaac ctcttcctgg gggtgggagt aggtaagggg tgggtgaggc    19620
cccaaacccc tctctggtag ggaaccgtgg ggatgaagat gaagcttata tgcagttctc    19680
ttctaggggc tgtgggcaaa gggcatttttg taattaatat tttcaagaat cagatgtctg    19740
gagtgtaggg gtgggcttgg tggtggtgga cgggcgggcc tgctggaggg ggagcttggt    19800
cgctgttgtg atttaggtt tgttttgtt ttgttttgaa tttgggggt tgtggattgt    19860 tgggggtagg gagattttt tttttaaag ctgcttcctc aactgtttca agctgcaaat    19920
gtttaagaga ataacagccc ccactcccac aggaaccgct gtaattaaat cagacagtag    19980
gaagactggg ctgctgccct caaagccaca gccttggat gttcctttc cgagagcaga    20040 aggtctaggc tacaggagg gggagattgg ctcccgtgag tcaggctgtg tttgggcttt    20100
gggccctggg attgggaaaa ggggatgggg cagactttgt aagcatatgc taggtatccg    20160
```

-continued

| | |
|---|---|
| atagtcctgt agaatttagt gaagaaacct tatacagttt ttaattttta tataaactat | 20220 |
| aactcagacc caagctacaa ggttggaatt ttggttggtt ttttttttaa gtaccctgcc | 20280 |
| tgtataattg catcagaatc ccccacccca cccccgccc ccgtgtttgt attttgggtt | 20340 |
| ggtttacact cgcacatact cagttttcag ttttcccctt tacagtcttc tcccctcacc | 20400 |
| tccaggaccc tccccctttt taaaaaataa atcgctgaca agtgtgaatc ccgtgaagac | 20460 |
| tttattttgt gttgtgtgta tcctgtacag caaggttggt ccttcgtaac aacgatgaa | 20520 |
| atggttccct tttttaaagc gccctctctc cctccaccct cagcgcccct gtccttggca | 20580 |
| tgttttgtat cagcgatcat tctgaactgt acatatttat gttgcgagag gcaaagggca | 20640 |
| agttttggat tttgcttctt ccaagtttgt ttttaaacga caaataaaaa aagaacattt | 20700 |
| taaatacaa | 20709 |

<210> SEQ ID NO 81
<211> LENGTH: 8490
<212> TYPE: DNA
<213> ORGANISM: Homo sapiens

<400> SEQUENCE: 81

| | |
|---|---|
| atggcggcgg cggcgggcgg cggcagttgc cccgggcctg gctccgcgcg gggccgcttc | 60 |
| ccgggccggc cgcggggcgc cggcggggc ggggccgcg gcggacgggg caacggggcc | 120 |
| gaaagagtgc gggtagctct gcggcgcggc ggtggcgcga cggggccggg cggagccgag | 180 |
| cccggggagg acacgcccct gctccgtttg ctggggctcc gccggggcct cgcccggctc | 240 |
| cgccgcctgt gggccggccc gcgggtccag cggggccggg gacggggtcg gggccggggc | 300 |
| tggggccccga gtcgaggctg cgtgccggag gaggagagca gtgacgggga atccgacgag | 360 |
| gaggagtttc agggttttca ttcagatgaa gatgtggccc ccagttccct gcgctctgcg | 420 |
| ctccgatccc agcgaggtcg agcgcccga ggtcggggtc gcaagcataa gacgaccccc | 480 |
| cttcctcctc ctcgcctagc agatgtggct cctacccccc caaagacccc tgcccggaaa | 540 |
| cggggtgagg aaggcacaga acggatggtg caggcactga ctgaacttct ccggcgggcc | 600 |
| caggcacccc aagcaccccg gagccgggca tgtgagcccc caccccccg gcggtctcgg | 660 |
| ggacggcccc caggacggcc agcaggcccc tgcaggagga agcagcaagc agtagtggtg | 720 |
| gcagaagcag ctgtgacaat ccccaaacct gagccccac ctcctgtggt tccagtgaaa | 780 |
| catcagactg gcagctggaa atgcaaggag gggcccggtc caggacctgg gaccccagg | 840 |
| cgtggaggac agtcaagccg tggaggccgt ggaggcaggg gccgcggccg aggtggtggg | 900 |
| ctccccttg tgatcaagtt tgtttcaagg gccaaaaag taaagatggg acaattgtcc | 960 |
| ttgggactcg aatcaggtca aggtcaaggt caacatgagg aaagttggca ggatgtcccc | 1020 |
| caaagaagag ttggatctgg acagggaggg agcccttgct ggaaaaagca ggaacagaag | 1080 |
| ctggatgacg aggaagaaga gaagaaagaa gaagaagaaa aagacaagga gggagaagag | 1140 |
| aaggaagaaa gagctgtagc tgaggagatg atgccagctg cggaaaagga agaggcaaag | 1200 |
| ctgccaccac cgcctctgac tcctccagcc ccttcacctc ctccaccct cccacccct | 1260 |
| tcgacatctc ctccaccccc actctgccct ccaccaccac cccagtgtc cccaccacct | 1320 |
| ctaccatccc ctccaccgcc tcctgcccaa gaggagcagg aggaatcccc tcctcctgtg | 1380 |
| gtcccagcta cgtgctccag gaaganggggc cggcctcccc tgactcccag ccagcgggcg | 1440 |
| gagcgggaag ctgctcgggc agggccagag ggcacctctc ctcccactcc aaccccagc | 1500 |

```
accgccacgg gaggccctcc ggaagacagt cccaccgtgg cccccaaaag caccaccttc      1560
ctgaagaata tccggcagtt tattatgcct gtggtgagtg cccgctcctc ccgtgtcatc      1620
aagacacccc ggcgatttat ggatgaagac ccccccaaac ccccaaaggt ggaggtctca      1680
cctgtcctgc gacctcccat taccacctcc ccacctgttc cccaggagcc agcaccagtc      1740
ccctctccac cacgtgcccc aactcctcca tctacgccag ttccactccc tgagaagaga      1800
cggtccatcc taagggaacc cacatttcgc tggacctcac tgacccggga gctgccccct      1860
cctcccccag ccccctccacc tcccccggcc ccctccccac ccctgctcc tgccacctcc      1920
tcccggaggc ccctactcct tcgggcccct cagtttaccc caagcgaagc ccacctgaag      1980
atctacgaat cggtgcttac tcctcctcct cttggggctc ctgaagcccc tgagccagag      2040
cctcctcctg ccgatgactc tccagctgag cctgagcctc gggcagtggg ccgcaccaac      2100
cacctcagcc tgcctcgatt cgccctgtg gtcaccactc ctgttaaggc cgaggtgtcc      2160
cctcacgggg ctccagctct gagcaacggg ccacagacac aggctcagct actgcagccc      2220
ctgcaggcct tgcaaaccca gctcctgccc caggcactac cgccaccaca gccacagctg      2280
cagccaccgc cgtcaccaca gcagatgcct cccctggaaa aagcccggat gcgggcgtg      2340
ggttccttgc cgctgtctgg ggtagaggag aagatgttca gcctcctcaa gagagccaaa      2400
gtgcagctat tcaagatcga tcagcagcag cagcagaagg tggcagcttc catgccgctg      2460
agccctggag ggcagatgga ggaggtggcc ggggctgtca agcagatctc cgacagaggc      2520
cctgtccggt ctgaagatga gtcggtggaa gctaagagag agcggccctc aggtcccgag      2580
tcccctgtgc aaggtccccg catcaaacat gtctgccgtc atgctgctgt ggccctgggt      2640
caggcccggg ccatggtgcc tgaagatgtc cctcgcctca gtgccctccc tctccgggat      2700
cggcaggacc tcgccacaga ggatacatca tcggcgtccg agactgagag tgtcccgtca      2760
cggtcccggc ggggaaaggt ggaggcagca ggccctgggg gagaatcaga gcccacaggt      2820
tctggaggga ccctggccca cacacccggg cgctcactgc cctcccatca cggcaagaag      2880
atgcgcatgg ctcgatgtgg acactgtcgg ggctgcctac gtgtgcagga ctgtgggtcc      2940
tgtgtcaact gcctagacaa gcccaagttt ggggggccta acaccaagaa gcagtgctgt      3000
gtataccgga agtgtgacaa aatagaggct cggaagatgg aacgactggc taaaaaaggc      3060
cggacgatag tgaagacgct gttgcccgtgg gattccgatg aatctcctga ggcctccccct      3120
ggtcctccag gcccacgccg gggggcggga gctgggggc cccgggagga ggtggtggcc      3180
cacccagggc ccgaggagca ggactccctc ctgcagcgca gtcagctcg cgctgcgtc      3240
aaacagcgac cctcctatga tatcttcgag gattcggatg actcggagcc cggggcccc      3300
cctgctcctc ggcgtcggac cccccgagaa aatgagctgc cactgccaga acctgaggag      3360
cagagccggc cccgcaaacc taccctgcag cctgtgttgc agctcaaggc ccgaaggcgc      3420
ctggacaagg atgctttggc ccctggcccc tttgcttctt ttcccaatgg ctggactgga      3480
aagcagaagt ctcccgatgg tgtgcaccgc gtccgtgtgg attttaagga ggattgtgat      3540
ttagagaacg tgtggctgat ggggggcctg agtgtgctca cctctgtgcc aggggggccc      3600
ccgatggtgt gcttgctgtg tgccagcaaa ggactccacg agctggtgtt ctgtcaagtc      3660
tgctgtgacc cattccaccc attctgcctg gaggaggccg agcggccct gccccagcat      3720
cacgacacct ggtgctgccg tcgctgcaaa ttctgccacg tctgtggacg caaaggtcgt      3780
ggatccaagc acctcctgga gtgcgagcgc tgccgcatg cataccaccc ggcctgtctg      3840
gggcccagct atccaacccg ggccacgcgc aaacggcgcc actggatctg ttcagcctgt      3900
```

```
gtgcgctgta agagctgtgg ggcaactcca ggcaagaact gggacgtcga gtggtctgga      3960
gattacagcc tctgccccag gtgcacccag ctatatgaga aaggaaacta ctgcccgatc      4020
tgtacacgct gctatgaaga caacgactat gagagcaaga tgatgcagtg cgcacagtgc      4080
gatcactggg tgcatgccaa gtgcgagggg ctctcagatg aagactacga gatcctttca      4140
ggactgccag actcggtgct gtacacctgc ggaccgtgtg ctggggcagc gcagccccgc      4200
tggcgagagg ccctgagcgg ggccctccag gggggcctgc gccaggtgct ccagggcctg      4260
ctgagctcca aggtggtggg cccactgctg ctctgcaccc agtgtgggcc agatgggaag      4320
caactgcacc caggaccctg cggcctgcaa gctgtgagtc agcgcttcga ggatggccac      4380
tacaagtctg tgcacagctt catggaggac atggtgggca tcctcatgcg gcactcggag      4440
gagggagaga ccccggaccg ccgggctgga ggccagatga aggggctcct gctgaagctg      4500
ctagaatctg cgttcggctg gttcgacgcc cacgacccca agtactggcg acggagtacc      4560
cggctgccaa acggagtcct tcccaatgcg gtgttgcccc catccctgga tcatgtctat      4620
gcgcagtgga gacagcagga accagagacc ccagaatcag ggcagcctcc aggggatccc      4680
tcagcagcat tccagggcaa ggatccggct gccttctcac acctggagga ccccgtcag       4740 tgtgcactct gcctcaaata cggggatgca gactccaagg aggcggggcg gctcttgtac      4800
atcgggcaga acgagtggac acacgtcaac tgtgccatct ggtcggcgga agtcttcgag      4860
gagaacgacg gctccctcaa gaatgtgcat gctgctgtgg cccgagggag gcagatgcgc      4920
tgcgagctct gcctgaagcc tggcgccacg gtgggctgct gcctgtcctc ctgcctcagc      4980
aacttccact tcatgtgtgc ccgggccagc tactgcatct tccaggatga caagaaagtc      5040
ttctgccaga aacacactga tctcctggat ggcaaggaaa ttgtgaaccc cgatggtttt      5100
gatgttctcc gccgagtcta tgtggacttc gagggcatca acttcaagcg gaagttcttg      5160
acggggcttg aacccgatgc catcaacgtg ctcattggtt ccatccgcat tgactccctg      5220
ggtactctgt ctgatctctc ggactgcgag ggacggctct tccccattgg ctaccagtgc      5280
tcccgtctgt actggagcac agtggatgct cggaggcgct gctggtatcg gtgccgaatt      5340
ctggagtatc ggccatgggg gccgagggaa gagccagctc acctggaggc tgcagaggag      5400
aaccagacca ttgtgcacag ccccgcccct tcctcagagc cccaggtgg tgaggacccc       5460 ccactggaca cagatgttct gtccctgga gctcctgagc gccactcgcc cattcagaac        5520
ctggaccctc cactgcggcc agattcaggc agcgcccctc ctccagcccc ccgttctttt      5580 tcggggctc gaatcaaagt gcccaactac tcgccatccc ggaggccctt ggggggtgtc        5640
tcctttggcc cctgccctc ccctggaagt ccatcttcac tgacccacca catccccaca       5700
gtgggagacc cggacttccc agctcccccc agacgttccc gtcgtcccag cccttttggct     5760 cccaggccgc ctccatcacg gtgggcctcc cctcctctaa aaacctcccc tcagctcagg      5820
gtgccccctc ctacctcagt cgtcacagcc ctcacaccta cctcagggga gctggctccc      5880
cctggcccgg cccatctcc accacccct gaagacctgg gcccagactt cgaggacatg        5940
gaggtggtgt caggactgag tgctgctgac ctggacttcg cggccagcct gctggggact      6000
gagcccttcc aggaagagat tgtagccgct ggggccatgg ggagcagcca cggggcccg       6060 ggggacagct ccgaggagga gtccagcccc acctcccgct acatccactt ccctgtgact      6120
gtggtgtccg ccctggtct ggcccccagc gctacccctg agccccccg cattgaacag         6180 ctggacggcg tggacgacgg cactgacagt gaggctgagg cggtgcagca gcctcggggc      6240
```

```
cagggcacgc ctccttcggg gccaggagta gtccgggcag gggtccttgg ggctgcaggg    6300
gacagggccc ggcctcctga ggacctgcca tcggaaattg tggattttgt gttgaagaac    6360
ctaggggggtc ctggggatgg aggtgctggc cctagagagg agtcactccc cccggcgcct    6420
cccctggcta atggcagcca gccctcccaa ggcctgaccg ccagcccagc tgaccccacc    6480
cgcacatttg cctggctccc aggggcccca ggggtccggg tgttaagcct tggccctgcc    6540
cctgagcccc ccaaacccgc cacatccaaa atcatacttg tcaacaagct ggggcaagta    6600
tttgtgaaga tggctgggga gggtgaacct gtcccacccc cagtgaagca gccacctttg    6660
cccccccacca tttcccccac ggctcccacc tcctggactc tgcccccagg ccccctcctc    6720
ggcgtgctgc ccgtggtcgg agtggtccgc cctgccccgc cccgccacc ccctcccctg    6780
acgctggtgc tgagcagtgg gccagccagc ccgccccgcc aggccatccg cgtcaagagg    6840
gtgtccactt tctccggccg gtccccgcca gcacctcccc catacaaagc cccccggctg    6900
gatgaagatg gagaggcctc agaggatacc cctcaggttc cagggcttgg cagtggcggg    6960
tttagccgtg tgaggatgaa acccccaca gtgcgtgggg tccttgacct ggatcggcct    7020
ggggagcccg ctggggaaga aagtcctggg cccctccagg aacggtcccc tttgctgcca    7080
cttccggaag atggtcctcc ccaggtcccc gatggtcccc cagacctgct gcttgagtcc    7140
cagtggcacc actattcagg tgaggcttcg agctctgagg aagagcctcc atccccagat    7200
gataaagaga accaggcccc aaaacggact ggcccacatc tgcgcttcga gatcagcagt    7260
gaggatgggt tcagcgttga ggcagagagc ttggagggg cgtggagaac tctgatcgag    7320
aaagtgcaag aggcccgagg gcatgcccga ctcagacatc tctcctttag tggaatgagt    7380
ggggcgagac tcctgggcat ccaccatgat gctgtcatct tcctggccga gcagctcccc    7440
ggagcccagc gttgccagca ctataagttc cgttaccacc agcagggaga gggccaggag    7500
gagccgcccc tgaatcccca tggggctgct cgggcagagg tctatctccg gaagtgcacc    7560
tttgacatgt tcaacttcct ggcctcccag caccgggtgc tccctgaggg ggccacctgt    7620
gatgaggaag aggatgaggt gcagctcagg tcaaccagac gtgccaccag cctggagctg    7680
cccatggcca tgcgtttttcg tcaccttaag aagacgtcca agaagctgt gggtgtctac    7740
agatcagcca tccacgggcg aggcctgttc tgtaagcgca acatcgacgc ggggagatg    7800
gtcatcgagt actctggcat tgtcatccgc tcggtgttga ctgacaagcg ggagaagttc    7860
tacgatggga agggcatcgg gtgctatatg ttccgcatgg atgactttga tgtagtggac    7920
gccacgatgc atggcaatgc cgcccgcttc atcaaccact cctgtgagcc caactgcttc    7980
tctcgggtca tccacgtgga gggccagaaa cacattgtta tcttcgccct gcgccgcatc    8040
ctgcgtggtg aggagctcac ctacgactac aagttcccca tcgaggatgc cagcaacaag    8100
ctgcctgca actgtggcgc caagcgctgc cgtcggttcc ttaactgagg ccgtggctgc    8160
ccaccacgac ccctcacacc tcctgctgcc gtcgctgcca tcttgcccct agcctgggg    8220
ctccctagcc cctcccagag catctcaccc ccaccctcat gttcagggtg gatgtgggca    8280
tgcaggtgac aagggccctg cctccacccc tccagcccat ccagcaatcg cccccttttct    8340
gccctggggg cccaggatgt agatattgta caaaggtttc taaatccctt cttttctatg    8400
cactttttta tttaagaggt ggggtcccag gtgggaaccc ccccacaata aagtctgtca    8460
atgtttggag aaaaaaaaaa aaaaaaaaa                                      8490
```

\<210\> SEQ ID NO 82
\<211\> LENGTH: 16872

<212> TYPE: DNA
<213> ORGANISM: Homo sapiens

<400> SEQUENCE: 82

```
gaggtgcgcg cgcccgcgcc gatgtgtgtg agtgcgtgtc ctgctcgctc catgttgccg      60
cctctcccgg tacctgctgc tgctcccggg gctgcgggaa atgcgagagg ctgagccggg     120
gaggaggaac ccgagcagca gcggcggcgg cggcggccgc ggcggcggga gccccccagg     180
aggaggaccg ggatccatgt gtctttcctg gtgactagga tgtcgtcgga ggaggacaag     240
agcgtggagc agccgcagcc gccgccacca cccccgagg agcctggagc cccggccccg      300
agccccgcag ccgcagacaa aagacctcgg ggccggcctc gcaaagatgg cgcttcccct     360
ttccagagag ccagaaagaa acctcgaagt aggggaaaa ctgcagtgga agatgaggac      420
agcatggatg ggctggagac aacagaaaca gaaacgattg tggaaacaga aatcaaagaa     480
caatctgcag aagaggatgc tgaagcagaa gtggataaca gcaaacagct aattccaact     540
cttcagcgat ctgtgtctga ggaatcggca aactccctgg tctctgttgg tgtagaagcc     600
aaaatcagtg aacagctctg cgcttttttgt tactgtgggg aaaaaagttc cttaggacaa     660
ggagacttaa acaattcag aataacgcct ggatttatct tgccatggag aaaccaacct      720
tctaacaaga aggacattga tgacaacagc aatggaacct atgagaaaat gcaaaactca      780
gcaccacgaa acaaagagg acagagaaaa gaacgatctc ctcagcagaa tatagtatct      840
tgtgtaagtg taagcaccca gacagcttca gatgatcaag ctggtaaact gtgggatgaa      900
ctcagtctgg ttgggcttcc agatgccatt gatatccaag ccttatttga ttctacaggc     960
acttgttggg ctcatcaccg ttgtgtggag tggtcactag gagtatgcca gatggaagaa    1020
ccattgttag tgaacgtgga caaagctgtt gtctcaggga gcacagaacg atgtgcattt    1080
tgtaagcacc ttggagccac tatcaaatgc tgtgaagaga aatgtaccca gatgtatcat    1140
tatccttgtg ctgcaggagc cggcaccttt caggatttca gtcacatctt cctgcttgt     1200
ccagaacaca ttgaccaagc tcctgaaaga tcgaaggaag atgcaaactg tgcagtgtgc    1260
gacagcccgg gagacctctt agatcagttc ttttgtacta cttgtggtca gcactatcat    1320
ggaatgtgcc tggatatagc ggttactcca ttaaaacgtg caggttggca atgtcctgag    1380
tgcaaagtgt gccagaactg caaacaatcg ggagaagata gcaagatgct agtgtgtgat    1440
acgtgtgaca aagggtatca tacttttgt cttcaaccag ttatgaaatc agtaccaacc    1500
aatggctgga atgcaaaaa ttgcagaata tgtatagagt gtggcacacg gtctagttct    1560
cagtggcacc acaattgcct gatatgtgac aattgttacc aacagcagga taacttatgt    1620
cccttctgtg ggaagtgtta tcatccagaa ttgcagaaag acatgcttca ttgtaatatg    1680
tgcaaaaggt gggttcacct agagtgtgac aaaccaacag atcatgaact ggatactcag    1740
ctcaaagaag agtatatctg catgtattgt aaacacctgg agctgagat ggatcgttta    1800
cagccaggtg aggaagtgga gatagctgag ctcactacag attataacaa tgaaatggaa    1860
gttgaaggcc ctgaagatca aatggtattc tcagagcagg cagctaataa agatgtcaac    1920
ggtcaggagt ccactcctgg aattgttcca gatgcggttc aagtccacac tgaagagcaa    1980
cagaagagtc atccctcaga aagtcttgac acagatagtc ttcttattgc tgtatcatcc    2040
caacatacag tgaatactga attggaaaaa cagatttcta atgaagttga tagtgaagac    2100
ctgaaaatgt cttctgaagt gaagcatatt tgtggcgaag atcaaattga agataaaatg    2160
gaagtgacag aaaacattga agtcgttaca caccagatca ctgtgcagca agaacaactg    2220
```

```
cagttgttag aggaacctga acagtggta tccagagaag aatcaaggcc tccaaaatta    2280
gtcatggaat ctgtcactct tccactagaa accttagtgt ccccacatga ggaaagtatt    2340
tcattatgtc ctgaggaaca gttggttata gaaaggctac aaggagaaaa ggaacagaaa    2400
gaaaattctg aactttctac tggattgatg gactctgaaa tgactcctac aattgagggt    2460
tgtgtgaaag atgtttcata ccaaggaggc aaatctataa agttatcatc tgagacagag    2520
tcatcatttt catcatcagc agacataagc aaggcagatg tgtcttcctc cccaacacct    2580
tcttcagact tgccttcgca tgacatgctg cataattacc cttcagctct tagttcctct    2640
gctgaaaaca tcatgccaac aacttacatc tcagtcactc caaaaattgg catgggtaaa    2700
ccagctatta ctaagagaaa atttttctcct ggtagacctc ggtccaaaca ggggcttgg    2760
agtacccata atacagtgag cccaccttcc tggtccccag acatttcaga aggtcgggaa    2820
attttttaaac ccaggcagct tcctggcagt gccatttgga gcatcaaagt gggccgtggg    2880
tctggatttc caggaaagcg gagacctcga ggtgcaggac tgtcggggcg aggtggccga    2940
ggcaggtcaa agctgaaaag tggaatcgga gctgttgtat acctgggggt gtctactgca    3000
gatatttcat caaataagga tgatgaagaa aactctatgc acaatacagt tgtgttgttt    3060
tctagcagtg acaagttcac tttgaatcag gatatgtgtg tagtttgtgg cagtttttggc    3120
caaggagcag aaggaagatt acttgcctgt tctcagtgtg gtcagtgtta ccatccatac    3180
tgtgtcagta ttaagatcac taaagtggtt cttagcaaag gttggaggtg tcttgagtgc    3240
actgtgtgtg aggcctgtgg gaaggcaact gacccaggaa gactcctgct gtgtgatgac    3300
tgtgacataa gttatcacac ctactgccta gaccctccat tgcagacagt tcccaaagga    3360
ggctggaagt gcaaatggtg tgtttggtgc agacactgtg gagcaacatc tgcaggtcta    3420
agatgtgaat ggcagaacaa ttacacacag tgcgctcctt gtgcaagctt atcttcctgt    3480
ccagtctgct atcgaaacta tagagaagaa gatcttattc tgcaatgtag acaatgtgat    3540
agatggatgc atgcagtttg tcagaactta aatactgagg aagaagtgga aaatgtagca    3600
gacattggtt ttgattgtag catgtgcaga ccctatatgc ctgcgtctaa tgtgccttcc    3660
tcagactgct gtgaatcttc acttgtagca caaattgtca caaaagtaaa agagctagac    3720
ccacccaaga cttataccca ggatggtgtg tgtttgactg aatcagggat gactcagtta    3780
cagagcctca cagttacagt tccaagaaga aaacggtcaa aaccaaaatt gaaattgaag    3840
attataaatc agaatagcgt ggccgtcctt cagacccctc cagacatcca atcagagcat    3900
tcaagggatg tgaaatgga tgatagtcga aaggagaac ttatggattg tgatggaaaa    3960
tcagaatcta gtcctgagcg ggaagctgtg gatgatgaaa ctaagggagt ggaaggaaca    4020
gatggtgtca aaagagaaa aaggaaacca tacagaccag gtattggtgg atttatggtg    4080
cggcaaagaa gtcgaactgg gcaagggaaa accaaaagat ctgtgatcag aaaagattcc    4140
tcaggctcta tttccgagca gttaccttgc agagatgatg gctggagtga gcagttacca    4200
gatactttag ttgatgaatc tgtttctgtt actgaaagca ctgaaaaaat aaagaagaga    4260
taccgaaaaa ggaaaaataa gcttgaagaa actttccctg cctatttaca agaagctttc    4320
tttgaaaag atcttctaga tacaagtaga caaagcaaga taagtttaga taatctgtca    4380
gaagatggag ctcagctttt atataaaaca aacatgaaca caggtttctt ggatccttcc    4440
ttagatccac tacttagttc atcctcggct ccaacaaaat ctggaactca cggtcctgct    4500
gatgacccat tagctgatat ttctgaagtt ttaaacacag atgatgacat tcttggaata    4560
atttcagatg atctagcaaa atcagttgat cattcagata ttggtcctgt cactgatgat    4620
```

```
ccttcctctt tgcctcagcc aaatgtcaat cagagttcac gaccattaag tgaagaacag    4680
ctagatggga tcctcagtcc tgaactagac aaaatggtca cagatggagc aattcttgga    4740
aaattatata aaattccaga gcttggcgga aaagatgttg aagacttatt tacagctgta    4800
cttagtcctg cgaacactca gccaactcca ttgccacagc ctcccccacc aacacagctg    4860
ttgccaatac acaatcagga tgcttttttca cggatgcctc tcatgaatgg ccttattgga    4920
tccagtcctc atctcccaca taattctttg ccacctggaa gcggactggg aactttctct    4980
gcaattgcac aatcctctta tcctgatgcc agggataaaa attcagcctt taatccaatg    5040
gcaagtgatc ctaacaactc ttggacatca tcagctccca ctgtggaagg agaaaatgac    5100
acaatgtcga atgcccagag aagcacgctt aagtgggaga agaggaggc tctgggtgaa    5160 atggcaactg ttgcccccagt tctctacacc aatattaatt tccccaactt aaaggaagaa    5220
ttccctgatt ggactactag agtgaagcaa attgccaaat tgtggagaaa agcaagctca    5280
caagaaagag caccatatgt gcaaaaagcc agagataaca gagctgcttt acgcattaat    5340
aaagtacaga tgtcaaatga ttccatgaaa aggcagcaac agcaagatag cattgatccc    5400
agctctcgta ttgattcgga gcttttttaaa gatcctttaa agcaaagaga atcagaacat    5460
gaacaggaat ggaaatttag acagcaaatg cgtcagaaaa gtaagcagca agctaaaatt    5520
gaagccacac agaaacttga acaggtgaaa aatgagcagc agcagcagca acaacagcaa    5580
tttggttctc agcatcttct ggtgcagtct ggttcagata caccaagtag tgggatacag    5640
agtcccttga cacctcagcc tggcaatgga aatatgtctc ctgcacagtc attccataaa    5700
gaactgttta caaaacagcc acccagtacc cctacgtcta catcttcaga tgatgtgttt    5760
gtaaagccac aagctccacc tcctcctcca gccccatccc ggattcccat ccaggatagt    5820
cttctctagg ctcagacttc tcagccaccc tcaccgcaag tgttttcacc tgggtcctct    5880
aactcacgac caccatctcc aatggatcca tatgcaaaaa tggttggtac ccctcgacca    5940
cctcctgtgg gccatagttt ttccagaaga aattctgctg caccagtgga aaactgtaca    6000
cctttatcat cggtatctag gccccttcaa atgaatgaga caacagcaaa taggccatcc    6060
cctgtcagag atttatgttc ttcttccacg acaaataatg accctatgc aaaacctcca    6120 gacacaccta ggcctgtgat gacagatcaa tttcccaaat ccttgggcct atcccggtct    6180
cctgtagttt cagaacaaac tgcaaaaggc cctatagcag ctggaaccag tgatcacttt    6240
actaaaccat ctcctagggc agatgtgttt caaagacaaa ggatacctga ctcatatgca    6300
cgacccttgt tgacacctgc acctcttgat agtggtcctg gacctttttaa gactccaatg    6360 caacctcctc catcctctca ggatccttat ggatcagtgt cacaggcatc aaggcgattg    6420
tctgttgacc cttatgaaag gcctgctttg acaccaagac ctatagataa tttttctcat    6480
aatcagtcaa atgatccata tagtcagcct cccctaccc cacatccagc agtgaatgaa    6540
tcttttgccc atccttcaag ggcttttttcc cagcctggaa ccatatcaag gccaacatct    6600
caggacccat actcccaacc cccaggaact ccacgacctg ttgtagattc ttattcccaa    6660
tcttcaggaa cagctaggtc caatacagac ccttactctc aacctcctgg aactccccgg    6720
cctactactg ttgacccata tagtcagcag ccccaaaccc caagaccatc tacacaaact    6780
gacttgtttg ttacacctgt aacaaatcag aggcattctg atccatatgc tcatcctcct    6840
ggaacaccaa gacctggaat ttctgtccct tactctcagc caccagcaac accaaggcca    6900
aggatttcag agggttttac taggtcctca atgacaagac cagtcctcat gccaaatcag    6960
```

```
gatcctttcc tgcaagcagc acaaaaccga ggaccagctt tacctggccc gttggtaagg    7020
ccacctgata catgttccca gacacctagg cccctggac ctggtctttc agacacattt    7080
agccgtgttt ccccatctgc tgcccgtgat ccctatgatc agtctccaat gactccaaga    7140
tctcagtctg actcttttgg aacaagtcaa actgcccatg atgttgctga tcagccaagg    7200
cctggatcag agggagctt ctgtgcatct tcaaactctc caatgcactc ccaaggccag     7260
cagttctctg gtgtctccca acttcctgga cctgtgccaa cttcaggagt aactgataca    7320
cagaatactg taaatatggc ccaagcagat acagagaaat tgagacagcg cagaagtta    7380 cgtgaaatca ttctccagca gcaacagcag aagaagattg caggtcgaca ggagaagggg    7440
tcacaggact cacccgcagt gcctcatcca gggcctcttc aacactggca accagagaat    7500
gttaaccagg ctttcaccag accccaccct ccctatcctg gaacattag gtctcctgtt    7560 gccccctcctt taggacctag atatgctgtt ttcccaaaag atcagcgtgg accctatcct    7620
cctgatgttg ctagtatggg gatgagacct catggattta gatttggatt tccaggaggt    7680
agtcatggta ccatgccgag tcaagagcgc ttccttgtgc ctcctcagca aatacaggga    7740
tctggagttt ctccacagct aagaagatca gtatctgtag atatgcctag gcctttaaat    7800
aactcacaaa tgaataatcc agttggactt cctcagcatt tttcaccaca gagcttgcca    7860
gttcagcagc acaacatact gggccaagca tatattgaac tgagacatag ggctcctgac    7920
ggaaggcaac ggctgccttt cagtgctcca cctggcagcg ttgtagaggc atcttctaat    7980
ctgagacatg gaaacttcat tccccggcca gactttccgg gccctagaca cacagacccc    8040
atgcgacgac ctccccaggg tctacctaat cagctacctg tgcacccaga tttggaacaa    8100
gtgccaccat ctcaacaaga gcaaggtcat tctgtccatt catcttctat ggtcatgagg    8160
actctgaacc atccactagg tggtgaattt tcagaagctc ctttgtcaac atctgtaccg    8220
tctgaaacaa cgtctgataa tttacagata accacccagc cttctgatgg tctagaggaa    8280
aaacttgatt ctgatgaccc ttctgtgaag gaactggatg ttaaagacct tgagggggtt    8340
gaagtcaaag acttagatga tgaagatctt gaaaacttaa atttagatac agaggatggc    8400
aaggtagttg aattggatac tttagataat ttggaaacta atgatcccaa cctggatgac    8460
ctcttaaggt caggagagtt tgatatcatt gcatatacag atccagaact tgacatggga    8520
gataagaaaa gcatgtttaa tgaggaacta gaccttccaa ttgatgataa gttagataat    8580
cagtgtgtat ctgttgaacc aaaaaaaag gaacaagaaa acaaaactct ggttctctct    8640
gataaacatt caccacagaa aaatccact gttaccaatg aggtaaaaac ggaagtactg    8700
tctccaaatt ctaaggtgga atccaaatgt gaaactgaaa aaaatgatga gaataaagat    8760
aatgttgaca ctccttgctc acaggcttct gctcactcag acctaaatga tggagaaaag    8820
acttctttgc atccttgtga tccagatcta tttgagaaaa gaaccaatcg agaaactgct    8880
ggccccagtg caaatgtcat tcaggcatcc actcaactac ctgctcaaga tgtaataaac    8940
tcttgtggca taactggatc aactccagtt ctctcaagtt tacttgctaa tgagaaatct    9000
gataattcag acattaggcc atcggggtct ccaccaccac caactctgcc ggcctcccca    9060
tccaatcatg tgtcaagttt gcctcctttc atagcaccgc ctggccgtgt tttggataat    9120
gccatgaatt ctaatgtgac agtagtctct agggtaaacc atgttttttc tcagggtgtg    9180
caggtaaacc cagggctcat tccaggtcaa tcaacagtta accacagtct ggggacagga    9240
aaacctgcaa ctcaaactgg gcctcaaaca agtcagtctg gtaccagtag catgtctgga    9300
ccccaacagc taatgattcc tcaaacatta gcacagcaga atagagagag gcccttcctt    9360
```

```
ctagaagaac agcctctact tctacaggat cttttggatc aagaaaggca agaacagcag    9420
cagcaaagac agatgcaagc catgattcgt cagcgatcag aaccgttctt ccctaatatt    9480
gattttgatg caattacaga tcctataatg aaagccaaaa tggtggccct aaaggtata    9540 aataaagtga tggcacaaaa caatctgggc atgccaccaa tggtgatgag caggttccct    9600
tttatgggcc aggtggtaac tggaacacag aacagtgaag acagaacct tggaccacag    9660 gccattcctc aggatggcag tataacacat cagatttcta ggcctaatcc tccaaatttt    9720
ggtccaggct tgtcaatga ttcacagcgt aagcagtatg aagagtggct ccaggagacc    9780
caacagctgc ttcaaatgca gcagaagtat cttgaagaac aaattggtgc tcacagaaaa    9840
tctaagaagg ccctttcagc taaacaacgt actgccaaga agctgggcg tgaatttcca    9900 gaggaagatg cagaacaact caagcatgtt actgaacagc aaagcatggt tcagaaacag    9960
ctagaacaga ttcgtaaaca acagaaagaa catgctgaat tgattgaaga ttatcggatc    10020
aaacagcagc agcaatgtgc aatggcccca cctaccatga tgcccagtgt ccagcccag    10080 ccaccctaa ttccaggtgc cactccaccc accatgagcc aacccacctt tcccatggtg    10140
ccacagcagc ttcagcacca gcagcacaca acagttattt ctggccatac tagccctgtt    10200
agaatgccca gtttacctgg atggcaaccc aacagtgctc ctgcccacct gccctcaat    10260 cctcctagaa ttcagccccc aattgcccag ttaccaataa aaacttgtac accagcccca    10320
gggacagtct caaatgcaaa tccacagagt ggaccaccac ctcgggtaga atttgatgac    10380
aacaatccct ttagtgaaag ttttcaagaa cgggaacgta aggaacgttt acgagaacag    10440
caagagagac aacggatcca actcatgcag gaggtagata gacaaagagc tttgcagcag    10500
aggatggaaa tggagcagca tggtatggtg ggctctgaga taagtagtag taggacatct    10560
gtgtcccaga ttcccttcta cagttccgac ttaccttgtg attttatgca acctctagga    10620 cccttcagc agtctccaca acaccaacag caaatgggc aggttttaca gcagcagaat    10680
atacaacaag gatcaattaa ttcaccctcc acccaaactt tcatgcagac taatgagcga    10740
aggcaggtag gccctccttc atttgttcct gattcaccat caatccctgt tggaagccca    10800
aatttttctt ctgtgaagca gggacatgga aatctttctg gaccagctt ccagcagtcc    10860 ccagtgaggc cttcttttac acctgcttta ccagcagcac ctccagtagc taatagcagt    10920
ctcccatgtg gccaagattc tactataacc catggacaca gttatccggg atcaacccaa    10980
tcgctcattc agttgtattc tgatataatc ccagaggaaa aagggaaaaa gaaaagaaca    11040
agaaagaaga aaagagatga tgatgcagaa tccaccaagg ctccatcaac tccccattca    11100
gatataactg ccccaccgac tccaggcatc tcagaaacta cctctactcc tgcagtgagc    11160
acacccagtg agcttcctca acaagccgac caagagtcgg tggaaccagt cggcccatcc    11220
actcccaata tggcagcagg ccagctatgt acagaattag agaacaaact gcccaatagt    11280
gatttctcac aagcaactcc aaatcaacag acgtatgcaa attcagaagt agacaagctc    11340
tccatggaaa cccctgccaa aacagaagag ataaaactgg aaaaggctga gacagagtcc    11400
tgcccaggcc aagaggagcc taaattggag gaacagaatg gtagtaaggt agaaggaaac    11460
gctgtagcct gtcctgtctc ctcagcacag agtcctcccc attctgctgg ggcccctgct    11520
gccaaaggag actcagggaa tgaacttctg aaacacttgt tgaaaaataa aaagtcatct    11580
tctcttttga atcaaaaacc tgagggcagt attttgttcag aagatgactg tacaaaggat    11640
aataaactag ttgagaagca gaacccagct gaaggactgc aaactttggg ggctcaaatg    11700
```

```
caaggtggtt ttggatgtgg caaccagttg ccaaaaacag atggaggaag tgaaaccaag    11760
aaacagcgaa gcaaacggac tcagaggacg ggtgagaaag cagcacctcg ctcaaagaaa    11820
aggaaaaagg acgaagagga gaaacaagct atgtactcta gcactgacac gtttacccac    11880
ttgaaacagc agaataattt aagtaatcct ccaacacccc ctgcctctct tcctcctaca    11940
ccacctccta tggcttgtca gaagatggcc aatggttttg caacaactga gaacttgct     12000 ggaaaagccg gagtgttagt gagccatgaa gttaccaaaa ctctaggacc taaaccattt    12060
cagctgccct tcagacccca ggacgacttg ttggcccgag ctcttgctca gggcccaag     12120 acagttgatg tgccagcctc cctcccaaca ccacctcata caatcagga gaattaagg      12180 atacaggatc actgtggtga tcgagatact cctgacagtt ttgttccctc atcctctcct    12240
gagagtgtgg ttggggtaga agtgagcagg tatccagatc tgtcattggt caaggaggag    12300
cctccagaac cggtgccgtc ccccatcatt ccaattcttc ctagcactgc tgggaaaagt    12360
tcagaatcaa gaaggaatga catcaaaact gagccaggca ctttatattt tgcgtcacct    12420
tttggtcctt ccccaaatgg tcccagatca ggtcttatat ctgtagcaat tactctgcat    12480
cctacagctg ctgagaacat tagcagtgtt gtggctgcat tttccgacct tcttcacgtc    12540
cgaatcccta acagctatga ggttagcagt gctccagatg tcccatccat gggtttggtc    12600
agtagccaca gaatcaaccc gggtttggag tatcgacagc atttacttct ccgtgggcct    12660
ccgccaggat ctgcaaaccc tcccagatta gtgagctctt accggctgaa gcagcctaat    12720
gtaccatttc ctccaacaag caatggtctt tctggatata aggattctag tcatggtatt    12780
gcagaaagcg cagcactcag accacagtgg tgttgtcatt gtaaagtggt tattcttgga    12840
agtggtgtgc ggaaatcttt caaagatctg acccttttga caaggattc ccgagaaagc     12900 accaagaggg tagagaagga cattgtcttc tgtagtaata actgctttat tctttattca    12960
tcaactgcac aagcgaaaaa ctcagaaaac aaggaatcca ttccttcatt gccacaatca    13020
cctatgagag aaacgccttc caaagcattt catcagtaca gcaacaacat ctccactttg    13080
gatgtgcact gtctccccca gctcccagag aaagcttctc cccctgcctc accacccatc    13140
gccttccctc ctgcttttga agcagcccaa gtcgaggcca agccagatga gctgaaggtg    13200
acagtcaagc tgaagcctcg gctaagagct gtccatggtg ggtttgaaga ttgcaggccg    13260
ctcaataaaa aatggagagg aatgaaatgg aagaagtgga gcattcatat tgtaatccct    13320
aaggggacat ttaaaccacc ttgtgaggat gaaatagatg aatttctaaa gaaattgggc    13380 acttcccttta aacctgatcc tgtgcccaaa gactatcgga aatgttgctt ttgtcatgaa    13440
gaaggtgatg gattgacaga tggaccagca aggctactca accttgactt ggatctgtgg    13500
gtccacttga actgcgctct gtggtccacg gaggtctatg agactcaggc tggtgcctta    13560
ataaatgtgg agctagctct gaggagaggc ctacaaatga aatgtgtctt ctgtcacaag    13620
acgggtgcca ctagtggatg ccacagattt cgatgcacca acatttatca cttcacttgc    13680
gccattaaag cacaatgcat gtttttttaag gacaaaacta gctttgccc catgcacaaa    13740 ccaaagggaa ttcatgagca agaattaagt tactttgcag tcttcaggag ggtctatgtt    13800
cagcgtgatg aggtgcgaca gattgctagc atcgtgcaac gaggagaacg ggaccatacc    13860
tttcgcgtgg gtagcctcat cttccacaca attggtcagc tgcttccaca gcagatgcaa    13920
gcattccatt tcctaaaagc actcttccct gtgggctatg aagccagccg gctgtactgg    13980
agcactcgct atgccaatag gcgctgccgc tacctgtgct ccattgagga gaaggatggg    14040
cgcccagtgt ttgtcatcag gattgtggaa caaggccatg aagacctggt tctaagtgac    14100
```

```
atctcaccta aaggtgtctg ggataagatt ttggagcctg tggcatgtgt gagaaaaaag   14160
tctgaaatgc tccagctttt cccagcgtat ttaaaaggag aggatctgtt tggcctgacc   14220
gtctctgcag tggcacgcat agcggaatca cttcctgggg ttgaggcatg tgaaaattat   14280
accttccgat acgccgaaa tcctctcatg gaacttcctc ttgccgttaa ccccacaggt    14340
tgtgcccgtt ctgaacctaa aatgagtgcc catgtcaaga ggtttgtgtt aaggcctcac   14400
accttaaaca gcaccagcac ctcaaagtca tttcagagca cagtcactgg agaactgaac   14460
gcaccttata gtaaacagtt tgttcactcc aagtcatcgc agtaccggaa gatgaaaact   14520
gaatggaaat ccaatgtgta tctggcacgg tctcggattc aggggctggg cctgtatgct   14580
gctcgagaca ttgagaaaca caccatggtc attgagtaca tcgggactat cattcgaaac   14640
gaagtagcca acaggaaaga gaagctttat gagtctcaga accgtggtgt gtacatgttc   14700
cgcatggata acgaccatgt gattgacgcg acgctcacag gagggcccgc aaggtatatc   14760
aaccattcgt gtgcacctaa ttgtgtggct gaagtggtga cttttgagag aggacacaaa   14820
attatcatca gctccagtcg gagaatccag aaaggagaag agctctgcta tgactataag   14880
tttgactttg aagatgacca gcacaagatt ccgtgtcact gtggagctgt gaactgccgg   14940
aagtggatga actgaaatgc attccttgct agctcagcgg gcggcttgtc cctaggaaga   15000
ggcgattcaa cacaccattg gaattttgca gacagaaaga gattttttgtt ttctgtttta   15060
tgacttttgt aaaaagcttc tgggagttct gatttcctca gtcctttagg ttaaagcagc   15120
gccaggagga agctgacaga agcagcgttc ctgaagtggc cgaggttaaa cggaatcaca   15180
gaatggtcca gcacttttgc ttttttttct ttccttttc tttttttttt gtttgttttt    15240
tgttttgttt ttcccttgtg ggtgggtttc attgttttgg ttttctagtc tcactaagga   15300
gaaacttttta ctggggcaaa gagccgatgg ctgccctgcc ccgggcaggg gccttcctat   15360
gaatgtaaga ctgaaatcac cagcgagggg gacagagagt gctggccacg gccttattaa   15420
aaaggggcag gccctctaac ttcaaaatgt ttttaaataa agtagacacc actgaacaag   15480
gaatgtactg aaatgacttc cttagggata gagctaaggg ataataactt gcactaaata   15540
catttaaata cttgattcca tgagtcagtt tattgtagtt tttgatttct gtaaaataag   15600
agaaactttt gtatttatta ttgaataagt gaatgaagct attttttaaat aaagttagaa  15660
gaaagccaag ctgctgctgt tacctgcaga actaacaaac cctgttactt tgtacagata   15720
tgtaaatatt ttgagaaaaa atacagtata aaaatagtta ttgaccaaat gctaccaggc   15780
tctgcagcag ctcgggggct tataaaatgt tcataggggat gttacaatat aattttgtgt   15840
tataaaatat gccattataa ttatgtaata accaaaattt caacctagag tgttgggggt   15900
ttttggaaa ccgcagtcta ttagtactca atggttttat acaccttact tctgacagag   15960
cggggcgtat gctacgacta caacttttat agctgttttg gtaatttaaa ctaattttttt  16020
catattatat tgttgcatcc ctacttcttc agtcaggttt ttttgtgctt acaatttgtg   16080
ataactgtga ataactgctt aaaaatacac ccaaatggag gctgaatttt tcttcagca    16140
aaagtagttt tgattagaac tttgtttcag ccacagagaa tcatgtaaac gtaataggat   16200
catgtagcag aaacttaaat ctaacccttt agccttctat ttaacacaaa atttgaaaa    16260
agttaaaaaa aaaaggaga tgtgattatg cttacagctg caggactctg gcaatagggt    16320
ttttggaaga tgtaatttta aaatgtgttt gtatgaactg tttgtttaca tttctttaat   16380
aaaaaaaaca ctgttttgtg tttgcttgta gaaacttaat cagcattttg aaccaggtta   16440
```

```
gcttttttatt ttgtacttaa aattctggta ctgacacttc acaggctaag tataaaatga     16500
agttttgtgt gcacaattca agtggactgt aaactgttgg tatattcagt gatgcagttc     16560
tgaacttgta tatggcatga tgtatttta tcttacagaa taaatcaatt gtatatattt      16620
ttctcttgat aaatagctgt atgaaatttg tttcctgaat attttcttc tcttgtacaa      16680 tatcctgaca tcctaccagt atttgtccta ccgggttttt gttgttttct gttctgtata     16740
atagtatcta atgttggcaa aaattgaatt ttttgaagta tacagagtgt tatgggtttt     16800
ggaatttgtg gacacagatt tagaagatca ccatttacaa ataaaatatt ttacatctat     16860
aaaaaaaaaa aa                                                         16872
```

```
<210> SEQ ID NO 83
<211> LENGTH: 1546
<212> TYPE: DNA
<213> ORGANISM: Homo sapiens

<400> SEQUENCE: 83
```

```
gtcacttccc ttcccgcgat ggcggcacag ggagctgctg cggcggttgc ggcggggact       60 tcagggtcg cggggagggg cgagcccggg cccggggaga atgcggccgc tgaggggacc      120
gccccatccc cgggccgcgt ctctccgccg accccgcgc gcggcgagcc ggaagtcacg      180
gtggagatcg gagaaacgta cctgtgccgg cgaccggata gcacctggca ttctgctgaa     240
gtgatccagt ctcgagtgaa cgaccaggag ggccgagagg aattctatgt acactacgtg     300
ggctttaacc ggcggctgga cgagtgggta gacaagaacc ggctggcgct gaccaagaca     360
gtgaaggatg ctgtacagaa gaactcagag aagtacctga gcgagctcgc agagcagcct     420
gagcgcaaga tcactcgcaa ccaaaagcgc aagcatgatg agatcaacca tgtgcagaag     480
acttatgcag agatggaccc caccacagca gccttggaga aggagcatga ggcgatcacc     540
aaggtgaagt atgtggacaa gatccacatc gggaactacg aaattgatgc ctggtatttc     600
tcaccattcc ccgaagacta tgggaaacag cccaagctct ggctctgcga gtactgcctc     660
aagtacatga aatatgagaa gagctaccgc ttccacttgg gtcagtgcca gtggcggcag     720
ccccccggga aagagatcta ccgcaagagc aacatctccg tgtacgaagt tgatggcaaa     780
gaccataaga tttactgtca gaacctgtgt ctgctggcca agctttttcct ggaccataag    840 acactgtact ttgacgtgga gccgttcgtc tttacatcc tgactgaggt ggaccggcag     900
ggggcccaca ttgttggcta cttctccaag gagaaggagt cccggatgg aaacaatgtg     960 gcctgcatcc tgaccttgcc cccctaccaa cgccgcggct acgggaagtt cctcatcgct    1020
ttcagttatg agctctccaa gctggagagc acagtcggct ccccggagaa gccactgtct    1080
gacctgggca agctcagcta ccgcagctac tggtcctggg tgctgctaga gatcctgcgg    1140
gacttccggg gcacactgtc catcaaggac ctcagccaga tgaccagtat cacccaaaat    1200
gacatcatca gtaccctgca atccctcaat atggtcaagt actggaaggg ccagcacgtg    1260
atctgtgtca cacccaagct ggtggaggag cacctcaaaa gtgcccagta taagaaacca    1320
cccatcacag tggactccgt ctgcctcaag tgggcacccc ccaagcacaa gcaagtcaag    1380
ctctccaaga agtgagcagc ctggcccctg cgtcggacc tgagcctcct ggctcccagc     1440
ctgtaaatat gtatagacct gttttgtcat ttttttaata aagtcagttc tggtggccct    1500
ggactttgga ggggaagggg aggccaagaa aaaaaaaaa aaaaaa                    1546
```

```
<210> SEQ ID NO 84
<211> LENGTH: 5941
```

<212> TYPE: DNA
<213> ORGANISM: Homo sapiens

<400> SEQUENCE: 84

```
gtgtgacaca attacaacaa ctttgtgctg gtgccgggga agtttgtgtc tccaacgaat      60
cccctcagtg ctccccagcc ccgcgcgctc cggccgttcc cgccgtcccc gcctgtggct     120
gccccctgcc caaccccgcg atgtgaccct acagccgaaa gccgccgctg ccgacccggg     180
ggctccgcag ccccctgccgc cgccgccgcc gccttcaccg ccgccgcgtt gggattttc     240
gtcgccgccg cccgcggcgg aggaggaggc ggcgataaag ttggtgtgct ggtcccgcgc     300
gcagattggg ggcgtcactg cgggcccgg tccgagggg ggtgtcggcg ttggagttgt      360
gaattcgctg cgtttccatg aaatcctgcg gagtgtcgct cgctaccgcc gccgctgccg     420
ccgccgcttt cggtgatgag gaaaagaaaa tggcggcggg aaaagcgagc ggcgagagcg     480
aggaggcgtc ccccagcctg acagccgagg agagggaggc gctcggcgga ctggacagcc     540
gcctctttgg gttcgtgaga tttcatgaag atggcgccag gacgaaggcc ctactgggca     600
aggctgttcg ctgctatgaa tctctaatct taaaagctga aggaaaagtg gagtctgatt     660
tcttttgtca attaggtcac ttcaacctct tattggaaga ttatccaaaa gcattatctg     720
cataccagag gtactacagt ttacagtctg actactggaa gaatgctgcc ttttatatg      780
gtcttggttt ggtctacttc cattataatg catttcagtg ggcaattaaa gcatttcagg     840
aggtgcttta tgttgatccc agcttttgtc gagccaagga aattcattta cgacttgggc     900
ttatgttcaa agtgaacaca gactatgagt ctagtttaaa gcattttcag ttagctttgg     960
ttgactgtaa tccctgcact ttgtccaatg ctgaaattca atttcacatt gcccacttat    1020
atgaaaccca gaggaaatat cattctgcaa aagaagctta tgaacaactt ttgcagacag    1080
agaatctttc tgcacaagta aaagcaactg tcttacaaca gttaggttgg atgcatcaca    1140
ctgtagatct cctgggagat aaagccacca aggaaagcta tgctattcag tatctccaaa    1200
agtccttgga agcagatcct aattctggcc agtcctggta tttcctcgga aggtgctatt    1260
caagtattgg gaaagttcag gatgccttta tatcttacag gcagtctatt gataaatcag    1320
aagcaagtgc agatacatgg tgttcaatag gtgtgctata tcagcagcaa aatcagccca    1380
tggatgcttt acaggcctat atttgtgctg tacaattgga ccatggccat gctgcagcct    1440
ggatggacct aggcactctc tatgaatcct gcaaccagcc tcaggatgcc attaaatgct    1500
acttaaatgc aactagaagc aaaagttgta gtaatacctc tgcacttgca gcacgaatta    1560
agtatttaca ggctcagttg tgtaaccttc cacaaggtag tctacagaat aaaactaaat    1620
tacttcctag tattgaggag gcgtggagcc taccaattcc cgcagagctt acctccaggc    1680
agggtgccat gaacacagca cagcaggcat gtaaacctca tcatccaaat actgaacctg    1740
tattaggcct cagtcaaaca ccaatttcac agcaatcctt gccactacac atgattcctt    1800
ctagccaagt agatgacctg tccagtcctg ccaagaggaa aagaacatct agtccaacaa    1860
agaatacttc tgacaattgg agtggtggac atgctgtgtc acatcctcca gtacagcaac    1920
aagctcattc atggtgtttg acaccacaga aattacagca tttggaacag ctccgcgcaa    1980
atagaaataa tttaaatcca gcacagaaac tgatgctgga acagctggaa agtcagtttg    2040
tcttaatgca acaacaccaa atgagaccaa caggagttgc acaggtacga tctactggaa    2100
ttcctaatgg gccaacagct gactcatcac tgcctacaaa ctcagtctct ggccagcagc    2160
cacagcttgc tctgaccaga gtgcctagcg tctctcagcc tggagtccgt cctgcctgcc    2220
```

-continued

```
ctgggcagcc tttggccaat ggacccttt  ctgcaggcca tgttccctgt agcacatcaa    2280
gaacgctggg aagtacagac actatttga  taggcaataa tcatataaca ggaagtggaa    2340
gtaatggaaa cgtgccttac ctgcagcgaa acgcactcac tctacctcat aaccgcacaa    2400
acctgaccag cagcgcagag gagccgtgga aaaaccaact atctaactcc actcaggggc    2460
ttcacaaagg tcagagttca cattcggcag gtcctaatgg tgaacgacct ctctcttcca    2520
ctgggccttc ccagcatctc caggcagctg gctctggtat tcagaatcag aacgacatc     2580 ccaccctgcc tagcaattca gtaacacagg gggctgctct caatcacctc tcctctcaca    2640
ctgctacctc aggtggacaa caaggcatta ccttaaccaa agagagcaag ccttcaggaa    2700
acatattgac ggtgcctgaa acaagcaggc acactggaga gacacctaac agcactgcca    2760
gtgtcgaggg acttcctaat catgtccatc agatgacggc agatgctgtt tgcagtccta    2820
gccatggaga ttctaagtca ccaggtttac taagttcaga caatcctcag ctctctgcct    2880
tgttgatggg aaaagccaat aacaatgtgg gtactggaac ctgtgacaaa gtcaataaca    2940
tccacccagc tgttcataca aagactgata actctgttgc ctcttcacca tcttcagcca    3000
tttcaacagc aacaccttct ccaaaatcca ctgagcagac aaccacaaac agtgttacca    3060
gccttaacag ccctcacagt gggctacaca caattaatgg agaagggatg gaagaatctc    3120
agagccccat gaaaacagat ctgcttctgg ttaaccacaa acctagtcca cagatcatac    3180
catcaatgtc tgtgtccata taccccagct cagcagaagt tctgaaggca tgcaggaatc    3240
taggtaaaaa tggcttatct aacagtagca ttttgttgga taaatgtcca cctccaagac    3300
caccatcttc accataccct cccttgccaa aggacaagtt gaatccacct acacctagta    3360
tttacttgga aaataaacgt gatgctttct ttcctccatt acatcaattt tgtacaaatc    3420
cgaacaaccc tgttacagta atacgtggcc ttgctggagc tcttaagtta gacctgggac    3480
ttttctctac taaaactttg gtggaagcta acaatgaaca tatggtagaa gtgaggacac    3540
agttgttgca gccagcagat gaaaactggg atcccactgg aacaaagaaa atctggcatt    3600
gtgaaagtaa tagatctcat actacaattg ctaaatatgc acagtaccag gcctcctcat    3660
tccaggaatc attgagagaa gaaaatgaaa aagaagtca  tcataaagac cactcagata    3720
gtgaatctac atcgtcagat aattctggga ggaggaggaa aggacccttt aaaaccataa    3780
agtttgggac caatattgac ctatctgatg acaaaaagtg gaagttgcag ctacatgagc    3840 tgactaaaact tcctgctttt gtgcgtgtcg tatcagcagg aaatcttcta agccatgttg    3900
gtcataccat attgggcatg aacacagttc aactatacat gaaagttcca gggagcagaa    3960
caccaggtca tcaggaaaat aacaacttct gttcagttaa cataaatatt ggcccaggtg    4020
actgtgaatg gtttgttgtt cctgaaggtt actgggtgt  tctgaatgac ttctgtgaaa    4080
aaaataattt gaatttccta atgggttctt ggtggcccaa tcttgaagat ctttatgaag    4140
caaatgttcc agtgtatagg tttattcagc gacctgaga  tttggtctgg ataaatgcag    4200
gcactgttca ttgggttcag gctattggct ggtgcaacaa cattgcttgg aatgttggtc    4260
cacttacagc ctgccagtat aaattggcag tggaacggta cgaatggaac aaattgcaaa    4320
gtgtgaagtc aatagtaccc atggttcatc ttttcctgga tatggcacga aatatcaagg    4380
tctcagatcc aaagctttt  gaaatgatta agtattgtct tctaagaact ctgaagcaat    4440
gtcagacatt gagggaagct ctcattgctg caggaaaaga gattatatgg catgggcgga    4500
caaaagaaga accagctcat tactgtagca tttgtgaagt ggaggttttt gatctgcttt    4560
ttgtcactaa tgagagtaat tcacgaaaga cctacatagt acattgccaa gattgtgcac    4620
```

-continued

```
gaaaaacaag cggaaacttg gaaaactttg tggtgctaga acagtacaaa atggaggacc      4680
tgatgcaagt ctatgaccaa tttacattag ctcctccatt accatccgcc tcatcttgat      4740
attgttccat ggacattaaa tgagaccttt tctgctattc aggaaataac ccagttctgc      4800
accactggtt tttgtagcta tctcgtaagg ctgctggctg aaaactgtgt ctatgcaacc      4860
ttccaagtgc ggagtgtcaa ccaactggac gggagagagt actgctccta ctccaggact      4920
ctcacaaagc tgatgagctg tacttcagaa aaaataata atttccatgt tttgtatata      4980
tctgacaaaa ctggcaacat cttacagact actgacttga agacaaccct ttttatattt      5040
ctctatttct gggctgatga atttgttttc atctgtcttt tcccccttca gaattttcct      5100
tggaaaaaaa atactagcct agctggtcat ttctttgtaa ggtagttagc aattttaagt      5160
ctttctttgg tcaactttt tttaatgtga aagttaggt aagacacttt tttactgctt         5220
ttatgttttt ctgtcttgtt ttgagaccat gatggttaca cttttggttc ctaaataaaa      5280
tttaaaaaat taacagccaa gtcacaaagg taatggattg cacatagact aaggaataaa      5340
cttcagattt gtgattttg tttctaatct tgatgtaaat ttacactatt tataaataca       5400
tatttattgc ttgaaaatat ttgtgaatgg aatgctgtta ttttttccag atttacctgc      5460
cattgaaatt ttaaggagtt ctgtaatttc aaacactact cctattacat tttctatgtg      5520
taaataaaac tgcttagcat tgtacagaaa cttttattaa aattgtttaa tgtttaaaga      5580
gttttctatt gtttgagttt taaaaagac tttatgtaca gtgcccagtt tttgttcatt       5640
tttgaaatct gattatatat atttatata tacttatgta tgtatatata atatatatag        5700
aaatctggat atatatgtat aaatctttag aacttaaatt tttctcgttt taagtttcac      5760
atctatggta gattttgag gtgtctactg taaagtattg cttacaaaaa gtatgattat       5820
ttttaaagaa atatatatgg tatgtatcct caagacctaa aatgtcagac tggtttattg      5880
ttaagttgca attactgcaa tgacagacca ataaacaatt gctgccaaaa tgtagtataa      5940
a                                                                     5941
```

<210> SEQ ID NO 85
<211> LENGTH: 7071
<212> TYPE: DNA
<213> ORGANISM: Homo sapiens

<400> SEQUENCE: 85

```
gtgaggccct gccgggtcgg gctgcgggcg gccgggcgcg ggcggcggga cagacgggcg       60
cacgcgagga ctgacggacg gacgcaccga gggcggcggg cacgcacggc ccgggccggc      120
gctccaaggc ccgcccggga gggccggggc cgcgctcaga attttgattt ggctgctggg      180
ctgctacctt gaaatccaag ccctaaaaat gccagcttct ttggacttag aagatgacct      240
ggataaatga taaaaattaa gaaagagatt ttgaagtttt cttattgtcc tcttggcata      300
tgcttctgga ataatattca ccatggtttt ggatgacctt ccaaacttag aagacatcta      360
tacttccttg tgttcatcaa caatggaaga ctcagagatg gattttgact ctggactaga      420
agatgatgac acaaaaagtg atagtatttt ggaggattcc acaattttg tggccttcaa       480 aggaaatata gatgataaag acttcaaatg gaaattagat gcaatattga aaacgtgcc       540 caatttgtta cacatggagt ccagcaagct aaaagtacag aaggtggagc cctggaacag      600
cgtgcgtgtg acattcaaca tccccgggga agcagcggag cggctacgga tccttgctca      660
gagcaacaac cagcagcttc gggatttagg gattctctcc gttcagattg aaggggaagg      720
```

```
tgctattaac ctggctttgg ctcagaaccg aagccaagat gtgagaatga atggacccat     780
gggagctgga aattcagtta ggatggaggc gggatttcct atggcaagtg gtccaggaat     840
aataaggatg aacaaccctg ccactgttat gatacccccg ggtggaaatg tgtcatcttc     900
catgatggca ccaggcccca atccagagct gcagcccagg actcctcgcc ctgcttctca     960
gtcagatgca atggatccac tcctctctgg gctccatata cagcagcaaa gtcatccctc    1020
aggatcttta gctcccccac atcacccaat gcagcctgtc tctgtgaaca gacaaatgaa    1080
cccagctaat tttccccagc tgcagcagca gcagcaacaa caacaacagc agcagcagca    1140
gcagcagcag caacaacagc aacagcagca acaacagttg caggcaagac ccccacagca    1200
acatcagcag caacagccac agggaattcg accccagttt actgccccaa ctcaggtgcc    1260
tgttcctcca ggctggaacc agctgccttc tggagccctt caacctcctc agcccagggg    1320
ttctctgggc acaatgactg caaaccaagg gtggaagaag gctcccttgc ccggcccaat    1380
gcaacagcaa ctccaggcaa gaccatcctt agccacggta cagacgcctt cccaccctcc    1440
ccctccatat cccttggca gccagcaagc ctcacaagcc cacacaaact ttcctcagat    1500
gagcaaccca ggccagttca cagctcctca gatgaagagt ttgcagggag ggccctctag    1560
ggtcccaact cccttgcagc agccccacct caccaacaag tctcctgcct cctcacccc     1620
ctccttccag cagggatccc ctgcatcctc cccaacggtt aaccaaactc agcagcagat    1680
gggaccaagg ccacctcaaa ataacccact tccccaggga tttcagcagc tgtcagctc    1740
tccgggtcgg aatcctatgg ttcaacaggg aaatgtgcca cctaacttca tggtgatgca    1800
gcagcaacca ccaaaccagg ggccacagag tttacatcca ggcctaggag gaatgcctaa    1860
acgcctccca cctggcttct cagcaggaca ggccaatccg aactttatgc aaggtcaggt    1920
gccttcgacc acagcaacca cccctgggaa ttcaggagcc cctcagctgc aagcaaatca    1980
aaatgtccag catgcaggtg gtcaaggagc tggtcctcct caaaaccaga tgcaggtgtc    2040
ccacgggccg ccaaatatga tgcagcccag cctcatggga attcatgca acatgaacaa    2100
tcagcaggct ggtacttctg gggttcctca agtgaacctc agcaacatgc aaggccagcc    2160
ccagcaggc ccaccatctc agctgatggg catgcaccag caaatcgtgc cctcccaggg    2220
ccagatggtc cagcaacaag gaaccttgaa ccctcagaac cctatgatcc tttcaagggc    2280
ccagcttatg ccacagggcc agatgatggt gaaccccccg agccaaaatc ttgggccctc    2340
gccccaaagg atgaccccac caagcagat gctttcccag cagggccacc aaatgatggc    2400
gccacataac cagatgatgg ggcctcaggg gcaggttttg ctccaacaga cccaatgat    2460
agagcagatt atgaccaatc aaatgcaggg gaataagcag cagtttaaca ctcagaacca    2520
gtccaatgtc atgccgggac cagcccgat aatgaggga ccaactccaa acatgcaagg    2580
aaatatggtg cagtttacgg gacagatgtc aggacagatg ctgccccagc aagggcctgt    2640
gaacaacagt ccatctcagg ttatgggcat tcagggacag gtcctgcgcc accagggcc    2700
cagcccacac atgcccagc agcatggtga tcctgctact acagcaaata acgatgtcag    2760
tttatctcag atgatgcctg atgttagcat tcaacaaacc aacatggtcc ccctcatgt    2820
gcaggccatg cagggaaaca gtgcctcggg aaaccactc tcaggccatg ggatgtcttt    2880
caatgcacct ttcagtggag ctcccaatgg aaatcagatg tcctgtggtc aaaatccagg    2940
cttcccagtc aataaggatg tcacgctaac gagcccattg ttggtcaact tattgcagag    3000
tgacatatct gcaggccatt ttggggtaaa caataagcaa aataatacca acgcaaataa    3060
accgaagaag aagaaacccc ctcggaagaa gaaaaatagt cagcaagatc taaacacccc    3120
```

-continued

```
agatactcgc ccagctggtc tggaagaggc tgatcagcca ccgttgcctg gagaacaagg    3180
aattaacttg ataactcag gccctaaact gccagaattt tcaaaccggc caccaggtta     3240
tccttctcaa ccagttgaac agaggccact tcagcagatg cctcctcaac tcatgcagca    3300
tgtggcaccc ccaccacagc caccacagca gcagccacag ccacaactgc ctcagcagca    3360
gcagccacca cctcccagtc agccacagtc tcagcagcag cagcagcagc agcaacaaat    3420
gatgatgatg ctcatgatgc agcaggatcc caaatcagtt aggcttccag tctctcaaaa    3480
tgtccatcct ccaaggggcc ccctgaaccc cgactcccag agaatgccca tgcaacagag    3540
tggcagtgtg cctgtcatgg tcagtctgca aggacctgcc tccgtgccac catcacctga    3600
taaacaaaga atgccaatgc ctgtgaatac tcccttggga agcaattcaa ggaaaatggt    3660
ctatcaggag agcccgcaga atccttccag ctcgccactg gcggagatgg cctcactccc    3720
tgaagcaagt ggcagtgaag caccatctgt cccaggaggc caaacaaca tgccttcaca     3780
tgtagtactt cccagaatc agttaatgat gacagggcca aaacctggac catcgcccct     3840
ttcagcaact caaggtgcaa ctccccagca accccctgta aattccctgc ccagctctca    3900
cggccaccac ttcccaaatg tggctgcgcc aacccagaca tctaggccca aaacaccaaa    3960
cagagccagc cccagaccct attatcctca gacacccaac aaccgccctc ccagcacaga    4020
accttcagaa atcagtctgt caccagaaag actcaatgcc tccatagcag gactcttccc    4080
tccacagatt aatattcctt tacctcctag gccaaattta acagggggct tgatcaaca     4140
aggcctaaat ccaacaactt tgaaggccat cgggcaagca ccttcaaatc ttaccatgaa    4200
tccttccaat tttgctaccc cacaaactca caaattagat tctgtggtag tgaattctgg    4260
aaagcagtct aattctggag caacaaaacg ggcaagtcca agcaacagtc gcaggtctag    4320
tcctgggtcc agtaggaaaa ccactccaag ccctgggagg caaaattcaa aagcccctaa    4380
acttactctg gcctctcaga caaatgcagc cctattgcag aatgtggagt tgccgagaaa    4440
tgtattggtc agtcccactc ctctggccaa tcccctgta cctgggagct tcctaacaa     4500
cagtgggctg aatcctcaga attctactgt gtctgtggct gcagttgggg gtgttgttga    4560
ggataacaag gagagcttga atgtgcctca ggacagtgat tgccagaatt cccagagtag    4620
gaaggaacag gtaaacattg aactaaaagc agtccctgcc caagaagtta aaatggttgt    4680
ccctgaagat cagtccaaaa aggatgggca gccttcggat cctaacaaac ttcccagtgt    4740
cgaagagaac aaaaatttgg tgtctcctgc tatgagggaa gcaccaacat cgttaagtca    4800
acttcttgac aactctggag ctcccaatgt gacaattaaa ccccctgggc ttacagatct    4860
ggaagtaaca cctccagtag tttctgggga ggacctcaaa aaagcatctg tcattcccac    4920
actgcaggat ctgtcttctt ctaaagaacc ttctaattcc ctaaacttac ctcacagtaa    4980
tgagctgtgt tcatcccttg tgcatcccga attgagtgag gtcagttcta acgttgcacc    5040
aagcatccct ccagtaatgt caagacctgt tagctcttcc tccatttcca ctcccttgcc    5100
cccaaatcaa ataactgtat ttgtcacttc caatcccatc acaacttcag ctaacacatc    5160
agcagctttg ccaactcact tgcagtctgc attgatgtca acagttgtca caatgcccaa    5220
tgcgggtagc aaggttatgg tttctgaggg acagtcagct gctcagtcta atgcccggcc    5280
tcagttcatt acacctgtct ttatcaattc atcctcaata attcaggtta tgaaaggatc    5340
acagccaagc acaattcctg cagccccact gacaaccaac tctggcctga tgcctccctc    5400
tgttgcagtt gttggccctt tacacatacc tcagaacata aaatttcttt ctgctcctgt    5460
```

```
accgcctaat gccctctcca gtagtcctgc tccaaacatc cagacaggtc gacctttggt    5520
ccttagctca cgagccaccc ctgttcagct tccttcccct ccttgtacgt cttctccagt    5580
tgtcccttct catcccsctg tgcagcaagt gaaagaattg aatccagatg aggctagccc    5640
```

```
accgcctaat gccctctcca gtagtcctgc tccaaacatc cagacaggtc gacctttggt    5520
ccttagctca cgagccaccc ctgttcagct tccttcccct ccttgtacgt cttctccagt    5580
tgtcccttct catcccsctg tgcagcaagt gaaagaattg aatccagatg aggctagccc    5640
tcaggtgaac acctcagcag atcagaacac tcttccctct tcacagtcaa ccacaatggt    5700
ttctccccct ttgaccaata gtccagggtc ctctggcaac cggcgaagcc cagtctcgtc    5760
tagtaagggc aaaggaaaag tggacaaaat tggccaaatt ttgttgacca aggcatgtaa    5820
gaaagttaca ggctctcttg agaaagggga agaacaatat ggtgcagatg agagactga    5880 aggccaaggg ctagacacca cagctccggg gctcatggga acagagcagt tatccacaga    5940
gctggacagt aaaaccccaa cgcccccagc acccactctg ctaaaaatga cctctagccc    6000
tgtgggcccg ggcactgcct cagcaggacc cagcttacct ggcggtgctc tcccaccag    6060 tgtacgctcg atagtaacca ctctggtacc ctccgagctc atctccgccg taccgaccac    6120
aaaaagcaat catggtggca tagcatctga gtcacttgcg ggtggcctag tggaggagaa    6180
ggtgggatcc catccagaac ttctacccag catgccccg tcgcagaatt tagtctcaaa    6240
ggaaacttca accacagcac tgcaggcctc tgttgccaga ccagagctgg aggtaaatgc    6300
tgccatagtc tctggacaaa gcagtgagcc caaagagata gttgaaaagt ccaaaatccc    6360
aggccgaaga aactcccgaa ctgaagagcc aactgtggcc tctgaaagtg tggaaaatgg    6420
acatcgtaaa cgatcttctc gacctgcttc agcctccagc tctactaaag acataaccag    6480
tgcggtgcaa tccaagcgaa gaaaatccaa gtaaacaagc aggactgcga cttgatactt    6540
ggaaatgtgt gtgactttta caaagagcaa ttttgagctg tgactttttt aaatcaattt    6600
ctgtacagtt agtaatttta ataatgtggc ccttttccta gtccctgcaa cctgtttcat    6660
aaagtgcaat ggggaaagca ggactgttga gccccttttgg tgttgcgagt tgaagttcaa    6720
ggtttctaaa atgttgtctt gtattgaaag gagctaatgc cattataaat gttactagtt    6780
ttcacatttc ctaagcagcc tagagtacag ggtgagcatt tttagatctc ctaatgatgt    6840
attgtgccgt ggaagtactg tgtgtgaata gcagtagtgg gggcaaaagc aatcttctca    6900
tttggaaatg ttgtaaataa ttttattata tagtgttttg gatgtatttg ttgtagaaat    6960
ggaccagtga ataaagagaa tctaaggatt tgtacaatgt gaaataacgt gttaaataaa    7020
tgtcattgtc atagaacata aagttatgtt attggtaagg gaaaaaaaa a              7071
```

<210> SEQ ID NO 86
<211> LENGTH: 3843
<212> TYPE: DNA
<213> ORGANISM: Homo sapiens

<400> SEQUENCE: 86

```
ggcgccgtgt ccgggtgtgg agaggggcgt cgtggaagcg agaagagtgg cccgtccctc      60 tcctcccct ttccctcttt cggaaagtgg tttctgcggg gcccgggagc ctcggagtac     120
cgaacctcga tctccggggc ggggtccttg gtggggactg agcgcccct cccggggacg     180 ggcggtctgg ccgcggagtc ccctgcggga gcgtgattgg ctggaaacgg tcccgaaccc     240
ccaggggagc ccgatccctg ggggaccctg gcttcggact ccagtatctg tcgtcgcagg     300
gtccctgccc tagtggccta tgtcccttgc tcggggccat ggagacactg cggccagtac     360
ggcggcgcct ctgtctgaag aaggggaagt gacctccggc ctccaggctc tggccgtgga     420
ggataccgga ggcccctctg cctcggccgg taaggccgag gacgagggg aaggaggccg     480 agaggagacc gagcgtgagg ggtccggggg cgaggaggcg cagggagaag tccccagcgc     540
```

-continued

```
tgggggagaa gagcctgccg aggaggactc cgaggactgg tgcgtgccct gcagcgacga    600
ggaggtggag ctgcctgcgg atgggcagcc ctggatgccc ccgccctccg aaatccagcg    660
gctctatgaa ctgctggctg cccacggtac tctggagctg caagccgaga tcctgccccg    720
ccggcctccc acgccggagg cccagagcga agaggagaga tccgatgagg agccggaggc    780
caaagaagag gaagaggaaa aaccacacat gcccacggaa tttgattttg atgatgagcc    840
agtgacacca aaggactccc tgattgaccg gagacgcacc ccaggaagct cagcccggag    900
ccagaaacgg gaggcccgcc tggacaaggt gctgtcggac atgaagagac aagaagct    960 ggaggagcag atccttcgta ccgggaggga cctcttcagc ctggactcgg aggacccag   1020 ccccgccagc cccccactcc gatcctccgg gagtagtctc ttccctcggc agcggaaata   1080
ctgattccca ctgctcctgc ctctagggtg cagtgtccgt acctgctgga gcctgggccc   1140
tccttcccca gcccagacat tgagaaactt gggaagaaga gagaaacctc aagctcccaa   1200
acagcacgtt gcgggaaaga ggaagagaga gtgtgagtgt gtgtgtgtgt tttttctatt   1260
gaacacctgt agagtgtgtg tgtgtgtttt ctattgaaca cctatagaga gagtgtgtgt   1320
gttttctatt gaacatctat atagagagag tgtgtgagtg tgtgttttct attgaacacc   1380
tattcagaga cctggactga attttctgag tctgaaataa aagatgcaga gctatcatct   1440
cttaaaagga gggctgtag ctgtagctca acagttaggc cccacttgaa gggagaggca   1500
gaattgtact cacccagatt ggaaaatgaa agccagatgg gtagaggtgc cctcagttag   1560
cacctgtccc atctcgggcc ctccaactcc tcccagtccc actccagtgc agccagctgg   1620
ctccaaggta gaaacccatg agcactcagg gagcagtgtg ccttcagctg cagcagaagc   1680
agcccggagg ataaaatgag aaccagctgc acacgggccc tttaactccc aagccccacc   1740
cctgggcttg gcctgccttg ccctgccggg aagtgatccc caaggcaggg tgagagttcc   1800
ccatctgagg cgtttgttgc agctaccgtc acttctagat gtgagtacat tgtactagcc   1860
ccccaaaccc caaatcaggg gcagatcttt gtatcccttg aggctctctt tagtcctgtc   1920
ttgctttgaa gggccttgct tctgctgggg cagggaaaac atgtctgaat cagagtgggg   1980
aaggaggatg ggtggtggct ttgcttttgg aggtttcact ttccaatagt tgggagtctt   2040
ctgggttttg aagtaaaggc agattaacac caacaccggt cccccacccc cctgcaactc   2100
tcaggcctct ctctgacttc agggtccac ctggaaatc aggtggggaa ccttacaggg    2160
tcattcagac cccatcttag ccctagatcg gtgcttgctc tactcacctg cactgtcctg   2220
gggacctggg ctctggcctg tcaccttgag ctccaagaat gtgacctgta cccattcagg   2280 cccccttaact ctgacagatg agggtttctt actcctccat gcagggctgg gccagctgtt   2340
ggtctcagtc gatcattcag gaagtcatta gcagagtgat ttccagaagg cgtagaattt   2400
agtgaccaag gttcttttcct ttttgggagg agaaagtgaa aactaggatg ctcagctgga   2460
cccaccagcc tgagattctg gggatttag agctgtccct tggggagcca agcacttggg   2520
ggtggaggtg atagcgaggc tgatggcccc tgtgttctca gctctctgcc tgggtagccc   2580
ctgggtgatg ggggagaggc cagctgtcac gtggggtatc aggtggctct gccagaaact   2640
cccttggcac acagagcact gggtcggccc tcggtgtgg ctgtttgggc aggacagccc   2700
tctgtatgta gccttgagca ggtaggggg ccaccttgag tgggtggccc agagacagcc   2760
tcagggctcc aaggtaacgg ggtgctcagg ttatcttggg tgctgccctc ccaggttctg   2820
ggggagcaga ggctgggcgc tggcccaact tacaggaaac actcacctttt gaactgccat   2880
```

| | |
|---|---|
| tagcaccatc tgggcagtac acagccccac ccaggtcctc tagttcttgt tctcggctta | 2940 |
| gaatctttgt gtttctgcct gagaagccac tgcctcctag tttgtggtct ctacagttat | 3000 |
| agccaggttg gacttccggc tccgtccttt gataactgtg tgctcttggg caaatttctt | 3060 |
| aacttgcagg ttcttgtgag gataacatga gttaattgag ggcacttaac actacctggc | 3120 |
| acagattaag ctcatctgaa gtgggagctg ttacttaggg gcgtttgcct agaacacagg | 3180 |
| gtccagagge tetetecegg aaacttagac ccagtgagtc agaagtgagg cctgcaaaaa | 3240 |
| gcagcaggag tggggttaag aattccagcc tagggctgga tgcggtggct caggcctgta | 3300 |
| atcccagtac tttgggaggc ccgaatggga ggatggcttg aggccaggag ttccagacca | 3360 |
| gcctgagcaa catagcgaga ccctgtctct gtttgtgtgt gtgtggttgg ggttttgttt | 3420 |
| tttttttttt tttaaagaat tatagctcag tcctatgatt aggcaagttg agaaaatatt | 3480 |
| gatgaagatc agggggtgctg aagcctggtt cctgggtcg cttctgatct aggcggttct | 3540 |
| tgcctctggt gactggtgtt aattggcagg agtgggagga gggaggacaa gtggaagtct | 3600 |
| aggctggctg agctgttctg tctcgaaaag ttcctaaaac tgtgctgctt taaaaaaaaa | 3660 |
| aaaagtaatt tatgagacac attctcaatt tccattaatc atctcctaaa gggggtaaac | 3720 |
| caggaagccg ctgggtgaaa acaggctgtt ggcaattcct gagtcatgtg acccattctc | 3780 |
| taaagactag aatatttaac ttaaatcagt gagaaactct gtgaaaaaaa aaaaaaaaa | 3840 |
| aaa | 3843 |

<210> SEQ ID NO 87
<211> LENGTH: 3723
<212> TYPE: DNA
<213> ORGANISM: Homo sapiens

<400> SEQUENCE: 87

| | |
|---|---|
| cggggccggg cgccgccgcg gagcctcccg ggccgccgcg atcatgtcgg accaggcgcc | 60 |
| caaagttcct gaggagatgt tcagggaggt caagtattac gcggtgggcg acatcgaccc | 120 |
| gcaggttatt cagcttctca aggctggaaa agcgaaggaa gtttcctaca atgcactagc | 180 |
| ctcacacata atctcagagg atggggacaa tccagaggtg ggagaagctc gggaagtctt | 240 |
| tgacttacct gttgtaaagc cttcttgggt gattctgtcc gttcagtgtg gaactcttct | 300 |
| gccagtaaat ggttttctc cagaatcatg tcagattttt tttggaatca ctgcctgcct | 360 |
| ttctcaggtg tcatctgaag acagaagtgc cctgtgggct ttggttacgt tctatggggg | 420 |
| agattgccag ctaaccctca ataagaaatg cacgcatttg attgttccag agccaaaggg | 480 |
| ggagaaatac gaatgtgctt taaagcgagc aagtattaaa attgtgactc ctgactgggt | 540 |
| tctggattgc gtatcagaga aaccaaaaa ggacgaagca ttttatcatc ctcgtctgat | 600 |
| tatttatgaa gaggaagaag aggaagagga agaggaggag gaagtagaaa atgaggaaca | 660 |
| agattctcag aatgagggta gtacagatga gaagtcaagc cctgccagct ctcaagaagg | 720 |
| gtctccttca ggtgaccagc agttttcacc taaatccaac actgaaaaat ctaaagggga | 780 |
| attaatgttt gatgattctt cagattcatc accggaaaaa caggagagaa atttaaactg | 840 |
| gacccggcc gaagtccac agttagctgc agcaaaacgc aggctgcctc agggaaagga | 900 |
| gcctgggttg attaacttgt gtgccaatgt cccacccgtc ccaggtaaca ttttgccccc | 960 |
| tgaggtccgg ggtaatttaa tggctgctgg acaaaacctc caaagttctg aaagatcaga | 1020 |
| aatgatagct acctggagtc cagctgtacg gacactgagg aatattacta ataatgctga | 1080 |
| cattcagcag atgaaccggc catcaaatgt agcacatatc ttacagactc tttcagcacc | 1140 |

```
tacgaaaaat ttagaacagc aggtgaatca cagccagcag ggacatacaa atgccaatgc    1200
agtgctgttt agccaagtga aagtgactcc agagacacac atgctacagc agcagcagca    1260
ggcccagcag cagcagcagc agcacccggt tttacacctt cagccccagc agataatgca    1320
gctccagcag cagcagcagc agcagatctc tcagcaacct taccccagc agccgccgca    1380 tccattttca cagcaacagc agcagcagca gcaagcccat ccgcatcagt tttcacagca    1440
acagctacag tttccacagc aacagttgca tcctccacag cagctgcatc gccctcagca    1500
gcagctccag ccctttcagc agcagcatgc cctgcagcag cagttccatc agctgcagca    1560
gcaccagctc cagcagcagc agcttgccca gctccagcag cagcacagcc tgctccagca    1620
gcagcagcaa cagcagattc agcagcagca gctccagcgc atgcaccagc agcagcagca    1680
gcagcagatg caaagtcaga cagcgccaca cttgagtcag acgtcacagg cgctgcagca    1740
tcaggttcca cctcagcagc ccccgcagca gcagcagcaa cagcagccac caccatcgcc    1800
tcagcagcat cagcttttg gacatgatcc agcagtggag attccagaag aaggcttctt    1860
attgggatgt gtgtttgcaa ttgcggatta ccagagcag atgtctgata agcaactgct    1920
ggccacctgg aaaaggataa tccaggcaca tggcggcact gttgaccca ccttcacgag    1980 tcgatgcacg caccttctct gtgagagtca agtcagcagc gcgtatgcac aggcaataag    2040
agaaagaaag agatgtgtta ctgcacactg gttaaacaca gtcttaaaga agaagaaaat    2100
ggtaccgccg caccgagccc ttcacttccc agtggccttc ccaccaggag gaaagccatg    2160
ttcacagcat attatttctg tgactggatt tgttgatagt gacagagatg acctaaaatt    2220
aatggcttat ttggcaggtg ccaaatatac gggttatcta tgccgcagca acacagtcct    2280
catctgtaaa gaaccaactg gtttaaagta tgaaaaagcc aaagagtgga ggataccctg    2340
tgtcaacgcc cagtggcttg gcgacattct tctgggaaac tttgaggcac tgaggcagat    2400
tcagtatagt cgctcacgg cattcagtct gcaggatcca tttgcccta cccagcattt    2460 agttttaaat cttttagatg cttggagagt tcccttaaaa gtgtctgcag agttgttgat    2520
gagtataaga ctacctccca aactgaaaca gaatgaagta gctaatgtcc agccttcttc    2580
caaaagagcc agaattgaag acgtaccacc tcccactaaa aagctaactc cagaattgac    2640
cccttttgtg cttttcactg gattcgagcc tgtccaggtt caacagtata ttaagaagct    2700
ctacattctt ggtggagagg ttgcggagtc tgcacagaag tgcacacacc tcattgccag    2760
caaagtgact cgcaccgtga agttcctgac ggcgatttct gtcgtgaagc acatagtgac    2820
gccagagtgg ctggaagaat gcttcaggtg tcagaagttc attgatgagc agaactacat    2880
tctccgagat gctgaggcag aagtactttt ctctttcagc ttggaagaat ccttaaaacg    2940
ggcacacgtt tctccactct ttaaggcaaa atattttac atcacacctg gaatctgccc    3000
aagtctttcc actatgaagg caatcgtaga gtgtgcagga ggaaaggtgt tatccaagca    3060
gccatctttc cggaagctca tggagcacaa gcagaactcg agtttgtcgg aaataatttt    3120
aatatcctgt gaaaatgacc ttcatttatg ccgagaatat tttgccagag gcatagatgt    3180
tcacaatgca gagttcgttc tgactggagt gctcactcaa acgctggact atgaatcata    3240
taagtttaac tgatggcgtc taggctgccg tgcatgtcga ctcctgcggt gcggggctgg    3300
ctgtctggct ggcgaggagc tgctgcgctt ccttcacatg ctcttgtttt ccagctgctt    3360 tcctgggga tcagactgtg aagcaggaag acagatataa taaatatact gcatcttttt    3420
aagatgtgca attttattct gaggaaacat aaattatgtt ttgtattata tgactttaag    3480
```

-continued

| | |
|---|---|
| agcccacatt aggtttttatg attcatttgc caggttttta aatgttttca caaaactgtt | 3540 |
| acgggacttc aactagaaat aaaatggtgt aaataaagac cttgctatct ctaaattatg | 3600 |
| gatgttaaag atttgaaatg ttttgtactt tgattatttt tatttcttat actctgtttt | 3660 |
| cttttatatt gatatcttgc ccacatttta aataaatgta cttttgaact taaaaaaaaa | 3720 |
| aaa | 3723 |

<210> SEQ ID NO 88
<211> LENGTH: 11784
<212> TYPE: DNA
<213> ORGANISM: Homo sapiens

<400> SEQUENCE: 88

| | |
|---|---|
| aggagtggaa ggttgagggg ggcgctaggc gcccttcgct ccctccctct ggaggagctg | 60 |
| ccgccgccac cgccgccact ctgctgctgc cgccgccgcc gccgccgctc ccgccgccat | 120 |
| tttgggttcg ctttgcggag gggagacgat cccagtctcg gttgcgggac ccgcctcccc | 180 |
| tcagtttgcc ccctttagcc ttccaccttt cccttctcct ctctcgcatt tccgccagtc | 240 |
| agcttacccg ctggccgcct cctgacaagc gggagggatc cgccgtggac ccagggaagc | 300 |
| ggaggagcct ggcggccacc ccctcttccc cacttccctg cactctcatc gctctcggcc | 360 |
| tcggcctcgg cctccgacac gagaaagatg ctggtttcga gttttggaga tccttgtttt | 420 |
| ttatggaaca cagttctgta aaattttcat aagattcctt ggcaataaca tacgcttgtg | 480 |
| atggacccta gaaatactgc tatgttagga ttgggttctg attccgaagg ttttttcaaga | 540 |
| aagagtcctt ctgccatcag tactggcaca ttggtcagta agagagaagt agagctagaa | 600 |
| aaaaacacaa aggaggaaga ggaccttcgc aaacggaatc gagaaagaaa catcgaagct | 660 |
| gggaaagatg atggtttgac tgatgcacag caacagtttt cagtgaaaga aacaaacttt | 720 |
| tcagagggaa atttaaaatt gaaaattggc ctccaggcta agagaactaa aaaacctcca | 780 |
| aagaacttgg agaactatgt atgtcgacct gccataaaaa caactattaa gcacccaagg | 840 |
| aaagcactta aagtggaaa gatgacggat gaaaagaatg aacactgtcc ttcaaaacga | 900 |
| gacccttcaa agttgtacaa gaaagcagat gatgttgcag ccattgaatg ccagtctgaa | 960 |
| gaagtcatcc gtcttcattc acagggagaa acaatccttt gtctaagaa gctgtctcca | 1020 |
| gtacactcag aaatggcaga ttatattaat gcaacgccat ctactcttct tggtagccgg | 1080 |
| gatcctgatt taaaggacag agcattactt aatggaggaa ctagtgtaac agaaaagttg | 1140 |
| gcacagctga ttgctacctg tcctccttcc aagtcttcca agacaaaacc gaagaagtta | 1200 |
| ggaactggca ctacagcagg attggttagc aaggatttga tcaggaaagc aggtgttggc | 1260 |
| tctgtagctg gaataataca taaggactta ataaaaaagc caaccatcag cacagcagtt | 1320 |
| ggattggtaa ctaaagatcc tgggaaaaag ccagtgttta atgcagcagt aggattggtc | 1380 |
| aataaggact ctgtgaaaaa actgggaact ggcactacag cggtattcat taataaaaac | 1440 |
| ttaggcaaaa agccaggaac tatcactaca gtaggactgc taagcaaaga ttcaggaaag | 1500 |
| aagctaggaa ttggtattgt tccaggttta gtgcataaag agtctggcaa gaagttagga | 1560 |
| cttggcactg tggttggact ggttaataaa gatttgggaa agaaattggg ttctactgtt | 1620 |
| ggcctagtgg ccaaggactg tgcaagaag attgtagcaa gttcagcaat gggattggtt | 1680 |
| aataaggaca ttggaaagaa actaatgagt tgtccttggg caggtctgat cagtaaagat | 1740 |
| gccataaacc ttaaagccga agcactgctc cccactcagg aaccgcttaa ggcttcttgt | 1800 |
| agtacaaaca tcaataatca ggaaagtcag gaactttctg aatccctgaa agatagtgcc | 1860 |

```
accagcaaaa cttttgaaaa gaatgttgta cggcagaata aagaaagcat attggaaaag   1920
ttctcagtac gaaaagaaat cattaatttg gagaaagaaa tgtttaatga aggaacatgc   1980
attcagcaag acagtttctc atccagtgaa aagggatctt atgaaacctc aaagcatgaa   2040
aagcagcctc ctgtatattg cacttctccg gactttaaaa tggggaggtgc ttctgatgta  2100
tctaccgcta aatccccatt cagtgcagta ggagaaagca atctcccttc cccatcacct   2160
actgtatctg ttaatccttt aaccagaagt cccctgaaa cttcttcaca gttggctcct    2220
aatccattac ttttaagttc tactacagaa ctaatcgaag aaatttctga atctgttgga   2280
aagaaccagt ttacttctga aagtacccac ttgaacgttg gtcataggtc agttggtcat   2340
agtataagta ttgaatgtaa agggattgat aaagaggtaa atgattcaaa aactacccat   2400
atagatattc caagaataag ctcttcccct ggaaaaaagc caagtttgac ttctgaatcc   2460
agcattcata ctattactcc ttcagttgtt aacttcacta gtttatttag taataagcct   2520
tttttaaaac tgggtgcagt atctgcatca gacaaacact gccaagttgc tgaaagccta   2580
agtactagtt tgcagtccaa accattaaaa aaaagaaaag gaagaaaacc tcggtggact   2640
aaagtggtgg caagaagcac atgccggtct ccaaaagggc tagaattaga agatcagag    2700
cttttaaaa acgtttcatg tagctcacta tcaaatagta attctgagcc agccaagttt    2760
atgaaaaaca ttggaccccc ttcatttgta gatcatgact tccttaaacg ccgattgcca   2820
aagttgagca aatccacagc tccatctctt gctctcttag ctgatagtga aaaaccatct   2880
cataagtctt ttgctactca caaactatcc tccagtatgt gtgtctctag tgaccttttg   2940
tctgatattt ataagcccaa aagaggaagg cctaaatcta aggagatgcc tcaactggaa   3000
gggccaccta aaaggacttt aaaaatccct gcttctaaag tgttttcttt acagtctaag   3060
gaagaacaag aaccccccaat tttacagcca gaaattgaaa tcccttcctt caaacaaggt  3120
ctgtctgtgt ctccttttcc aaaaagagag gcaggccta agaggcaaat gaggtcacca    3180
gtcaagatga agccacctgt actgtcagtg gctccatttg ttgccactga aagtccaagc   3240
aagctagaat ctgaaagtga caaccataga agtagcagtg atttctttga gagcgaggat   3300
caacttcagg atccagatga cctagatgac agtcataggc caagtgtctg tagtatgagt   3360
gaccttgaga tggaaccaga taaaaaaatt accaagagaa acaatggaca attaatgaaa   3420
acaattatcc gcaaaataaa taaatgaag actttaaaga gaaagaaact gttgaatcag    3480
attctttcaa gttctgtaga atcaagtaat aaagggaaag tgcaatccaa actccataat   3540
acggtatcaa gtcttgctgc cacatttggc tctaaattgg ccaacagat aaatgtcagc    3600
aagaaaggaa ccatttatat aggaaagaga agaggtcgca aaccaaaaac tgtcttaaat   3660
ggtattcttt ctggtagtcc tactagcctt gctgttcttg agcaaacagc tcaacaggca   3720
gctgggtcag cattaggaca gattcttccc ccattactgc cttcatctgc tagtagttct   3780
gagattcttc catcacctat ttgctctcag tcttctggga ctagtggagg tcagagccct   3840
gtaagtagtg atgcaggttt tgttgaaccc agttcagtgc catatttgca tttacactcc   3900
agacagggca gtatgattca gactcttgca atgaagaagg cctcaaaggg gaggaggcgg   3960
ttatctcctc ctactttgtt gccaaattct ccttcgcact tgagtgaact cacatctcta   4020
aagaagcta ctccttcccc aatcagtgag tctcatagtg atgagaccat tcccagtgat    4080
agtggaattg gaacagataa taacagcaca tcagacaggg cagagaaatt ttgtgggcaa   4140
aaaaagagga ggcattcttt tgagcatgtt tctctgattc cccctgaaac ctctacagtg   4200
```

```
ctaagcagtc ttaaagaaaa acataaacac aaatgtaagc gcaggaatca tgattacctc    4260
agctatgaca agatgaaaag gcagaaacga aaacggaaaa agaaatatcc ccagcttcga    4320
aatagacagg atccagactt tattgcagag ctggaggaac taataagtcg cctaagtgaa    4380
attcggatca ctcatcgaag tcatcatttt atccccgag atcttctgcc aactatcttt     4440
cgaatcaact ttaatagttt ctatacacat ccttctttcc ccttagaccc tttgcactac    4500
attcgaaaac ctgacttaaa aaagaaaaga gggagacccc ctaagatgag ggaggcaatg    4560
gctgaaatgc ctttttatgca cagccttagt tttcctctt ctagtactgg attctatcca    4620
tcttatggta tgccttactc tccttcaccc cttacagctg ctcccatagg attaggttac    4680 tatgaaggt atcctcccac tctttatcca cctcctccat ctccttcttt caccacgcca     4740
cttccacctc cttcctatat gcatgctggt catttacttc tcaatcctgc caaataccat    4800
aagaaaaagc ataagctact tcgacaggag gcctttctta caaccagcag gactcccctc    4860 cttccatga gtacctaccc cagtgttcct cctgagatgg cctatggttg gatggttgag      4920
cacaaacaca ggcaccgtca caaacacaga gaacaccgtt cttctgaaca ccccaggtt      4980 tctatggaca ctggctcttc ccgatctgtc ctggaatctt tgaagcgcta tagatttgga    5040
aaggatgctg ttggagagcg atataagcat aaggaaaagc accgttgtca catgtcctgc    5100
cctcatctct ctccttcaaa aagcttaata acagagagg aacagtgggt ccaccgagag     5160
ccttcagaat ctagtccatt ggccttggga ttgcagacac ctttacagat tgactgttca    5220
gaaagttctc caagcttatc ccttggagga ttcactccca actctgagcc agccagcagt    5280
gatgaacata caaaccttt cacaagtgca ataggcagct gcagagttc aaaccctaac      5340 tccagtggcc ggaagaaatt aactgacagc cctggactct tttctgcaca ggacacttca    5400
ctaaatcggc ttcacagaaa ggagtcactg ccttctaacg aaagggcagt acagactttg    5460
gcaggctccc agccaaccct tgataaaccc tcccagcggc catcagagag cacaaattgt    5520
agccctaccc ggaaaaggtc ttcatctgag agtacttctt caacagtaaa cggagttccc    5580
tctcgaagtc caagattagt tgcttctggg gatgactctg tggatagtct gctgcagcgg    5640
atggtacaaa atgaggacca agagcccatg gagaaaagta ttgatgctgt gattgcaact    5700
gcctctgcac caccttcttc cagtccaggc cgtagccaca gcaaggaccg aaccctggga    5760
aaaccagaca gccttttagt gcctgcagtc acaagtgact cttgcaataa tagcatctca    5820
ctcctatctg aaaagttgac aagcagctgt tccccccatc atatcaagag aagtgtagtg    5880
gaagctatgc aacgccaagc tcggaaaatg tgcaattacg acaaaatctt ggccacaaag    5940
aaaaacctag accatgtcaa taaaatctta aaagccaaaa aacttcaaag gcaggccagg    6000
acagggaata actttgtgaa acgtaggcca ggtcgacctc ggaaatgtcc ccttcaggct    6060
gtcgtatcaa tgcaagcatt ccaggctgct cagtttgtca acccagaatt gaacagagac    6120
gaggaaggag cagcactgca cctcagtcct gacacagtta cagatgtaat tgaggctgtt    6180
gttcagagtg taaatctgaa cccagaacat aaaaagggt tgaagagaaa aggttggcta    6240
ttggaagaac agaccagaaa aaagcagaag ccattaccag aggaagaaga gcaagagaat    6300
aataaaagct ttaatgaagc accagttgag attcccagtc cttctgaaac ccagctaaa    6360 ccttctgaac ctgaaagtac cttgcagcct gtgctttctc tcatcccaag ggaaaagaag    6420
cccccacgtc ccccaaagaa gaagtatcag aaagcagggc tgtattctga cgtttacaaa    6480
actacagacc caaagagtcg attgatccaa ttaaagaaag agaagctgga gtatactcca    6540
ggagagcatg aatatggatt atttccagcg cccattcatg ttggaaagta tctaagacaa    6600
```

```
aagagaattg acttccagct tccttatgat atcctttggc agtggaaaca caatcagcta    6660
tacaaaaagc cagatgtccc actatataag aaaattcgtt caaatgtcta cgttgatgtc    6720
aaaccccttt ctggttacga agctaccacc tgtaactgta agaagccaga tgatgacacc    6780
aggaagggct gtgttgatga ctgcctcaat agaatgatct tgctgagtg ttcccccaac     6840 acttgcccat gtggcgagca atgctgtaac cagaggatac agaggcatga atgggtgcaa    6900
tgtctagaac gatttcgagc tgaggaaaaa ggttggggaa tcagaaccaa agagcccta     6960 aaagctgggc agttcatcat tgaataccta ggggaggtcg tcagtgaaca ggagttcagg    7020
aacaggatga ttgagcagta tcataatcac agtgaccact actgcctgaa cctggatagt    7080
gggatggtga ttgacagtta ccgcatggga aatgaggccc gattcatcaa ccatagctgt    7140
gacccaaatt gtgaaatgca gaaatggtct gttaatggag tataccggat tggactctat    7200
gctcttaaag acatgccagc tgggactgaa ctcacttatg attataactt tcattccttc    7260
aatgtgaaaa acagcaact tgtaagtgt ggctttgaga atgtcgagg aatcatcgga       7320 ggcaagagtc agcgtgtgaa tggactcacc agcagcaaaa acagccagcc catggccaca    7380
cacaaaaaat ctggacggtc aaaagagaag agaaagtcta agcacaagct gaagaaaagg    7440
agaggccatc tctctgagga acccagtgaa aatatcaaca ccccaactag attgaccccc    7500
caattacaga tgaagccaat gtccaatcgt gaaaggaact ttgtgttaaa gcatcatgta    7560
ttcttggtcc gaaactggga aagattcgt caaaaacagg aggaagtaaa gcacaccagt     7620
gataatattc actcagcatc attatatacc cgttggaatg ggatctgccg agatgatggg    7680
aatatcaagt ctgatgtctt catgacccag ttctctgccc tgcagacagc tcgatctgtt    7740
cgaacaagac ggttggcagc tgcagaggaa aatattgaag tggctcgggc agcccgccta    7800
gcccagatct tcaaagaaat ttgtgatggt atcatctctt ataaagattc ttcccggcaa    7860
gcactggcag ctccactttt gaaccttccc ccaaagaaaa agaatgctga ttattatgag    7920
aagatctctg atcccctaga tcttatcacc atagagaagc agatcctcac tggttactat    7980
aagacagtgg aagcttttga tgctgacatg ctcaaagtct ttcggaatgc tgagaagtac    8040
tatgggcgta atccccagt tgggagagat gtttgtcgtc tacgaaaggc ctattacaat    8100
gcccggcatg aggcatcagc ccagattgat gagattgtgg gagagacagc aagtgaggca    8160
gacagcagtg agacctcagt ctctgaaaag gagaatgggc atgagaagga cgacgatgtt    8220
attcgctgta tctgtggcct ctacaaggat gaaggtctca tgatccagtg tgacaagtgc    8280
atggtatggc agcactgtga ttgtatggga gtgaactcag atgtggagca ctacctttgt    8340
gagcagtgtg acccaaggcc tgtggacagg gaggttccca tgatccctcg gccccactat    8400
gcccaacctg gctgtgtcta cttcatctgt ttgctccgag atgacttgct gcttcgtcag    8460
ggtgactgtg tgtatctgat gagggatagt cggcgcaccc ctgatggcca cccggtccgt    8520
cagtcctatc gactgttatc tcacattaac cgagataaac ttgacatctt tcgcattgag    8580
aagctttgga agaatgaaaa agaggaacgg tttgcctttg gtcaccatta tttccgtccc    8640
cacgaaacac accactctcc atcccgtcgg ttctatcata tgaactatt tcgggtgcca    8700 ctctatgaga tcattccctt ggaggctgta gtggggacct gctgtgtgtt ggacctttat    8760
acgtattgta aagggagacc caaaggagta aaggagcaag atgtgtacat ctgtgattat    8820
cggcttgaca agtcagcaca cctgttttac aagatccacc ggaaccgcta tcctgtctgc    8880 accaaacccct atgcttttga tcacttcccc aagaagctca ctcccaaaaa agatttctcg    8940
```

```
cctcattacg tcccagacaa ctacaagagg aatggaggac gatcatcctg gaagtctgag   9000
cgctcaaagc cacccctaaa agacttgggc caggaggatg atgctctacc cttgattgaa   9060
gaggttctag ccagtcaaga gcaagcagcc aatgagatac ccagcctgga ggagccagaa   9120
cgggaagggg ccactgctaa cgtcagtgag ggtgaaaaaa aaacagagga aagtagtcaa   9180 gaacccagt caacctgtac ccctgaggaa cgacggcata accaacggga acgactcaac    9240
cagatcttgc tcaatctcct tgaaaaaatc cctggaaaaa atgccattga tgtgacctac   9300
ttgctggagg aaggatcagg caggaaactg cgaaggcgta ctttgtttat cccagaaaac   9360
agctttcgaa agtgaccctc aaagaatgag aacctcaagc atctgggatc cagtggagct   9420
aatcagtcct gcctcctgct ctctgggtat agacaggggt gggaagggtc catctgggca   9480
aggggaatgg ggccatgttg ttgacattag gtacttaata agccttggag ctagtggaga   9540
gggagaggaa agggttctgt ccaagacagt tcaggttaat taattttctt ctccattgct   9600
tcaccttaag ggttaataat gtagagagga gggaggacca cattgatgac cagaacctac   9660
tggtacttta tagcatttgc cccaccccac agcttaggtt tttctgtcat cctcagatcc   9720
cacaggcatt gcgaagaagc tgcttcctat acccaggtat aactcaaaat ccaaagggat   9780
agggccagga tccctattcc tacccccatct attctctgtt ggctccaaga gctaccccag   9840
agacctaaaa cagaaacagt agctgaggct tcttcctaga tacctgacta gggaagtttg   9900
tctctccttt cttgcccaac caggtcaaag taaaatgtga gttgacagct caaagcactt   9960
gtaactgctg cccctccct acctctactc cccaaaatgg aatcatggga tagggaaggc   10020
ccccatgggg tcagaagggc acggtagttc ttgcaattat ttttgtttta cccttcataa  10080
cctgtcaaac atattttttt ctaatgagaa agccaggccc ccgccagcac acatgctgtt  10140
tttaatgcgc tgtagttctt gtgtgtctgc tgtgctgtgc aaatggagat tcagttcaaa  10200
ataaaatcat ttaaaaacct acataaaaag aactctaaac ccaccccctgc aacaaaagtc  10260 actacataaa ctgttcagca gtattcacct atcagatgt ttgttgtgag tatagattat    10320
caattgaaaa cactactctt gttttcttaa ttgtacagtt ttcaatgtcc ctttcttaaa   10380
gagacagtat atttctcttc accctagcc catcttccct cacccctg aatgacatca       10440 ggaggtatat ccagggtgtc tccttccttc ctactctctt gaccagaagt taacagacta   10500
tactgtctct ttaaaaataa aatttaaaaa gctttgttgt cttttcagac atacatatgc   10560
atatatgttt tagatgttct tataagagaa aagatggttt ttaaatgtgc caagttgtgt   10620
gtgtgtgtgt atatatatgt gtgtatgtgt gtgtatatat atatgtgtgt gtgtatatat   10680
atacacacac acacacacac ctgctgtgtg attggtaagc aatacaatag taaacatgtc   10740
cccattactt ttttctaata ttggaccaat gctgtcctaa ttgtacattt ccccttatgg   10800
tgacgatgct ctgactcgtt taggtagaca cattgaccac cttccattcc attaaatatt   10860 ttttccttt tccccttct gtgtcattct tgaggaaaaa acaaaagaga gagggggatgc    10920 caatgatccc cttgagcaga gaaaaagcaa aataaatatt ttattaaaga aaaagagaa    10980 ttaagaaaat agtttggagt attttcttac tgtagagaag cactgtacat tactaagaga   11040
cctgggtata agatactcac atgtggagct ggaaaaatcg catgtccaag cccgtttgag   11100
tggtttcttt tgttttcat tgcagggagt gggtgggagg gaggtgggac taggggcact    11160
ttgggggtct ccttttagtc aaaagcgaga aaatgacaag aaagagatta aaattcaatg   11220 tttccttttat agtgttaaac actaaaattt taaaaaagat gaaaagaaa aaaaactttt   11280 gtaaaatgcg agaacagaag caaaagacac tacgctctgt catttatct ttcttttgtt    11340
```

-continued

| | |
|---|---|
| gaaagactaa aaaaaaactg aaatgttttt tagacaatca aatgttaggt aagtgcaaaa | 11400 |
| acttgttttt tcttactggt gtagaaatta atgcctttt ttattttttca gttatttat | 11460 |
| aataacgaaa taaaaagaac cccccagctg ccaggcgggt tttggtgttt gaaatgcggg | 11520 |
| gcaaagcact acatcactgc aaatagatac agagttagtc tgcatgtctg taggctgtgt | 11580 |
| gattgcggaa aatataaatg ctgctaatat atttcctttt tacaaaagca tatctaaata | 11640 |
| gatgattgtt ttgatgttaa tctttgtaaa ttatgtatta ccaatttttaa cattggatgt | 11700 |
| aattgcatac aaagcttgca tctcaatcct tgaaagtcta gtattaaatg gaaaaaactt | 11760 |
| ttcctaactg tggaaaaaaa aaaa | 11784 |

<210> SEQ ID NO 89
<211> LENGTH: 5892
<212> TYPE: DNA
<213> ORGANISM: Homo sapiens

<400> SEQUENCE: 89

| | |
|---|---|
| gcgtcttccg gcgcccgcgg aggaggcgag ggtgggacgc tgggcggagc ccgagtttag | 60 |
| gaagaggagg ggacggctgt catcaatgaa gtcatattca taatctagtc ctctctccct | 120 |
| ctgtttctgt actctgggtg actcagagag ggaagagatt cagccagcac actcctcgcg | 180 |
| agcaagcatt actctactga ctggcagaga caggagaggt agatgtccac gcccacagac | 240 |
| cctggtgcga tgccccaccc agggccttcg ccggggcctg ggccttcccc tgggccaatt | 300 |
| cttgggccta gtccaggacc aggaccatcc ccaggttccg tccacagcat gatgggccca | 360 |
| agtcctggac ctccaagtgt ctcccatcct atgccgacga tggggtccac agacttccca | 420 |
| caggaaggca tgcatcaaat gcataagccc atcgatggta tacatgacaa ggggattgta | 480 |
| gaagacatcc attgtggatc catgaagggc actggtatgc gaccacctca cccaggcatg | 540 |
| ggccctcccc agagtccaat ggatcaacac agccaaggtt atatgtcacc acacccatct | 600 |
| ccattaggag ccccagagca cgtctccagc cctatgtctg gaggaggccc aactccacct | 660 |
| cagatgccac caagccagcc gggggccctc atcccaggtg atccgcaggc catgagccag | 720 |
| cccaacagag gtccctcacc tttcagtcct gtccagctgc atcagcttcg agctcagatt | 780 |
| ttagcttata aaatgctggc ccgaggccag cccctccccg aaacgctgca gcttgcagtc | 840 |
| caggggaaaa ggacgttgcc tggcttcag caacaacagc agcagcaaca gcagcagcag | 900 |
| cagcagcagc agcagcagca gcagcagcaa cagcagccgc agcagcagcc gccgcaacca | 960 |
| cagacgcagc aacaacagca gccggccctt gttaactaca acagaccatc tggcccgggg | 1020 |
| ccggagctga gcggcccgag caccccgcag aagctgccgg tgcccgcgcc cggcggccgg | 1080 |
| ccctcgcccg cgcccccgc agccgcgcag ccgcccgcgg ccgcagtgcc cgggccctca | 1140 |
| gtgccgcagc cggccccggg gcagccctcg cccgtcctcc agctgcagca aagcagagc | 1200 |
| cgcatcagcc ccatccagaa accgcaaggc ctggaccccg tggaaattct gcaagagcgg | 1260 |
| gaatacagac ttcaggcccg catagctcat aggatacaag aactggaaaa tctgcctggc | 1320 |
| tctttgccac cagattttaag aaccaaagca accgtggaac taaaagcact tcggttactc | 1380 |
| aatttccagc gtcagctgag acaggaggtg gtggcctgca tgcgcaggga cacgaccctg | 1440 |
| gagacggctc tcaactccaa agcatacaaa cggagcaagc gccagactct gagagaagct | 1500 |
| cgcatgaccg agaagctgga gaagcagcag aagattgagc aggagaggaa acgccgtcag | 1560 |
| aaacaccagg aatacctgaa cagtatttg caacatgcaa aagatttttaa ggaatatcat | 1620 |

```
cggtctgtgg ccggaaagat ccagaagctc tccaaagcag tggcaacttg gcatgccaac    1680
actgaaagag agcagaagaa ggagacagag cggattgaaa aggagagaat gcggcgactg    1740
atggctgaag atgaggaggg ttatagaaaa ctgattgatc aaaagaaaga caggcgttta    1800
gcttaccttt tgcagcagac cgatgagtat gtagccaatc tgaccaatct ggtttgggag    1860
cacaagcaag cccaggcagc caaagagaag aagaaggagga ggaggaggaa gaagaaggct    1920
gaggagaatg cagagggtgg ggagtctgcc ctgggaccgg atggagagcc catgatgag    1980 agcagccaga tgagtgacct ccctgtcaaa gtgactcaca cagaaaccgg caaggttctg    2040
ttcggaccag aagcacccaa agcaagtcag ctggacgcct ggctggaaat gaatcctggt    2100
tatgaagttg cccctagatc tgacagtgaa gagagtgatt ctgattatga ggaagaggat    2160
gaggaagaag agtccagtag gcaggaaacc gaagagaaaa tactcctgga tccaaatagc    2220
gaagaagttt ctgagaagga tgctaagcag atcattgaga cagctaagca agacgtggat    2280
gatgaataca gcatgcagta cagtgccagg ggctcccagt cctactacac cgtggctcat    2340
gccatctcgg agagggtgga gaaacagtct gccctcctaa ttaatgggac cctaaagcat    2400
taccagctcc agggcctgga atggatggtt tccctgtata taacaacttg aacggaatc    2460 ttagccgatg aaatggggct tggaaagacc atacagacca ttgcactcat cacttatctg    2520
atggagcaca aaagactcaa tggcccctat ctcatcattg ttccccttc gactctatct    2580 aactggacat atgaatttga caaatgggct ccttctgtgg tgaagatttc ttacaagggt    2640
actcctgcca tgcgtcgctc ccttgtcccc cagctacgga gtggcaaatt caatgtcctc    2700
ttgactactt atgagtatat tataaaagac aagcacattc ttgcaaagat tcggtggaaa    2760
tacatgatag tggacgaagg ccaccgaatg aagaatcacc actgcaagct gactcaggtc    2820
ttgaacactc actatgtggc ccccagaagg atcctcttga ctgggacccc gctgcagaat    2880
aagctccctg aactctgggc cctcctcaac ttcctcctcc caacaatttt taagagctgc    2940
agcacatttg aacaatggtt caatgctcca tttgccatga ctggtgaaag ggtgacttta    3000
aatgaagaag aaactatatt gatcatcagg cgtctacata aggtgttaag accatttta    3060 ctaaggagac tgaagaaaga agttgaatcc cagcttcccg aaaaagtgga atatgtgatc    3120
aagtgtgaca tgtcagctct gcagaagatt ctgtatcgcc atatgcaagc caggggatc    3180 cttctcacag atggttctga aaagataag aaggggaaag gaggtgctaa gacacttatg    3240
aacactatta tgcagttgag aaaaatctgc aaccaccat atatgtttca gcacattgag    3300
gaatcctttg ctgaacacct aggctattca aatggggtca tcaatggggc tgaactgtat    3360
cgggcctcag ggaagtttga gctgcttgat cgtattctgc aaaattgag agcgactaat    3420 caccgagtgc tgcttttctg ccagatgaca tctctcatga ccatcatgga ggattatttt    3480
gcttttcgga acttcctta cctacgcctt gatggcacca ccaagtctga agatcgtgct    3540
gctttgctga gaaaattcaa tgaacctgga tcccagtatt tcattttctt gctgagcaca    3600
agagctggtg gcctgggctt aaatcttcag gcagctgata cagtggtcat ctttgacagc    3660
gactggaatc ctcatcagga tctgcaggcc caagaccgag ctcaccgcat cgggcagcag    3720
aacgaggtcc gggtactgag gctctgtacc gtgaacagcg tggaggaaaa gatcctcgcg    3780
gccgcaaaat acaagctgaa cgtggatcag aaagtgatcc aggcgggcat gtttgaccaa    3840
aagtcttcaa gccacgagcg gagggcattc ctgcaggcca tcttggagca tgaggaggaa    3900
aatgaggaag aagatgaagt accggacgat gagactctga accaaatgat tgctcgacga    3960
gaagaagaat ttgacctttt tatgcggatg gacatggacc ggcggaggga agatgcccgg    4020
```

```
aacccgaaac ggaagccccg tttaatggag gaggatgagc tgccctcctg gatcattaag   4080
gatgacgctg aagtagaaag gctcacctgt gaagaagagg aggagaaaat atttgggagg   4140
gggtcccgcc agcgccgtga cgtggactac agtgacgccc tcacggagaa gcagtggcta   4200
agggccatcg aagacggcaa tttggaggaa atggaagagg aagtacggct taagaagcga   4260
aaagacgaa gaaatgtgga taaagatcct gcaaagaag atgtggaaaa agctaagaag   4320
agaagaggcc gccctcccgc tgagaaactg tcaccaaatc cccccaaact gacaaagcag   4380
atgaacgcta tcatcgatac tgtgataaac tacaaagata ggtgtaacgt ggagaaggtg   4440
cccagtaatt ctcagttgga aatagaagga aacagttcag ggcgacagct cagtgaagtc   4500
ttcattcagt taccttcaag gaaagaatta ccagaatact atgaattaat taggaagcca   4560
gtggatttca aaaaaataaa ggaaaggatt cgtaatcata agtaccggag cctaggcgac   4620
ctggagaagg atgtcatgct tctctgtcac aacgctcaga cgttcaacct ggagggatcc   4680
cagatctatg aagactccat cgtcttacag tcagtgttta agagtgcccg gcagaaaatt   4740
gccaaagagg aagagagtga ggatgaaagc aatgaagagg aggaagagga agatgaagaa   4800
gagtcagagt ccgaggcaaa atcagtcaag gtgaaaatta agctcaataa aaaagatgac   4860
aaaggccggg acaaagggaa aggcaagaaa aggccaaatc gaggaaaagc caaacctgta   4920
gtgagcgatt ttgacagcga tgaggagcag gatgaacgtg aacagtcaga aggaagtggg   4980
acggatgatg agtgatcagt atggaccttt ttccttggta gaactgaatt ccttcctccc   5040
ctgtctcatt tctacccagt gagttcattt gtcatatagg cactgggttg tttctatatc   5100
atcatcgtct ataaactagc tttaggatag tgccagacaa acatatgata tcatggtgta   5160
aaaaacacac acatacacaa atatttgtaa catattgtga ccaaatgggc ctcaaagatt   5220
cagattgaaa caaacaaaaa gcttttgatg gaaaatatgt gggtggatag tatatttcta   5280
tgggtgggtc taatttggta acggtttgat tgtgcctggt tttatcaccct gttcagatga   5340
gaagatttt gtcttttgta gcactgataa ccaggagaag ccattaaaag ccactggtta   5400
ttttatttt catcaggcaa ttttcgaggt ttttatttgt tcggtattgt ttttttacac   5460
tgtggtacat ataagcaact ttaataggtg ataaatgtac agtagttaga tttcacctgc   5520
atatacattt ttccatttta tgctctatga tctgaacaaa agcttttga attgtataag   5580
atttatgtct actgtaaaca ttgcttaatt tttttgctct tgatttaaaa aaagttttg   5640
ttgaaagcgc tattgaatat tgcaatctat atagtgtatt ggatggcttc ttttgtcacc   5700
ctgatctcct atgttaccaa tgtgtatcgt ctccttctcc ctaaagtgta cttaatcttt   5760
gctttctttg cacaatgtct ttggttgcaa gtcataagcc tgaggcaaat aaaattccag   5820
taatttcgaa gaatgtggtg ttggtgcttt cctaataaag aaataattta gcttgacaaa   5880
aaaaaaaaaa aa                                                       5892

<210> SEQ ID NO 90
<211> LENGTH: 5779
<212> TYPE: DNA
<213> ORGANISM: Homo sapiens

<400> SEQUENCE: 90
ggagaggccg ccgcggtgct gaggggggagg ggagccggcg agcgcgcgcg cagcgggggc    60
gcgggtggcg cgcgtgtgtg tgaaggggggg gcggtggccg aggcgggcgg gcgcgcgcgc   120
gaggcttccc ctcgtttggc ggcggcggcg gcttctttgt ttcgtgaaga gaagcgagac   180
```

```
gcccattctg ccccggccc cgcgcggagg ggcggggag gcgccgggaa gtcgacggcg    240
ccggcggctc ctgcgtctcg ccctttgcc caggctagag tgcagtggtg cggtcatggt    300
tcactgcagc ctcaacctcc tggactcagc aggaggccac tgtctgcagc tcccgtgaag    360
atgtccactc cagacccacc cctgggcgga actcctcggc caggtccttc cccgggccct    420
ggcccttccc ctggagccat gctgggccct agcccgggtc cctcgccggg ctccgcccac    480
agcatgatgg ggcccagccc agggccgccc tcagcaggac ccccatccc cacccagggg    540
cctggagggt accctcagga caacatgcac cagatgcaca agcccatgga gtccatgcat    600
gagaagggca tgtcggacga cccgcgctac aaccagatga aggaatggg gatgcggtca    660
ggggggccatg ctgggatggg gccccgccc agcccatgg accagcactc caaggttac    720
ccctcgcccc tgggtggctc tgagcatgcc tctagtccag ttccagccag tggcccgtct    780
tcggggcccc agatgtcttc cgggccagga ggtgccccgc tggatggtgc tgaccccag    840
gccttgggc agcagaaccg ggcccaacc ccatttaacc agaaccagct gcaccagctc    900
agagctcaga tcatggccta caagatgctg gccagggggc agccctccc cgaccacctg    960
cagatggcgg tgcagggcaa gcggccgatg cccgggatgc agcagcagat gccaacgcta   1020
cctccaccct cggtgtccgc aacaggaccc ggccctggcc ctggccctgg cccggcccg   1080
ggtcccggcc cggcacctcc aaattacagc aggcctcatg gtatgggagg cccaacatg   1140
cctcccccag accctcggg cgtgcccccc gggatgccag ccagcctcc tggagggcct   1200
cccaagccct ggcctgaagg acccatggcg aatgctgctg ccccacgag cacccctcag   1260
aagctgattc ccccgcagcc aacgggccgc ccttccccg cgcccctgc cgtcccaccc   1320
gccgcctcgc ccgtgatgcc accgcagacc cagtcccccg ggcagccggc ccagcccgcg   1380
cccatggtgc cactgcacca gaagcagagc cgcatcaccc ccatccagaa gccgcggggc   1440
ctcgaccctg tggagatcct gcaggagcgc gagtacaggc tgcaggctcg catcgcacac   1500
cgaattcagg aacttgaaaa ccttcccggg tccctggccg gggatttgcg aaccaaagcg   1560
accattgagc tcaaggccct caggctgctg aacttccaga ggcagctgcg ccaggaggtg   1620
gtggtgtgca tgcggaggga cacagcgctg gagacagccc tcaatgctaa ggcctacaag   1680
cgcagcaagc gccagtccct gcgcgaggcc cgcatcactg agaagctgga gaagcagcag   1740
aagatcgagc aggagcgcaa gcgccggcag aagcaccagg aatacctcaa tagcattctc   1800
cagcatgcca aggatttcaa ggaatatcac agatccgtca caggcaaaat ccagaagctg   1860
accaaggcag tggccacgta ccatgccaac acggagcggg agcagaagaa agagaacgag   1920
cggatcgaga aggagcgcat gcggaggctc atggctgaag atgaggaggg gtaccgcaag   1980
ctcatcgacc agaagaagga caagcgcctg gcctacctct gcagcagac agacgagtac   2040
gtggctaacc tcacggagct ggtgcggcag cacaaggctg cccaggtcgc caaggagaaa   2100
aagaagaaaa agaaaagaa gaaggcagaa aatgcagaag acagacgcc tgccattggg   2160
ccggatggcg agcctctgga cgagaccagc cagatgagcg acctcccggt gaaggtgatc   2220
cacgtggaga gtgggaagat cctcacaggc acagatgccc ccaaagccgg gcagctggag   2280
gcctggctcg agatgaaccc gggtgatgaa gtagctccga ggtctgatag tgaagaaagt   2340
ggctcagaag aagaggaaga ggaggaggag gaagagcagc cgcaggcagc acagcctccc   2400
accctgcccg tggaggagaa gaagaagatt ccagatccag acagcgatga cgtctctgag   2460
gtggacgcgc ggcacatcat tgagaatgcc aagcaagatg tcgatgatga atatggcgtg   2520
tcccaggccc ttgcacgtgg cctgcagtcc tactatgccg tggcccatgc tgtcactgag   2580
```

```
agagtggaca agcagtcagc gcttatggtc aatggtgtcc tcaaacagta ccagatcaaa    2640
ggtttggagt ggctggtgtc cctgtacaac aacaacctga acggcatcct ggccgacgag    2700
atgggcctgg ggaagaccat ccagaccatc gcgctcatca cgtacctcat ggagcacaaa    2760
cgcatcaatg ggcccttcct catcatcgtg cctctctcaa cgctgtccaa ctgggcgtac    2820
gagtttgaca gtgggcccc ctccgtggtg aaggtgtctt acaagggatc cccagcagca    2880
agacgggcct ttgtccccca gctccggagt gggaagttca acgtcttgct gacgacgtac    2940
gagtacatca tcaaagacaa gcacatcctc gccaagatcc gttggaagta catgattgtg    3000
gacgaaggtc accgcatgaa gaaccaccac tgcaagctga cgcaggtgct caacacgcac    3060
tatgtggcac cccgccgcct gctgctgacg ggcacaccgc tgcagaacaa gcttcccgag    3120
ctctgggcgc tgctcaactt cctgctgccc accatcttca agagctgcag caccttcgag    3180
cagtggttta acgcacccct tgccatgacc ggggaaaagg tggacctgaa tgaggaggaa    3240
accattctca tcatccggcg tctccacaaa gtgctgcggc ccttcttgct ccgacgactc    3300
aagaaggaag tcgaggccca gttgcccgaa aaggtggagt acgtcatcaa gtgcgacatg    3360
tctgcgctgc agcgagtgct ctaccgccac atgcaggcca agggcgtgct gctgactgat    3420
ggctccgaga aggacaagaa gggcaaaggc ggcaccaaga ccctgatgaa caccatcatg    3480
cagctgcgga gatctgcaa ccaccccta c atgttccagc acatcgagga gtccttttcc     3540
gagcacttgg ggttcactgg cggcattgtc caagggctgg acctgtaccg agcctcgggt    3600
aaatttgagc ttcttgatag aattcttccc aaactccgag caaccaacca caaagtgctg    3660
ctgttctgcc aaatgaccctc cctcatgacc atcatggaag attactttgc gtatcgcggc    3720
tttaaatacc tcaggcttga tggaaccacg aaggcggagg accggggcat gctgctgaaa    3780
accttcaacg agcccggctc tgagtacttc atcttcctgc tcagcacccg ggctggggg    3840 ctcggcctga acctccagtc ggcagacact gtgatcattt ttgacagcga ctggaatcct    3900
caccaggacc tgcaagcgca ggaccgagcc caccgcatcg ggcagcagaa cgaggtgcgt    3960
gtgctccgcc tctgcaccgt caacagcgtg gaggagaaga tcctagctgc agccaagtac    4020
aagctcaacg tggaccagaa ggtgatccag gccggcatgt tcgaccagaa gtcctccagc    4080
catgagcggc gcgccttcct gcaggccatc ctggagcacg aggagcagga tgagagcaga    4140
cactgcagca cgggcagcgg cagtgccagc ttcgcccaca ctgcccctcc gccagcgggc    4200
gtcaaccccg acttggagga gccacctcta aaggaggaag acgaggtgcc cgacgacgag    4260
accgtcaacc agatgatcgc ccggcacgag gaggagtttg atctgttcat gcgcatggac    4320
ctggaccgca ggcgcgagga ggcccgcaac cccaagcgga agccgcgcct catggaggag    4380
gacgagctcc cctcgtggat catcaaggac gacgcggagg tggagcggct gacctgtgag    4440
gaggaggagg agaagatgtt cggccgtggc tcccgccacc gcaaggaggt ggactacagc    4500
gactcactga cggagaagca gtggctcaag gccatcgagg agggcacgct ggaggagatc    4560
gaagaggagg tccggcagaa gaaatcatca cggaagcgca agcgagacag cgacgccggc    4620
tcctccaccc cgaccaccag cacccgcagc cgcgacaagg acgacgagag caagaagcag    4680
aagaagcgcg ggcggccgcc tgccgagaaa ctctcccccta acccacccaa cctcaccaag    4740
aagatgaaga agattgtgga tgccgtgatc aagtacaagg acagcagcag tggacgtcag    4800
ctcagcgagg tcttcatcca gctgcccctc gcgaaaggagc tgcccgagta ctacgagctc    4860
atccgcaagc ccgtggactt caagaagata aaggagcgca ttcgcaacca caagtaccgc    4920
```

| | |
|---|---|
| agcctcaacg acctagagaa ggacgtcatg ctcctgtgcc agaacgcaca gaccttcaac | 4980 |
| ctggagggct ccctgatcta tgaagactcc atcgtcttgc agtcggtctt caccagcgtg | 5040 |
| cggcagaaaa tcgagaagga ggatgacagt gaaggcgagg agagtgagga ggaggaagag | 5100 |
| ggcgaggagg aaggctccga atccgaatct cggtccgtca aagtgaagat caagcttggc | 5160 |
| cggaaggaga aggcacagga ccggctgaag ggcggccggc ggcggccgag ccgagggtcc | 5220 |
| cgagccaagc cggtcgtgag tgacgatgac agtgaggagg aacaagagga ggaccgctca | 5280 |
| ggaagtggca gcgaagaaga ctgagccccg acattccagt ctcgaccccg agccctcgt | 5340 |
| tccagagctg agatggcata ggccttagca gtaacgggta gcagcagatg tagtttcaga | 5400 |
| cttggagtaa aactgtataa acaaaagaat cttccatatt tatacagcag agaagctgta | 5460 |
| ggactgtttg tgactggccc tgtcctggca tcagtagcat ctgtaacagc attaactgtc | 5520 |
| ttaaagagag agagagagaa ttccgaattg gggaacacac gatacctgtt tttcttttcc | 5580 |
| gttgctggca gtactgttgc gccgcagttt ggagtcactg tagttaagtg tggatgcatg | 5640 |
| tgcgtcaccg tccactcctc ctactgtatt ttattggaca ggtcagactc gccgggggcc | 5700 |
| cggcgagggt atgtcagtgt cactggatgt caaacagtaa taaattaaac caacaacaaa | 5760 |
| acgcacagcc aaaaaaaaa | 5779 |

<210> SEQ ID NO 91
<211> LENGTH: 10914
<212> TYPE: DNA
<213> ORGANISM: Homo sapiens

<400> SEQUENCE: 91

| | |
|---|---|
| cgcccccct gcgcccgccc ctcccccttc gctttccttc tcccccgcc tcggctccga | 60 |
| catgagggc cggcggggca ggccgcccaa gcagcccgcg gctcccgctg cggagcgctg | 120 |
| cgccccggcc ccgccgccac cgccgccgcc gcccacgtcc ggacccatcg ggggctccg | 180 |
| ctcgcggcac cgcggcagca gccggggcag gtgggccgcc gcccaggctg aggtggcgcc | 240 |
| caagacgcgg ctgagctcgc caggggggg cagcagtagc cggaggaagc cgccgccgcc | 300 |
| gccgccggcc cccccagca ccagcgcccc gggccggggg gggcgaggag gcggggcgg | 360 |
| caggacgggg ggcggggggcg gcggcggcca cctggcccgg accaccgcgg cccggagggc | 420 |
| cgtcaacaaa gtggtgtacg atgaccacga gagcgaggag gaggaggaag aggaggacat | 480 |
| ggtctccgag gaggaggagg aggaggacgg cgacgccgag gagacccagg attctgagga | 540 |
| cgacgaggag gatgagatgg aagaggacga cgatgactcc gattatccgg aggagatgga | 600 |
| agacgacgac gacgacgcca gttactgcac ggaaagcagc ttcaggagcc atagtaccta | 660 |
| cagcagcact ccaggtaggc gaaaaccaag agtacatcgg cctcgttctc ctatattgga | 720 |
| agaaaaagac atcccgcccc ttgaatttcc caagtcctct gaggatttaa tggtgcctaa | 780 |
| tgagcatata atgaatgtca ttgccattta cgaggtactg cggaactttg gcactgtttt | 840 |
| gagattatct cctttcgct ttgaggactt ttgtgcagct ctggtgagcc aagagcagtg | 900 |
| cacactcatg gcagagatgc atgttgtgct tttgaaagca gttctgcgtg aagaagacac | 960 |
| ttccaatact acctttggac ctgctgatct gaaagatagc gttaattcca cactgtattt | 1020 |
| catagatggg atgacgtggc cagaggtgct gcgggtgtac tgtgagagtg ataaggagta | 1080 |
| ccatcacgtt cttccttacc aagaggcaga ggactaccca tatggaccag tagagaacaa | 1140 |
| gatcaaagtt ctacagtttc tagtcgatca gtttcttaca acaaatattg ctcgagagga | 1200 |
| attgatgtct gaaggggtga tacagtatga tgaccattgt agggtttgtc acaaacttgg | 1260 |

```
ggatttgctt tgctgtgaga catgttcagc agtataccat ttggaatgtg tgaagccacc    1320
tcttgaggag gtgccagagg acgagtggca gtgtgaagtc tgtgtagcac acaaggtgcc    1380
tggtgtgact gactgtgttg ctgaaatcca aaaaataaa ccatatattc gacatgaacc     1440
tattggatat gatagaagtc ggaggaaata ctggttcttg aaccgaagac tcataataga    1500
agaagataca gaaaatgaaa atgaaagaa aatttggtat tacagcacaa aggtccaact    1560
tgcagaatta attgactgtc tagacaaaga ttattgggaa gcagaactct gcaaaattct    1620
agaagaaatg cgtgaagaaa tccaccgaca catggacata actgaagacc tgaccaataa    1680
ggctcggggc agtaacaaat cctttctggc ggcagctaat gaagaaattt tggaatccat    1740
aagagccaaa aagggagaca ttgataatgt taaaagccca gaagaaacag aaaaagacaa    1800
gaatgagact gagaatgact ctaaagatgc tgagaaaaac agagaagaat ttgaagacca    1860
gtcccttgaa aaagacagtg acgacaaaac accagatgat gaccctgagc aaggaaaatc    1920
tgaggtaggt gatttcaaat cggagaagtc caacggggag ctaagtgaat ctcctggagc    1980
tggaaaagga gcatctggct caactcgaat catcaccaga ttgcggaatc cagatagcaa    2040
acttagtcag ctgaagagcc agcaggtggc agccgctgca catgaagcaa ataaattatt    2100
taaggagggc aaagaggtac tggtagttaa ctctcaagga gaaatttcac ggttgagcac    2160
caaaaaggaa gtgatcatga aggaaatat caacaattat tttaaattgg gtcaagaagg    2220
gaagtatcgc gtctaccaca atcaatactc caccaattca tttgctttga ataagcacca    2280
gcacagagaa gaccatgata agagaaggca tcttgcacat aagttctgtc tgactccagc    2340
aggagagttc aaatggaacg gttctgtcca tgggtccaaa gttcttacca tatctactct    2400
gagactgact atcacccaat agaaaacaa catcccttca tcctttcttc atcccaactg    2460
ggcatcacat agggcaaatt ggatcaaggc agttcagatg tgtagcaaac ccagagaatt    2520
tgcattggct ttagccattt tggagtgtgc agttaaacca gttgtgatgc taccaatatg    2580
gcgagaatct ttaggacata ccaggttaca ccggatgaca tcaattgaaa gagaagaaaa    2640
ggagaaagtc aaaaaaaaag agaagaaaca ggaagaagaa gaaacgatgc agcaagcgac    2700
atgggtaaaa tacacatttc cagttaagca tcaggtttgg aaacaaaaag gtgaagagta    2760
cagagtgaca ggatatggtg gttggagctg gattagtaaa actcatgttt ataggtttgt    2820
tcctaaattg ccaggcaata ctaatgtgaa ttacagaaag tcgttagaag gaaccaaaaa    2880
taatatggat gaaaatatgg atgagtcaga taaagaaaa tgttcacgaa gtccaaaaaa    2940
aataaaaata gagcctgatt ctgaaaaaga tgaggtaaaa ggttcagatg ctgcaaaagg    3000
agcagaccaa aatgaaatgg atatctcaaa gattactgag aagaaggacc aagatgtgaa    3060
ggagctctta gattctgaca gtgataaacc ctgcaaggaa gaaccaatgg aagtagcgca    3120
tgacatgaaa acagagtcac atgtaaattg tcaggagagt tctcaagtag atgtggtcaa    3180
tgttagtgag ggttttcatc taaggactag ttacaaaaag aaaacaaaat catccaaact    3240
agatggactt cttgaaaagga gaattaaaca gtttacactg gaagaaaaac agcgactcga    3300
aaaaatcaag ttggagggtg gaattaaggg tataggaaag acttctacaa attcttcaaa    3360
aaatctctct gaatcaccag taataacgaa agcaaaagaa gggtgtcaga gtgactcgat    3420
gagacaagaa cagagcccaa atgcaaataa tgatcaacct gaggacttga ttcagggatg    3480
ttcagaaagt gattcctcag ttcttagaat gagtgatcct agtcatacca caacaaact     3540 ttatccaaaa gatcgagtgt tagatgatgt ctccattcgg agcccagaaa caaaatgtcc    3600
```

```
gaaacaaaat tccattgaaa atgacataga agaaaaagtc tctgaccttg ccagtagagg    3660
ccaggaaccc agtaagagta aaacaaaagg aaatgatttt ttcatcgatg actctaaact    3720
agccagtgca gatgatattg gtactttgat ctgtaagaac aaaaaaccgc tcatacagga    3780
ggaaagtgac accattgttt cttcttccaa gagtgcttta cattcatcag tgcctaaaag    3840
taccaatgac agagatgcca cacctctgtc aagagcaatg gactttgaag gaaaactggg    3900
atgtgactct gaatctaata gcactttgga aaatagttct gataccgtgt ctattcagga    3960
tagcagtgaa gaagatatga ttgttcagaa tagcaatgaa agcatttctg aacagttcag    4020
aactcgagaa caagatgttg aagtcttgga gccgttaaag tgtgagttgg tttctggtga    4080
gtccactgga aactgtgagg acaggctgcc ggtcaagggg actgaagcaa atggtaaaaa    4140
accaagtcag cagaagaaat tagaggagag accagttaat aaatgtagtg atcaaataaa    4200
gctaaaaaat accactgaca aaaagaataa tgaaaatcga gagtctgaaa agaaaggaca    4260
gagaacaagt acatttcaaa taatggaaa agataataaa cccaaaatat atttgaaagg    4320
tgaatgcttg aaagaaattt ctgagagtag agtagtaagt ggtaatgttg aaccaaaggt    4380
taataatata aataaaataa tccctgagaa tgatattaaa tcattgactg ttaaagaatc    4440
tgctataagg ccattcatta atggtgatgt catcatggaa gattttaatg aaagaaacag    4500
ctccgaaaca aaatcgcatt tgctgagttc ttcagatgct gaaggtaact accgagatag    4560
ccttgagacc ctgccatcaa ccaaagagtc tgacagtaca cagacgacca caccctcagc    4620
atcttgtcca gaaagcaatt cagttaatca ggtagaagat atggaaatag aaacctcaga    4680
agttaagaaa gttacttcat cacctattac ttctgaagag gaatctaatc tcagtaatga    4740
ctttattgat gaaaatggtc tgcccatcaa caaaaatgaa aatgtcaatg gagaatctaa    4800
aagaaaaacc gtcatcacag aagtcaccac gatgacctcc acagtggcca cagaatcaaa    4860
aactgtgatc aaggtagaaa aaggcgataa gcaaactgtg gtttcttcca cagaaaattg    4920
tgcaaaatcc actgtcacaa ccaccactac aacagtgacc aagctttcca cacccttccac    4980
aggcggcagt gtggacatca tctctgtaaa ggagcagagc aaaaccgtgg tcaccacgac    5040
agtgacagac tccctgacca ccacgggagg cacactggtt acatctatga ctgtgagcaa    5100
agagtattcc acacgagaca aagtgaaact gatgaaattt tcaagaccaa agaagactcg    5160
ttcaggtaca gctctgccat cctatagaaa atttgttacc aagagcagca agaagagcat    5220
ttttgttttg cctaatgatg acttaaaaaa gttggcccga aaaggaggaa tccgagaggt    5280
cccttatttt aattacaatg caaaacctgc tttggatata tggccatatc cttctcctag    5340
accgaccttt ggcatcactt ggaggtatag acttcagaca gtaaagtcct tagctggagt    5400
gagcctgatg ttacggttac tgtgggcaag tttgagatgg gatgatatgg cggccaaggc    5460
tcctccagga ggagggacta cacggacaga aacatccgaa actgaaatca aacaacaga    5520
aataattaag aggagagatg ttggtcctta tggcattcga tctgaatatt gtatcaggaa    5580
aatcatttgt cccattggag ttccagaaac accaaaagaa acgcctacac ctcagaggaa    5640
aggccttcga tcaagtgcac tgcggccaaa gagaccagaa acgcccaagc aaactggccc    5700
tgttattatt gaacctgggt agcagaagag aaactggaat tgtgggagat cagggcatt    5760
tgctgagaga gtggagaaag aaaaggcaca agcagttgag caacaggcta agaaacgact    5820
ggagcagcag aagccgacag tgattgcaac ttccactact tccccaacaa gcagtacaac    5880
cagcaccatc tctccagcac agaaggttat ggtggccccc ataagtggct cagttacaac    5940
tggaaccaaa atggtactaa ctactaaagt tggatctcca gctacagtaa cattccaaca    6000
```

```
aaacaagaac tttcatcaaa cctttgctac atgggttaag caaggccagt caaattcagg    6060
cgttgttcaa gtacagcaga aagtcctggg tatcattcca tcaagtacag gtaccagtca    6120
gcaaaccttt acttcattcc agcccaggac agcaacagtc acaattaggc ccaatacctc    6180
aggctctgga ggaaccacaa gcaattcaca agtaatcaca gggcctcaga ttcgccctgg    6240
tatgaccgtg attagaacac cactccaaca gtcaacacta ggaaaggcaa ttattcgaac    6300
acctgtgatg gtacagccag gtgctcctca gcaagtgatg actcaaatca tcagggggca    6360
gcctgtctcc actgcagtct ccgcccctaa cacggtttcc tcaacacctg gcagaaaag    6420 cttaacttca gcaacgtcca cttcaaatat acagtcttca gcctcacaac cccctcgccc    6480
ccaacaagga caagtgaagc tcaccatggc tcaacttact cagttaacac agggccacgg    6540
tggcaatcaa ggtttgacag tagtaattca aggacaaggt caaactactg gacagttgca    6600
gttgatacct caaggggtga ctgtactccc aggcccaggc cagcagctaa tgcaagctgc    6660
aatgccaaat ggtactgttc agcgattcct ctttacccca ttggcaacaa cagccaccac    6720
agccagcacc accaccacca ctgtttccac gacagcagca ggtacaggtg aacaaaggca    6780
gagtaaactg tcaccccaga tgcaggtaca tcaagacaaa accctgccac cagctcagtc    6840
atcaagtgtg ggtccagcag aagcccagcc acagactgct cagccttcag ctcagcccca    6900
gccccaaacc cagccccagt ccccagctca gcctgaagtt cagactcagc ctgaagttca    6960
gacccaaaca actgtttcat cccatgtccc ttctgaagca caacccaccc acgcacagtc    7020
atccaagccc caagttgcag cacagtctca gcctcaaagt aatgtccaag acagtctcc    7080 tgttcgtgtc caaagtccat cacagactcg aatacgtcca tcaactccat cccaactgtc    7140
tcctggacaa caatcccagg ttcagactac aacctcacaa ccgattccaa ttcaaccaca    7200
tacatctctt cagataccct tcccaaggcca gccacagtca caacccccagg tacagtcttc    7260 aactcaaact ctttcatcag gacaaacttt aaatcaagtt actgtttcat ccccatcccg    7320
tcctcagcta caaatacagc agccacagcc ccaagtcatt gctgtgcctc agctgcaaca    7380
acaagtccag gttctctctc agatccagtc acaggttgtg gctcagatac aggctcagca    7440
aagtggtgtg cccagcaaa tcaaactcca gttacctatc caaattcagc aaagcagtgc    7500
tgtgcagact caccagattc agaatgtggt tacagtgcag gcagccagtg tgcaagagca    7560
gttgcaaagg gttcagcaac tcagggatca gcagcaaaag aagaaacagc aacagataga    7620
aattaagcgt gaacacaccc tccaagcttc taatcaaagt gaaatcattc agaaacaggt    7680
ggtgatgaag cataatgctg taatagaaca tttaaaacag aaaaagagca tgactccagc    7740
tgaaagagaa gagaatcaaa gaatgattgt ctgtaaccag gtgatgaagt atattttgga    7800
taagatagat aaagaagaaa acaggcagc aaaaaaacgg aagcgtgaag agagtgtgga    7860
gcagaaacgt agcaagcaga atgccactaa gctgtcagct ctgctcttca agcacaaaga    7920
gcagctcaga gccgagatcc tgaagaagag agcactcctg gacaaggatc tgcaaattga    7980
agtgcaggaa gagctgaaga gagacctgaa aattaagaaa gaaaaagacc tgatgcagtt    8040
ggctcaggcc acagcagtag ctgcacccct ccccccagtg acaccagctc ctccagcccc    8100
tccagcccct ccaccttcac ctccccctcc acctgctgtg caacacacag gccttctgtc    8160
cacgcccacc ttacctgctg cttcccagaa gaggaagcgg gaagaggaaa aagactccag    8220
ctcaaagtcc aagaaaaaga aaatgatctc tactacctca aaggaaacta gaaggacac    8280 aaagctttac tgtatctgta aaacgcctta tgatgaatct aaatttttata ttggctgtga    8340
```

```
tcggtgtcag aattggtacc atgggcgctg cgttggcatc ttgcaaagtg aggcagagct   8400
cattgatgag tatgtctgtc cacagtgcca gtcaacagag gatgccatga cagtgctcac   8460
gccactaaca gagaaggatt atgaggggtt gaagagggtg ctccgttcct tacaggccca   8520
taagatggcc tggcctttcc ttgaaccagt agaccctaat gatgcaccag attattatgg   8580
tgttattaag gaacctatgg accttgccac catggaagaa agagtacaaa gacgatatta   8640
tgaaaagctg acggaatttg tggcagatat gaccaaaatt tttgataact gtcgttacta   8700
caatccaagt gactccccat tttaccagtg tgcagaagtt ctcgaatcat tctttgtaca   8760
gaaattgaaa ggcttcaaag ctagcaggtc tcataacaac aaactgcagt ctacagcttc   8820
ttaaagttca gcgtgttaac ctaacataaa acacagcaag aatctggttg tctgaactat   8880
tttaaattaa ggagccagat gttttagtc aggctatcct gacaagactt gacctaaact   8940
tcgtttttat tggtcataac agtccaatta tattcttggc caattttgtc caacggacaa   9000
gaaaaagca agtcaacga caccattatc ttgtcaagat cagatggttt tactattgtg   9060
gcagaagcga gaaaactttg tttattgaaa aaaaagaaa aagaaagcaa gaaaaaaga   9120
tactatgggg tcaagtgtaa ctccatggaa atgccacgtc tgctcttcag tgaagaagct   9180
ggtttagagt ctcacagaaa acttttgact gtatttattt attgttgcaa aaaagacgct   9240
tttttattgc tgccctcatt tgtcagctaa ttatttttc ttataaaatc cagccccggt   9300
tacatataat catctgtatc ttatcatgat tcctgtaggt aaaagtacaa gacgacctct   9360
agatgtcttt tctttctatg aaaggagctg ctatgtacac atgtgcacac acacacaact   9420
gggaatcaac aatgagttta ttgttcatgg tagattaaaa ttaagcttgc ataaaggttg   9480
ggctaagtgg tcctggacta cagactctgt tgccttgaat ataacagtac aatttgtcaa   9540
ttactctgca ccaggctaaa atgagtaaaa tctatttgaa ggtatcttgt ttgtaaacat   9600
ttgtcagatt ctaatttttt tcttttgtat aaaattcaa ctatggatgt atatgaaaca   9660
aaataaatgg agataatttt tctcccacag acagaggtgt ctttgaatgt gcgctaatga   9720
ttatctgtaa gccttttgtgg ggagggaggc ctgcaaggtc atgaaaggca gaagagtcta   9780
attgtgcctg gatttctcca ggacagcagt ggccctcgt tttatcattc ccagtccatt   9840
gtcatcacgt cagagaaaaa tcttcagggg tgctaatcct gttgcatcag ttgatcatac   9900
taacgagaac ggtaatgcga caagatacac attgccttca tctgtacatt ctgtgatacc   9960
aggcaaatta ccaattacac acagctactt atattttatg aagggcattt tttagatgac  10020
ctcatcctct gtgttatttg ttgattgggt ttgttttctg tttgttggtt tgtttgtttc  10080
ttccacgtaa ggaaaagtag tgtaaacagt agcgagaaaa tggaaaccac agaggaagat  10140
gtattttgca tgttttttcct ttcagtgttc ttacacgttg tatcactgca ttgtggtaat  10200
agcttctata aaatctgcca tagttggatt atgcagcttt gcaaaaattt ttactagatt  10260
ttgcactaac tcatattagc tttgtcctac caacttctgg aatttatcta attattgttt  10320
ttcaaagttt cttcctttt aatgtttccc tgctatgcaa aaccttccc agacctcagt  10380
ttcttaaaag aaagatgttg ctacagttcc cgattctttc ttattacagg ctcaggtgta  10440
caggttattc tgggttaatt ttatctaatg aagcccattc cttttgtac ataaagatgt  10500
cacttaaact tatgcttaca aactaaagac taatcgctca atatgaaaac atgaaaaaat  10560
ttttgcttaa agtattaaga tggaagtagt taaatatggg ttattttgtc ctttacttt  10620
tttaaaaaat gttacatatt gtatgcactg tgctgatgca agaattctac attttaatga  10680
gttataaaat tattctgcat ctcatcacgt cacagtattt ctgtactatt tattcatata  10740
```

| | | | | |
|---|---|---|---|---|
| tataaatata | tatgggctta | atcatttaaa | atttgttgca | gcaagaactt tcctacctgt | 10800 |
| aggcaataga | ttgctatgtt | tttaacaaat | tgtggcaaat | tctaaacagc aattcttttg | 10860 |
| tacgtaatag | gacatttcat | cctagaaaaa | taaagtaatg | tttttgacat tgga | 10914 |

<210> SEQ ID NO 92
<211> LENGTH: 4025
<212> TYPE: DNA
<213> ORGANISM: Homo sapiens

<400> SEQUENCE: 92

| | | | | |
|---|---|---|---|---|
| ggcctgagcg | aaggggttgg | aagcggagtg | attccccacc | cctgctccat ctagctcttt | 60 |
| ccagtgcagc | cactgccgcc | gcccaggagc | cctcgtcccc | tgccttgtcc ccctactcgt | 120 |
| tcccgctccc | acggcatgga | gcaggacact | gccgcagtgg | cagccaccgt ggcagccgcg | 180 |
| gatgcgaccg | ccactatcgt | ggtcatagag | gacgagcagc | ccgggccgtc cacctctcag | 240 |
| gaggagggag | cggccgccgc | ggccaccgaa | gccaccgcgg | ccacggagaa gggcgagaag | 300 |
| aagaaggaga | aaacgtttc | ttcatttcaa | ctcaaacttg | ctgctaaagc gcctaaatct | 360 |
| gaaaaggaaa | tggacccaga | atatgaagag | aaaatgaaag | ccgaccgagc aaagagattt | 420 |
| gaattttttac | tgaagcagac | agaacttttt | gcacatttca | ttcagccttc agcacagaaa | 480 |
| tctccaacat | ctccactgaa | catgaaattg | gacgtcccc | gaataaagaa agatgaaaag | 540 |
| cagagcttaa | tttctgctgg | agactaccgc | cataggcgca | cagagcaaga agaagatgaa | 600 |
| gagctactgt | ctgagagtcg | gaaaacatct | aatgtgtgta | ttagatttga ggtgtcacct | 660 |
| tcatatgtga | aagggggggcc | actgagagat | tatcagattc | gaggactgaa ttggttgatc | 720 |
| tctttatatg | aaaatggagt | caatggcatt | ttggctgatg | aaatgggcct tgggaaaact | 780 |
| ttacaaacaa | ttgctttgct | tggttacctg | aaacactacc | gaaatattcc tggacctcac | 840 |
| atggttttag | ttccaaagtc | tactttacac | aactggatga | atgaatttaa acgatgggtc | 900 |
| ccatctctcc | gtgtcatttg | ttttgtcgga | gacaaggatg | ccagagctgc tttttattcgt | 960 |
| gatgaaatga | tgccaggaga | gtgggatgtt | tgcgttactt | cttatgagat ggtaattaaa | 1020 |
| gaaaaatctg | tattcaaaaa | gtttcactgg | cgatacctgg | tcattgatga agctcacaga | 1080 |
| ataaagaatg | aaaaatctaa | gctttcagag | attgttcgtg | agttcaagtc gactaaccgc | 1140 |
| ttgctcctaa | ctggaacacc | tttgcagaat | aacctgcatg | aactgtgggc cttactcaac | 1200 |
| tttttattgc | ctgatgtctt | taattctgca | gatgactttg | attcttggtt tgacactaaa | 1260 |
| aattgtcttg | gtgatcaaaa | actcgtggaa | agacttcatg | cagttttaaa accatttttg | 1320 |
| ttacgccgta | taaaaactga | tgtagagaag | agtctgccac | ctaaaaagga ataaagatt | 1380 |
| tacttggggc | tgagtaagat | gcaacgagaa | tggtatacaa | aaatcctgat gaaagatatt | 1440 |
| gatgttttaa | actcttctgg | caagatggac | aagatgcgac | tcttaaacat tctgatgcag | 1500 |
| cttcgaaagt | gttgtaatca | tccatatctg | tttgatggtg | ctgaacctgg tccacctat | 1560 |
| accactgatg | agcatattgt | cagcaacagt | ggtaaaatgg | tagttctgga taaactattg | 1620 |
| gccaaactca | agaacaggg | ttcaagggt | ctcatttca | gccagatgac tcgcttgctg | 1680 |
| gatattttgg | aagattattg | catgtggcgt | ggttatgagt | attgtcgact ggatggacaa | 1740 |
| accccgcatg | aagaaagaga | ggataaattc | ctagaagtgg | aatttctggg tcaaagggaa | 1800 |
| gcaatagagg | cttttaatgc | tcctaatagt | agcaaattca | tctttatgct aagtaccagg | 1860 |
| gctggaggtc | tcggaattaa | cctggcaagt | gctgatgtgg | ttatactata tgattcagac | 1920 |

| | | | | |
|---|---|---|---|---|
| tggaacccac | aggttgatct | acaagctatg | gatcgagcac | atcgtattgg tcagaagaaa | 1980 |
| ccagtacgtg | tattccgtct | catcactgac | aacactgttg | aagagaggat tgtagaaaga | 2040 |
| gctgagataa | aactgagact | cgattcaatt | gttatacaac | aaggaagact cattgaccaa | 2100 |
| cagtctaaca | agctggcaaa | agaggaaatg | ttacaaatga | tacggcatgg agccacccat | 2160 |
| gtttttgctt | ctaaagagag | tgagttgaca | gatgaagaca | ttacaactat tctggaaaga | 2220 |
| ggggaaaaga | agactgcaga | gatgaatgaa | cgcctgcaaa | aaatgggaga gtcttctcta | 2280 |
| agaaatttta | gaatggacat | tgaacaaagt | ttatacaaat | ttgagggaga agattataga | 2340 |
| gaaaaacaga | agcttggcat | ggtggaatgg | attgaacctc | ctaaacgaga acgcaaagca | 2400 |
| aactacgcag | tggatgccta | ctttagagag | gctttgcgtg | tcagcgagcc aaagattcca | 2460 |
| aaggctccac | ggcctccaaa | acagccaaat | gttcaggatt | ttcaattttt cccaccacgc | 2520 |
| ttatttgagc | tcctggaaaa | ggaaattctt | tattatcgga | agacaatagg ctataaggtt | 2580 |
| ccaaggaatc | ctgatatccc | aaatccagct | ctggctcaaa | gagaagagca aaaaaagatt | 2640 |
| gatggagctg | aacctcttac | accagaagag | actgaagaaa | aggaaaaact tctcacacaa | 2700 |
| ggtttcacaa | actggactaa | acgagatttt | aaccagttta | ttaaagctaa tgagaaatat | 2760 |
| ggaagagatg | acattgataa | catagctcga | gaggtagagg | gcaaatcccc tgaggaggtc | 2820 |
| atggagtatt | cagctgtatt | tgggaacgt | tgcaatgaat | tacaggacat tgagaaaatt | 2880 |
| atggctcaaa | ttgaacgtgg | agaagcaaga | attcaacgaa | ggatcagtat caagaaagcc | 2940 |
| ctggatgcca | aaattgcaag | atacaaggct | ccatttcatc | agttgcgcat tcagtatgga | 3000 |
| accagcaaag | gaaagaacta | tactgaggaa | gaagatagat | tcttgatttg tatgttacac | 3060 |
| aaaatgggct | tgatagaga | aaatgtatat | gaagaattaa | gacagtgtgt acgaaatgct | 3120 |
| ccccagttta | gatttgactg | gtttatcaag | tctaggactg | ccatggaatt ccagagacgc | 3180 |
| tgtaacactc | tgatttcatt | gattgagaaa | gaaaatatgg | aaattgagga aagagagaga | 3240 |
| gcagaaaaga | agaaacgggc | aactaaaact | ccaatgtcac | agaaaagaaa agcagagtca | 3300 |
| gctactgaga | gctctggaaa | gaaggatgtc | aagaaggtga | atcctaaag cctagaaata | 3360 |
| aagtttaaa | tgggaaactg | ctattttctt | gttcccatct | tcaaatgcta attgccagtt | 3420 |
| ccagtgtatt | catggtactc | taagaaaaat | ctctttggtt | ttgatttctt gcatatttta | 3480 |
| tatattttac | aatgctttct | acctgaaatg | tgtagcttta | tattttatgg cattctagta | 3540 |
| tttttgtgta | ctgtattttg | tgcatttcat | gtcttcatca | aaatcctctc agtccttgtt | 3600 |
| cttttgaagc | ttgtgctgag | gttttagctt | ttctatgttt | tatatgccgc tgctttgaaa | 3660 |
| gagaacctag | attctatagt | tgtattattg | ttgtttcata | ctttaaattt atatggctgt | 3720 |
| ggaaaaacga | attaaaatgt | tttgaggaga | aagactttt | cacttctttg ttgctttctt | 3780 |
| ttctattgag | tctgggcttg | tttgtgttac | tgcatactgt | gattagcata ataattgttt | 3840 |
| ctttgaggtc | atctaaatat | ttttttccta | aggaataaa | gggtgaggaa agaaaaatat | 3900 |
| taaaaaagct | aatatttgat | actgtgcttg | ctgtcagtat | gcattacatt taaattattc | 3960 |
| tctattcaag | tgggaaaata | taataaagaa | atgtctataa | gaaatttaaa aaaaaaaaa | 4020 |
| aaaaa | | | | | 4025 |

<210> SEQ ID NO 93
<211> LENGTH: 351
<212> TYPE: PRT
<213> ORGANISM: Bos taurus

<400> SEQUENCE: 93

```
Met Ala Ala Ala Asn Ser Gly Ser Ser Leu Pro Leu Phe Asp Cys
1               5                   10                  15

Pro Thr Trp Ala Gly Lys Pro Pro Gly Leu His Leu Asp Val Val
            20                  25                  30

Lys Gly Asp Lys Leu Ile Glu Lys Leu Ile Ile Asp Glu Lys Tyr
            35                  40                  45

Tyr Leu Phe Gly Arg Asn Pro Asp Leu Cys Asp Phe Thr Ile Asp His
    50                  55                  60

Gln Ser Cys Ser Arg Val His Ala Ala Leu Val Tyr His Lys His Leu
65                  70                  75                  80

Lys Arg Val Phe Leu Ile Asp Leu Asn Ser Thr His Gly Thr Phe Leu
                85                  90                  95

Gly His Ile Arg Leu Glu Pro His Lys Pro Gln Gln Ile Pro Ile Asp
                100                 105                 110

Ser Thr Val Ser Phe Gly Ala Ser Thr Arg Ala Tyr Thr Leu Arg Glu
                115                 120                 125

Lys Pro Gln Thr Leu Pro Ser Ala Val Lys Gly Asp Glu Lys Met Gly
            130                 135                 140

Gly Glu Asp Asp Glu Leu Lys Gly Leu Leu Gly Leu Pro Glu Glu Glu
145                 150                 155                 160

Thr Glu Leu Asp Asn Leu Thr Glu Phe Asn Thr Ala His Asn Lys Arg
                165                 170                 175

Ile Ser Thr Leu Thr Ile Glu Glu Gly Asn Leu Asp Ile Gln Arg Pro
                180                 185                 190

Lys Arg Lys Arg Lys Asn Ser Arg Val Thr Phe Ser Glu Asp Asp Glu
                195                 200                 205

Ile Ile Asn Pro Glu Asp Val Asp Pro Ser Val Gly Arg Phe Arg Asn
                210                 215                 220

Met Val Gln Thr Ala Val Val Pro Val Lys Lys Arg Val Glu Gly
225                 230                 235                 240

Pro Gly Ser Leu Val Leu Glu Glu Ser Gly Ser Arg Arg Met Gln Asn
                245                 250                 255

Phe Ala Phe Ser Gly Gly Leu Tyr Gly Gly Leu Pro Pro Thr His Ser
                260                 265                 270

Glu Ala Gly Ser Gln Pro His Gly Ile His Gly Thr Ala Leu Ile Gly
                275                 280                 285

Gly Leu Pro Met Pro Tyr Pro Asn Leu Ala Pro Asp Val Asp Leu Thr
                290                 295                 300

Pro Val Val Pro Ser Ala Val Asn Met Asn Pro Ala Pro Asn Pro Ala
305                 310                 315                 320

Val Tyr Asn Pro Glu Ala Val Asn Glu Pro Lys Lys Lys Tyr Ala
                325                 330                 335

Lys Glu Ala Trp Pro Gly Lys Lys Pro Thr Pro Ser Leu Leu Ile
                340                 345                 350
```

US 11,103,538 B2

TARGETING EPIGENETIC REGULATORS USING A BACTERIAL DELIVERY SYSTEM

CROSS-REFERENCE TO RELATED APPLICATION

This application is a U.S. National Stage Filing under 35 U.S.C. 371 from International Application No. PCT/US2015/044831, filed on Aug. 12, 2015, and published as WO 2016/025582 on Feb. 18, 2016, which claims the benefit of priority to U.S. Provisional Application Ser. No. 62/036,579, filed on Aug. 12, 2014, which are incorporated by reference herein in their entireties.

BACKGROUND OF THE INVENTION

Cancer is generally characterized by an uncontrolled and invasive growth of cells. These cells may spread to other parts of the body (metastasis). Conventional anticancer therapies, consisting of surgical resection, radiotherapy and chemotherapy, can be effective for some cancers/patients; however, they are not effective for many cancer sufferers. Thus, further medical treatments are needed.

The role of bacteria as an anticancer agent has been recognized for over 100 years, and many genera of bacteria, including *Clostridium, Bifidus,* and *Salmonella,* have been shown to preferentially accumulate in tumor tissue and cause regression.

The use of *Salmonella typhimurium* to treat solid tumors began with the development of a nonpathogenic strain, VNP20009. Well-tolerated in mice and humans, this strain has been shown to preferentially accumulate (>2000-fold) in tumors over the liver, spleen, lung, heart and skin, retarding tumor growth between 38-79%, and prolonging survival of tumor-bearing mice. In initial clinical trials, *S. typhimurium* was found to be tolerated at high dose and able to effectively colonize human tumors.

SUMMARY OF THE INVENTION

A major problem with using bacteria as an anti-cancer agent is their toxicity at the dose required for therapeutic efficacy and an obstacle in cancer gene therapy is the specific targeting of therapy directly to the cancer. One approach to overcome these two limitations is to use bacteria which are genetically engineered to express a specific DNA, RNA or protein molecule.

A novel therapeutic platform for controlled gene and protein delivery into cancer cells, and therefore treatment for cancer, is provided herein. Transient delivery of genes and proteins with bacteria enable direct targeting of proteins and functions specifically in cancer cells.

One embodiment provides an attenuated *Salmonella* strain comprising a lysis gene or cassette operably linked to an intracellularly induced *Salmonella* promoter.

In one embodiment, the lysis cassette is Lysin E from phage phiX174, phage iEPS5, or lambda phage.

In one embodiment, the sifA gene has been deleted or expression of sifA has been reduced (sifA is a member of the *Salmonella* translocated effector (STE) family; Brown et al. Microbiology. 2006 August; 152(Pt 8): 2323-43). In one embodiment, the promoter is a promoter for one of the genes in *Salmonella* pathogenicity island 2 type III secretion system (SPI2-T3SS), including SpiC/SsaB, SseF, SseG, SseI, SseJ, SseK1, SseK2, SifA, SifB, PipB, PipB2, SopD2, GogB, SseL, SteC, SspH1, SspH2, and/or SirP.

In another embodiment, an essential *Salmonella* gene is under the regulation of an inducible promoter, including ftsW, ftsA, ftsZ, murE, mukF, imp, secF, eno, hemH, tmk, dxs, uppS, cdsA, accA, pssA, msbA, tsf, trmD, cca, infB, rpoA, rpoB, rpoC, holA, dnaC, and eng.

In one embodiment the inducible promoter is tightly regulated and induced by a small molecule that is safe to inject into humans, including but not limited to, pBAD (L-arabinose), LacI (IPTG) or nahR (acetyl salicylic acid (ASA).

In one embodiment, the addition of an inducer agent causes lysis. In another embodiment, the withholding of an inducer agent causes lysis.

In one embodiment, the *Salmonella* strain further comprises a plasmid that expresses DNA, shRNA, non-coding RNA and/or a peptide. In one embodiment, the shRNA molecule is complimentary to a gene, or portion thereof, in which the gene codes for a cytoplasmic protein that promotes survival of a cancer cell. In another embodiment, the shRNA molecule or peptide inhibits, suppresses or blocks expression and/or activity of an epigenetic target. In one embodiment, the epigenetic target is at least one of EZH2, NIPP1, or PP1. In another embodiment, the epigenetic target is at least one (e.g., mRNA) of NIPP1 (accession No. NM 002713); EZH2 (accession No. NM_004456); PP1α (accession No. NM_002708); PP1β (accession No. NM_206876); PP_1γ (accession No. NM_002710); Suz12 (accession No. NM_015355); EED (accession No. NM_003797); EZH1 (accession No. NM_001991); RbAp48 (accession No. NM_005610); Jarid2 (accession No. NM_004973); YY1 (accession No. NM_003403); CBX2 (accession No. NM_005189); CBX4 (accession No. NM_003655); CBX6 (accession No. NM_014292); CBX7 (accession No. NM_175709); PHC1 (accession No. NM_004426); PHC2 (accession No. NM_198040); PHC3 (accession No. NM_024947); BMI1 (accession No. NM_005180); PCGF2 (accession No. NM_007144); ZNF134 (accession No. NM_003435); RING1 (accession No. NM_002931); RNF2 (accession No. NM_0072120; PHF1 (accession No. NM_024165); MTF2 (accession No. NM_007358); PHF19 (accession No. NM_001286840); SETD1A (accession No. XM_005255723); SETD1B (accession No. NM_015048); CXXC1 (accession No. NM_001101654); ASH2L (accession No. NM_004674); DPY30 (accession No. NM_032574); RBBP5 (accession No. NM_005057); WDR5 (accession No. NM_017588); KMT2A (accession No. NM_001197104); KMT2D (accession No. XM 006719616); KMT2B (accession No. NM_014727); KMT2C (accession No. NM_170606); KAT8 (accession No. NM_032188); KDM6A (accession No. NM_001291415); NCOA6 (accession No. NM_014071); PAGR1 (accession No. NM_024516); PAXIP1 (accession No. NM_007349); ASH1L (accession No. NM_018489); SMARCA2 (accession No. NM_003070); SMARCA4 (accession No. NM_001128844); BPTF (accession No. NM_182641); or SMARCA1 (accession No. NM_001282874). In one embodiment, the peptide comprises amino acids 143-224 of NIPP1, including amino acids 191-210 of NIPP1 (numbering based on bovine NIPP1; accession number NM_174582.2). The amino acid sequence corresponding to NM_174582.2 is as follows:

(SEQ ID NO: 93)
MAAAANSGSSLPLFDCPTWAGKPPPGLHLDVVKGDKLIEKLIIDEKKYYLF

GRNPDLCDFTIDHQSCSRVHAALVYHKHLKRVFLIDLNSTHGTFLGHIRLE

PHKPQQIPIDSTVSFGASTRAYTLREKPQTLPSAVKGDEKMGGEDDELKGL

LGLPEEETELDNLTEFNTAHNKRISTLTIEEGNLDIQRPKRKRKNSRVTFS

EDDEIINPEDVDPSVGRFRNMVQTAVVPVKKKRVEGPGSLVLEESGSRRMQ

-continued

NFAFSGGLYGGLPPTHSEAGSQPHGIHGTALIGGLPMPYPNLAPDVDLTPV

VPSAVNMNPAPNPAVYNPEAVNEPKKKKYAKEAWPGKKPTPSLLI.

In one embodiment, the *Salmonella* strain is VNP20009 with a sifA deletion, an intracellularly induced lysis gene or cassette, a plasmid that expresses at least one DNA, shRNA or peptide and wherein the tsf gene of the *Salmonella* strain is under the regulation of an inducible promoter.

As would be understood by those skilled in the art, the *Salmonella* strains described herein can be used an in vitro or in vivo method.

One embodiment provides a method to treat cancer comprising administering to subject in need thereof an effective amount of an attenuated *Salmonella* strain described herein or a composition comprising such a strain so as to treat said cancer.

Another embodiment provides a method of inhibiting tumor growth/proliferation or reducing the volume/size of tumor comprising administering to subject in need thereof an effective amount of an attenuated *Salmonella* strain described herein or a composition comprising such a strain so as to suppress tumor growth or reduce the volume of the tumor.

Another embodiment provides a method to treat, reduce formation/number or inhibit spread of metastases comprising administering to subject in need thereof an effective amount of an attenuated *Salmonella* strain described herein or a composition comprising such a strain so as to treat, reduce formation/number or inhibit spread of metastases.

One embodiment provides a method to reduce expression of a gene or activity of a protein in a tumor cell comprising contacting said cell with an attenuated *Salmonella* strain described herein or a composition comprising such a strain so as to reduce expression of a gene or activity of a protein in a tumor cell.

In one embodiment, the cancer is selected from the group consisting of lung cancer, liver cancer, kidney cancer, breast cancer, prostate cancer, pancreatic cancer, colon cancer, head and neck cancer, ovarian cancer and gastroenterological cancer.

Accordingly, the present invention can also be directed to a pharmaceutical composition, as can be used in conjunction with the method(s) of this invention. One embodiment provides a composition comprising an attenuated *Salmonella* strain described herein and pharmaceutically acceptable carrier.

DETAILED DESCRIPTION OF THE INVENTION

Figure 1:
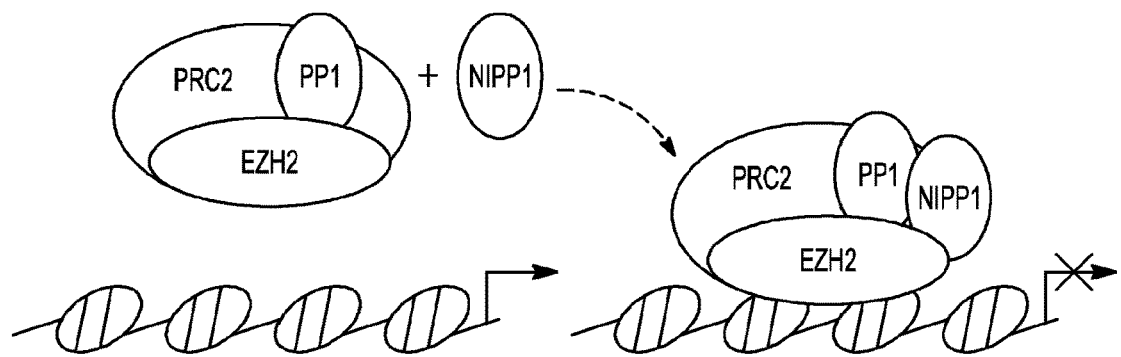
FIG. 1. The NIPP1:PP1 complex regulates the association of EZH2 with proliferation-related genes. The phosphatase PP1 dephosphorylates EZH2, which releases it from proliferation-related genes. When NIPP1 is associated with PP1 and EZH2, NIPP1 inhibits PP1 activity, regulating the association of EZH2 with its target genes.

To date, there has not been a system to modify epigenetic targets in whole organisms. There is much promise to treat many diseases by modulating epigenetic targets and bacterial delivery is a viable way to do it. Described herein is the use of bacteria to target intracellular protein-protein interaction in cancer cells.

The onset and progression of cancer is controlled by epigenetic events. Described herein are therapies against the epigenetic regulators EZH2, NIPP1 and the phosphatase PP1 (and others described herein). Together they regulate the expression of proliferation genes (8, 9). Targeting the EZH2-NIPP1-PP1 complex would disrupt malignant gene expression profiles and would be an effective treatment for disease, including metastatic disease. There are currently no clinical therapies against EZH2, NIPP1 or PP1.

The methyltransferase EZH2 (Enhancer of Zeste Homolog 2) is a member of the PcG proteins, which are regulators of stem cell pluripotency and development (1). EZH2 is part of the Polycomb Repressive Complex 2 (PRC2) that initiates gene silencing by trimethylating histone H3 at lysine 27 (H3K27me3) on target promoters. EZH2 is an oncogene. Overexpression of EZH2 promotes cell proliferation, migration and neoplastic transformation (2, 3). Depletion of EZH2 in cancer cells reduces tumor proliferation and inhibits tumor cell invasion (4, 63-65). The expression level of EZH2 is elevated in a broad range of neoplastic malignancies and is positively correlated with aggressive tumors and poor prognosis (2, 3).

NIPP1 (Nuclear Inhibitor of Protein Phosphatase 1) is a multifunctional scaffold protein that exerts its functions via its interactors. NIPP1 interacts with EZH2 via which it induces transcriptional repression. In addition, NIPP1 also interacts with the phosphatase PP1. The NIPP1:PP1 complex determines the occupancy of EZH2 on proliferation-related target genes, modulating the expression status of these genes (8, 9). When bound to PP1, NIPP1 inhibits the phosphatase from dephosphorylating EZH2 and results in the continued association of EZH2 with NIPP1-specific target genes (FIG. 1). NIPP1 is involved in embryonic development. Nipp1−/− mice die before gastrulation at E6.5 and a Nipp1−/− ES cell line cannot be derived (7). Depletion of NIPP1 in PC-3 prostate cancer cells and U2OS osteosarcoma cells impairs proliferation, indicating the potential of NIPP1 as a target for therapy (10).

Figure 2A:
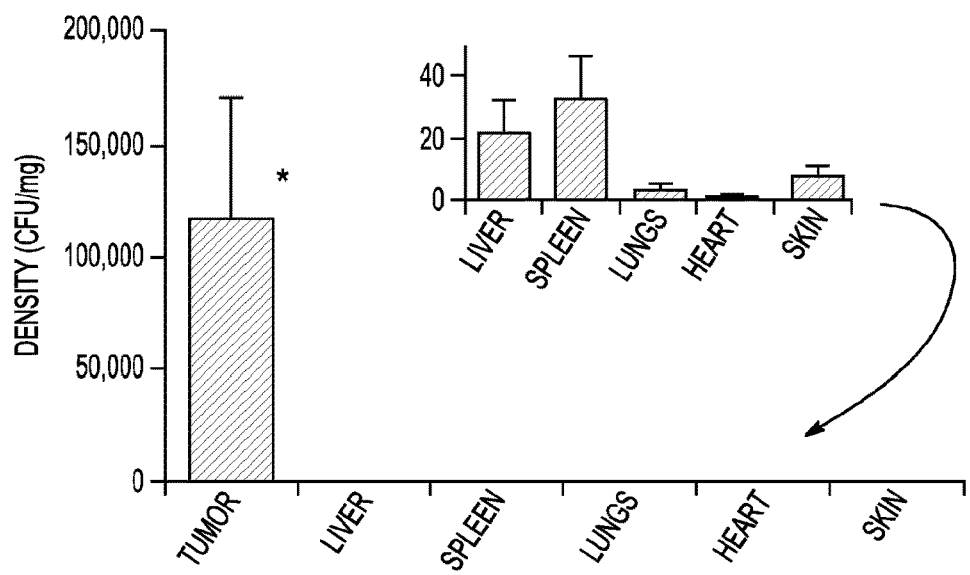
FIGS. 2A-B. *Salmonella* preferentially accumulate in tumors. A) Biodistribution in the organs of tumor-bearing mice, one week after systemic tail-vein injection of 2 million *Salmonella*/mouse. More bacteria accumulate in tumors than the liver and spleen (*, P<0.05), the major clearance organs. (Forbes N S, et al. Cancer Res 2003, 63(17):5188-5193) B) After systemic injection, *Salmonella* colonies (arrows, red) spread throughout tumor tissue. Scale bar is 50 µm.
Figure 2B:
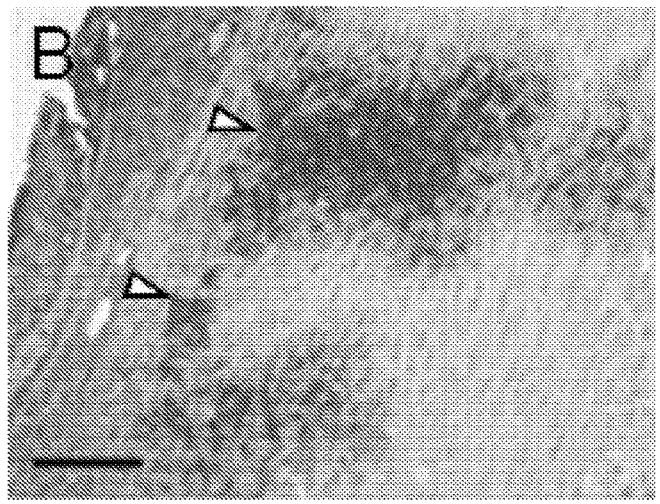
Figure 3A:
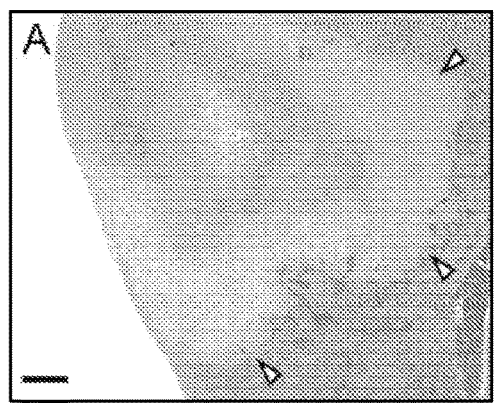
FIGS. 3A-D. *Salmonella* accumulate in metastases. A) Hepatic metastasis (arrows) spread from a dorsal mammary tumor. Scale bar is 250 µm. B) After systemic injection, *Salmonella* were present in the metastatic tissue (arrows) and not the normal liver tissue. C) Pulmonary metastasis formed by injecting 4T1 cells into the tail vein. D) After systemic injection, the center of each metastasis (C, arrow) had an associated *Salmonella* colony (D, arrow).
Figure 3B:
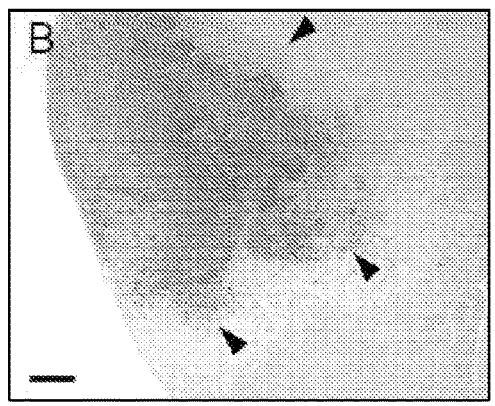
Figure 3C:
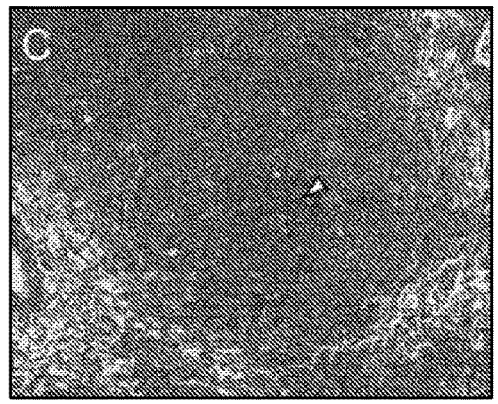
Figure 3D:
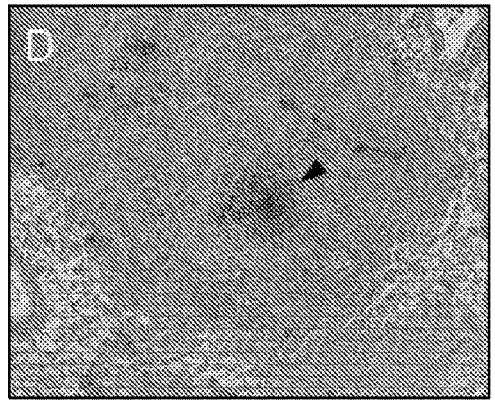

Systemic therapy against EZH2 and NIPP1 is unfeasible because it would cause severe side effects in actively differentiating tissues, such as skin and intestines (11). Bacterial delivery would enable inhibition of EZH2, NIPP1, and PP1 specifically in tumor cells. Bacterial delivery of dissociative peptides would interrupt protein-protein interactions, a goal that has been difficult to achieve with other delivery modalities. Facultative aerobic bacteria, such as *Salmonella*, selectively accumulate and replicate in tumor tissue (66). After systemic administration, the bacterial density in tumors is typically 3,500 times more than other organs (FIG. 2A), and once colonized, bacteria spread throughout tumor tissue (FIG. 2B). Initially, *Salmonella* bacteria flood into tumors following inflammation (67) and they become entrapped in the vasculature (68). Small molecules produced by tumors draw bacteria into the tissue, where they preferentially replicate in the favorable tumor microenvironment (66, 69). The privileged tumor environment prevents clearance by the immune system (70).

A therapy against EZH2 and NIPP1 can eliminate and/or reduce cancer stem cells (CSC) and prevent and/or reduce metastasis formation. Inhibiting epigenetic targets such EZH2, NIPP1 and/or PP1 can return cancer stem cells to normal behavior, and prevent cancer spreading and malignancy.

Figure 4:
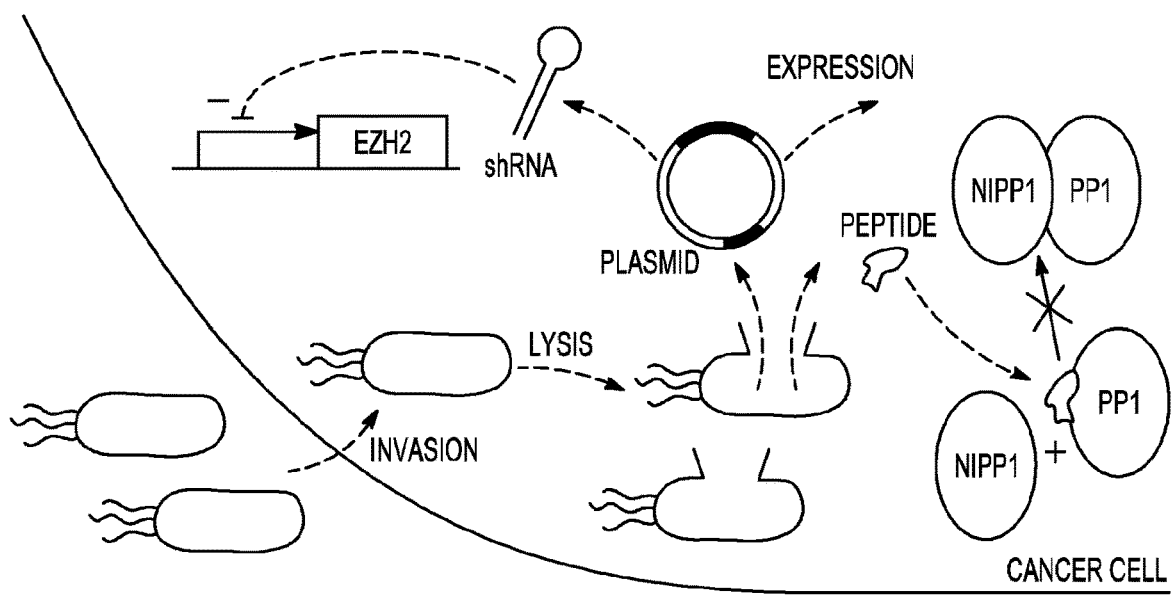
FIG. 4. Delivery platform for RNA, DNA and peptides. A bacterial delivery system (BDS) to deliver peptides and plasmids was developed. This bacterial system can specifically invade cancer cells and lyse upon entry, releasing the content into the mammalian cytosol. Delivered plasmids can create, for example, shRNAs to silence genes or can be directly expressed. Delivered peptides will interfere with epigenetic regulators within cancer cells.

Described herein is a novel therapeutic platform for gene and protein delivery (FIG. 4); specifically, targeting NIPP1, PP1 and EZH2 as a treatment that targets cancer and/or metastasis. Bacterial gene delivery can be used for both primary tumors and metastatic lesions due to its inherent capabilities. Bacterial delivery enables targeted epigenetic therapy and elimination of cancer stem cells. Compared to other forms of gene therapy, bacterial delivery of shRNA transiently silence genes, and therefore, modifications are not permanently incorporated into the genome and therefore unwanted genomic incorporation in non-cancer tissues is prevented. Further, insertion of a failsafe circuit into the bacterial vector prevents unwanted infection and defines the end of therapy without the need for antibiotics to remove the bacteria (e.g., *Salmonella*).

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, several embodiments with regards to methods and materials are described herein. As used herein, each of the following terms has the meaning associated with it in this section.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The articles "a" and "an" are used herein to refer to one or to more than one (i.e. to at least one) of the grammatical object of the article. By way of example, "an element" means one element or more than one element.

The phrase "and/or," as used herein, should be understood to mean "either or both" of the elements so conjoined, e.g., elements that are conjunctively present in some cases and disjunctively present in other cases.

As used herein, "or" should be understood to have the same meaning as "and/or" as defined above. For example, when separating a listing of items, "and/or" or "or" shall be interpreted as being inclusive, e.g., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

The terms "individual," "subject" and "patient" are used interchangeably herein and refer to any subject for whom diagnosis, treatment, or therapy is desired, including a mammal Mammals include, but are not limited to, humans, farm animals, sport animals and pets. A "subject" is a vertebrate, such as a mammal, including a human. Mammals include, but are not limited to, humans, farm animals, sport animals and companion animals. Included in the term "animal" is dog, cat, fish, gerbil, guinea pig, hamster, horse, rabbit, swine, mouse, monkey (e.g., ape, gorilla, chimpanzee, orangutan) rat, sheep, goat, cow and bird.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease.

The terms "inhibit", "inhibiting", and "inhibition" refer to the slowing, halting, or reversing the growth or progression of a disease, infection, condition, group of cells, protein or its expression. The inhibition can be greater than about 20%, 40%, 60%, 80%, 90%, 95%, or 99%, for example, compared to the growth or progression that occurs in the absence of the treatment or contacting.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" is an amount sufficient to effect beneficial or desired result, such a preclinical or clinical results. An effective amount can be administered in one or more administrations.

The terms "cell," "cell line," and "cell culture" as used herein may be used interchangeably. All of these terms also include their progeny, which are any and all subsequent generations. It is understood that all progeny may not be identical due to deliberate or inadvertent mutations.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). Thus, it is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, an "essentially pure" preparation of a particular protein or peptide is a preparation wherein at least about 95%, and preferably at least about 99%, by weight, of the protein or peptide in the preparation is the particular protein or peptide.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, a "functional" biological molecule is a biological molecule in a form in which it exhibits a property by which it is characterized. A functional enzyme, for example, is one which exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site having the universal resource locator using the BLAST tool at the NCBI website. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

The term "nucleic acid" typically refers to large polynucleotides. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "nucleic acid construct," as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

The term "otherwise identical sample", as used herein, refers to a sample similar to a first sample, that is, it is obtained in the same manner from the same subject from the same tissue or fluid, or it refers a similar sample obtained from a different subject. The term "otherwise identical sample from an unaffected subject" refers to a sample obtained from a subject not known to have the disease or disorder being examined. The sample may of course be a standard sample. By analogy, the term "otherwise identical" can also be used regarding regions or tissues in a subject or in an unaffected subject.

"Substantially homologous nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. Preferably, the substantially identical nucleic acid sequence encodes the peptide encoded by the reference nucleic acid sequence. The percentage of identity between the substantially similar nucleic acid sequence and the reference nucleic acid sequence is at least about 50%, 65%, 75%, 85%, 95%, 99% or more. Substantial identity of nucleic acid sequences can be determined by comparing the sequence identity of two sequences, for example by physical/chemical methods (i.e., hybridization) or by sequence alignment via computer algorithm. Suitable nucleic acid hybridization conditions to determine if a nucleotide sequence is substantially similar to a reference nucleotide sequence are: 7% sodium dodecyl sulfate SDS, 0.5 M $NaPO_4$, 1 mM EDTA at 50° C. with washing in 2× standard saline citrate (SSC), 0.1% SDS at 50° C.; preferably in 7% (SDS), 0.5 M $NaPO_4$, 1 mM EDTA at 50° C. with washing in 1×SSC, 0.1% SDS at 50° C.; preferably 7% SDS, 0.5 M $NaPO_4$, 1 mM EDTA at 50° C. with washing in 0.5×SSC, 0.1% SDS at 50° C.; and more preferably in 7% SDS, 0.5 M $NaPO_4$, 1 mM EDTA at 50° C. with washing in 0.1×SSC, 0.1% SDS at 65° C. Suitable computer algorithms to determine substantial similarity between two nucleic acid sequences include, GCS program package (Devereux et al., 1984 Nucl. Acids Res. 12:387), and the BLASTN or FASTA programs (Altschul et al., 1990 Proc. Natl. Acad. Sci. USA. 1990 87:14:5509-13; Altschul et al., J. Mol. Biol. 1990 215:3:403-10; Altschul et al., 1997 Nucleic Acids Res. 25:3389-3402). The default settings provided with these programs are suitable for determining substantial similarity of nucleic acid sequences for purposes of the present invention.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, the term "pharmaceutically-acceptable carrier" means a chemical composition with which an appropriate compound or derivative can be combined and which, following the combination, can be used to administer the appropriate compound to a subject. "Pharmaceutically acceptable" means physiologically tolerable, for either human or veterinary application. As used herein, "pharmaceutical compositions" include formulations for human and veterinary use.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure. In particular, purified sperm cell DNA refers to DNA that does not produce significant detectable levels of non-sperm cell DNA upon PCR amplification of the purified sperm cell DNA and subsequent analysis of that amplified DNA. A "significant detectable level" is an amount of contaminate that would be visible in the presented data and would need to be addressed/explained during analysis of the forensic evidence.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

A "recombinant cell" is a cell that comprises a transgene. Such a cell may be a eukaryotic or a prokaryotic cell. Also, the transgenic cell encompasses, but is not limited to, an embryonic stem cell comprising the transgene, a cell obtained from a chimeric mammal derived from a transgenic embryonic stem cell where the cell comprises the transgene, a cell obtained from a transgenic mammal, or fetal or placental tissue thereof, and a prokaryotic cell comprising the transgene.

The term "regulate" refers to either stimulating or inhibiting a function or activity of interest.

By "small interfering RNAs (siRNAs)" is meant, inter alia, an isolated dsRNA molecule comprised of both a sense and an anti-sense strand. In one aspect, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

By the term "specifically binds to", as used herein, is meant when a compound or ligand functions in a binding reaction or assay conditions which is determinative of the presence of the compound in a sample of heterogeneous compounds, or it means that one molecule, such as a binding moiety, e.g., an oligonucleotide or antibody, binds preferentially to another molecule, such as a target molecule, e.g., a nucleic acid or a protein, in the presence of other molecules in a sample.

The terms "specific binding" or "specifically binding" when used in reference to the interaction of a peptide (ligand) and a receptor (molecule) also refers to an interaction that is dependent upon the presence of a particular structure (i.e., an amino sequence of a ligand or a ligand binding domain within a protein); in other words the peptide comprises a structure allowing recognition and binding to a specific protein structure within a binding partner rather than to molecules in general. For example, if a ligand is specific for binding pocket "A," in a reaction containing labeled peptide ligand "A" (such as an isolated phage displayed peptide or isolated synthetic peptide) and unlabeled "A" in the presence of a protein comprising a binding pocket A the unlabeled peptide ligand will reduce the amount of labeled peptide ligand bound to the binding partner, in other words a competitive binding assay.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

Methods involving conventional molecular biology techniques are described herein. Such techniques are generally known in the art and are described in detail in methodology treatises, such as Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Methods for chemical synthesis of nucleic acids are discussed, for example, in Beaucage and Carruthers, Tetra. Letts. 22: 1859-1862, 1981, and Matteucci et al., J. Am. Chem. Soc. 103:3185, 1981.

As used herein, the terms "including", "includes", "having", "has", "with", or variants thereof, are intended to be inclusive similar to the term "comprising."

The terms "comprises", "comprising", and the like can have the meaning ascribed to them in U.S. Patent Law and can mean "includes", "including" and the like. As used herein, "including" or "includes" or the like means including, without limitation.

I. Salmonella

Examples of *Salmonella* strains which can be employed in the present invention include *Salmonella typhi* (ATCC No. 7251) and *S. typhimurium* (ATCC No. 13311). Attenuated *Salmonella* strains include *S. typhi*-aroC-aroD (Hone et al. Vacc. 9:810 (1991) *S. typhimurium*-aroA mutant (Mastroeni et al. Micro. Pathol. 13:477 (1992)) and *Salmonella typhimurium* 7207. Additional attenuated *Salmonella* strains that can be used in the invention include one or more other attenuating mutations such as (i) auxotrophic mutations, such as aro (Hoiseth et al. Nature, 291:238-239 (1981)), gua (McFarland et al Microbiol. Path., 3:129-141 (1987)), nad (Park et al. J. Bact, 170:3725-3730 (1988), thy (Nnalue et al. Infect. Immun, 55:955-962 (1987)), and asd (Curtiss, supra) mutations; (ii) mutations that inactivate global regulatory functions, such as cya (Curtiss et al. Infect. Immun, 55:3035-3043 (1987)), crp (Curtiss et al (1987), supra), phoP/phoQ (Groisman et al. Proc. Natl. Acad. Sci., USA, 86:7077-7081 (1989); and Miller et al. Proc. Natl. Acad. Sci., USA, 86:5054-5058 (1989)), phop.sup.c (Miller et al. J. Bact, 172:2485-2490 (1990)) or ompR (Dorman et al. Infect. Immun, 57:2136-2140 (1989)) mutations; (iii) mutations that modify the stress response, such as recA (Buchmeier et al. Mol. Micro., 7:933-936 (1993)), htrA (Johnson et al. Mol. Micro., 5:401-407 (1991)), htpR (Neidhardt et al. Biochem. Biophys. Res. Com., 100:894-900 (1981)), hsp (Neidhardt et al. Ann. Rev. Genet, 18:295-329 (1984)) and groEL (Buchmeier et al. Sci., 248:730-732 (1990)) mutations; mutations in specific virulence factors, such as lsyA (Libby et al. Proc. Natl. Acad. Sci., USA, 91:489-493 (1994)), pag or prg (Miller et al (1990), supra; and Miller et al (1989), supra), iscA or virG (d'Hauteville et al. Mol. Micro., 6:833-841 (1992)), plcA (Mengaud et al. Mol. Microbiol., 5:367-72 (1991); Camilli et al. J. Exp. Med, 173:751-754 (1991)), and act (Brundage et al. Proc. Natl. Acad. Sci., USA, 90:11890-11894 (1993)) mutations; (v) mutations that affect DNA topology, such as top A (Galan et al. Infect. Immun., 58: 1879-1885 (1990)); (vi) mutations that disrupt or modify the cell cycle, such as min (de Boer et al. Cell, 56:641-649 (1989)); (vii) introduction of a gene encoding a suicide system, such as sacB (Recorbet et al. App. Environ. Micro., 59:1361-1366 (1993); Quandt et al. Gene, 127:15-21 (1993)), nuc (Ahrenholtz et al. App. Environ. Micro., 60:3746-3751 (1994)), hok, gef, kil, or phlA (Molin et al. Ann. Rev. Microbiol., 47:139-166 (1993)); (viii) mutations that alter the biogenesis of lipopolysaccharide and/or lipid A, such as rFb (Raetz in *Esherishia coli* and *Salmonella typhimurium*, Neidhardt et al, Ed., ASM Press, Washington D.C. pp 1035-1063 (1996)), galE (Hone et al. J. Infect. Dis., 156:164-167 (1987)) and htrB (Raetz, supra), msbB (Reatz, supra; and U.S. Pat. No. 7,514,089); and (ix) introduction of a bacteriophage lysis system, such as lysogens encoded by P22 (Rennell et al. Virol, 143:280-289 (1985)), lamda murein transglycosylase (Bienkowska-Szewczyk et al. Mol. Gen. Genet., 184:111-114 (1981)) or S-gene (Reader et al. Virol, 43:623-628 (1971)).

The attenuating mutations can be either constitutively expressed or under the control of inducible promoters, such as the temperature sensitive heat shock family of promoters (Neidhardt et al. supra), or the anaerobically induced nirB promoter (Harborne et al. Mol. Micro., 6:2805-2813 (1992)) or repressible promoters, such as uapA (Gorfinkiel et al. J. Biol. Chem., 268:23376-23381 (1993)) or gcv (Stauffer et al. J. Bact, 176:6159-6164 (1994)).

In one embodiment, the bacterial delivery system is safe and based on a non-toxic, attenuated *Salmonella* strain that has a partial deletion of the msbB gene. This deletion diminishes the TNF immune response to bacterial lipopolysaccharides and prevents septic shock. In another embodiment, it also has a partial deletion of the purI gene. This deletion makes the bacteria dependent on external sources of purines and speeds clearance from non-cancerous tissues (13). In mice, the virulence ($LD_{50}$) of the therapeutic strain is 10,000-fold less than wild-type *Salmonella* (72, 73). In pre-clinical trials, attenuated *Salmonella* has been administered systemically into mice and dogs without toxic side effects (17, 27). Two FDA-approved phase I clinical trials have been performed and showed that this therapeutic strain can be safely administered to patients (20). In one embodiment, the strain of bacteria is VNP20009, a derivative strain of *Salmonella typhimurium*. Deletion of two of its genes—msbB and purI—resulted in its complete attenuation (by preventing toxic shock in animal hosts) and dependence on external sources of purine for survival. This dependence renders the organism incapable of replicating in normal tissue such as the liver or spleen, but still capable of growing in tumors where purine is available.

Further, insertion of a failsafe circuit into the bacterial vector prevents unwanted infection and defines the end of therapy without the need for antibiotics to remove the bacteria (e.g., *Salmonella*).

II. Vectors/Plasmids

In the present compositions and/or methods, DNA, RNA (e.g., a nucleic acid-based gene interfering agent) or protein may be produced by recombinant methods. The nucleic acid is inserted into a replicable vector for expression. Many such vectors are available. The vector components generally include, but are not limited to, one or more of the following: an origin of replication, one or more marker genes, an enhancer element, a promoter, and a transcription termination sequence. In some embodiments, for example in the utilization of bacterial delivery agents such as *Salmonella*, the gene may be integrated into the host cell chromosome or may be presented on, for example, a plasmid/vector.

Expression vectors usually contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media.

Expression vectors can contain a promoter that is recognized by the host organism and is operably linked to the nucleic acid-based gene interfering agent sequence. Promoters are untranslated sequences located upstream (5') to the start codon of a structural gene (generally within about 100 to 1000 bp) that control the transcription of particular nucleic acid sequence to which they are operably linked. In bacterial cells, the region controlling overall regulation can be referred to as the operator. Promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known.

Promoters suitable for use with prokaryotic hosts include the β-lactamase and lactose promoter systems, alkaline phosphatase, a tryptophan (trp) promoter system, hybrid promoters such as the tac promoter, and starvation promoters (Matin, A. (1994) Recombinant DNA Technology II, Annals of New York Academy of Sciences, 722:277-291). However, other known bacterial promoters are also suitable. Such nucleotide sequences have been published, thereby enabling a skilled worker to operably ligate them to a DNA coding sequence. Promoters for use in bacterial systems also can contain a Shine-Dalgarno (S.D.) sequence operably linked to the coding sequence.

Construction of suitable vectors containing one or more of the above-listed components employs standard ligation techniques. Isolated plasmids or DNA fragments are cleaved, tailored, and re-ligated in the form desired to generate the plasmids required.

In some embodiments of the invention, the expression vector is a plasmid or bacteriophage vector suitable for use in *Salmonella*, and the DNA, RNA and/or protein is provided to a patient through expression by an attenuated *Salmonella* administered to the patient. The term "plasmid" as used herein refers to any nucleic acid encoding an expressible gene and includes linear or circular nucleic acids and double or single stranded nucleic acids. The nucleic acid can be DNA or RNA and may comprise modified nucleotides or ribonucleotides, and may be chemically modified by such means as methylation or the inclusion of protecting groups or cap- or tail structures.

One embodiment provides an attenuated *Salmonella* strain comprising a lysis gene or cassette operably linked to an intracellularly induced *Salmonella* promoter. In one embodiment, promoter is a promoter for one of the genes in *Salmonella* pathogenicity island 2 type III secretion system (SPI2-T3SS) selected from the group SpiC/SsaB (accession no. CBW17423.1), SseF (accession no. CBW17434.1), SseG (accession no. CBW17435.1), SseI (accession no. CBW17087.1), SseJ (accession no. CBW17656.1), SseK1 (accession no. CBW20184.1), SseK2 (accession no. CBW18209.1), SifA (accession no. CBW17257.1), SifB (accession no. CBW17627.1), PipB (accession no. CBW17123.1), PipB2 (accession no. CBW18862.1), SopD2 (accession no. CBW17005.1), GogB (accession no. CBW18646.2), SseL (accession no. CBW18358.1), SteC (accession no. CBW17723.1), SspH1 (accession no. STM14_1483), SspH2 (accession no. CBW18313.1), or SirP (examples/an embodiment of sequences that can be used in the instant compositions/methods are provided for by accession numbers and sequences provided throughout the specification; other sequences, including those with greater than about 80%, 85%, 90%, 95%, 96%, 97%, 98%, 99% and 100% identity may also be used in the composition/methods of the invention).

```
SpiC/SsaB (accession no. CBW17423.1):
  1    mseegfmlav lkgipliqdi raegnsrswi mtidghparg eifseafsis lflndleslp
 61    kpclayvtll laahpdvhdy aiqltadggw lngyyttsss seliaieiek hlaltcilkn
121    virnhhklys ggv SseF (accession no. CBW17434.1):
  1    mkihipsaas nivdgnspps diQakevsfp ppeipapgtp aapvlltpeq irqqrdyaih
 61    fmqytiralg atvvfglsva aavisggagl piailagaal viaigdacca yhnyQsicqg
121    keplqtasds valvvsalal kcgaslncan tlanclslli rsgiaismlv lplqfplpaa
181    eniaasldmg svitsyslta igavldycla rpsgddgens vdelhadpsv llaeqmaalc
241    qsattpalmd ssdhtsrgep SseG (accession no. CBW17435.1):
  1    mkpvspnaqv ggqrpvnape esppcpslph petnmesgri gpqqgkervl aglakrviec
 61    fpkeifswqt vilggqilcc sagialtvls gggaplvala giglaiaiad vacliyhhkh
121    hlpmandsig navfyiancf anQrksmaia kayslggrla ltatvmthsy wsgslglqph
181    llerindity glmsftrfgm dgmamtgmqv ssplyrllaq vtpeqrape SseI (accession no. CBW17087.1):
  1    mpfhigsgcl paiisnrriy riawsdtppe msswekmkef fcsthqaeal eciwtichpp
 61    agttredvvs rfellrtlay dgweenihsg lhgenyfcil dedsqeilsv tlddvgnytv
121    ncqgysethh ltmatepgve rtditynits didaaaylee lkqnpiinnk imnpvgqces
181    lmtpvsnfmn ekgfdniryr gifiwdkpte eiptnhfavv gnkegkdyvf dvsahQfenr
241    gmsnlngpli lsadewvcky rmatrrkliy ytdfsnssia anaydalpre lesesmagkv
301    fvtsprwfnt fkkqkyslig km SseJ (accession no. CBW17656.1):
  1    mplsvgqgyf tssissekfn aikesarlpe lslwekikay fftthhaeal ecifnlyhhq
 61    elnitpvqvr gayiklrala sqgckeqfii esqehadkli ikddngenil sievechpea
121    fglakeinks hpkpknislg ditrlvffgd slsdslgrmf ekthhilpsy gqyfggrftn
181    gftwteflss phflgkemln faeggstsas yscfncigdf vsntdrqvas ytpshqdlai
241    fllgandymt lhkdnvimvv eqqiddieki isggvnnvlv mgipdlsltp ygkhsdekrk
301    lkdesiahna llktnveelk ekypqhkicy yetadafkvi meaasnigyd tenpythhgy
361    vhvpgakdpq ldicpqyvfn dlvhptclevh hcfaimlesf iahhyste SseK1 (accession no. CBW20184.1):
  1    mippinryvp alsknelvkt vtnrdiqfts fngkdyplcf ldektpllfq wfernparfg
 61    kndipiinte knpylnniik aatiekerli gifvdgdffp gqkdafskle ydyenikviy
121    rndidfsmyd kklseiymen iskqesmpee krdchllqll kkelsdigeg ndsliksyll
181    dkghgwfdfy rnmamlkagq lfleadkvgc ydlstnsgci yldadmiite klggiyipdg
241    iavhveridg rasmengiia vdrnnhpall agleimhtkf dadpysdgvc ngirkhfnys
301    lnedynsfcd fiefkhdnii mntsqftgss warhvq SseK2 (accession no. CBW18209.1):
  1    marfnaaftr ikimfsrirg liscqsntqt iaptlsppss ghvsfagidy pllpinhqtp
 61    lvfqwfernp drfggneipi intqknpyln niinaaiiek eriigifvdg dfskgqrkal
121    gklegnyrni kviynsdlny smydkkltti ylenitklea qsaserdevl lngvkksled
181    vlknnpeetl isshnkdkgh lwfdfyrnlf llkgsdafle agkpgchhlq pgggciylda
```

```
241    dmlltdklgt lylpdgiaih vsrkdnhvsl engiiavnrs ehpalikgle imhskpygdp
301    yndwlskglr hyfdgshiqd ydafcdfief kheniimnts sltasswr
SifA (accession no. CBW17257.1):
  1    mpitigngfl kseiltnspr ntkeawwkvl wekikdfffs tgkakadrcl hemlfaerap
 61    trerlteiff elkelacasq rdrfqvhnph endatiilri mdqneenell ritqntdtfs
121    cevmgnlyfl mkdrpdilks hpqmtamikr ryseivdypl psticlnpag apilsvpldn
181    iegylytelr kghldgwkaq ekatylaaki gsgiekttri lhhanisest qqnafletma
241    mcglkqleip pphthipiek mvkevlladk tfqaflvtdp stsqsmlaei veaisdqvfh
301    aifridpgai qkmaeeqltt lhvrseggsg ciccfl
SifB (accession no. CBW17627.1):
  1    mpitigrgfl ksemfsqsai sqrsfftllw ekikdffcdt qrstadqyik elcdvasppd
 61    aqrlfdlfck lyelsspscr gnfhfqhykd aecqytnlci kdgediplci mirqdhyyye
121    imnrtvlcvd tqsahlkrys dinikastyv ceplcclfpe rlqlslsggi tfsvdlknie
181    etliamaekg nlcdwkeQer kaaissrinl giagagvtai ddaiknkiaa kvientnlkn
241    aafepnyaqs svtgivyscl fkneilmnml eessshgllc lnelteyvtl qvhnslfsed
301    lsslvettkn eahhqs
PipB (accession no. CBW17123.1):
  1    mpitnaspen ilrylhaagt gtkeamksat sprgilewfv nfftcggvrr snerwfrevi
 61    gklttsllyv nknaffdgnk ifledvngct iclscgaase ntdpmviiev nkngktvtdk
121    vdserfwnvc rmlklmskhn iqqpdslite dgflnlrgvn lahkdfQged lskidasnad
181    frettlsnvn lvganlccan lhavnlmgsn mtkanithad ltcanmsgvn ltaailfgsd
241    ltdtklngak ldkialtlak altgadltgs qhtptplpdy ndrtlfphpi f
PipB2 (accession no. CBW18862.1):
  1    mersldslag maksafgagt saamrqatsp ktileyiinf ftcggirrrn etqygeliet
 61    maetlkstmp drgaplpeni ilddmdgcry efnlpgenne agqvivrvsk gdhsetreip
121    lasfekicra llfrcefslp gdsviltaqg gmnlkgavlt ganitsenlc dadlsganle
181    gavlfmadce ganfkganls gtslgdsnfk nacledsimc gatldhanit ganlghasll
241    gcsmiecncs ganmdhtnls gatliradms gatlqgatim aaimegavlt ranlrkasfi
301    stnldgadla eanlnntcfk dctltdlrte datmststqt lfnefyseni
SopD2 (accession no. CBW17005.1):
  1    mpvtlsfgnr hnyeinhsrl arlmspdkee alymgvwdrf kdcfrthkkg evlevlytli
 61    hgcerenqae lnvditgmek ihaftqlkey anpsqqdrfv mrfdmnqtqv lfeidgkvid
121    kcnlhrllnv sencifkvme edeeelflki cikygekisr ypellegfan klkdavnedd
181    dvkdevyklm rsgedrkmec vewngtltee eknklrclqm gsfnittqff kigywelege
241    vlfdmvhptl syllqaykps lssdlietnt mlfsdvinkd yddyQnnkre idailrriyr
301    shnntlfise ksscrnmli
GogB (accession no. CBW18646.2):
  1    mqyaytsnea tsnlellnkw riespdieke ernsiydkii eanhtgslsi tahhvtsipv
 61    fpdnlselnl sscytlesip nlpdglkslt isgnQtikis yfpdslesls idmQayeeny
121    tfpalpyglk sftacygkfl pplpphlssl slqnfseilc aelpykldkl dlqncpflpl
181    mkmlpeelke lsielirtvp gtviddilpd klkklsinfc dniklpvklp vnlksinlss
241    rtpiaweipt cnlpahidis tdgyvklnpe fltrsditfs nkpagdvlsf qpgdvvyglc
301    kardrvntiv nslyyfskkd iiiqntltda vwdrknravf nkdekiaerl ndvqrgiffr
```

```
361  eflsqhkkyn itedkysdls neecwiktsk aglefqtrlr ersvifvidn lvdaisdian
421  ktgkhgnsit ahelrwvyrn rhddlvkqnv kfflngeais hedvfslvgw dkykpknrnr
```

SseL (accession no. CBW18358.1):
```
  1  msdealtllf savengdqnc idllcnlalr nddlghrvek flfdlfsgkr tgssdidkki
 61  nqaclvlhqi annditkdnt ewkklhapsr llymagsatt dlskkigiah kimgdgfaqt
121  dgeqvgvenl wcgarmlssd elaaatqglv qespllsvny piglihpttk enilstqlle
181  kiagsglshn evflvntgdh wllclfykla ekikclifnt yydlnentkQ eiieaakiag
241  isesdevnfi emnlqnnvpn gcglfcyhti qllsnaggnd pattlrefae nfltlsveeq
301  alfntqtrrq iyeyslq
```

SteC (accession no. CBW17723.1):
```
  1  mpftfqignh scgiserylr diidnkrehv fstcekfidf frniftrrsl isdyreiynl
 61  lcqkkehpdi kgpfspgpfs krdedctrwr pllgyiklid asrpetidky tvevlahgen
121  mlllqmfydg vlvtetecse rcvdflketm fnynngeitl aalgndnlpp seagsngiye
181  afeqrlidfl ttpatasgye sgaidqtdas qpaaieafin spefqknirm rdieknkigs
241  gsygtvyrlh ddfvvkipvn ergikvdvns pehrnchpdr vskylnmand dknfsrsaim
301  ningkdvtvl vskyiqggef dvedednyrm aeallksrgv ymhdinilgn ilvkegvlff
361  vdgdgivlsq esrqqrsysl atrqleeqik ahhmiklkra etegntedve yyksllitdld
421  aligeeeqtp apgrrfklaa peegtivakv lkdelkk
```

SspH1 (accession no. STM14_1483):
```
  1  mfnirntgps vsmqaiagaa apeaspeeiv wekiqvffpq enyeeaggcl aelchpargm
 61  lpdhissqfa rlkaltfpaw eeniqcnrdg inqfcildag skeilsitld dagnytvncq
121  gyseandfim dtepgeecte faegasgtsl rpattvsqka aeydavwskw erdapagesp
181  graavvqemr dclnngnpvl nvgasglttl pdrlpphitt lvipdnnits lpelpeglre
241  levsgnlqlt slpslpqglq klwaynnwla slptlppglg dlaysnnqlt slpemppalr
301  elrvsgnnit slpalpsglq klwaynnrlt slpemspglq eldvshnqlt rlpqsltgls
361  saarvyldgn plsvrtlqal rdiighsgir ihfdmagpsv prearalhla vadwltsare
421  geaaqadrwq afglednaaa fslvldrlre tenfkkdagf kagisswltq laedaalrak
481  tfamateats tcedrvthal hqmnnvqlvh naekgeydnn lqglvstgre mfrlatleqi
541  arekagtlal vddvevylaf qnklkeslel tsvtsemrff dvsgvtvsdl qaaelqvkta
601  ensgfskwil qwgplhsvle rkvperfnal rekqisdyed tyrklydevl kssglvddtd
661  aertigvsam dsakkefldg lralvdevlg syltarwrin
```

SspH2 (accession no. CBW18313.1):
```
  1  mpfhigsgcl patisnrriy riawsdtppe msswekmkef fcsthqteal eciwtichpp
 61  agttredvin rfellrtlay agweesihsg qhgenyfcil dedsqeilsv tlddagnytv
121  ncqgysethr ltldtaggee gtghaegasg tfrtsflpat tapqtpaeyd avwsawrraa
181  paeesrgraa vvqkmracln ngnavinvge sglttlpdcl pahittivip dnnitslpal
241  ppelrtlevs gnqltslpvl ppgllelsif snplthlpal psglcklwif gnqltslpvl
301  ppglqelsys dnglaslpal pselcklway nnqltslpml psglqelsys dnglaslptl
361  pselyklway nnrltslpal psglkelivs gnrltslpvl pselkelmvs gnrltslpml
421  psgllslsvy rnqltrlpes lihlssettv nlegnplser tlqalreits apgysgpiir
481  fdmagasapr etralhlaaa dwlvparege papadrwhmf gqednadafs lfldrlsete
541  nfikdagfka gisswlaqla edealrantf amateatssc edrvtfflhq mknvqlvhna
601  ekgqydndla alvatgremf rlgklegiar ekvrtlalvd eievwlayqn klkkslglts
```

```
661   vtsemrffdv sgvtvtdlqd aelqvkaaek sefrewilqw gplhrvlerk apervnalre 721   kgisdyeety rmlsdtelrp sglvgntdae rtigarames akktfldglr plveemlgsy 781   lnvqwrrn
```

In one embodiment, the *Salmonella* gene under the regulation of an inducible promoter is selected from ftsW (accession no. CBW16230.1), ftsA (accession no. CBW16235.1), ftsZ (accession no. CBW16236.1), murE (accession no. CBW16226.1), mukF (accession no. CBW17025.1), imp (accession no. CBW16196.1), secF (accession no. CBW16503.1), eno (accession no. CBW19030.1), hemH (accession no. CBW16582.1), tmk (accession no. CBW17233.1), dxs (accession no. CBW16516.1), uppS (accession no. CBW16324.1), cdsA (accession no. CBW16325.1), accA (accession no. CBW16335.1), pssA (accession no. CBW18718.1), msbA (accession no. CBW17017.1), tsf (accession no. CBW16320.1), trmD (accession no. CBW18749.1), cca (accession no. CBW19276.1), infB (accession no. CBW19355.1), rpoA (accession no. CBW19477.1), rpoB (accession no. CBW20180.1), rpoC (accession no. CBW20181.1), holA (accession no. CBW16734.1), dnaC (accession no. CBW20563.1), or eng (EngA accession no. CBW18582.1; EngB accession no. CBW20039.1).

```
ftsW (accession no. CBW16230.1):
  1   mmasrdkdad slimydrtll wltfglaaig fvmvtsasmp vgqrlandpf lfakrdalyi 61   flafclamvt lrlpmtfwqk ysttmliasi imllivlvvg ssvngasrwi algplriqpa 121   eftklslfcy lanylvrkvd evrnnlrgfl kpmgvilvla vlllaqpdlg tvvvlfvttl 181   amlflagakl wqfiaiigmg isavillila epyrirrvts fwnpwedpfg sgyqltqslm 241   afgrgeiwgq glgnsvqkle ylpeahtdfi faiigeelgy igvvlallmv ffvaframsi 301   grkaleidhr fsgflacsig iwfsfqalvn vgaaagmlpt kgltlplisy ggssllimst 361   aimfllridy etrlekaqaf trgsr ftsA (accession no. CBW16235.1):
  1   mikatdrklv vgleigtakv aalvgevlpd gmvniigvgs cpsrgmdkgg vndlesvvkc 61   vqraidqael madcqissvy lalsgkhisc qneigmvpis eeevtqedve nvvhtaksvr 121   vrdehrvlhv ipqeyaidyq egiknpvgls gvrmqakvhl itchndmakn ivkavercgl 181   kvdqlifagl aasysvlted erelgvcvvd igggtmdiav ytggalrhtk vipyagnvvt 241   sdiayafgtp psdaeaikvr hgcalgsivg kdesvevpsv ggrpprslqr qtlaeviepr 301   ytellnlvne eilqlqeqlr qqgvkhhlaa givltggaaq ieglaacaqr vfhtqvriga 361   pinitgltdy aqepyystav gllhygkesh lngeaevekr vtasvgswik rinswlrkef ftsZ (accession no. CBW16236.1):
  1   mfepmeltnd avikvigvgg gggnavehmv reriegveff avntdaqalr ktavgqtiqi 61   gsgitkglga ganpevgrna adedrealra alegadmvfi aagmgggtgt gaapvvaeva 121   kdlgiltvav vtkpfnfegk krmafaeqgi telskhvdsl itipndkllk vlgrgislld 181   afgaandvlk gavqgiaeli trpglmnvdf advrtvmsem gyammgsgva sgedraeeaa 241   emaissplle didlsgargv lvnitagfdl rldefetvgn tirafasdna tvvigtsldp 301   dmndelrvtv vatgigmdkr peitivtnkq vqqpvldryq qhgmapltqe qktvakvvnd 361   ntpqaakepd yldipaflrk qad murE (accession no. CBW16226.1):
  1   madrnlrdll apwvaglpar elremtldsr vaaagdlfva vvghqadgrr yipqaiaqgv 61   aaiiaeakde asdgeiremh gvpvvylsql nerlsalagr fyhepsenmr lvavtgtngk 121   ttttqllaqw sqllgetsav mgtvgngllg kviptenttg savdvqhvla slvaqgatfg 181   amevsshglv qhrvaalkfa asvftnlsrd hldyhgdmah yeaakwmlys thhhgqaivn 241   addevgrrwl aslpdavays meghinpnch grwlkaeave yhdrgatirf asswgegeie 301   srlmgafnvs nillalatll algypltdll ktaarlqpvc grmevftapg kptvvvdyah
```

-continued

```
361    tpdalekalq  aarlhcagkl  wcvfgcggdr  dkgkrplmga  iaeefadivv  vtddnprtee
421    praiindila  gmldagqvry  megraeavtn  aimqakdndv  vliagkghed  yqivgtqrld
481    ysdrvtaarl  lgvia
``` mukF (accession no. CBW17025.1):
```
  1    msefsqtvpe  lvawarkndf  sislpvdrls  fllavatlng  erldgemseg  elvdafrhvs
 61    dafeqtseti  gvrannaind  mvrqrllnrf  tseqaegnai  yrltplgigi  tdyyirqref
121    stlrlsmqls  ivagelkraa  daaaeggdef  hwhrnvyapl  kysvaeifds  idltqrimde
181    qqqqvkddia  qllnkdwraa  isscelllse  tsgtlrelqd  tleaagdklq  anllriqdat
241    mthddlhfvd  rlvfdlqskl  driiswgqqs  idlwigydrh  vhkfirtaid  mdknrvfaqr
301    lrqsvqtyfd  dpwaltyana  drlldmrdee  malrddevtg  elppdleyee  fneireqlaa
361    iieeqlaiyk  trqtpldlgl  vvreylaqyp  rarhfdvari  vidqavrlgv  aqadftglpa
421    kwqpindyga  kvqahvidky
``` imp (accession no. CBW16196.1):
```
  1    mkkriptlla  tmiasalysh  qglaadlasq  cmlgvpsydr  plvkgdtndl  pvtinadnak
 61    gnypddavft  gnvdimqgns  rlqadevqlh  qkqaegqpep  vrtvdalgnv  hyddnqvilk
121    gpkgwanlnt  kdtnvwegdy  qmvgrqgrgk  adlmkqrgen  rytilengsf  tsclpgsdtw
181    svvgsevihd  reeqvaeiwn  arfkvgpvpi  fyspylqlpv  gdkrrsgfli  pnakyttkny
241    fefylpyywn  iapnmdatit  phymhrrgni  mwenefrylt  qagegvmeld  ylpsdkvyed
301    dhpkegdkhr  wlfnwqhsgv  mdqvwrfnvd  ytkvsdssyf  ndfdskygss  tdgyatqkfs
361    vgyavqnfda  tvstkqfqvf  ndqntssysa  epqldvnyyh  ndlgpfdtri  ygqavhfvnt
421    kdnmpeatry  hleptinlpl  snrwgslnte  aklmathyqq  tnldsynsdp  nnknkledsv
481    nrvmpqfkvd  gkliferdma  mlapgytqtl  eprvqylyvp  yrdqsgiyny  dssllqsdyn
541    glfrdrtygg  ldriasanqv  ttgvttriyd  daaverfnvs  vgqiyyftes  rtgddnikwe
601    nddktgslvw  agdtywrise  rwglrsgvqy  dtrldsvats  sssleyrrdq  drlvqlnyry
661    aspeyiqatl  psyystaeqy  knginqvgav  aswpiadrws  ivgayyfdtn  sskpadqmlg
721    lqynsccyai  rvgyerklng  wdndkqhaiy  dnaigfniel  rglssnyglg  tqemlrsnil
781    pyqssm
``` secF (accession no. CBW16503.1):
```
  1    maqeytveql  nhgrkvydfm  rwdfwafgis  gllliaaivi  mgvrgfnwgl  dftggtviei
 61    tlekpaemdv  mrealqkagy  eepqlqnfgs  shdimvrmpp  tegetggqvl  gskvvtiine
121    atnqnaavkr  iefvgpsvga  dlaqtgamal  lvalisilvy  vgfrfewrla  agvvialand
181    viitlgilsl  fhieidltiv  aslmsvigys  lndsivvsdr  irenfrkirr  gtpyeifnvs
241    ltqtlhrtli  tsgttivvil  mlylfggpvl  egfsltmlig  vsigtassiy  vasalalklg
301    mkrehmlqqk  vekegadqps  up
``` eno (accession no. CBW19030.1):
```
  1    mskivkvigr  eiidsrgnpt  veaevhlegg  fvgmaaapsg  astgsreale  lrdgdksrfl
 61    gkgvtkavga  vngpiaqail  gkdakdqagi  dkimidldgt  enksnfgana  ilayslanak
121    aaaaakgmpl  yehiaelngt  pgkysmpvpm  mniinggeha  dnnvdiqefm  iqpvgaktvk
181    eairmgsevf  hhlakvlkgk  gmntavgdeg  gyapnlgsna  ealaviaeav  kaagyelgkd
241    itlamdcaas  efykdgkyvl  agegnkafts  eefthfleel  tkqypivsie  dgldesdwdg
301    fayqtkvlgd  kiqlvgddlf  vtntkilkeg  iekgiansil  ikfnqigslt  etlaaikmak
361    dagytavish  rsgetedati  adlavgtaag  qiktgsmsrs  drvakynqli  rieealgeka
421    pyngrkeikg  qa
```

```
hemH (accession no. CBW16582.1):
  1 mrqtktgill anlgtpdapt peavkrylkq flsdrrvvdt prllwwpllr gvilplrspr
 61 vaklyqsiwm dggsplmvys reqqqalaar lpdtpvalgm sygspslesa vdellasdvd
121 hivvlplypq yscstvgavw delgrilark rripgisfir dyaddgayid alaksaresf
181 arhgepdvll lsyhgipqry adegddypqr crdttrelvs alglppekvm mtfqsrfgre
241 pwltpytdet lkmlgekgtg hiqvmcpgfa adcletleei aeqnreifle aggkkyayip
301 alnatpehid mmlkltapyr tmk (accession no. CBW17233.1):
  1 mgsnyivieg legagkttar dvvvetleql girnmiftre pggtqlaekl rslvldirsv
 61 gdevitdkae vlmfyaarvq lvetvikpal aqgvwvigdr hdlstqayqg ggrgidqtml
121 atlrdavlgd frpdltlyld vtpevglkra rargdldrie qesfdffnrt rarylelaaq
181 dsrirtidat qpldavmrdi ratvtkwvqe qaa dxs (accession no. CBW16516.1):
  1 msfdiakypt lalvdstgel rllpkeslpk lcdelrryll dsysrssghf asglgtvelt
 61 valhyvyntp fdqliwdvgh qayphkiltg rrdkigtirq kgglhpfpwr geseydvlsv
121 ghsstsisag igiavaaeke gkdrrtvcvi gdgaitagma feamnhagdi rpdmlvilnd
181 nemsisenvg alnnhlaqll sgklysslre ggkkvfsgvp pikellkrte ehikgmvvpg
241 tlfeelgfny igpvdghdvm glistlknmr dlkgpqflhi mtkkgrgyep aekdpitfha
301 vpkfdpssgc lpkssgglpg yskifgdwlc etaakdsklm aitpamregs gmvefsrkfp
361 dryfdvaiae qhavtfaagl aiggykpvva iystflqray dqvihdvaiq klpvmfaidr
421 agivgadgqt hqgafdlsyl rcipdmvimt psdenecrqm lftgyhyndg ptavryprgn
481 aqgvaltple klpigkglvk rhgeklailn fgtlmpeaak vaealnativ dmrfvkpldd
541 tlilemaaqh dalvtleena imggagsgvn evlmahrkpv pviniglpdf fipqgtqeea
601 raelgldaag ieakikawla uppS (accession no. CBW16324.1):
  1 mlsatqpvse nlpahgcrhv aiimdgngrw akkqgkiraf ghkagaksvr raysfaanng
 61 idaltlyafs senwnrpaqe vsalmelfvw aldsevkslh rhnvrlriig disrfnsrlq
121 erirksealt ahntgltlni aanyggrwdi vqgvrqlaeq vqagvlrpdq ideerlgqqi
181 cmhelapvdl virtggehri snfllwqiay aelyftdvlw pdfdeqdfeg alhafanrer
241 rfggtepgdd ka cdsA (accession no. CBW16325.1):
  1 mlkyrlisaf vlipaviaal fllppvgfai itivvcmlaa wewgqlsgfa arsqrvwlav
 61 lcglllalml fllpeyhhni rqplvemslw aslgwwvval llvlfypgsa aiwrnsktlr
121 lifglltivp ffwgmlalra whydenhysg aiwllyvmil vwgadsgaym fgklfgkhkl
181 apkvspgktw qgfigglata aviswgygmw anlnvapvil licsvvaala svlgdltesm
241 fkreagikds ghlipghggi ldridsltaa vpvfacllll vfrtl accA (accession no. CBW16335.1):
  1 mslnfldfeq piaeleakid sltaysrqde kldinideev hrlreksvel trkifadlga
 61 wqvaqlarhp qrpytldyvr lafdefdela gdrayaddka ivggiarleg rpvmiighqk
121 gretkekirr nfgmpapegy rkalrlmema erfnmpiitf idtpgaypgv gaeergqsea
181 iarnlremsr lnvpvictvi geggsggala igvgdkvnml qystysvisp egcasilwks
241 adkaplaaea mgiiaprlke lklidsiipe plggahrnpe amaaslkaql ledladldvl
301 stddlknrry qrlmsygya
```

```
pssA (accession no. CBW18718.1):
    1  mlskfkrnkh qqhlaqlpki sqsvddvdff ytpatfretl lekiasatqr icivalyleq 61  ddggkgilda lyaakrqrpe ldvrvlvdwh raqrgrigaa asntnadwyc rlaqenpgid 121  vpvygvpint realgvlhfk gfiiddsvly sgaslndvyl hqhdkyrydr yqlirnrqma 181  dimfdwvtqn lmngrgvnrl dntqrpkspe ikndirlyrq elrdasyhfq gdandeqlsv 241  tplvglgkss llnktifhlm pcaehkltic tpyfnlpavl vrniiqllrd gkkveiivgd 301  ktandfyipe depfkiigal pylyeinlrr flsrlqyyvn tdqlvvrlwk dddntyhlkg 361  mwvddkwmll tgnnlnpraw rldlenaili hdpkqelapq rekelelirt httivkhyrd 421  lqsiadypik vrklirrlrr iridrlisri l msbA (accession no. CBW17017.1):
    1  mhndkdlstw qtfrrlwpti apfkagliva gialilnaas dtfmlsllkp llddgfgktd 61  rsvllwmplv viglmilrgi tsyissycis wvsgkvvmtm rrrlfghmmg mpvaffdkqs 121  tgtllsrity dseqvasssss galitvvreg asiiglfimm fyyswqlsii lvvlapivsi 181  airvvskrfr sisknmqntm gqvttsaeqm lkghkevlif ggqevetkrf dkvsnkmrlq 241  gmkmvsassi sdpiiqlias lalafvlyaa sfpsvmdslt agtitvvfss mialmrplks 301  ltnvnaqfqr gmaacqtlfa ildseqekde gkrvidratg dlefrnvtft ypgrevpalr 361  ninlkipagk tvalvgrsgs gkstiaslit rfydideghi lmdghdlrey tlaslrnqva 421  lvsqnvhlfn dtvanniaya rteeysreqi eeaarmayam dfinkmdngl dtiigengvl 481  lsggqrqria iarallrdsp ilildeatsa ldteseraiq aaldelqknr tslviahrls 541  tieqadeivv vedgiiverg thsellaqhg vyaqlhkmqf gq tsf (accession no. CBW16320.1):
    1  maeitaslvk elrertgagm mdckkaltea ngdielaien mrksgaikaa kkagnvaadg 61  viktkidgnv afilevncqt dfvakdagfq afadkvldaa vagkitdvev lkaqfeeery 121  alvakigeni nirrvasleg dvlgsyqhga rigvlvaakg adeelvkqla mhvaaskpef 181  vkpedvsadv vekeyqvqld iamqsgkpke iaekmvegrm kkftgevslt gqpfvmepsk 241  svgqllkehn advtgfirfe vgegiekvet dfaaevaams kqs trmD (accession no. CBW18749.1):
    1  mfigivslfp emfraitdyg vtgravkkgl lniqswsprd fandrhrtvd drpygggpgm 61  lmmvqplrda ihaakaaage gakviylspq grkldqagvs elatnqklil vcgryegvde 121  rviqteidee wsigdyvlsg gelpamtlid svarfipgvl gheasaieds fadglldcph 181  ytrpevlegm evppvllsgn haeirrwrlk qslgrtwlrr pellenlalt eeqarllaef 241  ktehaqqqhk hdgma cca (accession no. CBW19276.1):
    1  mkiylvggav rdallglpvk dkdwvvvgat pqemldagyq qvgrdfpvfl hpqtheeyal 61  arterksgsg ytgftcyaap dvtleadlqr rdltinalar ddagqiidpy hgrrdlearl 121  lrhvspafge dplrvlrvar faaryahlsf riadetlalm remtaagele hltpervwke 181  tenalttrnp qvyfqvlrdc galrvlfpei dalfgvpapa kwhpeidtgv htlmtlsmaa 241  mlspqldvrf atichdlgkg ltpknlwprh hghgpagvkl veqlcqrlry pndlrdlakl 301  vaeyhdliht fpilqpktiv klfdaidawr kpqrveqial tseadvrgrt gfeasdypqg 361  rwlreawqva qavptkevve agfkgieire eltkrriaav anwkekrcpn pas infB (accession no. CBW19355.1):
    1  mtdvtlkala aerqvsvdrl vqqfadagir ksaddsysaq ekqtllahln reaysgpdkl 61  tlqrktrstl nipgtggksk svqievrkkr tfvkrdpqea erlaaeeqaq reaeeqarre 121  aeeqakreaq qkaereaaeq akreaaekak reaaekdkvs nqqtddmtkt aqaekarren
```

-continued

```
 181    eaaelkrkae eeearrkleee arrvaeeearr maeenkwtat pepvedtsdy hvttsqharq
 241    aedendreve ggrgrgrnak aarpakkgkh aeskadreea raavrggkgg krkgsslqqg
 301    fqkpaqavnr dvvigetitv gelankmavk gsqvikammk lgamatinqv idgetaqlva
 361    eemghkvilr reneleeavm sdrdtgaaae prapvvtimg hvdhgktsll dyirstkvas
 421    geaggitqhi gayhvetdng mitfldtpgh aaftsmrarg aqatdivvlv vaaddgvmpq
 481    tieaighaka agvpvvvavn kidkpeadpd rvknelsqyg ilpeewgges qfvhvsakag
 541    tgidelldai llqaevlelk avrkgmasga viesfldkgr gpvatvlvre gtlhkgdivl
 601    cgfeygrvra mrnelgqevl eagpsipvei lglsgvpaag devtvvrdek karevalyrq
 661    gkfrevklar qqksklenmf anmtegevhe vnivlkadvq gsveaisdsl lklstdevkv
 721    kiigsgvggi tetdatlaaa snailvgfnv radasarkvi eseslldlryy sviynlidev
 781    kaamsgmlsp elkqqiigla evrdvfkspk fgaiagcmvt egtikrhnpi rvlrdnvviy
 841    egeleslrrf kddvnevrng mecgigvkny ndvrvgdmie vfeiieiqrt ia
``` rpoA (accession no. CBW19477.1):
```
   1    mqgsvteflk prlvdieqvs sthakvtlep lergfghtlg nalrrillss mpgcavteve
  61    idgvlheyst kegvqedile illnlkglav rvqgkdevil tlnksgigpv taadithdgd
 121    veivkpqhvi chltdenasi smrikvqrgr gyvpastrih seederpigr llvdacyspv
 181    eriaynveaa rveqrtldlk lviemetngt idpeeairra atilaeqlea fvdlrdvrqp
 241    evkeekpefd pillrpvddl eltvrsancl kaeaihyigd lvqrtevell ktpnlgkksl
 301    teikdvlasr glslgmrlen wppasiade
``` rpoB (accession no. CBW20180.1):
```
   1    mvysytekkr irkdfgkrpq vldvpyllsi qldsfqkfie gdpeggygle aafrsvfpiq
  61    sysgnselqy vsyrlgepvf dvqecgirgv tysaplrvkl rlviyereap egtvkdikeq
 121    evymgeiplm tdngtfving tervivsqlh rspgvffdsd kgkthssgkv lynariipyr
 181    gswldfefdp kdnlfvridr rrklpatiil ralnytteqi ldlffekvvf eirdnklqme
 241    liperlrget asfdieangk vyvekgrrit arhirqlekd dikhievpve yiagkvvskd
 301    yvdestgeli caanmelsld llaklsgsgh krietlftnd ldhgpyiset vrvdptndrl
 361    salveiyrmm rpgepptrea aeslfenlff sedrydlsav grmkfnrsll rdeiegsgil
 421    skddiidvmk klidirngkg evddidhlgn rrirsvgema enqfrvglvr veravkerls
 481    lgdldtlmpq dminakpisa avkeffgssq lsqfmdqnnp lseithkrri salgpggltr
 541    eragfevrdv hpthygrvcp ietpegpnig linslsvyaq tneygfletp yrrvvdgvvt
 601    deihylsaie egnyviagan snlddeghfv edlvtcrskg esslfsrdqv dymdvstqqv
 661    vsvgaslipf lehddanral mganmqrgav ptlradkplv gtgmeravav dsgvtavakr
 721    ggtvqyvdas rivikvnede mypgeagidi ynitkytrsn qntcinqmpc vslgepverg
 781    dvladgpstd lgelalgqnm rvafmpwngy nfedsilvse rvvqedrftt ihigelacvs
 841    rdtklgpeei tadipnvgea alskldesgi vyigaevtgg dilvgkvtpk getqltpeek
 901    llraifgeka sdvkdsslry pngvsgtvid vqvftrdgve kdkraleiee mqlkqakkdl
 961    seelqileag lfsriravlv ssgveaekld klprdrwlel gltdeekqnq leglaegyde
1021    lkhefekkle akrrkitqgd dlapgvlkiv kvylavkrri qpgdkmagrh gnkgviskin
1081    piedmpyden gtpvdivinp lgvpsrmnig qilethlgma akgigdkina mlkqqqevak
1141    lrefiqrayd lgadvrqkvd lstfsddevl rlaenlrkgm piatpvfdga keaeikellk
1201    lgdlptsgqi tlfdgrtgeq ferpvtvgym ymlklnhlvd dkmharstgs yslvtqqplg
```

-continued

```
1261    gkagfggqrf gemevwalea ygaaytlqem ltvksddvng rtkmyknivd gnhqmepgmp 1321    esfnvllkei rslginiele de rpoC (accession no. CBW20181.1):
   1    mkdllkflka qtkteefdai kialaspdmi rswsfgevkk petinyrtfk perdglfcar 61    ifgpvkdyec lcgkykrlkh rgvicekcgv evtqtkvrre rmghielasp tahiwflksl 121    psriglllldm plrdiervly fesyvviegg mtnlergqil teeqyldale efgdefdakm 181    gaeaigallk smdleqecet lreelnetns etkrkkltkr iklleafvqs gnkpewmilt 241    vlpvlppdlr plvpldggrf atsdlndlyr rvinrnnrlk rlldlaapdi ivrnekrmlq 301    eavdalldng rrgraitgsn krplksladm ikgkqgrfrq nllgkrvdys grsvitvgpy 361    lrlhqcglpk kmalelfkpf iygklelrgl attikaakkm vereeavvwd ildevirehp 421    vllnraptlh rlgiqafepv liegkaiqlh plvcaaynad fdgdqmavhv pltleaqlea 481    ralmmstnni lspangepii vpsqdvvlgl yymtrdcvna kgegmvltgp keaeriyrag 541    laslharvkv riteyekden gefvahtslk dttvgrailw mivpkglpfs ivnqalgkka 601    iskmlntcyr ilglkptvif adqtmytgfa yaarsgasvg iddmvipekk heiiseaeae 661    vaeigegfqs glvtageryn kvidiwaaan drvskammdn lqtetvinrd gqeeqqvsfn 721    siymmadsga rgsaaqirql agmrglmakp dgsiietpit anfreglnvl qyfisthgar 781    kgladtalkt ansgyltrrl vdvaqdlvvt eddcgthegi lmtpviegg d vkeplrdrvl 841    grvtaedvlk pgtadilvpr ntllheqwcd lleansvdav kvrsvvscdt dfgvcahcyg 901    rdlarghiin kgeaigviaa qsigepgtql tmrtfhigga asraaaessi qvknkgsikl 961    snvksvvnss gklvitsrnt elklidefgr tkesykvpyg avmakgdgeq vaggetvanw 1021    dphtmpvite vsgfirftdm idgqtitrqt deltglsslv vldsaerttg gkdlrpalki 1081    vdaqgndvli pgtdmpaqyf lpgkaivqle dgvgissgdt laripqesgg tkditgglpr 1141    vadlfearrp kepailaeia givsfgketk gkrrlvitpv dgsdpyeemi pkwrqlnvfe 1201    gervergdvi sdgpeaphdi lrlrgvhavt ryivnevqdv yrlqgvkind khievivrqm 1261    lrkatiesag ssdflegeqv eysrvkianr eleangkvga tfsrdllgit kaslatesfi 1321    saasfqettr vlteaavagk rdelrglken vivgrlipag tgyayhqdrm rrraagegpa 1381    tpqvtaedas aslaellnag lggsdne holA (accession no. CBW16734.1):
   1    mirlypeqlr aqlneglraa ylllgndpll lqesqdairl aaasqgfeeh haftldpstd 61    wgslfslcqa mslfasrqtl vlqlpengpn aamneglatl sellhddlll ivrgnkltka 121    genaawytal adrsvqvscq tpeqaqlprw vaarakagnl qlddaanqll cycyegnlla 181    lagalerlsl lwpdgkltlp rvegavndaa hftpfhwvda llmgkskral hilqqlrleg 241    sepvillrtl grellllvnl krqsahtplr alfdkhrvwq nrrpmigdal qrlhpaqlrq 301    avqlltrtei tlkqdyggsv wadleglsll lchkaladvf idg dnaC (accession no. CBW20563.1):
   1    mknvgdlmqr lqkmmpahit pafktgeell awqkeggeir aaalarenra mkmqrtfnrs 61    girplhqncs fdnyrvecdg qmnalskarq yvdefdgnia sfvfsgkpgt gknhlaaaic 121    nelllrgksv liitvadims amkdtfsnre tseeqllndl snvdllvide igvqtesrye 181    kviingivdr rssskrptgm ltnsnmeemt kmlgervmdr mrlgnslwvn ftwdsyrsry 241    tgkey eng (EngA accession no. CBW18582.1):
   1    mvpvvalvgr pnvgkstlfn rltrtrdalv adfpgltrdr kygraevegr eficidtggi 61    dgtedgvetr maeqsllaie eadvvlfmvd araglmpade aiakhlrsre kptflvankt
```

-continued

```
121    dgldpdgavv  dfyslglgei  ypiaashgrg  vlsllehvll  pwmddvapqe  evdedaeywa 181    qfeaeqngee  apeddfdpqs  lpiklaivgr  pnvgkstltn  rilgeervvv  ydmpgttrds 241    iyipmerder  eyvlidtagv  rkrgkitdav  ekfsviktlq  aiedanvvll  vidaregisd 301    qdlsllgfil  nsgrslvivv  nkwdglsqev  keqvketldf  rlgfidfary  hfisalhgsg 361    vgnlfesvre  aydsstrrvs  tamltrimtm  avedhqpplv  rgrrvklkya  haggynppiv 421    vihgnqvkdl  pdsykrylmn  yfrkslevmg  tpiriqfkeg  enpyankrnt  ltptqmrkrk 481    rlmkhikksk EngB (accession no. CBW20039.1):
  1    mmsapdirhl  psdcgievaf  agrsnagkss  alntltnqks  lartsktpgr  tqlinlfevv 61    dgkrlvdlpg  ygyaevpeem  krkwqralge  ylekrqslqg  lvvlmdirhp  lkdldqqmiq 121    wavesniqvl  vlltkadkla  sgarkaglnm  vreavlafng  dvqveafssl  kkqgvdklrq 181    kldswfsela  pveeicidge
```

III. Therapeutic DNA, RNA and Peptides

The present invention delivers therapeutic DNA, RNA and/or peptides to cancer cells.

Gene silencing through RNAi (RNA-interference) by use of short interfering RNA (siRNA) can be used for therapeutic gene silencing. Short hairpin RNA (shRNA) transcribed from small DNA plasmids within the target cell has also been shown to mediate stable gene silencing and achieve gene knockdown at levels comparable to those obtained by transfection with chemically synthesized siRNA.

RNAi agents are agents that modulate expression of an RNA by a RNA interference mechanism. The RNAi agents employed in one embodiment of the subject invention are small ribonucleic acid molecules (also referred to herein as interfering ribonucleic acids), i.e., oligoribonucleotides, that are present in duplex structures, e.g., two distinct oligoribonucleotides hybridized to each other (e.g., an siRNA) or a single ribooligonucleotide that assumes a small hairpin formation to produce a duplex structure (e.g, shRNA).

dsRNA can be prepared according to any of a number of methods that are available in the art, including in vitro and in vivo methods, as well as by synthetic chemistry approaches. Single-stranded RNA can also be produced using a combination of enzymatic and organic synthesis or by total organic synthesis. The use of synthetic chemical methods enables one to introduce desired modified nucleotides or nucleotide analogs into the dsRNA.

In certain embodiments, instead of the RNAi agent being an interfering ribonucleic acid, e.g., an siRNA or shRNA as described above, the RNAi agent may encode an interfering ribonucleic acid, e.g., an shRNA, as described above. In other words, the RNAi agent may be a transcriptional template of the interfering ribonucleic acid. In these embodiments, the transcriptional template is typically a DNA that encodes the interfering ribonucleic acid. The DNA may be present in a vector, where a variety of different vectors are known in the art, e.g., a plasmid vector, a viral vector, etc.

Alternative the active agent may be a ribozyme. The term "ribozyme" as used herein for the purposes of specification and claims is interchangeable with "catalytic RNA" and means an RNA molecule that is capable of catalyzing a chemical reaction.

Exemplary target genes include, but are not limited to, EZH2 (accession number for human EZH2 mRNA is NM_004456), NIPP1 (accession number for human NIPP1 mRNA is NM_002713) and PP1 (accession numbers for human PP1 mRNA are PP1α mRNA: NM_002708; PP1β mRNA: NM_206876; PP1γ mRNA: NM_002710). EZH2, NIPP1 and PP1, would disrupt cancer cell processes and eliminate and/or diminish cancer stems cells. This will stop tumors from spreading/growing and prevent metastasis formation.

In another embodiment, the epigenetic target is at least one (e.g., mRNA) of NIPP1 (accession No. NM_002713); EZH2 (accession No. NM_004456); PP1α (accession No. NM_002708); PP1β (accession No. NM_206876); PP1γ (accession No. NM_002710); Suz12 (accession No. NM_015355); EED (accession No. NM_003797); EZH1 (accession No. NM_001991); RbAp48 (accession No. NM_005610); Jarid2 (accession No. NM_004973); YY1 (accession No. NM_003403); CBX2 (accession No. NM_005189); CBX4 (accession No. NM_003655); CBX6 (accession No. NM_014292); CBX7 (accession No. NM_175709); PHC1 (accession No. NM_004426); PHC2 (accession No. NM_198040); PHC3 (accession No. NM_024947); BMI1 (accession No. NM_005180); PCGF2 (accession No. NM_007144); ZNF134 (accession No. NM_003435); RING1 (accession No. NM_002931); RNF2 (accession No. NM_0072120; PHF1 (accession No. NM_024165); MTF2 (accession No. NM_007358); PHF19 (accession No. NM_001286840); SETD1A (accession No. XM_005255723); SETD1B (accession No. NM_015048); CXXC1 (accession No. NM_001101654); ASH2L (accession No. NM_004674); DPY30 (accession No. NM_032574); RBBP5 (accession No. NM_005057); WDR5 (accession No. NM_017588); KMT2A (accession No. NM_001197104); KMT2D (accession No. XM_006719616); KMT2B (accession No. NM_014727); KMT2C (accession No. NM_170606); KAT8 (accession No. NM_032188); KDM6A (accession No. NM_001291415); NCOA6 (accession No. NM_014071); PAGR1 (accession No. NM_024516); PAXIP1 (accession No. NM_007349); ASH1L (accession No. NM_018489); SMARCA2 (accession No. NM_003070); SMARCA4 (accession No. NM_001128844); BPTF (accession No. NM_182641); or SMARCA1 (accession No. NM_001282874).

NIPP1 (accession No. NM_002713):

```
   1    aaatgggagg gggagacgca agatggcggc agccgcgaac tccggctcta gcctcccgct
  61    gttcgactgc ccaacctggt gagtggcggc gcggccaggg ctagagtggc ccggccggag
 121    ctagcctggg ctggaagggc ggctcttttt ttacttttct gctgcgagcc gaacggctca
 181    gaaaccccgg aatggttgag gaaaaactgt ttgctgcacc gggccgggcg acgtgttgaa
 241    gaaccgagag cctggagccc aggcccagga actgaagaaa cccggggttg ggggctcaaa
 301    ggcgctcact taggcagccc ctttgagcga ttagccagtc gccggagcgc ttcgaggcct
 361    tggcccgaac ttacgcccaa ctcttgactg agtgcctggt gctctcgtgg agcatcgcat
 421    ctggcccctt cctgtacgtc ccgagcgcgc tcgagccagc cccggcccca accctacctc
 481    caagccccgc atccctctgt ggttgctgca tccctcgtgc ggcacttgtc tgtctgccac
 541    agagaatacg aggggcaggt aagcccctc ccggtttaca tctggatgta gtcaaaggag
 601    acaaactaat tgagaaactg attattgatg agaagaagta ttacttattt gggagaaacc
 661    ctgatttgtg tgactttacc attgaccacc agtcttgctc tcgggtccat gctgcacttg
 721    tctaccacaa gcatctgaag agagttttcc tgatagatct caacagtaaa cctgacagag
 781    ttcaacactg cccacaacaa gcggatttct accccttacca ttgaggaggg aaatctggac
 841    attcaaagac caaagaggaa gaggaagaac tcacgggtga cattcagtga ggatgatgag
 901    atcatcaacc cagaggatgt ggatccctca gttggtcgat tcaggaacat ggtgcaaact
 961    gcagtggtcc cagtcaagaa gaagcgtgtg gagggccctg ctccctggg cctggaggaa
1021    tcagggagca ggcgcatgca gaactttgcc ttcagcggag gactctacgg gggcctgccc
1081    cccacacaca gtgaagcagg ctcccagcca catggcatcc atgggacagc actcatcggt
1141    ggcttgccca tgccataccc aaaccttgcc cctgatgtgg acttgactcc tgttgtgccg
1201    tcagcagtga acatgaaccc tgcaccaaac cctgcagtct ataaccctga agctgtaaat
1261    gaacccaaga agaagaaata tgcaaaagag gcttggccag gcaagaagcc cacaccttcc
1321    ttgctgattt gatattttg gtcatggaga agggtgggat tgggtgggaa tggggtggaa
1381    gggtgatggg gagctaatga actaggaga aaaactttcc atgtgtgcg tatcgtcttt
1441    cagaatgtct cctggcatcc taaccatgta atatgacaat tggggtggg gttgaaatag
1501    cccataaaga cctgtcttca caacacttgc attgtagaga aaggcttctt atatccttt
1561    caatagactg ccctggctct ttcctaggcc ttccactacc tccttcttt ctcccacttt
1621    ctaggatcat ttttatgtaa agtcacatat cccaggccct caggttgaat ccagagctgt
1681    agaggttaca gtagcatcac cagccttggg ggtccagagc ctaatttata ttcactatcc
1741    ttccaagtcc cgggtagcag aagggttgcc atagatctca gtttgatcaa aaagaaggct
1801    tagaattctg cagttaagct gaggtttaaa ctaaaaaatg tttccttggg tcagtggttt
1861    tgaggtccag tagctaggct tttctctttt gtccttcctg ttggaatgaa acatttcga
1921    ttttccttca tctgtgactg gtgccataga cacaggttta tagttttaac ttacagtatt
1981    gtttgaaatt tacctgtttt tcttgtcaaa cctgagcact cctcctgctg aagtttctta
2041    tttaattcca gagtactgtc ctctactcta aggcattact tttaagtgta ttatgaaggc
2101    agtttcaaa ggatatgacc agttgggta attcaaatta aaaggaaaa gatttgttg
2161    gaagtaactg tgtctctaa gaggaattt tagatgtcag tttggaggct ctttcccccc
2221    tcaattgaga gctcttgtta ttcagagctc caagactaga cctggctaac aaacatagga
2281    gacaaagtta ggaaacattg atacaagctt tgtacagaga tttgtacatt tgtgtaatag
2341    gccttttcat gctttatgtg tagctttta cctgtaacct ttattacatt gtaaattaaa
```

-continued

```
2401  cgtaactttt gtcatttggg tgcaggctgt gaatttgtct ctcagtcact gattgccact
2461  gccatctgga aatgtttgct aaaggcacag tcactgggct tgggaggcaa tgctccatcc
2521  ccattatatt acaaataaag atgccctaaa tgagtgtg
```

EZH2 (accession No. NM_004456)

```
   1  ggcggcgctt gattgggctg gggggggccaa ataaaagcga tggcgattgg gctgccgcgt
  61  ttggcgctcg gtccggtcgc gtccgacacc cggtgggact cagaaggcag tggagccccg
 121  gcggcggcgg cggcggcgcg cggggcgac gcgcgggaac aacgcgagtc ggcgcgcggg
 181  acgaagaata atcatgggcc agactgggaa gaaatctgag aagggaccag tttgttggcg
 241  gaagcgtgta aaatcagagt acatgcgact gagacagctc aagaggttca gacgagctga
 301  tgaagtaaag agtatgttta gttccaatcg tcagaaaatt ttggaaagaa cggaaatctt
 361  aaaccaagaa tggaaacagc gaaggataca gcctgtgcac atcctgactt ctgtgagctc
 421  attgcgcggg actagggagt gttcggtgac cagtgacttg gattttccaa cacaagtcat
 481  cccattaaag actctgaatg cagttgcttc agtacccata atgtattctt ggtctcccct
 541  acagcagaat tttatggtgg aagatgaaac tgttttacat aacattcctt atatgggaga
 601  tgaagttta gatcaggatg gtactttcat tgaagaacta ataaaaaatt atgatgggaa
 661  agtacacggg gatagagaat gtgggtttat aaatgatgaa atttttgtgg agttggtgaa
 721  tgcccttggt caatataatg atgatgacga tgatgatgat ggagacgatc ctgaagaaag
 781  agaagaaaag cagaaagatc tggaggatca ccgagatgat aaagaaagcc gcccacctcg
 841  gaaatttcct tctgataaaa ttttttgaagc catttcctca atgtttccag ataagggcac
 901  agcagaagaa ctaaaggaaa atataaaga actcaccgaa cagcagctcc caggcgcact
 961  tcctcctgaa tgtaccccca acatagatgg accaaatgct aaatctgttc agagagagca
1021  aagcttacac tcctttcata cgcttttctg taggcgatgt tttaaatatg actgcttcct
1081  acatcgtaag tgcaattatt cttttcatgc aacacccaac acttataagc ggaagaacac
1141  agaaacagct ctagacaaca aaccttgtgg accacagtgt taccagcatt tggagggagc
1201  aaaggagttt gctgctgctc tcaccgctga gcggataaag accccaccaa aacgtccagg
1261  aggccgcaga agaggacggc ttcccaataa cagtagcagg cccagcaccc ccaccattaa
1321  tgtgctggaa tcaaaggata cagacagtga tagggaagca gggactgaaa cggggggaga
1381  gaacaatgat aaagaagaag aagagaagaa agatgaaact tcgagctcct ctgaagcaaa
1441  ttctcggtgt caaacaccaa taaagatgaa gccaaatatt gaacctctg agaatgtgga
1501  gtggagtggt gctgaagcct caatgtttag agtcctcatt ggcacttact atgacaattt
1561  ctgtgccatt gctaggttaa ttgggaccaa acatgtagac aggtgtatg agtttagagt
1621  caaagaatct agcatcatag ctccagctcc cgctgaggat gtggatactc tccaaggaa
1681  aaagaagagg aaacaccggt tgtgggctgc acactgcaga aagatacagc tgaaaaagga
1741  cggctcctct aaccatgttt acaactatca accctgtgat catccacggc agccttgtga
1801  cagttcgtgc ccttgtgtga tagcacaaaa ttttttgtgaa agttttgtc aatgtagttc
1861  agagtgtcaa aaccgctttc cgggatgccg ctgcaaagca cagtgcaaca ccaagcagtg
1921  cccgtgctac ctggctgtcc gagagtgtga ccctgacctc tgtcttactt gtggagccgc
1981  tgaccattgg acagtaaaa atgtgtcctg caagaactgc agtattcagc ggggctccaa
2041  aaagcatcta ttgctggcac catctgacgt ggcaggctgg gggatttta tcaaagatcc
2101  tgtgcagaaa aatgaattca tctcagaata ctgtgagag attatttctc aagatgaagc
2161  tgacagaaga gggaaagtgt atgataaata catgtgcagc tttctgttca acttgaacaa
```

-continued

```
2221    tgattttgtg gtggatgcaa cccgcaaggg taacaaaatt cgttttgcaa atcattcggt
2281    aaatccaaac tgctatgcaa aagttatgat ggttaacggt gatcacagga taggtatttt
2341    tgccaagaga gccatccaga ctggcgaaga gctgtttttt gattacagat acagccaggc
2401    tgatgccctg aagtatgtcg gcatcgaaag agaaatggaa atcccttgac atctgctacc
2461    tcctccccccc tcctctgaaa cagctgcctt agcttcagga acctcgagta ctgtgggcaa
2521    tttagaaaaa gaacatgcag tttgaaattc tgaatttgca aagtactgta agaataattt
2581    atagtaatga gtttaaaaat caactttta ttgccttctc accagctgca aagtgttttg
2641    taccagtgaa ttttgcaat aatgcagtat ggtacatttt tcaactttga ataaagaata
2701    cttgaacttg tccttgttga atc
```

PP1α (accession No. NM_002708)
```
   1    gcggggccgc gggccggggg cggactgggg cggcggaag gagagccagg ccggaaggag
  61    gctgccggag ggcgggaggc aggagcgggc caggagctgc tgggctggag cggcggcgcc
 121    gccatgtccg acagcgagaa gctcaacctg gactcgatca tcgggcgcct gctggaagtg
 181    cagggctcgc ggcctggcaa gaatgtacag ctgacagaga cgagatccg cggtctgtgc
 241    ctgaaatccc gggagatttt tctgagccag cccattcttc tggagctgga ggcacccctc
 301    aagatctgcg gtgacataca cggccagtac tacgaccttc tgcgactatt tgagtatggc
 361    ggtttccctc ccgagagcaa ctacctcttt ctgggggact atgtggacag gggcaagcag
 421    tccttggaga ccatctgcct gctgctggcc tataagatca gtaccccga gaacttcttc
 481    ctgctccgtg gaaccacga gtgtgccagc atcaaccgca tctatggttt ctacgatgag
 541    tgcaagagac gctacaacat caaactgtgg aaaaccttca ctgactgctt caactgcctg
 601    cccatcgcgg ccatagtgga cgaaaagatc ttctgctgcc acggaggcct gtccccggac
 661    ctgcagtcta tggagcagat tcggcggatc atgcggccca gatgtgcc tgaccagggc
 721    ctgctgtgtg acctgctgtg gtctgaccct gacaaggacg tgcagggctg gggcgagaac
 781    gaccgtggcg tctcttttac ctttggagcc gaggtggtgg ccaagttcct ccacaagcac
 841    gacttggacc tcatctgccg agcacaccag gtggtagaag acggctacga gttctttgcc
 901    aagcggcagc tggtgacact ttctcagct cccaactact gtggcgagtt tgacaatgct
 961    ggcgccatga tgagtgtgga cgagaccctc atgtgctctt ccagatcct caagcccgcc
1021    gacaagaaca aggggaagta cgggcagttc agtggcctga accctggagg ccgaccatc
1081    accccaccc gcaattccgc caaagccaag aaatagcccc cgcacaccac cctgtgcccc
1141    agatgatgga ttgattgtac agaaatcatg ctgccatgct gggggggggt caccccgacc
1201    cctcaggccc acctgtcacg gggaacatgg agccttggtg tatttttctt ttctttttt
1261    aatgaatcaa tagcagcgtc cagtccccca gggctgcttc ctgcctgcac ctgcggtgac
1321    tgtgagcagg atcctggggc cgaggctgca gctcagggca acggcaggcc aggtcgtggg
1381    tctccagccg tgcttggcct cagggctggc agccggatcc tggggcaacc catctggtct
1441    cttgaataaa ggtcaaagct ggattctcgc aaaaaaaaaa aaaaaaa
```

PP1β (accession No. NM_206876)
```
   1    gctgcgtgac gcggcggcgc gcaagggacg tgcggagtga gtggcgctgc gggtggggcc
  61    gtcggcggcg ctggtgagag aacgccgagc cgtcgccgca gcctccgccg ccgagaagcc
 121    cttgttcccg ctgctgggaa ggagagtctg tgccgacaag atggcggacg gggagctgaa
 181    cgtggacagc ctcatcaccc ggctgctgga ggtacgagga tgtcgtccag gaaagattgt
 241    gcagatgact gaagcagaag ttcgaggctt atgtatcaag tctcgggaga tctttctcag
 301    ccagcctatt cttttggaat tggaagcacc gctgaaaatt tgtggagata ttcatggaca
```

-continued

```
 361   atatacagat ttactgagat tatttgaata tggaggtttc ccaccagaag ccaactatct
 421   tttcttagga gattatgtgg acagaggaaa gcagtctttg gaaaccattt gtttgctatt
 481   ggcttataaa atcaaatatc cagagaactt ctttctctta agaggaaacc atgagtgtgc
 541   tagcatcaat cgcatttatg gattctatga tgaatgcaaa cgaagattta atattaaatt
 601   gtggaagacc ttcactgatt gttttaactg tctgcctata gcagccattg tggatgagaa
 661   gatcttctgt tgtcatggag gattgtcacc agacctgcaa tctatggagc agattcggag
 721   aattatgaga cctactgatg tccctgatac aggtttgctc tgtgatttgc tatggtctga
 781   tccagataag gatgtgcaag gctggggaga aaatgatcgt ggtgtttcct ttacttttgg
 841   agctgatgta gtcagtaaat ttctgaatcg tcatgattta gatttgattt gtcgagctca
 901   tcaggtggtg gaagatggat atgaattttt tgctaaacga cagttggtaa ccttattttc
 961   agccccaaat tactgtggcg agtttgataa tgctggtgga atgatgagtg tggatgaaac
1021   tttgatgtgt tcatttcaga tattgaaacc atctgaaaag aaagctaaat accagtatgg
1081   tggactgaat tctggacgtc ctgtcactcc acctcgaaca gctaatccgc cgaagaaaag
1141   gtgaagaaag gaattctgta aagaaaccat cagatttgtt aaggacatac ttcataatat
1201   ataagtgtgc actgtaaaac catccagcca tttgacaccc tttatgatgt cacaccttta
1261   acttaaggag acgggtaaag gatcttaaat tttttttctaa tagaaagatg tgctacactg
1321   tattgtaata agtatactct gttatagtca acaaagttaa atccaaattc aaaattatcc
1381   attaaagtta catcttcatg tatcacaatt tttaaagttg aaaagcatcc cagttaaact
1441   agatgtgata gttaaaccag atgaaagcat gatgatccat ctgtgtaatg tggttttagt
1501   gttgcttggt tgtttaatta ttttgagctt gttttgtttt tgtttgtttt cactagaata
1561   atggcaaata cttctaattt ttttccctaa acatttttaa aagtgaaata tgggaagagc
1621   tttacagaca ttcaccaact attattttcc cttgtttatc tacttagata tctgtttaat
1681   cttactaaga aaactttcgc ctcattacat taaaaaggaa ttttagagat tgattgtttt
1741   aaaaaaaaat acgcacattg tccaatccag tgattttaat catacagttt gactgggcaa
1801   actttacagc tgatagtgaa tattttgctt tatacaggaa ttgacactga tttggatttg
1861   tgcactctaa tttttaactt attgatgctc tattgtgcag tagcatttca tttaagataa
1921   ggctcatata gtattaccca actagttggt aatgtgatta tgtggtacct tggctttagg
1981   ttttcattcg cacggaacac cttttggcat gcttaacttc ctggtaacac cttcacctgc
2041   attggttttc tttttctttt ttctttcttt tttttttttt tttttttttt gagttgttgt
2101   ttgtttttag atccacagta catgagaatc ctttttttgac aagccttgga aagctgacac
2161   tgtctctttt tcctccctct atacgaagga tgtatttaaa tgaatgctgg tcagtgggac
2221   attttgtcaa ctatgggtat tgggtgctta actgtctaat attgccatgt gaatgttgta
2281   tacgattgta aggcttatgt cactaaagat ttttattctg attttttcat aatcaaaggt
2341   catatgatac tgtatagaca agctttgtag tgaagtatag tagcaataat ttctgtacct
2401   gatcaagttt attgcagcct ttctttcct atttctttt tttaagggt agtattaaca
2461   aatggcaatg agtagaaaag ttaacatgaa gattttagaa ggagagaact tacaggacac
2521   agatttgtga ttctttgact gtgacactat tggatgtgat tctaaaagct tttattgagc
2581   attgtcaaat ttgtaagctt catagggatg gacatcatat ctataatgcc cttctatatg
2641   tgctaccata gatgtgacat ttttgacctt aatatcgtct ttgaaaatgt taaattgaga
2701   aacctgttaa cttacatttt atgaattggc acattgtatt acttactgca agagatattt
```

-continued

```
2761  cattttcagc acagtgcaaa agttctttaa aatgcatatg tctttttttc taattccgtt
2821  ttgttttaaa gcacatttta aatgtagttt tctcatttag taaaagttgt ctaattgata
2881  tgaagcctga ctgattttt ttttccttac agtgagacat ttaagcacac attttattca
2941  catagatact atgtccttga catattgaaa tgattctttt ctgaaagtat tcatgatctg
3001  catatgatgt attaggttag gtcacaaagg ttttatctga ggtgatttaa ataacttcct
3061  gattggagtg tgtaagctga gcgatttcta ataaaatttt agttgtacac ttttagtagt
3121  catagtgaag caggtctaga aaataagcct ttggcaggga aaaagggcaa tgttgattaa
3181  tctcagtatt aaaccacatt aatctgtatc ccattgtctg cttttgtaa attcatccag
3241  gtcaagacta agtatgttgg ttaataggaa tccttttttt ttttttaaa gactaaatgt
3301  gaaaaaataa tcactactta agctaattaa tattggtcat taaatttaaa ggatggaaat
3361  ttatcatgtt taaaaattat tcaagcactc ttaaaaccac ttaaacagcc tccagtcata
3421  aaaatgtgtt ctttacaaat atttgcttgg caacacgact tgaaataaat aaaactttgt
3481  ttcttaggag aaaatgattc tgtaattcca gtgtcactaa tttatattgt tctttcctct
3541  gatttttttc aggttagtga ttttttttgta tacaatttaa tccaaatgtt atgacattca
3601  gaaatcatga acacagtag atatctgtta taatgtggtg tatcacatgg attataaagc
3661  aaagttatgg tcgatttcta ttcttgaaag aatcaactac agtgaatcct ttgcatttga
3721  agccttaaca tgcattgctt taattttgcc cagggacaaa ttttaataat cagcaagact
3781  ggtttgtgca aagcgttgag tcatcaggta tttagagcct agccagctac ccagtatcca
3841  tgctgccata tcccttcatt gtaaaaagta cctaaacatt cgtgaaatga ttttttttag
3901  ctgaaaaatg ctggcaagaa gaattttaaa gcttaaaata ggtggtaaat ttgaagtatg
3961  agtgtgttca cgagaaacat aggcttttca aaaaatttt tattcaaggc aaagcaagga
4021  acatcttgag atatgtctca agaatataaa gatgtattat tttaagccaa ggagctgaaa
4081  tatatctcag tttataaatt caggtatatt cttttttgtct ccatggcaac cataactttt
4141  gaaccaaaaa aaattgtttt tacatcttta tgctgaaaat gtgtttagat taggaatatg
4201  gtcgggctga atttgctgtt gctccctaac caaatccacc tcttgttttc cttgtgagtc
4261  catggctaaa tcaaagctgc ccctgagaag agacttaatc caagcctgat tgtactagtg
4321  gcatcactta gaagtaggct ttccctcttc ctagtagatc tcaatgtttt ataattcctt
4381  aaaacagctg aaaattggga caacatactt tacgcaatga acagtagtta ataggaaat
4441  aaactagttc catataagta tacacctaga gttttaatta cctttataat gtttcttaaa
4501  agtgaaactt agatacaatt gtgattggat acttagatac taagtgaaac ttagtgtaac
4561  aattttgatc tgttaaattg gatttttacat gtacatttga atgccagaat tctaaataa
4621  atcccctggt taggaaattt taaaagtcaa agcttgtttt cttcaaccac taccttctac
4681  attggttgac ttagaccgta agcttttaa gtttctcatt gtaatttacc ttctcatgca
4741  gattgctgat gttttattaa accttatttt tacaaaaatg aaaaaa
```

PP1γ (accession No. NM_002710)
```
  1  taaagaagtc ccggccgggc cgctgcactc cccgcgcgca tccgtgcgcc gcccgaggct
 61  gtctaaggag tcggcggcca ttttgttctt ctcgtggttc cagtggggag agaaggagga
121  agtagggagc ggggtggcag ggggggacc cgccgcggct gctgccaccc ccgccaccac
181  cgcctctgct cgtggcgtgg gaaaggaggt gtgagtcccg ggcgcgagcc ggcggcggcg
241  ccgctgcggg agggtcggcg gtgggaaggc gatggcggat ttagataaac tcaacatcga
301  cagcattatc caacggctgc tggaagtgag agggtccaag cctggtaaga atgtccagct
```

-continued

```
 361   tcaggagaat gaaatcagag gactgtgctt aaagtctcgt gaaatctttc tcagtcagcc
 421   tatcctacta gaacttgaag caccactcaa aatatgtggt gacatccatg gacaatacta
 481   tgatttgctg cgactttttg agtacggtgg tttcccacca gaaagcaact acctgtttct
 541   tggggactat gtggacaggg gaaagcagtc attggagacg atctgcctct tactggccta
 601   caaaataaaa tatcctgaga attttttttct tctcagaggg aaccatgaat gtgccagcat
 661   caacagaatt tatggatttt atgatgaatg taaaagaaga tacaacatta aactatggaa
 721   aactttcaca gactgtttta actgtttacc gatagcagcc atcgtggatg agaagatatt
 781   ctgctgtcat ggaggtttat caccagatct tcaatctatg agcagattc ggcgaattat
 841   gcgaccaact gatgtaccag atcaaggtct tctttgtgat cttttgtggt ctgaccccga
 901   taaagatgtc ttaggctggg gtgaaaatga cagaggagtg tccttcacat tggtgcaga
 961   agtggttgca aaatttctcc ataagcatga tttggatctt atatgtagag cccatcaggt
1021   ggttgaagat ggatatgaat tttttgcaaa gaggcagttg gtcactctgt tttctgcgcc
1081   caattattgc ggagagtttg acaatgcagg tgccatgatg agtgtggatg aaacactaat
1141   gtgttctttt cagattttaa agcctgcaga gaaaaagaag ccaaatgcca cgagacctgt
1201   aacgcctcca aggggtatga tcacaaagca agcaaagaaa tagatgtcgt tttgacactg
1261   cctagtcggg acttgtaaca tagagtatat aaccttcatt tttaagactg taatgtgtac
1321   tggtcagctt gctcagatag atctgtgttt gtgggggccc ttccttccat ttttgattta
1381   gtgaatggca tttgctggtt ataacagcaa atgaaagact cttcactcca aaaagaaaag
1441   tgttttgttt tttaattctc tgttcctttt gcaaacaatt ttaatgatgg tgttaaagct
1501   gtacacccca ggacagttta tcctgtctga ggagtaagtg tacaattgat ctttttaat
1561   tcagtacaac ccataatcat gtaaatgctc attttcttta ggacataaag agagccctag
1621   ggtgctctga atctgtacat gttcttgtca taaaatgcat actgttgata caaaccactg
1681   tgaacatttt ttatttgaga attttgtttc aaagggattg cttttttcctc tcattgtctt
1741   gttatgtaca aactagtttt tatagctatc aacattagga gtaactttca accttgccag
1801   catcactggt atgatgtata tttaattaaa gcacactttt ccccgaccgt atacttaaaa
1861   tgacaaagcc attctttttaa atatttgtga ctcttttccta aagccaaagt ttctgttgaa
1921   ttatgttttg acacacccct aagtacaagg tggtatggtt gtatacacat gctgccttct
1981   tggggattca aaaacaggtt tttgatttttg aatagcaatt agtgatatag tgctgtttaa
2041   gctactaacg ataaaaggta ataacatttt atacaatttc catatagtct attcattaag
2101   taatcttttt acagttgcat caggcctgaa cccgtccatt cagaaagctt caaattatag
2161   aaacaatact gttctatacg agtgaccgat tatgctttct ttggcctaca ttctttattc
2221   tgcggtgaag ttgaggctta aagttaaaa caaggaact aacttactgt ccaccagttt
2281   atacagaact cacagtacct atgactttt taaactaaga tctgttaaaa aagaaatctg
2341   tttcaacaga tgaccgtgta caataccgtg tggtgaaaat gaattcagac ttattaaatg
2401   atgaacttgt taaatcttct cagtgtctat ttatcagcac aatacacaca ggagaactgt
2461   tgatggcata ttgaatagat tttcctgaat aaattgctct ggaaaccaca caaaaaaaaa
2521   aaaaaa
```

Suz12 (accession No. NM_015355):

```
   1   ggtgagcggc ctccgaagcg gagcggggct ctgaggagac acttttttttt tcctccctcc
  61   ttccctcctc tcctcctccc ttcccttccc ctctcctccc ctctctcctc cttcccccct
 121   cggtccgccg gagcctgctg gggcgagcgg ttggtattgc aggcgcttgc tctccggggc
```

-continued

```
 181   cgcccggcgg gtagctggcg gggggaggag gcaggaaccg cgatggcgcc tcagaagcac
 241   ggcggtgggg gaggggcgg ctcggggccc agcgcgggt ccggggagg cggcttcggg
 301   ggttcggcgg cggtggcggc ggcgacggct tcgggcggca atccggcgg cgggagctgt
 361   ggagggggtg gcagttactc ggcctcctcc tcctcctccg cggcggcagc ggcgggggct
 421   gcggtgttac cggtgaagaa gccgaaaatg gagcacgtcc aggctgacca cgagcttttc
 481   ctccaggcct tgagaagcc aacacagatc tatagatttc ttcgaactcg gaatctcata
 541   gcaccaatat ttttgcacag aactcttact tacatgtctc atcgaaactc cagaacaaac
 601   atcaaaagga aaacatttaa agttgatgat atgttatcaa agtagagaa atgaaagga
 661   gagcaagaat ctcatagctt gtcagctcat ttgcagctta cgtttactgg tttcttccac
 721   aaaaatgata agccatcacc aaactcagaa atgaacaaa attctgttac cctggaagtc
 781   ctgcttgtga agtttgcca caaaaaaga aaggatgtaa gttgtccaat aaggcaagtt
 841   cccacaggta aaagcaggt gcctttgaat cctgacctca atcaaacaaa acccgaaat
 901   ttcccgtccc ttgcagtttc agtaatgaa tttgaaccta gtaacagcca tatggtgaag
 961   tcttactcgt tgctatttag agtgactcgt ccaggaagaa gagagtttaa tggaatgatt
1021   aatggagaaa ccaatgaaaa tattgatgtc aatgaagagc ttccagccag aagaaaacga
1081   aatcgtgagg atggggaaaa gacatttgtt gcacaaatga cagtatttga taaaaacagg
1141   cgcttacagc ttttagatgg ggaatatgaa gtagccatgc aggaaatgga agaatgtcca
1201   ataagcaaga aaagagcaac atgggagact attcttgatg gaagaggct gcctccattc
1261   gaaacatttt ctcagggacc tacgttgcag ttcactcttc gttggacagg agagaccaat
1321   gataaatcta cggctcctat tgccaaacct cttgccacta gaaattcaga gagtctccat
1381   caggaaaaca agcctggttc agttaaacct actcaaacta ttgctgttaa agaatcattg
1441   actacagatc tacaaacaag aaaagaaag gatactccaa atgaaaaccg acaaaaatta
1501   agaatatttt atcagtttct ctataacaac aatacaaggc aacaaactga agcaagagat
1561   gacctgcatt gcccttggtg tactctgaac tgccgcaaac tttatagttt actcaagcat
1621   cttaaactct gccatagcag atttatcttc aactatgttt atcatccaaa aggtgctagg
1681   atagatgttt ctatcaatga gtgttatgat ggctcctatg caggaaatcc tcaggatatt
1741   catcgccaac ctggatttgc ttttagtcgc aacggaccag ttaagagaac acctatcaca
1801   catattcttg tgtgcaggcc aaaacgaaca aaagcaagca tgtctgaatt tcttgaatct
1861   gaagatgggg aagtagaaca gcaaagaaca tatagtagtg ccacaatcg tctgtatttc
1921   catagtgata cctgcttacc tctccgtcca caagaaatgg aagtagatag tgaagatgaa
1981   aaggatcctg aatggctaag agaaaaaacc attacacaa ttgaagagtt ttctgatgtt
2041   aatgaaggag agaaagaagt gatgaaactc tggaatctcc atgtcatgaa gcatgggttt
2101   attgctgaca atcaaatgaa tcatgcctgt atgctgtttg tagaaaatta tggacagaaa
2161   ataattaaga agaatttatg tcgaaacttc atgcttcatc tagtcagcat gcatgacttt
2221   aatcttatta gcataatgtc aatagataaa gctgttacca agctccgtga aatgcagcaa
2281   aaattagaaa aggggaatc tgcttcccct gcaaacgaag aaataactga agaacaaaat
2341   gggacagcaa atggatttag tgaaattaac tcaaaagaga agctttgga aacagatagt
2401   gtctcagggg tttcaaaaca gagcaaaaaa caaaaactct gaaagctct aaccccatgt
2461   tatggacaaa cactgaaatt acattttagg gaattcatcc tctaagaatt atgttttgt
2521   ttttaatcat atgttccaaa caggcactgt tagatgaagt aaatgatttc aacaaggata
2581   tttgtatcag ggttctactt cacttcatta tgcagcatta catgtatatc acttttattg
```

-continued

```
2641    atgtcattaa aacattctgt actttaagca tgaaaagcaa tatttcaaag tatttttaaa
2701    ctcaacaaat gtcatcaaat atgttgaatt gatctagaaa ttatttcata tataaatcag
2761    aatttttttg catttatgaa cggctgtttt tctactttgt aattgtgaga cattttcttg
2821    gggagggaaa attggaatgg ttccctttt tagaaattga agtggtcttc atatgtcaac
2881    tacagaaaag gaaaaaaata gaaattgaag gattttttatg aaattatatt gcattactat
2941    ttgcagtcaa actttgatcc ttgtttttga aatcatttgt caattcgaa tgaaaaatta
3001    taatgtaatt ttacattaca taagttcctt ttacaattaa aaaatagcac ttcttcatct
3061    tatgcctgtt tgagaagata ttaaattttc acattgttga cagtgaaatg ctatgttggt
3121    ttataagatt acagaccatt tgttttcatg tggataattt tagtgcattg ctcacccggt
3181    atgttttttt tttttaactt gaacattttg cttgttttgt ttttcttttt taattagata
3241    atcacacgga aaattaagct gttcatatct ttaaattagg attgcaaacc aaggaaagaa
3301    cgcatttgag attttaagat gtcacttata aggggagaag tgttcttaaa aagtcaacca
3361    gaaaactgtt atgcctttta tttgtttgca aggatgtctt tgtaatgtgt ttcatgaata
3421    gaatatccaa tagagataag ctgacttgaa tcattttgag caattttgcc ctgtgttata
3481    tgtgtttcac gcacatattt gcagttggat tttctccaac agaaagtgga ttcactactg
3541    gcacattaac aagcaccaat aggttttat tccaactccg agcactgtgg ttgagtaaca
3601    tcacctcaat tttttattat ccttaaagat attgcatttt catattcttt atttataaag
3661    gatcaatgct gctgtaaata caggtatttt taattttaaa atttcattcc accaccatca
3721    gatgcagttc cctattttgt ttaatgaagg gatatataag ctttctaatg gtgtcttcag
3781    aaatttataa aatgtaaata ctgatttgac tggtctttaa gatgtgttta actgtgaggc
3841    tatttaacga atagtgtgga tgtgatttgt catccagtat taagttctta gtcattgatt
3901    tttgtgttta aaaaaaaata ggaaagaggg aaactgcagc tttcattaca gattccttga
3961    ttggtaagct ctccaaatga tgagttctag taaactctga ttttttgcctc tggatagtag
4021    atctcgagcg tttatctcgg gctttaattt gctaaagctg tgcacatatg taaaaaaaaa
4081    aaaaaaaaga ttattttagg ggagatgtag gtgtagaatt attgcttatg tcatttctta
4141    agcagttatg ctcttaatgc ttaaaagaag gctagcattg tttgcacaaa aagttggtga
4201    ttcccacccc aaatagtaat aaaaattactt ctgttgagta aactttttat gtcatcgtaa
4261    aagctgaaaa aatcccttg ttctatttta taaaaaagt gcttttctat atgtacccctt
4321    gataacagat tttgaagaaa tcctgtaaga tgataaagca tttgaatggt acagtagatg
4381    taaaaaaaat tcagtttaaa agaacatttg ttttttacatt aaatgtttat ttgaaatcaa
4441    atgattttgt acataaagtt caataatata aaagctg
```

EED (accession No. NM_003797):

```
  1    cgctttgaaa tccaccctgg gattcggaaa ccgggtagaa aactacctgg ttcagcaaac
 61    gagaattcaa acagaggagg ggcttggagg aggcgggttt cgacgaaccc agcgcaagag
121    tacgccacgg cgcctgcgca tcccctgacg ggtactttcc attcgccaga tgggggaagc
181    caggggggaag caggttactg ttttttgcatt tctatcttca aggaagaatt aggttatgaa
241    tagttccgtg aatagtcagg aagcgctgtc ctccaagttc aagattaagg aaacgtggca
301    tgcacagcta aagcaagagg tgacgtcttg tatcttcccc cgttcctgg acattggtg
361    gtgtagccca ttccacagac tttcgctccc tagcagcggg tcggagatcg aaggaacggg
421    ccaattgcgg ctgaaacgtc tttggaagga ggaaggggt gagggagcat cccttttgagt
481    ttcgcctctt ctcgaggcgg tggtgggaag ggagacatac ttaatactgc cctcttaatc
```

-continued

```
 541  caacggacct tacatcgtgt agactgccgg gagggcggcg ggaaagggc aagacgggag
 601  ttggggaagg gaaggagcca ggaagccgcg cggagggcg cgcgcgcgcg ccccttttc
 661  agcagtgtgg cggggtcgca cgcacgcccg cctcggcggc tgggcgcgat ttgcgacagt
 721  ggggggggcg gtggaggtgg cggcggcagc ggcaactttg cggcaagctc gggccgggct
 781  tgcttgacgg cggtgtggcg gaggccccgc cccaggcggc aggaacctgg agggaggcgg
 841  aggaatatgt ccgagaggga agtgtcgact gcgccggcgg gaacagacat gcctgcggcc
 901  aagaagcaga agctgagcag tgacgagaac agcaatccag acctctctgg agacgagaat
 961  gatgacgctg tcagtataga aagtggtaca aacactgaac gccctgatac acctacaaac
1021  acgccaaatg cacctggaag gaaaagttgg ggaaagggaa aatggaagtc aaagaaatgc
1081  aaatattctt tcaaatgtgt aaatagtctc aaggaagatc ataaccaacc attgtttgga
1141  gttcagttta actggcacag taaagaagga gatccattag tgtttgcaac tgtaggaagc
1201  aacagagtta ccttgtatga atgtcattca caaggagaaa tccggttgtt gcaatcttac
1261  gtggatgctg atgctgatga aaacttttac acttgtgcat ggacctatga tagcaatacg
1321  agccatcctc tgctggctgt agctggatct agaggcataa ttaggataat aaatcctata
1381  acaatgcagt gtataaagca ctatgttggc catggaaatg ctatcaatga gctgaaattc
1441  catccaagag atccaaatct tctcctgtca gtaagtaaag atcatgcttt acgattatgg
1501  aatatccaga cggacactct ggtggcaata tttggaggcg tagaagggca cagagatgaa
1561  gttctaagtg ctgattatga tcttttgggt gaaaaataa tgtcctgtgg tatggatcat
1621  tctcttaaac tttggaggat caattcaaag agaatgatga atgcaattaa ggaatcttat
1681  gattataatc caaataaaac taacaggcca tttatttctc agaaaatcca ttttcctgat
1741  ttttctacca gagacataca taggaattat gttgattgtg tgcgatggtt aggcgatttg
1801  atactttcta gtcttgtga aaatgccatt gtgtgctgga acctggcaa gatggaagat
1861  gatatagata aaattaaacc cagtgaatct aatgtgacta ttcttgggcg atttgattac
1921  agccagtgtg acatttggta catgaggttt tctatggatt tctggcaaaa gatgcttgca
1981  ttgggcaatc aagttggcaa actttatgtt tgggatttag aagtagaaga tcctcataaa
2041  gccaaatgta caacactgac tcatcataaa tgtggtgctg ctattcgaca aaccagtttt
2101  agcagggata gcagcattct tatagctgtt tgtgatgatg ccagtatttg gcgctgggat
2161  cgacttcgat aaaatacttt tgcctaatca aaattagagt gtgtttgttg tctgtgtaaa
2221  atagaattaa tgtatcttgc tagtaagggc acgtagagca tttagagttg tctttcagca
2281  ttcaatcagg ctgagctgaa tgtagtgatg tttacattgt ttacattctt tgtactgtct
2341  tcctgctcag actctactgc ttttaataaa aatttatttt tgtaaagctg tgtgtttagt
2401  tactttcatt gtggtgaaaa aaagttaaaa gtaataaaat tatgccttat cttttaaaa
2461  aaaaaaaaaa aaaaaa
```

EZH1 (accession No. NM_001991):
```
   1  gcgcatgcgt cctagcagcg ggacccgcgg ctcgggatgg aggctggaca cctgttctgc
  61  tgttgtgtcc tgccattctc ctgaagaaca gaggcacact gtaaaaccca acacttcccc
 121  ttgcattcta taagattaca gcaagatgga aataccaaat cccctacct ccaaatgtat
 181  cacttactgg aaaagaaaag tgaaatctga atacatgcga cttcgacaac ttaaacggct
 241  tcaggcaaat atgggtgcaa aggctttgta tgtggcaaat tttgcaaagg ttcaagaaaa
 301  aacccagatc ctcaatgaag aatggaagaa gcttcgtgtc caacctgttc agtcaatgaa
 361  gcctgtgagt ggacacccctt ttctcaaaaa gtgtaccata gagagcattt tcccgggatt
```

-continued

```
 421   tgcaagccaa catatgttaa tgaggtcact gaacacagtt gcattggttc ccatcatgta
 481   ttcctggtcc cctctccaac agaactttat ggtagaagat gagacggttt tgtgcaatat
 541   tccctacatg ggagatgaag tgaagaaga agatgagact tttattgagg agctgatcaa
 601   taactatgat gggaaagtcc atggtgaaga agagatgatc cctggatccg ttctgattag
 661   tgatgctgtt tttctggagt tggtcgatgc cctgaatcag tactcagatg aggaggagga
 721   agggcacaat gacacctcag atggaaagca ggatgacagc aaagaagatc tgccagtaac
 781   aagaaagaga aagcgacatg ctattgaagg caacaaaaag agttccaaga aacagttccc
 841   aaatgacatg atcttcagtg caattgcctc aatgttccct gagaatggtg tcccagatga
 901   catgaaggag aggtatcgag aactaacaga gatgtcagac cccaatgcac ttccccctca
 961   gtgcacaccc aacatcgatg gccccaatgc caagtctgtg cagcgggagc aatctctgca
1021   ctccttccac acactttttt gccggcgctg ctttaaatac gactgcttcc ttcaccctt
1081   tcatgccacc cctaatgtat ataaacgcaa gaataaagaa atcaagattg aaccagaacc
1141   atgtggcaca gactgcttcc ttttgctgga aggagcaaag gagtatgcca tgctccacaa
1201   cccccgctcc aagtgctctg gtcgtcgccg gagaaggcac cacatagtca gtgcttcctg
1261   ctccaatgcc tcagcctctg ctgtggctga gactaaagaa ggagacagtg acagggacac
1321   aggcaatgac tgggcctcca gttcttcaga ggctaactct cgctgtcaga ctcccacaaa
1381   acagaaggct agtccagccc cacctcaact ctgcgtagtg aagcaccct cggagcctgt
1441   ggaatggact ggggctgaag aatctctttt tcgagtcttc catggcacct acttcaacaa
1501   cttctgttca atagccaggc ttctggggac caagacgtgc aagcaggtct ttcagtttgc
1561   agtcaaagaa tcacttatcc tgaagctgcc aacagatgag ctcatgaacc cctcacagaa
1621   gaagaaaaga aagcacagat tgtgggctgc acactgcagg aagattcagc tgaagaaaga
1681   taactcttcc acacaagtgt acaactacca accctgcgac cacccagacc gccctgtga
1741   cagcaccttgc ccctgcatca tgactcagaa tttctgtgag aagttctgcc agtgcaaccc
1801   agactgtcag aatcgtttcc ctggctgtcg ctgtaagacc cagtgcaata ccaagcaatg
1861   tccttgctat ctggcagtgc gagaatgtga ccctgacctg tgtctcacct gtggggcctc
1921   agagcactgg gactgcaagg tggtttcctg taaaaactgc agcatccagc gtggacttaa
1981   gaagcacctg ctgctggccc cctctgatgt ggccggatgg gcaccttca taaaggagtc
2041   tgtgcagaag aacgaattca tttctgaata ctgtggtgag ctcatctctc aggatgaggc
2101   tgatcgacgc ggaaaggtct atgacaaata catgtccagc ttcctcttca acctcaataa
2161   tgattttgta gtggatgcta ctcggaaagg aaacaaaatt cgatttgcaa atcattcagt
2221   gaatcccaac tgttatgcca aagtggtcat ggtgaatgga gaccatcgga ttgggatctt
2281   tgccaagagg gcaattcaag ctggcgaaga gctcttcttt gattacaggt acagccaagc
2341   tgatgctctc aagtacgtgg ggatcgagag ggagaccgac gtcctttagc cctcccaggc
2401   cccacggcag cacttatggt agcggcactg tcttggcttt cgtgctcaca ccactgctgc
2461   tcgagtctcc tgcactgtgt ctcccacact gagaaacccc caacccact ccctctgtag
2521   tgaggcctct gccatgtcca gagggcacaa aactgtctca atgagagggg agacagaggc
2581   agctagggct tggtctccca ggacagagag ttacagaaat gggagactgt ttctctggcc
2641   tcagaagaag cgagcacagg ctggggtgga tgacttatgc gtgatttcgt gtcggctccc
2701   caggctgtgg cctcaggaat caacttaggc agttcccaac aagcgctagc ctgtaattgt
2761   agctttccac atcaagagtc cttatgttat tgggatgcag gcaaacctct gtggtcctaa
```

```
                                    -continued
2821   gacctggaga ggacaggcta agtgaagtgt ggtccctgga gcctacaagt ggtctgggtt
2881   agaggcgagc ctggcaggca gcacagactg aactcagagg tagacaggtc accttactac
2941   ctcctccctc gtggcagggc tcaaactgaa agagtgtggg ttctaagtac aggcattcaa
3001   ggctggggga aggaaagcta cgccatcctt ccttagccag agagggagaa ccagccagat
3061   gatagtagtt aaactgctaa gcttgggccc aggaggcttt gagaaagcct tctctgtgta
3121   ctctggagat agatggagaa gtgttttcag attcctggga acagacacca gtgctccagc
3181   tcctccaaag ttctggctta gcagctgcag gcaagcatta tgctgctatt gaagaagcat
3241   taggggtatg cctggcaggt gtgagcatcc tggctcgctg gatttgtggg tgtttttcagg
3301   ccttccattc cccatagagg caaggcccaa tggccagtgt tgcttatcgc ttcagggtag
3361   gtgggcacag gcttggacta gagaggagaa agattggtgt aatctgcttt cctgtctgta
3421   gtgcctgctg tttggaaagg gtgagttaga atatgttcca aggttggtga ggggctaaat
3481   tgcacgcgtt taggctggca ccccgtgtgc agggcacact ggcagagggt atctgaagtg
3541   ggagaagaag caggtagacc acctgtccca ggctgtggtg ccaccctctc tggcattcat
3601   gcagagcaaa gcactttaac catttctttt aaaaggtcta tagattgggg tagagtttgg
3661   cctaaggtct ctagggtccc tgcctaaatc ccactcctga gggaggggga agaagagagg
3721   gtgggagatt ctcctccagt cctgtctcat ctcctgggag aggcagacga gtgagtttca
3781   cacagaagaa tttcatgtga atggggccag caagagctgc cctgtgtcca tggtgggtgt
3841   gccgggctgg ctgggaacaa ggagcagtat gttgagtaga aagggtgtgg gcgggtatag
3901   attggcctgg gagtgttaca gtagggagca ggcttctccc ttctttctgg gactcagagc
3961   cccgcttctt cccactccac ttgttgtccc atgaaggaag aagtgggggtt cctcctgacc
4021   cagctgcctc ttacggtttg gtatgggaca tgcacacaca ctcacatgct ctcactcacc
4081   acactggagg gcacacacgt accccgcacc cagcaactcc tgacagaaag ctcctcccac
4141   ccaaatgggc caggcccag catgatcctg aaatctgcat ccgccgtggt ttgtattcat
4201   tgtgcatatc agggataccc tcaagctgga ctgtgggttc caaattactc atagaggaga
4261   aaaccagaga aagatgaaga ggaggagtta ggtctatttg aaatgccagg ggctcgctgt
4321   gaggaatagg tgaaaaaaaa cttttcacca gcctttgaga gactagactg accccaccct
4381   tccttcagtg agcagaatca ctgtggtcag tctcctgtcc cagcttcagt tcatgaatac
4441   tcctgttcct ccagtttccc atcctttgtc cctgctgtcc cccacttttta aagatgggtc
4501   tcaaccccctc cccaccacgt catgatggat ggggcaaggt ggtggggact aggggagcct
4561   ggtatacatg cggcttcatt gccaataaat ttcatgcact ttaaagtcct gtggcttgtg
4621   acctcttaat aaagtgttag aatccaaaaa aaaa
RbAp48 (accession No. NM_005610):
   1   gctcccattg gctgatgttg gcgcgaaggt gcgcgagtca gccctcgcgc tgggggcgca
  61   ggaaacaata gaggccgcgc gcacagagcg agctcttgca gcctccccgc cctcccgca
 121   acgctcgacc ccaggattcc cccggctcgc ctgcccgcca tggccgacaa ggaagcagcc
 181   ttcgacgacg cagtggaaga acgagtgatc aacgaggaat acaaaatatg gaaaagaac
 241   accccttttc tttatgattt ggtgatgacc catgctctgg agtggcccag cctaactgcc
 301   cagtggctcc cagatgtaac cagaccagaa gggaaagatt tcagcattca tcgacttgtc
 361   ctggggacac acacatcgga tgaacaaaac catcttgtta tagccagtgt gcagctccct
 421   aatgatgatg ctcagtttga tgcgtcacac tacgacagtg agaaaggaga atttggaggt
 481   tttggttcag ttagtggaaa aattgaaata gaaatcaaga tcaaccatga aggagaagta
```

-continued

```
 541   aacagggccc gttatatgcc ccagaaccct tgtatcatcg caacaaagac tccttccagt
 601   gatgttcttg tttttgacta tacaaaacat ccttctaaac cagatccttc tggagagtgc
 661   aacccagact tgcgtctccg tggacatcag aaggaaggct atgggctttc ttggaaccca
 721   aatctcagtg ggcacttact tagtgcttca gatgaccata ccatctgcct gtgggacatc
 781   agtgccgttc caaaggaggg aaaagtggta gatgcgaaga ccatctttac agggcatacg
 841   gcagtagtag aagatgtttc ctggcatcta ctccatgagt ctctgtttgg gtcagttgct
 901   gatgatcaga aacttatgat tgggatact cgttcaaaca atacttccaa accaagccac
 961   tcagttgatg ctcacactgc tgaagtgaac tgccttctt tcaatcctta tagtgagttc
1021   attcttgcca caggatcagc tgacaagact gttgccttgt gggatctgag aaatctgaaa
1081   cttaagttgc attcctttga gtcacataag gatgaaatat tccaggttca gtggtcacct
1141   cacaatgaga ctattttagc ttccagtggt actgatcgca gactgaatgt ctgggattta
1201   agtaaaattg gagaggaaca atccccagaa gatgcagaag acgggccacc agagttgttg
1261   tttattcatg gtggtcatac tgccaagata tctgatttct cctggaatcc caatgaacct
1321   tgggtgattt gttctgtatc agaagacaat atcatgcaag tgtggcaaat ggcagagaac
1381   atttataatg atgaagaccc tgaaggaagc gtggatccag aaggacaagg gtcctagata
1441   tgtctttact tgttgtgatt ttagactccc ctttttttctt ctcaaccctg agagtgattt
1501   aacactggtt ttgagacaga ctttattcag ctatccctct atataatagg taccaccgat
1561   aatgctatta gcccaaaccg tgggtgtttt ctaaatatta ataggggggc ttgattcaac
1621   aaagccacag acttaacgtt gaaattttct tcaggaattt tctagtaacc caggtctaaa
1681   gtagctacag aaaggggaat attatgtgtg attattttc ttcttatgct atatccccaa
1741   gttttcaga ctcatttaag taaaggctag agtgagtaag gaatagagcc aaatgaggta
1801   ggtgtctgag ccatgaagta taaatactga aagatgtcac ttttattcag gaaatagggg
1861   gagattcaag tcatatagat tcctactcga aaatcttgac acctgacttt ccaggatgca
1921   cattttcata cgtagaccag tttcctcttg gtttcttcag ttaagtcaaa caacacgtt
1981   cctctttccc catatattca tatattttg ctcgttagtg tatttcttga gctgttttca
2041   tgttgtttat ttcctgtctg tgaaatggtg tttttttttt tgttgttggt tttttttttt
2101   tttttttaa cttgggacca ccaagttgta aagatgtatg tttttacctg acagttatac
2161   cacaggtaga ctgtcaagtt gagaagagtg aatcaataac ttgtatttgt tttaaaaatt
2221   aaattaatcc ttgataagag ttgctttttt tttttaggag ttagtccttg accactagtt
2281   tgatgccatc tccattttgg gtgacctgtt tcaccagcag gcctgttact ctccatgact
2341   aactgtgtaa gtgcttaaaa tggaataaat tgcttttcta cataacccca tgctgatggg
2401   ttttatttag tataaaacat ccatcaaaca ccagtctctg gcttctagaa gagtccttca
2461   gatgacagtt gttgtccatg gtctttgact atcaagagca gaattaaatg taatagtccc
2521   agagctgtag aaaagaactt tactccttcc cagggaaagt gaaagacata aaacactgaa
2581   tcagaggtgg cacagattag tctttgataa ggtaacgttt ctttgaagtc tatctgtaga
2641   gaactacatg gacttccaag agtgtcaaag gcagtgtggt agagagaatt taaggcaaga
2701   tttaaatttg gaaaggtgc ttgaacctttt tctcagaggt tttatttccc cagtatgttt
2761   ttcactgggg cctttactta ggttagaaat aataggcttt gaaggcctct atcaccagat
2821   gcaataacca gataaaaattc ctgttttttc ccaatcgctt agttttttgt tgttgttgtt
2881   ttttaactga gtagatcatt ctgacccaga actactttca tgaggtaaga tcttgggaa
2941   aatctgaata gcgttaacca ttagattcaa atctcaaatg gtttcttttc aagtctagtt
```

-continued

```
3001  gttttagagt atagtgagaa ataccttgac acaattttaa gagtaaacta tatgggtcag
3061  catatccttg aacaaaaagt agactttgta aaagtattca tttaaattct aacactcgtg
3121  gcacaaaaga atggaaattg taaacccatg taatggaaat tggctatctt tttgacccca
3181  catgtgcccc tcaaaaatgt ttttggtttg ggtcaacaca aggcaagata cattctttaa
3241  aatactccca gatgtgtcca tacattcatc cttcactcag tgcatatgtg agggttgttg
3301  ctggaagaca ggaggctcat ctttcctttc cttggtgcat tgagatcagt atcaacagca
3361  gatgaaatag aatccagcaa agagttgaca tgttctgcct ccggccaact ctagaatctt
3421  tttaagcagg tcagccagta tttgcaactt ccacaggatg aattgcttgc caagtttctg
3481  gcactcttgt ctggttggaa gagtacatcc aaagggtact tagtgatcct ttgctaagaa
3541  gttttttgct gtttccgggt tacagatttg gccatatatt tctaaacagc ccctgtaaag
3601  ttgaaagaaa aagtttataa cagtgaactt ctgaggttta gttactgcag gctttgttga
3661  gaagagattg ttacagtgtg atttatggat gatcagggat gactttcccc tagcaaatat
3721  ttggatgcct cctgtttgtc aaatagaatg aatggtgatg gtgatgggag ggatagttaa
3781  acgttttctc tgctaggtta acttcttaca ggtataatta caatgcctga aattctgtag
3841  tttcatttct ttggattagt cgttgtcttt tccagattgt acacaatctg atcaacacaa
3901  aggtagttag tagatcatta acctcaattg caaggttata atttctcaaa cattaagcat
3961  attatcagtc atgtggattc aaacacagta taagaaaatc ctcaaggctg ggtgtgatgg
4021  cttatgcctg taatcccagc tacttagcag gctgaggcag gagtattgtt tgaacccagg
4081  aggcagagtt gcagtgagcc aagatcgtgc cactactcca gcctgggcaa aatagcaaga
4141  cccgaccccc catctctact aaaaagaaat ttaaaaaaat aaatcctag aaaattagaa
4201  aaagcaacaa tagttacttg tgggccaggc gcggtggttc acgcctgtaa tcccagcact
4261  ttgagaggct gaggcacgtg gatcacaagg tcaggagttc aagaccagcc tggccaagat
4321  ggtgaaaccc cgtttctact aaaaatacaa aaactagctg gccgtggtgg catgctcctg
4381  tagtcccagc tactcaggag gctgaggcag gaaaatcact tgaacccagg aggtggaggt
4441  tgcagtgaac tgagaccgtg ccactgcact ccagcctggg tggcagagcg agactgtctc
4501  aaaaaaaaaa gaaagttgtg aatttgatgt aagcttagga aatgaataaa atttataggc
4561  atctgtataa tgtacaactt gacacggact ttcttttatc cttagttcct ttcacggact
4621  ctagaacttt tatcagaata tactggtaaa acattggggg agggatcctg agtaggtgat
4681  tggtcagaaa gatgccttca gttttgtcag tgtctaaaag ttaagtctgt ttaggccaag
4741  catggtggct cacacctgaa atcccagcac tctgggaggc cgaggcaagt ggatcacaag
4801  gtcaggagat gagaccatct tagccaacat ggtgaaaccc cgtctctact aaaatacaaa
4861  aaaattagcc aggcgtggtg gtgcgtgcct ataatcccag ctacttggga ggctgaggca
4921  ggggaatcgc ttgaacccgg gaggcagagg tcacgccact gcactccagc ctggcaacag
4981  agcaagactc cgtctcaaaa aaaaaaaaa aaaaaagag taagtctgtg taacatgaac
5041  atctctgctt ccacccaaaa ccacagcctt tgaatattat ataaggaact taatggatag
5101  atatgtttat tatttttgat agcacaactg ctttctctgc tattataagg aaaactgaga
5161  atagcaggtg ggtagggtag gatgaggaaa caagatgccc aaagcctaga tgccacagaa
5221  ttcatggtga taatcagggc atattttgag tcctactaga aacaaacatt ccaaatgaac
5281  tctgaatgcc tgactcaggc gttttggagg tttgggttat ccccttgtca ttaggcacac
5341  aagggttttt tgttgttttt gttttttggg ttttttgttt gttttgaggc agtctcactc
```

-continued

```
5401  tgttgtacaa gctggagtgc tgtattgtga tcttgactca ctgcaacctc tgcctcctgg
5461  ttcaagcgat tctcctgcct tggcctcctg agtagctggg attataagtg cctgccacta
5521  tgcccggcta atttttgtat ttttagtgga gatggagttt tgccatgttg gccaggctgg
5581  tcttgaactc ctgactccag gtgatccacc ctcctcagcc tcccaaagtg ctaggattac
5641  aggcgtgagc caccccgtcc ggcctgtttt taaggcatta attagtattg ttaggaaagc
5701  agtaacaatg caaacaccac tcttctcttc acaaagatca ccttgagact gtgtctccat
5761  tccacctgcc tgagaagtgg gagcatcagc ctgttccagg ctcttgggta gtagcatagc
5821  ccttttaaaaa gagagagcca ttttccatgt gttttttggat aagcacaatt tgaaaatcat
5881  ttcccaaatc ctcttttttgt ttttgattct aaggtaaaat tttccctaag ccctcccacc
5941  atcccctcag ccagtattag atgagatttg tatagcagca gaaactgact tataagtaga
6001  gagctcttca gcaagactga gccttagctg ttccatctct ttgttcttct gttgctggag
6061  ttgcacccca tttcttaact gcctctggcg ttcttccatt tcctccagct gttcctgcat
6121  gagatggcca agaacatttc taatgagcca aacaataaaa actcacattg tccactctta
6181  cttataaaac acttttttgt tcattgttta atcttgatag cagtattgag ctggtattt
6241  atatgatagg ttatgaaaca ggttcaaaga agttgtgtct tggaaaaaaa gtgacaatgc
6301  ttttgaaaat gatgacgaaa aaggcatctt gtctgttaac cacagcttgc tttaatagaa
6361  tcctggggagg gtgattggga cttttttagta ttacaacctt agtgtcattg aggaggattt
6421  tggtctagtt agtgggctga gtttcatata cctctcctc catgtgcagg tttgttaaga
6481  taattggtag ttttttaataa tataaaatac ttaagttgaa atacaaaagt gtggcaacaa
6541  ttattaaata ttggctagaa ttctaggaga gttacacaac tagtggaagt ccatgtttag
6601  aaaataaatg gcttgtttaa ggaaaagttt ttgtgtccaa agctccttaa agtcagagag
6661  atttctacct ggtacttaac atcatatgga aattgatgct ttagtgaggg tgttggctat
6721  cctattgcta atttcctgca tcctttttttc ttctttatttt ttgtatagag acagggtctc
6781  gctatgttgc ccaggctggt cttgttcctg ggctcaagca gtcctcccgc ctcggtctcc
6841  caaagtgctg ggattacagg tgtgagccac tgtgcccagc ttatcctttt ttcattacac
6901  aaaaagactg aatttggtta gttctaagtt ggaagataaa gatggtatgc acaggaggcc
6961  cttgggagcc ctcagataac tttctcattc ttccagaatc aggctgggat gcattctgta
7021  aattttccct gcctaggatg tatacctgag gaataaggta aggaagatgt cagcaagtca
7081  gtctctggtt tacctgctag ctggcatgga tccttaagga agcaggaggg agttgggaag
7141  agaggaaggg gtgaagttgg tatcttttaa agcgagagtg atttttacctc agattttgaa
7201  gaatactaag gaatccagtt gttggggtac atgctattat tagaaggatc tagataattt
7261  gtcctctgag tcatacttga cattgtacct gtggcacatc aatccgcact gtttgatact
7321  ctggctgaat ctcagcttc accaacattg tcaaaggacc ttttttagtc cccagccatg
7381  cctaagagtg tgtcatctga agagggaagc atctgcatac tgctgtcctg attgctcagt
7441  cctcactacc taccagaccc gttggtaagg tacaaaagta catgcttgga aaagcagtct
7501  gcaccaccag tgataagctg tgacagagtg aacagcctc aatgaaatga aggaaggatt
7561  gctacagtgg cattaaggat ggtctcttaa tcctgtgtta accactagat taactttaca
7621  atcaactcaa aatccttcaa aggctttcca ctttctttag tggcattcag accccctcta
7681  gtttgacccc tacctccaac ttgaacctct gttactcttc cgtatgaaca ttttcctcta
7741  gccctggact actagtaccg aagtcactag tcatagga ctcatttgaa atatgactag
7801  tctcaattga gatgtaatgt aagtgtaaaa tacacagcag atttctaaga cagcacacaa
```

-continued

```
7861  aatgtaaaat atgtcaaaaa tatttgatac tgattacatg ttgaaatata tgtgttgggt
7921  taaataaaat gcattaaagt taa
```

Jarid2 (accession No. NM_004973):
```
   1  tggatagcct ctctctcatt ggttaggggg cttggaaaaa agagactcgg cgagccctcg
  61  ctgtggtgct gccgccgccg ccgccgccgc cgctggagtt gactcttctg ctcgcactgc
 121  tgctgcagca caaacgtgac ttccaacatt ttttatttat ctttcccttt tcttttccaa
 181  gatgtaacta cggatcagac actaaggacc ttcacgtttc gctgatgtag ttttggagg
 241  aaaagggggg gggagtgaag ggcgtcggtt ttttttgtg tgtgtgtgta tgtgtttcgg
 301  gggaaatttt ccattatgag tgttttacta aagtgaattt ttttttgttt gcttcgttcg
 361  tctttggctc ttttttttc cttcccaatt tcggatttat ttcaaggcga atctggcttt
 421  gggggaagag gaagaaaagt cggattacaa gatcaaccac caccaacaac aataaaaacc
 481  accaggatat tttttttgcaa atttctgacg gctttaaatt catgaagcaa ttgtcccctt
 541  ttgcaatcag catttggatc tcagaatgag caaggaaaga cccaaggaga atatcattca
 601  gaagaaatac gatgacagtg atgggattcc gtggtcagaa aacgggtgg tacgtaaagt
 661  cctttatttg tctctgaagg agttcaagaa ttcccagaag aggcagcatg cggaaggcat
 721  tgctgggagc ctgaaaactg tgaatgggct ccttggtaat gaccagtcta agggattagg
 781  accagcatca gaacagtcag agaatgaaaa ggacgatgca tcccaagtgt cctccactag
 841  caacgatgtt agttcttcag attttgaaga agggccgtcg aggaaaaggc ccaggctgca
 901  agcacaaagg aagtttgctc agtctcagcc gaatagtccc agcacaactc cagtaaagat
 961  agtggagcca ttgctacccc ctccagctac tcagatatca gacctctcta aaaggaagcc
1021  taagacagaa gatttttctta cctttctctg ccttcgaggt tctcctgcgc tgcccaacag
1081  catggtgtat tttggaagct ctcaggatga ggaggaagtc gaggaggaag atgatgagac
1141  agaagacgtc aaaacagcca ccaacaatgc ttcatcttca tgccagtcga cccccaggaa
1201  aggaaaaacc cacaaacatg ttcacaacgg gcatgttttc aatggttcca gcaggtcaac
1261  acgggagaag gaacctgttc aaaaacacaa agcaaagag gccactcccg caaggagaa
1321  gcacagcgat caccgggctg acagccgccg ggagcaggct tcagctaacc accccgcagc
1381  ggcccctcc acgggttcct cggccaaggg gcttgctgcc acccatcacc acccccctct
1441  gcatcggtcg gctcaggact tacggaaaca ggtttctaag gtaaacggag tcactcgaat
1501  gtcatctctg ggtgcaggtg taaccagtgc caaaaagatg cgcgaggtca gaccttcacc
1561  atccaaaact gtgaagtaca ctgccacggt gacgaagggg gctgtcacat acaccaaagc
1621  caagagagaa ctggtcaagg acaccaaacc caatcaccac aagcccagtt ccgctgtcaa
1681  ccacacaatc tcagggaaaa ctgaaagtag caatgcaaaa acccgcaaac aggtgctatc
1741  cctcgggggg gcgtccaagt ccactgggcc cgccgtcaat ggcctcaagg tcagtggcag
1801  gttgaaccca aagtcatgca ctaaggaggt gggggggcgg cagctgcggg agggcctgca
1861  gctgcgggag gggctgcgga actccaagag gagactggaa gaggcacacc aggcggagaa
1921  gccgcagtcg cccccaaga agatgaaagg ggcggctggc cccgccgaag gccctggcaa
1981  gaaggccccg gccgagagag gtctgctgaa cggacacgtg aagaaggaag tgccggagcg
2041  cagtctggag aggaatcggc cgaagcgggc cacggccggg aagagcacgc caggcagaca
2101  agcacatggc aaggcggaca gcgcctcctg tgaaaatcgt tctacctcgc aaccggagtc
2161  cgtgcacaag ccgcaggact cgggcaaggc cgaagaggc ggcggcaagg ccgggtgggc
2221  ggccatggac gagatccccg tcctcaggcc ctccgccaag gagttccacg atccgctcat
```

-continued

```
2281  ctacatcgag tcggtccgcg ctcaggtgga gaagttcggg atgtgcaggg tgatcccccc
2341  tccggactgg cggcccgagt gcaagctcaa cgatgagatg cggtttgtca cgcagattca
2401  gcacatccac aagctgggcc ggcgctgggg ccccaacgtg cagcggctgg cctgcatcaa
2461  gaagcacctc aaatctcagg gcatcaccat ggacgagctc ccgctcatag ggggctgtga
2521  gctcgacctg gcctgctttt tccggctgat taatgagatg ggcggcatgc agcaagtgac
2581  tgacctcaaa aaatggaaca aactagcaga catgctgcgc atccccgaaa ctgcccagga
2641  ccggctggcc aagctgcagg aggcctactg ccagtaccta ctctcctacg actccctgtc
2701  cccagaggag caccggcggc tggagaagga ggtgctgatg agaaggaga tcctggagaa
2761  gcgcaagggg ccgctggaag gccacacaga gaacgaccac cacaagttcc accctctgcc
2821  ccgcttcgag cccaagaatg ggctcatcca cggcgtggcc cccaggaacg gcttccgcag
2881  caagctcaag gaggtgggcc aggcccagtt gaagactggc cggcggcgac tcttcgctca
2941  ggaaaaagaa gtggtcaagg aagaggagga ggacaaaggc gtcctcaatg acttccacaa
3001  gtgcatctat aagggaaggt ctgtttctct aacaactttt tatcgaacag cgaggaatat
3061  catgagcatg tgtttcagca aggagcctgc cccagccgaa atcgagcaag agtactggag
3121  gctagtggaa gagaaggact gccacgtggc agtgcactgc ggcaaggtgg acaccaacac
3181  tcacggcagt ggattcccag taggaaaatc agaacccttt tcgaggcatg gatggaacct
3241  caccgtcctc cccaataaca cagggtccat cctgcgtcac ctcggtgctg tgcctggagt
3301  gactattccc tggctaaata ttggcatggt cttttctacc tcatgctggt ctcgagacca
3361  aaatcaccct tccatacatt g actacttaca cactggtgct gactgcattt ggtattgcat
3421  tcctgctgag gaggagaaca agctggaaga tgtggtccac accctgctgc aagccaatgg
3481  caccccaggg ctgcagatgc tggaaagcaa cgtcatgatc tccccggagg tgctgtgcaa
3541  agagggatc aaggtgcaca ggaccgtgca gcagagtggc cagtttgtcg tctgcttccc
3601  gggatccttt gtgtccaaag tgtgctgtgg gtacagcgtg tctgaaaccg tgcactttgc
3661  taccacccag tggacaagta tgggctttga ccgccaag gaaatgaagc gtcgccatat
3721  agctaagcca ttctccatgg agaagttact ctaccagatt gcacaagcag aagcaaaaaa
3781  agaaaacggt cccactctca gtaccatctc agccctcctg gatgagctca gggatacaga
3841  gctgcggcag cgcaggcagc tgttcgaggc tggcctccac tcctccgcac gctatggcag
3901  ccacgatggc agcagcacgg tggcggacgg gaagaaaaag cctcgaaagt ggctgcagtt
3961  ggagacgtca gagaggaggt gtcagatctg ccagcacctg tgctacctgt ccatggtggt
4021  acaagagaac gaaaacgtcg tgttctgtct ggagtgtgct ctgcgccacg tggagaaaca
4081  gaagtcctgc cgagggctga agttgatgta ccgctacgat gaggaacaga ttatcagtct
4141  ggtcaatcag atctgcggca aagtgtctgg taaaaacggc agcattgaga actgtctcag
4201  taaacccaca ccaaaaagag gtccccgcaa gagagcgaca gtggacgtgc ccccctcccg
4261  tctgtcagcc tccagttcat ccaaaagtgc ttcgagctca tcatgaagat gccaacgccc
4321  gtggtcgatt tatatatatt ttttgtaat tattatattc tagttttgag tacttgctgt
4381  aggattcaag ctgtctttgc actagctcta aagaagattt tcttctggtt ttagagaact
4441  aattttgttt tagcattaaa ctgttgaact ttttttgta cttagaaaac ctagatactg
4501  cagtcagatt ttggaaactg ccgtatagtc actgttttaa aaaccccgga ggggctgtat
4561  taatttgtat tgccccatgg ctgacaaaag ccttttttttt tggttttgat ttttttttt
4621  ttgtaactgt tggggggaaa aaggcttttt aacccatttt tgaagagggt gaagtttgga
```

-continued

```
4681    gaacaaattt aaaaaccatc agtcatgtga gcagattttt tagaagggat aggagacaca
4741    cgcgcacaca cacacacaca cgaaacttga aatggctttg ctttggctgt cgtcttctgc
4801    cgtgtgccag atgagcttgt gatctgggaa gccggggcac cccgttttg  tttctctggg
4861    cggttgtggc agctgaaggc ggacgttgtt tcctaaccat aggtggaacg aggagacggg
4921    agcgagtggg ctctccacca gcacatcact atgcatctgt tccaggaaag aagaaaagcg
4981    agcgaggaag acggaaaaga ctgcctgcct tggaggggtc acatgaggga gacctgtgcc
5041    tgatttcatt aggaaatcca ttctgttatt ttttggtgct gttggctact ttatcaaaaa
5101    acccttcaat agcatcctta agatttaaaa aaaaaaaaa  aaaaaaggaa aaaaaagtga
5161    tggaagccgt aagtgcttct ttgtcatcga cgtgcaatct ttctaacatt ccatctccat
5221    ctcaccgctt cttgtttgac accttcacaa gtcagcatta atctttcttt taaaacttgt
5281    ttcatttatg atcatgtaga gagccactag gaggcctgca gttattttg  aatgtgaaaa
5341    tgcatttgcg ttcatcttgt ctatttttc  tcttcatgtt gtaacaaaaa ggaaaaaaga
5401    aaaaaaatc  ccatcccttt tgtacatatg cctgtaaatt gttttaaata cttgagcctt
5461    tttctcggtg ggggtgggg  aggggggtga aagacaaga  tgaagaaaag ccttacattt
5521    cagtttcttc atcggttgga ttggatgctt acagggtttt tcttgtaaca tttataagtg
5581    ctgcttacat cactgaacaa caacaaaaaa ataataatgg agtagctgtt gcccttctcc
5641    ggttgtgtgt acagtatgtg tggaataaaa aagggaaact gttttcacaa gctgttcttt
5701    gtttcataat tggattcatc aatcccgtag ctacccatat tgcactgagc ttgccagtgg
5761    tgactgccag gaacgtccta tgatccactt tgttggttgt tgttgcagaa gactgaactg
5821    ttttggaata tttaacaatt acagaaacag tcaagtgttt tccaatgtgg ttgtccggtt
5881    tctatggcct tgctgtgtac tttccctctt tttgacagta aacttctgcc tatggcttac
5941    agtttgacat ttaatttatt agcgctgctc tgcaccctc  ccttgggagg gagacttcat
6001    gtggtttatt gcgagttttt tgtttacttt tcaggtttgt actacaaggt ttaataataa
6061    aaacaaagtt ttttggacat ttgtctgtct tgtggaaaaa aaaaaaaaaa aa
```

YY1 (accession No. NM_003403):

```
   1    agggcgaacg ggcgagtggc agcgaggcgg ggcgggctga ggccagcgcg gaagtctcgc
  61    gaggccgggc ccgagcagag tgtggcggcg gcggcgagat ctgggctcgg gttgaggagt
 121    tggtatttgt gtggaaggag gcggaggcgc aggaggaagg gggaagcgga gcgccggccc
 181    ggagggcggg aggaggcgcg gccagggcgg gcggttgcgg cgaggcgagg cgaggcgggg
 241    agccgagacg agcagcggcc gagcgagcgc gggcgcgggc gcaccgaggc gagggaggcg
 301    gggaagcccc gccgccgccg cggcgcccgc cccttccccc gccgcccgcc ccctctcccc
 361    ccgcccgctc gccgccttcc tccctctgcc ttccttcccc acggccggcc gcctcctcgc
 421    ccgcccgccc gcagccgagg agccgaggcc gccgcggccg tggcggcgga gccctcagcc
 481    atggcctcgg gcgacaccct tacatcgcc  acgacggct  cggagatgcc ggccgagatc
 541    gtggagctgc acgagatcga ggtggagacc atcccggtgg agaccatcga gaccacagtg
 601    gtgggcgagg aggaggagga ggacgacgac gacgaggacg gcggcggtgg cgaccacggc
 661    ggcggggcg  gccacgggca cgccggccac caccaccacc accatcacca ccaccaccac
 721    ccgcccatga tcgctctgca gccgctggtc accgacgacc cgacccaggt gcaccaccac
 781    caggaggtga tcctggtgca gacgcgcgag gaggtggtgg gcggcgacga ctcggacggg
 841    ctgcgcgccg aggacggctt cgaggatcag attctcatcc cggtgccgc  gccggccggc
 901    ggcgacgacg actacattga acaaacgctg gtcaccgtgg cggcggccgg caagagcggc
```

-continued

```
 961   ggcggcggct cgtcgtcgtc gggaggcggc cgcgtcaaga agggcggcgg caagaagagc
1021   ggcaagaaga gttacctcag cggcggggcc ggcgcggcgg gcggcggcgg cgccgacccg
1081   ggcaacaaga agtgggagca gaagcaggtg cagatcaaga ccctggaggg cgagttctcg
1141   gtcaccatgt ggtcctcaga tgaaaaaaaa gatattgacc atgagacagt ggttgaagaa
1201   cagatcattg gagagaactc acctcctgat tattcagaat atatgacagg aaagaaactt
1261   cctcctggag gaatacctgg cattgacctc tcagatccca acaactggc agaatttgct
1321   agaatgaagc caagaaaaat taaagaagat gatgctccaa gaacaatagc ttgccctcat
1381   aaaggctgca caaagatgtt cagggataac tcggccatga aaaacatct gcacacccac
1441   ggtcccagag tccacgtctg tgcagaatgt ggcaaagctt ttgttgagag ttcaaaacta
1501   aaacgacacc aactggttca tactggagag aagcccttc agtgcacgtt cgaaggctgt
1561   gggaaacgct tttcactgga cttcaatttg cgcacacatg tgcgaatcca taccggagac
1621   aggccctatg tgtgccccct cgatggttgt aataagaagt ttgctcagtc aactaacctg
1681   aaatctcaca tcttaacaca tgctaaggcc aaaaacaacc agtgaaaaga agagagaaga
1741   cccttctcga ccacgggaag catcttccag aagtgtgatt gggaataaat atgcctctcc
1801   tttgtatatt atttctagga agaattttaa aaatgaatcc tacacaccta agggacatgt
1861   tttgataaag tagtaaaaat taaaaaaaaa aaactttact aagatgacat tgctaagatg
1921   ctctatcttg ctctgtaatc tcgtttcaaa aacacagtgt ttttgtaaag tgtggtccca
1981   acaggaggac aattcatgaa cttcgcatca aagacaatt ctttatacaa cagtgctaaa
2041   aatgggactt cttttcacat tcttataaat atgaagctca cctgttgctt acaattttt
2101   taatttgta ttttccaagt gtgcatattg tacactttt tggggatatg cttagtaatg
2161   ctacgtgtga ttttctgga ggttgataac tttgcttgca gtagatttc tttaaagaa
2221   tgggcagtta catgcatact tcaaaagtat tttcctgtaa aaaaaaaaaa gttatatagg
2281   ttttgtttgc tatcttaatt ttggttgtat tctttgatgt taacacattt tgtataattg
2341   tatcgtatag ctgtattgaa tcatgtagta tcaaatatta gatgtgattt aatagtgtta
2401   atcaatttaa acccatttta gtcacttttt ttttccaaaa aatactgcc agatgctgat
2461   gttcagtgta atttctttgc ctgttcagtt acagaaagtg gtgctcagtt gtagaatgta
2521   ttgtacctt taacacctga tgtgtacatc ccatgtaaca gaaagggcaa caataaaata
2581   gcaatcctaa agcaagaata tggcagaaca agatctgtaa gcacagtctt attttatttt
2641   gttgtccaga atacttataa ttcttgagcc tcccagaaat tggaagctaa ataaagcaac
2701   tcaagtttcc tttatttgc actcaattac agtgattatt gatgaaagcg atgcatggat
2761   attttaatac ttcctacatg tcctgacttc tgaaagagag taggtaacag gcatcccgag
2821   ttcaggaact acctcagaac accccaggcc aggttggtca taggctgtga ttttagcccc
2881   cggcaagtgt gagtgaagca tctgtaccac cgcgcaggct gagcgcctgc gcagggtaag
2941   gtgccacctg gcagtggggc acacagaggg aagaccaggc ctgtccatca gccggctgcc
3001   ttcagaggca gctccagcag gaccttggct tgtctgacag gaaatgcttg tggtcgttgg
3061   ttatttggtt tgagagccct tgttcctcca tctagtggag tccttattaa atgctagcaa
3121   tgtggcaatt gagtgccagt agcttaattt catgtttct
```

CBX2 (accession No. NM_005189):
```
   1   ggcggtccgg gcgggtgact ggcggcgggc gccgcggtcg ggctggctgc cgggcagcat
  61   ggaggagctg agcagcgtgg gcgagcaggt cttcgccgcc gagtgcatcc tgagcaagcg
 121   gctccgcaag ggcaagctgg agtacctggt caagtggcgc ggctggtcct ccaaacataa
```

-continued

```
 181   cagctgggag ccggaggaga acatcctgga cccgaggctg ctcctggcct tccagaagaa
 241   ggaacatgag aaggaggtgc agaaccggaa gagaggcaag aggccgagag gccggccaag
 301   gaagctcact gccatgtcct cctgcagccg gcgctccaag ctcaaggaac ccgatgctcc
 361   ctccaaatcc aagtccagca gttcctcctc ttcctccacg tcatcctcct cttcctcaga
 421   tgaagaggat gacagtgact tagatgctaa gaggggtccc cggggccgcg agacccaccc
 481   agtgccgcag aagaaggccc agatcctggt ggccaaaccc gagctgaagg atcccatccg
 541   gaagaagcgg ggacgaaagc ccctgccccc agagcaaaag gcaacccgaa gacccgtgag
 601   cctggccaag gtgctgaaga ccgcccggaa ggatctgggg gccccggcca gcaagctgcc
 661   ccctccactc agcgcccccg ttgcaggcct ggcagctctg aaggcccacg ccaaggaggc
 721   ctgtggcggc ccagtgcca tggccacccc agagaacctg gccagcctaa tgaagggcat
 781   ggccagtagc cccggccggg gtggcatcag ctggcagagc tccatcgtgc actacatgaa
 841   ccggatgacc cagagccagg cccaggctgc cagcaggttg gcgctgaagg cccaggccac
 901   caacaagtgc ggcctcgggc tggacctgaa ggtgaggacg cagaaagggg agctgggaat
 961   gagccctcca ggaagcaaaa tcccgaaggc ccccagcggt ggggctgtgg agcagaaagt
1021   ggggaacaca gggggccccc cgcacaccca tggtgccagc agggtgcctg ctgggtgccc
1081   aggcccccag ccagcaccca cccaggagct gagcctccag gtcttggact tgcagagtgt
1141   caagaatggc atgcccgggg tgggtctcct tgcccgccac gccaccgcca ccaagggtgt
1201   cccggccacc aacccagccc ctgggaaggg cactgggagt ggcctcattg ggccagcgg
1261   ggccaccatg cccaccgaca caagcaaaag tgagaagctg gcttccgag cagtggcgcc
1321   acccaccccct gccagcaaga gggactgtgt caagggcagt gctaccccca gtgggcagga
1381   gagccgcaca gccccgggag aagcccgcaa ggcggccaca ctgccagaga tgagcgcagg
1441   tgaggagagt agcagctcgg actccgaccc cgactccgcc tcgccgccca gcactggaca
1501   gaacccgtca gtgtccgttc agaccagcca ggactggaag cccacccgca gcctcatcga
1561   gcacgtattt gtcaccgacg tcactgccaa cctcatcacc gtcacagtga aggagtctcc
1621   caccagcgtg ggcttcttca acctgaggca ttactgaagc cccggcgcca ccagctgcgc
1681   ggtcttactc cccttcctg cctatggtgt cgcttggcta agtgactccc agcccaagcc
1741   ccctcaagag tctgggtcgg ggaggagga gtgggtggcc tccttgatgg gcaggcttgg
1801   aagggacttc tcccgcaccc cactctgtcc caggacatag gcaggggggc ctcactgcct
1861   tgttggtctc caccttgttc ctacctctgc aggcctcttt gctctcccct cttgcctcag
1921   gaaacccggt ggcacctgtg gctccaggtg actgtcttga acagagcggg cttcttcatg
1981   gctgcgttgt tgctgagttt gaactgctcc tccctggcct gcgtgactga atcacagctt
2041   tggtccctgt cttgcagggg ctgaggtgtc aggaggggac ttctggccca ccttgccttc
2101   agccctggag tgggcagaga gtattgtggg gaggcatggc cagtgggact agtgttccct
2161   ccatctggcc acagcttttg ggagatgggg tgggcagggg tggtcctggc tggcattgcc
2221   tgagccggca gtgatgaagt ggggagcttg cccttgacag gtgggggctg gctggggcct
2281   taatgtgaaa agacagtggc aggcagctga gtagagcga gcccagcagc cctaaaaggc
2341   tgccttcatg gccatctagc cccagttcag ggcagcatcc atagcccaca agccagcgtg
2401   ggtggggcgg gggtggtccc acagctgggt tccacctgaa gagcctccgt gcctcggagc
2461   aggagaggca ggctatggct gccaccctcc ctcctgcctg tgtcccagtg agaactgacc
2521   tgagtcccct tccaaaccca gaccacctc ctgccccagg cccactgaag catgttccat
2581   ttctaaaaag cccagagttc agtgtgtccc aaggaaaacc caaagtggag gtgctcaggt
```

-continued

```
2641  ccaggggagt ccagtgggca ggacccttgg caggcaagcc cctcccttca ctcccaggac
2701  ctaccttctg ctagtaaagg actggcttca ttctaattat ggcccacaga ctgccccgga
2761  gacctggagg acagcagtgc tggcacttgg gtgtccatgg gcccgtctgc cggctctgcc
2821  tgtgctgcaa gtgttggccg tgggtccagc caacaactcc ctacgtcctg tgtggggccc
2881  tgcccaagtg gatgaggcat tccttgagga gtatcatttt ccctgacaat ccccatcacc
2941  tttaggggtt ccctgcttgg ctccttttcca gctgaaaaac tagacctgtg ccattgggga
3001  agctggacaa agtctagggg gcccgcctgg tagagggtcc cgggaagctg gatctgtcag
3061  cctcggccct gaggcccctg ttaactcaag actgtgagct gcctctaggt ggtcacgtct
3121  gggagctagc ttgtatggct tctgaccagt atcaggattt ctgttctgag agcagcgtgg
3181  gcagcaaggc agggcagccc agaggtggca gcggcaggca atctggtcac taggtctttg
3241  tgatgccaaa aataaaagag ggtggggtgg gtgctttctg ttcctctgat tggatggagt
3301  ccgccagcag gcatgggggct acattccagt gcctgactat agggaggcac tcctgattcc
3361  atggagcagc ccggactttg agaatgggct ctggtttgcg ggggcaggc gtaccagact
3421  gcaagacccc ccagtacctc accgtgccaa ataggaagag gtggccttgg tgtagccaaa
3481  tggatctttt taacagtgtg cctttgggga gggacccatg tccatggctt cgttgagggc
3541  catccatatg ccagctgggg gccagcccac agtggccata ttggctgcag caggaatggt
3601  gcccacctcg gcgaattgaa gggctaagag tcccagatag ctaggccaga gctggaagca
3661  gacagtaagg ggaagagctg ctcccacagg agagggagag attccagctc actgcgcagc
3721  ctgggaggag gcgtggatcc tggcacgctg agcctcaggc accagcctcc ctgtgctcga
3781  cagcaaagtc ttgactcctt cctgctgagc actgtgctac cttcactgct ccaaagccag
3841  actaacagct ctccaagccc ttggggtgac tcggcttcca ggagctgttg gagaaatgag
3901  gatgtctgtc cctgtctgcc tgggcaggcc agattcctcc ccagcagccg ggtctctcca
3961  gaccctgatt cggtgccttt ctgtttacca gctacttcaa tcccaaagtt tgaatctgca
4021  gataccttac tcccagccac tttgccttct tactgtgttg tgtgtttttc ctggtgcttc
4081  aagagcgtgt gcagggcaag tgccgtcact gggaactgca ccagatgctc agacttggtt
4141  gtcttatgtt taccaataaa taaaagtaga ctttttctat ttttatttgc tgctatttgt
4201  gtgtgtgttt gtgtttgtgt agctaggtat ctggcacttc tgacgatgca ttgttgcttt
4261  tttcc
```

CBX4 (accession No. NM_003655):
```
  1  agccggggcg ggcgcgggca gcggcgggcc ggccgggctg tgcggggcga gcggcggcgg
 61  cggcggggc gcttcggccg gggcggcagc tgggcgccgg cgggagctag cagcgtctgc
121  agccgcgccg gccgccagcg ccccggcgcg ctccggctcg gccatggagc tgccagctgt
181  tggcgagcac gtcttcgcgg tggagagcat cgagaagaag cggatccgca agggcagagt
241  ggagtatctg gtgaaatgga ggctggtc gcccaaatat aacacgtggg aaccggagga
301  gaacatcctg gaccccaggc tgctgatcgc cttccagaac agggaacgga ggagcagct
361  gatgggatat cggaagagag ggccgaagcc caaaccgcta gtggtgcagg tgcctacctt
421  tgcccgtcgt tccaatgtcc tgaccggcct ccaggactcc tccactgaca accgtgccaa
481  gctggatttg ggcgcgcagg ggaagggcca gggcatcag tacgagctca acagcaagaa
541  gcaccaccag taccagccgc acagcaagga gcgggcgggc aagccccgc gccgggcaa
601  gagcggcaag tactactacc agctcaacag caagaagcac cacccctacc agcccgaccc
661  caaaatgtac gacctgcagt accagggcgg ccacaaggag gcgcccagcc ccacctgccc
```

-continued

```
 721   ggacctgggg gccaagagcc acccgcccga caagtgggcg caaggtgcgg gggccaaagg
 781   ctacctgggg gcggtgaagc ccctggccgg tgcggcgggt gctccaggca aaggctccga
 841   gaagggcccc cccaacggaa tgatgccggc ccccaaagag gctgtgacgg gcaacgggat
 901   tgggggcaag atgaagatag tcaagaacaa gaacaagaac ggacgcatcg tgatcgtgat
 961   gagcaaatac atggagaacg gcatgcaggc ggtgaagatc aagtccggcg aggtggcaga
1021   ggggaggct cgctccccca gccacaagaa gcgggcagcc gacgagcgcc accctcctgc
1081   cgacaggact tttaaaaagg cggcgggcgc agaggagaag aaggtggagg cgccgcccaa
1141   gaggagggag gaggaggtgt ccggggttag cgatccgcag ccccaggatg ccggctcccg
1201   caagctgtcc ccgaccaagg aggcctttgg agagcagccc ctgcagctca ccaccaagcc
1261   cgacctgctt gcctgggacc cggcccggaa cacgcacccg ccctcacacc cccgcaccc
1321   gcacccccat caccaccacc accaccacca ccaccaccac cacgccgtcg gcctgaatct
1381   ctcccacgtg cgcaagcgct gcctctccga cccacggc gagcgcgagc cctgcaagaa
1441   gcggctgact gcgcgcagca tcagcacccc cacctgcctg gggcagcc cagccgctga
1501   gcgcccggcc gacctgccac cagccgccgc cctcccgcag cccgaggtca tcctgctaga
1561   ctcagacctg gatgaaccca tagacttgcg ctgcgtcaag acgcgcagcg aggccgggga
1621   gccgcccagc tccctccagg tgaagcccga caccggcg tcggcggcgg tggcggtggc
1681   ggcggcagcg gcacccacca cgacggcgga gaagcctcca gccgaggccc aggacgaacc
1741   tgcagagtcg ctgagcgagt caagcccctt ctttgggaat ataattatca ccgacgtcac
1801   cgcgaactgc ctcaccgtta ctttcaagga gtacgtgacg gtgtagccga agggcgtcgg
1861   aaggggaagc gccattcccg cggggggcg gggagctgag cacctggggc ctcggggcgg
1921   gctcccctct cgccaaccg ccaaccgcga gagacccagg ctggccccca gggtgaggac
1981   gcccggagcg gaggtaacca tgttcccct gcggcggctg tcagacctgg gcggaggccc
2041   cttccacgcg gtgccggcgg ggctcgccct ctcctgccct tccccgctgg agatggaccc
2101   ccggaacgga cagggcagct ctgcgcccgg cctcagagtt ctagtattat attttaaccg
2161   tgctaacttg tcaagtgctg actctactcc cgtttgtacg tggtgttatt attgaaatgt
2221   attgtttgag ctcaaaaggc ccgaccaccc cccttcgggc tgctatatat atatttattt
2281   gtaggtattt atatattgaa atataaaaac ctagatttat ggagtttcct ctagatcatg
2341   ttatattcta tatcagacaa actatttct tttgaccttt cttccctcc atccagtatt
2401   tcggttgatt tcattttctc ccctctcttc cccttccacg aactgcaata ccagtaacct
2461   tggtatatat tttttgatac tgtacacatg gatgtcttgt ttctatgtgc aaaaaaaaaa
2521   aaaaaaaaaa gtttgttaaa aggctacacg agctctctag aaactgctgc tactagaaat
2581   gtctaaacta taagcttcca actattacct gcttgaatgt aaatattaaa tggagatgtt
2641   gaaggtgcaa aaaaa
```

CBX6 (accession No. NM_014292):
```
   1   gtgacggccc gcagctggaa cgcgagcgcg cgcccgccg cgctcccgcc cgccggggcc
  61   tgggcgctgc ggcgcgtgcg cgagcggtgc cgcaccggcc gcgggcgcag ggagtattat
 121   gggctgtggg tgccgctgag caagatggag ctgtctgcag tgggcgagcg ggtcttcgcg
 181   gccgaatcca tcatcaaacg gcggatccga aagggacgca tcgagtacct ggtgaaatgg
 241   aaggggtggg cgatcaagta cagcacttgg gagcccgagg agaacatcct ggactcgcgg
 301   ctcattgcag ccttcgaaca aaaggagagg gagcgtgagc tgtatgggcc aagaagagg
 361   ggacccaaac ccaaaacttt cctcctgaag gcgcgggccc aggccgaggc cctccgcatc
```

-continued

```
 421   agtgatgtgc atttctctgt caagccgagc gccagtgcct cctcgcccaa gctgcactcc
 481   agcgcagccg tgcaccggct caagaaggac atccgccgct gccaccgtat gtcccgccgt
 541   cccctgcccc gcccggaccc gcagggggc agccccggac tgcgcccgcc catttcgccc
 601   ttctcggaga cggtgcgcat catcaaccgc aaggtgaagc cgcgggagcc caagcggaac
 661   cgcatcatcc tgaacctgaa ggtgatcgac aagggcgctg cggcgggggg cgccgggcag
 721   ggggccgggg cgctggcccg ccccaaagtc ccctcgcgga accgcgttat aggcaagagc
 781   aagaagttca gcgagagcgt cctgcgtaca cagatccgcc acatgaagtt cggcgccttt
 841   gcgctgtaca agcctccgcc cgccccctg gtagcccgt ccccggcaa ggctgaggcc
 901   tcagccccgg gccctgggct acttctggcc gccccgccg ccccctacga cgcccgcagc
 961   tctggctcct ccggctgccc ctcgcctaca ccacagtcct ctgacccga cgacacgccc
1021   cccaagctcc tccccgagac cgtgagccca tccgccccca gctggcgcga gccggaggtg
1081   ctcgacctgt ccctccctcc cgagtcggca gccaccagca agcgggcacc gcctgaggtc
1141   acagctgctg ccggcccggc acctcccacg gcccctgagc ccgccggtgc ctcctccgag
1201   cccgaggctg gggactggcg ccccgagatg tcaccctgct ccaatgtggt cgtcaccgat
1261   gtcaccagca acctcctgac ggtcacaatc aaggaattct gcaaccctga ggatttcgag
1321   aaggtggctg ctggggtagc aggcgccgct gggggcggtg gcagcattgg ggcgagcaag
1381   tgaggggct ccaccaagga gggggcttg gggggccct cctgcccgaa gtcatactct
1441   tgctcccacc ccacccttgc ccccagcct ctctccctgt gctttgcttg tctcaaatgg
1501   ctcggtgttg acccagggat ggggctgggt agttggggtc ccagaaagcc gggggtaggg
1561   gccaccctgg aatggggcag gggaagggca cccccctgc ccatgcatgg tagcccactg
1621   ggtggtttct ggaaagccct agaaactagg gttcctctgc cccttccaca tcccacctgt
1681   ctctctagct tgcttcctgc tctcctgtgc ggcgtctgat ttctcggtgc taacctggca
1741   gctgtggggc ccttaggagc ccccaccga gggtggacac agtccctttc cttcctgcag
1801   atgcctaggc aggaggaggg cttcctgcct gtttggcaaa gtcccaggca gaggccaagg
1861   atgaggcctg actcggctcc tccctccaca tcagccaggg catcagaagt tgggccaggg
1921   cggggtcttc cctgctcgat tttggacgag gctaagtag acccctatg ccctgcccca
1981   gccctggctc tttcctaacc ccctcaacgg tgggaggaac tggcagaggg tgcgcctggc
2041   cacagcctcc ccgcatctaa aggccccttc agttcttgac caaaggtgct acgagaacct
2101   gccgtggaaa cttccagttg tgcgtctgcc ccactcgctg tgtttgtccg tgggttcata
2161   catgcattgg gtgctaggcc ccaggctgcc gggtggcacc ctttacagtt cctttgaaca
2221   ggggcattga aggcctggac tgcctctcgc ctcagtaggc ctggggacca ggcttgggtc
2281   tggaggttg ctgtggaagt caccaggcct cccctcctgg cccaggtgtg ctgggggcac
2341   cgtgcccccc accccctgc cctcctcagg gtggtcagcc caacctgtcg gaccttcact
2401   tcacatcatg gtggggaccg agatagagag ggagacccca ttccaagctc cctcttcctc
2461   cgggtgtttg gggaggatgc tgaagaatcc attccgagg gcctcccggc ttgtcccagc
2521   ccctctttg cttctgacca cggaggcttt ctcacagccc agcctgcctg aagcaaagga
2581   ggctcccgtg tcctgggcag cttctgtttc cctctgctgc ctgggagctg aggcacccgt
2641   gccagtggca gaggccacag ccccagcctt aggccaggcc ctgggagggc aggcaggcaa
2701   aggggagacc agagggtctg tgttctccag gagaatgagg gtgttggtcc cagaattggg
2761   accggggccc cgctggccag ccctgggcca cttcccgggt ctccattgtg cgtgggtggc
```

-continued

```
2821  gtgttccagg cgtggctgga gctggcttcc tggctgtgct gccatgggcc cctccctcag
2881  aagcacgttg gcaggaggcc gatcagaacc ctagcgcctt tggtcctaag aatgggaggc
2941  tgccttcctt cccaatctcc ctgccagggc ccacagcgtg gccctagccc tcccctcccc
3001  gggatgtaga acggggaccc tcgcagggtt ggggcggggg ctgatactcc tcggcccctc
3061  cctaccctgc cctgtgtgtt ggctttgtgg ccgtccaagt gccaattggc ttttcgccca
3121  aataagggct ggtatttctc ctctgtcctt ggaggtgatt tcccctgac cccctccccc
3181  aggtgagtga ccacctgggt gccagttaca ggtgtttcca gagaccatag aaatgtgttt
3241  tcctgagagt tcgtgtcatt cgtgactttt ttgtaaagaa gttgtgtttt cagaggtgat
3301  tttatgacag gaaagtgaaa gaattagttt tgcaaaaaaa caaaacaaa aaagaggaa
3361  aaaaaaaga aatagaaaaa aatattgtgg gattcctatg gggggtggc ggggagaaa
3421  gagctattta agaaaaaata gtaacgcagt gattgcacag gtgaggtggc aatgtcagga
3481  tggggcggag gcctgggccc agctggcagg tccctggca tcgcaggcac tgtggagagg
3541  gcctggaccc agatctccac acccgtgctt gctcaaaggg aaggacaaca gcgggccccc
3601  gggagctaac ccaagctgca ggtcccggca agctgaggtt tgggagggtg ggggttgtca
3661  ctggtgattt tctccagggg gctggtgagt gggcagtttg gtttcttgcc cccttctgtt
3721  cctttcccag ttgttgggcc atctggtccc caccaccgcc accctatggg ggagacctcc
3781  ctccccacgg gtcaccctaa agccacaac ctctctgagc ctccctggcc tgaaagggga
3841  tgcaggcttc aggaggcaag aagctgggcc cctgggggtg gctggggaga gggaatgcat
3901  ttcccttgcc acaggtggtc tgcttctgct ggcctgagct ccaagtggag cagcccgggc
3961  cagccttggt gcatgaagag gcaccaggca caccgccttg aggtgggcag tgcccatggg
4021  ggcccgagtg gatgggaccg agggtgagtg gagcctcctt cctccccctct ctagtacccc
4081  cgcctcccac acacttgcac ggatcggcct cccttgggag atcagcctcc atgggcccct
4141  cgtccaccct tgctgctttc catttgccta attaccaagc agaagttgca atctggtttg
4201  ctttattttt gtatgtgaaa taaccccaa agcccaatct cctcctacgt tcaatattgg
4261  ttggggcatc cgtcatctcc ccttaagtgc gcccctccc cacccaagta tcataggaaa
4321  ccggtgaggt ctggtgtctc tggttttgaga cggtaagttg ggaccccatcc ctgtctgggt
4381  gcccactctg acctttagtt tgcccttctg tgaaatgggt gtattgggta gcaagccctc
4441  ttcagaaagc gctgctggtg tcagagcagc tgcccagtac caggtggggg gtcaaggttg
4501  ctggtactgg ggcccccagc tgcccacaac ccctctttgt tctcaccctg caaagggtc
4561  aaggtcaaaa tgagcctcat ccttcctatg atctgggaag aggtgatgat caagtcccca
4621  acttcagtgt gaggtggaca gagttggggg gatggcccct ttttgaagag gtgaaaatgg
4681  ttttggagaa gcgcagctgc ttcactgggg gaatgcggca gggactgggg cccaggatgc
4741  tttggcctat ggggaaaagc cctttaaaag gcagggccca ggccctggag ccagcacaag
4801  actggcctcg agccctgag ccaggaggtc ctggaggaga gccaggccgg tgggcccgcc
4861  caaggctgga gggtcagccc aacagggag ctgggttggc caggggctg gactgctacc
4921  agcctctctg gcctatgggg acccaagagg acacatcccc cttttgccca ctcttctgtg
4981  tcattttgtt gttttggttt gtggtggttt tcttttttc tttgtttt cttttttctt
5041  tctttctttt ttttttttt tttttttttt tttgcacttc gcccacacag gacagtggag
5101  ccccacctgg tcagttccac ttccgggctc ccatgcactt gcccaaggcg gcctctttgg
5161  gacggggatg gtttgaggaa acacttttaa agaaaaaagg aagcattga aaggtttag
5221  tttcttccct atctgcatgt cctctcatat agaaagccca gaattagggg ctagaactcc
```

-continued

```
5281  aggagagggt ctccccgact catctcttgc tgacggtcac caggatgcag aaatagggag
5341  atggttagtg ggggccaaag atgcccctc ccaggccttc gtggttccct cctccgcccc
5401  ctgcaatctt tggaggagtc agtgcctcac tccagcagtg agtgcctact gtatgcaggt
5461  agtcagccag gcaaagagag actaacggtc tcatggggga accctcttgc ggaggccgg
5521  gtagctggag cgaagcgttc cggctgccct tgctgctggg tggagtggag agggagactt
5581  ctttttgttg gttttaattt aaaaacacaa aggcctaaag aaatacgtat cttataattt
5641  ttttaatttt tgagacgttc atttaatgaa ttgtgcacga atgaattcta tatatataaa
5701  atatacatat atagctctat atttggggag gggcactgtc tcttttttct ctcatttta
5761  aaatgaagtg ttgttgcctt tgtatgtggt tcaaccatcc agctcccagc tggctaaact
5821  ttgcctccag tggtcaaaga tgggaaaaga gtggggttgg caggagatgg aaaacggagg
5881  tgccgcccca gcatgggggg caggtccccc agtccaccct gcccctcccc ctgtggagaa
5941  gacgcttagt tgggggtgtg ggtttgggct ccattctgga ttcggcggtt ccggggagg
6001  ggtgggtctg tgccgattac tctgtcttgt acgtttgttc tgctgctctt caatattgta
6061  tcaacgccag gaaggggggg tgaaaagcct cttttacccc ccaaataaat tgtcacattc
6121  cgaagctgag gcctagcccc taggttgggg tgtgtctgtg tcttc
```

CBX7 (accession No. NM_175709):

```
   1  ccagccccag catcgcgcgc cgcagccgcg ccccgcagc tccgcccccg gcccggcccg
  61  gccccgggcc cgctcgcccg ccgccccgca tggagctgtc agccatcggc gagcaggtgt
 121  tcgccgtgga gagcatccgg aagaagcgcg tgcggaaggg taaagtcgag tatctggtga
 181  agtggaaagg atggcccca agtacagca cgtgggagcc agaagagcac atcttggacc
 241  cccgcctcgt catggcctac gaggagaagg aggagagaga ccgagcatcg gggtatagga
 301  agagaggtcc gaaacccaag cggcttctgc tgcagcggct gtacagcatg gacctgcgga
 361  gctcccacaa ggccaagggc aaggagaagc tctgcttctc cctgacgtgc ccactcggca
 421  gcgggagccc tgaggggtg gtcaaggcgg gggcacctga gctggtggac aagggcccct
 481  tggtgcccac cctgcccttc ccgctccgca gccccgaaa ggcccacaag tacctgcggc
 541  tctcgcgcaa gaagttcccg ccccgcgggc ccaacctgga gagccacagc catcgacggg
 601  agctcttcct gcaggagcca ccggccccag acgtcctgca ggcggctggc gagtgggagc
 661  ctgctgcgca gccccctgaa gaggaggcag atgccgacct ggccgagggg ccccctccct
 721  ggacacctgc gctcccctca agtgaggtga ccgtgaccga catcaccgcc aactccatca
 781  ccgtcacctt ccgcgaggcc caggcagctg agggcttctt ccgagaccgc agtgggaagt
 841  tctgaatcac cgttttact cttcttaaac tgttttcttt tgggcttggg gtgggacttc
 901  cagagatagg gatgggttgg gggcgggta attattttat ttaaaaaaat accgagcagc
 961  aaaagggag aagatcccac tactctccca ccacctgccc tttctctgag ggacgtttac
1021  cacgaggcct caggctgggg atggagagag ttgctctggg agttggggta ccacccccag
1081  ggcaggatgg ggacaggatc acctgcccgg acaccacca ttatcattct cctctagtga
1141  cgcagcagct ggttctggga gttaaggag cattggaagg cccaaaccct ctcccttgag
1201  tggccacccc agcctggttg gctggttttc ccttttctc ttgtttcaat tgggtcttta
1261  ccttgaactc tcctctctgg ctttgcggtg ggctgtggag gctggttttg accaaaagtg
1321  agtggggcgg gaggaagggg caggaggaag ggttgaggtt acttgggggcg agtcccttcc
1381  ccttcagaga ggcttctatc cttcccaggg aggaggcgcc gctgagaccc ttctgctgag
1441  agctctgccc tcccctcatc acctggcctg tgcagaaacg ctcatgcaca cctggctgca
```

-continued

```
1501  caggtgtgca cgcattaccc ttcgcgtgta cgttcccatg tgccccgtga agcatgtgt
1561  ggctgcagac gtgtccacat gggccttgcg aacctgggtt agaaccctg gccaggcgaa
1621  cgtggggtga ttcacagcac aaaagacctc accaccacac ctgcactcac cccaccttgc
1681  atgcaccttg ctacctgctt gcggctttca gtggagggca ggggtctggc acaggtgcga
1741  tggcacccca tgctccaggc atacagatgt ggtttctcgg ctgcaccggg ccaggctgcg
1801  ggtgtgcagg cgtctgctaa gttgtgtgat gtatcagcac aggctttgag acgtctggac
1861  cctgtccttc ctcccgtgag gggttcttgt tctttctgac tcaggtgact tttcagccct
1921  tccaattccc ctcttttct gccctcccct ccaactcagc caacccaggt gtgggcagtc
1981  agggagggag ggagtgtccc accacgttct cagggcagcc cttgactcct aagccccttc
2041  ctccttccat tctgcatccc ctccccatcc aacctaaatg ccacagctgg ggctgagctg
2101  tattcctgtg gagggacctc tgccgtgcct ctctgaggtc aggctgtgct gtgtgatggg
2161  caggctttgc cccagcccac ccctggcaag gtgcacttgt tttctggttt gtacaaggtg
2221  tcctgggggc ccgtggcttc cctgccagtg aggagtgact tctccctctc ttccagtcct
2281  gtaggggaga caaaaccaga ttgggggggcc caaggggagc atggaaaagg ccggctcccc
2341  tgtctttcct tggctgtcag agtcagggta acacacacca agagtggagt gcggccagca
2401  agtttgagac ctgcccgccc tcctcgcagc tctgctctgt gtcctcagga agtcacagag
2461  tctactgagg caaggagagg gtgattcttt ccccaaatcc cttcttccct ggttcccaaa
2521  ccaaagacag cctgcagccc tttctgcatg gggtgctctg ttgacaggct tcccagatcc
2581  ctgagtctct cttttccttcc tcctcgatct ttagttgtcc acggtcaatt cagtgcttcc
2641  attgggggac agtccccctcc gggatgacct gattcacctc cagcccaggg aatggaatct
2701  agaggaatac gtggggtggg tctggacaag gagcggcagg aatcaccacc catctccagc
2761  tgtggagccc tgtggagggg aagggggaagc ttggggttca gaggggactc ttccaggaga
2821  ggggtgccca gcggaggtaa agatgataga gggttgtggg gggtctctag ttgaatgttt
2881  tggcccatga ctttggaaca tggctggcag cttccagcag aagtcacgct ccccatcccc
2941  caggggacat aggaccttt tcctgcttcc tggtcacttt caaagaacta tttgcgcaat
3001  ctgtgggtct gtggattcac ggggctttct gtgtgggtgc tgcagttgct tttgtctgca
3061  gcagcaggac acatctttcc tcttactcag ccctttatgg cccatgggga actccgtggc
3121  tcagggagag ctgaactcca ggggtgtgac ctgggacggg tgggcctgag gtgcccagct
3181  cagggcagcc aggtggctca tgggctgtag tgagccagct ccctggggga aaggctgtg
3241  ggccgttagg accatcctcc aggacaggtg acctctatga ggtcacctac ggctgtggcc
3301  gtgcaggcct ccttccagcc cagagtggcc cagtagagca aggcagacag tgacctccac
3361  ccccgcagcc ctcttaaaag gccagtactc ttgggggtgg ggggagggtt tagaaagcat
3421  ttgcccatct gcctttcttt ccccagccc ccacccgctt gaatgtaga acccgtgggg
3481  cacttttcct tttgtggtgg ggggtgcgga ggaggtaccc ccacccctgg cacagccgcc
3541  tggaatgcag gactgtcact gctgttcggg tgatgacctc gttgccaagc tcctcctgtc
3601  cccttgttct ggggcaggc gctgtgcttc tgtgaggtgg tttagctttt gctttcgaag
3661  tggccagctg cggccaccag gtctcagcac aagagcgctt cctttgcaca gaatgagctt
3721  cgagctttgt tcagactaaa tgaatgtatc tgggaggggt cggggcacg agttgattcc
3781  aagcacatgc ctttgctgag tgtgtgtgtg ctgggagagt cagagtggat gtagagcgcg
3841  gttttatttt tgtactgaca ttggtaagag actgtatagc atctatttat ttagatgatt
```

-continued

```
3901    tatctggtaa atgaggcaaa aaaattatta aaaatacatt aaagatgatt taaaaaaaag 3961    aaaa
```

PHC1 (accession No. NM_004426):
```
   1    cccgccgcgg aggccgagcg agcccccagc ccagcctggc gactggggac cccggcacat 61    gaggtggacg cccccgggga agacttgggt gcacagccag gcgagaaggt cttgagtcag 121    acagagcacc agccttgggg accctggacc actatcatgg agactgagag cgagcagaac 181    tccaattcca ccaatgggag ttctagctca gggggcagct ctcggcccca gatagctcaa 241    atgtcacttt atgaacgaca agcagtgcag gctctgcaag cactgcagcg gcagcccaat 301    gcagctcagt atttccacca gttcatgctc cagcagcagc tcagtaatgc ccagctgcat 361    agcctggctg ccgtccagca ggccacaatt gctgccagtc ggcaggccag ctccccaaac 421    accagcacta cacagcagca gactaccacc acccaggcct cgatcaatct ggccaccaca 481    tcggccgccc agctcatcag ccgatcccag agtgtgagct ctcccagtgc taccaccttg 541    acccaatctg tgctactggg aacaccacc tccccacccc tcaaccagtc tcaggcccag 601    atgtatctac ggccacagct gggaaaccta ttgcaggtaa accgaaccct gggtcggaat 661    gtgcctctag cctcccaact catcctgatg cctaatgggg cggtggctgc agtccagcag 721    gaggtgccat ctgctcagtc tcctggagtt catgcagatg cagatcaggt tcagaacttg 781    gcagtaagga atcaacaggc ctcagctcaa ggacctcaga tgcaaggctc cactcagaag 841    gccattcctc caggagcctc ccctgtctct agcctctccc aggcctctag ccaggcccta 901    gcggtggcac aggcttcctc tggggccaca aaccagtccc tcaacctag tcaagctggt 961    ggaggcagtg ggaatagcat cccagggtcc atgggtccag gtggaggtgg gcaggcacat 1021    ggtggtttgg gtcagttgcc ttcctcagga atgggtggtg ggagctgtcc cagaaagggt 1081    acaggagtgg tgcagcccct tgcctgcagcc caaacagtga ctgtgagcca gggcagccag 1141    acagaggcag aaagtgcagc agccaagaag gcagaagcag atgggagtgg ccagcagaat 1201    gtgggcatga acctgacacg gacagccaca cctgcgccca gccagacact tattagctca 1261    gccacctaca cacagatcca gccccattca ctgattcagc aacagcaaca gatccacctc 1321    cagcagaaac aggtggtgat ccagcagcag attgccatcc accaccagca gcagttccag 1381    caccggcagt cccagctcct tcacacagct acacacctcc agttggcgca gcagcagcag 1441    cagcaacaac agcaacagca gcaacagcag cagccgcaag ccaccacccc tcactgcccct 1501    cagccaccac aggtcccacc tactcagcag gtcccacctt cccagtccca gcagcaagcc 1561    caaaccctgg tcgttcagcc catgcttcag tcttcaccct tgtctcttcc acctgatgca 1621    gcccctaagc caccaattcc catccaatcc aaaccacctg tagcacctat caagccgcct 1681    cagttagggg ccgctaagat gtcagctgcc cagcaaccac caccccatat ccctgtgcaa 1741    gttgtaggca ctcgacagcc aggtacagcc caggcacagg ctttgggggtt ggcacagctg 1801    gcagctgctg tacctacttc ccggggatg ccaggtacag tgcagtctgg tcaggcccat 1861    ttggcctcct cgccaccttc atcccaggct cctggtgcac tgcaggagtg ccctcccaca 1921    ttggccctg ggatgaccct tgctcctgtg caggggacag cacatgtggt aaagggtggg 1981    gctaccacct cctcacctgt tgtagcccag gtccctgctg ccttctatat gcagtctgtg 2041    cacttgccgg gtaaacccca gacattggct gtcaaacgca aggctgactc tgaggaggag 2101    agagatgatg tctccacatt gggttcaatg cttcctgcca aggcatctcc agtagcagaa 2161    agcccaaaag tcatggacga aagagcagt cttggagaaa aagctgaatc agtggctaat 2221    gtgaatgcta atactccaag cagtgaacta gtagccttga cccccgcccc ttcagtaccg
```

-continued

```
2281  cctcctacac tagccatggt gtctagacaa atgggtgact caaaccccc  acaggccatc
2341  gtgaagcccc agattctcac ccacatcatt gaaggctttg ttatccagga aggagcagaa
2401  cctttcccgg tgggttgttc tcagttactg aaggagtctg agaagccact acagactggc
2461  cttccgacag ggctgactga gaatcagtca ggtggccctt gggagtgga  cagcccatct
2521  gctgagttag ataagaaggc gaatctcctg aagtgcgagt actgtgggaa gtacgccccc
2581  gcagagcagt ttcgtggctc taagaggttc tgctccatga cttgcgctaa gaggtacaat
2641  gtgagctgta gccatcagtt ccggctgaag aggaaaaaaa tgaaagagtt tcaagaagcc
2701  aactatgctc gcgttcgcag gcgtggaccc cgccgcagct cctctgacat tgcccgtgcc
2761  aagattcagg gcaagtgcca ccggggtcaa gaagactcta gccggggttc agataattcc
2821  agttatgatg aagcactctc tccaacatct cctgggcctt tatcagtaag agctgggcat
2881  ggagaacgtg acctggggaa tcccaataca gctccaccta caccggaatt acatggcatc
2941  aaccctgtgt tcctgtccag taatcccagc cgttggagtg tagaggaggt gtacgagttt
3001  attgcttctc tccaaggctg ccaagagatt gcagaggaat ttcgctcaca ggagattgat
3061  ggacaggccc ttttattact taaagaagaa catcttatga gtgccatgaa catcaagctg
3121  ggccctgccc tcaagatctg cgccaagata aatgtcctca aggagaccta aggtggccct
3181  cttgcacaaa ccagcctaag gcagacactc tccactgtcc aggttataac ctggtaccag
3241  cagactttgc agggaagaaa gagttgttcc aatcatgtaa ccttctgtag gggattactg
3301  agacagggaa gagaagtgca agaattggtt gctggtgcta catggcggca gctttgacat
3361  tttctctggg ttctacttta tttttttaaaa tctttacagt tctcaccatt tcacgtacct
3421  taatccaatc tttataaaag aggcagtcta gagaactagg actgctcagc cttatcctgg
3481  agtggagcat ttagcccagg tcttaattct ccaagaggag gaatacatag tatggtaagg
3541  caaggaactg ggtggaatgt caggttgcct gcccaatggg agaggtaggg ttttttctagc
3601  ttgtgtgaca gaagtagcaa aatctggtcc tcccccctcc cagtgtagct gtggctcaga
3661  gttttttctt tttgttgtca cttactccct tgtgattgaa ttttttctcc tgcatccatg
3721  gcaggatccc cagccagtat agagacttgg ttggcatctt ctgctgcagg gactaaaagt
3781  atttgactgg ggcacatgtg gctgttgtca ttctttctgc atcccactgt tcccctccaa
3841  tttatgttat tttctaccct gttttttcagt tccatctctg ctctgtccta tagctttata
3901  aaaccagagt gtgtggggct gaggtcagga gtataagtac ctgccttagg cactattcct
3961  tatataacaa aaatattaaa tatttttttc ctcagtaaaa ggatgaaaat tggtttcagt
4021  tgtcttactc tattccagtc tttgcccact ttcacacaaa tgacaaggcc aatatgtttt
4081  gtttgttttt taatcattaa gagttttttgt acaaaaggtg atggtttttt ttcttcattt
4141  taaaacacca gggtgtgggg gagggatgca aacaaataac aaaaaagatg cttttgtaac
4201  attatttttcc ctgtttagaa agaaaaaaat cactccaata gtattgaaaa gtccaaagat
4261  gaaatagttt catttttcttt tcctaaggct tataaaaggc cccctgcctg ttgattccat
4321  ccctcttttg tgtccagtgg agccatgtta ctcttcagtg gcccaggggt tcactattaa
4381  agaaagatca gtccaggttt ctgggcacat ggcctaaaca ggaagatgga agcatcagag
4441  gattaaaaac cttttccccac agaaatgtgg gcaagaagac acttccctga ccagcagaa
4501  gggacaggtg cagcagcatt ccacacccag cgcagaggac agcagagccc tcgatgtccc
4561  acttctgctt ccgttccctt tctagaagat tgaaaaaaag gtcaaaacca catgcctgtg
4621  gagaaagtgc gacatgttta gaaatactgg tagggaacca ggagtaagaa aagctttacc
4681  agcttttact acaaatggat gaaagacatc aggatcccac caccgcaagg taaagtgact
```

```
4741  tccctttct  ggaaccctg   tggcacagga  gtaccaattt  tcctttccaa  cgaactggat
4801  ttctggatag  gcattttggc  tgtatgtgga  cagataagac  cacagtcctt  agcccaatcc
4861  cagctataca  gtcaccccaa  tttccacaaa  tgatgtgatg  gtaccgtata  atcctgtaat
4921  tgggaaattt  cacatttttc  ctgtcctaat  ctcagaggtg  ggagaagcaa  gtctagaaca
4981  tctccaggct  cagactaaac  gagagtactt  ggactgcaac  caagtaatca  ctgcaaagta
5041  gttccaagca  gcaagaaata  ccagattctc  atggaggcta  ctatagggta  cagaataaca
5101  acatgaaagc  aatcaaccct  gtataaataa  tgtttcttgg  cattttttt   ttaattaaag
5161  aaatccagtg  tctcaaaaaa  aaaaaaaaa   aaaaaaaaaa  aaaaaa
```

PHC2 (accession No. NM_198040):

```
   1  catctgcctg  cccttctgcc  atccgagcgc  cctgactgcg  ccacactgca  ggccatggag
  61  aatgagctgc  cagtcccaca  tacatctagc  agtgcctgtg  ccaccagcag  taccagcggg
 121  gccagtagca  gcagtggctg  caacaacagc  agcagtggtg  gaagtggccg  ccccaccggg
 181  ccccagattt  ctgtgtacag  tggtattcca  gaccggcaga  ccgtgcaggt  gatccagcag
 241  gccctgcaca  gacagcccag  cacggccgct  cagtacctgc  agcagatgta  cgccgcccag
 301  cagcagcacc  tcatgctgca  gaccgcggcg  ctccagcagc  agcacctcag  cagcgcccag
 361  ctccagagcc  tggcagccgt  acagcaggca  agcctggtat  ccaatagaca  aggaagcact
 421  tcaggcagca  atgtgtctgc  gcaggccccg  gcccagtcat  cttcgatcaa  cctggcagcc
 481  tccccagcag  cagcccagct  cctcaaccgg  gcccagagtg  tgaactctgc  agcagcctca
 541  ggcatcgctc  agcaggctgt  gctcttgggc  aacacgtctt  ccccagcccct dactgcaagc
 601  caagcacaga  tgtatctgag  ggcacagatg  ctcatcttca  cgcccacggc  caccgtcgct
 661  actgtgcagc  ctgagctcgg  cactggctcc  ccgcccggc   ccccacccc   cgcccaggta
 721  cagaacttga  ccctccgaac  acagcagaca  ccagcggcag  cagcctcggg  ccccaccccc
 781  actcagcctg  tcctgcccag  cttggccctg  aaaccacgc   cgggcggtag  ccagcctctg
 841  cctaccccag  cacagagcag  aaatactgct  caggcttccc  ctgcaggtgc  caagcctggc
 901  atagctgaca  gtgtgatgga  gccacacaag  aaaggagatg  gcaacagcag  tgtgccaggg
 961  agcatggaag  gccgggctgg  gctcagccgg  acggttcctg  ctgtggctgc  caccccctc
1021  attgcaccag  cctatgctca  gctgcagcca  caccagctcc  tcccacagcc  atcctcaaag
1081  cacctgcagc  cccaatttgt  gatccagcag  cagccacagc  cacaacagca  gcagccgccg
1141  ccccagcagt  cacggcctgt  gctccaagct  gagccccacc  ccagctcgc   ctcagtctct
1201  ccaagcgtgg  ccctccagcc  cagctcagag  gcccatgcca  tgccactagg  cccggttaca
1261  cccgccctgc  cactccagtg  tcccactgcc  aacctgcaca  agcctggcgg  cagtcagcag
1321  tgtcaccctc  ccacacctga  tactgggcct  cagaatggac  atcccgaggg  cgtgccccac
1381  acccctcaac  gcaggttcca  gcacacttca  gctgtcatct  tacaactgca  gcctgcttca
1441  ccaccccagc  agtgtgtccc  tgatgactgg  aaagaagtgg  caccaggga  gaaaagtgtg
1501  cctgagacgc  ggtctggccc  atcaccacat  cagcaggcta  ttgtcactgc  catgcctggt
1561  ggcctgcctg  tacccacgag  ccctaacatc  cagccgtccc  cagctcacga  gacagggcag
1621  ggcattgttc  atgcactgac  cgacctcagc  agccccggca  tgacctcagg  gaacggaaac
1681  tctgcctcca  gcatcgccgg  cactgccccc  cagaatggtg  agaataaacc  accacaggcc
1741  attgtgaaac  cccaaatcct  gacgcatgtt  atcgaagggt  ttgtgatcca  ggaggggcg
1801  gagcctttcc  cggtgggacg  ctcgtccctg  ctggtgggga  atctcaagaa  gaagtatgca
1861  caggggttcc  tgcctgagaa  acttccacag  caggatcaca  ccaccaccac  tgactcggag
```

-continued

```
1921   atggaggagc cctatctgca agaatccaaa gaggagggtg ctcccctcaa actcaagtgt
1981   gagctctgtg gccgggtgga ctttgcctat aagttcaagc gttccaagcg cttctgttcc
2041   atggcttgtg caaagaggta caacgtggga tgcaccaaac gggtgggact tttccactca
2101   gaccggagca agctgcagaa ggcaggagct gcgacccaca accgcgtcg ggccagcaaa
2161   gccagtctgc caccacttac aaggatacc aagaagcagc caacaggcac tgtgccccctt
2221   tcggttactg ctgctttgca gctaacacac agccaggaag actccagccg ttgctcagat
2281   aactcaagct atgaggaacc cttgtcaccc atctcagcca gctcatctac ttcccgccgg
2341   cgacaaggcc agcgggacct ggagctcccc gacatgcata tgcgggacct ggtgggcatg
2401   ggacaccact tcctgccaag tgagcccacc aagtggaatg tagaagacgt ctacgaattc
2461   atccgctctc tgccaggctg ccaggagata gcaggaat tccgtgccca ggaaatcgac
2521   gggcaagccc tgctgctgct caaggaggac caccctgatga gcgccatgaa catcaagctg
2581   gggcccgccc tgaagatcta cgcccgcatc agcatgctca aggactccta gggctggtgg
2641   cagccaggat tctggcccag ggcgcctcct cccgactgag cagagccaga cagacattcc
2701   tgaggggccc agaaatgggg ccggttggag ggcaggggct ctccctaggg gcatagctgg
2761   tgaggaggtc tgggcacctc ctccatggct ctcaggggcc tttcatttct gtgggagggg
2821   cagagaggta ggtggacag aagatggggc tttatgcttg taaatattga tagcactggc
2881   ttcctccaaa gtcccaatac tctagccccg ctctcttccc ctctttctgt cccccatttt
2941   ccaggggggta tatggtcagg gctccccaac ctgagttggg ttacttcaag ggcagccagc
3001   aggcctggat ggaggcctag aaagcccttg ccttccttcc tcccacttct ttctccaggc
3061   ctggttaact cttccgttgt cagcttctcc cccttcagcc tgtttctgca gcagccaggg
3121   ttctcccccc tacaccctct gcaggtggag agagagaagc tgggcccagc cgggccgtgc
3181   ctgctggcac agacgcctta acgctgtgtg tatgactgtg tgactgtgtg ggagcctgga
3241   ctgacagata ggccaagggc tactctctgg catctccagg tgttttgtag caaacagcca
3301   cttagtgctt tgtcctggac tccactcagc ctcaggatgg ggaatagcca agaatggcag
3361   cctcagcgca gaggcaaggt cagaaagaga cggcgcttca gagtttcctt tccagacacc
3421   cctccccgca ctgtgaagtt cccctgaccg ccctcctggt tcacaaagag cattaagaaa
3481   gctgcggtgg tctgagcaac atagcccaaa gggctgagcc tcctggcctg cctgcccgcc
3541   caccctggga gtcccagtgg tgaggctcag agaactgcta aggggaaaga acagctggag
3601   tttctgttga tgtgaagaag gcagctcttg gcctcccact cccacacttc tttgcctata
3661   aatcttccta gcagcaattt gagctacctg aggaggaggc agggcagaaa gggcgagggc
3721   ctgcctctga cctgccgtgt cctttgcagg aaggaggtag gcacctttct gagcttattc
3781   tattccccac ccacaccccc aggcagggtt ggaaatgaag gactnttta acctttgttt
3841   tgttttttaa aataaatct gtaaatctg tct
```

PHC3 (accession No. NM_024947):

```
  1    atgcgcagcc catgttagtg atggaggaga gaagatggcg gaagcggaat ttaaggacca
 61    tagtacagct atggatactg aaccaaaccc gggaacatct tctgtgtcaa caacaaccag
121    cagtaccacc accaccacca tcaccacttc ctcctctcga atgcagcagc cacagatctc
181    tgtctacagt ggttcagacc gacatgctgt acaggtaatt caacaggcat tgcatcggcc
241    ccccagctca gctgctcagt accttcagca aatgtatgca gcccaacaac agcacttgat
301    gctgcatact gcagctcttc agcagcagca tttaagcagc tcccagcttc agagccttgc
361    tgctgttcag gcaagtttgt ccagtggaag accatctaca tctcccacag gaagtgtcac
```

-continued

```
 421   acagcagtca agtatgtccc aaacgtctat caacctctcc acttctccta cacctgcaca
 481   gttaataagc cgttcccagg cttccagttc taccagcggc agtattaccc aacagactat
 541   gttactaggg agtacttccc ctaccctaac ggcaagccaa gctcaaatgt atctccgagc
 601   tcaaatgctg attttcacac ccgctaccac tgtggctgct gtacagtctg acattcctgt
 661   tgtctcgtcg tcatcgtcat cttcctgtca gtctgcagct actcaggttc agaatttaac
 721   attacgcagc cagaagttgg gtgtattatc tagctcacag aatggtccac caaaaagcac
 781   tagtcaaact cagtcattga caatttgtca taacaaaaca acagtgacca gttctaaaat
 841   cagccaacga gatccttctc cagaaagtaa taagaaagga gagagcccaa gcctggaatc
 901   acgaagcaca gctgtcaccc ggacatcaag tattcaccag ttaatagcac cagcttcata
 961   ttctccaatt cagcctcatt ctctaataaa acatcagcag attcctcttc attcaccacc
1021   ttccaaagtt tcccatcatc agctgatatt acaacagcag caacagcaaa ttcagccaat
1081   cacacttcag aattcaactc aagacccacc cccatcccag cactgtatac cactccagaa
1141   ccatggcctt cctccagctc ccagtaatgc ccagtcacag cattgttcac cgattcagag
1201   tcatccctct cctttaacag tgtctcctaa tcagtcacag tcagcacagc agtctgtagt
1261   ggtgtctcct ccaccacctc attcaccaag tcagtctcct actataatta ttcatccaca
1321   agcacttatt cagccacacc ctcttgtgtc atcagctctc cagccagggc caaatttgca
1381   gcagtccact gctaatcagg tgcaagctac agcacagttg aatcttccat cccatcttcc
1441   acttccagct tcccctgttg tacacattgg cccagttcag cagtctgcct tggtatcccc
1501   aggccagcag attgtctctc catcacacca gcaatattca tccctgcagt cctctccaat
1561   cccaattgca agtcctccac agatgtcgac atctcctcca gctcagattc caccactgcc
1621   cttgcagtct atgcagtctt tacaagtgca gcctgaaatt ctgtcccagg gccaggtttt
1681   ggtgcagaat gctttggtgt cagaagagga acttccagct gcagaagctt tggtccagtt
1741   gccatttcag actcttcctc ctccacagac tgttgcggta aacctacaag tgcaaccacc
1801   agcacctgtt gatccaccag tggtttatca ggtagaagat gtgtgtgaag aagaaatgcc
1861   agaagagtca gatgaatgtg tccggatgga tagaaccccca ccaccaccca ctttgtctcc
1921   agcagctata acagtgggga gaggagaaga tttgacttct gaacatcctt tgttagagca
1981   agtggaatta cctgctgtgg catcagtcag tgcttcagta attaaatctc catcagatcc
2041   ctcacatgtt tctgttccac cacctccatt gttacttcca gctgccacca aaggagtaa
2101   cagtacatct atgcacagta gcattcccag tatagagaac aaacctccac aggctattgt
2161   taaaccacag atcctaaccc atgttattga aggctttgtg attcaggagg gattggagcc
2221   atttcctgtg agtcgttcct ctttgctaat agaacagcct gtgaaaaaac ggcctctttt
2281   ggataatcag gtgataaatt cagtgtgtgt tcagccagag ctacagaata atacaaaaca
2341   tgcggataat tcatctgaca cagagatgga agacatgatt gctgaagaga cattagaaga
2401   aatggacagt gagttgctca agtgtgaatt ctgtgggaaa atgggatatg ctaatgaatt
2461   tttgcggtca aaacgattct gcactatgtc atgtgccaaa aggtacaatg ttagctgttc
2521   taaaaaattt gcacttagtc gttggaatcg taagcctgat aatcaaagtc ttgggcatcg
2581   tggccgtcgt ccaagtggcc ctgatgggc agcgagagaa catatcctta ggcagcttcc
2641   aattacttat ccatctgcag aagaagactt ggcttctcat gaagattctg tgccatctgc
2701   tatgacaact cgtctgcgca ggcagagcga gcgggaaaga gaacgtgagc ttcgggatgt
2761   gagaattcgg aaaatgcctg agaacagtga cttgctacca gttgcacaaa cagagccatc
```

-continued

```
2821  tatatggaca gttgatgatg tctgggcctt catccattct ttgcctggct gccaggatat
2881  cgcagatgaa ttcagagcac aggagattga tggacaggcc cttctcttgc tgaaagaaga
2941  ccatctcatg agtgcaatga atatcaagct aggcccagcc ctgaagatct gtgcacgcat
3001  caactctctg aaggaatctt aacaggaaca tgaagccttg ataaaacagc agttttactt
3061  ttctcacaaa aacttgtaag gtaaaggcct aacttggtct agaatatgac acttattgtg
3121  gtggatagcc aagcacattg ggatctccac atcaaatact gacatttctt ctacaggtat
3181  aataattcat catgcatttt cataattaat aaacattggt aaaattaatt ttacaggtta
3241  catgaaacat tgaaagactt gttacagagg gccatgatat ttttcaaaga aatgtgttat
3301  actagataat ttttttaaag gtgatgttta tcattaatat aaagaatcct tttaaaagta
3361  atttaatgat ttacatttct cctcttttga ttcaattttc ttatacattt tttctaccct
3421  attagttttc taaaggttgt catgagaggt atattatgga ataatttagt agtccagtga
3481  cagaatcgta tgaaatcagt gtacattta aaaacatgt cttttagaca tatgctttat
3541  ctataaaaaa ggaattgtgt tctagtatga acaatactga tctggaagtg agaagagtta
3601  gtttctattc caaacttgac caagaatttg gtttgactga aacgttttc ctctcagttt
3661  ttgtacattt atttagagca gtggttctca gtggaggtca gttttgatcg ccaggggaca
3721  tctggcaatg ttgagacatt ttggttgtca cagcttgggg gtgggttcag gggagggttg
3781  ctactggtgt ctagtagtta aagccagag atgtttctaa acatcttata atgcacagga
3841  cagcacccct ccactgtaaa gaattattgg ttcaaaaata tcggtactgc caaggttgag
3901  aaactctgat atagaaggag tgataaaatat tgttttcacc caaaggaata cttttaaagg
3961  atgaagctta ctaaacatat atgatggaag tattattcag ataacattaa tattctgctg
4021  aataatttt tctagtttaa tcatactaga aaagaaaaa aaatctacaa attgtcctat
4081  aaaataagga caaacatgca ataatttaa ctctcagaaa gtactaattc attctgatta
4141  tctttcatac ctctgtgctc ctctgcactg acgaagacat aatatgatta tacctatgaa
4201  ctagtgcaca gccttttctg gcaagaaaat agtttgtagc agatacgtgg ttgctctttg
4261  gatttttttc tattgttgaa catgctggga ctagctagaa tgcacattcc tacttccttt
4321  accaaacgtt tgcatgcttc ctgcaaagca cttaccaagt gatttctctt gaaccatcgg
4381  atataatttt gtatgtacat gtttgaggaa aaaaatgtaa agcaaaacct tttactgaac
4441  agtgttctat agaattatga cactaaaaca aaattgtttg tggaagcct gaaagcttta
4501  tagtcctgga catcaaaaat tttatttgag atgatgaatg ttttgttttc atcttttctt
4561  atattaccac aattgagata ttttagtaat tgaaggaaca tacacagata tttggcagaa
4621  gtcgagtaag gaggggaaaa aaagagtccg tgagtttcag tcattttcac tgctctttc
4681  aaaaagattg tgttgagctg gtagaagact aaagatgtca ctgaagcat cacagatact
4741  atatttatct tttggctttg tgtacattag agaatgttga ttatttttat acaaaaatac
4801  agcgggtaat tttttttaatc tttagatgcc tcttgtttga atgtatgctt tgtggaattc
4861  tttgtgtagt aatgttttaa aaaaagatgt ttactgatag ttacatgtag gattagaata
4921  tgtaatataa tataaggctc atgttccaga cctacgatag cttgtagtct atgttacgta
4981  tttctttata tcacattttt aatcattgga ttaaagtatc aaggaaagct aggtactcta
5041  taatgagttt tcatttatta gcagttaatc atcatgacag aattgtcata tgcttgactt
5101  ttccctcttc ttggaatttc agaacacaaa tacaggctaa gcattagtaa gagatggccc
5161  acagtatgag agagagaggt gcaacgaaa atctcgcctg gaattaaaac ttttcataga
5221  ttatccacgg ttaatacaaa atttattata tggggataga ctgctccagc aataatgatt
```

```
5281  acatcctata actgtattac ctatggcctt taaggtatca attttgaact gtgttgtagg
5341  ctctccttt atttgttctc tttcctaata gcagccattc tgtacttatt gaaagcccct
5401  gtgcctactg ctgtcttaag tattcaggag gggcttacaa gagggttttc tattggagaa
5461  taccgtataa tcttaaatct agtccagatc tctgttgtcc ccactcaaaa catacacaaa
5521  atatgcactt gcttttttca agtgagtttt tatttaaaaa tggcttgttt gctatcacat
5581  tggtgcagct gtttctttca agatgagtta atcatcttaa tttcaaagct tcagctatat
5641  ataatggata tatagacaac actgagcatc cacctctctc ctgagcttta aagcagagtt
5701  tcagtatgat ataggtgggg agagtaaatt gttttcatat cctttcatac tactactaat
5761  agtttagga ttttgactgg ggagagataa tgacaaacag aaagggaaca tggaggttct
5821  tcctactttt gctacctaag tttgcatttt ctgacttcct tgcagtgttg cactctttgt
5881  cccattggga taaaaagcat aagtttgaaa ttttgcttta agccttgtgt tcctggggaa
5941  gttaaacaac taagagagct gatttgtaaa aattatttt tatatgacat taatattcat
6001  caagccttgt gtaggcatgt gtaagacaca gctatgcagc tttgagtagt caatatagta
6061  tgagatagag tgttgtccca atcctcctg tcacttttta agtagcatat tatttccctg
6121  atggtcctgt tactttgctg ttgaatgctc taaacagaac tttttaaaag gtgtgtttta
6181  agagcagtca cctaggagta gacaaggtgg aatgggagga gagaaatggt aatgcaaaag
6241  cttgagcatg ggaagagtca gaggaggagg ccatcatcct tgttagctta gcctacttca
6301  acactgagca catttctgca cttttgaagt gaaattcatg ttttacttag aagaaataat
6361  tttctttcat tagggatccc agttgatttt tgtttcctgg tgtatcaaaa tacttagaac
6421  tatgaaacaa gtattattgt gatcatgcct ttgaataatt tttgacgtag cttatcttca
6481  tgtatcaagt ataaaattat aatgagacat ctattcacaa atacaagtct tagattgaat
6541  tgaaatgtgt tatagtgccc tgtctcccac tgacttgttc agttaaatgt cttaaagtac
6601  attatgtaca tcttcaggct tttggtacca caatggcaca agtatggtag ggaggcaata
6661  tagtcttagg ctatatgcct atattaagtg tgtataaaca atttttgaaa gaatacacta
6721  ttatagatgt atgtgagtga tgctgacctg acagccatat ccagtggatg aaactgactg
6781  gacacactgt taaaatgttt taaagatgta ttttcagcca gaacagcctg gttatagttt
6841  gtggttttca ccttggtgga ttgcaggaac acatgcagcc tactggcatt gagcattagc
6901  taatggcatg aaagggcctc atctcactac ctctctaagg cctctagctc caagaaaacc
6961  atgaaaactt ctttcttgga gagatctttg tctcagaatc cttagagagg atttcgtatg
7021  ggggctaact ttaggaaggg aggcagctgg ggcaggactt tctgatacct gacagtcatg
7081  ttccagagca acctttgggc agtggaaact ggcgcatcta tgcaaaatga ttgctcaatc
7141  tctatcttgt gtactacata tgtaactagc tgggccctaa ggaaggtttt ctaggggaa
7201  ggatagggaa gtagaggagg agacaagtag gaggaacaaa gcattctaga cccaagagga
7261  tagaagatat ttaggataga tatggctttc atccatagtt caaaataatg cgttttgtta
7321  gatgccagtt atagcagtaa ataggttata gttttatat gtcaagattt acctgtaatc
7381  agactcattc tttcactctc tatacccact gtctccatgc ttgggagcat ggatattaat
7441  agttccagtg atgtagaagt tagtgatttt tgattctga aaaggtgag aacctttat
7501  tacagttgga gaatatttgt caaaaattca aaggttgttg taattgagtt gccagaatta
7561  cagagtttcc attttcagat atcacagttg aatcacctct gtagattgtt ataagagag
7621  gcattttaag atagtatttt atttgctagg ttgtgtctca gtctaagaat tgggaaaaga
```

-continued

```
7681  agagctatag gtttctcttt cctagtctgg atttcagtaa acacaagcct acctctgctt 7741  ctttggttca cagcagtgtg gatcatgaaa tgaactgttt acccacattc atcaatattg 7801  gtattttaca aatctacttg gagcatttaa tttcatctca aagattgtga tccactttag 7861  ataagcacaa atacagtatt aggaaaagta aatatgcaat cttactaaaa tttcaacttg 7921  ttaagctgta tatcttaaaa gaaattattt ggggctgggc atggtggctc acacctgtaa 7981  tcccagcact ttgggaggct gaggtgggta gatcacctga ggtcaggagt tcgagaccag 8041  cctgaccaat atggtgaaac cctatctcta ctaaaaacac aaaaattagc tgggtgtggt 8101  ggcatgcacc tgtaattcca gctacttggg aggctgagac aggagaattg cttgaaccca 8161  ggtggtggag gttgcagtga gccaagatca caccctgca ctccagcctg ggtgacagag 8221  cgagactcca tctcaaaaaa acaaaacaaa aaattatttg ggaagatacg tcctcttta 8281  ttagaagttc ataaaatgta tcatatagtt ttgttcacag tagttatata agctttcttc 8341  aaataaattt aaaattagat taccttcttt ggaaaaagaa tttcctaaat ttttaagaat 8401  tttcaaagtt ttacatatta gtttttagaa cctaatccgt tttaaaattg tactatgaga 8461  aagctttttt ttgaaagttg taaagcatta atacaaataa tacaaatata attattacca 8521  tcacattcca gagaatatgg ctttttctaa actttcaatt tagaaaacat acattaaggg 8581  agaatctctg ccctcctttt cagctctgaa gatcagcttt tctactcaga cacatgcaca 8641  caccccttcc aagtgtcatg tttatgggaa catttgggaa atgttttcca gatgttttat 8701  ttttccctt ttatagtttg ttgacattta attttactta aagatgacaa ttttaatcgg 8761  aaatgttaga ggtacaacat agtgaggttc tagctagctt tatacttttg aaaaatattt 8821  ttgtttctac tgcttttac aagtactagt cctctcagtg atactggtgg tgttcagtat 8881  gaatccatag aaagaaaaca aaatttgttg tttaaaaaaa gcagagtaat gaatgaattt 8941  cagttttgaa acaacataa tttgaaaaca ctgttatact aacatggcaa ggtgttaatt 9001  aaatataaga gtaaggtagt aagttctttt agagcacctg tttaaattta ctccagtaat 9061  catcttaagg attgatagtc accatcactt attggcttaa aagttatatt tcatggaata 9121  ttatcagtgt taaatccaag ctttgtggag ctttaagtga tggtggtgaa aagttggtg 9181  tttatgagag agtggtgggg tgtctagtca ttagtgaagt taaacatcaa cctgttttag 9241  aaagaatttt ttagtcttgc ctaaagtaaa ccagaagtgt ctagtgttta aatctttatt 9301  tagaatgctt ctcttaaaag tatttttgt tttgggtagt attaaataat cagtaaataa 9361  tctatttcag tagtaaataa tgaattaaga tgatgatgaa tgaggattaa cacactggtc 9421  tggagactgg ggtttatttt cagtgggtta gctgtgtgtg acatgttggg caattactca 9481  gctgttttaa cagcttccag atatgcagta tggtgcctgt actactcaaa agttgatttt 9541  ggtttaattc atctttaagg tacctcccag ctctaaaact atgattctag gctgtgtaat 9601  ggggttatte ctactttatt ctctttcctt ttttaagggt tcattttata cttaataagc 9661  atccatttct tgggtcacct acagtctttg ttctcctaag gattaaaata gaaaattcat 9721  acataacaag caaatgatga cattttccta aatgctcctt attggttaac cactgaatat 9781  atgaacacat atgaatattg tcattcatgt acttaaattc atttagcaaa ctatttgaac 9841  acttacatgt gcagtgtttg gtgaacatga catgaggaac tagtagtaag taaaatcttc 9901  cccccaaaat tcattgtggc ttaaataaat atgaacataa tcattactac ttaatatact 9961  gagagggaat cttaataaac ttggaactgg gagggaatat ttgtatacat tgggtaaagg 10021 gttaggctag atgacatcta aggggtctga gtgaatcata tcataatttt tataacacat 10081 ttcacatact aaacatcagt tggccccata cctgattaag ttacaaaatt taggagactt
```

-continued

```
10141 aacattaagg acttacaggt tgagacagcc cgtatttcac aacattattt tgacacttga
10201 ctctattcca gagttgttgc tatacaaggc atgtggcaga acaaaaaaaa agctggtgtt
10261 gatataagag cttttttaccc agtattgaca gtgagcaact ttctttcttt ttttttttttt
10321 ttctttttttt ttttttttgag atgggttcgc tctgttgccc aggctggtgt gcagtggtgc
10381 gatctcagct cactgcaacc tccacctccc gggttgaagc gattgtcttg cctcagcctt
10441 ccaagtagct ggaattacag gtgcccgccg ccacacctgg ctaatttttg tatttttagt
10501 agagacgggg cttcaccatg ttggccaggc tagtctcgaa ctcttgacct caagtgatcc
10561 acctgccttg gcctccctaa gtgctgggat tacaggcatg agccaccaca cctgtccgac
10621 agtgtagcaa ctttctaaaa ctgaaaaatc tcaaaggaga tcattggaac tgacttgttc
10681 atttattttt tgtttttaaa ttaagaaaga ttacacaaaa taagtgttac tgtactttaa
10741 gctattacaa atatccaact tttaaagata tgtaagaatc agtaatattc tagaaagcac
10801 atatatagta aaagggcatc ctttaaatgt agaacgggta acatgaaac agttccatgc
10861 ttgaattgtt aagtatctag ggggtaaaca ttgaatggga gaatcattta ttgggttaag
10921 gtcccttcct tgtcattctg ggatctgtga atcacattgt aattcctgtt gacaaagctt
10981 tacttgttaa catcagttga tactgacatt ctccataaag atatagaatg aaaatatcta
11041 ttaaaaatag tttatcattg ttttagcttt tttgttttgt ttgttttgag acagagtctc
11101 actgtcaccc aggcttgagt gcagcggtgt gatcttggct caatgcaacc tccacctccc
11161 aggttcaata gattctccca ccttggcctc ccaagtagct gggattactg catgcacca
11221 ctatgcctgg ccagtttttt gtatttttag tagagatggg gtttcaccat gttggccagg
11281 ctggactcga actcctgacc tcaagtgatc cgcccacctc agcctcccaa agtgccggga
11341 ttataggcat gagccactgc gcctagcctg ttgcagctt ttaaagcagg aaaatatcca
11401 tataaactgt tgggttagaa tctatattag aatctttcaa actaattgaa acaggaaga
11461 ctatcatcta agtagccaga taatctgggt ttcaaaaagt tattccatgg tactggttta
11521 aaaaatactt ttcaagtgtt ttaattttta aagtgtaact aattcttcaa atatgttatg
11581 ctgttaaaat atgtattcca taagtacttt ttgtatatgt attcttaaat tttaaaaagt
11641 caactgaatg cgcaaagatg atataatttt ggatgtagac atttaaacta gattcccagt
11701 cctctccttc aaaagcttgg tctttgtttt tcctataggg aaaaaagtca aaataagttc
11761 caaaaactat cctcaaagta gtattgtgct tgtagtaaat gaaggttgga tggatggata
11821 ctgacaatgg tggcaggcat ttcaagcctt ttaaattagt acttttttgtc gtcttgctta
11881 ttaaaatttt gttaatttta gcaaagacca attgttgtga taaactggtg ttttttttggat
11941 gcttcaagca cacgttaacc aattttttaa ttcccctttt ggttcctccc attgttctaa
12001 aataggactt tcatattatt aaaacctcaa aagatgatcc acccaggatg aacaaagatc
12061 accaagggga agaaaaacat tttttatctt tacagaaaac atgttaagat tatatataga
12121 tgtattcttt acattggata ttgtattaga gtcctcctta caagaaatga aatagttttt
12181 agcactctta gcattagagt tcctagattg gtgttgatag ctacagtttt aaaatgtata
12241 acctgaaaat gaaggttaat tttgcattgt aagagcacat ttgatctatg taaaaagtgt
12301 ccatttggtg tattttttta aaaagagaa agcactttca tattaagtag catgtgtatg
12361 aatttagatt ttcatatttg ttgtgtctgt attcagtgaa gtaaattgag catttaaatg
12421 tttgttgatg gcaacattaa ctattaaatt aaagcacctt atactctgct gcttaacttg
12481 cttgtaattg cacctttgtt acctgcacat tttcatatag aatattgttg taacattgct
```

-continued

```
12541   tcatgtgggt ctggatggaa gattagtggg cctacaggat catttatttta tattgtttat 12601   attacaataa tatattgtag atcagttgta agttcatttc tttacaaata aaagcctctt 12661   ccatttgact ggaaaaaaaa aaaaaaa
```

BMI1 (accession No. NM_005180):
```
   1    acagcaacta tgaaataatc gtagtatgag aggcagagat cggggcgaga caatggggat 61    gtgggcgcgg gagccccgtt ccggcttagc agcacctccc agccccgcag aataaaaccg 121    atcgcgcccc ctccgcgcgc gccctccccc gagtgcggag cgggaggagg cggcggcggc 181    cgaggaggag gaggaggagg ccccggagga ggaggcgttg gaggtcgagg cggaggcgga 241    ggaggaggag gccgaggcgc cggaggaggc cgaggcgccg gagcaggagg aggccggccg 301    gaggcggcat gagacgagcg tggcggccgc ggctgctcgg ggccgcgctg gttgcccatt 361    gacagcggcg tctgcagctc gcttcaagat ggccgcttgg ctcgcattca ttttctgctg 421    aacgactttt aactttcatt gtcttttccg cccgcttcga tcgcctcgcg ccggctgctc 481    tttccgggat tttttatcaa gcagaaatgc atcgaacaac gagaatcaag atcactgagc 541    taaatcccca cctgatgtgt gtgctttgtg gagggtactt cattgatgcc acaaccataa 601    tagaatgtct acattccttc tgtaaaacgt gtattgttcg ttacctggag accagcaagt 661    attgtcctat ttgtgatgtc caagttcaca agaccagacc actactgaat ataaggtcag 721    ataaaactct ccaagatatt gtatacaaat tagttccagg cttttcaaa aatgaaatga 781    agagaagaag ggattttat gcagctcatc cttctgctga tgctgccaat ggctctaatg 841    aagatagagg agaggttgca gatgaagata agagaattat aactgatgat gagataataa 901    gcttatccat tgaattcttt gaccagaaca gattggatcg gaaagtaaac aaagacaaag 961    agaaatctaa ggaggaggtg aatgataaaa gatacttacg atgcccagca gcaatgactg 1021    tgatgcactt aagaaagttt ctcagaagta aaatggacat acctaatact ttccagattg 1081    atgtcatgta tgaggaggaa cctttaaagg attattatac actaatggat attgcctaca 1141    tttatacctg gagaaggaat ggtccacttc cattgaaata cagagttcga cctacttgta 1201    aagaatgaa gatcagtcac cagagagatg gactgacaaa tgctggagaa ctggaaagtg 1261    actctgggag tgacaaggcc aacagcccag caggaggtat tccctccacc tcttcttgtt 1321    tgcctagccc cagtactcca gtgcagtctc ctcatccaca gtttcctcac atttccagta 1381    ctatgaatgg aaccagcaac agccccagcg gtaaccacca atcttctttt gccaatagac 1441    ctcgaaaatc atcagtaaat gggtcatcag caacttcttc tggttgatac ctgagactgt 1501    taaggaaaaa aattttaaac ccctgattta tatagatatc ttcatgccat tacagctttc 1561    tagatgctaa tacatgtgac tatcgtccaa tttgctttct tttgtagtga cattaaattt 1621    ggctataaaa gatggactac atgtgatact cctatggacg ttaattgaaa agaaagattg 1681    ttgttataaa gaattggttt cttggaaagc aggcaagact ttttctctgt gttaggaaag 1741    atgggaaatg gtttctgtaa ccattgtttg gatttggaag tactctgcag tggacataag 1801    cattgggcca tagtttgtta atctcaacta acgcctacat tacattctcc ttgatcgttc 1861    ttgttattac gctgttttgt gaacctgtag aaaacaagtg ctttttatct tgaaattcaa 1921    ccaacggaaa gaatatgcat agaataatgc attctatgta gccatgtcac tgtgaataac 1981    gatttcttgc atatttagcc attttgattc ctgtttgatt tatacttctc tgttgctacg 2041    caaaaccgat caaagaaaag tgaacttcag ttttacaatc tgtatgccta aaagcgggta 2101    ctaccgttta ttttactgac ttgtttaaat gattcgcttt tgtaagaatc agatggcatt 2161    atgcttgttg tacaatgcca tattggtata tgcataaca ggaaacagta ttgtatgata
```

-continued

```
2221  tatttataaa tgctataaag aaatattgtg tttcatgcat tcagaaatga ttgttaaaat
2281  tctcccaact ggttcgacct ttgcagatac ccataaccta tgttgagcct tgcttaccag
2341  caaagaatat ttttaatgtg gatatctaat tctaaagtct gttccattag aagcaattgg
2401  cacatctttc tatactttat atacttttct ccagtaatac atgtttactt taaagattgt
2461  tgcagtgaag aaaaacettt aactgagaaa tatggaaacc gtcttaattt tccattggct
2521  atgatggaat taatattgta ttttaaaaat gcatattgat cactataatt ctaaaacaat
2581  ttttaaaata aaccagcagg ttgctaaaag aaggcatttt atctaaagtt attttaatag
2641  gtggtatagc agtaatttta aatttaagag ttgcttttac agttaacaat ggaatatgcc
2701  ttctctgcta tgtctgaaaa tagaagctat ttattatgag cttctacagg tattttaaa
2761  tagagcaagc atgttgaatt taaaatatga ataacccac ccaacaattt tcagtttatt
2821  ttttgctttg gtcgaacttg gtgtgtgttc atcacccatc agttatttgt gagggtgttt
2881  attctatatg aatattgttt catgtttgta tgggaaaatt gtagctaaac atttcattgt
2941  ccccagtctg caaagaagc acaattctat tgctttgtct tgcttatagt cattaaatca
3001  ttacttttac atatattgct gttacttctg ctttctttaa aaatatagta aaggatgttt
3061  tatgaagtca caagatacat atattttat tttgacctaa atttgtacag tcccattgta
3121  agtgttgttt ctaattatag atgtaaaatg aaatttcatt tgtaattgga aaaaatccaa
3181  taaaaaggat attcatttag aaaatagcta agatctttaa taaaaatttg atatgaaaag
3241  cacaatgtgc agaagttatg gaaaacctat agaggattac aacaggtaaa cgttaaagag
3301  aatacattgc tgacttatag tgatgtggc aagaagtaca tgctttgttg taaaattgct
3361  tgaaagccca ttgaaagatg tatctgttta tttacagtct ttgaagtaaa agttaccaat
3421  gtttgccaat aaaaa
```
PCGF2 (accession No. NM_007144):
```
   1  tctcccctcc cgccgcccgg gcgagcgaca cggctgcggc ccccctcccc tcccttccct
  61  ccctccctcc catcccccc tccccgagac ccaccggacc ccgaacccag atggccgaaa
 121  cgggctcccc gtcttaacga tttggcgtct ccctcgacca ccacctcttt gtgcagcagc
 181  ccccgggcag accctgttcc gagggcaacg ctccccagtc ccccaccccc cgaccccgga
 241  atcatgcatc ggactacacg gatcaaaatc acagagctga accccacct catgtgtgcc
 301  ctctgcgggg ggtacttcat cgacgccacc actatcgtgg agtgcctgca ttccttctgc
 361  aaaacctgca tcgtgcgcta cctggagacc aacaaatact gccccatgtg tgacgtgcag
 421  gtccataaaa cccggccgct gctgagcatc aggtctgaca aaacacttca agacattgtc
 481  tacaaattgg tccctgggct ttttaaagat gagatgaaac ggcggcggga tttctatgca
 541  gcgtacccc tgacggaggt ccccaacggc tccaatgagg accgcggcga ggtcttggag
 601  caggagaagg gggctctgag tgatgatgag attgtcagcc tctccatcga attctacgaa
 661  ggtgccaggg accgggacga aagaagggc ccctggaga atggggatgg ggacaaagag
 721  aaaacagggg tgcgcttcct gcgatgccca gcagccatga ccgtcatgca tcttgccaag
 781  tttctccgca acaagatgga tgtgcccagc aagtacaagg tggaggttct gtacgaggac
 841  gagccactga aggaatacta caccctcatg gacatcgcct acatctaccc ctggcggcgg
 901  aacgggcctc tcccctcaa gtaccgtgtc cagccagcct gcaagcggct caccctagcc
 961  acggtgccca ccccctccga gggcaccaac accagcgggg cgtccgagtg tgagtcagtc
1021  agcgacaagg ctcccagccc tgccaccctg ccagccacct cctcctcct gcccagccca
1081  gccaccccat ccatggctc tcccagttcc catgggcctc cagccaccca ccctacctcc
```

```
1141  cccactcccc cttcgacagc cagtggggcc accacagctg ccaacggggg tagcttgaac
1201  tgcctgcaga caccatcctc caccagcagg gggcgcaaga tgactgtcaa cggcgctccc
1261  gtgccccect taacttgagg ccagggaccc tctcccttct tccagccaag cctctccact
1321  ccttccactt tttctgggcc cttttttcca cctcttctac tttccccagc tcttcccacc
1381  ttggggtgg ggggcgggtt ttataaataa atatatatat atatgtacat aggaaaaacc
1441  aaatatacat acttattttc tatggaccaa ccagattaat ttaaatgcca caggaaacaa
1501  actttatgtg tgtgtgtatg tgtggaaaat ggtgttcatt tttttggg ggggtcttgt
1561  gtaatttgct gtttttgggg gtgcctggag atgaactgga tgggccactg gagtctcaat
1621  aaagctctgc accatcctcg ctgtttccca aggcaggtgg tgtgttgggg gccccttcag
1681  acccaaagct ttaggcatga ttccaactgg ctgcatatag gagtcagtta gaatcgtttc
1741  tttctctccc cgtttctctc cccatcttgg ctgctgtcct gcctctgacc agtggccgcc
1801  ccccacgttg ttgaatgtcc agaaattgct aagaacagtg ccttttacaa atgcagttta
1861  tccctggttc tgaggagcaa gtgcagggtg gaggtggcac ctgcatcacc tcctcctctt
1921  gcagtggaaa ctttgtgcaa agaatagata gttctgcctc tttttttttt tttcctgtgt
1981  gtgtggcctt tgcatcattt atcttgtgga aaagaagatt caggccctga gaggtctcag
2041  ctcttggagg agggctaagg ctttagcatt gtgaagcgct gcaccccccac caaccttacc
2101  ctcaccgggg aaccctcact agcaggactg gtggtggagt ctcacctggg gcctagagtg
2161  gaagtggggg tgggttaacc tcacacaagc acagatccca gactttgcca gaggcaaaca
2221  gccttccaat tgcccctcca ccccagctg aggcccggtc acctggtcag gacagagcaa
2281  ctgcatctaa aagcacaaga agacagaaac ctgtaagctc tgaccccacc cccaccccctt
2341  gagaggtcag cggaccacct ccttagggac agaccctggc aggtcgctgc caccgagat
2401  ttcctcaagt gtgcatagat ctgagaggag tcgggagtcg agactcgaga ttccatcata
2461  gcgtaggtgt gtggggttgg gagcccctg atgggcttgt ctgtgtttgc accttgtcct
2521  gtgtctgagg tcctgtgact gtaccctcct ttgccctggg acatctgtat ctcttggctt
2581  tgtaataaat gctgcatact ttctaaaaaa aaaaaaaaaa aa
```
ZNF134 (accession No. NM_003435):
```
   1  cgaactgtga tggcggcggc cgcggtgatg ggcccggcgc agatcctctg tggttgttga
  61  attgtaacaa gagagagaac tctggctgcc tgagagggca tgactctagt cacagcagga
 121  ggggcttgga caggccctgg ttgttggcat gaagtgaagg atgaagagtc atcttctgaa
 181  cagagcattt ctatagcagt gtcacatgtt aatacttcca aggcaggttt gcccgcacag
 241  acggctctcc cttgtgacat atgtggcccc atcttgaaag atattttgca cctggatgaa
 301  caccaggggta cacaccatgg actgaaactt cacacatgtg gggcatgtgg agacaattc
 361  tggttcagtg caaaccttca tcagtaccag aagtgttaca gtatagagca accctttaaga
 421  agggataaaa gtgaggcctc aattgtgaag aactgcacag ttagcaaaga acctcatccg
 481  tcagagaagc cctttacgtg taaggaggag cagaaaaact tccaggctac tttgggtggc
 541  tgccaacaaa aggccatcca agtaagagg aagacacaca ggagcactga gagtggggat
 601  gcatttcatg gtgaacaaat gcattacaag tgcagtgaat gtgggaaagc tttcagccgc
 661  aaagacacac ttgtccagca ccagagaatt catagtggag agaagcctta tgagtgcagc
 721  gaatgtggga aagccttcag ccgcaaagct acacttgtcc agcatcagag aatccatact
 781  ggagaaaggc cttatgaatg cagcgaatgt ggaaaaacct tcagtcgaaa agacaacctt
 841  actcagcaca agagaatcca cactggagaa atgccttata agtgcaatga atgtgggaaa
```

```
 901   tattttagcc atcactccaa tctaattgta caccagagag ttcacaatgg agcaaggcct
 961   tataagtgca gtgattgtgg gaaagtcttc agacacaaat ctacacttgt tcagcatgag
1021   agtattcaca ctggagaaaa tccttatgat tgcagtgatt gtgggaaatc ctttggccac
1081   aaatacaccc tcattaaaca tcagcgaatt cacactgagt caaagccgtt tgagtgcatt
1141   gaatgcggga aattctttag tcgaagttct gactatattg caccagagag ggttcacact
1201   ggtgaaaggc cttttgtgtg cagtaaatgt gggaaagact ttatcagaac ctcccacctt
1261   gttcgacacc aaagagttca cactggagaa aggccatatg agtgcagtga atgtgggaag
1321   gcctacagct taagctccca cctcaatcgg caccagaaag ttcacactgc aggcaggctt
1381   taggagtgct ttgaatacaa caggactcat caatcagatg ttgaatttca tgtatctgaa
1441   cattgacaca aaggagatac cttatggtgc caggtacgtg ggaaccttct agggatatgt
1501   tgcactttct gacttgctca ggttttttgc cagagttatg tcactgtcaa tccatgtggc
1561   cgaaaccatc ttaactctac cagctaagat accccagcat tggggaaggc agggttttgt
1621   attgtccagt ccctggagaa aatcatgaaa tgcctgagtt cattgggggt cctcattccc
1681   ttctgtatga caggtatagg tatggatatg acccattttt agccaagagg gtctgagctg
1741   tatctgctgg tggcttatac aaaaagttta ctttcttcat ggatattctt ggtctcacat
1801   acttgtaatc aagttttttcc agcctccaag tcacctggcc tgggaaagta cttgcctcat
1861   gttgctctgg tttgtgataa taaaggcttt acagtttaag ccacatttaa tcttggggct
1921   tcttcttatg gtctggggtg gattgaaaac aggctctgcc aaactgaaga cagcctttgt
1981   gcggtgcctc caactttgcc tcaaatggga cagtgggttg agggagaaca gttcttagtc
2041   cagttttgat gttaacttcc atagctgaca aagcttgtta agtaagaatt aagatcttgt
2101   gtagacctga tttgtctgga ttttagagtt atttgagagc ccatatttca ccttgaggag
2161   ggtgctgctg ctgtgacagc ctgcagtgtt ttgaaacagc atggattggg tgtcttgttt
2221   gcagcatgtg tcccatgttc cccaacac
```
RING1 (accession No. NM_002931):
```
   1   cagcgcccgg gccatggcgg cggcggtggc gggagctgct gtctgagcag cggttgcgga
  61   ccgagcgaac ttggcccagg agcccgggcc tagggagagg cgcggcggcg gcgggagcgc
 121   gaacggctgg agctggcctt cttcgccttc tcctcggctg tggagccctg gtgggggtc
 181   tgcgcccggt caccatgacg acgccgcgcga atgcccagaa tgccagcaaa acgtgggaac
 241   tgagtctgta tgagctgcac cggaccccgc aggaagccat aatggatggc acagagattg
 301   ctgtttcccc tcggtcactg cattcagaac tcatgtgccc tatctgcctg gacatgctga
 361   agaatacgat gaccaccaag gagtgcctcc acagattctg ctctgactgc attgtcacag
 421   ccctacggag cgggaacaag gagtgtccta cctgccgaaa gaagctggtg tccaagcgat
 481   ccctacggcc agaccccaac tttgatgccc tgatctctaa gatctatcct gccgggagg
 541   aatacgaggc ccatcaagac cgagtgctta tccgcctgag ccgcctgcac aaccagcagg
 601   cattgagctc cagcattgag gaggggctac gcatgcaggc catgcacagg gcccagcgtg
 661   tgaggcggcc gataccaggg tcagatcaga ccacaacgat gagtgggggg aaggagagc
 721   ccgggagg agaaggggat ggagaagatg tgagctcaga ctccgcccct gactctgccc
 781   caggccctgc tcccaagcga ccccgtggag gggcgcagg gggagcagt gtagggacag
 841   gggaggcgg cactggtggg gtgggtgggg gtgccggttc ggaagactct ggtgaccggg
 901   gagggactct gggagggga acgctgggcc cccaagccc tcctgggcc cccagccccc
 961   cagagccagg tggagaaatt gagctcgtgt tccggcccca ccccctgctc gtggagaagg
```

-continued

```
1021   gagaatactg ccagacgagg tatgtgaaga caactgggaa tgccacagtg gaccacctct
1081   ccaagtactt ggccctgcgc attgccctcg agcggaggca acagcaggaa gcaggggagc
1141   caggagggcc tggagggggc gcctctgaca ccggaggacc tgatgggtgt ggcggggagg
1201   gtggggtgc cggaggaggt gacggtcctg aggagcctgc tttgcccagc ctggagggcg
1261   tcagtgaaaa gcagtacacc atctacatcg cacctggagg cggggcgttc acgacgttga
1321   atggctcgct gaccctggag ctggtgaatg agaaattctg gaaggtgtcc cggccactgg
1381   agctgtgcta tgctcccacc aaggatccaa agtgacccca ccaggggaca gccagaggaa
1441   ggggaccatg gggtatccct gtgtcctggt ctatcacccc agcttctttg tcccccagta
1501   cccccagccc agccagccaa taagaggaca caaatgagga cacgtggctt ttatacaaag
1561   tatctatatg agattcttct atattgtaca gagtggggca aaacacgccc ccatctgctg
1621   ccttttctat tgccctgcaa cgtcccatct atacgaggtg ttggagaagg tgaagaaccc
1681   tcccattcac gcccgcctac aacaacaaa cgtgcttttt tcctctttga aacctgcaaa
1741   aaaa
```

RNF2 (accession No. NM_007212):
```
   1   gcgcctccgc ccctcgctcg ctcgctcctt cccgcccctcc ccgcagcgcc ggccgagccg
  61   gcttcccctc agtctctcat gaatattgag cggcccctgt tgtatttccc gagctccatt
 121   gcggaagctg aggctcgcca tattgtgcgg cggcgccggc gtccgcggca gctgatacca
 181   gagtcttgct ccggccgcgg ccagcggagc cctgggctgg ggcaggagcc gcaatgtctc
 241   aggctgtgca gacaaacgga actcaaccat taagcaaaac atgggaactc agtttatatg
 301   agttacaacg aacacctcag gaggcaataa cagatggctt agaaattgtg gtttcacctc
 361   gaagtctaca cagtgaatta atgtgcccaa tttgtttgga tatgttgaag aacaccatga
 421   ctacaaagga gtgtttacat cgttttgtg cagactgcat catcacagcc cttagaagtg
 481   gcaacaaaga atgtcctacc tgtcggaaaa aactagtttc caaaagatca ctaaggccag
 541   acccaaactt tgatgcactc atcagcaaaa tttatccaag tcgtgatgag tatgaagctc
 601   atcaagagag agtattagcc aggatcaaca gcacaataa tcagcaagca ctcagtcaca
 661   gcattgagga aggactgaag atacaggcca tgaacagact gcagcgaggc aagaaacaac
 721   agattgaaaa tggtagtgga gcagaagata atggtgacag ttcacactgc agtaatgcat
 781   ccacacatag caatcaggaa gcaggcccta gtaacaaacg gaccaaaaca tctgatgatt
 841   ctgggctaga gcttgataat aacaatgcag caatggcaat tgatccagta atggatggtg
 901   ctagtgaaat tgaattagta ttcaggcctc atcccacact tatggaaaaa gatgacagtg
 961   cacagacgag atacataaag acttctggta acgccactgt tgatcactta tccaagtatc
1021   tggctgtgag gttagcttta gaagaacttc gaagcaaagg tgaatcaaac cagatgaacc
1081   ttgatacagc cagtgagaag cagtatacca tttatatagc aacagccagt ggccagttca
1141   ctgtattaaa tggctctttt tctttggaat tggtcagtga gaatactgg aaagtgaaca
1201   aacccatgga actttattac gcacctacaa aggagcacaa atgagccttt aaaaaccaat
1261   tctgagactg aactttttta tagcctattt ctttaatatt aaagatgtac tggcattact
1321   tttatggaca gatcttggat atgttgttca attttctttc tgagccagac tagtttacgc
1381   tattcaaatc ttttcccctt tatttaagat ttccttttg gaagggactg caattattca
1441   gtatttttttt ctttccttta aaaaaatata tctgaagttt cttgtgtttt tttttttccc
1501   cacaaagtgt gtttccactt ggagcaccat tttgacccag gaattttca tagtttctgt
1561   attcttataa gattcagttg gctgtccttt tcctgctccc ctcaaaagat ttttagtcat
```

-continued

```
1621   acagaatgtt aaatattatg tattctgact ttttttttcc cccggagtct tgtatattta
1681   tagttttcta tataaactgt agtatcttca tgaagaccca aggctcaaat ttactgtcct
1741   taaaaacaat tctcatagga ttattctttt catggtattt tcttccataa tatctcattt
1801   taaaagaag ttctttatga acttagtgtc cattgtcatg caatgttttt ttttttccat
1861   tcttttccc tgtaattttg gaatttctgg tcctgggaag aatcaaacaa aatcttaagt
1921   tctatgagaa cttggttcat tgacatattc tgctgaagaa agaaaaatta aattggtagt
1981   aaaatatagt cttcaagtat acgtttgaga gtgcttttt tgtattagt tctgctgtca
2041   cttcatttcc tgtattatat gtgatgtttt tccccattaa ataccagag ataatggaga
2101   tattttgcac tttagccttg atgaaaagta caagatatgt tcaaagcttc cctaattttt
2161   ttcttatttg tagccacata agtttcaaga ataacatggc acacagaaca atggaaaaaa
2221   gtttgtttcc attggaaaat tatatcattt tgggttgcca catcagttta taaatttggc
2281   gctcttttaa ttacactctg tagaaggtta atagagcttg agccctgctt taatatgtag
2341   tgaaagataa ttctgtagaa aaacgtcagc cagtagggta aagtcattct actgttctta
2401   attttatat tgaggaacaa tattgggtgt ttgggagcca gaaagctttg ttgacagatc
2461   agaaataaga ttgacttggg tgttatattt catctctctc cagactctag gtatatttcc
2521   aactttatat atcacagtat ttaaaaagac atgtttgcat tgagaaatta accctaaagg
2581   gttttcaata gggtgtagac ctccagtacc tttgtaacta aagtctgtct agtcattgta
2641   aatatttatc tgtcagtttt gacagattgg ggccagcttg atgttttaaa tcttcagccc
2701   ggtatgaaaa cttaaaggta tatattcaat ttttttaccat tttatggaaa atatttaaaa
2761   tctgttttta caggtttttt tttttttttt tttttttgta atctgtgcca tgaaatttga
2821   aaaccaccaa aaatcaaggg aacttttata tattcaattc ctttctggt gtaatgttaa
2881   agttgtatag attattaatg catgcccact gaatataacc ctggttttgt gataaaactg
2941   cttagatttt gttgatgaca ttagattagt agttgcatta aataactaaa ttcccattgt
3001   gattaattga aattttgtct ttaagcagag agttatttgt gactataagc tttgtgctta
3061   gagaatgtat gtgttttat ctgtcagtat gggaggatat aaactgcatc attagtgaaa
3121   ttattggttg tgtaatcctt tgtgaaatat aattctaggt atttgatagg gtattgagtg
3181   tattttgtgt gtgtgtggat gtgtgttttg gggtacgggg agaggcgatg ctattggcca
3241   tcactaccaa ccagggtttc aaaaagtatt acctaagtaa tttctttat cactatctca
3301   actgaggaag aaaaggctca ccacaagtgg tgtgaaggct ttgggtactt agttctaaat
3361   ttttttatgg taacatatac atagccacat ttacagtttt aaccatttta aggcatgtaa
3421   ttcagtgggg ttaggtacat tcacaatgtt gtgtaatgat caccgctgtc tacttgtaaa
3481   acttttcat caccccaaac agaaactctg tgtgcaatta agtaatgca tttctcttct
3541   tcttaccccc t
```

PHF1 (accession No. NM_024165):

```
  1    ctccctcccc cccgccgcct cctcctcctg ccgctgccgc tgctttggct gctgcgtcat
 61    acgccccaga gccgccggga cggaggggc gggcctgggg accccccggc ctccgcctgc
121    acgccccccc acgcccggac gtgccctctc cgcgcggggg actcgcctag gtctcctacg
181    tctgccctg cccggctccc ggcggcccca gctgtcaccg gcccccccag gatgcaatgg
241    cgcagccccc ccggctgagc cgctctggtg cctcctcact ttgggaccca gcttctcctg
301    ctcccacctc tggccccagg cctcggcttt ggagggtca agatgtgctg gccagatgga
361    ctgatgggct gctatacttg ggtaccatca aaaaggtgga cagtgctagg gaggtgtgtc
```

-continued

```
 421   tggtccagtt tgaggatgat tcgcagtttc tggttctatg gaaagacatt agccctgctg
 481   ccctccctgg agaggaactc ctctgttgtg tctgtcgctc tgagactgtg gtccctggga
 541   accggctggt cagctgtgag aagtgtcgcc atgcttatca ccaggactgc catgttccca
 601   gggctccagc ccctggagag ggagagggca catcctgggt atgccgccag tgtgtctttg
 661   cgatcgccac aagagggga ggtgccctga agaagggccc ctatgcccgg gccatgctgg
 721   gtatgaagct ttctctgcca tatggactga aggggctgga ctgggatgct ggacatctga
 781   gcaaccgaca gcagagttac tgttactgtg gtggccctgg ggagtggaac ctgaaaatgc
 841   tgcagtgccg gagctgcctg cagtggttcc atgaggcctg cacccagtgt ctgagcaagc
 901   ccctcctcta tggggacagg ttctatgaat ttgaatgctg tgtgtgtcgc ggggccctg
 961   agaaagtccg agactacag cttcgctggg tggatgtggc ccatcttgtc ctgtatcacc
1021   tcagtgtttg ctgtaagaag aaatactttg attttgatcg tgagatcctc cccttcactt
1081   ctgagaattg ggacagtttg ctcctggggg agctttcaga caccccaaa ggagaacgtt
1141   cttccaagct cctctctgct cttaacagcc acaaggaccg tttcatttca gggagagaga
1201   ttaagaagag gaaatgtttg tttggtctcc atgctcggat gcctcccct gtggagcccc
1261   ctactggaga tggagcactc accagcttcc cttcagggca gggcctggg gagggtct
1321   cacgtcccct ggggaagcgc cggaggccgg agccagagcc cctgaggagg aggcagaagg
1381   ggaaagtgga ggagctgggg ccaccctcag cagtgcgcaa tcagcccgag ccccaggagc
1441   agagggagcg ggctcatctg cagagggcac tgcaggcctc agtgtctcca ccatccccca
1501   gccctaacca gagttaccag ggcagcagcg gctacaactt ccggcccaca gatgcccgct
1561   gcctgcccag cagcccatc cggatgtttg cttccttcca cccttctgcc agcaccgcag
1621   ggacctctgg ggacagtgga ccccagaca ggtcacccct ggaacttcac attggtttcc
1681   ccacagacat ccctaaaagt gcccccact cgatgactgc ctcatcttcc tcagtttcat
1741   ccccatcccc aggtcttcct agacgctcag cacccccttc tccctgtgc cgtagtttgt
1801   ctcctgggac tgggggagga gtccgaggtg gggttggtta cctgtcccga ggggacccctg
1861   tccgggtcct tgctcggaga gtacggcctg atggctctgt gcagtacctg gttgagtggg
1921   gaggaggggg catcttctga acagcctgcc tctgcccagc tccccattca cacacaccgg
1981   cactttcata ccctgacctc tgacctcacc tacagctggg atgtacctgg agagatagg
2041   ggtagttctc cctactgccc aggctggaat ccaagagtgg ggagtgggga agaggccctc
2101   ttctctaccc tccttcatga ttcctgaccc ctcccatcct tcccatttcc tttgatgtta
2161   ttttgttaca gctttttaaa tatttttaa aattatttaa cccctggggg cagagactga
2221   ggagggagga tgataaggga tcccggactc tgtatgattg aaataaagag aaataaacaa
2281   atctagcagc tctgaaaaaa aaaaaaaaa aa
```

MTF2 (accession No. NM_007358):

```
   1   gctgccattc ggcaccgag tcgctccgcg ctcccagaat gcaccggcag tccgcgggaa
  61   accaaaatgg cgagggctg tattgaagtg ggctgtgttt gaggccggtg taagaacgct
 121   cattctaccc ccaacccttg tctccaagga cctcggtttg tgcgtgcata tgtgccgggt
 181   acccggtggg gcgggtgccc agtaagtgct cggactcgca ggggaagcgc ccacggggac
 241   ggattggttg tttttcctg tatgaagcgc ttggcaccac tgaagtgacc gaatgagaga
 301   ctctacaggg gcaggtaatt cactggtcca caagcggtct cctttacgtc gaaaccaaaa
 361   gaccccaaca tccttgacca agctgtcttt acaggatgga cataaagcca aaagccagc
 421   atgtaaattt gaagagggtc aggatgtcct agctagatgg tcagatggct tgttttatct
```

-continued

```
 481   tggcactatc aaaaagataa acatattgaa acagagctgc ttcatcatat ttgaagacag
 541   ttctaaatcc tgggttctct ggaaggacat tcaaacagga gccactggaa gtggggaaat
 601   ggtctgtaca atatgtcaag aagagtattc agaagctccc aatgaaatgg ttatatgtga
 661   caagtgtggc caaggatatc atcagttgtg tcacacacct catattgatt ccagtgtgat
 721   tgattcagat gaaaaatggc tctgtcggca gtgtgttttt gcaacaacaa caaagagggg
 781   tggtgcactt aagaaaggac caaatgccaa agcattgcaa gtcatgaagc agacattacc
 841   ctatagtgtg gcagaccttg aatgggatgc aggtcataaa accaatgtcc agcagtgtta
 901   ctgctattgt ggaggccctg gagactggta tttgaagatg ctacagtgct gcaaatgtaa
 961   gcagtggttt catgaggctt gtgtgcaatg ccttcaaaag ccaatgctat ttggagacag
1021   attttatacg tttatatgct ctgtctgcag ttctggacca gaataccctca aacgtctacc
1081   attacagtgg gtagatatag cacacctatg cctttacaac ctaagtgtta ttcataagaa
1141   gaaatacttt gattctgaac ttgagcttat gacatacatt aatgaaaact gggatagatt
1201   gcaccctgga gagctggcag acacaccaaa atctgaaaga tatgagcatg ttctggaggc
1261   attaaatgat tacaagacca tgtttatgtc tgggaaagaa ataaagaaga agaagcattt
1321   gtttgggttg cgaattcgtg ttcctcctgt gccaccaaat gtggctttca aagcagagaa
1381   agaacctgaa ggaacatctc atgaatttaa aattaaaggc agaaaggcat ccaaacctat
1441   atctgattca agggaagtaa gcaatggcat agaaaaaaaa ggaaagaaaa atctgtagg
1501   tcgtccacct ggcccatata caagaaaaat gattcaaaaa actgctgagc cacttttgga
1561   taaggaatca atttcagaga atcctacttt ggatttacct tgttctatag ggagaactga
1621   gggaactgca cattcatcca atacctcaga tgtggatttc acgggtgctt ccagtgcaaa
1681   agaaactacc tcgtctagca ttttccaggca ttatggatta tctgactcca gaaaaagaac
1741   gcgtacagga agatcttggc ctgctgcaat accacatttg cggagaagaa gaggtcgtct
1801   tccaagaaga gcactccaga ctcagaactc agaaattgta aaagatgatg aaggcaaaga
1861   agattatcag tttgatgaac tcaacacaga gattctgaat aacttagcag atcaggagtt
1921   acaactcaat catctaaaga actccattac cagttatttt ggtgctgcag gtagaatagc
1981   atgtggcgaa aaataccgag ttttggcacg tcgggtgaca cttgatggaa aggtgcagta
2041   tcttgtggaa tgggaaggag caactgcatc ctgactgtag gactgaacat tatgttcact
2101   gcactctgat tttctgtagg tacagttcaa agccctaaag gagtctggct tttactatct
2161   ttcttaaaaa aaaaaaaaag tcaaaaaaat tcaaaaaagg ggatgatact agccttaaca
2221   tgtacctgtc aatgttatgg atattgtcat aaaaaggtat cttttaaaaa tcagaacaga
2281   gacttaattt tttaaatctt aagatttgta gaatgtttct aggataggat attaaaaatg
2341   attgaaaccc atgcatggtg ttagacaatt tttctaatta ttccattgag tcagtttttt
2401   gtgattagtg attatcagag caaacatcat gtagatagca caagtatttg gagaaacgtt
2461   gtttgttttg ttaccaaaat gttggaaaaa tttatttcaa tacctttttag atttcataaa
2521   gtgcagtgta tataatgcct actgaaagac tgtaaaatat tgaaatttc tttcaagcaa
2581   agtgtaaaaa aatatattga gcctgtaaat tgctctgtga ctagacttca ttgtcgtctt
2641   aatatattct tgcatgtgca tatatataca cacgtgtata tatatgtgtg tgattatgtg
2701   acctatgcaa tacaaattat gggaatgggc agctttggag tatatatccc ataattcttt
2761   tttcaggaat agttgcagta tttacacagc agcatttctt ctcaggcttt tattgggtgc
2821   tgttgcttgc tatgtatgaa gagaaatgtg tcagacaagt ttagtgtgtt ctgaagaagg
2881   gtgtgaacaa cagtgttcat gggcttttag aatgcttttc actttttagtc cttgtaactc
```

-continued

```
2941  agctgttcag tacctaaaac aaattcaaat aatatgaaca ttatctccta ctagaagtaa
3001  cgttttcaag ttttcatggc acattattgat tgtaaatgtc tctcattttt aacagtaagt
3061  ctataggagt cccgtgaaga ttcctgaaat gtctgtagta actgttagtc atgtttgaat
3121  aagtgtagta tgaacaaagt attttattgc acagggttaa caaacagtat gttgccagct
3181  gaggctactg ctgttttatt acaacattac ctcttgtttt tataaagtgt accaagattt
3241  aaattgataa ctttattta cttgtaaaaa aaagtttct tttatcacca gtgttacagt
3301  tgtcttctgt ttcttttgt tttgtttttt ttgtttcct ttttagccaa agagtgaaca
3361  gaagattttc ttattttggt ggctattcat tttacttta aaagtgattg gtggatttta
3421  gactaattat gggggaattt gccaccaaaa taaaaaatat gtaaagtgta gtgattacag
3481  agtggttaaa atgtgggtta gtacttattt attccattaa ttgattattt gactgtttat
3541  aaagaaagtt gctttattc tttaaacatc ttcaaaagat gatcctttct tgtcacatta
3601  tagccaaaag aagcagagaa cttcattgtc tgcatttggt tcctggttgg ccaggtataa
3661  atgagcttta caaaagtgca aattaaaaac tgttacttct gtttacctcc accaaaactt
3721  gattttcccc tagctattaa tttaaggttg cctttcctgc agctgcaata ttttgaataa
3781  cacacagagt ttgtgttgat ttttgaatgt ttgtttatat ctaggggtaa tgaaaaatgt
3841  aaatcccgtg tatccttatt cactccacct gtatcatatt atttcatttt ccccaaagtc
3901  ctttaattct aactgaacac cagcagtatt tttagaaatt tttctttaac atacttggaa
3961  gatgatttat ccagctgaac tgtctttaga cgtaattatt gtgaatgtct gttttatttt
4021  ctcatggtgg ttcacatggc tctgatgttc agtttgtatt tttggaattg ctttacttag
4081  aaattaaaac agaccaacat taaatgtgtg tattttttaa agagctaaaa aaaaaaaaaa
4141  aaaa
```

PHF19 (accession No. NM_001286840):
```
   1  accagtaagt cgtgtattta gcattcattc atcaaagcct ccggatgcct cctacgtgcc
  61  ctgcactatg ctggtcttgg taatccgtgg tccctatccc agcgcccagt gtcagggaa
 121  gctgatggag aatcgagctc tggatccagg gactcgggac tcctatggtg ccaccagcca
 181  cctccccaac aagggggccc tggcgaaggt caagaacaac ttcaaagact tgatgtccaa
 241  actgacggag ggccagtatg tgctgtgccg gtggacagat ggcctgtact acctcgggaa
 301  gatcaagagg gtcagcagct ctaagcaaag ctgcctcgtg actttcgaag ataattccaa
 361  atactgggtc ctatggaagg acatacagca tgccggtgtt ccaggagagg agcccaagtg
 421  caacatctgc ctaggaagga catcagggcc gctgaatgag atcctcatct gcgggaagtg
 481  tggcctgggt taccaccagc agtgccacat ccccatagcg ggcagtgctg accagcccct
 541  gctcacacct tggttctgcc gacgctgcat cttcgcactg ctgtgcggga aggcggcgc
 601  gctgaagaag ggcgccatcg ccaggacgct gcaggccgtg aagatggtgc tgtcctacca
 661  gcccgaggag ctcgagtggg actcgcccca tcgcaccaac cagcagcaat gctactgcta
 721  ctgcggcggg cccggagaat ggtacctgcg gatgctgcaa tgttaccggg caggcagtg
 781  gttccacgag gcctgcaccc agtgcctcaa tgagcccatg atgtttggag accggtttta
 841  cctgttcttc tgctccgtgt gtaaccaggg cccagagtac atcgagaggc tgcccctgcg
 901  atgggtggat gtggttcacc tggccctcta taatctgggg gtacagagca agaagaagta
 961  ctttgacttt gaggagattc tggccttgt caaccaccac tgggagctcc tgcagcttgg
1021  caagctcacc agcacccag tgacagatcg aggaccacat ctcctcaacg ctctgaacag
1081  ttataaaagc cggttcctct gcggcaagga gatcaagaag aagaagtgca tcttccgcct
```

-continued

```
1141   gcgcatccgc gtcccaccca acccgccagg gaagctgctg cctgacaaag gactgctgcc
1201   aaatgagaac agcgcctcct ctgagctgcg taagagagga aagagcaagc ctggtttgtt
1261   gcctcacgaa ttccagcagc agaaaaggcg agtttataga agaaaaagat caaagttttt
1321   gctggaagat gctattccca gtagtgactt cacctcagcc tggagcacca accaccacct
1381   ggctagcata tttgacttca cgctggatga aattcaaagt ttaaaaagtg ccagctcagg
1441   ccagaccttc ttctcagatg tcgactccac cgacgctgcc agcacctctg gctctgcctc
1501   caccagcctc tcctatgact ccagatggac agtgggcagc cgaaagagga agctggcagc
1561   caaggcatac atgcccctgc gggcaaagcg gtgggcagct gagctggatg acgctgccc
1621   ctcggacagc agtgcagagg gggcttcagt ccccgagcgg ccagacgaag gcattgacag
1681   ccacacattt gagagcatca gtgaagatga ctcatccctg tcccacctca agtcatctat
1741   caccaactac tttggtgcag ctgggcggtt ggcctgtggg gagaagtacc aggtgttggc
1801   tcggagggtc acacctgagg caaggttca gtacctggtg gagtgggaag ggaccacccc
1861   ttactgacta gccccgggg gtgccagggg tcctgaaaac caaaggagga gcagcagaag
1921   ccataggctc cccagctttc tccaggctgg ggtgggagaa ggaagcagga cagagctgca
1981   agtgcctggc agaatgccct gcctgcctgc ctgccaggcc aaggcctgcg tctctctgct
2041   gtaccagctc tgttccaggg cctcctcagg ctcgttaccc ctgtgcctgt gtctctacac
2101   actccacacc ccctcaaact ctgtttatct gttctctgac cttgtgtccc ctgcgctggg
2161   accttcctc ctgaggccca ggtctttgtc cccagttgtg tgccttgacc tctctcgccc
2221   ctttctgggt gtgttcgcac atcctgtgtg tgcacagctg tccctccact ggatcccctt
2281   cacacgtgac ccgtggggca gccagtcctc ccagggacta cataacaggc acctttgaga
2341   gagcatggga gaaggtggat aagaggatgc tgctcagtgc ttttctcttc cactttcctg
2401   ccactcccca ctaccctcgg agagaggtgg tgggatggga gagagcccct gtgaaagcct
2461   gtgaggatct gaagagtaaa gggctgggtc tgcctcagaa ggcaccagca ccagggccca
2521   ggtattaagg ctgagagtga aggctgccaa tgtcagcttt ggaggtccca gaagtcttct
2581   gttctctggc ctcacccct cagtcgccat agagctgggc ctggccttgc tggaatggag
2641   gcatccttcc aaacctgggg gacgggggtg gggggtggta gtggtgggag ggaaaccatg
2701   tcttgctaaa cctgtttctg gtgcctccca tccccagacc caccagacac cacacagcag
2761   acaatacaca cccactcgca caagcttcca tccacatgtg ttgtactttc agctctaggc
2821   atgcagacaa ccccacacgg ccacaccacc acatgcccaa gtgtacacac acagagccac
2881   accgtccctc tgggcctgct ggctcctccc ttggcttttcc cttggcccac ttccagggcc
2941   caggtgctgc aactaaatgt gaaagctcag tggccgctcc ttctttcagc ccatcaacca
3001   gcattggtcc catagggaag cacaggggac tcaccctctt tcatatccct gccctgccc
3061   tgaaatggac aatcactttt tgggataggt tgaaattttt aaagagcctg catcatttgg
3121   ttccctcaaa gggaagccct tgccagtggg ggtttgaaag agaatttttg gaaccaacat
3181   tcaaattctg cctcatctgg agggaaacca aaattgggag ggggaagagg acccctgatg
3241   ttttgctgct tccagagata ttagaaactg actcacttga ttggaaaatg gacaaaagtg
3301   ccttgacgtg gagggtgggc accagatggg gaccagcctt gccaactgct gctgtggcct
3361   ccagcttggc tggttttgca ggccgccagc aggaaggcga aggtggtagt acagcaagag
3421   gcactggcgg ggcagcaggc ctgcaggagc tgttttttcca ttgctaggcc tgacccctct
3481   ctacctgtga gcgttcaggg ggtccctgag atagtttaga tgccccccca tcttagacct
```

```
3541  cagctcccac agtgcctttt aaggggacc tcacctcctg tgcacagccc acccactttc
3601  ctctgcttcc ctggcacagc ccaggcatag acgagctggc gttggaccca gttcttcccc
3661  cttttcagcc ccacagctgc tgccacaggg gccaactagg gccaggtgga aggggagctg
3721  agaagccaac ccctagccca ggggtgctgt gggaactggg atccaatttg tagcttcctg
3781  cctggcttca gagagcccag caaccttcta ggcctgcttt ccagacttct gagatagcct
3841  gggatgagca atcctgttat agtacatctg gaccttccct acctgggctc tggggaggct
3901  gtgggcctgg agagggaaaa ggagggaggg ggtgtctgca ccacctggga agatagcaca
3961  aggcctaatg aggtcaccct gactccccac cccagcattt cattcatacc agataatagc
4021  tgcattactg ccaactgacc ttataaccct ctgcaccttc aaaaagattc atggttttta
4081  attgctgctt ttaataacat ttgttaaagt tataattaat gtgtctgatt tatgatttaa
4141  aacctcccct tgaacaatca aaaaaaaaa aaaaaaaaa a
```

SETD1A (accession No. XM_005255723):
```
   1  agtggtgttt ggtgcgcgcg ccggggaggt ggtggtgggg gggcgccgcc gccgccaccg
  61  ctgcggggcc gggtctcgcg ctgccgctgc cgccgcctcg cgccgctgag gtgccgcgcg
 121  aggtgggggg aggggagcc gctcgccggg agcggtgtaa atgagcaaag atggatcagg
 181  aaggtggggg agatgggcag aaggccccga gcttccagtg gcggaactac aagctcatcg
 241  tggatcctgc cttggaccct gccctgcgca ggcttctca gaaggtgtac cgctatgatg
 301  gagtccactt cagtgtcaac gactcaaagt atataccagt cgaagacctc caagaccccc
 361  gttgccatgt caggtccaaa acagagact tttccctccc agtccctaag tttaagctgg
 421  acgagttcta tattggacag attccactga aggaagtgac ttttgcaagg ctgaatgaca
 481  acgtgcggga gaccttcctg aaggatatgt gccgtaagta cggtgaggtg aagaggtag
 541  agatcctcct tcaccccgt acgcgcaagc acctgggcct ggcccgtgtg ctcttcacca
 601  gcactcgggg cgccaaggaa acggtcaaaa acctccacct tacctccgtc atgggcaaca
 661  tcatccatgc ccagcttgac atcaaaggac aacaacgaat gaaatactat gaactaattg
 721  tcaatggctc ctacacccct cagactgtgc ccactggggg caaggccctg agtgagaagt
 781  tccaaggctc gggtgcagcc actgagacgg ccgaatcccg ccgccgctct tcctctgaca
 841  cagctgccta cccagcaggc accactgcgg tgggcactcc tggcaacggc acccctgct
 901  cccaggacac aagcttctcc agcagccgac aagataccc atcttccttt ggccagttca
 961  cacctcagtc ctcccaagga accccctaca cgtctcgggg cagcaccccc tactctcagg
1021  actctgccta ctccagcagc accacttcaa cctccttcaa gccccggcgg tcagagaaca
1081  gctaccaaga tgccttttcc cgccgccact tctctgcatc ttcagcctcc acaaccgcct
1141  ccacggccat cgccgccacc actgcagcca ctgcctcatc ctccgcctct tcctcctcat
1201  tgtcctcgtc ctcctcgtca tcctcttcct cctcgtcctc tcagtttcgt agttctgatg
1261  caaactaccc agcgtattat gaaagctgga atcgctacca cgccatact tcctacccac
1321  cacgccgggc cacacgggag aacccctg gagcccttt tgctgaaaat acagctgagc
1381  gcttcccacc ttcttacacc tcctacctgc cccccgagcc cagccggccc accgaccagg
1441  actaccggcc tcctgcctca gaggctccac cccggagcc tccagaacct ggtggaggcg
1501  ggggtggagg agggcccagc cctgagagag aagaagttcg gacttccccc cgcccagcct
1561  cccctgcccg ctctggctcc ccagccccgg agaccaccaa tgagagtgtg cccttcgccc
1621  agcacagcag cctggattcc cgcatcgaga tgctgctgaa ggagcagcgc tccaagtttt
1681  ccttcttggc ctctgacaca gaggaggagg aagagaacag cagcatggtc cttgggcca
```

-continued

```
1741   gagatacagg gagtgaggtg ccttctgggt cagggcatgg gccctgcaca ccccctccgg
1801   ccccagctaa ttttgaggat gtggcaccta cagggagcgg ggagccaggg gctacccggg
1861   agtctcccaa ggcaaatgga cagaaccagg cttctccatg ctcttctgga gacgacatgg
1921   agatctccga cgacgaccgg ggtggctcac cccctccggc ccgacgcccc cctcagcagc
1981   ctccgccacc tcccctccc ccgccgcctc ctcctcccta cctggcgtcc cttcctcttg
2041   gttatcctcc ccaccaacct gcctacctcc tcccacccag acctgatggg ccgccgcccc
2101   ctgagtaccc cccacctcct ccaccacccc cgcacatcta tgactttgtg aactccttgg
2161   agctcatgga ccgacttggg gctcagtggg gagggatgcc catgtccttc cagatgcaga
2221   cccagatgtt aactcggctc catcagctgc ggcagggcaa gggattgatt gccgcctcag
2281   ctggcccccc cggtgggggcc tttggggagg ccttcctccc gtttccaccc ccgcaggagg
2341   cagcctacgg cttgccgtat gctctatatg cacaggggca ggagggcaga ggggcatact
2401   cacgggaggc ctaccacctg cccatgccaa tggcagccga gcccctgccc tcctcctcag
2461   tctcgggaga ggaggccggg ctgccaccca gggaagaagc agagctggca gagggcaaga
2521   ccctcccgac agcaggcacc gtgggccgtg tgctcgccat gctggtccag gagatgaaga
2581   gcatcatgca gcgagacctc aaccgcaaga tggtggagaa cgtggccttc ggagcctttg
2641   accagtggtg ggagagcaag gaggagaagg ccaagccatt ccagaacgcg gccaagcagc
2701   aagccaagga ggaggataaa gagaagacga agctgaagga gcctggcctg ctgtccctcg
2761   tggactgggc caagagcggg ggcactacgg gcatcgaggc tttcgccttt gggtcagggc
2821   tgagaggggc cctgcgctg ccttcattca aggtaaagcg gaaagagcca tcggaaattt
2881   ccgaggccag tgaggaaaag aggcctcgtc cctccactcc tgctgaggaa gatgaagacg
2941   accctgaaca agagaaggag gctggagagc aggacgtcc ggggaccaag ccccccgaagc
3001   gggacgaaga gcgaggcaag acccagggca agcaccgcaa gtcctttgct ctggacagcg
3061   aaggggagga ggcatcccag gagtcctcct cggagaagga tgaggaggat gacgaggaag
3121   atgaggaaga tgaagatcga gaggaagctg tggataccac aaagaaggag acagaggtgt
3181   cggatggcga ggacgaggaa agcgattcgt cttccaaatg ttctctgtat gctgactcag
3241   atggcgaaaa tgacagcaca tcagactccg agagcagcag ctcttccagc tcctcatcct
3301   cctcctcctc ctcgtcctca tcctcctcgt cctcttcatc ctctgagtcc tcctctgaag
3361   atgaagagga agaggagcgg ccagcagccc ttccctcagc ctccccgccc cccagagaag
3421   tcccagtgcc cacgccagca cctgtggagg tgccagtgcc ggaaagggtt gcaggctccc
3481   cagtcacacc cctgcccgaa caggaggcgt ctccagcaag gcctgcaggc cccacggagg
3541   agtcaccccc cagtgcgcct ctgcgtcccc cagaaccacc tgctgggccc ccggccctg
3601   ccccacgccc cgatgagcgt ccctcttctc ccatcccct cctgccccca cccaagaaac
3661   gccggaaaac tgtctccttc tctgccatcg aggtggtgcc agccccggag cccctccag
3721   ccacaccgcc gcaggccaag tttcccggcc cagcctcccg caaggctccc cggggcgtgg
3781   agcggaccat ccgcaacctg cccctggacc acgcatctct ggtcaagagt ggcccgagg
3841   aggtgtcccg aggaggccgg agccgggctg gaggccgagg ccgcctcacc gaggaagagg
3901   aggctgagcc agggacagag gtgggacctgg cggtcctggc cgacctggcc ctgacccctg
3961   cccggcgcgg gctgcctgcc ctgcctgctg ttgaagactc agaggccaca gagacatcgg
4021   acgaggccga gcgccctagg ccctgctca gccacatcct cctggagcac aactatgccc
4081   tggccgtcaa gcccacgccc ctgcgccag cctgcggcc cccggagcca gtgcccgcac
4141   ccgccgccct cttcagttcc ccagctgatg aggtcctgga ggcccccgag gtggtggtgg
```

-continued

```
4201  ctgaggcgga ggagcccaag ccgcagcaac tgcagcagca gcgggaggag ggcgaagagg
4261  aggggagga agaggggag gaagaggag aggagtcctc tgacagcagc agcagcagcg
4321  atggggaggg cgccctccgg aggcgcagcc tccgctccca cgccggcgc cgccgccctc
4381  cgccccacc cccgccgcca ccgcccgcg cctacgagcc acgcagtgag tttgaacaga
4441  tgaccatcct gtatgacatt tggaactcgg gcctggactc agaggacatg agttacctgc
4501  ggcttacgta cgagcggctg ctgcagcaga caagcggggc tgactggctc aacgacactc
4561  actgggtcca tcacacaatc accaacctga ccaccccaaa acgcaagcgg cggccccagg
4621  atgggccccg ggagcaccag acaggctcag cccgcagcga aggctactac cccatcagca
4681  agaaggagaa ggacaagtac ctggacgtgt gcccagtctc ggcccggcag ctggagggcg
4741  tggacactca ggggacgaac cgcgtgctgt ccgagcgccg gtccgagcag cggcggctgc
4801  tgagcgccat cggtacctcc gccatcatgg acagtgacct gctgaaactc aaccagctca
4861  agttccggaa gaagaagctc cgatttggcc ggagccggat ccacgagtgg ggtctgtttg
4921  ccatggaacc cattgctgct gacgagatgg tcatcgaata cgtgggtcag aacatccgtc
4981  agatggtggc cgacatgcgc gagaagcgct acgtgcagga gggcattggc agcagctacc
5041  tgttccgggt ggaccacgac accatcatcg atgccaccaa gtgtggcaac ctggccagat
5101  tcatcaacca ctgctgcacg cctaactgct acgccaaggt catcaccatc gagtcccaga
5161  agaagatcgt gatctactcc aagcagccca ttggcgtgga cgaggagatc acctacgact
5221  acaagttccc actggaagac aacaagatcc cgtgtctgtg tggcacagag agctgccggg
5281  gctccctaaa ctgaggtggg gcaggatggg tgcccacacc cctatttatt cccctggtg
5341  ccctgagctc ccagcacccc ccagcctta gtgggctcag cagggccac atgcccccat
5401  ctccaagcgt ggggttgggg gcccaagcc cagcgaggga gcctcagtcc ctggaggcag
5461  cttctgcctc tcctgtcacc cctgcccacc acccctgat tgtttttctt tgcggagaag
5521  aagctgtaaa tgtttttgtag cagccagcag ctgtttcctg tggaaacctg gggtgccggc
5581  ctgtacagat tctgtcctgg ggggctacac agtcctcttg ctttgtgtta atggggactt
5641  ccccttacgc cctgcgtgta cccctcccca gtttaggggt ctctggggca gtggccatgt
5701  tctccccctg gggggctct gcaccccag tcctggggac tccgtgcctg gaaccctgcc
5761  tcatctgttc ctgccagacc ctgagggtca cccttccacc ctggtgtcac tccccggctc
5821  agccaggcca ggatggcggg gtgggtccct tttgctgggc tggactgtac atatgttaat
5881  agcgcaaacc cgacgccaca tttttataat tgtgattaaa ctttattgta caaaa
```

SETD1B (accession No. NM_015048):

```
  1  aacggcatgg agaacagtca cccccccac caccaccacc agcagccccc gccgcagccc
 61  ggcccttcgg gcgagaggag gaaccaccat tggagaagtt acaagttgat gattgacccg
121  gctctgaaaa aggggcatca taaactgtac cgctacgatg gcagcatttt cagcctggcg
181  atgtccagca accgcccggt ggaaattgtc gaagatcccc gggtcgtcgg gatctggacc
241  aaaaacaagg agctggagct gtcggtgccc aaattcaaga tcgatgagtt ctacgtgggc
301  ccggtgcctc cgaagcaggt gacatttgcc aagctgaatg ataacatccg tgaaaacttc
361  ctgagggaca tgtgcaagaa gtatggggag gtggaggagg tggagatttt gtacaacccc
421  aagaccaaga agcacctggg catcgccaag gtggtctttg ccacggtccg gggagccaag
481  gatgccgttc agcacttgca cagcacttcc gtcatgggca acattatcca cgtggagctg
541  gacaccaaag gggaaacccg aatgcggttc tatgaactgt tggtcactgg ccgatacacc
601  ccccagaccc tcccagtggg cgagctggac gctgtctctc caatcgtgaa tgagaccctg
```

-continued

```
 661   cagctgtcag atgccctgaa gcgcctcaag gatggaggcc tgtctgcagg ctgtggctcc
 721   ggctcctcct ctgtcacccc caatagcggt gggacaccct tctcccagga cacagcttat
 781   tccagctgcc gcctggacac acccaactcc tatggacagg gcaccccgct cacaccgcgc
 841   ctgggcaccc ctttctcaca ggactccagc tactccagcc gccagcccac accctcatac
 901   ctcttcagcc aggaccctgc agtgaccttc aaggcccggc gccacgagag caagttcacg
 961   gacgcctaca accgccgcca cgaacatcat tatgtacaca attctcccgc ggtcactgcg
1021   gtggccgggg ccacagccgc tttccggggt tcctcggacc tcccgttcgg agcagtcggc
1081   ggcactgggg gcagcagcgg tcccccgttc aaggctcaac acaggattc agccacattt
1141   gcccacactc caccacccgc ccaagcaacc cctgctcctg gattcaagtc tgctttctct
1201   ccgtatcaga ccccagtggc ccacttccct ccaccccgg aagagcccac cgccacagcc
1261   gcttttgggg cccgcgacag tggggagttc cggagggcac cggcgccccc acccctgcca
1321   cctgctgagc ctctggccaa ggagaagcca ggcacgccac ccggcccgcc gcccccgac
1381   accaacagca tggagctggg cggccggccc accttcggct ggagtcctga gccctgtgac
1441   agccctggca cgcccacgct ggagtcgtcc cctgcagggc cagagaaacc ccacgacagc
1501   ctggactcgc gcatcgagat gctgctgaag gagcagcgca ccaagctgct cttcctgagg
1561   gagccggact cggacaccga gctgcagatg gagggcagcc ccatctcctc ctcctcctcc
1621   cagctctccc cactggcccc ctttggcacc aactcccagc caggcttccg gggcccacg
1681   cccccctcgt cacgccctc cagcaccggc ctggaggata tcagcccaac acccctccca
1741   gactccgacg aggacgagga gctcgacctg ggccttgggc tcggcctcc acctgagcca
1801   ggcccccgg accctgctgg gcttctgagc cagacagctg aggtggcctt ggacctggtt
1861   ggagacagaa ccccgacctc agagaagatg gatgagggcc agcagtcctc aggcgaggac
1921   atggagatct cggatgacga gatgccctcg gcccccatca ccagcgctga ctgccccaag
1981   cccatggtgg tgaccccagg agcggcagcc gtggcagccc cttctgtgct agccccaacc
2041   ctgccgctgc cccgccacc tggcttcccc ccgctgcccc cccaccacc accaccccca
2101   ccgcagcctg gcttccccat gccccaccg ctgcccccac cgccgccccc acccctcca
2161   gcccaccctg ctgtgacagt gcccccacca cccttgccag cgccgctgg agtcccgccc
2221   ccacccatcc tgccaccact gcccccttt ccgccgggcc tgttccctgt gatgcaggtg
2281   gacatgagcc acgtgctggg tggccagtgg ggcggcatgc ccatgtcctt ccagatgcaa
2341   acgcaggtgc tcagccggct gatgacgggc cagggcgcct gcccctaccg gcccttcatg
2401   gccgctgcgg ccgccgctgc ctcagctggg ctccagtttg tcaacctgcc gccctaccgg
2461   ggccccttct ccctgagcaa ctccggccca ggccgcgggc agcactggcc accactgccc
2521   aagtttgacc cgtcagtgcc tccaccaggc tacatgccac gccaggagga cccacacaaa
2581   gccacggtgg atggcgtcct gctggtggtc ctcaaagaac tcaaggccat catgaagcgt
2641   gacctgaacc gcaagatggt ggaagtggtg gctttccggg cctttgacga gtggtgggac
2701   aagaaggagc ggatggccaa ggcctcgctg accccggtga agtcgggcga gcacaaggac
2761   gaggacaggc cgaagcccaa ggaccgcatc gcctcgtgcc tgctggagtc atggggcaag
2821   ggcgagggcc tgggctacga gggcctgggc ctgggcattg gctgcgtgg ggccattcgc
2881   ctgccctcct tcaaggtcaa gaggaaggag ccaccagaca ccacctcatc tggcgaccag
2941   aagcggctgc ggccctcgac ctctgtggat gaggaagatg aagagtccga gcgagagcga
3001   gaccgggata tggcagacac cccctgtgag ctcgccaagc gggaccccaa gggcgtgggt
```

-continued

```
3061  gtgcggcggc ggccggcgcg gcctctggag ctggacagtg gtggggagga ggacgagaag
3121  gagtcattgt cggaggaaca ggagagcacc gaggaggaag aggaggcgga ggaggaggag
3181  gaggaggaag atgacgacga tgacgacagt gatgaccggg acgagtctga gaacgatgac
3241  gaggacacag ccctgtcaga ggcgagtgag aaggacgaag gggactcgga tgaagaggag
3301  acagtgagca ttgtaacctc caaggccgaa gccacgtcgt ccagtgagag ttccgagtct
3361  tctgagtttg agtcaagctc cgagtcctcg ccctcatcct cggaggatga ggaggaggta
3421  gtggccaggg aagaggagga agaagaggag gaggaggaga tggtggccga ggaaaagcatg
3481  gcttctgcag gccctgagga ctttgagcag gacggggagg aagcggctct ggccccgggg
3541  gcacctgcag tggactcgtt gggcatggaa gaggaggtgg acatcgagac tgaggctgtg
3601  gccctgagg agcggccctc catgctggac gagcccccct tgcctgtggg tgttgaagag
3661  ccagcggact ccagggagcc gcctgaggaa ccaggcctga gccaggaagg ggccatgttg
3721  ctgtctccag agcccctgc caaggaggtg gaggctcgac ccccattgtc ccctgagcga
3781  gctccagaac atgacctgga agtggagccg gagcccccta tgatgctccc cttgccgctg
3841  caaccaccat gccgcccccc acgaccaccc cggccaccca gcccaccgcc ggagcctgag
3901  accacagatg cctcacaccc atctgtccct ccggagcccc ttgccgagga ccaccccccg
3961  catactccag gcctctgtgg cagcctggcc aagtcgcaga gcacagagac ggtgccagcc
4021  acaccaggcg gggagccccc gctatcaggg ggcagcagtg gcctgtccct gagctctccg
4081  caagtgcccg gcagcccctt ctcctaccca gccccgtccc ctagcttgag cagtgggggc
4141  ctccctcgga cacctggccg ggacttcagc ttcacaccca ccttctccga gcccagcggg
4201  cccttgctcc tgcccgtctg cccactcccc actggccgac gcgatgaacg ctccgggccc
4261  ctggcctccc cggtgctcct ggagacgggc ctgcccctcc ctctgcccct tccctgccc
4321  ttgcccttgg cattgcccgc cgtcttgcgg gccaggctc gtgcgcccac cccgctgcca
4381  cccctgctgc ccgcccccct ggcctcttgc cctcccccaa tgaagaggaa gccgggccgg
4441  ccccggcgat ccccaccatc tatgctctcc ttggatgggc ccttggtccg accaccagca
4501  ggggccgccc ttggaaggga actcctgctc ctgccgggcc agccacagac ccccgtcttc
4561  cccagcaccc atgaccccg gacggtgacc ctggacttcc ggaacgcggg gatcccagcc
4621  cctccaccac cccttccccc cagccacccc caccccac ctcccccacc tgtagagccc
4681  accaagctgc cctttaagga gctagacaac cagtggccct ccgaggccat tcctccgggc
4741  ccccgtgggc gcgatgaggt cactgaggaa tacatggagt tggccaagag ccggggccgg
4801  tggcgccggc cacctaagaa gcgccatgag gacctggtgc cacctgcggg ctcgcccgaa
4861  ctctcgccac cccagcccct cttccggccc cgctcggagt ttgaggagat gaccatcctg
4921  tatgacatct ggaacggtgg catcgatgag gaggacatcc gcttcctgtg tgtcacctac
4981  gagcgactgc tacagcagga caatggcatg gactggctta cgacacgct ctgggtctac
5041  catccctcca ccagcctctc ttcagctaag aagaagaaac gggacgatgg catccgcgag
5101  cacgtgacgg gctgtgcccg cagtgagggc ttctacacca tcgacaagaa ggacaagctc
5161  agatacctca acagcagccg tgccagcacc gatgagcccc ccgcagacac ccagggcatg
5221  agcatcccag cacagcccca cgcctccacc cgggcaggct cggagcggcg tccggagcag
5281  cgccgcctgc tgtcctcctt cactggcagc tgtgacagtg acctgctcaa gttcaaccag
5341  ctcaagttcc ggaagaaaaa gctcaagttc tgcaagagcc acattcacga ctggggcttg
5401  ttcgccatgg agcccatcgc ggctgacgag atggtcatcg agtacgtggg ccagaatatc
5461  cgtcaggtga tcgcagacat gcgggagaag cgttatgagg acgagggcat cgggagcagc
```

-continued

```
5521  tacatgttcc gggtggacca tgacaccatc atcgacgcca ccaagtgcgg caacttcgcg
5581  cgcttcatca accacagctg caaccccaac tgctatgcca aggtgatcac ggtggagtca
5641  cagaagaaga tagtcatcta ctcgaagcag cacattaacg tcaatgagga gattacctat
5701  gactataagt tccccatcga ggacgtcaag atcccctgcc tctgtggctc cgagaactgc
5761  cggggaccc tcaactaggc cccggcacca gactcaaagg atgtcagccg tagccctggg
5821  actcccgagc gtggagcccc tggcccggg gccggcccc ccgcgcccgc ccccatttca
5881  ggtgctgtcc tctacccagc ggccattcag ggcctggcgc cccacactac cccctggagc
5941  ccctggctcc ggcccctccg cgggaaaggg cttctctgtc gttcagccca cgtctctctc
6001  attttaacaa cgcccttt caggatttct gtttaactcc agcatcagct tctctctctc
6061  cgtctctcct cccctctctc tcttctctgt ctcttctctc tcccaccatc accctcggcc
6121  tcttcctgtg aatgctgcta cgttgttttg tcttctctat ttttttcctc gttgtgagaa
6181  aagacattta accgttgaaa tgtgaaggtg aatcagaga ggggcccgc ggggtctgc
6241  agaggcctca gtgtggctgt gcgtggcccg tgtcctggaa gccacccgga cctggacgca
6301  gggccaggtg ctgtgggaag atggaggcc cccacggcct tgacctcaga acactacgcc
6361  ctgaaagcgc ccctcactgc ccgtgggcac agtgaggaga ccccacacct ttccccaccc
6421  gagctgcagc ctgttccttc cccagaggcc tggggcacca ctgacccggt ggaccctgat
6481  ggagctaagc tgtcccaggc aggggtctcc gctctgggct ttccctgcca cctcacaccc
6541  cagcaccccc taaaccttgg gttcaatgtt tactttctca ttcggatgcc agcaacgcgg
6601  gagcctctcg gaggcccag tgcaggtgag gggcgctgag aacgcgggca gccactctct
6661  tctgcccttg ccttcgccct gggtgggaca gggctcccaa gggcaggcgg gtcccccagt
6721  cccgccatta cgggttgtca gaccgtctgc gtgtggcatt ttttggctta taagcttcac
6781  ccactcaccc caacccaca ccccacatcc ccctgccggc agcccctcaa cctaagaagg
6841  ccagagcata tttattttcg gagggagcag attacttctc ccagagaaag gaaaatcttg
6901  gaaaagattt aaaaacacaa atctaagcct tgacggtttt ttttcccctt ttgaccccct
6961  tcccatctct tcagaattta ttcccatggc tttttttttt cttgtgcgtg tataaaatca
7021  aaaggaaggg gaaaaaggtt tttgaagttc agaaccaact tctgtatata gaggctgccg
7081  caaaggactt tctcttggga acattgtttc ttgtagaaac atgcgggaag acatttttg
7141  ctcatttctt tgtacttcca aaaaaaagg aaaaaaaga caaaagcaag tcccccgta
7201  ccccagaaag cagaggaggc gtgtaaataa tttctggaaa gtgactgttg tgacccggag
7261  tcctcatcaa gatgagcgcg ctccatgagg gagctgctcc caccctgcgg acgcaggcgg
7321  ccggagcctc tggtatctca gcttgtgtca agcttgttat catgtaaatt ctgtacaaag
7381  aattgttatt tttctctttt ttgttgttgg tggttttgtt gtgtgttttt tgttgttttt
7441  ttttttattcc tttccccccag gccctctcta tttgagactg tgcccgccgg tttcaagatc
7501  aaggaaattg gtggcaacaa gacacagatg gggtacctgg gcacagcggc gaacttctct
7561  tccgtttgcg gttttctgcc taattgtgca actgaggaaa taattttattt ttcacatgag
7621  gaaatgcgta gcttgtagag acggctgatt caagttacat gtacagcctc caaagggctg
7681  tctccattct gtccccttcc cataaaagaa gtggggtgt tcgagaagac cagggaaggg
7741  acccttgcct caccctccc cctggcctca ccttgctccc agccatcgtg cccagtgtta
7801  acctcggctg gccttcacta aggggactag acctccctct ccccaggagc cccagcccca
7861  gagtggttg caataatcaa gatatgtgtc gagtcatttt tctttcaact ccctcatttt
```

-continued

```
7921  tcattgaaca aatctctgct tttcaagagt tgggggtttc tgctatttt  tgctttctct
7981  ccctccccct gcaaagatga gaaccaatga gttttaggga tgtttgtgcg ggtagactcc
8041  atcatccata tgtaacttgt tttgaagaga agtgtttccg ttgtgtgtct tgatgtaaat
8101  atttgttcat attttgtga attcaatact atgtaccatt gtattatagt aacttttata
8161  aagcaaacca taaatatact gacttttctt acaga
```

CXXC1 (accession No. NM_001101654):
```
   1  ggaaagagtg gtggcaggtg aagtcggaga cgacagagga actggtttcc tccgccccgc
  61  aaggcacaca gcctgccgac gccccattaa tacatgtgga aggggaaaga gactgaatgg
 121  aggaatgaat acaacttgat ccaggtcgtg cttcggaagc ggtcacttta cctgtgaacc
 181  tctctgcctg acaaacgggc aatgtacgga atcaaccacc aagatggcgg cgcccgtgaa
 241  gaatccgcaa ttaggtcgcc gtcatatgtc gcctaggaac gtacggaatt cgacccacgt
 301  acggaatcgg attccaagat gacggcatct atgaggaagt cacgcagtag gtgcagccat
 361  gttgcctgta cgtcgaggcc gtacaagcag ccgccgtacg gactctactg caaggtggc
 421  ggcgccctcg ggaaagccac attagagcgc ggccatgttc ccggcgaaca tatggattcg
 481  gccaccatac ggatacgata agcaagatgg cggcgcctga ggggtcttgg gggctctagg
 541  ccggccacct actggtttgc agcggagacg acgcatgggg cctgcgcaat aggagtacgc
 601  tgcctgggag gcgtgactag aagcggaagt agttgtgggc gcctttgcaa ccgcctggga
 661  cgccgccgag tggtctgtgc aggttcgcgg gtcgctggcg ggggtcgtga gggagtgcgc
 721  cgggagcgga gatatggagg agatggttc agacccagag cctccagatg ccggggagga
 781  cagcaagtcc gagaatgggg agaatgcgcc catctactgc atctgccgca aaccggacat
 841  caactgcttc atgatcgggt gtgacaactg caatgagtgg ttccatgggg actgcatccg
 901  gatcactgag aagatggcca aggccatccg ggagtggtac tgtcgggagt gcagagagaa
 961  agaccccaag ctagagattc gctatcggca caagaagtca cgggagcggg atggcaatga
1021  gcgggacagc agtgagcccc gggatgaggg tgagggcgc aagaggcctg tccctgatcc
1081  agacctgcag cgccgggcag ggtcagggac aggggttggg gccatgcttg ctcggggctc
1141  tgcttcgccc cacaaatcct ctccgcagcc cttggtggcc acacccagcc agcatcacca
1201  gcagcagcag cagcagatca acggtcagc ccgcatgtgt ggtgagtgtg aggcatgtcg
1261  gcgcactgag gactgtggtc actgtgattt ctgtcgggac atgaagaagt tcggggggccc
1321  caacaagatc cggcagaagt gccggctgcg ccagtgccag ctgcgggccc ggaatcgta
1381  caagtacttc ccttcctcgc tctcaccagt gacgccctca gagtccctgc aaggcccccg
1441  ccggccactg cccacccaac agcagccaca gccatcacag aagttagggc gcatccgtga
1501  agatgagggg gcagtggcgt catcaacagt caaggagcct cctgaggcta cagccacacc
1561  tgagccactc tcagatgagg acctacctct ggatcctgac ctgtatcagg acttctgtgc
1621  agggggccttt gatgaccatg gcctgccctg gatgagcgac acagaagagt ccccattcct
1681  ggaccccgcg ctgcggaaga gggcagtgaa agtgaagcat gtgaagcgtc gggagaagaa
1741  gtctgagaag aaggtgatgg agaggaagga ggagcgatac aagcggcatc ggcagaagca
1801  gaagcacaag gataaatgga acacccaga gagggctgat gccaaggacc ctgcgtcact
1861  gccccagtgc ctggggcccg gctgtgtgcg cccgcccag cccagctcca agtattgctc
1921  agatgactgt ggcatgaagc tggcagccaa ccgcatctac gagatcctcc cccagcgcat
1981  ccagcagtgg cagcagagcc cttgcattgc tgaagagcac ggcaagaagc tgctcgaacg
2041  cattcgccga gagcagcaga gtgcccgcac tcgccttcag gaaatggaac gccgattcca
```

-continued

```
2101  tgagcttgag gccatcattc tacgtgccaa gcagcaggct gtgcgcgagg atgaggagag
2161  caacgagggt gacagtgatg acacagacct gcagatcttc tgtgtttcct gtgggcaccc
2221  catcaaccca cgtgttgcct tgcgccacat ggagcgctgc tacgccaagt atgagagcca
2281  gacgtccttt gggtccatgt accccacacg cattgaaggg ccacacgac  tcttctgtga
2341  tgtgtataat cctcagagca aaacatactg taagcggctc caggtgctgt gccccgagca
2401  ctcacgggac cccaaagtgc cagctgacga ggtatgcggg tgccccttg  tacgtgatgt
2461  ctttgagctc acgggtgact tctgccgcct gcccaagcgc cagtgcaatc gccattactg
2521  ctgggagaag ctgcggcgtg cggaagtgga cttggagcgc gtgcgtgtgt ggtacaagct
2581  ggacgagctg tttgagcagg agcgcaatgt gcgcacagcc atgacaaacc gcgcgggatt
2641  gctggccctg atgctgcacc agacgatcca gcacgatccc ctcactaccg acctgcgctc
2701  cagtgccgac cgctgagcct cctggcccgg accccttaca ccctgcattc cagatggggg
2761  agccgcccgg tgcccgtgtg tccgttcctc cactcatctg tttctccggt tctccctgtg
2821  cccatccacc ggttgaccgc ccatctgcct ttatcagagg gactgtcccc gtcgacatgt
2881  tcagtgcctg gtggggctgc ggagtccact catccttgcc tcctctccct gggttttgtt
2941  aataaaattt tgaagaaacc aaggaaaaaa aaaaaa
```

ASH2L (accession No. NM_004674):
```
   1  cacagcaacg cgcgcgagag aagagagtat tctcgcgaga agtccagggg tggccgtgat
  61  ggcggcggca ggagcaggac ctggccagga agcgggtgcc gggcctggcc caggagcggt
 121  cgcaaatgca acaggggcag aagaggggga gatgaagccg gtggcagcgg gagcagccgc
 181  tcctcctgga gagggatct  ctgctgctcc gacagttgag cccagttccg gggaggctga
 241  aggcggggag gcaaacttgg tcgatgtaag cggtggcttg gagacagaat catctaatgg
 301  aaaagataca ctagaaggtg ctggggatac atcagaggtg atggatactc aggcgggctc
 361  cgtggatgaa gagaatggcc gacagttggg tgaggtagag ctgcaatgtg ggatttgtac
 421  aaaatggttc acggctgaca catttggcat agatacctca tcctgtctac ctttcatgac
 481  caactacagt tttcattgca acgtctgcca tcacagtggg aatacctatt tcctccggaa
 541  gcaagcaaac ttgaaggaaa tgtgccttag tgctttggcc aacctgacat ggcagtcccg
 601  aacacaggat gaacatccga agacaatgtt ctccaaagat aaggatatta taccatttat
 661  tgataaatac tgggagtgca tgacaaccag acagagacct gggaaaatga cttggccaaa
 721  taacattgtt aaaacaatga gtaaagaaag atgtgtattc ttggtaaagg aacacccaga
 781  tccaggcagt aaagatccag aagaagatta ccccaaattt ggacttttgg atcaggacct
 841  tagtaacatt ggtcctgctt atgacaacca aaaacagagc agtgctgtgt ctactagtgg
 901  gaatttaaat ggggaattg  cagcaggaag cagcggaaaa ggacgaggag ccaagcgcaa
 961  acagcaggat ggagggacca cagggaccac caagaaggcc cggagtgacc ctttgttttc
1021  tgctcagcgc cttccccctc atggctaccc attggaacac ccgtttaaca aagatggcta
1081  tcggtatatt ctagctgagc ctgatccgca cgccctgac  cccgagaagc tggaacttga
1141  ctgctgggca ggaaaaccta ttcctggaga cctctacaga gcctgctgt  atgaacgggt
1201  tttgttagcc ctacatgatc gagctcccca gttaaagatc tcagatgacc ggctgactgt
1261  ggttggagag aagggctact ctatggtgag ggcctctcat ggagtacgga aggtgcctg
1321  gtattttgaa atcactgtgg atgagatgcc accagatacc gctgccagac tggttggtc
1381  ccagccccta ggaaaccttc aagctccttt aggttatgat aaatttagct attcttggcg
1441  gagcaaaaag ggaaccaagt tccaccagtc cattggcaaa cactactctt ctggctatgg
```

-continued

```
1501  acagggagac gtcctgggat tttatattaa tcttcctgaa gacacagaga cagccaagtc 1561  attgccagac acatacaaag ataaggcttt gataaaattc aagagttatt tgtattttga 1621  ggaaaaagac tttgtggata aagcagagaa gagcctgaag cagactcccc atagtgagat 1681  aatattttat aaaaatggtg tcaatcaagg tgtggcttac aaagatattt tgagggggt 1741  ttacttccca gccatctcac tgtacaagag ctgcacggtt ccattaact ttggaccatg 1801  cttcaagtat cctccgaagg atctcactta ccgccctatg agtgacatgg gctggggcgc 1861  cgtggtagag cacaccctgg ctgacgtctt gtatcacgtg gagacagaag tggatgggag 1921  gcgcagtccc ccatgggaac cctgaccagg tccctctttt ctgtcaagga ctttctggga 1981  ataatactgg gggttttgtt tttgattttg aactgtctca aatgttctcc caaagatgct 2041  aaaaacacag cctctccttt tagcaagtta aaaggctggg taggactgcg ggagactgcc 2101  tgcctttcac cattttctcc ccacttccag tgactgctct tattttgtgt accataagcc 2161  aacaaccgct gactccagga ttgcataagc ccctgtgaa atcggtgctg tactgcatac 2221  cctgccagct gtgacttgtt atcctactat attttctaag gagtgaataa tattgtccga 2281  gtaactaact tatttaaaag acatttcctt ctgtgggcat tgactgtatc ccacctgttt 2341  tccaaggaaa tggtaacctg tttctgagaa cacctgaaat caatggctat acattccaaa 2401  ccaatctaaa cgctatttcc ttttggtgtg ggtttggttt tgttcatttt gaaatacact 2461  tttgaacact gagatccgta aaactactag atctctggaa gtgtaattgt gaaagaaact 2521  tgcttgcagc tttaacaaaa tgagaaactt cccaaataaa acttgttttg aagtttatgt 2581  gacactttgc ttcccttcag attgggtgcc tcttggtgac agtgttcaga aatgtaagca 2641  gcacgaggaa gggagctggc actgggagga agagccgggt ttctgagttg tgttttggct 2701  gctttcctat tgctcccatt cttgccaatc agccacccc tttcctgtga aaatctgcca 2761  ccttgaggag aggaacaaga gtttaaaagg gctaatgatc tccctcccgg tcttcccttg 2821  gaacatggat gttgatatat gtgcgggtgg tttcctgtct tgcttatctt ccttttgccct 2881  gagctgatgg ctaaagggca gttttcggac tattaaagac tgaaatgtaa gaatgagcct 2941  tctaggctgg gcgc
```

DPY30 (accession No. NM_032574):
```
   1  tggcgcggtg cagggctctt aagaacgaac ggcttgggcg cgggtaatca gctcccttc 61  ccccactttc tcacttattc taggtacttg ggactgtcgt agagtttcca gaccccatgt 121  aggcgcccag tcgtggactg tcccactctg ctgctctact gctcgtggtg ctcccgcgcc 181  cagactggta tccggggact gtgacttgca gggtccgcca tggagccaga gcagatgctg 241  gagggacaaa cgcaggttgc agaaaatcct cactctgagt acggtctcac agacaacgtt 301  gagagaatag tagaaaatga aagattaat gcagaaaagt catcaaagca gaaggtagat 361  ctccagtctt tgccaactcg tgcctaccctg gatcagacag ttgtgcctat cttattacag 421  ggacttgctg tgcttgcaaa ggaaagacca ccaaatccca ttgaatttct agcatcttat 481  ctttttaaaaa acaaggcaca gtttgaagat cgaaactgac ttaatgggaa gaacagaaaa 541  atttagttgc tactgtagat ttacatgatt aagaggcagc tttaattgcc atgatcattc 601  cctctttttg gatgtataag aaccttccgg acaacagaac ctatttctgg aattgcagaa 661  gataacatat ttcccttatt ttgatttaat caccataaac catacctatt taatgagtgt 721  attctgtgca attttttttct cagattgtct ttaactttgt ttttaaaatg accttcaaaa 781  taaactgtca aaacaccatt
```

-continued

RBBP5 (accession No. NM_005057):

```
   1  ggaagccgcg gggccttcta aggccgaaag tcttcggagc ttgcgccagt ctcttcgcgg
  61  cgtccaccac ttagacgcaa gttgctgaag ccggccgggg agaaggtgtt gttgccggag
 121  ctgagaccgg gcggccacag tccgcaggga tgaacctcga gttgctggag tcctttgggc
 181  agaactatcc agaggaagct gatggaactt tggattgtat cagcatggct ttgacttgca
 241  cctttaacag gtggggcaca ctgcttgcag ttggctgtaa tgatggccga attgtcatct
 301  gggatttctt gacaagaggc attgctaaaa taattagtgc acacatccat ccagtgtgtt
 361  ctttatgctg gagccgagat ggtcataaac tcgtgagtgc ttccactgat aacatagtgt
 421  cacagtggga tgttctttca ggcgactgtg accagaggtt tcgattccct tcacccatct
 481  taaaagtcca atatcatcca cgagatcaga acaaggttct cgtgtgtccc atgaaatctg
 541  ctcctgtcat gttgacccct tcagattcca acatgttgt tctgccggtg gacgatgact
 601  ccgatttgaa cgttgtggca tcttttgata ggcgagggga atatatttat acgggaaacg
 661  caaaaggcaa gattttggtc ctaaaaacag attctcagga tcttgttgct tccttcagag
 721  tgacaactgg aacaagcaat accacagcca ttaagtcaat tgagtttgcc cggaagggga
 781  gttgcttttt aattaacacg gcagatcgaa taatcagagt ttatgatggc agagaaatct
 841  taacatgtgg aagagatgga gagcctgaac ctatgcagaa attgcaggat ttggtgaata
 901  ggacccatg gaagaaatgt tgtttctctg gggatgggga atacatcgtg gcaggttctg
 961  cccggcagca tgccctgtac atctgggaga gagcattgg caacctggtg aagattctcc
1021  atgggacgag aggagaactc ctcttggatg tagcttggca tcctgttcga cccatcatag
1081  catccatttc cagtggagtg gtatctatct gggcacagaa tcaagtagaa aactggagtg
1141  catttgcacc agacttcaaa gaattggatg aaaatgtaga atacgaagaa agggaatcag
1201  agtttgatat tgaagatgaa gataagagtg agcctgagca gacaggggct gatgctgcag
1261  aagatgagga agtggatgtc accagcgtgg accctattgc tgccttctgt agcagtgatg
1321  aagagctgga agattcaaag gctctattgt atttacccat tgcccctgag gtagaagacc
1381  cagaagaaaa tccttacggc cccccaccgg atgcagtcca aacctccttg atggatgaag
1441  gggctagttc agagaagaag aggcagtcct cagcagatgg gtcccagcca cctaagaaga
1501  aacccaaaac aaccaatata gaacttcaag gagtaccaaa tgatgaagtc catccactac
1561  tgggtgtgaa gggggatggc aaatccaaga gaagcaagc aggccggcct aaaggatcaa
1621  aaggtaaaga gaaagattct ccatttaaac cgaaactcta caaggggac agaggtttac
1681  ctctggaagg atcagcgaag ggtaaagtgc aggcggaact cagccagccc ttgacagcag
1741  gaggagcaat ctcagaactg ttatgaagac cttcgaagtt cttcattctt tctcactttg
1801  ccatcatgtg gcctctggac actgtggtca gtcatttgaa aattgacttt aatttaaaac
1861  aaaggcctgt gcctcccacc caggaggtgg gagggtgaat tttatgttta atgaagaag
1921  tgaattatgg aagaagagta tacgaccttc ccttcccttt caagcataag tccaaataga
1981  ctctcaggaa tgaagatttg tgaagacatc agataggaat tttgactcat ttaaactttg
2041  atgcttagtt atgttgctgg agaaaagata cttatgtttt gctcatctaa cttcattgta
2101  cccagcgtca ttttgacatg tcatttccta tctcccattt gccttcggtc tcaatgcat
2161  gtctttgagt gacttcttat ctgaaatttt gctactggta tcctaggaaa gcttttgttg
2221  gatactctca ttttaaactt ctcctctccc cagatacctc ctatatttcc atattgtgtg
2281  caaaggatgg gcagaaaaga aagtgcttga agatttcaa attttcgaaa agggaacaac
2341  gaaggccctc tcttcctctc ataccacgtt ttgctcaaga agctgggctg taacaattca
```

-continued

```
2401  gggttttccc ttgttttcct ctcattgcat gtttccctcc aatattggtt cattgtcatc
2461  aatcatggtt tttgaagata gctagtttta tccatctcca gcaaagaatc atcaatagtt
2521  tatattgctt tacctgtgct ggcttccaga gatggaaaca aacccaggtg tctctcaaca
2581  agctactttt ttactggggt ggggaatct atgcaaggag taaagtaaaa ccatccagaa
2641  tcaaagcagc aaccacatag ttcaaatcaa agatcaaggt gaatttttg tatcactgcc
2701  tgtggaaatc tatcctcatc agtcattgca ttttcctg cctatacctg tgctccttt
2761  tcttactgtg ttcagtca cttcctttct gtgaaaggtt gcttagcttt tttttgaca
2821  tttgttgttc tttataaaaa taacagattg gatagatgtg tacatttggt gtttgaaatt
2881  ctctgaaaat cccattagga aaccaggtgt gaaaagggct cagtagcttc tctgagtggc
2941  gttttagct gactggaagt gcttaatctg gatcgtcttt tttttttttt ttttttttc
3001  aatattttaa aaggagaatt taaatactgt gcttactgtg aaatatatca gttggtgagc
3061  cgggcgtggt gggtcacgcc tgtaatccca gcactttggg aggccaaggc gggttgatca
3121  cccgaggtca ggagttcaag accagcctgg ccaacgtggt gaaagcctgt atctattaaa
3181  agacaaaaat tagctgggcg tggtagtaca tgcctgtaat cccagctaca ctggaggctg
3241  agtcaggaga atcacttgaa cgtgggaggc agaggttgca gtgagtggag atcgcaccac
3301  tgccctccag cctaggtgac agaatgagac tctatctcaa aaaaaaaaaa aaaatgatat
3361  cagttggtgg atgctcctat aggtagccaa acacattgat tacctgttag attttaggat
3421  agaaatcaaa gtagagcacg tcagcaagag cctcttttgtc tcactccatc atttaaaacc
3481  agtatattca gtagttgaag aaagagctct ccctgagtca gttgcaaaac gtctatattt
3541  ttagatgcca ctactttttt cttaaatatt cattttgaga ctgtcatgag ttagaccagt
3601  ggttgagatt agtagatggc tcactagaca tgttttgtt ttgcagacat tatatccatt
3661  ccagtcctct gcactgtaca ctgcagcagt gtgcaaacta tgggacttag agggtttctg
3721  ccatctttcc acgtgtgaag tagcttggtt tcctctgcct gtgcatttgg atgtttgtgc
3781  tatgtccacc tcctaaactg gctactgaga aaatcatctt cagccctgtc agattgtctc
3841  tggcagtagc tcctaataat tatttatgtt ttggaattt ttttttcaac tttaaaaaa
3901  ccttctatcc atttcaattt gaattatttg atttgtacaa tatatgtata ttctcttctt
3961  ccttttttgtc atccctgccc tgccaccccc aaaattttgt ttttaaaaat attctgggct
4021  gggcatggtg gctcacacct gtaatcccag cacttgggga ggccgaggct ggtggatcat
4081  ctgaggtcag gtgtttgaga ccagcctggt caacatggtg aaaccccgtc tctactaaaa
4141  atacaaaaat tagctgggcg tggtggcggg cacctgtaat cctagctact cgggaggctg
4201  aggcaggaga attgcttgaa tccaggaggc agaggttgca gtgagctgag attgcgccac
4261  tgcactccag cctgggtgac agagcaagac tccatctcaa aaaaaaaaa aaaaaaaat
4321  ctgtagtttt gtacaagatg agacttagcc ttgggtactt cttgctgaag ctttaatgct
4381  ttgtaaataa aatcggatgt ttattaaaga aaaaaaaaa aaa
WDR5 (accession No. NM_017588):
   1  gccgcctggc gccgcccga gctgccgcct tgtcgagctg agtccgcgct cccgcccagg
  61  cggcggccga cgcgacgccc cgagcgcccg gccccgccgc cgcggcccgg cagactgcct
 121  ctgtcaccgg gtccctccac ccttgtctcc tgtgcggcca gcgtcagagc catggcgacg
 181  gaggagaaga gcccgagac cgaggccgcc agagcacagc caacccttc gtcatccgcc
 241  actcagagca agcctacacc tgtgaagcca aactatgctc taaagttcac ccttgctggc
 301  cacaccaaag cagtgtcctc cgtgaaattc agcccgaatg gagagtggct ggcaagttca
```

-continued

```
 361  tctgctgata aacttattaa aatttggggc gcgtatgatg ggaaatttga gaaaaccata
 421  tctggtcaca agctgggaat atccgatgta gcctggtcgt cagattctaa ccttcttgtt
 481  tctgcctcag atgacaaaac cttgaagata tgggacgtga gctcgggcaa gtgtctgaaa
 541  accctgaagg gacacagtaa ttatgtcttt tgctgcaact tcaatcccca gtccaacctt
 601  attgtctcag gatcctttga cgaaagcgtg aggatatggg atgtgaaaac agggaagtgc
 661  ctcaagactt tgccagctca ctcggatcca gtctcggccg ttcattttaa tcgtgatgga
 721  tccttgatag tttcaagtag ctatgatggt ctctgtcgca tctgggacac cgcctcaggc
 781  cagtgcctga agacgctcat cgatgacgac aaccccccg tgtcttttgt gaagttctcc
 841  ccgaacggca aatacatcct ggccgccacg ctggacaaca ctctgaagct ctgggactac
 901  agcaagggga agtgcctgaa gacgtacact ggccacaaga atgagaaata ctgcatattt
 961  gccaatttct ctgttactgg tgggaagtgg attgtgtctg gctcagagga taaccttgtt
1021  tacatctgga accttcagac gaaagagatt gtacagaaac tacaaggcca cacagatgtc
1081  gtgatctcaa cagcttgtca cccaacagaa aacatcatcg cctctgctgc gctagaaaat
1141  gacaaaacaa ttaaactgtg aagagtgac tgctaagtcc ctttgctcct gcccgcgaga
1201  gactgtcggg aagttgaccc ggattggcaa gaaacagggt gtcttggagg tggtccccca
1261  gatctgcgcc tggggtcag gacagggcct gatttgagcc tcctctctga agatgatttg
1321  gccgagcgga aggtgtggac caccggaaag ttcttaaaag ttgctggtga catttcttgc
1381  caattctaac actgtctagg aagagttcc tagtctattg tgttcaaaca gagtcaacaa
1441  aagttttaa ttttttatta cagaagggtg aagttcaatt taacatgcgt tgtgtttttt
1501  cagtaaacgt tctgtatctt tttgatattc catgacccag tgcacgcgtg ggcctgtcac
1561  cgccaccgtg gccccgccag ctggcctccc ctttggccca cgccggccgc ccccattctc
1621  tgctgcgtag atgccctggc ccagggccct gactcctcca ttcccgccag tagctgttcc
1681  tagtgtattt tcgtctttct ggaaaacagc attgagtggt tgttttctgt gtaaagagcc
1741  gtttgtgtct tgggagtttg tggcccacat gccgatagca cggtcatcgc acatgactct
1801  cccgtttgtc tcagtgtccc tgcaacaagc agcaccgcag actgtaataa aaggtggggt
1861  tttgtgaatg gttgtggcaa gtgcgtcctt gtgaagctcg tctccatgtg gctttcttgg
1921  agaaaggctc ccctggggca agagggtgga aggtttcttt ggacaggagg tgctgaggct
1981  ggctgcacct gctctctgaa gacgccttcc tctctaggtt cattgttcag tgttgctggg
2041  ggcggggaac gggggtgggg aggttcttag ttgcgaagga gccaagctcc tgatggactt
2101  gcgttgggat gtgggggaca cctgtggcat ggtaaggctc cctgagtccc ttactccagg
2161  tcagatgcca gtgggactca tgcgccctat gagggctgca gggccagtgc tgcccctcgg
2221  actcctcgag gggttgggtg ctaagcgcga gcctcgccgt cctgctgga gccctcgcct
2281  gcctgcccct ctgcctgtgc tcctggcagt gtggcttccc ggtgctcacc tgcacagcag
2341  ttaacagcag aggccgagcg ggagcctctg gggagcgagg ctgaaacctg aacctgccca
2401  tggagacagt tgtggtgagg gttgccacac acagtgaggg cggagcaggg tggctgaggg
2461  cacaggtgcc tgggtctgtc ccacggggca gggctttggg gctgtgatgc tctgggaagc
2521  cagcttgggt cctgggtcta cagagggccc tggcccccgga gcccagccag ctctgcctct
2581  ctcagggcct ggagtcctgg gggagctcag ccagctctgc ctttctcagg gcctggagtc
2641  ctggatgaat cctgcaggtt tttggttgca ccggcccagg aggaagcgg ggggtttgtc
2701  aggtgggctc tcctggaggt cctcgagtgg caggggtgag gagggatta tctgaggcat
```

-continued

```
2761  ctggagatgt atatcctgtg gtttcccctg cccctctgtt tccgatgagg tgtacggatg
2821  agtgacctgc actaagaagt gagttgccac agtgaaaatg ggttggtttt tgtcttcgac
2881  gctcagggtc tgggcgcctc gcatttgcag tctgttgtga cagacacggg gagctccgcg
2941  tgccagcctg tggctgccct gctgtggggg tcctgggcc ggcgaggccc cttcagtctt
3001  gttctggggg gacggcccac tccggggagg gggtgtgctg tgctgagcgc tgtatccctg
3061  aatatagttt attttttcta catttgaatt ctgttgtaga tttatgtaaa aatacattct
3121  ttttgaaaat aaaaattttc atgtcttcta atttaaaaaa aaa
```

KMT2A (accession No. NM_001197104):

```
   1  ctgcttcact tcacggggcg aacatggcgc acagctgtcg gtggcgcttc cccgcccgac
  61  ccgggaccac cggggggcggc ggcggcgggg ggcgccgggg cctaggggc gccccgcggc
 121  aacgcgtccc ggccctgctg cttccccccg gccccccggt cggcggtggc ggccccgggg
 181  cgcccccctc ccccccggct gtggcggccg cggcggcggc ggcgggaagc agcggggctg
 241  gggttccagg gggagcggcc gccgcctcag cagcctcctc gtcgtccgcc tcgtcttcgt
 301  cttcgtcatc gtcctcagcc tcttcagggc cggccctgct ccgggtgggc ccgggcttcg
 361  acgcggcgct gcaggtctcg gccgccatcg gcaccaacct cgcgcggttc cgggccgtgt
 421  tgggggagag cggcggggga ggcggcagcg gagaggatga gcaattctta ggttttggct
 481  cagatgaaga agtcagagtg cgaagtccca caaggtctcc ttcagttaaa actagtcctc
 541  gaaaacctcg tgggagacct agaagtggct ctgaccgaaa ttcagctatc ctctcagatc
 601  catctgtgtt ttcccctcta aataaatcag agaccaaatc tggagataag atcaagaaga
 661  aagattctaa aagtatagaa aagaagagag gaagacctcc caccttccct ggagtaaaaa
 721  tcaaaataac acatggaaag gacatttcag agttaccaaa gggaaacaaa gaagatagcc
 781  tgaaaaaaat taaaaggaca ccttctgcta cgtttcagca agccacaaag attaaaaaat
 841  taagagcagg taaactctct cctctcaagt ctaagtttaa gacagggaag cttcaaatag
 901  gaaggaaggg ggtacaaatt gtacgacgga gaggaaggcc tccatcaaca gaaaggataa
 961  agaccccttc gggtctcctc attaattctg aactggaaaa gccccagaaa gtccggaaag
1021  acaaggaagg aacacctcca cttacaaaag aagataagac agttgtcaga caaagccctc
1081  gaaggattaa gccagttagg attattcctt cttcaaaaag gacagatgca accattgcta
1141  agcaactctt acagagggca aaaaagggg ctcaaaagaa aattgaaaaa gaagcagctc
1201  agctgcaggg aagaaaggtg aagacacagg tcaaaaatat tcgacagttc atcatgcctg
1261  ttgtcagtgc tatctcctcg cggatcatta agacccctcg gcggtttata gaggatgagg
1321  attatgaccc tccaattaaa attgcccgat tagagtctac accgaatagt agattcagtg
1381  ccccgtcctg tggatcttct gaaaaatcaa gtgcagcttc tcagcactcc tctcaaatgt
1441  cttcagactc ctctcgatct agtagcccca gtgttgatac ctccacagac tctcaggctt
1501  ctgaggagat tcaggtactt cctgaggagc ggagcgatac ccctgaagtt catcctccac
1561  tgcccatttc ccagtcccca gaaaatgaga gtaatgatag gagaagcaga aggtattcag
1621  tgtcggagag aagttttgga tctagaacga cgaaaaaatt atcaactcta caaagtgccc
1681  cccagcagca gacctcctcg tctccaccct cacctctgct gactccaccg ccaccactgc
1741  agccagcctc cagtatctct gaccacacac cttggcttat gcctccaaca atccccttag
1801  catcaccatt tttgcctgct tccactgctc ctatgcaagg gaagcgaaaa tctattttgc
1861  gagaaccgac atttaggtgg acttctttaa agcattctag gtcagagcca caatactttt
1921  cctcagcaaa gtatgccaaa gaaggtctta ttcgcaaacc aatatttgat aatttccgac
```

-continued

```
1981  cccctccact aactcccgag gacgttggct ttgcatctgg ttttctgca tctggtaccg
2041  ctgcttcagc ccgattgttt tcgccactcc attctggaac aaggtttgat atgcacaaaa
2101  ggagccctct tctgagagct ccaagattta ctccaagtga ggctcactct agaatatttg
2161  agtctgtaac cttgcctagt aatcgaactt ctgctggaac atcttcttca ggagtatcca
2221  atagaaaaag gaaagaaaa gtgtttagtc ctattcgatc tgaaccaaga tctccttctc
2281  actccatgag gacaagaagt ggaaggctta gtagttctga gctctcacct ctcaccccc
2341  cgtcttctgt ctcttcctcg ttaagcattt ctgttagtcc tcttgccact agtgccttaa
2401  acccaacttt tacttttcct tctcattccc tgactcagtc tggggaatct gcagagaaaa
2461  atcagagacc aaggaagcag actagtgctc cggcagagcc attttcatca agtagtccta
2521  ctcctctctt cccttggttt accccaggct ctcagactga agagggaga aataaagaca
2581  aggcccccga ggagctgtcc aaagatcgag atgctgacaa gagcgtggag aaggacaaga
2641  gtagagagag agaccgggag agagaaaagg agaataagcg ggagtcaagg aaagagaaaa
2701  ggaaaaaggg atcagaaatt cagagtagtt ctgctttgta tcctgtgggt agggtttcca
2761  aagagaaggt tgttggtgaa gatgttgcca cttcatcttc tgccaaaaaa gcaacagggc
2821  ggaagaagtc ttcatcacat gattctggga ctgatattac ttctgtgact cttggggata
2881  caacagctgt caaaaccaaa atacttataa agaaagggag aggaaatctg gaaaaaacca
2941  acttggacct cggcccaact gccccatccc tggagaagga gaaaccctc tgcctttcca
3001  ctccttcatc tagcactgtt aaacattcca cttcctccat aggctccatg ttggctcagg
3061  cagacaagct tccaatgact gacaagaggg ttgccagcct cctaaaaaag gccaaagctc
3121  agctctgcaa gattgagaag agtaagagtc ttaaacaaac cgaccagccc aaagcacagg
3181  gtcaagaaag tgactcatca gagacctctg tgcgaggacc ccggattaaa catgtctgca
3241  gaagagcagc tgttgccctt ggccgaaaac gagctgtgtt tcctgatgac atgcccaccc
3301  tgagtgcctt accatgggaa gaacgagaaa agattttgtc ttccatgggg aatgatgaca
3361  agtcatcaat tgctggctca gaagatgctg aacctcttgc tccacccatc aaaccaatta
3421  aacctgtcac tagaaacaag gcaccccagg aacctccagt aaagaaagga cgtcgatcga
3481  ggcggtgtgg gcagtgtccc ggctgccagg tgcctgagga ctgtggtgtt tgtactaatt
3541  gcttagataa gcccaagttt ggtggtcgca atataaagaa gcagtgctgc aagatgagaa
3601  aatgtcagaa tctacaatgg atgccttcca aagcctacct gcagaagcaa gctaaagctg
3661  tgaaaagaa agagaaaaag tctaagacca gtgaaaagaa agacagcaaa gagagcagtg
3721  ttgtgaagaa cgtggtggac tctagtcaga aacctacccc atcagcaaga gaggatcctg
3781  ccccaaagaa aagcagtagt gagcctcctc cacgaaagcc cgtcgaggaa aagagtgaag
3841  aagggaatgt ctcggcccct gggcctgaat ccaaacaggc caccactcca gcttccagga
3901  agtcaagcaa gcaggtctcc cagccagcac tggtcatccc gcctcagcca cctactacag
3961  gaccgccaag aaaagaagtt cccaaaacca ctcctagtga gcccaagaaa agcagcctc
4021  caccaccaga atcaggtcca gagcagagca acagaaaaa agtggctccc cgcccaagta
4081  tccctgtaaa acaaaaacca aagaaaaagg aaaaccacc tccggtcaat aagcaggaga
4141  atgcaggcac tttgaacatc ctcagcactc tctccaatgg caatagttct aagcaaaaaa
4201  ttccagcaga tggagtccac aggatcagag tggactttaa ggaggattgt gaagcagaaa
4261  atgtgtggga gatgggaggc ttaggaatct tgacttctgt tcctataaca cccagggtgg
4321  tttgctttct ctgtgccagt agtgggcatg tagagtttgt gtattgccaa gtctgttgtg
4381  agcccttcca caagttttgt ttagaggaga acgagcgccc tctggaggac cagctggaaa
```

-continued

```
4441  attggtgttg tcgtcgttgc aaattctgtc acgtttgtgg aaggcaacat caggctacaa
4501  agcagctgct ggagtgtaat aagtgccgaa acagctatca ccctgagtgc ctgggaccaa
4561  actaccccac caaacccaca agaagaaga aagtctggat ctgtaccaag tgtgttcgct
4621  gtaagagctg tggatccaca actccaggca aagggtggga tgcacagtgg tctcatgatt
4681  tctcactgtg tcatgattgc gccaagctct ttgctaaagg aaacttctgc cctctctgtg
4741  acaaatgtta tgatgatgat gactatgaga gtaagatgat gcaatgtgga aagtgtgatc
4801  gctgggtcca ttccaaatgt gagaatcttt caggtacaga agatgagatg tatgagattc
4861  tatctaatct gccagaaagt gtggcctaca cttgtgtgaa ctgtactgag cggcaccctg
4921  cagagtggcg actggccctt gaaaaagagc tgcagatttc tctgaagcaa gttctgacag
4981  ctttgttgaa ttctcggact accagccatt tgctacgcta ccggcaggct gccaagcctc
5041  cagacttaaa tcccgagaca gaggagagta taccttcccg cagctccccc gaaggacctg
5101  atccaccagt tcttactgag gtcagcaaac aggatgatca gcagccttta gatctagaag
5161  gagtcaagag gaagatggac caagggaatt acacatctgt gttggagttc agtgatgata
5221  ttgtgaagat cattcaagca gccattaatt cagatggagg acagccagaa attaaaaaag
5281  ccaacagcat ggtcaagtcc ttcttcattc ggcaaatgga acgtgttttt ccatggttca
5341  gtgtcaaaaa gtccaggttt tgggagccaa ataaagtatc aagcaacagt gggatgttac
5401  caaacgcagt gcttccacct tcacttgacc ataattatgc tcagtggcag gagcgagagg
5461  aaaacagcca cactgagcag cctcctttaa tgaagaaaat cattccagct cccaaaccca
5521  aaggtcctgg agaaccagac tcaccaactc ctctgcatcc tcctacacca ccaattttga
5581  gtactgatag gagtcgagaa gacagtccag agctgaaccc accccaggca atagaagaca
5641  atagacagtg tgcgttatgt ttgacttatg gtgatgacag tgctaatgat gctggtcgtt
5701  tactatatat tggccaaaat gagtggacac atgtaaattg tgctttgtgg tcagcggaag
5761  tgtttgaaga tgatgacgga tcactaaaga atgtgcatat ggctgtgatc agggcaagc
5821  agctgagatg tgaattctgc caaaagccag gagccaccgt gggttgctgt ctcacatcct
5881  gcaccagcaa ctatcacttc atgtgttccc gagccaagaa ctgtgtcttt ctggatgata
5941  aaaaagtata ttgccaacga catcgggatt tgatcaaagg cgaagtggtt cctgagaatg
6001  gatttgaagt tttcagaaga gtgtttgtgg actttaagg aatcagcttg agaaggaagt
6061  ttctcaatgg cttggaacca gaaaatatcc acatgatgat tgggtctatg caatcgact
6121  gcttaggaat tctaaatgat ctctccgact gtgaagataa gctctttcct attggatatc
6181  agtgttccag ggtatactgg agcaccacag atgctcgcaa cgctgtgta tacatgca
6241  agatagtgga gtgccgtcct ccagtcgtag agccggatat caacagcact gttgaacatg
6301  atgaaaacag gaccattgcc catagtccaa catcttttac agaaagttca tcaaaagaga
6361  gtcaaaacac agctgaaatt ataagtcctc catcaccaga ccgacctcct cattcacaaa
6421  cctctggctc ctgttattat catgtcatct caaaggtccc caggattcga acacccagtt
6481  attctccaac acagagatcc cctggctgtc gaccgttgcc ttctgcagga agtcctaccc
6541  caaccactca tgaaatagtc acagtaggtg atcctttact ctcctctgga cttcgaagca
6601  ttggctccag gcgtcacagt acctcttcct tatcacccca gcggtccaaa ctccggataa
6661  tgtctccaat gagaactggg aatacttact ctaggaataa tgtttcctca gtctccacca
6721  ccgggaccgc tactgatctt gaatcaagtg ccaaagtagt tgatcatgtc ttagggccac
6781  tgaattcaag tactagttta gggcaaaaca cttccaccct ttcaaatttg caaaggacag
```

-continued

```
6841   tggttactgt aggcaataaa aacagtcact tggatggatc ttcatcttca gaaatgaagc
6901   agtccagtgc ttcagacttg gtgtccaaga gctcctcttt aaagggagag aagaccaaag
6961   tgctgagttc caagagctca gagggatctg cacataatgt ggcttaccct ggaattccta
7021   aactggcccc acaggttcat aacacaacat ctagagaact gaatgttagt aaaatcggct
7081   cctttgctga accctcttca gtgtcgtttt cttctaaaga ggccctctcc ttcccacacc
7141   tccatttgag agggcaaagg aatgatcgag accaacacac agattctacc caatcagcaa
7201   actcctctcc agatgaagat actgaagtca aaaccttgaa gctatctgga atgagcaaca
7261   gatcatccat tatcaacgaa catatgggat ctagttccag agataggaga cagaaaggga
7321   aaaaatcctg taaagaaact ttcaaagaaa agcattccag taaatctttt ttggaacctg
7381   gtcaggtgac aactggtgag gaaggaaact gaagccaga gtttatggat gaggttttga
7441   ctcctgagta tatgggccaa cgaccatgta acaatgtttc ttctgataag attggtgata
7501   aaggcctttc tatgccagga gtccccaaag ctccacccat gcaagtagaa ggatctgcca
7561   aggaattaca ggcaccacgg aaacgcacag tcaaagtgac actgacacct ctaaaaatgg
7621   aaaatgagag tcaatccaaa aatgccctga agaaagtag tcctgcttcc cctttgcaaa
7681   tagagtcaac atctcccaca gaaccaattt cagcctctga aaatccagga gatggtccag
7741   tggcccaacc aagccccaat aatacctcat gccaggattc tcaaagtaac aactatcaga
7801   atcttccagt acaggacaga aacctaatgc ttccagatgg ccccaaacct caggaggatg
7861   gctctttta aaggaggtat ccccgtcgca gtgcccgtgc acgttctaac atgttttttg
7921   ggcttacccc actctatgga gtaagatcct atggtgaaga agacattcca ttctacagca
7981   gctcaactgg gaagaagcga ggcaagagat cagctgaagg acaggtggat ggggccgatg
8041   acttaagcac ttcagatgaa gacgacttat actattacaa cttcactaga acagtgattt
8101   cttcaggtgg agaggaacga ctggcatccc ataatttatt tcgggaggag gaacagtgtg
8161   atcttccaaa aatctcacag ttggatggtg ttgatgatgg gacagagagt gatactagtg
8221   tcacagccac aacaaggaaa agcagccaga ttccaaaaag aaatggtaaa gaaaatggaa
8281   cagagaactt aaagattgat agacctgaag atgctgggga gaaagaacat gtcactaaga
8341   gttctgttgg ccacaaaaat gagccaaaga tggataactg ccattctgta agcagagtta
8401   aaacacaggg acaagattcc ttggaagctc agctcagctc attggagtca agccgcagag
8461   tccacacaag taccccctcc gacaaaaatt tactggacac ctataatact gagctcctga
8521   aatcagattc agacaataac aacagtgatg actgtgggaa tatcctgcct tcagacatta
8581   tggactttgt actaaagaat actccatcca tgcaggcttt gggtgagagc ccagagtcat
8641   cttcatcaga actcctgaat cttggtgaag gattgggtct tgacagtaat cgtgaaaaag
8701   acatgggtct ttttgaagta ttttctcagc agctgcctac aacagaacct gtggatagta
8761   gtgtctcttc ctctatctca gcagaggaac agtttgagtt gcctctagag ctaccatctg
8821   atctgtctgt cttgaccacc cggagtccca ctgtccccag ccagaatccc agtagactag
8881   ctgttatctc agactcaggg gagaagagag taaccatcac agaaaaatct gtagcctcct
8941   ctgaaagtga cccagcactg ctgagcccag gagtagatcc aactcctgaa ggccacatga
9001   ctcctgatca ttttatccaa ggacacatgg atgcagacca catctctagc cctccttgtg
9061   gttcagtaga gcaaggtcat ggcaacaatc aggatttaac taggaacagt agcacccctg
9121   gccttcaggt acctgttttcc ccaactgttc ccatccagaa ccagaagtat gtgcccaatt
9181   ctactgatag tcctggcccg tctcagattt ccaatgcagc tgtccagacc actccacccc
9241   acctgaagcc agccactgag aaactcatag ttgttaacca gaacatgcag ccactttatg
```

-continued

```
 9301 ttctccaaac tcttccaaat ggagtgaccc aaaaaatcca attgacctct tctgttagtt
 9361 ctacacccag tgtgatggag acaaatactt cagtattggg acccatggga ggtggtctca
 9421 cccttaccac aggactaaat ccaagcttgc caacttctca atctttgttc ccttctgcta
 9481 gcaaaggatt gctacccatg tctcatcacc agcacttaca ttccttccct gcagctactc
 9541 aaagtagttt cccaccaaac atcagcaatc ctccttcagg cctgcttatt ggggttcagc
 9601 ctcctccgga tccccaactt ttggtttcag aatccagcca gaggacagac ctcagtacca
 9661 cagtagccac tccatcctct ggactcaaga aaagacccat atctcgtcta cagacccgaa
 9721 agaataaaaa acttgctccc tctagtaccc cttcaaacat gccccttct gatgtggttt
 9781 ctaatatgac attgattaac ttcacaccct cccagcttcc taatcatcca agtctgttag
 9841 atttggggtc acttaatact tcatctcacc gaactgtccc caacatcata aaaagatcta
 9901 aatctagcat catgtatttt gaaccggcac ccctgttacc acagagtgtg ggaggaactg
 9961 ctgccacagc ggcaggcaca tcaacaataa gccaggatac tagccacctc acatcagggt
10021 ctgtgtctgg cttggcatcc agttcctctg tcttgaatgt tgtatccatg caaactacca
10081 caaccctac aagtagtgcg tcagttccag gacacgtcac cttaaccaac ccaaggttgc
10141 ttggtacccc agatattggc tcaataagca atcttttaat caaagctagc cagcagagcc
10201 tggggattca ggaccagcct gtggctttac cgccaagttc aggaatgttt ccacaactgg
10261 ggacatcaca gacccctct actgctgcaa taacagcggc atctagcatc tgtgtgctcc
10321 cctccactca gactacgggc ataacagccg cttcaccttc tggggaagca gacgaacact
10381 atcagcttca gcatgtgaac cagctccttg ccagcaaaac tgggattcat tcttcccagc
10441 gtgatcttga ttctgcttca gggccccagg tatccaactt tacccagacg gtagacgctc
10501 ctaatagcat gggactggag cagaacaagg ctttatcctc agctgtgcaa gccagcccca
10561 cctctcctgg gggttctcca tcctctccat cttctggaca gcggtcagca agcccttcag
10621 tgccgggtcc cactaaaccc aaaccaaaaa ccaaacggtt tcagctgcct ctagacaaag
10681 ggaatggcaa gaagcacaaa gtttcccatt tgcggaccag ttcttctgaa gcacacattc
10741 cagaccaaga aacgacatcc ctgacctcag gcacagggac tccaggagca gaggctgagc
10801 agcaggatac agctagcgtg gagcagtcct cccagaagga gtgtgggcaa cctgcagggc
10861 aagtcgctgt tcttccggaa gttcaggtga cccaaaatcc agcaaatgaa caagaaagtg
10921 cagaacctaa aacagtggaa gaagaggaaa gtaatttcag ctccccactg atgctttggc
10981 ttcagcaaga acaaaagcgg aaggaaagca ttactgagaa aaaacccaag aaaggacttg
11041 tttttgaaat ttccagtgat gatggctttc agatctgtgc agaaagtatt gaagatgcct
11101 ggaagtcatt gacagataaa gtccaggaag ctcgatcaaa tgcccgccta agcagctct
11161 catttgcagg tgttaacggt ttgaggatgc tggggattct ccatgatgca gttgtgttcc
11221 tcattgagca gctgtctggt gccaagcact gtcgaaatta caattccgt ttccacaagc
11281 cagaggaggc caatgaaccc cccttgaacc ctcacggctc agccagggct gaagtccacc
11341 tcaggaagtc agcatttgac atgttttaact tcctggcttc taaacatcgt cagcctcctg
11401 aatacaaccc caatgatgaa gaagaggagg aggtacagct gaagtcagct cggagggcaa
11461 ctagcatgga tctgccaatg cccatgcgct tccggcactt aaaaaagact tctaaggagg
11521 cagttggtgt ctacaggtct cccatccatg gccgggtct tttctgtaag agaaacattg
11581 atgcaggtga gatggtgatt gagtatgccg gcaacgtcat ccgctccatc cagactgaca
11641 agcgggaaaa gtattacgac agcaagggca ttggttgcta tatgttccga attgatgact
```

```
11701  cagaggtagt ggatgccacc atgcatggaa atgctgcacg cttcatcaat cactcgtgtg
11761  agcctaactg ctattctcgg gtcatcaata ttgatgggca gaagcacatt gtcatctttg
11821  ccatgcgtaa gatctaccga ggagaggaac tcacttacga ctataagttc cccattgagg
11881  atgccagcaa caagctgccc tgcaactgtg gcgccaagaa atgccggaag ttcctaaact
11941  aaagctgctc ttctccccca gtgttggagt gcaaggaggc ggggccatcc aaagcaacgc
12001  tgaaggcctt ttccagcagc tgggagctcc cggattgcgt ggcacagctg aggggcctct
12061  gtgatggctg agctctctta tgtcctatac tcacatcaga catgtgatca tagtcccaga
12121  gacagagttg aggtctcgaa gaaaagatcc atgatcggct ttctcctggg gcccctccaa
12181  ttgtttactg ttagaaagtg ggaatggggt ccctagcaga cttgcctgga aggagcctat
12241  tatagagggt tggttatgtt gggagattgg gcctgaattt ctccacagaa ataagttgcc
12301  atcctcaggt tggcccttc ccaagcactg taagtgagtg ggtcaggcaa agccccaaat
12361  ggagggttgg ttagattcct gacagtttgc cagccaggcc ccacctacag cgtctgtcga
12421  acaaacagag gtctggtggt tttccctact atcctcccac tcgagagttc acttctggtt
12481  gggagacagg attcctagca cctccggtgt caaaaggctg tcatggggtt gtgccaatta
12541  attaccaaac attgagcctg caggctttga gtgggagtgt tgcccccagg agccttatct
12601  cagccaatta cctttcttga cagtaggagc ggcttccctc tcccattccc tcttcactcc
12661  ctttcttcc tttcccctgt cttcatgcca ctgctttccc atgcttcttt cgggttgtag
12721  gggagactga ctgcctgctc aaggacactc cctgctgggc ataggatgtg cctgcaaaaa
12781  gttccctgag cctgtaagca ctccaggtgg ggaagtggac aggagccatt ggtcataacc
12841  agacagaatt tggaaacatt ttcataaagc tccatggaga gttttaaaga aacatatgta
12901  gcatgatttt gtaggagagg aaaaagatta tttaaatagg atttaaatca tgcaacaacg
12961  agagtatcac agccaggatg acccttgggt cccattccta agacatggtt actttatttt
13021  ccccttgtta agacatagga agacttaatt tttaaacggt cagtgtccag ttgaaggcag
13081  aacactaatc agatttcaag gcccacaact tggggactag accaccttat gttgagggaa
13141  ctctgccacc tgcgtgcaac ccacagctaa agtaaattca atgacactac tgccctgatt
13201  actccttagg atgtggtcaa aacagcatca aatgtttctt ctcttccttt ccccaagaca
13261  gagtcctgaa cctgttaaat taagtcattg gattttactc tgttctgttt acagtttact
13321  atttaaggtt ttataaatgt aaatatattt tgtatatttt tctatgagaa gcacttcata
13381  gggagaagca cttatgacaa ggctattttt taaaccgcgg tattatccta atttaaaaga
13441  agatcggttt ttaataattt tttattttca taggatgaag ttagagaaaa tattcagctg
13501  tacacacaaa gtctggtttt tcctgcccaa cttccccctg gaaggtgtac ttttgttgt
13561  ttaatgtgta gcttgtttgt gccctgttga cataaatgtt tcctgggttt gctctttgac
13621  aataaatgga gaaggaaggt cacccaactc cattgggcca ctcccctcct tcccctattg
13681  aagctcctca aaaggctaca gtaatatctt gatacaacag attctcttct ttcccgcctc
13741  tctcctttcc ggcgcaactt ccagagtggt gggagacggc aatctttaca tttccctcat
13801  ctttcttact tcagagttag caaacaacaa gttgaatggc aacttgacat ttttgcatca
13861  ccatctgcct cataggccac tctttccttt ccctctgccc accaagtcct catatctgca
13921  gagaacccat tgatcacctt gtgccctctt tgggggcagc tgttgaaac tgaagcacag
13981  tctgaccact cacgataaag cagatttttc tctgcctctg ccacaaggtt tcagagtagt
14041  gtagtccaag tagagggtgg ggcacccttt tctcgccgca agaagcccat tcctatggaa
14101  gtctagcaaa gcaatacgac tcagcccagc actctctgcc ccaggactca tggctctgct
```

```
14161  gtgccttcca tcctgggctc ccttctctcc tgtgacctta agaactttgt ctggtggctt
14221  tgctggaaca ttgtcactgt tttcactgtc atgcagggag cccagcactg tggccaggat
14281  ggcagagact tccttgtcat catggagaag tgccagcagg ggactgggaa aagcactcta
14341  cccagacctc acctcccttc ctccttttgc ccatgaacaa gatgcagtgg ccctagggt
14401  tccactagtg tctgctttcc tttattattg cactgtgtga ggttttttg taaatccttg
14461  tattcctatt ttttttaaag aaaaaaaaa aaccttaagc tgcatttgtt actgaaatga
14521  ttaatgcact gatgggtcct gaattcacct tgagaaagac ccaaaggcca gtcagggggt
14581  gggggaact cagctaaata gacctagtta ctgccctgct aggccatgct gtactgtgag
14641  cccctcctca ctctctacca accctaaacc ctgaggacag gggaggaacc cacagcttcc
14701  ttctcctgcc agctgcagat ggtttgcctt gcctttccac cccctaattg tcaaccacaa
14761  aaatgagaaa ttcctcttct agctcagcct tgagtccatt gccaaatttt cagcacacct
14821  gccagcaact tggggaata agcgaaggtt tccctacaag agggaaagaa ggcaaaaacg
14881  gcacagctat ctccaaacac atctgagttc atttcaaaag tgaccaaggg aatctccgca
14941  caaaagtgca gattgaggaa ttgtgatggg tcattcccaa gaatccccca aggggcatcc
15001  caaatccctg aggagtaaca gctgcaaacc tggtcagttc tcagtgagag ccagctcact
15061  tatagctttg ctgctagaac ctgttgtggc tgcatttcct ggtggccagt gacaactgtg
15121  taaccagaat agctgcatgg cgctgaccct ttggccggaa cttggtctct tggctccctc
15181  cttggccacc caccacctct cgcacagccc ctctgttttt acaccaataa caagaattaa
15241  gggggaagcc ctggcagcta tacgttttca accagactcc tttgccggga cccagcccgc
15301  caccctgctc gcctccgtca aaccccggc caatgcagtg agcaccatgt agctcccttg
15361  atttaaaaaa ataaaaaat aaaaaaaaaa ggaaaaaaaa atacaacaca cacacaaaaa
15421  taaaaaaaat attctaatga atgtatcttt ctaaaggact gacgttcaat caaatatctg
15481  aaaatactaa aggtcaaaac cttgtcagat gttaacttct aagttcggtt tgggattttt
15541  ttttttaat agaaatcaag ttgttttgt tttaaggaa aagcgggtca ttgcaaaggg
15601  ctgggtgtaa ttttatgttt catttccttc atttttaaagc aatacaaggt tatggagcag
15661  atggttttgt gccgaatcat gaatactagt caagtcacac actctggaaa cttgcaactt
15721  tttgtttgtt ttggttttca ataaaatata aatatgatat atataggaac taatatagta
15781  atgcaccatg taacaaagcc tagttcagtc catggctttt aattctctta acactataga
15841  taaggattgt gttacagttg ctagtagcgg caggaagatg tcaggctcac tttcctctga
15901  ttcccgaaat gggggaacc tctaaccata aaggaatggt agaacagtcc attcctcgga
15961  tcagagaaaa atgcagacat ggtgtcacct ggattttttt ctgcccatga atgttgccag
16021  tcagtacctg tcctccttgt ttctctattt ttggttatga atgttggggt taccacctgc
16081  atttagggga aaattgtgtt ctgtgctttc ctggtatctt gttccgaggt actctagttc
16141  tgtctttcaa ccaagaaaat agaattgtgg tgtttctttt attgaacttt taacagtctc
16201  tttagtaaat acaggtagtt gaataattgt ttcaagagct caacagatga caagcttctt
16261  ttctagaaat aagacatttt ttgacaactt tatcatgtat aacagatctg ttttttttcc
16321  ttgtgttctt ccaagcttct ggttagagaa aaagagaaaa aaaaaaagg aaaatgtgtc
16381  taaagtccat cagtgttaac tccctgtgac agggatgaag gaaaatactt taatagttca
16441  aaaaataata atgctgaaag ctctctacga aagactgaat gtaaaagtaa aaagtgtaca
```

-continued

```
16501 tagttgtaaa aaaaaggagt ttttaaacat gtttattttc tatgcacttt tttttattta
16561 agtgatagtt taattaataa acatgtcaag tttaaaaaaa aaaaaaaa
```

KMT2D (accession No. XM_006719616):
```
   1 agcggaagga tcccgcagcg tgtgcgtaga actgcagagt cacagccttt cctccgagag
  61 ggcgggatcc ctccgccgct ccgctccaac acaaaatagg gccgcctctt ctcctttctc
 121 cccctctcga gtggggtgcc ccgggcaaaa ggccccccg gatctagcgc cgaaggcttc
 181 acgaatcttc acgaccgctg cccagctctt gggccaggaa atagcccctt cgcaggaacc
 241 accctaccgg ccgaacagga ggcggagggg gggaggcgga gcggcgccgc gctgcactac
 301 tttcctctcc ggttgcaaat ggctgcctcg ttccccactt tccgctcagt ttcctgaccc
 361 cccggtgccg ggagccgggg ttgggccatg cacctctagg ccgcctgcga tcacagtcag
 421 ccggggtcg aggggtgcc accgaccaga gccggccagg ccggggggcgg ggcagctccc
 481 gaggccagag gggaagggag gcgagcgcag ggcctggagc ggccggaggg gagcgggcag
 541 agggctcgca ccgcccgccc cttccttttc ctcgcctacc tagcctcctc ccttccccgg
 601 ggggagcaga aggtggggg ctcgaagccg ccgagggtga gcgctcgggg tcgagaagcc
 661 cggcgctggg tgtgtgtcag gttcagcccc gcggccccgc cggccccgcg tcgccgtagc
 721 tcgcgcggcc ccgggcgccg gccggggcgg ggagagggc tcggcgctcc tgcgagggtc
 781 tcacgttcca tccgggccag gcgcggggcg gcgcggcatt ccttccgggc tgctggggag
 841 gcgcctcgac gttccatctg gagagcctcg acgttccgcc cgagcccggc gcgggcggcc
 901 ggggcgctgg ccgggcccta ggactgagag gccgcccggc gacgcggatg cggagcctgc
 961 tcgcccaaga tcaaagccac cggtgctctc tttgtgtccg ctcgggattc gccgccctgg
1021 ggctgtccat ggaaacctaa actgctggaa cctgaggcag agaaccctc tttggcttct
1081 tgctgttttt ttgtggggg agggtggcca ctccgacctg gatttaccgt tcttggcccc
1141 cctaagcccc ccgtgcggg gggcggctgt gatcgctctg gcggttggag gtcggggagc
1201 ggcccgggct ctggccatgt tctcggatga ggatttctgg atcgccctgt gaagaggtct
1261 ccccgagagg gccctgccca gtcggagaga gggatggaca gccagaagct ggctggtgag
1321 gataaagatt cagaaccggc agctgatgga cctgcagctt ctgaggaccc aagtgccact
1381 gagtcagacc tgcccaaccc acatgtggga gaggtctctg tccttagttc tgggagtccc
1441 aggcttcagg agactcctca ggactgcagt ggggtccgg tgcggcgttg tgctctctgt
1501 aactgcgggg agcccagtct acacgggcag cggagctac ggcgctttga gttgccattt
1561 gattggcccc ggtgtccagt ggtgtcccct ggggggagcc cagggcccaa tgaggcagtg
1621 ctgcccagtg aggacctatc acagattggt ttccctgagg ccttacacc tgcccaccta
1681 ggagaacctg gagggtcctg ctgggctcac cattggtgtg ctgcatggtc ggcaggcgta
1741 tgggggcagg agggcccaga actatgtggt gtggacaagg ccatcttctc agggatctca
1801 cagcgctgct cccactgcac caggctcggt gcctccatcc cttgccgctc acctggatgt
1861 ccacggcttt accacttccc ctgcgcgact gccagcggtt ccttcctatc catgaaaaca
1921 ctgcagctgc tatgcccaga gcacagtgag ggggctgcat atctggagga ggctcgctgt
1981 gcagtgtgtg aggggccagg ggagttgtgt gacctgttct tctgtaccag ctgtgggcat
2041 cactatcacg gggcctgcct ggacactgct ctgactgccc gcaaacgtgc tggctggcag
2101 tgccctgaat gcaaagtgtg ccaagcctgc aggaaacctg ggaatgactc taagatgttg
2161 gtttgtgaga cgtgtgacaa aggataccat actttctgcc taaaaccacc catggaggaa
2221 ctgcctgctc actcttggaa gtgcaaggcg tgccgggtgt gccgggcctg tggggcgggc
```

-continued

```
2281  tcagcagaac tgaatcccaa ctcggagtgg tttgagaact actctctctg tcaccgctgt
2341  cacaaagccc agggaggtca gactatccgc tccgttgctg agcagcatac cccggtgtgt
2401  agcagatttt cacccccaga gcctggcgat accccactg acgagcccga tgctctgtac
2461  gttgcatgcc aagggcagcc aaagggtggg cacgtgacct ctatgcaacc caaggaacca
2521  gggcccctgc aatgtgaagc caaaccacta gggaaagcag gggtccaact tgagccccag
2581  ttggaggccc ccctaaacga ggagatgcca ctgctgcccc cacctgagga gtcacccctg
2641  tccccaccac ctgaggaatc acccacgtcc ccaccacctg aggcatcacg cctgtcacca
2701  ccacctgagg aattgcccgc atccccactt cctgaggcat tgcacctgtc ccggccgctg
2761  gaggaatcgc ccctctctcc gccgcctgag gagtctcctc tgtctccccc acctgaatca
2821  tcaccttttt ctccactgga ggagtcgccc ttgtctccac cggaagagtc accccatct
2881  cctgcacttg agacgcctct atccccacca cctgaagcat cgcccctgtc cccaccattt
2941  gaagaatctc ctttgtcccc gccacctgag gaattgccca cttccccgcc acctgaagca
3001  tctcgcctgt ctccaccacc tgaggagtca cccatgtccc ctccacctga agagtcaccc
3061  atgtctccac caccggaggc atctcgtctg ttcccaccat ttgaagagtc tcctctgtcc
3121  cctccacctg aggagtctcc cctttcccca ccacctgagg catcacgcct gtccccacca
3181  cctgaggact cgcctatgtc cccaccacct gaagaatcac ctatgtcccc cccacctgag
3241  gtatcgcgcc tatccccct gcctgtggtg tcacgcctgt ctccaccgcc tgaggaatct
3301  cccttgtccc caccgcctga ggagtctccc acgtcccctc cacctgaggc ttcacgcctc
3361  tccccaccac ctgaggactc ccccacatcc ccaccacctg aggactcacc tgcttcccca
3421  ccaccggagg actcgctcat gtccctgccg ctggaggagt caccctgtt gccactacct
3481  gaggagccgc aactctgccc ccggtccgag gggccgcacc tgtcaccccg gcctgaggag
3541  ccgcacctgt cccccggcc tgaggagcca cacctatctc cgcaggctga ggagccacac
3601  ctgtccccc agcctgagga gccatgccta tgcgctgtgc ctgaggagcc acacttgtcc
3661  ccccaggctg agggaccaca tctgtcccct cagcctgagg aattgcacct gtcccccccag
3721  actgaggagc cgcacctgtc tcctgtgcct gaggagccat gcttgtcccc ccaacctgag
3781  gaatcacacc tgtcccccca gtctgaggag ccatgcctgt cccccggcc tgaggaatcg
3841  catctgtccc ctgagcttga aagccaccc ctgtccctc ggcctgaaaa gccccctgag
3901  gagccaggcc aatgccctgc acctgaggag ctgcccttgt tccctccccc tggggaacca
3961  tccttatctc ccttgcttgg agagccagcc ctgtctgagc ctggggaacc acctctgtcc
4021  cctctgcccg aggagctgcc gttgtcccca tctggggagc catccttgtc gcctcagctg
4081  atgccaccag atcccccttcc tcctccactc tcacccatca tcacagctgc ggccccaccg
4141  gccctgtctc ctttgggga gttagagtac cccctttggtg ccaaagggga cagtgaccct
4201  gagtcaccgt tggctgcccc catcctggag acacccatca gccctccacc agaagctaac
4261  tgcactgacc ctgagcctgt ccccctatg atccttcccc catctccagg ctccccagtg
4321  gggccggctt ctcccatcct gatggagccc cttcctcctc agtgttcgcc actccttcag
4381  cattccctgg ttccccaaaa ctcccctcct tcccagtgct ctcctcctgc cctaccactg
4441  tccgttccct ccccgttgag tcccataggg aaggtagtgg gggtctcaga tgaggctgag
4501  ctgcacgaga tggagactga gaaagtttca gaacctgaat gcccagcctt ggaacccagt
4561  gccaccagtc ctctcccctc ccaatggggg gaccttcct gccccgcccc cagccctgcc
4621  ccagccctgg atgacttctc tggcctaggg gaagacacag cccctctgga tgggattgat
```

```
-continued
4681  gctccgggtt cacagccaga gcctggacag acccctggca gtttggctag tgaacttaaa
4741  ggctcccctg tgctcctgga ccccgaggag ctggcccctg tgaccccctat ggaggtctac
4801  cccgaatgca agcagacagc agggcagggc tcaccatgtg aagaacagga agagccacgt
4861  gcaccggtgg cccccacacc acccactctc atcaaatccg acatcgttaa cgagatctct
4921  aatctgagcc agggtgatgc cagtgccagt tttcctggct cagagcccct cctgggctct
4981  ccagacccgg agggggtgg ctccctgtcc atggagttgg gggtctctac ggatgttagt
5041  ccagcccgag atgagggctc cctacggctc tgtactgact cactgccaga gactgatgac
5101  tcactattgt gcgatgctgg gacagctatc agcggaggca aagctgaggg ggagaagggg
5161  cggcggcgca gctccccagc ccgttcccgc atcaaacagg gtcgcagcag cagtttccca
5221  ggaagacgcc ggcctcgtgg aggagcccat ggaggacgtg gtagaggacg ggcccggcta
5281  aagtcaactg cttcttccat tgagactctg gttgctgaca ttgatagctc tcccagtaag
5341  gaggaggagg aagaagatga tgacaccatg cagaataccg tggttctctt ctccaacaca
5401  gacaaatttg tcctaatgca ggacatgtgt gtggtatgtg gcagctttgg ccgggggca
5461  gagggccacc tccttgcctg ttcgcagtgc tctcagtgct atcacccttaa ctgtgtcaac
5521  agcaagatca ccaaggtgat gctgctcaag gctggcgttt gtgtggagtg tattgtgtgt
5581  gaggtgtgtg ccaggcctc cgacccctca cgcctgctgc tctgtgatga ctgtgatatt
5641  agctaccaca catactgcct ggaccccccca ctgctcaccg tccccaaggg cggctggaag
5701  tgcaagtggt gtgtgtcctg tatgcagtgt ggggctgctt cccctggctt ccactgtgaa
5761  tggcagaata gttacacaca ctgtgggccc tgtgccagcc tggtgacctg ccctatctgt
5821  catgctcctt acgtagaaga ggacctacta atccagtgcc gccactgtga acggtggatg
5881  catgcaggct gtgagagcct cttcacagag gacgatgtgg agcaggcagc cgatgaaggc
5941  tttgactgtg tctcctgcca gccctacgtg gtaaagcctg tggcgcctgt tgcacctcca
6001  gagctggtgc ccatgaaggt gaaagagcca gagccccagt actttcgctt cgaaggtgtg
6061  tggctgacag aaactggcat ggccttgctg cgtaacctga ccatgtcacc actgcacaag
6121  cggcgccaac ggcgaggacg gcttggcctc ccaggcgagg caggattgga gggttctgag
6181  ccctcagatg cccttggccc tgatgacaag aaggatgggg acctggacac cgatgagctg
6241  ctcaagggtg aaggtggtgt ggagcacatg gagtgcgaaa ttaaactgga gggccccgtc
6301  agccctgatg tggagcctgg caaagaggag accgaggaaa gcaaaaaacg caagcgtaaa
6361  ccatatcggc ctggcattgg tggtttcatg gtgcgacagc ggaaatccca cacacgcacg
6421  aaaaagggc ctgctgcaca ggcggaggtg ttgagtgggg atgggcagcc cgacgaggtg
6481  atacctgctg acctgcctgc agagggcgcc gtggagcaga gcttagctga aggggatgag
6541  aagaagaagc aacagcggcg agggcgcaag aagagcaaac tggaggacat gttccctgct
6601  tacttgcagg aagccttctt tgggaaggag ctgctggacc tgagccgtaa ggccctttt
6661  gcagttgggg tggccggcc aagctttgga ctagggaccc caaaagccaa gggagatgga
6721  ggctcagaaa ggaaggaact ccccacatcg cagaaggag atgatggtcc agatattgca
6781  gatgaagaat cccgtggcct cgagggcaaa gccgatacac caggacctga ggatgggggc
6841  gtgaaggcat cccccagtgcc cagtgaccct gagaagccag gcacccagg tgaagggatg
6901  cttagctctg acttagacag gatttccaca gaagaactgc caagatgga atccaaggac
6961  ctgcagcagc tcttcaagga tgttctgggc tctgaacgag aacagcatct gggttgtgga
7021  accctggcc tagaaggcag ccgtacgcca ctgcagaggc cctttcttca aggtggactc
7081  cctttgggca atctgccctc cagcagccca atggactcct acccaggcct ctgccagtcc
```

-continued

```
7141  ccgttcctgg attctaggga gcgcgggggc ttctttagcc cggaacccgg tgagcccgac
7201  agcccctgga cgggctcagg tggcaccacg ccctccaccc ccacaacccc caccacggag
7261  ggtgagggcg acggactctc ctataaccag cggagtcttc agcgctggga aaggatgag
7321  gagttgggcc agctgtccac catctcacct gtgctctatg ccaacattaa ttttcctaat
7381  ctcaagcaag actacccaga ctggtcaagc cgttgcaaac aaatcatgaa gctctggaga
7441  aaggttccag cagctgacaa agcccctac ctgcaaaagg ccaaagataa ccgggcagct
7501  caccgcatca acaaggtgca gaagcaggct gagagccaga tcaacaagca gaccaaggtg
7561  ggcgacatag cccgtaagac tgaccgaccg ccctacatc tccgcattcc cccgcagcca
7621  ggggcactgg gcagcccgcc ccccgctgct gcccccacca ttttcattgg cagccccact
7681  acccccgccg gcttgtctac ctctgcggac gggttcctga agccgccggc gggctcggtg
7741  cctggccctg actcgcctgg tgagctcttc ctcaagctcc caccccaggt gcccgcccaa
7801  gtgccttcgc aggacccctt tggactggcc cctgcctatc ccctggagcc ccgcttcccc
7861  acggcaccgc ccacctatcc cccctatcct agtcctacgg gggcccctgc gcagcccccg
7921  atgctgggcg cctcatctcg tcctggggct ggccagccag gggaattcca cactacccca
7981  cctggcaccc ccagacacca gccctccaca cctgacccat tcctcaaacc ccgctgcccc
8041  tcgctggata acttggctgt gcctgagagc cctggggtag ggggaggcaa agcttccgag
8101  ccctgctct cgcccccacc ttttgggag tccggaagg ccctagaggt gaagaaggaa
8161  gagcttgggg catcctctcc tagctatggg ccccaaaacc tgggctttgt tgactcaccc
8221  tcctcaggca cccacctggg tggcctggag ttaaagacac ctgatgtctt caaagccccc
8281  ctgaccccctc gggcatctca ggtagagccc cagagcccgg gcttgggcct aaggccccag
8341  gagccacccc ctgccaggc tttggcacct tctcctccaa gtcacccaga catctttcgc
8401  cctggctcct acactgaccc atatgctcag cccccattga ctcctcggcc ccaacctccg
8461  cccctgaga gctgctgtgc tctgccccct cgctcactgc cctccgaccc tttctcccga
8521  gtgcctgcca gtcctcagtc ccagtccagc tcccagtctc cactgacacc ccggcctctg
8581  tctgctgaag cttttttgccc atcacccgtt acccctcgct tccagtcccc tgacccttat
8641  tctcgcccac cctcacgccc tcagtcccgt gacccatttg ccccattgca taagccaccc
8701  cgaccccagc cccctgaagt tgcctttaag gctgggtctc tagcccacac ttcgctgggg
8761  gctgggggt tcccagcagc cctgcccgcg gggccagcag gtgagctcca tgccaaggtc
8821  ccaagtgggc agccccccaa ttttgtccgg tccctggga cgggtgcatt tgtgggcacc
8881  ccctctccca tgcgtttcac tttccctcag gcagtagggg agccttccct aaagcccct
8941  gtccctcagc ctggtctccc gccaccccat gggatcaaca gccattttgg gcccggcccc
9001  accttgggca agcctcaaag cacaaactac acagtagcca cagggaactt ccacccatcg
9061  ggcagccccc tggggcccag cagcgggtcc acaggggaga gctatgggct gtccccacta
9121  cgccctccgt cggttctgcc accacctgca cccgacggat ccctccccta cctgtcccat
9181  ggagcctcac agcgatcagg catcacctct cctgtcgaaa agcgagaaga cccagggact
9241  ggaatgggta gctctttggc gacagctgaa ctcccaggta cccaggaccc aggcatgtcc
9301  ggccttagcc aaacagagct ggagaagcaa cggcagcgcc agcgactacg agagctgctg
9361  attcggcagc agatccagcg caacaccctg cggcaggaga aggaaacagc tgcagcagct
9421  gcaggagcag tggggcctcc aggcagctgg ggtgctgagc ccagcagccc tgcctttgag
9481  cagctgagtc gaggccagac ccccttgct gggacacagg acaagagcag ccttgtgggg
```

-continued

```
 9541 ttgccccaa gcaagctgag tggccccatc ctggggccag ggtccttccc tagcgatgac
 9601 cgactctccc ggccacctcc accagccacg ccttcctcta tggatgtgaa cagccggcaa
 9661 ctggtaggag gctcccaagc tttctatcag cgagcaccct atcctgggtc cctgccctta
 9721 cagcagcaac agcaacaact gtggcagcaa caacaggcaa cagcagcaac ctccatgcga
 9781 tttgccatgt cagctcgctt tccatcaact cctggacctg aacttggccg ccaagcccta
 9841 ggttccccgt tggcgggaat tccacccgt ctgccaggcc ctggtgagcc agtgcctggt
 9901 ccagctggtc ctgcccagtt cattgagctg cggcacaatg tacagaaagg actgggacct
 9961 gggggcactc cgtttcctgg tcagggccca cctcagagac cccgttttta ccctgtaagt
10021 gaggaccccc accgactggc tcctgaaggg cttcggggcc tggcggtatc aggtatccc
10081 ccacagaaac cctcagcccc accggcccct gaattgaaca acagtcttca tccaacaccc
10141 cacaccaagg gtcctaccct gccaactggt ttggagctgg tcaaccggcc cccgtcgagc
10201 actgagcttg gccgccccaa tcctctggcc ctggaagctg ggaagttgcc ctgtgaggat
10261 cccgagctgg atgacgattt tgatgcccac aaggccctag aggatgatga agagcttgct
10321 cacctgggtc tgggtgtgga tgtggccaag ggtgatgatg aacttggcac cttagaaaac
10381 ctggagacca atgaccccca cttggatgac ctgctcaatg agacgagtt tgacctgctg
10441 gcatatactg atcctgagct ggacactggg gacaagaagg atatcttcaa tgagcacctg
10501 aggctggtag aatcggctaa tgagaaggct gaacgggagg ccctgctgcg gggggtggag
10561 ccaggaccct tgggccctga ggagcgccct cccctgctg ctgatgcctc tgaaccccgc
10621 ctggcatctg tgctccctga ggtgaagccc aaggtggagg agggtggacg ccaccttct
10681 ccttgccaat tcaccattgc tacccccaag gtagagcccg cacctgctgc caattccctt
10741 ggcctggggc taaagccagg acagagcatg atgggcagcc gggatacccg gatgggcaca
10801 gggccatttt ctagcagtgg gcacacagct gagaaggcct cctttgggc cacgggagga
10861 ccaccagctc acctgctgac ccccagccca ctgagtggcc caggaggatc ctccctgctg
10921 gaaaagtttg agctcgagag tggggctttg accttgcctg gtggacctgc agcatctggg
10981 gatgagctag acaagatgga gagctcactg gtagccagcg agttacccct gctcattgag
11041 gacctgttgg agcatgagaa gaaggagctg cagaagaagc agcagctttc agcacagttg
11101 cagcctgccc agcagcagca gcaacagcag cagcagcatt ccctactgtc tgcaccaggc
11161 cctgcccagg ccatgtctttt gccacatgag ggctcttctc ccagtttggc tgggtcccaa
11221 cagcagcttt ccctgggtct tgcaggtgcc cgacagccag gtttgcccca gccactgatg
11281 cccacccagc caccagctca tgccctccag caacgcctgg ctccatccat ggctatggtg
11341 tccaatcaag gcatatgct aagtgggcag catggagggc aggcaggctt ggtaccccag
11401 cagagctcac agccagtgct atcacagaag cccatgggca ccatgccacc ttccatgtgc
11461 atgaagccgc agcaattggc aatgcagcag cagctggcaa acagcttctt cccagataca
11521 gacctggaca aatttgctgc agaagatatc attgatccca ttgcaaaggc caagatggtg
11581 gctttgaaag gcatcaagaa agtgatggct cagggcagca ttggggtggc acctggtatg
11641 aacagacagc aagtgtctct gctagcccga aggctctcgg ggggacctag cagtgatctg
11701 cagaaccatg tggcagctgg gagtggccag gagcggagtg ctggtgatcc ctcccagcct
11761 cgtcccaacc cgcccacttt tgctcaggga gtgatcaatg aagctgacca gcggcagtat
11821 gaggagtggc tgttccatac ccagcagctc ctacagatgc agctgaaggt gctagaggag
11881 cagattggtg tacaccgcaa gtcccggaag gctctgtgtg ccaagcagcg cactgccaaa
11941 aaagctggcc gtgagttccc agaagctgat gctgagaagc tcaagctggt tacagagcag
```

-continued

```
12001  cagagcaaga tccagaaaca actggatcag gtccggaaac agcagaagga gcacactaat
12061  ctcatggcag aatatcggaa caagcagcag caacaacagc agcagcagca gcaacaacag
12121  caacagcact cagctgtgct ggctctcagc ccttcccaga gtccccggct gctcaccaag
12181  ctccctggtc agctgctccc tggccatggg ctgcagccac cacagggggcc tccgggtggg
12241  caagccggag gtcttcgcct gaccccktggg ggtatggcac tacctggaca gcctggtggc
12301  cccttcctta atacagctct ggcccaacag cagcaacagc aacattctgt ggggctgga
12361  tccctggctg gcccttcagg gggcttcttc cctggcaacc ttgctcttcg aagcctcgga
12421  cctgattcaa ggcttttaca ggaaaggcag ctgcagctgc agcagcaacg tatgcagctg
12481  gcccagaaac tgcagcagca gcagcagcag caacagcagc agcagcacct tctaggacag
12541  gtggcaatcc agcagcaaca gcagcagggt cctggagtac agacaaacca agctctgggt
12601  cccaagcccc agggccttat gcctcccagc agccaccaag gcctcctggt ccagcagctg
12661  tcccctcaac caccccaggg gccccagggc atgctgggcc ctgcccaggt ggctgtgttg
12721  cagcagcagc accctggagc tttgggcccc cagggccctc acagacaggt gcttatgacc
12781  cagtcccggg tgctcagttc ccccagctg gcacagcagg gtcagggcct tatgggacac
12841  aggctggtca cagcccagca gcagcagcag caacaacagc accaacagca agggtccatg
12901  gcagggctgt cccatcttca gcagagtctg atgtcacaca gtgggcagcc caaactgagc
12961  gctcagccca tgggctcttt acagcagctt cagcagcagc agcagctgca acagcaacag
13021  caacttcagc agcagcagca gcagcagcta caacagcaac agcaacttca gcagcaacag
13081  cttcaacagc agcaacagca gcagcagctt caacaacagc agcagcaaca gcttcaacag
13141  cagcaacagc agctacaaca gcaacagcaa caacaacagc agcagtttca acagcagcag
13201  caacagcagc agatgggcct tttaaaccag agtcgaactt tactgtctcc tcagcaacaa
13261  cagcagcagc aagtggcact tggccctggc atgccagcaa gcctcttca acacttttct
13321  agccctggag ccctgggtcc aaccctcctc ctgacgggca aggaacaaaa caccgtagac
13381  ccagccgttt cttcagaggc cactgagggg ccctctacac atcagggagg gccgttagca
13441  ataggaacta cccctgagtc aatggccact gaaccaggag aggtaaagcc ctcactctct
13501  ggggactcac aactcctgct tgtccaaccc cagccccagc ctcagcccag ctctctgcag
13561  ctgcagccac ctctgaggct tccaggacaa cagcagcagc aagttagcct gctccacaca
13621  gcaggtggag gaagccatgg gcagctaggc agtggatcat cttctgaggc ctcatctgtg
13681  ccccacctgc tggctcagcc ctctgtttcc ttaggggatc agcctgggtc catgacccag
13741  aaccttctgg gcccccaaca gcccatgcta gagcggccca tgcaaaataa tacagggcca
13801  caacctccca aaccaggacc tgtcctccag tctgggcagg gtctgcctgg ggttggaatc
13861  atgcctacgg tgggtcagct tcgagcacag ctccaaggag tcctggccaa aaacccacag
13921  ctgcggcact taagtcctca gcagcagcag cagctacagg cactcctcat gcagcggcag
13981  ctgcagcaga gtcaggcagt acgccagacc ccaccctacc aggagcctgg gacccagacc
14041  tctccccctcc agggcctcct gggctgccaa cctcaacttg ggggcttccc tggaccacag
14101  acaggccccc tccaggagct aggggcaggg cctcgacctc agggcccacc ccggctccct
14161  gccccaccag gagccttatc tacaggacca gtccttggcc ctgtccatcc cacacctcca
14221  ccatccagcc ctcaagagcc aaagagacct tcacaattac cttcccccag ctcccagctt
14281  cccactgagg cccagctccc tcccacccat ccagggaccc caaacctca ggggccaacc
14341  ttggagccgc ctcctgggag ggtctcacct gctgctgccc agcttgcaga taccttgttt
```

```
                              -continued
14401  agcaagggtc tgggaccttg ggatccccca gacaacctag cagaaaccca gaagccagag 14461  cagagcagcc tggtacctgg gcatctggac caggtgaatg gacaggtggt gcctgaggca 14521  tcccaactca gcatcaagca ggaacctcgg gaagagccat gtgccctggg agcccagtca 14581  gtgaagaggg aggccaatgg ggagccaata ggggcaccag gaaccagcaa ccacctcctg 14641  ctggcaggcc ctcgctcaga agctgggcat ctgctcttgc agaagctact ccgggcaaag 14701  aatgtgcaac tcagcactgg gcggggggtcc gaggggctgc gagctgagat caacgggcac 14761  attgacagca agctggctgg gctggagcag aaactacagg gtaccccccag caacaaggag 14821  gatgcagcag caaggaagcc tttgacaccg aagcccaagc gggtacagaa ggcaagcgac 14881  aggttggtga gctcccgaaa gaagctgcgg aaggaggacg gggtcagggc cagcgaggcc 14941  ttgctgaaac agctgaaaca ggagctgtcc ctgctgcccc taacggagcc tgctatcacc 15001  gccaatttta gcctctttgc ccccctttggc agtggctgcc cagtcaatgg gcagagccag 15061  ctgaggggggg cctttggaag tggggcgctg cccactggcc ctgactacta ttcccagctg 15121  cttaccaaga ataacctgag taacccgccg acaccaccct cgtcgctgcc ccccacccca 15181  cccccatcgg tgcagcagaa gatggtgaat ggcgtcaccc catctgaaga gctggggggag 15241  caccccaagg atgctgcctc tgcccgggat agtgaaaggg cactgaggga tacttcagag 15301  gtgaagagtc tagacctgct ggctgccttg cctacacccc ctcacaatca gactgaggat 15361  gtcaggatgg agagtgatga ggatagcgat tctcctgaca gcattgtgcc agcttcatcc 15421  cctgagagca tcttgggggga ggaggcccct cgtttccctc atctgggctc aggccggtgg 15481  gagcaagagg accgggccct ctcccctgtc atcccccctca ttcctcgggc cagcatccca 15541  gtcttcccag ataccaaacc ttatggggcc cttggcctgg aggtccctgg aaagctgcct 15601  gtcacaactt gggaaaaggg caaaggaagt gaggtgtcag tcatgctcac agtctctgct 15661  gctgcagcca agaacctgaa tggcgtgatg gtggcagtgg cggagctgct gagcatgaag 15721  atccccaact cctatgaggt gctgttccca gagagccccg cccgggcagg cactgagcca 15781  aagaaggggg aagctgaggg tcctggtggg aaggaaaagg gtctggaagg caagagccca 15841  gacactggcc ctgattggct gaagcagttt gatgcagtgt tgcctggcta taccctgaag 15901  agccaactag acatcttgag cctcctgaaa caggagagcc ccgccccaga gccacccact 15961  cagcacagct atacctacaa tgtctccaat ctggatgtgc acagctctc ggccccacct 16021  cctgaagaac cctccccgcc cccttccccc ttggcacctt ctcctgccag tccccctact 16081  gagcccttgg ttgaacttcc caccgaaccc ttggctgagc cacccgtccc ctcacctctg 16141  ccactggcct catcccctga atcagcccga cccaagcccc gtgcccggcc ccctgaagaa 16201  ggtgaagatt cccgtcctcc tcgcctcaag aaaatggaaag gagtgcgctg gaagcggctt 16261  cggctgctgc tgaccatcca gaagggcagt gggcggcagg aggatgagcg ggaagtggca 16321  gagtttatgg agcagcttgg cacagccttg cgacctgaca aggtaccgcg agacatgcgt 16381  cgctgctgtt tctgtcatga ggagggtgac ggggccactg atgggcctgc ccgtctgctg 16441  aacctggacc tggacctgtg ggtgcacctc aactgtgccc tttggtccac ggaggtgtat 16501  gagacccagg gcgggggcact gatgaatgtg gaggttgccc tgcaccgagg actgctaacc 16561  aagtgctccc tgtgccagcg aactggtgcc accagcagct gcaatcgcat gcgttgcccc 16621  aatgtctacc attttgcttg tgccatccgt gccaagtgca tgttcttcaa ggacaagacc 16681  atgctgtgtc caatgcataa gatcaagggg ccctgtgagc aagagctgag ctcttttgct 16741  gtcttccggc gggtctacat tgagcgggac gaggtgaagc aaatcgctag catcattcag 16801  cggggagaac ggctgcacat gttccgtgtg gggggccttg tgttccacgc catcggacag
```

```
-continued
16861  ctgctgcctc accagatggc tgactttcat agtgccactg ccctctatcc cgtgggctac
16921  gaggccacgc gcatctattg gagcctccgc accaacaatc gtcgctgctg ctatcgctgt
16981  tctattggtg agaacaacgg gcggccggag tttgtaatca aagtcatcga gcagggcctg
17041  gaggacctgg tcttcactga cgcctctccc caggccgtgt ggaatcgcat cattgagcct
17101  gtggctgcca tgagaaaaga ggctgacatg ctgcgactct ccctgagta tctgaagggc
17161  gaggagctct ttgggctgac ggtgcatgcc gtgcttcgca tagctgaatc actgcccggg
17221  gtggagagct gtcaaaacta tttattccgc tatgggcgcc accccttat ggagctgcca
17281  ctcatgatca accccactgg ctgtgcccga tcagagccta aaatcctcac acactacaaa
17341  cggccccata ccctgaacag caccagcatg tctaaggcat atcagagcac cttcacaggc
17401  gagaccaaca cccctacag caagcagttt gtgcactcca agtcatctca gtaccggcgg
17461  ctgcgcaccg aatggaagaa caacgtgtac ctggctcgct cccgtatcca gggcctgggg
17521  ctctatgcag ccaaggacct agaaaagcac acaatggtta tcgagtacat tggcaccatc
17581  attcggaacg aggtggccaa ccggcgggag aaaatctacg aagagcagaa tcgaggcatc
17641  tacatgttcc gaataaacaa tgaacatgtg attgatgcta cgttgaccgc cggccctgcc
17701  aggtacatta accattcctg tgccctaac tgtgtggccg aagtcgtgac atttgacaaa
17761  gaggacaaaa tcatcatcat ctccagccgg cgaatcccca aggagagga gctaacctat
17821  gactatcagt ttgattttga ggacgatcag cacaagatcc cctgccactg tggagcctgg
17881  aattgtcgga aatggatgaa ctaagaagct ttgaggctac caggcagggg agtcccccta
17941  cccacaacct cttccctgaa agggatgagg gggaagagag gtagcagcca gagccaggac
18001  ccagggttgg ggctgccggc tgacccggag cccctggagc aggaggctgg ggcagagggc
18061  cctaggccaa gcccaccctg ggcaccaggg acaatcctct tccccaccac cggccctcag
18121  gctggcatct ctgccccag ctccaggagg ggccagacag aagcagccat tgggcatctc
18181  aggtttgagg gggatatggg ccgggaacta cccagaagca tctgggaggc agcagggtgg
18241  gggaagagga tgtgtggccg ggcctcacag ccctgctgct cccactgacc tctccggccc
18301  aactcacggc tgcaaagaga cttgactaag cttgacaatc ccaaaggccg ggtcccacac
18361  ctggccctgc ctgccgggtc ctgcccccac cctcaccccc atccccctcc ctcttgatct
18421  gtctctgttt ccctcttttc ctctgtgttt ctgtctctct atgggttgtg tttccttgtt
18481  ttccactctg acaaatgcaa catgaacggg aaagaggcgc ccagctgcct aggagggcaa
18541  gctgggcaag ccgggcaagg agacccccgca cccacaccta cctcatttaa gtgttggatt
18601  ttttgctgtt ttgaaatgtg agaccctctc caagcccct actgccccaa ccctctcccc
18661  cacctcactg ccctcttctg agtgggtgga aggggggtag gaggaggaag aaaaacaaca
18721  acaaaaaatc catctttgtt tttaattatg ggcatgggat ggtggttgag gcaaatgatg
18781  atgaagattg gggatgactg gcccctagtt gctctaggac ttccttctcc atctggacat
18841  gggggcagga gggagctaaa cctaggacca ggatatctcc ctcctgtttt cccaacctca
18901  tcatgagcct gtttgccctc cagcccctgg acgggttggg tgggggtag ggtgagggct
18961  atccctgagt ggcatgccca tacctagtga ggcagggtgt ggcccggagc tcccactttc
19021  cctcagtcac caaactgctg ctggtctggt gggaagggt ggtgatgtgg ggtggggga
19081  gcttagtgtc agcgcgggga gggtgggggg tatttatcta tttatacatg ggattgtaca
19141  tagtccttgtg gggcatgggg gagcggctg gaggtgagaa ccctcccctc tccccccacc
19201  ccccggggag agcaaatgta aaactactaa ttttgtgct ttatatattc tatataaata
```

-continued

```
19261 tatctatttt cttttacaa aaccagttta taaatggtag gggggtgtgg ggcggacaca
19321 tggagctccc cttgtggggg ggcccctcc attacccgac ctaccgccct tttcctcacc
19381 ccccacccca ctccccaccc cctggctgtg actgctgtaa gatgggggta tagaggctgg
19441 gcaattccca cccctgttg tatagttgga ctatgttata acgcacaaaa gagagctgac
19501 cccagggga gccagagggt gatgggttcc ttgcctccct ttccttcccc tttctgccca
19561 agcttgtgct gcagttgaac ctcttcctgg gggtgggagt aggtaagggg tgggtgaggc
19621 cccaaacccc tctctggtag ggaaccgtgg ggatgaagat gaagcttata tgcagttctc
19681 ttctaggggc tgtgggcaaa gggcattttg taattaatat tttcaagaat cagatgtctg
19741 gagtgtaggg gtgggcttgg tggtggtgga cgggcgggcc tgctggaggg ggagcttggt
19801 cgctgttgtg attttaggtt tgttttgtt ttgttttgaa tttgggggt tgtggattgt
19861 tgggggtagg gagattttt ttttttaaag ctgcttcctc aactgtttca agctgcaaat
19921 gtttaagaga ataacagccc ccactcccac aggaaccgct gtaattaaat cagacagtag
19981 gaagactggg ctgctgccct caaagccaca gcccttggat gttccttttc cgagagcaga
20041 aggtctaggc tacagggagg gggagattgg ctcccgtgag tcaggctgtg tttggggctt
20101 gggccctggg attgggaaaa ggggatgggg cagactttgt aagcatatgc taggtatccg
20161 atagtcctgt agaatttagt gaagaaacct tatacagttt ttaatttta tataaactat
20221 aactcagacc caagctacaa ggttggaatt ttggttggtt tttttttaa gtaccctgcc
20281 tgtataattg catcagaatc ccccacccca ccccccgccc ccgtgtttgt attttgggtt
20341 ggtttacact cgcacatact cagttttcag ttttcccctt tacagtcttc tcccctcacc
20401 tccaggaccc tccccctttt taaaaaataa atcgctgaca agtgtgaatc ccgtgaagac
20461 tttatttgt gttgtgtgta tcctgtacag caaggttggt ccttcgtaac aacggatgaa
20521 atggttccct ttttaaagc gccctctctc cctccaccct cagcgcccct gtccttggca
20581 tgttttgtat cagcgatcat tctgaactgt acatatttat gttgcgagag gcaaagggca
20641 agttttggat tttgcttctt ccaagtttgt ttttaaacga caaataaaaa aagaacattt
20701 taaatacaa
```

KMT2B (accession No. NM_014727):

```
   1 atggcggcgg cggcgggcgg cggcagttgc cccgggcctg gctccgcgcg gggccgcttc
  61 ccgggccggc cgcggggcgc cggcgggggc ggggccgcg gcggacgggg caacggggcc
 121 gaaagagtgc gggtagctct gcggcgcggc ggtggcgcga cggggccggg cggagccgag
 181 cccggggagg acacggccct gctccgtttg ctgggctcc gccggggcct gcgccggctc
 241 cgccgcctgt gggccggccc gcgggtccag cggggccggg acggggtcg gggccggggc
 301 tggggcccga gtcgaggctg cgtgccggag gaggagagca gtgacgggga atccgacgag
 361 gaggagtttc agggtttca ttcagatgaa gatgtggccc ccagttccct gcgctctgcg
 421 ctccgatccc agcgaggtcg agcgccccga ggtcgggtc gcaagcataa gacgaccccc
 481 cttcctcctc ctcgcctagc agatgtggct cctacccccc caaagacccc tgcccggaaa
 541 cggggtgagg aaggcacaga acggatggtg caggcactga ctgaacttct ccggcgggcc
 601 caggcacccc aagcaccccg gagccgggca tgtgagccct ccaccccccg gcggtctcgg
 661 ggacggcccc caggacggcc agcaggcccc tgcaggagga agcagcaagc agtagtggtg
 721 gcagaagcag ctgtgacaat ccccaaacct gagcccccac ctcctgtggt tccagtgaaa
 781 catcagactg gcagctggaa atgcaaggag gggcccggtc caggacctgg gaccccagg
 841 cgtggaggac agtcaagccg tggaggccgt ggaggcaggg gccgcggccg aggtggtggg
```

```
 901  ctcccctttg tgatcaagtt tgtttcaagg gccaaaaaag taaagatggg acaattgtcc
 961  ttgggactcg aatcaggtca aggtcaaggt caacatgagg aaagttggca ggatgtcccc
1021  caaagaagag ttggatctgg acagggaggg agcccttgct ggaaaaagca ggaacagaag
1081  ctggatgacg aggaagaaga gaagaaagaa gaagaagaaa agacaagga gggagaagag
1141  aaggaagaaa gagctgtagc tgaggagatg atgccagctg cggaaaagga gaggcaaag
1201  ctgccaccac cgcctctgac tcctccagcc ccttcacctc ctccaccccct ccacccccct
1261  tcgacatctc ctccaccccc actctgccct ccaccaccac ccccagtgtc cccaccacct
1321  ctaccatccc ctccaccgcc tcctgcccaa gaggagcagg aggaatcccc tcctcctgtg
1381  gtcccagcta cgtgctccag gaagaggggc cggcctcccc tgactcccag ccagcgggcg
1441  gagcgggaag ctgctcgggc agggccagag ggcacctctc ctcccactcc aaccccccagc
1501  accgccacgg gaggccctcc ggaagacagt cccaccgtgg cccccaaaag caccaccttc
1561  ctgaagaata tccggcagtt tattatgcct gtggtgagtg cccgctcctc ccgtgtcatc
1621  aagacacccc ggcgatttat ggatgaagac cccccaaaac ccccaaaggt ggaggtctca
1681  cctgtcctgc gacctcccat taccacctcc ccacctgttc cccaggagca agcaccagtc
1741  ccctctccac cacgtgcccc aactcctcca tctaccccag ttccactccc tgagaagaga
1801  cggtccatcc taagggaacc cacatttcgc tggacctcac tgacccggga gctgccccct
1861  cctcccccag cccctccacc tcccccggcc ccctcccac ccctgctcc tgccacctcc
1921  tcccggaggc ccctactcct tcgggcccct cagtttaccc caagcgaagc ccacctgaag
1981  atctacgaat cggtgcttac tcctcctcct cttggggctc ctgaagcccc tgagccagag
2041  cctcctcctg ccgatgactc tccagctgag cctgagcctc gggcagtggg ccgcaccaac
2101  cacctcagcc tgcctcgatt cgcccctgtg gtcaccactc ctgttaaggc cgaggtgtcc
2161  cctcacgggg ctccagctct gagcaacggg ccacagacac aggctcagct actgcagccc
2221  ctgcaggcct tgcaaaccca gctcctgccc caggcactac cgccaccaca gccacagctg
2281  cagccaccgc cgtcaccaca gcagatgcct cccctggaaa agcccggat tgcgggcgtg
2341  ggttccttgc cgctgtctgg ggtagaggag aagatgttca gcctcctcaa gagagccaaa
2401  gtgcagctat tcaagatcga tcagcagcag cagcagaagg tggcagcttc catgccgctg
2461  agccctggag ggcagatgga ggaggtggcc ggggctgtca agcagatctc cgacagaggc
2521  cctgtccggt ctgaagatga gtcggtggaa gctaagagag agcggccctc aggtcccgag
2581  tcccctgtgc aaggtccccg catcaaacat gtctgccgtc atgctgctgt ggccctgggt
2641  caggcccggg ccatggtgcc tgaagatgtc cctcgcctca gtgccctccc tctccgggat
2701  cggcaggacc tcgccacaga ggatacatca tcggcgtccg agactgagag tgtcccgtca
2761  cggtcccggc ggggaaaggt ggaggcagca ggccctgggg gagaatcaga gcccacaggt
2821  tctggaggga ccctggccca cacaccccgg cgctcactgc cctcccatca cggcaagaag
2881  atgcgcatgg ctcgatgtgg acactgtcgg ggctgcctac gtgtgcagga ctgtgggtcc
2941  tgtgtcaact gcctagacaa gcccaagttt ggggccccta acaccaagaa gcagtgctgt
3001  gtataccgga agtgtgacaa aatagaggct cggaagatgg aacgactggc taaaaaaggc
3061  cggacgatag tgaagacgct gttgccctgg gattccgatg aatctcctga ggcctcccct
3121  ggtcctccag gcccacgccg ggggcgggga gctgggggc ccggggagga ggtggtggcc
3181  cacccagggc ccgaggagca ggactccctc ctgcagcgca agtcagctcg gcgctgcgtc
3241  aaacagcgac cctcctatga tatcttcgag gattcggatg actcggagcc cggggggcccc
3301  cctgctcctc ggcgtcggac ccccgagaa aatgagctgc cactgccaga acctgaggag
```

-continued

```
3361  cagagccggc cccgcaaacc taccctgcag cctgtgttgc agctcaaggc ccgaaggcgc
3421  ctggacaagg atgctttggc ccctggcccc tttgcttctt ttcccaatgg ctggactgga
3481  aagcagaagt ctcccgatgg tgtgcaccgc gtccgtgtgg attttaagga ggattgtgat
3541  ttagagaacg tgtggctgat ggggggcctg agtgtgctca cctctgtgcc agggggcccc
3601  ccgatggtgt gcttgctgtg tgccagcaaa ggactccacg agctggtgtt ctgtcaagtc
3661  tgctgtgacc cattccaccc attctgcctg gaggaggccg agcggcccct gccccagcat
3721  cacgacacct ggtgctgccg tcgctgcaaa ttctgccacg tctgtggacg caaaggtcgt
3781  ggatccaagc acctcctgga gtgcgagcgc tgccgccatg cataccaccc ggcctgtctg
3841  gggcccagct atccaacccg ggccacgcgc aaacggcgcc actggatctg ttcagcctgt
3901  gtgcgctgta agagctgtgg ggcaactcca ggcaagaact gggacgtcga gtggtctgga
3961  gattacagcc tctgccccag gtgcacccag ctatatgaga aggaaacta ctgcccgatc
4021  tgtacacgct gctatgaaga caacgactat gagagcaaga tgatgcagtg cgcacagtgc
4081  gatcactggg tgcatgccaa gtgcgagggg ctctcagatg aagactacga gatcctttca
4141  ggactgccag actcggtgct gtacacctgc ggaccgtgtg ctggggcagc gcagccccgc
4201  tggcgagagg ccctgagcgg ggccctccag gggggcctgc gccaggtgct ccagggcctg
4261  ctgagctcca aggtggtggg cccactgctg ctctgcaccc agtgtgggcc agatgggaag
4321  caactgcacc caggaccctg cggcctgcaa gctgtgagtc agcgcttcga ggatggccac
4381  tacaagtctg tgcacagctt catggaggac atggtgggca tcctcatgcg gcactggag
4441  gagggagaga ccccggaccg ccgggctgga ggccagatga aggggctcct gctgaagctg
4501  ctagaatctg cgttcggctg gttcgacgcc cacgacccca gtactggcga acggagtacc
4561  cggctgccaa acggagtcct tcccaatgcg gtgttgcccc catccctgga tcatgtctat
4621  gcgcagtgga gacagcagga accagagacc ccagaatcag ggcagcctcc aggggatccc
4681  tcagcagcat tccagggcaa ggatccggct gccttctcac acctggagga ccccgtcag
4741  tgtgcactct gcctcaaata cggggatgca gactccaagg aggcggggcg gctcttgtac
4801  atcgggcaga acgagtggac acacgtcaac tgtgccatct ggtcggcgga agtcttcgag
4861  gagaacgacg gctccctcaa gaatgtgcat gctgctgtgg cccgagggag gcagatgcgc
4921  tgcgagctct gcctgaagcc tggcgccacg gtgggctgct gcctgtcctc ctgcctcagc
4981  aacttccact tcatgtgtgc ccgggccagc tactgcatct tccaggatga caagaaagtc
5041  ttctgccaga aacacactga tctcctggat ggcaaggaaa ttgtgaaccc cgatggtttt
5101  gatgttctcc gccgagtcta tgtggacttc gagggcatca acttcaagcg gaagttcttg
5161  acggggcttg aacccgatgc catcaacgtg ctcattggtt ccatccgcat tgactccctg
5221  ggtactctgt ctgatctctc ggactgcgag gacggctct tccccattgg ctaccagtgc
5281  tcccgtctgt actggagcac agtggatgct cggaggcgct gctggtatcg gtgccgaatt
5341  ctggagtatc ggccatgggg gccgagggaa gagccagctc acctggaggc tgcagaggag
5401  aaccagacca ttgtgcacag ccccgcccct tcctcagagc cccaggtgg tgaggacccc
5461  ccactggaca cagatgttct tgtccctgga gctcctgagc gccactcgcc cattcagaac
5521  ctggaccctc cactgcggcc agattcaggc agcgcccctc ctccagcccc cgttcttttt
5581  tcggggctc gaatcaaagt gcccaactac tcgccatccc ggaggccctt ggggggtgtc
5641  tcctttggcc ccctgccctc cctggaagt ccatcttcac tgacccacca catccccaca
5701  gtgggagacc cggacttccc agctcccccc agacgttccc gtcgtcccag ccctttggct
```

-continued

```
5761   cccaggccgc ctccatcacg gtgggcctcc cctcctctaa aaacctcccc tcagctcagg
5821   gtgcccctc  ctacctcagt cgtcacagcc ctcacaccta cctcagggga gctggctccc
5881   cctggcccgg ccccatctcc accacccct  gaagacctgg gcccagactt cgaggacatg
5941   gaggtggtgt caggactgag tgctgctgac ctggacttcg cggccagcct gctggggact
6001   gagcccttcc aggaagagat tgtagccgct ggggccatgg ggagcagcca cgggggcccg
6061   ggggacagct ccgaggagga gtccagcccc acctcccgct acatccactt ccctgtgact
6121   gtggtgtccg cccctggtct ggccccagc  gctacccctg agcccccg   cattgaacag
6181   ctggacggcg tggacgacg  cactgacagt gaggctgagg cggtgcagca gcctcgggc
6241   cagggcacgc ctccttcggg gccaggagta gtccgggcag gggtccttgg ggctgcaggg
6301   gacagggccc ggcctcctga ggacctgcca tcggaaattg tggattttgt gttgaagaac
6361   ctagggggtc ctggggatgg aggtgctggc cctagagagg agtcactccc ccggcgcct
6421   cccctggcta atggcagcca gccctcccaa ggcctgaccg ccagcccagc tgaccccacc
6481   cgcacatttg cctggctccc aggggcccca ggggtccggg tgttaagcct tggccctgcc
6541   cctgagcccc ccaaacccgc cacatccaaa atcatacttg tcaacaagct ggggcaagta
6601   tttgtgaaga tggctgggga gggtgaacct gtcccacccc cagtgaagca gccacctttg
6661   ccccccacca tttcccccac ggctcccacc tcctggactc tgccccagg  ccccctcctc
6721   ggcgtgctgc ccgtggtcgg agtggtccgc cctgccccgc ccccgccacc ccctcccctg
6781   acgctggtgc tgagcagtgg gccagccagc ccgccccgcc aggccatccg cgtcaagagg
6841   gtgtccactt ctccggccg  gtccccgcca gcacctcccc catacaaagc ccccggctg
6901   gatgaagatg gagaggcctc agaggatacc cctcaggttc cagggcttgg cagtggcggg
6961   tttagccgtg tgaggatgaa accccccaca gtgcgtgggg tccttgacct ggatcggcct
7021   ggggagcccg ctggggaaga aagtcctggg ccctccagg  aacggtcccc tttgctgcca
7081   cttccggaag atggtcctcc ccaggtcccc gatggtcccc cagacctgct gcttgagtcc
7141   cagtggcacc actattcagg tgaggcttcg agctctgagg aagagcctcc atccccagat
7201   gataaagaga accaggcccc aaaacggact ggcccacatc tgcgcttcga gatcagcagt
7261   gaggatgggt tcagcgttga ggcagagagc ttggagggg  cgtggagaac tctgatcgag
7321   aaagtgcaag aggcccgagg gcatgcccga ctcagacatc tctccttag  tggaatgagt
7381   ggggcgagac tcctgggcat ccaccatgat gctgtcatct tcctggccga gcagctcccc
7441   ggagcccagc gttgccagca ctataagttc cgttaccacc agcagggaga gggccaggag
7501   gagccgcccc tgaatcccca tggggctgct cgggcagagg tctatctccg gaagtgcacc
7561   tttgacatgt tcaacttcct ggcctcccag caccgggtgc tccctgaggg ggccacctgt
7621   gatgaggaag aggatgaggt gcagctcagg tcaaccagac gtgccaccag cctggagctg
7681   cccatggcca tgcgttttcg tcaccttaag aagacgtcca agaagctgtg gggtgtctac
7741   agatcagcca tccacgggcg aggcctgttc tgtaagcgca acatcgacgc ggggagatg
7801   gtcatcgagt actctggcat tgtcatccgc tcggtgttga ctgacaagcg ggagaagttc
7861   tacgatggga agggcatcgg gtgctatatg ttccgcatgg atgactttga tgtagtggac
7921   gccacgatgc atggcaatgc cgcccgcttc atcaaccact cctgtgagcc caactgcttc
7981   tctcgggtca tccacgtgga gggcagaaa  cacattgtta tcttcgccct gcgccgcatc
8041   ctgcgtggtg aggagctcac ctacgactac aagttccccc tcgaggatgc cagcaacaag
8101   ctgcccctgca actgtggcgc caagcgctgc cgtcggttcc ttaactgagg ccgtggctgc
8161   ccaccacgac ccctcacacc tcctgctgcc gtcgctgcca tcttgcccct agcctggggg
```

-continued

```
8221 ctccctagcc cctcccagag catctcaccc ccaccctcat gttcagggtg gatgtgggca
8281 tgcaggtgac aagggccctg cctccacccc tccagcccat ccagcaatcg cccccttct
8341 gccctggggg cccaggatgt agatattgta caaaggtttc taaatccctt cttttctatg
8401 cacttttta tttaagaggt ggggtcccag gtgggaaccc cccacaata aagtctgtca
8461 atgtttggag aaaaaaaaaa aaaaaaaaa
```

KMT2C (accession No. NM_170606):
```
   1 gaggtgcgcg cgcccgcgcc gatgtgtgtg agtgcgtgtc ctgctcgctc catgttgccg
  61 cctctcccgg tacctgctgc tgctcccggg gctgcgggaa atgcgagagg ctgagccggg
 121 gaggaggaac ccgagcagca gcggcggcgc cggcggccgc ggcggcggga gcccccagg
 181 aggaggaccg ggatccatgt gtctttcctg gtgactagga gtcgtcgga ggaggacaag
 241 agcgtggagc agccgcagcc gccgccacca cccccccgagg agcctggagc cccggccccg
 301 agccccgcag ccgcagacaa aagacctcgg ggccggcctc gcaaagatgg cgcttcccct
 361 ttccagagag ccagaaagaa acctcgaagt aggggggaaaa ctgcagtgga agatgaggac
 421 agcatggatg ggctggagac aacagaaaca gaaacgattg tggaaacaga aatcaaagaa
 481 caatctgcag aagaggatgc tgaagcagaa gtggataaca gcaaacagct aattccaact
 541 cttcagcgat ctgtgtctga ggaatcggca aactccctgg tctctgttgg tgtagaagcc
 601 aaaatcagtg aacagctctg cgcttttttgt tactgtgggg aaaaaagttc cttaggacaa
 661 ggagacttaa acaattcag aataacgcct ggatttatct tgccatggag aaaccaacct
 721 tctaacaaga aggacattga tgacaacagc aatggaacct atgagaaaat gcaaaaactca
 781 gcaccacgaa acaaagagg acagagaaaa gaacgatctc ctcagcagaa tatagtatct
 841 tgtgtaagtg taagcaccca gacagcttca gatgatcaag ctggtaaact gtgggatgaa
 901 ctcagtctgg ttgggcttcc agatgccatt gatatccaag ccttatttga ttctacaggc
 961 acttgttggg ctcatcaccg ttgtgtggag tggtcactag gagtatgcca gatggaagaa
1021 ccattgttag tgaacgtgga caaagctgtt gtctcaggga gcacagaacg atgtgcattt
1081 tgtaagcacc ttggagccac tatcaaatgc tgtgaagaga atgtaccca gatgtatcat
1141 tatccttgtg ctgcaggagc cggcaccttt caggatttca gtcacatctt cctgctttgt
1201 ccagaacaca ttgaccaagc tcctgaaaga tcgaaggaag atgcaaactg tgcagtgtgc
1261 gacagcccgg gagacctctt agatcagttc tttgtacta cttgtggtca gcactatcat
1321 ggaatgtgcc tggatatagc ggttactcca ttaaaacgtg caggttggca atgtcctgag
1381 tgcaaagtgt gccagaactg caaacaatcg ggagaagata gcaagatgct agtgtgtgat
1441 acgtgtgaca aagggtatca tactttttgt cttcaaccag ttatgaaatc agtaccaacc
1501 aatggctgga atgcaaaaa ttgcagaata tgtatagagt gtggcacacg gtctagttct
1561 cagtggcacc acaattgcct gatatgtgac aattgttacc aacagcagga taacttatgt
1621 cccttctgtg ggaagtgtta tcatccagaa ttgcagaaag acatgcttca ttgtaatatg
1681 tgcaaaaggt gggttcacct agagtgtgac aaaccaacag atcatgaact ggatactcag
1741 ctcaaagaag agtatatctg catgtatttgt aaacacctgg gagctgagat ggatcgttta
1801 cagccaggtg aggaagtgga gatagctgag ctcactacag attataacaa tgaaatggaa
1861 gttgaaggcc ctgaagatca aatggtattc tcagagcagg cagctaataa agatgtcaac
1921 ggtcaggagt ccactcctgg aattgttcca gatgcggttc aagtccacac tgaagagcaa
1981 cagaagagtc atccctcaga aagtcttgac acagatagtc ttcttattgc tgtatcatcc
2041 caacatacag tgaatactga attggaaaaa cagatttcta atgaagttga tagtgaagac
```

-continued

```
2101  ctgaaaatgt cttctgaagt gaagcatatt tgtggcgaag atcaaattga agataaaatg
2161  gaagtgacag aaaacattga agtcgttaca caccagatca ctgtgcagca agaacaactg
2221  cagttgttag aggaacctga acagtggta tccagagaag aatcaaggcc tccaaaatta
2281  gtcatggaat ctgtcactct tccactagaa accttagtgt ccccacatga ggaaagtatt
2341  tcattatgtc ctgaggaaca gttggttata gaaaggctac aaggagaaaa ggaacagaaa
2401  gaaaattctg aactttctac tggattgatg gactctgaaa tgactcctac aattgagggt
2461  tgtgtgaaag atgtttcata ccaaggaggc aaatctataa agttatcatc tgagacagag
2521  tcatcatttt catcatcagc agacataagc aaggcagatg tgtcttcctc cccaacacct
2581  tcttcagact tgccttcgca tgacatgctg cataattacc cttcagctct tagttcctct
2641  gctggaaaca tcatgccaac aacttacatc tcagtcactc caaaaattgg catgggtaaa
2701  ccagctatta ctaagagaaa attttctcct ggtagacctc ggtccaaaca gggggcttgg
2761  agtacccata atacagtgag cccaccttcc tggtccccag acatttcaga aggtcgggaa
2821  attttttaaac ccaggcagct tcctggcagt gccatttgga gcatcaaagt gggccgtggg
2881  tctggatttc caggaaagcg gagacctcga ggtgcaggac tgtcggggcg aggtggccga
2941  ggcaggtcaa agctgaaaag tggaatcgga gctgttgtat acctgggggt gtctactgca
3001  gatatttcat caaataagga tgatgaagaa aactctatgc acaatacagt tgtgttgttt
3061  tctagcagtg acaagttcac tttgaatcag gatatgtgtg tagtttgtgg cagttttggc
3121  caaggagcag aaggaagatt acttgcctgt tctcagtgtg gtcagtgtta ccatccatac
3181  tgtgtcagta ttaagatcac taaagtggtt cttagcaaag gttggaggtg tcttgagtgc
3241  actgtgtgtg aggcctgtgg gaaggcaact gacccaggaa gactcctgct gtgtgatgac
3301  tgtgacataa gttatcacac ctactgccta gaccctccat tgcagacagt tcccaaagga
3361  ggctggaagt gcaaatggtg tgtttggtgc agacactgtg gagcaacatc tgcaggtcta
3421  agatgtgaat ggcagaacaa ttacacacag tgcgctcctt gtgcaagctt atcttcctgt
3481  ccagtctgct atcgaaacta tagagaagaa gatcttattc tgcaatgtag acaatgtgat
3541  agatggatgc atgcagtttg tcagaactta aatactgagg aagaagtgga aaatgtagca
3601  gacattggtt ttgattgtag catgtgcaga ccctatatgc ctgcgtctaa tgtgccttcc
3661  tcagactgct gtgaatcttc acttgtagca caaattgtca caaaagtaaa agagctagac
3721  ccacccaaga cttatatccca ggatggtgtg tgtttgactg aatcagggat gactcagtta
3781  cagagcctca cagttacagt tccaagaaga aaacggtcaa aaccaaaatt gaaattgaag
3841  attataaatc agaatagcgt ggccgtcctt cagacccctc cagacatcca atcagagcat
3901  tcaagggatg gtgaaatgga tgatagtcga gaaggagaac ttatggattg tgatggaaaa
3961  tcagaatcta gtcctgagcg ggaagctgtg gatgatgaaa ctaagggagt ggaaggaaca
4021  gatggtgtca aaagagaaa aaggaaacca tacagaccag gtattggtgg atttatggtg
4081  cggcaaagaa gtcgaactgg gcaagggaaa accaaaagat ctgtgatcag aaaagattcc
4141  tcaggctcta tttccgagca gttaccttgc agagatgatg gctggagtga gcagttacca
4201  gatactttag ttgatgaatc tgtttctgtt actgaaagca ctgaaaaaat aaagaagaga
4261  taccgaaaaa ggaaaaataa gcttgaagaa actttccctg cctatttaca agaagctttc
4321  tttggaaaag atcttctaga tacaagtaga caaagcaaga taagtttaga taatctgtca
4381  gaagatggag ctcagctttt atataaaaca aacatgaaca caggtttctt ggatccttcc
4441  ttagatccac tacttagttc atcctcggct ccaacaaaat ctggaactca cggtcctgct
```

```
4501  gatgacccat tagctgatat ttctgaagtt ttaaacacag atgatgacat tcttggaata
4561  atttcagatg atctagcaaa atcagttgat cattcagata ttggtcctgt cactgatgat
4621  ccttcctctt tgcctcagcc aaatgtcaat cagagttcac gaccattaag tgaagaacag
4681  ctagatggga tcctcagtcc tgaactagac aaaatggtca cagatggagc aattcttgga
4741  aaattatata aaattccaga gcttggcgga aaagatgttg aagacttatt tacagctgta
4801  cttagtcctg cgaacactca gccaactcca ttgccacagc ctccccacc aacacagctg
4861  ttgccaatac acaatcagga tgcttttca cggatgcctc tcatgaatgg ccttattgga
4921  tccagtcctc atctcccaca taattctttg ccacctggaa gcggactggg aactttctct
4981  gcaattgcac aatcctctta tcctgatgcc agggataaaa attcagcctt taatccaatg
5041  gcaagtgatc ctaacaactc ttggacatca tcagctccca ctgtggaagg agaaaatgac
5101  acaatgtcga atgcccagag aagcacgctt aagtgggaga aagaggaggc tctgggtgaa
5161  atggcaactg ttgccccagt tctctacacc aatattaatt tccccaactt aaaggaagaa
5221  ttccctgatt ggactactag agtgaagcaa attgccaaat gtggagaaa agcaagctca
5281  caagaaagag caccatatgt gcaaaaagcc agagataaca gagctgcttt acgcattaat
5341  aaagtacaga tgtcaaatga ttccatgaaa aggcagcaac agcaagatag cattgatccc
5401  agctctcgta ttgattcgga gcttttaaa gatcctttaa agcaaagaga atcagaacat
5461  gaacaggaat ggaaatttag acagcaaatg cgtcagaaaa gtaagcagca agctaaaatt
5521  gaagccacac agaaacttga acaggtgaaa aatgagcagc agcagcagca acaacagcaa
5581  tttggttctc agcatcttct ggtgcagtct ggttcagata caccaagtag tgggatacag
5641  agtcccttga cacctcagcc tggcaatgga aatatgtctc ctgcacagtc attccataaa
5701  gaactgttta caaaacagcc acccagtacc cctacgtcta catcttcaga tgatgtgttt
5761  gtaaagccac aagctccacc tcctcctcca gccccatccc ggattcccat ccaggatagt
5821  ctttctcagg ctcagacttc tcagccaccc tcaccgcaag tgttttcacc tgggtcctct
5881  aactcacgac caccatctcc aatggatcca tatgcaaaaa tggttggtac ccctcgacca
5941  cctcctgtgg gccatagttt ttccagaaga aattctgctg caccagtgga aaactgtaca
6001  cctttatcat cggtatctag gccccttcaa atgaatgaga caacagcaaa taggccatcc
6061  cctgtcagag atttatgttc ttcttccacg acaaataatg accctatgc aaaacctcca
6121  gacacaccta ggcctgtgat gacagatcaa tttcccaaat ccttgggcct atcccggtct
6181  cctgtagttt cagaacaaac tgcaaaaggc cctatagcag ctggaaccag tgatcacttt
6241  actaaaccat ctcctagggc agatgtgttt caaagacaaa ggatacctga ctcatatgca
6301  cgaccttgt tgacacctgc acctcttgat agtggtcctg gacctttaa gactccaatg
6361  caacctcctc catcctctca ggatccttat ggatcagtgt cacaggcatc aaggcgattg
6421  tctgttgacc cttatgaaag gcctgctttg acaccaagac ctatagataa ttttttctcat
6481  aatcagtcaa atgatccata tagtcagcct ccccttaccc cacatccagc agtgaatgaa
6541  tcttttgccc atccttcaag ggctttttcc cagcctggaa ccatatcaag gccaacatct
6601  caggacccat actcccaacc cccaggaact ccacgacctg ttgtagattc ttattcccaa
6661  tcttcaggaa cagctaggtc aatacagac ccttactctc aacctcctgg aactccccgg
6721  cctactactg ttgaccccata tagtcagcag ccccaaaccc caagaccatc tacacaaact
6781  gacttgtttg ttacacctgt aacaaatcag aggcattctg atccatatgc tcatcctcct
6841  ggaacaccaa gacctggaat ttctgtccct tactctcagc caccagcaac accaaggcca
6901  aggatttcag agggttttac taggtcctca atgacaagac cagtcctcat gccaaatcag
```

-continued

```
6961  gatcctttcc tgcaagcagc acaaaaccga ggaccagctt tacctggccc gttggtaagg
7021  ccacctgata catgttccca gacacctagg cccctggac ctggtctttc agacacattt
7081  agccgtgttt ccccatctgc tgcccgtgat ccctatgatc agtctccaat gactccaaga
7141  tctcagtctg actcttttgg aacaagtcaa actgcccatg atgttgctga tcagccaagg
7201  cctggatcag aggggagctt ctgtgcatct tcaaactctc caatgcactc caaggccag
7261  cagttctctg gtgtctccca acttcctgga cctgtgccaa cttcaggagt aactgataca
7321  cagaatactg taaatatggc ccaagcagat acagagaaat tgagacagcg gcagaagtta
7381  cgtgaaatca ttctccagca gcaacagcag aagaagattg caggtcgaca ggagaagggg
7441  tcacaggact cacccgcagt gcctcatcca gggcctcttc aacactggca accagagaat
7501  gttaaccagg ctttcaccag acccccacct ccctatcctg gaacattag gtctcctgtt
7561  gcccctcctt taggacctag atatgctgtt ttcccaaaag atcagcgtgg accctatcct
7621  cctgatgttg ctagtatggg gatgagaccc catggattta gatttggatt tccaggaggt
7681  agtcatggta ccatgccgag tcaagagcgc ttccttgtgc ctcctcagca aatacaggga
7741  tctggagttt ctccacagct aagaagatca gtatctgtag atatgcctag gcctttaaat
7801  aactcacaaa tgaataatcc agttggactt cctcagcatt tttcaccaca gagcttgcca
7861  gttcagcagc acaacatact gggccaagca tatattgaac tgagacatag ggctcctgac
7921  ggaaggcaac ggctgccttt cagtgctcca cctggcagcg ttgtagaggc atcttctaat
7981  ctgagacatg gaaacttcat tccccggcca gactttccgg gccctagaca cacagacccc
8041  atgcgacgac ctccccaggg tctacctaat cagctacctg tgcacccaga tttggaacaa
8101  gtgccaccat ctcaacaaga gcaaggtcat tctgtccatt catcttctat ggtcatgagg
8161  actctgaacc atccactagg tggtgaattt cagaagctc ctttgtcaac atctgtaccg
8221  tctgaaacaa cgtctgataa tttacagata accacccagc cttctgatgt tctagaggaa
8281  aaacttgatt ctgatgaccc ttctgtgaag gaactggatg ttaaagacct tgagggggtt
8341  gaagtcaaag acttagatga tgaagatctt gaaaacttaa atttagatac agaggatggc
8401  aaggtagttg aattggatac tttagataat ttggaaacta atgatcccaa cctggatgac
8461  ctcttaaggt caggagagtt tgatatcatt gcatatacag atccagaact tgacatggga
8521  gataagaaaa gcatgtttaa tgaggaacta gaccttccaa ttgatgataa gttagataat
8581  cagtgtgtat ctgttgaacc aaaaaaaaag gaacaagaaa acaaaactct ggttctctct
8641  gataaacatt caccacagaa aaaatccact gttaccaatg aggtaaaaac ggaagtactg
8701  tctccaaatt ctaaggtgga atccaaatgt gaaactgaaa aaaatgatga gaataaagat
8761  aatgttgaca ctccttgctc acaggcttct gctcactcag acctaaatga tggagaaaag
8821  acttctttgc atccttgtga tccagatcta tttgagaaaa gaaccaatcg agaaactgct
8881  ggcccagtg caaatgtcat tcaggcatcc actcaactac tgctcaaga tgtaataaac
8941  tcttgtggca taactggatc aactccagtt ctctcaagtt tacttgctaa tgagaaatct
9001  gataattcag acattaggcc atcgggtct ccaccaccac caactctgcc ggcctcccca
9061  tccaatcatg tgtcaagttt gcctcctttc atagcaccgc ctggccgtgt tttggataat
9121  gccatgaatt ctaatgtgac agtagtctct agggtaaacc atgtttttc tcagggtgtg
9181  caggtaaacc cagggctcat tccaggtcaa tcaacagtta accacagtct ggggacagga
9241  aaacctgcaa ctcaaactgg gcctcaaaca agtcagtctg gtaccagtag catgtctgga
9301  ccccaacagc taatgattcc tcaaacatta gcacagcaga atagagagag gcccttctt
```

```
 9361 ctagaagaac agcctctact tctacaggat cttttggatc aagaaaggca agaacagcag
 9421 cagcaaagac agatgcaagc catgattcgt cagcgatcag aaccgttctt ccctaatatt
 9481 gattttgatg caattacaga tcctataatg aaagccaaaa tggtggccct taaaggtata
 9541 aataaagtga tggcacaaaa caatctgggc atgccaccaa tggtgatgag caggttccct
 9601 tttatgggcc aggtggtaac tggaacacag aacagtgaag acagaacct  tggaccacag
 9661 gccattcctc aggatggcag tataacacat cagatttcta ggcctaatcc tccaaatttt
 9721 ggtccaggct tgtcaatga  ttcacagcgt aagcagtatg aagagtggct ccaggagacc
 9781 caacagctgc ttcaaatgca gcagaagtat cttgaagaac aaattggtgc tcacagaaaa
 9841 tctaagaagg ccctttcagc taaacaacgt actgccaaga agctgggcg  tgaatttcca
 9901 gaggaagatg cagaacaact caagcatgtt actgaacagc aaagcatggt tcagaaacag
 9961 ctagaacaga ttcgtaaaca acagaaagaa catgctgaat tgattgaaga ttatcggatc
10021 aaacagcagc agcaatgtgc aatggcccca cctaccatga tgcccagtgt ccagccccag
10081 ccaccctaa  ttccaggtgc cactccaccc accatgagcc aacccacctt tcccatggtg
10141 ccacagcagc ttcagcacca gcagcacaca acagttattt ctggccatac tagccctgtt
10201 agaatgccca gtttacctgg atggcaaccc aacagtgctc ctgcccacct gcccctcaat
10261 cctcctagaa ttcagccccc aattgcccag ttaccaataa aacttgtac  accagcccca
10321 gggacagtct caaatgcaaa tccacagagt ggaccaccac ctcgggtaga atttgatgac
10381 aacaatccct ttagtgaaag ttttcaagaa cgggaacgta aggaacgttt acgagaacag
10441 caagagagac aacggatcca actcatgcag gaggtagata gacaaagagc tttgcagcag
10501 aggatggaaa tggagcagca tggtatggtg ggctctgaga taagtagtag taggacatct
10561 gtgtcccaga ttcccttcta cagttccgac ttaccttgtg attttatgca acctctagga
10621 ccccttcagc agtctccaca acaccaacag caaatggggc aggttttaca gcagcagaat
10681 atacaacaag gatcaattaa ttcaccctcc acccaaactt tcatgcagac taatgagcga
10741 aggcaggtag gccctccttc atttgttcct gattcaccat caatccctgt tggaagccca
10801 aattttttctt ctgtgaagca gggacatgga atctttctg  ggaccagctt ccagcagtcc
10861 ccagtgaggc cttcttttac acctgcttta ccagcagcac ctccagtagc taatagcagt
10921 ctcccatgtg ccaagattc  tactataacc catggacaca gttatccggg atcaacccaa
10981 tcgctcattc agttgtattc tgatataatc ccagaggaaa aagggaaaaa gaaaagaaca
11041 agaaagaaga aaagagatga tgatgcagaa tccaccaagg ctccatcaac tccccattca
11101 gatataactg ccccaccgac tccaggcatc tcagaaacta cctctactcc tgcagtgagc
11161 acacccagtg agcttcctca acaagccgac caagagtcgg tggaaccagt cggcccatcc
11221 actcccaata tggcagcagg ccagctatgt acagaattag agaacaaact gcccaatagt
11281 gatttctcac aagcaactcc aaatcaacag acgtatgcaa attcagaagt agacaagctc
11341 tccatggaaa  ccctgccaa aacagaagag ataaaactgg aaaaggctga gacagagtcc
11401 tgcccaggcc aagaggagc  taaattggag aacagaatg  gtagtaaggt agaaggaaac
11461 gctgtagcct gtcctgtctc ctcagcacag agtcctcccc attctgctgg ggccctgct
11521 gccaaaggag actcaggaa  tgaacttctg aaacacttgt tgaaaaataa aaagtcatct
11581 tctctttgga atcaaaaacc tgagggcagt atttgttcag aagatgactg tacaaaggat
11641 aataaactag ttgagaagca gaacccagct gaaggactgc aaactttggg ggctcaaatg
11701 caaggtggtt ttggatgtgg caaccagttg ccaaaaacag atggaggaag tgaaaccaag
11761 aaacagcgaa gcaaacggac tcagaggacg ggtgagaaag cagcacctcg ctcaaagaaa
```

-continued

```
11821   aggaaaaagg acgaagagga gaaacaagct atgtactcta gcactgacac gtttacccac
11881   ttgaaacagc agaataattt aagtaatcct ccaacacccc ctgcctctct tcctcctaca
11941   ccacctccta tggcttgtca gaagatggcc aatggttttg caacaactga agaacttgct
12001   ggaaaagccg gagtgttagt gagccatgaa gttaccaaaa ctctaggacc taaaccattt
12061   cagctgccct tcagacccca ggacgacttg ttggcccgag ctcttgctca gggccccaag
12121   acagttgatg tgccagcctc cctcccaaca ccacctcata caatcagga agaattaagg
12181   atacaggatc actgtggtga tcgagatact cctgacagtt ttgttccctc atcctctcct
12241   gagagtgtgg ttggggtaga agtgagcagg tatccagatc tgtcattggt caaggaggag
12301   cctccagaac cggtgccgtc ccccatcatt ccaattcttc ctagcactgc tgggaaaagt
12361   tcagaatcaa gaaggaatga catcaaaact gagccaggca ctttatattt tgcgtcacct
12421   tttggtcctt ccccaaatgg tcccagatca ggtcttatat ctgtagcaat tactctgcat
12481   cctacagctg ctgagaacat tagcagtgtt gtggctgcat tttccgacct tcttcacgtc
12541   cgaatcccta acagctatga ggttagcagt gctccagatg tcccatccat gggtttggtc
12601   agtagccaca gaatcaaccc gggtttggag tatcgacagc atttacttcc ccgtgggcct
12661   ccgccaggat ctgcaaaccc tcccagatta gtgagctctt accggctgaa gcagcctaat
12721   gtaccatttc ctccaacaag caatggtctt tctggatata aggattctag tcatggtatt
12781   gcagaaagcg cagcactcag accacagtgg tgttgtcatt gtaaagtggt tattcttgga
12841   agtggtgtgc ggaaatcttt caaagatctg accctttga caaggattcc ccgagaaagc
12901   accaagaggg tagagaagga cattgtcttc tgtagtaata actgctttat tctttattca
12961   tcaactgcac aagcgaaaaa ctcagaaaac aaggaatcca ttccttcatt gccacaatca
13021   cctatgagag aaacgccttc caaagcattt catcagtaca gcaacaacat ctccactttg
13081   gatgtgcact gtctccccca gctcccagag aaagcttctc cccctgcctc accacccatc
13141   gccttccctc ctgcttttga agcagcccaa gtcgaggcca agccagatga gctgaaggtg
13201   acagtcaagc tgaagcctcg gctaagagct gtccatggtg ggtttgaaga ttgcaggccg
13261   ctcaataaaa aatggagagg aatgaaatgg aagaagtgga gcattcatat tgtaatccct
13321   aagggacat ttaaaccacc ttgtgaggat gaaatagatg aatttctaaa gaaattgggc
13381   acttcccta aacctgatcc tgtgcccaaa gactatcgga aatgttgctt ttgtcatgaa
13441   gaaggtgatg gattgacaga tggaccagca aggctactca accttgactt ggatctgtgg
13501   gtccacttga actgcgctct gtggtccacg gaggtctatg agactcaggc tggtgcctta
13561   ataaatgtgg agctagctct gaggagaggc ctacaaatga aatgtgtctt ctgtcacaag
13621   acgggtgcca ctagtggatg ccacagattt cgatgcacca acatttatca cttcacttgc
13681   gccattaaag cacaatgcat gtttttttaag gacaaaacta gctttgccc catgcacaaa
13741   ccaaagggaa ttcatgagca agaattaagt tactttgcag tcttcaggag ggtctatgtt
13801   cagcgtgatg aggtgcgaca gattgctagc atcgtgcaac gaggagaacg ggaccatacc
13861   tttcgcgtgg gtagcctcat cttccacaca attggtcagc tgcttccaca gcagatgcaa
13921   gcattccatt ctcctaaagc actcttccct gtgggctatg aagccagccg gctgtactgg
13981   agcactcgct atgccaatag gcgctgccgc tacctgtgct ccattgagga aaggatggg
14041   cgcccagtgt ttgtcatcag gattgtggaa caaggccatg aagacctggt tctaagtgac
14101   atctcaccta aaggtgtctg ggataagatt ttggagcctg tggcatgtgt gagaaaaaag
14161   tctgaaatgc tccagctttt cccagcgtat ttaaaaggag aggatctgtt tggcctgacc
```

```
-continued
14221  gtctctgcag tggcacgcat agcggaatca cttcctgggg ttgaggcatg tgaaaattat
14281  accttccgat acggccgaaa tcctctcatg gaacttcctc ttgccgttaa ccccacaggt
14341  tgtgcccgtt ctgaacctaa aatgagtgcc catgtcaaga ggtttgtgtt aaggcctcac
14401  accttaaaca gcaccagcac ctcaaagtca tttcagagca cagtcactgg agaactgaac
14461  gcaccttata gtaaacagtt tgttcactcc aagtcatcgc agtaccggaa gatgaaaact
14521  gaatggaaat ccaatgtgta tctggcacgg tctcggattc aggggctggg cctgtatgct
14581  gctcgagaca ttgagaaaca caccatggtc attgagtaca tcgggactat cattcgaaac
14641  gaagtagcca acaggaaaga gaagctttat gagtctcaga accgtggtgt gtacatgttc
14701  cgcatggata acgaccatgt gattgacgcg acgctcacag gagggcccgc aaggtatatc
14761  aaccattcgt gtgcacctaa ttgtgtggct gaagtggtga cttttgagag aggacacaaa
14821  attatcatca gctccagtcg gagaatccag aaaggagaag agctctgcta tgactataag
14881  tttgactttg aagatgacca gcacaagatt ccgtgtcact gtggagctgt gaactgccgg
14941  aagtggatga actgaaatgc attccttgct agctcagcgg gcggcttgtc cctaggaaga
15001  ggcgattcaa cacaccattg gaattttgca gacagaaaga gattttttgtt ttctgttttta
15061  tgacttttttg aaaaagcttc tgggagttct gatttcctca gtcctttagg ttaaagcagc
15121  gccaggagga agctgacaga agcagcgttc ctgaagtggc cgaggttaaa cggaatcaca
15181  gaatggtcca gcactttttgc ttttttttct tttccttttc tttttttttt gtttgttttt
15241  tgttttgttt ttcccttgtg ggtgggtttc attgttttgg ttttctagtc tcactaagga
15301  gaaactttta ctggggcaaa gagccgatgg ctgccctgcc ccgggcaggg gccttcctat
15361  gaatgtaaga ctgaaatcac cagcgagggg gacagagagt gctggccacg gccttattaa
15421  aaaggggcag gccctctaac ttcaaaatgt ttttaaataa agtagacacc actgaacaag
15481  gaatgtactg aaatgacttc cttagggata gagctaaggg ataataactt gcactaaata
15541  catttaaata cttgattcca tgagtcagtt tattgtagtt tttgatttct gtaaaataag
15601  agaaactttt gtatttatta ttgaataagt gaatgaagct attttttaaat aaagttagaa
15661  gaaagccaag ctgctgctgt tacctgcaga actaacaaac cctgttactt tgtacagata
15721  tgtaaatatt ttgagaaaaa atacagtata aaaatagtta ttgaccaaat gctaccaggc
15781  tctgcagcag ctcggggggct tataaaatgt tcatagggat gttacaatat aattttgtgt
15841  tataaaatat gccattataa ttatgtaata accaaaattt caacctagag tgttgggggt
15901  tttttggaaa ccgcagtcta ttagtactca atggttttat acaccttact tctgacagag
15961  cggggcgtat gctacgacta caacttttat agctgttttg gtaatttaaa ctaattttttt
16021  catattatat tgttgcatcc ctacttcttc agtcaggttt ttttgtgctt acaatttgtg
16081  ataactgtga ataactgctt aaaaatacac ccaaatggag gctgaatttt tccttcagca
16141  aaagtagttt tgattagaac tttgtttcag ccacagagaa tcatgtaaac gtaataggat
16201  catgtagcag aaacttaaat ctaacccttt agccttctat ttaacacaaa aatttgaaaa
16261  agttaaaaaa aaaaaggaga tgtgattatg cttacagctg caggactctg gcaataggt
16321  ttttggaaga tgtaattttta aaatgtgttt gtatgaactg tttgtttaca tttcttttaat
16381  aaaaaaaaca ctgttttgtg tttgcttgta gaaacttaat cagcattttg aaccaggtta
16441  gcttttttatt ttgtacttaa aattctggta ctgacacttc acaggctaag tataaaatga
16501  agttttgtgt gcacaattca agtggactgt aaactgttgg tatattcagt gatgcagttc
16561  tgaacttgta tatggcatga tgtattttta tcttacagaa taaatcaatt gtatatattt
16621  ttctcttgat aaatagctgt atgaaatttg tttcctgaat atttttcttc tcttgtacaa
```

-continued

```
16681 tatcctgaca tcctaccagt atttgtccta ccgggttttt gttgttttct gttctgtata
16741 atagtatcta atgttggcaa aaattgaatt ttttgaagta tacagagtgt tatgggtttt
16801 ggaatttgtg gacacagatt tagaagatca ccatttacaa ataaaatatt ttacatctat
16861 aaaaaaaaaa aa
```

KAT8 (accession No. NM_032188):
```
   1 gtcacttccc ttcccgcgat ggcggcacag ggagctgctg cggcggttgc ggcggggact
  61 tcagggtcg cggggaggg cgagcccggg cccggggaga atgcggccgc tgaggggacc
 121 gccccatccc cgggccgcgt ctctccgccg accccggcgc gcggcgagcc ggaagtcacg
 181 gtggagatcg gagaaacgta cctgtgccgg cgaccggata gcacctggca ttctgctgaa
 241 gtgatccagt ctcgagtgaa cgaccaggag ggccgagagg aattctatgt acactacgtg
 301 ggcttttaacc ggcggctgga cgagtgggta gacaagaacc ggctggcgct gaccaagaca
 361 gtgaaggatg ctgtacagaa gaactcagag aagtacctga gcagctcgc agagcagcct
 421 gagcgcaaga tcactcgcaa ccaaaagcgc aagcatgatg agatcaacca tgtgcagaag
 481 acttatgcag agatggaccc caccacagca gccttggaga aggagcatga ggcgatcacc
 541 aaggtgaagt atgtggacaa gatccacatc gggaactacg aaattgatgc ctggtatttc
 601 tcaccattcc ccgaagacta tgggaaacag cccaagctct ggctctgcga gtactgcctc
 661 aagtacatga aatatgaaga gagctaccgc ttccacttgg gtcagtgcca gtggcggcag
 721 cccccccggga aagagatcta ccgcaagagc aacatctccg tgtacgaagt tgatggcaaa
 781 gaccataaga tttactgtca gaacctgtgt ctgctggcca agcttttcct ggaccataag
 841 acactgtact ttgacgtgga gccgttcgtc ttttacatcc tgactgaggt ggaccggcag
 901 ggggcccaca ttgttggcta cttctccaag gagaaggagt ccccggatgg aaacaatgtg
 961 gcctgcatcc tgaccttgcc cccctaccaa cgccgcggct acgggaagtt cctcatcgct
1021 ttcagttatg agctctccaa gctggagagc acagtcggct ccccggagaa gccactgtct
1081 gacctgggca agctcagcta ccgcagctac tggtcctggg tgctgctaga gatcctgcgg
1141 gacttccggg gcacactgtc catcaaggac ctcagccaga tgaccagtat cacccaaaat
1201 gacatcatca gtaccctgca atccctcaat atggtcaagt actggaaggg ccagcacgtg
1261 atctgtgtca cacccaagct ggtggaggag cacctcaaaa gtgcccagta taagaaacca
1321 cccatcacag tggactccgt ctgcctcaag tgggcacccc ccaagcacaa gcaagtcaag
1381 ctctccaaga agtgagcagc ctggcccctg ctgtcggacc tgagcctcct ggctcccagc
1441 ctgtaaatat gtatagacct gttttgtcat ttttttaata aagtcagttc tggtggccct
1501 ggactttgga ggggaagggg aggccaagaa aaaaaaaaaa aaaaaa
```

KDM6A (accession No. NM_001291415):
```
   1 gtgtgacaca attacaacaa ctttgtgctg gtgccgggga gtttgtgtc tccaacgaat
  61 cccctcagtg ctcccccagcc ccgcgcgctc cggccgttcc cgccgtcccc gcctgtggct
 121 gccccctgcc caaccccgcg atgtgaccct acagccgaaa gccgccgctg ccgacccggg
 181 ggctccgcag cccctgccgc cgccgccgcc gccttcaccg ccgccgcgtt gggatttttc
 241 gtcgccgccg cccgcggcgg aggaggaggc ggcgataaag ttggtgtgct ggtcccgcgc
 301 gcagattggg ggcgtcactg cgggcccccgg tccgagggggg ggtgtcggcg ttggagttgt
 361 gaattcgctg cgtttccatg aaatcctgcg gagtgtcgct cgctaccgcc gccgctgccg
 421 ccgccgcttt cggtgatgag gaaaagaaaa tggcggcggg aaaagcgagc ggcgagagcg
 481 aggaggcgtc ccccagcctg acagccgagg agagggaggc gctcggcgga ctggacagcc
```

-continued

```
 541   gcctctttgg gttcgtgaga tttcatgaag atggcgccag gacgaaggcc ctactgggca
 601   aggctgttcg ctgctatgaa tctctaatct taaaagctga aggaaaagtg gagtctgatt
 661   tcttttgtca attaggtcac ttcaacctct tattggaaga ttatccaaaa gcattatctg
 721   cataccagag gtactacagt ttacagtctg actactggaa gaatgctgcc tttttatatg
 781   gtcttggttt ggtctacttc cattataatg catttcagtg ggcaattaaa gcatttcagg
 841   aggtgcttta tgttgatccc agcttttgtc gagccaagga aattcattta cgacttgggc
 901   ttatgttcaa agtgaacaca gactatgagt ctagtttaaa gcattttcag ttagctttgg
 961   ttgactgtaa tccctgcact ttgtccaatg ctgaaattca atttcacatt gcccacttat
1021   atgaaaccca gaggaaatat cattctgcaa aagaagctta tgaacaactt ttgcagacag
1081   agaatctttc tgcacaagta aaagcaactg tcttacaaca gttaggttgg atgcatcaca
1141   ctgtagatct cctgggagat aaagccacca ggaaagcta tgctattcag tatctccaaa
1201   agtccttgga agcagatcct aattctggcc agtcctggta tttcctcgga aggtgctatt
1261   caagtattgg gaaagttcag gatgccttta tatcttacag gcagtctatt gataaatcag
1321   aagcaagtgc agatacatgg tgttcaatag gtgtgctata tcagcagcaa aatcagccca
1381   tggatgcttt acaggcctat atttgtgctg tacaattgga ccatggccat gctgcagcct
1441   ggatggacct aggcactctc tatgaatcct gcaaccagcc tcaggatgcc attaaatgct
1501   acttaaatgc aactagaagc aaaagttgta gtaataccct gcacttgca gcacgaatta
1561   agtatttaca ggctcagttg tgtaaccttc cacaaggtag tctacagaat aaaactaaat
1621   tacttcctag tattgaggag gcgtggagcc taccaattcc cgcagagctt acctccaggc
1681   agggtgccat gaacacagca cagcaggcat gtaaacctca tcatccaaat actgaacctg
1741   tattaggcct cagtcaaaca ccaatttcac agcaatcctt gccactacac atgattcctt
1801   ctagccaagt agatgacctg tccagtcctg ccaagaggaa aagaacatct agtccaacaa
1861   agaatacttc tgacaattgg agtggtggac atgctgtgtc acatcctcca gtacagcaac
1921   aagctcattc atggtgtttg acaccacaga aattacagca tttggaacag ctccgcgcaa
1981   atagaaataa tttaaatcca gcacagaaac tgatgctgga acagctgaaa agtcagtttg
2041   tcttaatgca acaaccaa atgagaccaa caggagttgc acaggtacga tctactggaa
2101   ttcctaatgg gccaacagct gactcatcac tgcctacaaa ctcagtctct ggccagcagc
2161   cacagcttgc tctgaccaga gtgcctagcg tctctcagcc tggagtccgt cctgcctgcc
2221   ctgggcagcc tttgccaat ggaccctttt ctgcaggcca tgttccctgt agcacatcaa
2281   gaacgctggg aagtacagac actattttga taggcaataa tcatataaca ggaagtggaa
2341   gtaatggaaa cgtgccttac ctgcagcgaa acgcactcac tctacctcat aaccgcacaa
2401   acctgaccag cagcgcagag gagccgtgga aaaaccaact atctaactcc actcaggggc
2461   ttcacaaagg tcagagttca cattcggcag gtcctaatgg tgaacgacct ctctcttcca
2521   ctgggccttc ccagcatctc caggcagctg gctctggtat tcagaatcag aacggacatc
2581   ccaccctgcc tagcaattca gtaacacagg gggctgctct caatcacctc tcctctcaca
2641   ctgctacctc aggtggacaa caaggcatta ccttaaccaa agagagcaag ccttcaggaa
2701   acatattgac ggtgcctgaa acaagcaggc acactggaga gacacctaac agcactgcca
2761   gtgtcgaggg acttcctaat catgtccatc agatgacggc agatgctgtt tgcagtccta
2821   gccatggaga ttctaagtca ccaggtttac taagttcaga caatcctcag ctctctgcct
2881   tgttgatggg aaaagccaat aacaatgtgg gtactggaac ctgtgacaaa gtcaataaca
2941   tccacccagc tgttcataca aagactgata actctgttgc ctcttcacca tcttcagcca
```

-continued

```
3001  tttcaacagc aacaccttct ccaaaatcca ctgagcagac aaccacaaac agtgttacca
3061  gccttaacag ccctcacagt gggctacaca caattaatgg agaagggatg aagaatctc
3121  agagccccat gaaaacagat ctgcttctgg ttaaccacaa acctagtcca cagatcatac
3181  catcaatgtc tgtgtccata tacccagct cagcagaagt tctgaaggca tgcaggaatc
3241  taggtaaaaa tggcttatct aacagtagca ttttgttgga taaatgtcca cctccaagac
3301  caccatcttc accataccct cccttgccaa aggacaagtt gaatccacct acacctagta
3361  tttacttgga aaataaacgt gatgctttct ttcctccatt acatcaattt tgtacaaatc
3421  cgaacaaccc tgttacagta atacgtggcc ttgctggagc tcttaagtta gacctgggac
3481  ttttctctac taaaactttg gtggaagcta acaatgaaca tatggtagaa gtgaggacac
3541  agttgttgca gccagcagat gaaaactggg atcccactgg aacaaagaaa atctggcatt
3601  gtgaaagtaa tagatctcat actacaattg ctaaatatgc acagtaccag gcctcctcat
3661  tccaggaatc attgagagaa gaaaatgaaa aagaagtca tcataaagac cactcagata
3721  gtgaatctac atcgtcagat aattctggga ggaggaggaa aggacccttt aaaaccataa
3781  agtttgggac caatattgac ctatctgatg acaaaaagtg gaagttgcag ctacatgagc
3841  tgactaaaact tcctgctttt gtgcgtgtcg tatcagcagg aaatcttcta agccatgttg
3901  gtcataccat attgggcatg aacacagttc aactatacat gaaagttcca gggagcagaa
3961  caccaggtca tcaggaaaat aacaacttct gttcagttaa cataaatatt ggcccaggtg
4021  actgtgaatg gtttgttgtt cctgaaggtt actggggtgt tctgaatgac ttctgtgaaa
4081  aaaataattt gaatttccta atgggttctt ggtggcccaa tcttgaagat ctttatgaag
4141  caaatgttcc agtgtatagg tttattcagc gacctggaga tttggtctgg ataaatgcag
4201  gcactgttca ttgggttcag gctattggct ggtgcaacaa cattgcttgg aatgttggtc
4261  cacttacagc ctgccagtat aaattggcag tggaacggta cgaatggaac aaattgcaaa
4321  gtgtgaagtc aatagtaccc atggttcatc tttcctggaa tatggcacga atatcaagg
4381  tctcagatcc aaagcttttt gaaatgatta agtattgtct tctaagaact ctgaagcaat
4441  gtcagacatt gagggaagct ctcattgctg caggaaaaga gattatatgg catgggcgga
4501  caaaagaaga accagctcat tactgtagca tttgtgaagt ggaggttttt gatctgcttt
4561  ttgtcactaa tgagagtaat tcacgaaaga cctacatagt acattgccaa gattgtgcac
4621  gaaaaacaag cggaaacttg gaaaactttg tggtgctaga acagtacaaa atggaggacc
4681  tgatgcaagt ctatgaccaa tttacattag ctcctccatt accatccgcc tcatcttgat
4741  attgttccat ggacattaaa tgagacctttt tctgctattc aggaaataac ccagttctgc
4801  accactggtt tttgtagcta tctcgtaagg ctgctggctg aaaactgtgt ctatgcaacc
4861  ttccaagtgc ggagtgtcaa ccaactggac gggagagagt actgctccta ctccaggact
4921  ctcacaaagc tgatgagctg tacttcagaa aaaaataata atttccatgt tttgtatata
4981  tctgacaaaa ctggcaacat cttacagact actgacttga agacaacctc ttttatattt
5041  ctctatttct gggctgatga atttgttttc atctgtcttt tccccttca gaattttcct
5101  tggaaaaaaa atactagcct agctggtcat ttctttgtaa ggtagttagc aattttaagt
5161  ctttctttgg tcaacttttt tttaatgtga aaagttaggt aagcactttt tttactgctt
5221  ttatgttttt ctgtcttgtt ttgagaccat gatggttaca cttttggttc ctaaataaaa
5281  tttaaaaaat taacagccaa gtcacaaagg taatggattg cacatagact aaggaataaa
5341  cttcagattt gtgattttg tttctaatct tgatgtaaat ttacactatt tataaataca
```

-continued

```
5401  tatttattgc ttgaaaatat ttgtgaatgg aatgctgtta ttttttccag atttacctgc 5461  cattgaaatt ttaaggagtt ctgtaatttc aaacactact cctattacat tttctatgtg 5521  taaataaaac tgcttagcat tgtacagaaa cttttattaa aattgtttaa tgtttaaaga 5581  gttttctatt gtttgagttt taaaaaagac tttatgtaca gtgcccagtt tttgttcatt 5641  tttgaaatct gattatatat attttatata tacttatgta tgtatatata atatatatag 5701  aaatctggat atatatgtat aaatctttag aacttaaatt tttctcgttt taagtttcac 5761  atctatggta gattttttgag gtgtctactg taaagtattg cttacaaaaa gtatgattat 5821  ttttaaagaa atatatatgg tatgtatcct caagacctaa aatgtcagac tggtttattg 5881  ttaagttgca attactgcaa tgacagacca ataacaatt gctgccaaaa tgtagtataa 5941  a
```

NCOA6 (accession No. NM_014071):

```
   1  gtgaggccct gccgggtcgg gctgcgggcg gccgggcgcg ggcggcggga cagacgggcg 61  cacgcgagga ctgacggacg acgcaccga gggcggcggg cacgcacggc ccggggccggc 121  gctccaaggc ccgcccggga gggccggggc cgcgctcaga attttgattt ggctgctggg 181  ctgctacctt gaaatccaag ccctaaaaat gccagcttct ttggacttag aagatgacct 241  ggataaatga taaaaattaa gaaagagatt ttgaagtttt cttattgtcc tcttggcata 301  tgcttctgga ataatattca ccatggtttt ggatgacctt ccaaacttag aagacatcta 361  tacttccttg tgttcatcaa caatggaaga ctcagagatg gattttgact ctggactaga 421  agatgatgac acaaaaagtg atagtatttt ggaggattcc acaattttg tggccttcaa 481  aggaaatata tgatgataaag acttcaaatg gaaattagat gcaatattga aaaacgtgcc 541  caatttgtta cacatggagt ccagcaagct aaaagtacag aaggtggagc cctggaacag 601  cgtgcgtgtg acattcaaca tcccccggga agcagcggag cggctacgga tccttgctca 661  gagcaacaac cagcagcttc gggatttagg gattctctcc gttcagattt aagggggaagg 721  tgctattaac ctggctttgg ctcagaaccg aagccaagat gtgagaatga atggacccat 781  gggagctgga aattcagtta ggatggaggc gggatttcct atggcaagtg gtccaggaat 841  aataaggatg aacaaccctg ccactgttat gatacccccg ggtggaaatg tgtcatcttc 901  catgatggca ccaggcccca atccagagct gcagcccagg actcctcgcc ctgcttctca 961  gtcagatgca atggatccac tcctctctgg gctccatata cagcagcaaa gtcatccctc 1021  aggatcttta gctcccccac atcacccaat gcagcctgtc tctgtgaaca gacaaatgaa 1081  cccagctaat tttcccccagc tgcagcagca gcagcaacaa caacaacagc agcagcagca 1141  gcagcagcag caacaacagc aacagcagca acaacagttg caggcaagac cccacagca 1201  acatcagcag caacagccac agggaattcg accccagttt actgcccaa ctcaggtgcc 1261  tgttcctcca ggctggaacc agctgccttc tggagccctt caacctcctc cagcccaggg 1321  ttctctgggc acaatgactg caaaccaagg gtggaagaag ctccccttgc ccggcccaat 1381  gcaacagcaa ctccaggcaa gaccatcctt agccacggta cagacgcctt cccacccctcc 1441  ccctccatat cccttggca gccagcaagc ctcacaagcc cacacaaact ttcctcagat 1501  gagcaaccca ggccagttca cagctcctca gatgaagagt ttgcagggag ggccctctag 1561  ggtcccaact cccttgcagc agccccacct caccaacaag tctcctgcct cctcaccctc 1621  ctccttccag cagggatccc ctgcatcctc cccaacggtt aaccaaactc agcagcagat 1681  gggaccaagg ccacctcaaa ataacccact tccccaggga tttcagcagc ctgtcagctc 1741  tccgggtcgg aatcctatgg ttcaacaggg aaatgtgcca cctaacttca tggtgatgca
```

```
-continued
1801  gcagcaacca ccaaaccagg ggccacagag tttacatcca ggcctaggag gaatgcctaa
1861  acgcctccca cctggcttct cagcaggaca ggccaatccg aactttatgc aaggtcaggt
1921  gccttcgacc acagcaacca cccctgggaa ttcaggagcc cctcagctgc aagcaaatca
1981  aaatgtccag catgcaggtg gtcaaggagc tggtcctcct caaaaccaga tgcaggtgtc
2041  ccacgggccg ccaaatatga tgcagcccag cctcatggga attcatggca acatgaacaa
2101  tcagcaggct ggtacttctg gggttcctca agtgaacctc agcaacatgc aaggccagcc
2161  ccagcagggc ccaccatctc agctgatggg catgcaccag caaatcgtgc cctcccaggg
2221  ccagatggtc cagcaacaag gaaccttgaa ccctcagaac cctatgatcc tttcaagggc
2281  ccagcttatg ccacagggcc agatgatggt gaaccccccg agccaaaatc ttgggccctc
2341  gccccaaagg atgacccccac ccaagcagat gctttcccag cagggcccac aaatgatggc
2401  gccacataac cagatgatgg ggcctcaggg gcaggttttg ctccaacaga acccaatgat
2461  agagcagatt atgaccaatc aaatgcaggg gaataagcag cagtttaaca ctcagaacca
2521  gtccaatgtc atgccgggac cagcccagat aatgagggga ccaactccaa acatgcaagg
2581  aaatatggtg cagtttacgg acagatgtc aggacagatg ctgccccagc aagggcctgt
2641  gaacaacagt ccatctcagg ttatgggcat tcaggacag gtcctgcggc caccagggcc
2701  cagcccacac atggcccagc agcatggtga tcctgctact acagcaaata cgatgtcag
2761  tttatctcag atgatgcctg atgttagcat tcaacaaacc aacatggtcc cccctcatgt
2821  gcaggccatg cagggaaaca gtgcctcggg aaaccacttc tcaggccatg ggatgtcttt
2881  caatgcacct ttcagtggag ctcccaatgg aaatcagatg tcctgtggtc aaaatccagg
2941  cttcccagtc aataaggatg tcacgctaac gagcccattg ttggtcaact tattgcagag
3001  tgacatatct gcaggccatt ttggggtaaa caataagcaa ataatacca acgcaaataa
3061  accgaagaag aagaaacccc ctcggaagaa gaaaaatagt cagcaagatc taaacacccc
3121  agatactcgc ccagctggtc tggaagaggc tgatcagcca ccgttgcctg gagaacaagg
3181  aattaacttg gataactcag gccctaaact gccagaattt tcaaaccggc caccaggtta
3241  tccttctcaa ccagttgaac agaggccact tcagcagatg cctcctcaac tcatgcagca
3301  tgtggcaccc ccaccacagc caccacagca gcagccacag ccacaactgc ctcagcagca
3361  gcagccacca cctcccagtc agccacagtc tcagcagcag cagcagcagc agcaacaaat
3421  gatgatgatg ctcatgatgc agcaggatcc caaatcagtt aggcttccag tctctcaaaa
3481  tgtccatcct ccaagggggcc ccctgaaccc cgactcccag agaatgccca tgcaacagag
3541  tggcagtgtg cctgtcatgg tcagtctgca aggacctgcc tccgtgccac catcacctga
3601  taaacaaaga atgccaatgc ctgtgaatac tcccttggga agcaattcaa ggaaaatggt
3661  ctatcaggag agcccgcaga atccttccag ctcgccactg gcggagatgg cctcactccc
3721  tgaagcaagt ggcagtgaag caccatctgt cccaggaggc ccaaacaaca tgccttcaca
3781  tgtagtactt ccccagaatc agttaatgat gacagggcca aaacctggac catcgcccct
3841  ttcagcaact caaggtgcaa ctccccagca ccccctgta aattccctgc ccagctctca
3901  cggccaccac ttcccaaatg tggctgcgcc aacccagaca tctaggccca aacaccaaa
3961  cagagccagc cccagaccct attatcctca gacacccaac aaccgccctc ccagcacaga
4021  accttcagaa atcagtctgt caccagaaag actcaatgcc tccatagcag gactcttccc
4081  tccacagatt aatattcctt tacctcctag gccaaattta acaggggct ttgatcaaca
4141  aggcctaaat ccaacaactt tgaaggccat cggcaagca ccttcaaatc ttaccatgaa
4201  tccttccaat tttgctaccc cacaaactca caaattagat tctgtggtag tgaattctgg
```

-continued

```
4261  aaagcagtct aattctggag caacaaaacg ggcaagtcca agcaacagtc gcaggtctag
4321  tcctgggtcc agtaggaaaa ccactccaag ccctgggagg caaaattcaa aagcccctaa
4381  acttactctg gcctctcaga caaatgcagc cctattgcag aatgtggagt tgccgagaaa
4441  tgtattggtc agtcccactc ctctggccaa tcccctgta cctgggagct ttcctaacaa
4501  cagtgggctg aatcctcaga attctactgt gtctgtggct gcagttgggg gtgttgttga
4561  ggataacaag gagagcttga atgtgcctca ggacagtgat tgccagaatt cccagagtag
4621  gaaggaacag gtaaacattg aactaaaagc agtccctgcc caagaagtta aaatggttgt
4681  ccctgaagat cagtccaaaa aggatgggca gccttcggat cctaacaaac ttcccagtgt
4741  cgaagagaac aaaaatttgg tgtctcctgc tatgagggaa gcaccaacat cgttaagtca
4801  acttcttgac aactctggag ctcccaatgt gacaattaaa cccctgggc ttacagatct
4861  ggaagtaaca cctccagtag tttctgggga ggacctcaaa aaagcatctg tcattcccac
4921  actgcaggat ctgtcttctt ctaaagaacc ttctaattcc ctaaacttac ctcacagtaa
4981  tgagctgtgt tcatcccttg tgcatcccga attgagtgag gtcagttcta acgttgcacc
5041  aagcatccct ccagtaatgt caagacctgt tagctcttcc tccatttcca ctcccttgcc
5101  cccaaatcaa ataactgtat ttgtcacttc caatcccatc acaacttcag ctaacacatc
5161  agcagctttg ccaactcact tgcagtctgc attgatgtca acagttgtca caatgcccaa
5221  tgcgggtagc aaggttatgg tttctgaggg acagtcagct gctcagtcta atgcccggcc
5281  tcagttcatt acacctgtct ttatcaattc atcctcaata attcaggtta tgaaaggatc
5341  acagccaagc acaattcctg cagccccact gacaaccaac tctggcctga tgcctccctc
5401  tgttgcagtt gttggcccctt tacacatacc tcagaacata aaattttctt ctgctcctgt
5461  accgcctaat gccctctcca gtagtcctgc tccaaacatc cagacaggtc gacctttggt
5521  ccttagctca cgagccaccc ctgttcagct tccttcccct ccttgtacgt cttctccagt
5581  tgtcccttct catcccctg tgcagcaagt gaaagaattg aatccagatg aggctagccc
5641  tcaggtgaac acctcagcag atcagaacac tcttccctct tcacagtcaa ccacaatggt
5701  ttctcccctt ttgaccaata gtccagggtc ctctggcaac cggcgaagcc cagtctcgtc
5761  tagtaagggc aaggaaaag tggacaaaat tggccaaatt ttgttgacca aggcatgtaa
5821  gaaagttaca ggctctcttg agaaagggga agaacaatat ggtgcagatg gagagactga
5881  aggccaaggg ctagacacca cagctccggg gctcatggga acagagcagt tatccacaga
5941  gctggacagt aaaacccaa cgcccccagc acccactctg ctaaaaatga cctctagccc
6001  tgtgggcccg ggcactgcct cagcaggacc cagcttacct ggcggtgctc tccccaccag
6061  tgtacgctcg atagtaacca ctctggtacc ctccgagctc atctccgccg taccgaccac
6121  aaaaagcaat catggtggca tagcatctga gtcacttgcg ggtggcctag tggaggagaa
6181  ggtgggatcc catccagaac ttctacccag catagccccg tcgcagaatt tagtctcaaa
6241  ggaaacttca accacagcac tgcaggcctc tgttgccaga ccagagctgg aggtaaatgc
6301  tgccatagtc tctggacaaa gcagtgagcc caaagagata gttgaaaagt ccaaaatccc
6361  aggccgaaga aactcccgaa ctgaagagcc aactgtggcc tctgaaagtg tggaaaatgg
6421  acatcgtaaa cgatcttctc gacctgcttc agcctccagc tctactaaag acataaccag
6481  tgcggtgcaa tccaagcgaa gaaaatccaa gtaaacaagc aggactgcga cttgatactt
6541  ggaaatgtgt gtgacttta caaagagcaa ttttgagctg tgactttttt aaatcaattt
6601  ctgtacagtt agtaatttta ataatgtggc cctttttccta gtccctgcaa cctgtttcat
```

-continued

```
6661   aaagtgcaat ggggaaagca ggactgttga gcccttttgg tgttgcgagt tgaagttcaa
6721   ggtttctaaa atgttgtctt gtattgaaag gagctaatgc cattataaat gttactagtt
6781   ttcacatttc ctaagcagcc tagagtacag ggtgagcatt tttagatctc ctaatgatgt
6841   attgtgccgt ggaagtactg tgtgtgaata gcagtagtgg gggcaaaagc aatcttctca
6901   tttggaaatg ttgtaaataa ttttattata tagtgttttg gatgtatttg ttgtagaaat
6961   ggaccagtga ataaagaaa tctaaggatt tgtacaatgt gaaataacgt gttaaataaa
7021   tgtcattgtc atagaacata aagttatgtt attggtaagg gaaaaaaaaa a
```

PAGR1 (accession No. NM_024516):
```
   1   ggcgccgtgt ccgggtgtgg agagggcgt cgtggaagcg agaagagtgg cccgtccctc
  61   tcctccccct ttccctcttt cggaaagtgg tttctgcggg gcccgggagc ctcggagtac
 121   cgaacctcga tctccggggc ggggtccttg gtggggactg agcgcccccc cccggggacg
 181   ggcggtctgg ccgcggagtc ccctgcggga gcgtgattgg ctggaaacgg tcccgaaccc
 241   ccagggagc ccgatccctg ggggaccctg gcttcggact ccagtatctg tcgtcgcagg
 301   gtccctgccc tagtggccta tgtcccttgc tcggggccat ggagacactg cggccagtac
 361   ggcggcgcct ctgtctgaag aaggggaagt gacctccggc ctccaggctc tggccgtgga
 421   ggataccgga ggcccctctg cctcggccgg taaggccgag acgaggggg aaggaggccg
 481   agaggagacc gagcgtgagg ggtccggggg cgaggaggcg cagggagaag tccccagcgc
 541   tgggggagaa gagcctgccg aggaggactc cgaggactgg tgcgtgccct gcagcgacga
 601   ggaggtggag ctgctgcgcg atgggcagcc ctggatgccc ccgccctccg aaatccagcg
 661   gctctatgaa ctgctggctg cccacggtac tctggagctg caagccgaga tcctgccccg
 721   ccggcctccc acgccggagg cccagagcga agaggagaga tccgatgagg agccggaggc
 781   caaagaagag gaagaggaaa aaccacacat gcccacggaa tttgattttg atgatgagcc
 841   agtgacacca aaggactccc tgattgaccg gagacgcacc ccaggaagct cagcccggag
 901   ccagaaacgg gaggcccgcc tggacaaggt gctgtcggac atgaagagac acaagaagct
 961   ggaggagcag atccttcgta ccgggaggga cctcttcagc ctggactcgg aggaccccag
1021   ccccgccagc ccccactcc gatcctccgg gagtagtctc ttccctcggc agcggaaata
1081   ctgattccca ctgctcctgc ctctagggtg cagtgtccgt acctgctgga gcctgggccc
1141   tccttcccca gcccagacat tgagaaactt gggaagaaga gagaaacctc aagctcccaa
1201   acagcacgtt gcgggaaaga ggaagagaga gtgtgagtgt gtgtgtgtgt ttttctatt
1261   gaacacctgt agagtgtgtg tgtgtgtttt ctattgaaca cctatagaga gagtgtgtgt
1321   gttttctatt gaacatctat atagagagag tgtgtgagtg tgtgttttct attgaacacc
1381   tattcagaga cctggactga attttctgag tctgaaataa agatgcaga gctatcatct
1441   cttaaaagga ggggctgtag ctgtagctca acagttaggc cccacttgaa gggagaggca
1501   gaattgtact cacccagatt ggaaaatgaa agccagatgg gtagaggtgc cctcagttag
1561   cacctgtccc atctcgggcc ctccaactcc tcccagtccc actccagtgc agccagctgg
1621   ctccaaggta gaaacccatg agcactcagg gagcagtgtg ccttcagctg cagcagaagc
1681   agcccggagg ataaaatgag aaccagctgc acacgggccc tttaactccc aagccccacc
1741   cctgggcttg gcctgccttg ccctgccggg aagtgatccc caaggcaggg tgagagttcc
1801   ccatctgagg cgtttgttgc agctacctgc acttctagat gtgagtacat tgtactagcc
1861   ccccaaaccc caaatcaggg gcagatcttt gtatcccttg aggctctctt tagtcctgtc
1921   ttgctttgaa gggccttgct tctgctgggg cagggaaaac atgtctgaat cagagtgggg
```

-continued

```
1981  aaggaggatg ggtggtggct ttgcttttgg aggtttcact ttccaatagt tgggagtctt 2041  ctgggttttg aagtaaaggc agattaacac caacaccggt cccccacccc cctgcaactc 2101  tcaggcctct ctctgacttc agggtcccac ctgggaaatc aggtggggaa ccttacaggg 2161  tcattcagac cccatcttag ccctagatcg gtgcttgctc tactcacctg cactgtcctg 2221  gggacctggg ctctggcctg tcaccttgag ctccaagaat gtgacctgta cccattcagg 2281  cccctttaact ctgacagatg agggtttctt actcctccat gcagggctgg gccagctgtt 2341  ggtctcagtc gatcattcag gaagtcatta gcagagtgat ttccagaagg cgtagaattt 2401  agtgaccaag gttctttcct ttttgggagg agaaagtgaa aactaggatg ctcagctgga 2461  cccaccagcc tgagattctg gggattttag agctgtccct tggggagcca agcacttggg 2521  ggtggaggtg atagcgaggc tgatggcccc tgtgttctca gctctctgcc tgggtagccc 2581  ctgggtgatg ggggagaggc cagctgtcac gtggggtatc aggtggctct gccagaaact 2641  cccttggcac acagagcact gggtcggccc tcgggtgtgg ctgtttgggc aggacagccc 2701  tctgtatgta gccttgagca ggtagggggg ccaccttgag tgggtggccc agagacagcc 2761  tcagggctcc aaggtaacgg ggtgctcagg ttatcttggg tgctgccctc ccaggttctg 2821  ggggagcaga ggctgggcgc tggcccaact tacaggaaac actcacctttt gaactgccat 2881  tagcaccatc tgggcagtac acagccccac ccaggtcctc tagttcttgt tctcggctta 2941  gaatctttgt gtttctgcct gagaagccac tgcctcctag tttgtggtct ctacagttat 3001  agccaggttg gacttccggc tccgtccttt gataactgtg tgctcttggg caaatttctt 3061  aacttgcagg ttcttgtgag gataacatga gttaattgag ggcacttaac actacctggc 3121  acagattaag ctcatctgaa gtgggagctg ttacttaggg gcgtttgcct agaacacagg 3181  gtccagaggc tctctcccgg aaacttagac ccagtgagtc agaagtgagg cctgcaaaaa 3241  gcagcaggag tggggttaag aattccagcc tagggctgga tgcggtggct caggcctgta 3301  atcccagtac tttgggaggc ccgaatggga ggatggcttg aggccaggag ttccagacca 3361  gcctgagcaa catagcgaga ccctgtctct gtttgtgtgt gtgtggttgg ggttttgttt 3421  tttttttttt tttaaagaat tatagctcag tcctatgatt aggcaagttg agaaaatatt 3481  gatgaagatc aggggtgctg aagcctggtt cctggggtcg cttctgatct aggcggttct 3541  tgcctctggt gactggtgtt aattggcagg agtgggagga gggaggacaa gtgaagtct 3601  aggctggctg agctgttctg tctcgaaaag ttcctaaaac tgtgctgctt taaaaaaaaa 3661  aaaagtaatt tatgagacac attctcaatt tccattaatc atctcctaaa gggggtaaac 3721  caggaagccg ctgggtgaaa acaggctgtt ggcaattcct gagtcatgtg acccattctc 3781  taaagactag aatatttaac ttaaatcagt gagaaactct gtgaaaaaaa aaaaaaaaa 3841  aaa
```

PAXIP1 (accession No. NM_007349):

```
  1  cggggccggg cgccgccgcg gagcctcccg ggccgccgcg atcatgtcgg accaggcgcc 61  caaagttcct gaggagatgt tcagggaggt caagtattac gcggtgggcg acatcgaccc 121  gcaggttatt cagcttctca aggctgaaaa agcgaaggaa gtttcctaca atgcactagc 181  ctcacacata atctcagagg atggggacaa tccagaggtg ggagaagctc gggaagtctt 241  tgacttacct gttgtaaagc cttcttgggt gattctgtcc gttcagtgtg gaactcttct 301  gccagtaaat ggttttttctc cagaatcatg tcagattttt tttggaatca ctgcctgcct 361  ttctcaggtg tcatctgaag acagaagtgc cctgtgggct ttggttacgt tctatggggg 421  agattgccag ctaaccctca ataagaaatg cacgcatttg attgttccag agccaaaggg
```

-continued

```
 481   ggagaaatac gaatgtgctt taaagcgagc aagtattaaa attgtgactc ctgactgggt
 541   tctggattgc gtatcagaga aaccaaaaa ggacgaagca ttttatcatc ctcgtctgat
 601   tatttatgaa gaggaagaag aggaagagga agaggaggag gaagtagaaa atgaggaaca
 661   agattctcag aatgagggta gtacagatga aagtcaagc cctgccagct ctcaagaagg
 721   gtctccttca ggtgaccagc agttttcacc taaatccaac actgaaaaat ctaaagggga
 781   attaatgttt gatgattctt cagattcatc accggaaaaa caggagagaa atttaaactg
 841   gaccccggcc gaagtccac agttagctgc agcaaaacgc aggctgcctc agggaaagga
 901   gcctggggttg attaacttgt gtgccaatgt cccacccgtc ccaggtaaca ttttgccccc
 961   tgaggtccgg ggtaatttaa tggctgctgg acaaaacctc caaagttctg aaagatcaga
1021   aatgatagct acctggagtc cagctgtacg gacactgagg aatattacta ataatgctga
1081   cattcagcag atgaaccggc catcaaatgt agcacatatc ttacagactc tttcagcacc
1141   tacgaaaaat ttagaacagc aggtgaatca cagccagcag ggacataaa atgccaatgc
1201   agtgctgttt agccaagtga aagtgactcc agagacacac atgctacagc agcagcagca
1261   ggcccagcag cagcagcagc agcacccggt tttacacctt cagccccagc agataatgca
1321   gctccagcag cagcagcagc agcagatctc tcagcaacct taccccccagc agccgccgca
1381   tccattttca cagcaacagc agcagcagca gcaagcccat ccgcatcagt tttcacagca
1441   acagctacag tttccacagc aacagttgca tcctccacag cagctgcatc gccctcagca
1501   gcagctccag cccttttcagc agcagcatgc cctgcagcag cagttccatc agctgcagca
1561   gcaccagctc cagcagcagc agcttgccca gctccagcag cagcacagcc tgctccagca
1621   gcagcagcaa cagcagattc agcagcagca gctccagcgc atgcaccagc agcagcagca
1681   gcagcagatg caaagtcaga cagcgccaca cttgagtcag acgtcacagg cgctgcagca
1741   tcaggttcca cctcagcagc ccccgcagca gcagcagcaa cagcagccac caccatcgcc
1801   tcagcagcat cagctttttg acatgatcc agcagtggag attccagaag aaggcttctt
1861   attgggatgt gtgtttgcaa ttgcggatta ccagagcag atgtctgata agcaactgct
1921   ggccacctgg aaaaggataa tccaggcaca tggcggcact gttgaccca ccttcacgag
1981   tcgatgcacg caccttctct gtgagagtca agtcagcagc gcgtatgcac aggcaataag
2041   agaaagaaag agatgtgtta ctgcacactg gttaaacaca gtcttaaaga agaagaaat
2101   ggtaccgccg caccgagccc ttcacttccc agtggccttc ccaccaggag gaaagccatg
2161   ttcacagcat attatttctg tgactggatt tgttgatagt gacagagatg acctaaaatt
2221   aatggcttat ttggcaggtg ccaaatatac gggttatcta tgccgcagca acacagtcct
2281   catctgtaaa gaaccaactg gtttaaagta tgaaaaagcc aaagagtgga ggataccctg
2341   tgtcaacgcc cagtggcttg gcgacattct tctgggaaac tttgaggcac tgaggcagat
2401   tcagtatagt cgctacacgg cattcagtct gcaggatcca tttgcccta cccagcattt
2461   agttttaaat cttttagatg cttggagagt tcccttaaaa gtgtctgcag agttgttgat
2521   gagtataaga ctacctccca aactgaaaca gaatgaagta gctaatgtcc agccttcttc
2581   caaaagagcc agaattgaag acgtaccacc tcccactaaa aagctaactc cagaattgac
2641   ccctttttgtg cttttcactg gattcgagcc tgtccaggtt caacagtata ttaagaagct
2701   ctacattctt ggtggagagg ttgcggagtc tgcacagaag tgcacacacc tcattgccag
2761   caaagtgact cgcaccgtga agttcctgac ggcgatttct gtcgtgaagc acatagtgac
2821   gccagagtgg ctgaagaat gcttcaggtg tcagagttc attgatgagc agaactacat
2881   tctccgagat gctgaggcag aagtacttttt ctctttcagc ttggaagaat ccttaaaacg
```

-continued

```
2941    ggcacacgtt tctccactct ttaaggcaaa atattttac atcacacctg gaatctgccc
3001    aagtctttcc actatgaagg caatcgtaga gtgtgcagga ggaaaggtgt tatccaagca
3061    gccatctttc cggaagctca tggagcacaa gcagaactcg agtttgtcgg aaataatttt
3121    aatatcctgt gaaaatgacc ttcatttatg ccgagaatat tttgccagag catagatgt
3181    tcacaatgca gagttcgttc tgactggagt gctcactcaa acgctggact atgaatcata
3241    taagtttaac tgatggcgtc taggctgccg tgcatgtcga ctcctgcggt gcggggctgg
3301    ctgtctggct ggcgaggagc tgctgcgctt ccttcacatg ctcttgtttt ccagctgctt
3361    tcctggggga tcagactgtg aagcaggaag acagatataa taaatatact gcatcttttt
3421    aagatgtgca attttattct gaggaaacat aaattatgtt ttgtattata tgactttaag
3481    agcccacatt aggttttatg attcatttgc caggttttta aatgttttca caaaactgtt
3541    acgggacttc aactagaaat aaaatggtgt aaataaagac cttgctatct ctaaattatg
3601    gatgttaaag atttgaaatg ttttgtactt tgattatttt tatttcttat actctgtttt
3661    cttttatatt gatatcttgc ccacatttta aataaatgta cttttgaact taaaaaaaaa
3721    aaa
```

ASH1L (accession No. NM_018489):
```
   1    aggagtggaa ggttgagggg ggcgctaggc gcccttcgct ccctccctct ggaggagctg
  61    ccgccgccac cgccgccact ctgctgctgc cgccgccgcc gccgccgctc ccgccgccat
 121    tttgggttcg ctttgcggag gggagacgat cccagtctcg gttgcgggac ccgcctcccc
 181    tcagtttgcc cccttagcc ttccaccttt ccttctcct ctctcgcatt ccgccagtc
 241    agcttacccg ctggccgcct cctgacaagc gggagggatc cgccgtggac ccagggaagc
 301    ggaggagcct ggcggccacc ccctcttccc cacttccctg cactctcatc gctctcggcc
 361    tcggcctcgg cctccgacac gagaaagatg ctggtttcga gttttggaga tccttgtttt
 421    ttatggaaca cagttctgta aaattttcat aagattcctt ggcaataaca tacgcttgtg
 481    atggaccta gaaatactgc tatgttagga ttgggttctg attccgaagg ttttcaaga
 541    aagagtcctt ctgccatcag tactggcaca ttggtcagta agagagaagt agagctagaa
 601    aaaaacacaa aggaggaaga ggaccttcgc aaacggaatc gagaaagaaa catcgaagct
 661    gggaaagatg atggtttgac tgatgcacag caacagtttt cagtgaaaga aacaaacttt
 721    tcagagggaa atttaaaatt gaaaattggc ctccaggcta agagaactaa aaaacctcca
 781    aagaacttgg agaactatgt atgtcgacct gccataaaaa caactattaa gcacccaagg
 841    aaagcactta aaagtggaaa gatgacggat gaaaagaatg aacactgtcc ttcaaaacga
 901    gacccttcaa agttgtacaa gaaagcagat gatgttgcag ccattgaatg ccagtctgaa
 961    gaagtcatcc gtcttcattc acagggagaa aacaatcctt tgtctaagaa gctgtctcca
1021    gtacactcag aaatggcaga ttatattaat gcaacgccat ctactcttct tggtagccgg
1081    gatcctgatt taaggacag agcattactt aatggaggaa ctagtgtaac agaaaagttg
1141    gcacagctga ttgctacctg tcctccttcc aagtcttcca agacaaaacc gaagaagtta
1201    ggaactggca ctacagcagg attggttagc aaggatttga tcaggaaagc aggtgttggc
1261    tctgtagctg gaataataca taaggactta ataaaaaagc caaccatcag cacagcagtt
1321    ggattggtaa ctaaagatcc tgggaaaaag ccagtgttta atgcagcagt aggattggtc
1381    aataaggact ctgtgaaaaa actgggaact ggcactacag cggtattcat taataaaaac
1441    ttaggcaaaa agccaggaac tatcactaca gtaggactgc taagcaaaga ttcaggaaag
1501    aagctaggaa ttggtattgt tccaggttta gtgcataaag agtctggcaa gaagttagga
```

```
-continued
1561  cttggcactg tggttggact ggttaataaa gatttgggaa agaaattggg ttctactgtt
1621  ggcctagtgg ccaaggactg tgcaaagaag attgtagcaa gttcagcaat gggattggtt
1681  aataaggaca ttggaaagaa actaatgagt tgtcctttgg caggtctgat cagtaaagat
1741  gccataaacc ttaaagccga agcactgctc cccactcagg aaccgcttaa ggcttcttgt
1801  agtacaaaca tcaataatca ggaaagtcag gaactttctg aatccctgaa agatagtgcc
1861  accagcaaaa cttttgaaaa gaatgttgta cggcagaata agaaagcat attggaaaag
1921  ttctcagtac gaaaagaaat cattaatttg gagaaagaaa tgtttaatga aggaacatgc
1981  attcagcaag acagtttctc atccagtgaa aagggatctt atgaaacctc aaagcatgaa
2041  aagcagcctc ctgtatattg cacttctccg gactttaaaa tgggaggtgc ttctgatgta
2101  tctaccgcta aatccccatt cagtgcagta ggagaaagca atctcccttc cccatcacct
2161  actgtatctg ttaatccttt aaccagaagt cccctgaaa cttcttcaca gttggctcct
2221  aatccattac ttttaagttc tactacagaa ctaatcgaag aaatttctga atctgttgga
2281  aagaaccagt ttacttctga agtacccac ttgaacgttg gtcataggtc agttggtcat
2341  agtataagta ttgaatgtaa agggattgat aaagaggtaa atgattcaaa aactacccat
2401  atagatattc caagaataag ctcttccctt ggaaaaaagc caagtttgac ttctgaatcc
2461  agcattcata ctattactcc ttcagttgtt aacttcacta gtttatttag taataagcct
2521  tttttaaaac tgggtgcagt atctgcatca gacaaacact gccaagttgc tgaaagccta
2581  agtactagtt tgcagtccaa accattaaaa aaaagaaaag gaagaaaacc tcggtggact
2641  aaagtggtgg caagaagcac atgccggtct ccaaaagggc tagaattaga aagatcagag
2701  cttttttaaaa acgtttcatg tagctcacta tcaaatagta attctgagcc agccaagttt
2761  atgaaaaaca ttggaccccc ttcatttgta gatcatgact tccttaaacg ccgattgcca
2821  aagttgagca atccacagc tccatctctt gctctcttag ctgatagtga aaaaccatct
2881  cataagtctt tgctactca caaactatcc tccagtatgt gtgtctctag tgaccttttg
2941  tctgatattt ataagcccaa aagaggaagg cctaaatcta aggagatgcc tcaactggaa
3001  gggccaccta aaaggacttt aaaaatcct gcttctaaag tgttttcttt acagtctaag
3061  gaagaacaag acccccaat tttacagcca gaaattgaaa tcccttcctt caaacaaggt
3121  ctgtctgtgt ctccttttcc aaaaaagaga ggcaggccta agaggcaaat gaggtcacca
3181  gtcaagatga agccacctgt actgtcagtg gctccatttg ttgccactga aagtccaagc
3241  aagctagaat ctgaaagtga caaccataga agtagcagtg atttctttga gagcgaggat
3301  caacttcagg atccagatga cctagatgac agtcataggc caagtgtctg tagtatgagt
3361  gaccttgaga tggaaccaga taaaaaaatt accaagagaa acaatggaca attaatgaaa
3421  acaattatcc gcaaaataaa taaatgaag actttaaaga gaagaaact gttgaatcag
3481  attctttcaa gttctgtaga atcaagtaat aaagggaaag tgcaatccaa actccataat
3541  acggtatcaa gtcttgctgc cacatttggc tctaaattgg gccaacagat aaatgtcagc
3601  aagaaaggaa ccatttatat aggaaagaga gaggtcgca aaccaaaaac tgtcttaaat
3661  ggtattcttt ctggtagtcc tactagcctt gctgttcttg agcaaacagc tcaacaggca
3721  gctgggtcag cattaggaca gattcttccc ccattactgc cttcatctgc tagtagttct
3781  gagattcttc catcacctat ttgctctcag tcttctggga ctagtggagg tcagagccct
3841  gtaagtagtg atgcaggttt tgttgaaccc agttcagtgc catatttgca tttacactcc
3901  agacagggca gtatgattca gactcttgca atgaagaagg cctcaaaggg gaggaggcgg
```

-continued

```
3961  ttatctcctc ctactttgtt gccaaattct ccttcgcact tgagtgaact cacatctcta
4021  aaagaagcta ctccttcccc aatcagtgag tctcatagtg atgagaccat tcccagtgat
4081  agtggaattg aacagataa taacagcaca tcagacaggg cagagaaatt ttgtgggcaa
4141  aaaaagagga ggcattcttt tgagcatgtt tctctgattc cccctgaaac ctctacagtg
4201  ctaagcagtc ttaaagaaaa acataaacac aaatgtaagc gcaggaatca tgattacctc
4261  agctatgaca agatgaaaag gcagaaacga aaacggaaaa agaaatatcc ccagcttcga
4321  aatagacagg atccagactt tattgcagag ctggaggaac taataagtcg cctaagtgaa
4381  attcggatca ctcatcgaag tcatcatttt atcccccgag atcttctgcc aactatcttt
4441  cgaatcaact ttaatagttt ctatacacat ccttctttcc ccttagaccc tttgcactac
4501  attcgaaaac ctgacttaaa aagaaaaga gggagacccc taagatgag ggaggcaatg
4561  gctgaaatgc cttttatgca cagccttagt tttcctcttt ctagtactgg attctatcca
4621  tcttatggta tgccttactc tccttcaccc cttacagctg ctcccatagg attaggttac
4681  tatggaaggt atcctcccac tctttatcca cctcctccat ctccttcttt caccacgcca
4741  cttccacctc cttcctatat gcatgctggt catttacttc tcaatcctgc caaataccat
4801  aagaaaaagc ataagctact tcgacaggag gccttttctta caaccagcag gactcccctc
4861  ctttccatga gtacctaccc cagtgttcct cctgagatgg cctatggttg gatggttgag
4921  cacaaacaca ggcaccgtca caaacacaga gaacaccgtt cttctgaaca accccaggtt
4981  tctatggaca ctggctcttc ccgatctgtc ctggaatctt tgaagcgcta tagatttgga
5041  aaggatgctg ttggagagcg atataagcat aaggaaaagc accgttgtca catgtcctgc
5101  cctcatctct ctccttcaaa aagcttaata aacagagagg aacagtgggt ccaccgagag
5161  ccttcagaat ctagtccatt ggccttggga ttgcagacac ctttacagat tgactgttca
5221  gaaagttctc caagcttatc ccttggagga ttcactccca actctgagcc agccagcagt
5281  gatgaacata caaaccttt cacaagtgca ataggcagct gcagagtttc aaaccctaac
5341  tccagtggcc ggaagaaatt aactgacagc cctggactct tttctgcaca ggacacttca
5401  ctaaatcggc ttcacagaaa ggagtcactg ccttctaacg aaagggcagt acagactttg
5461  gcaggctccc agccaacctc tgataaaccc tcccagcggc catcagagag cacaaattgt
5521  agcccctaccc ggaaaaggtc ttcatctgag agtacttctt caacagtaaa cggagttccc
5581  tctcgaagtc caagattagt tgcttctggg gatgactctg tggatagtct gctgcagcgg
5641  atggtacaaa atgaggacca agagcccatg gagaaaagta ttgatgctgt gattgcaact
5701  gcctctgcac caccttcttc cagtccaggc cgtagccaca gcaaggaccg aaccctggga
5761  aaaccagaca gccttttagt gcctgcagtc acaagtgact cttgcaataa tagcatctca
5821  ctcctatctg aaaagttgac aagcagctgt tcccccatc atatcaagag aagtgtagtg
5881  gaagctatgc aacgccaagc tcggaaaatg tgcaattacg acaaaatctt ggccacaaag
5941  aaaaacctag accatgtcaa taaaatctta aaagccaaaa aacttcaaag gcaggccagg
6001  acagggaata actttgtgaa acgtaggcca ggtcgacctc ggaaatgtcc ccttcaggct
6061  gtcgtatcaa tgcaagcatt ccaggctgct cagtttgtca acccagaatt gaacagagac
6121  gaggaaggag cagcactgca cctcagtcct gacacagtta cagatgtaat tgaggctgtt
6181  gttcagagtg taaatctgaa cccagaacat aaaaaggggt tgaagagaaa aggttggcta
6241  ttggaagaac agaccagaaa aaagcagaag ccattaccag aggaagaaga gcaagagaat
6301  aataaaagct ttaatgaagc accagttgag attcccagtc cttctgaaac cccagctaaa
6361  ccttctgaac ctgaaagtac cttgcagcct gtgctttctc tcatcccaag ggaaaagaag
```

-continued

```
6421  cccccacgtc ccccaaagaa gaagtatcag aaagcagggc tgtattctga cgtttacaaa
6481  actacagacc caaagagtcg attgatccaa ttaaagaaag agaagctgga gtatactcca
6541  ggagagcatg aatatggatt atttccagcg cccattcatg ttggaaagta tctaagacaa
6601  aagagaattg acttccagct tccttatgat atcctttggc agtggaaaca caatcagcta
6661  tacaaaaagc cagatgtccc actatataag aaaattcgtt caaatgtcta cgttgatgtc
6721  aaacccttt ctggttacga agctaccacc tgtaactgta agaagccaga tgatgacacc
6781  aggaagggct gtgttgatga ctgcctcaat agaatgatct tgctgagtg ttcccccaac
6841  acttgcccat gtggcgagca atgctgtaac cagaggatac agaggcatga atgggtgcaa
6901  tgtctagaac gatttcgagc tgaggaaaaa ggttggggaa tcagaaccaa agagcccta
6961  aaagctgggc agttcatcat tgaatacca ggggaggtcg tcagtgaaca ggagttcagg
7021  aacaggatga ttgagcagta tcataatcac agtgaccact actgcctgaa cctggatagt
7081  gggatggtga ttgacagtta ccgcatggga aatgaggccc gattcatcaa ccatagctgt
7141  gacccaaatt gtgaaatgca gaaatggtct gttaatggag tataccggat tggactctat
7201  gctcttaaag acatgccagc tgggactgaa ctcacttatg attataactt tcattccttc
7261  aatgtggaaa aacagcaact tgtaagtgt ggctttgaga atgtcgagg aatcatcgga
7321  ggcaagagtc agcgtgtgaa tggactcacc agcagcaaaa acagccagcc catggccaca
7381  cacaaaaat ctggacggtc aaaagagaag agaaagtcta agcacaagct gaagaaaagg
7441  agaggccatc tctctgagga acccagtgaa aatatcaaca ccccaactag attgacccc
7501  caattacaga tgaagccaat gtccaatcgt gaaaggaact tgtgttaaa gcatcatgta
7561  ttcttggtcc gaaactggga agagattcgt caaaaacagg aggaagtaaa gcacaccagt
7621  gataatattc actcagcatc attatatacc cgttggaatg ggatctgccg agatgatggg
7681  aatatcaagt ctgatgtctt catgacccag ttctctgccc tgcagacagc tcgatctgtt
7741  cgaacaagac ggttggcagc tgcagaggaa aatattgaag tggctcgggc agcccgccta
7801  gcccagatct tcaaagaaat ttgtgatggt atcatctctt ataaagattc ttcccggcaa
7861  gcactggcag ctccactttt gaaccttccc ccaaagaaaa agaatgctga ttattatgag
7921  aagatctctg atcccctaga tcttatcacc atagagaagc agatcctcac tggttactat
7981  aagacagtgg aagcttttga tgctgacatg ctcaaagtct ttcggaatgc tgagaagtac
8041  tatgggcgta atcccccagt tgggagagat gtttgtcgtc tacgaaaggc ctattacaat
8101  gcccggcatg aggcatcagc ccagattgat gagattgtgg agagacagc aagtgaggca
8161  gacagcagtg agacctcagt ctctgaaaag gagaatgggc atgagaagga cgacgatgtt
8221  attcgctgta tctgtggcct ctacaaggat gaaggtctca tgatccagtg tgacaagtgc
8281  atggtatggc agcactgtga ttgtatggga gtgaactcag atgtggagca ctacctttgt
8341  gagcagtgtg acccaaggcc tgtgacagg gaggttccca tgatccctcg gccccactat
8401  gcccaacctg gctgtgtcta cttcatctgt ttgctccgag atgacttgct gcttcgtcag
8461  ggtgactgtg tgtatctgat gagggatagt cggcgcaccc ctgatggcca ccggtccgt
8521  cagtcctatc gactgttatc tcacattaac cgagataaac ttgacatctt tcgcattgag
8581  aagctttgga gaatgaaaa agaggaacgg tttgcctttg gtcaccatta tttccgtccc
8641  cacgaaacac accactctcc atcccgtcgg ttctatcata tgaactatt tcgggtgcca
8701  ctctatgaga tcattcctt ggaggctgta gtgggacct gctgtgtgtt ggacctttat
8761  acgtattgta aagggagacc caaaggagta aaggagcaag atgtgtacat ctgtgattat
```

-continued

```
8821  cggcttgaca agtcagcaca cctgttttac aagatccacc ggaaccgcta tcctgtctgc
8881  accaaaccct atgcttttga tcacttcccc aagaagctca ctcccaaaaa agatttctcg
8941  cctcattacg tcccagacaa ctacaagagg aatggaggac gatcatcctg gaagtctgag
9001  cgctcaaagc caccoctaaa agacttgggc caggaggatg atgctctacc cttgattgaa
9061  gaggttctag ccagtcaaga gcaagcagcc aatgagatac ccagcctgga ggagccagaa
9121  cgggaagggg ccactgctaa cgtcagtgag ggtgaaaaaa aaacagagga aagtagtcaa
9181  gaaccccagt caacctgtac ccctgaggaa cgacggcata accaacggga acgactcaac
9241  cagatcttgc tcaatctcct tgaaaaaatc cctggaaaaa atgccattga tgtgacctac
9301  ttgctggagg aaggatcagg caggaaactg cgaaggcgta ctttgtttat cccagaaaac
9361  agctttcgaa agtgaccctc aaagaatgag aacctcaagc atctgggatc cagtggagct
9421  aatcagtcct gcctcctgct ctctgggtat agacaggggt gggaagggtc atctgggca
9481  aggggaatgg ggccatgttg ttgacattag gtacttaata agccttggag ctagtggaga
9541  gggagaggaa agggttctgt ccaagacagt tcaggttaat taattttctt ctccattgct
9601  tcaccttaag ggttaataat gtagagagga gggaggacca cattgatgac cagaacctac
9661  tggtacttta tagcatttgc cccaccccac agcttaggtt tttctgtcat cctcagatcc
9721  cacaggcatt gcgaagaagc tgcttcctat acccaggtat aactcaaaat ccaagggat
9781  agggccagga tccctattcc taccccatct attctctgtt ggctccaaga gctaccccag
9841  agaccttaaa cagaaacagt agctgaggct tcttcctaga tacctgacta gggaagtttg
9901  tctctccttt cttgcccaac caggtcaaag taaatgtga gttgacagct caaagcactt
9961  gtaactgctg ccccctccct acctctactc cccaaaatgg aatcatggga tagggaaggc
10021 ccccatgggg tcagaagggc acggtagttc ttgcaattat ttttgtttta cccttcataa
10081 cctgtcaaac atatttttt ctaatgagaa agccaggccc ccgccagcac acatgctgtt
10141 tttaatgcgc tgtagttctt gtgtgtctgc tgtgctgtgc aaatggagat tcagttcaaa
10201 ataaaatcat ttaaaaacct acataaaaag aactctaaac ccaccctgc aacaaagtc
10261 actacataaa ctgttcagca gtattcacct atcagagtat tgttgtgag tatagattat
10321 caattgaaaa cactactctt gttttcttaa ttgtacagtt tcaatgtcc ctttcttaaa
10381 gagacagtat atttctcttc accoctagcc catcttccct cacccctcctg aatgacatca
10441 ggaggtatat ccagggtgtc tccttccttc ctactctctt gaccagaagt taacagacta
10501 tactgtctct ttaaaaataa aatttaaaaa gctttgttgt cttttcagac atacatatgc
10561 atatatgttt tagatgttct tataagagaa aagatggttt ttaaatgtgc caagttgtgt
10621 gtgtgtgtgt atatatatgt gtgtatgtgt gtgtatatat atatgtgtgt gtgtatatat
10681 atacacacac acacacacac ctgctgtgtg attggtaagc aatacaatag taaacatgtc
10741 cccattactt ttttctaata ttggaccaat gctgtcctaa ttgtacattt cccctattgg
10801 tgacgatgct ctgactcgtt taggtagaca cattgaccac cttccattcc attaaatatt
10861 ttttcctttt tccccttct gtgtcattct tgaggaaaaa acaaaagaga gagggatgc
10921 caatgatccc cttgagcaga gaaaagcaa ataaatatt ttattaaga aaaagagaa
10981 ttaagaaaat agtttggagt attttcttac tgtagagaag cactgtacat tactaagaga
11041 cctgggtata agatactcac atgtggagct ggaaaaatcg catgtccaag cccgtttgag
11101 tggtttcttt tgttttcat tgcaggagt gggtgggagg gaggtgggac taggggcact
11161 ttgggggtct ccttttagtc aaaagcgaga aaatgacaag aaagagatta aaattcaatg
11221 tttcctttat agtgttaaac actaaaattt taaaaaagat gaaaagaaa aaaaactt
```

-continued

```
11281  gtaaaatgcg agaacagaag caaaagacac tacgctctgt cattttatct ttattttgtt
11341  gaaagactaa aaaaaaactg aaatgttttt tagacaatca aatgttaggt aagtgcaaaa
11401  acttgttttt tcttactggt gtagaaatta atgccttttt ttattttttca gttattttat
11461  aataacgaaa taaaagaac ccccagctg ccaggcgggt tttggtgttt gaaatgcggg
11521  gcaaagcact acatcactgc aaatagatac agagttagtc tgcatgtctg taggctgtgt
11581  gattgcggaa aatataaatg ctgctaatat atttcctttt tacaaaagca tatctaaata
11641  gatgattgtt ttgatgttaa tattgttaaa ttatgtatta ccaattttaa cattggatgt
11701  aattgcatac aaagcttgca tctcaatcct tgaaagtcta gtattaaatg gaaaaaactt
11761  ttcctaactg tggaaaaaaa aaaa
```

SMARCA2 (accession No. NM_003070):

```
    1  gcgtcttccg gcgcccgcgg aggaggcgag ggtgggacgc tgggcggagc ccgagtttag
   61  gaagaggagg ggacggctgt catcaatgaa gtcatattca taatctagtc ctctctccct
  121  ctgtttctgt actctgggtg actcagagag ggaagagatt cagccagcac actcctcgcg
  181  agcaagcatt actctactga ctggcagaga caggagaggt agatgtccac gcccacagac
  241  cctggtgcga tgccccaccc agggccttcg ccggggcctg ggccttcccc tgggccaatt
  301  cttgggccta gtccaggacc aggaccatcc ccaggttccg tccacagcat gatggggcca
  361  agtcctggac ctccaagtgt ctcccatcct atgccgacga tggggtccac agacttccca
  421  caggaaggca tgcatcaaat gcataagccc atcgatggta tacatgacaa ggggattgta
  481  gaagacatcc attgtggatc catgaagggc actggtatgc gaccacctca cccaggcatg
  541  ggccctcccc agagtccaat ggatcaacac agccaaggtt atatgtcacc acacccatct
  601  ccattaggag ccccagagca cgtctccagc cctatgtctg gaggaggccc aactccacct
  661  cagatgccac caagccagcc gggggccctc atcccaggtg atccgcaggc catgagccag
  721  cccaacagag gtccctcacc tttcagtcct gtccagctgc atcagcttcg agctcagatt
  781  ttagcttata aaatgctggc ccgaggccag cccctccccg aaacgctgca gcttgcagtc
  841  caggggaaaa ggacgttgcc tggcttgcag caacaacagc agcagcaaca gcagcagcag
  901  cagcagcagc agcagcagca gcagcagcaa cagcagccgc agcagcagcc gccgcaacca
  961  cagacgcagc aacaacagca gccggcccct gttaactaca acagaccatc tggcccgggg
 1021  ccggagctga gcggcccgag caccccgcag aagctgccgg tgcccgcgcc cggcggccgg
 1081  ccctcgcccg cgcccccgcg agccgcgcag ccgccgcgcg gccgcagtgcc cgggccctca
 1141  gtgccgcagc cggccccggg gcagccctcg cccgtcctcc agctgcagca gaagcagagc
 1201  cgcatcagcc ccatccgaa accgcaaggc ctggacccgg tggaaattct gcaagagcgg
 1261  gaatacagac ttcaggcccg catagctcat aggatacaag aactggaaaa tctgcctggc
 1321  tctttgccac cagatttaag aaccaaagca accgtggaac taaaagcact tcggttactc
 1381  aatttccagc gtcagctgag acaggaggtg gtggcctgca tgcgcaggga cacgacctg
 1441  gagacggctc tcaactccaa agcatacaaa cggagcaagc gccagactct gagagaagct
 1501  cgcatgaccg agaagctgga gaagcagcag aagattgagc aggagaggaa acgccgtcag
 1561  aaacaccagg aatacctgaa cagtattttg caacatgcaa agatttttaa ggaatatcat
 1621  cggtctgtgg ccggaaagat ccagaagctc tccaaagcag tggcaacttg gcatgccaac
 1681  actgaaagag agcagaagaa ggagacagag cggattgaaa aggagagaat gcggcgactg
 1741  atggctgaag atgaggaggg ttatagaaaa ctgattgatc aaaagaaaga caggcgttta
 1801  gcttaccttt tgcagcagac cgatgagtat gtagccaatc tgaccaatct ggtttgggag
```

```
1861  cacaagcaag cccaggcagc caaagagaag aagaagagga ggaggaggaa gaagaaggct
1921  gaggagaatg cagagggtgg ggagtctgcc ctgggaccgg atggagagcc catagatgag
1981  agcagccaga tgagtgacct ccctgtcaaa gtgactcaca cagaaaccgg caaggttctg
2041  ttcggaccag aagcacccaa agcaagtcag ctggacgcct ggctggaaat gaatcctggt
2101  tatgaagttg cccctagatc tgacagtgaa gagagtgatt ctgattatga ggaagaggat
2161  gaggaagaag agtccagtag gcaggaaacc gaagagaaaa tactcctgga tccaaatagc
2221  gaagaagttt ctgagaagga tgctaagcag atcattgaga cagctaagca agacgtggat
2281  gatgaataca gcatgcagta cagtgccagg ggctcccagt cctactacac cgtggctcat
2341  gccatctcgg agagggtgga gaaacagtct gccctcctaa ttaatgggac cctaaagcat
2401  taccagctcc agggcctgga atggatggtt tccctgtata ataacaactt gaacggaatc
2461  ttagccgatg aaatggggct tggaagacc atacagacca ttgcactcat cacttatctg
2521  atggagcaca aaagactcaa tggcccctat ctcatcattg ttccccttc gactctatct
2581  aactggacat atgaatttga caaatgggct ccttctgtgg tgaagatttc ttacaagggt
2641  actcctgcca tgcgtcgctc ccttgtcccc cagctacgga gtggcaaatt caatgtcctc
2701  ttgactactt atgagtatat tataaaagac aagcacattc ttgcaaagat tcggtggaaa
2761  tacatgatag tggacgaagg ccaccgaatg aagaatcacc actgcaagct gactcaggtc
2821  ttgaacactc actatgtggc ccccagaagg atcctcttga ctgggacccc gctgcagaat
2881  aagctccctg aactctgggc cctcctcaac ttcctcctcc aacaatttt taagagctgc
2941  agcacatttg aacaatggtt caatgctcca tttgccatga ctggtgaaag ggtggactta
3001  aatgaagaag aaactatatt gatcatcagg cgtctacata aggtgttaag accatttta
3061  ctaaggagac tgaagaaaga agttgaatcc cagcttcccg aaaaagtgga atatgtgatc
3121  aagtgtgaca tgtcagctct gcagaagatt ctgtatcgcc atatgcaagc caagggggatc
3181  cttctcacag atggttctga aaagataag aaggggaaag gaggtgctaa gacacttatg
3241  aacactatta tgcagttgag aaaaatctgc aaccacccat atatgtttca gcacattgag
3301  gaatcctttg ctgaacacct aggctattca aatggggtca tcaatggggc tgaactgtat
3361  cgggcctcag ggaagtttga gctgcttgat cgtattctgc caaaattgag agcgactaat
3421  caccgagtgc tgcttttctg ccagatgaca tctctcatga ccatcatgga ggattatttt
3481  gcttttcgga acttccttta cctacgcctt gatggcacca ccaagtctga agatcgtgct
3541  gctttgctga agaaattcaa tgaacctgga tcccagtatt tcattttctt gctgagcaca
3601  agagctggtg gcctgggctt aaatcttcag gcagctgata cagtggtcat ctttgacagc
3661  gactggaatc ctcatcagga tctgcaggcc aagaccgag ctcaccgcat cgggcagcag
3721  aacgaggtcc gggtactgag gctctgtacc gtgaacagcg tggaggaaaa gatcctcgcg
3781  gccgcaaaat acaagctgaa cgtggatcag aaagtgatcc aggcgggcat gtttgaccaa
3841  aagtcttcaa gccacgagcg gagggcattc ctgcaggcca tcttggagca tgaggaggaa
3901  aatgaggaag aagatgaagt accggacgat gagactctga accaaatgat tgctcgacga
3961  gaagaagaat ttgacctttt tatgcggatg gacatggacc ggcggaggga agatgcccgg
4021  aacccgaaac ggaagcccg tttaatggag gaggatgagc tgccctcctg gatcattaag
4081  gatgacgctg aagtagaaag gctcacctgt gaagaagagg aggagaaaat atttgggagg
4141  gggtcccgcc agcgccgtga cgtggactac agtgacgccc tcacggagaa gcagtggcta
4201  agggccatcg aagacggcaa tttggaggaa atggaagagg aagtacggct taagaagcga
```

-continued

```
4261  aaaagacgaa gaaatgtgga taaagatcct gcaaaagaag atgtggaaaa agctaagaag
4321  agaagaggcc gccctcccgc tgagaaactg tcaccaaatc cccccaaact gacaaagcag
4381  atgaacgcta tcatcgatac tgtgataaac tacaaagata ggtgtaacgt ggagaaggtg
4441  cccagtaatt ctcagttgga aatagaagga aacagttcag ggcgacagct cagtgaagtc
4501  ttcattcagt taccttcaag gaaagaatta ccagaatact atgaattaat taggaagcca
4561  gtggatttca aaaaaataaa ggaaaggatt cgtaatcata agtaccggag cctaggcgac
4621  ctggagaagg atgtcatgct tctctgtcac aacgctcaga cgttcaacct ggagggatcc
4681  cagatctatg aagactccat cgtcttacag tcagtgttta agagtgcccg gcagaaaatt
4741  gccaaagagg aagagagtga ggatgaaagc aatgaagagg aggaagagga agatgaagaa
4801  gagtcagagt ccgaggcaaa atcagtcaag gtgaaaatta agctcaataa aaaagatgac
4861  aaaggccggg acaaagggaa aggcaagaaa aggccaaatc gaggaaaagc caaacctgta
4921  gtgagcgatt ttgacagcga tgaggagcag gatgaacgtg aacagtcaga aggaagtggg
4981  acggatgatg agtgatcagt atggaccttt ttccttggta gaactgaatt ccttcctccc
5041  ctgtctcatt tctacccagt gagttcattt gtcatatagg cactgggttg tttctatatc
5101  atcatcgtct ataaactagc tttaggatag tgccagacaa acatatgata tcatggtgta
5161  aaaacacac acatacacaa atatttgtaa catattgtga ccaaatgggc ctcaaagatt
5221  cagattgaaa caaacaaaaa gcttttgatg gaaatatgt gggtggatag tatatttcta
5281  tgggtgggtc taatttggta acggtttgat tgtgcctggt tttatcacct gttcagatga
5341  gaagattttt gtcttttgta gcactgataa ccaggagaag ccattaaaag ccactggtta
5401  ttttatttt catcaggcaa ttttcgaggt ttttatttgt tcggtattgt ttttttacac
5461  tgtggtacat ataagcaact ttaataggtg ataaatgtac agtagttaga tttcacctgc
5521  atatacattt ttccatttta tgctctatga tctgaacaaa gcttttga attgtataag
5581  atttatgtct actgtaaaca ttgcttaatt ttttgctct tgatttaaaa aaaagttttg
5641  ttgaaagcgc tattgaatat tgcaatctat atagtgtatt ggatggcttc ttttgtcacc
5701  ctgatctcct atgttaccaa tgtgtatcgt ctccttctcc ctaaagtgta cttaatcttt
5761  gctttctttg cacaatgtct ttggttgcaa gtcataagcc tgaggcaaat aaaattccag
5821  taatttcgaa gaatgtggtg ttggtgcttt cctaataaag aaataattta gcttgacaaa
5881  aaaaaaaaaa aa
```

SMARCA4 (accession No. NM_001128844):

```
  1  ggagaggccg ccgcggtgct gagggggagg ggagccggcg agcgcgcgcg cagcggggc
 61  gcgggtggcg cgcgtgtgtg tgaagggggg gcggtggccg aggcgggcgg gcgcgcgcgc
121  gaggcttccc ctcgtttggc ggcggcggc gcttctttgt ttcgtgaaga gaagcgagac
181  gcccattctg ccccggccc cgcgcggagg ggcggggag gcgccgggaa gtcgacggcg
241  ccggcggctc ctgcgtctcg ccctttgcc caggctagag tgcagtggtg cggtcatggt
301  tcactgcagc ctcaacctcc tggactcagc aggaggccac tgtctgcagc tcccgtgaag
361  atgtccactc cagacccacc cctgggcgga actcctcggc caggtccttc cccgggccct
421  ggcccttccc ctggagccat gctgggccct agcccgggtc cctcgccggg ctccgcccac
481  agcatgatgg ggcccagccc agggccgccc tcagcaggac accccatccc cacccagggg
541  cctggagggt accctcagga caacatgcac cagatgcaca gcccatggga gtccatgcat
601  gagaagggca gtcggacga cccgcgctac aaccagatga aggaatgggg gatgcggtca
661  gggggccatg ctgggatggg gccccgccc agccccatgg accagcactc ccaaggttac
```

-continued

```
 721   ccctcgcccc tgggtggctc tgagcatgcc tctagtccag ttccagccag tggcccgtct
 781   tcggggcccc agatgtcttc cgggccagga ggtgccccgc tggatggtgc tgacccccag
 841   gccttggggc agcagaaccg gggcccaacc ccatttaacc agaaccagct gcaccagctc
 901   agagctcaga tcatggccta caagatgctg ccagggggc agcccctccc cgaccacctg
 961   cagatggcgg tgcagggcaa gcggccgatg cccgggatgc agcagcagat gccaacgcta
1021   cctccaccct cggtgtccgc aacaggaccc ggccctggcc ctggccctgg cccggcccg
1081   ggtcccggcc cggcacctcc aaattacagc aggcctcatg gtatgggagg gcccaacatg
1141   cctcccccag gaccctcggg cgtgccccc gggatgccag gccagcctcc tggagggcct
1201   cccaagccct ggcctgaagg acccatggcg aatgctgctg ccccacgag cacccctcag
1261   aagctgattc ccccgcagcc aacgggccgc ccttcccccg cgccccctgc cgtcccaccc
1321   gccgcctcgc ccgtgatgcc accgcagacc cagtccccg gcagccggc ccagcccgcg
1381   cccatggtgc cactgcacca aagcagagc cgcatcaccc ccatccagaa gccgcgggc
1441   ctcgaccctg tggagatcct gcaggagcgc gagtacaggc tgcaggctcg catcgcacac
1501   cgaattcagg aacttgaaaa ccttcccggg tccctggccg gggatttgcg aaccaaagcg
1561   accattgagc tcaaggccct caggctgctg aacttccaga ggcagctgcg ccaggaggtg
1621   gtggtgtgca tgcggaggga cacagcgctg gagacagccc tcaatgctaa ggcctacaag
1681   cgcagcaagc gccagtccct gcgcgaggcc cgcatcactg agaagctgga gaagcagcag
1741   aagatcgagc aggagcgcaa gcgccggcag aagcaccagg aatacctcaa tagcattctc
1801   cagcatgcca aggatttcaa ggaatatcac agatccgtca caggcaaaat ccagaagctg
1861   accaaggcag tggccacgta ccatgccaac acggagcggg agcagaagaa agagaacgag
1921   cggatcgaga aggagcgcat gcggaggctc atggctgaag atgaggaggg gtaccgcaag
1981   ctcatcgacc agaagaagga caagcgcctg gcctacctct gcagcagac agacgagtac
2041   gtggctaacc tcacggagct ggtgcggcag cacaaggctg cccaggtcgc aaggagaaa
2101   aagaagaaaa agaaaaagaa gaaggcagaa aatgcagaag acagacgcc tgccattggg
2161   ccggatggcg agcctctgga cgagaccagc cagatgagcg acctcccggt gaaggtgatc
2221   cacgtggaga gtgggaagat cctcacaggc acagatgccc ccaaagccgg gcagctggag
2281   gcctggctcg agatgaaccc ggggtatgaa gtagctccga ggtctgatag tgaagaaagt
2341   ggctcagaag aagaggaaga ggaggaggag gaagagcagc cgcaggcagc acagcctccc
2401   accctgcccg tggaggagaa gaagaagatt ccagatccag acagcgatga cgtctctgag
2461   gtggacgcgc ggcacatcat tgagaatgcc aagcaagatg tcgatgatga atatggcgtg
2521   tcccaggccc ttgcacgtgg cctgcagtcc tactatgccg tggcccatgc tgtcactgag
2581   agagtggaca agcagtcagc gcttatggtc aatggtgtcc tcaaacagta ccagatcaaa
2641   ggtttggagt ggctggtgtc cctgtacaac aacaacctga acggcatcct ggccgacgag
2701   atgggcctgg ggaagaccat ccagaccatc cgcctcatca cgtacctcat ggagcacaaa
2761   cgcatcaatg gccccttcct catcatcgtg cctctctcaa cgctgtccaa ctgggcgtac
2821   gagtttgaca gtgggcccc ctccgtggtg aaggtgtctt acaagggatc cccagcagca
2881   agacgggcct ttgtccccca gctccggagt gggaagttca cgtcttgct gacgacgtac
2941   gagtacatca tcaaagacaa gcacatcctc gccaagatcc gttggaagta catgattgtg
3001   gacgaaggtc accgcatgaa gaaccaccac tgcaagctga cgcaggtgct caacacgcac
3061   tatgtggcac cccgccgcct gctgctgacg gcacaccgc tgcagaacaa gcttcccgag
3121   ctctgggcgc tgctcaactt cctgctgccc accatcttca gagctgcag caccttcgag
```

-continued

```
3181  cagtggttta acgcacccct tgccatgacc ggggaaaagg tggacctgaa tgaggaggaa
3241  accattctca tcatccggcg tctccacaaa gtgctgcggc ccttcttgct ccgacgactc
3301  aagaaggaag tcgaggccca gttgcccgaa aaggtggagt acgtcatcaa gtgcgacatg
3361  tctgcgctgc agcgagtgct ctaccgccac atgcaggcca agggcgtgct gctgactgat
3421  ggctccgaga aggacaagaa gggcaaaggc ggcaccaaga ccctgatgaa caccatcatg
3481  cagctgcgga agatctgcaa ccaccctac atgttccagc acatcgagga gtccttttcc
3541  gagcacttgg ggttcactgg cggcattgtc caagggctgg acctgtaccg agcctcgggt
3601  aaatttgagc ttcttgatag aattcttccc aaactccgag caaccaacca caaagtgctg
3661  ctgttctgcc aaatgacctc cctcatgacc atcatggaag attactttgc gtatcgcggc
3721  tttaaatacc tcaggcttga tggaaccacg aaggcggagg accggggcat gctgctgaaa
3781  accttcaacg agcccggctc tgagtacttc atcttcctgc tcagcacccg ggctggggg
3841  ctcggcctga acctccagtc ggcagacact gtgatcattt ttgacagcga ctggaatcct
3901  caccaggacc tgcaagcgca ggaccgagcc caccgcatcg ggcagcagaa cgaggtgcgt
3961  gtgctccgcc tctgcaccgt caacagcgtg gaggagaaga tcctagctgc agccaagtac
4021  aagctcaacg tggaccagaa ggtgatccag gccggcatgt tcgaccagaa gtcctccagc
4081  catgagcggc gcgccttcct gcaggccatc ctggagcacg aggagcagga tgagagcaga
4141  cactgcagca cgggcagcgg cagtgccagc ttcgcccaca ctgcccctcc gccagcgggc
4201  gtcaaccccg acttggagga gccacctcta aaggaggaag acgaggtgcc cgacgacgag
4261  accgtcaacc agatgatcgc ccggcacgag gaggagtttg atctgttcat gcgcatggac
4321  ctggaccgca ggcgcgagga ggcccgcaac cccaagcgga agccgcgcct catggaggag
4381  gacgagctcc cctcgtggat catcaaggac gacgcggagg tggagcggct gacctgtgag
4441  gaggaggagg agaagatgtt cggccgtggc tcccgccacc gcaaggaggg ggactacagc
4501  gactcactga cggagaagca gtggctcaag gccatcgagg agggcacgct ggaggagatc
4561  gaagaggagg tccggcagaa gaaatcatca cggaagcgca agcgagacag cgacgccggc
4621  tcctccaccc cgaccaccag caccccgcagc cgcgacaagg acgacgagag caagaagcag
4681  aagaagcgcg ggcggccgcc tgccgagaaa ctctccccta acccacccaa cctcaccaag
4741  aagatgaaga agattgtgga tgccgtgatc aagtacaagg acagcagcag tggacgtcag
4801  ctcagcgagg tcttcatcca gctgcccctcg cgaaaggagc tgcccgagta ctacgagctc
4861  atccgcaagc ccgtggactt caagaagata aaggagcgca ttcgcaacca caagtaccgc
4921  agcctcaacg acctagagaa ggacgtcatg ctcctgtgcc agaacgcaca gaccttcaac
4981  ctggagggct ccctgatcta tgaagactcc atcgtcttgc agtcggtctt caccagcgtg
5041  cggcagaaaa tcgagaagga ggatgacagt gaaggcgagg agagtgagga ggaggaagag
5101  ggcgaggagg aaggctccga atccgaatct cggtccgtca aagtgaagat caagcttggc
5161  cggaaggaga aggcacagga ccggctgaag ggcggccggc ggcggccgag ccgagggtcc
5221  cgagccaagc cggtcgtgag tgacgatgac agtgaggagg aacaagagga ggaccgctca
5281  ggaagtggca gcgaagaaga ctgagccccg acattccagt ctcgaccccg agcccctcgt
5341  tccagagctg agatggcata ggccttagca gtaacgggta gcagcagatg tagtttcaga
5401  cttggagtaa aactgtataa acaaaagaat cttccatatt tatacagcag agaagctgta
5461  ggactgtttg tgactggccc tgtcctggca tcagtagcat ctgtaacagc attaactgtc
5521  ttaaagagag agagagagaa ttccgaattg gggaacacac gatacctgtt tttcttttcc
```

-continued

```
5581  gttgctggca gtactgttgc gccgcagttt ggagtcactg tagttaagtg tggatgcatg
5641  tgcgtcaccg tccactcctc ctactgtatt ttattggaca ggtcagactg ccgggggcc
5701  cggcgagggt atgtcagtgt cactggatgt caaacagtaa taaattaaac caacaacaaa
5761  acgcacagcc aaaaaaaaa
```

BPTF (accession No. NM_182641):
```
   1  cgccccccct gcgcccgccc ctccccttc gctttccttc tccccccgcc tcggctccga
  61  catgaggggc cggcggggca ggccgcccaa gcagcccgcg gctcccgctg cggagcgctg
 121  cgccccggcc ccgccgccac cgccgccgcc gcccacgtcc ggacccatcg gggggctccg
 181  ctcgcggcac cgcggcagca gccggggcag gtgggccgcc gcccaggctg aggtggcgcc
 241  caagacgcgg ctgagctcgc ccagggggg cagcagtagc cggaggaagc cgccgccgcc
 301  gccgccggcc cccccagca ccagcgcccc gggccggggg gggcgaggag gcggggggcgg
 361  caggacgggg ggcgggggcg gcggcggcca cctggcccgg accaccgcgg cccggagggc
 421  cgtcaacaaa gtggtgtacg atgaccacga gagcgaggag gaggaggaag aggaggacat
 481  ggtctccgag gaggaggagg aggaggacgg cgacgccgag gagacccagg attctgagga
 541  cgacgaggag gatgagatgg aagaggacga cgatgactcc gattatccga aggagatgga
 601  agacgacgac gacgacgcca gttactgcac ggaaagcagc ttcaggagcc atagtaccta
 661  cagcagcact ccaggtaggc gaaaaccaag agtacatcgg cctcgttctc ctatattgga
 721  agaaaaagac atcccgcccc ttgaatttcc caagtcctct gaggatttaa tggtgcctaa
 781  tgagcatata atgaatgtca ttgccattta cgaggtactg cggaactttg gcactgtttt
 841  gagattatct cctttcgct ttgaggactt ttgtgcagct ctggtgagcc aagagcagtg
 901  cacactcatg gcagagatgc atgttgtgct tttgaaagca gttctgcgtg aagaagacac
 961  ttccaatact accttggac ctgctgatct gaaagatagc gttaattcca cactgtattt
1021  catagatggg atgacgtggc cagaggtgct gcgggtgtac tgtgagagtg ataaggagta
1081  ccatcacgtt cttccttacc aagaggcaga ggactaccca tatggaccag tagagaacaa
1141  gatcaaagtt ctacagtttc tagtcgatca gtttcttaca acaaatattg ctcgagagga
1201  attgatgtct gaaggggtga tacagtatga tgaccattgt agggtttgtc acaaacttgg
1261  ggatttgctt tgctgtgaga catgttcagc agtataccat ttggaatgtg tgaagccacc
1321  tcttgaggag gtgccagagg acgagtggca gtgtgaagtc tgtgtagcac acaaggtgcc
1381  tggtgtgact gactgtgttg ctgaaatcca aaaaaataaa ccatatattc gacatgaacc
1441  tattggatat gatagaagtc ggaggaaata ctggttcttg aaccgaagac tcataataga
1501  agaagataca gaaaatgaaa atgaaaagaa aatttggtat tacagcacaa aggtccaact
1561  tgcagaatta ttgactgtc tagacaaaga ttattgggaa gcagaactct gcaaaattct
1621  agaagaaatg cgtgaagaaa tccaccgaca catggacata actgaagacc tgaccaataa
1681  ggctcgggc agtaacaaat cctttctggc ggcagctaat gaagaaattt tggaatccat
1741  aagagccaaa aagggagaca ttgataatgt taaagcccca gaagaaacag aaaaagacaa
1801  gaatgagact gagaatgact ctaaagatgc tgagaaaaac agagaagaat ttgaagacca
1861  gtcccttgaa aaagacagtg acgacaaaac accagatgat gaccctgagc aaggaaaatc
1921  tgaggtaggt gatttcaaat cggagaagtc caacggggag ctaagtgaat ctcctggagc
1981  tggaaaagga gcatctggct caactcgaat catcaccaga ttgcggaatc cagatagcaa
2041  acttagtcag ctgaagagcc agcaggtggc agccgctgca catgaagcaa ataaattatt
2101  taaggagggc aaagaggtac tggtagttaa ctctcaagga gaaatttcac ggttgagcac
```

```
2161  caaaaaggaa gtgatcatga aaggaaatat caacaattat tttaaattgg gtcaagaagg
2221  gaagtatcgc gtctaccaca atcaatactc caccaattca tttgctttga ataagcacca
2281  gcacagagaa gaccatgata agagaaggca tcttgcacat aagttctgtc tgactccagc
2341  aggagagttc aaatggaacg gttctgtcca tgggtccaaa gttcttacca tatctactct
2401  gagactgact atcacccaat tagaaaacaa catcccttca tcctttcttc atcccaactg
2461  ggcatcacat agggcaaatt ggatcaaggc agttcagatg tgtagcaaac ccagagaatt
2521  tgcattggct ttagccattt tggagtgtgc agttaaacca gttgtgatgc taccaatatg
2581  gcgagaatct ttaggacata ccaggttaca ccggatgaca tcaattgaaa gagaagaaaa
2641  ggagaaagtc aaaaaaaaag agaagaaaca ggaagaagaa gaaacgatgc agcaagcgac
2701  atgggtaaaa tacacatttc cagttaagca tcaggtttgg aaacaaaaag gtgaagagta
2761  cagagtgaca ggatatggtg gttggagctg gattagtaaa actcatgttt ataggtttgt
2821  tcctaaattg ccaggcaata ctaatgtgaa ttacagaaag tcgttagaag gaaccaaaaa
2881  taatatggat gaaaatatgg atgagtcaga taaagaaaaa tgttcacgaa gtccaaaaaa
2941  aataaaaata gagcctgatt ctgaaaaaga tgaggtaaaa ggttcagatg ctgcaaaagg
3001  agcagaccaa aatgaaatgg atatctcaaa gattactgag aagaaggacc aagatgtgaa
3061  ggagctctta gattctgaca gtgataaacc ctgcaaggaa gaaccaatgg aagtagacga
3121  tgacatgaaa acagagtcac atgtaaattg tcaggagagt tctcaagtag atgtggtcaa
3181  tgttagtgag ggttttcatc taaggactag ttacaaaaag aaaacaaaat catccaaact
3241  agatggactt cttgaaagga gaattaaaca gtttacactg gaagaaaaac agcgactcga
3301  aaaaatcaag ttggagggtg gaattaaggg tataggaaag acttctacaa attcttcaaa
3361  aaatctctct gaatcaccag taataacgaa agcaaaagaa gggtgtcaga gtgactcgat
3421  gagacaagaa cagagcccaa atgcaaataa tgatcaacct gaggacttga ttcagggatg
3481  ttcagaaagt gattcctcag ttcttagaat gagtgatcct agtcatacca caaacaaact
3541  ttatccaaaa gatcgagtgt tagatgatgt ctccattcgg agcccagaaa caaaatgtcc
3601  gaaacaaaat tccattgaaa atgacataga agaaaagtc tctgaccttg ccagtagagg
3661  ccaggaaccc agtaagagta aaacaaaagg aaatgatttt ttcatcgatg actctaaact
3721  agccagtgca gatgatattg gtactttgat ctgtaagaac aaaaaaccgc tcatacagga
3781  ggaaagtgac accattgttt cttcttccaa gagtgcttta cattcatcag tgcctaaaag
3841  taccaatgac agagatgcca cacctctgtc aagagcaatg gactttgaag gaaaactggg
3901  atgtgactct gaatctaata gcactttgga aaatagttct gataccgtgt ctattcagga
3961  tagcagtgaa gaagatatga ttgttcagaa tagcaatgaa agcatttctg aacagttcag
4021  aactcgagaa caagatgttg aagtcttgga gccgttaaag tgtgagttgg tttctggtga
4081  gtccactgga aactgtgagg acaggctgcc ggtcaagggg actgaagcaa atggtaaaaa
4141  accaagtcag cagaagaaat tagaggagag accagttaat aaatgtagtg atcaaataaa
4201  gctaaaaaat accactgaca aaaagaataa tgaaaatcga gagtctgaaa agaaaggaca
4261  gagaacaagt acatttcaaa taaatggaaa agataataaa cccaaaatat atttgaaagg
4321  tgaatgcttg aaagaaattt ctgagagtag agtagtaagt ggtaatgttg aaccaaaggt
4381  taataatata aataaaataa tccctgagaa tgatattaaa tcattgactg ttaaagaatc
4441  tgctataagg ccattcatta atggtgatgt catcatggaa gattttaatg aaagaaacag
4501  ctccgaaaca aaatcgcatt tgctgagttc ttcagatgct gaaggtaact accgagatag
4561  ccttgagacc ctgccatcaa ccaaagagtc tgacagtaca cagacgacca caccctcagc
```

```
4621  atcttgtcca gaaagcaatt cagttaatca ggtagaagat atggaaatag aaacctcaga
4681  agttaagaaa gttacttcat cacctattac ttctgaagag gaatctaatc tcagtaatga
4741  ctttattgat gaaaatggtc tgcccatcaa caaaaatgaa aatgtcaatg gagaatctaa
4801  aagaaaaacc gtcatcacag aagtcaccac gatgacctcc acagtggcca cagaatcaaa
4861  aactgtgatc aaggtagaaa aaggcgataa gcaaactgtg gtttcttcca cagaaaattg
4921  tgcaaaatcc actgtcacaa ccaccactac aacagtgacc aagctttcca caccctccac
4981  aggcggcagt gtggacatca tctctgtaaa ggagcagagc aaaaccgtgg tcaccacgac
5041  agtgacagac tccctgacca ccacgggagg cacactggtt acatctatga ctgtgagcaa
5101  agagtattcc acacgagaca aagtgaaact gatgaaattt tcaagaccaa agaagactcg
5161  ttcaggtaca gctctgccat cctatagaaa atttgttacc aagagcagca agaagagcat
5221  ttttgttttg cctaatgatg acttaaaaaa gttggcccga aaaggaggaa tccgagaggt
5281  cccttatttt aattacaatg caaaacctgc tttggatata tggccatatc cttctcctag
5341  accgaccttt ggcatcactt ggaggtatag acttcagaca gtaaagtcct tagctggagt
5401  gagcctgatg ttacggttac tgtgggcaag tttgagatgg gatgatatg cggccaaggc
5461  tcctccagga ggagggacta cacggacaga aacatccgaa actgaaatca caacaacaga
5521  aataattaag aggagagatg ttggtcctta tggcattcga tctgaatatt gtatcaggaa
5581  aatcatttgt cccattggag ttccagaaac accaaaagaa acgcctacac ctcagaggaa
5641  aggccttcga tcaagtgcac tgcggccaaa gagaccagaa acgcccaagc aaactggccc
5701  tgttattatt gaaacctggg tagcagaaga agaactggaa ttgtgggaga tcagggcatt
5761  tgctgagaga gtggagaaag aaaaaggcac agcagttgag caacaggcta agaaacgact
5821  ggagcagcag aagccgacag tgattgcaac ttccactact tccccaacaa gcagtacaac
5881  cagcaccatc tctccagcac agaaggttat ggtggccccc ataagtggct cagttacaac
5941  tggaaccaaa atggtactaa ctactaaagt tggatctcca gctacagtaa cattccaaca
6001  aaacaagaac tttcatcaaa cctttgctac atgggttaag caaggccagt caaattcagg
6061  cgttgttcaa gtacagcaga aagtcctggg tatcattcca tcaagtacag gtaccagtca
6121  gcaaaccttt acttcattcc agcccaggac agcaacagtc acaattaggc ccaatacctc
6181  aggctctgga ggaaccacaa gcaattcaca gtaatcaca gggcctcaga ttcgccctgg
6241  tatgaccgtg attagaacac cactccaaca gtcaacacta ggaaaggcaa ttattcgaac
6301  acctgtgatg gtacagccag gtgctcctca gcaagtgatg actcaaatca tcaggggca
6361  gcctgtctcc actgcagtct ccgcccctaa cacggtttcc tcaacacctg gcagaaaag
6421  cttaacttca gcaacgtcca cttcaaatat acagtcttca gcctcacaac ccctcgccc
6481  ccaacaagga caagtgaagc tcaccatggc tcaacttact cagttaacac agggccacgg
6541  tggcaatcaa ggtttgacag tagtaattca aggacaaggt caaactactg acagttgca
6601  gttgatacct caagggggtga ctgtactccc aggcccaggc cagcagctaa tgcaagctgc
6661  aatgccaaat ggtactgttc agcgattcct ctttacccca ttggcaacaa cagccaccac
6721  agccagcacc accaccacca ctgtttccac gacagcagca ggtacaggtg aacaaaggca
6781  gagtaaactg tcaccccaga tgcaggtaca tcaagacaaa accctgccac cagctcagtc
6841  atcaagtgtg ggtccagcag aagcccagcc acagactgct cagccttcag ctcagcccca
6901  gccccaaacc cagccccagt ccccagctca gcctgaagtt cagactcagc ctgaagttca
6961  gacccaaaca actgtttcat cccatgtccc ttctgaagca caacccaccc acgcacagtc
```

-continued

```
7021  atccaagccc caagttgcag cacagtctca gcctcaaagt aatgtccaag gacagtctcc
7081  tgttcgtgtc caaagtccat cacagactcg aatacgtcca tcaactccat cccaactgtc
7141  tcctggacaa caatcccagg ttcagactac aacctcacaa ccgattccaa ttcaaccaca
7201  tacatctctt cagatacctt cccaaggcca gccacagtca caaccccagg tacagtcttc
7261  aactcaaact ctttcatcag gacaaacttt aaatcaagtt actgtttcat ccccatcccg
7321  tcctcagcta caaatacagc agccacagcc ccaagtcatt gctgtgcctc agctgcaaca
7381  acaagtccag gttctctctc agatccagtc acaggttgtg gctcagatac aggctcagca
7441  aagtggtgtg ccccagcaaa tcaaactcca gttacctatc caaattcagc aaagcagtgc
7501  tgtgcagact caccagattc agaatgtggt tacagtgcag gcagccagtg tgcaagagca
7561  gttgcaaagg gttcagcaac tcagggatca gcagcaaaag aagaaacagc aacagataga
7621  aattaagcgt gaacacaccc tccaagcttc taatcaaagt gaaatcattc agaaacaggt
7681  ggtgatgaag cataatgctg taatagaaca tttaaaacag aaaaagagca tgactccagc
7741  tgaaagagaa gagaatcaaa gaatgattgt ctgtaaccag gtgatgaagt atattttgga
7801  taagatagat aaagaagaaa acaggcagc aaaaaaacgg aagcgtgaag agagtgtgga
7861  gcagaaacgt agcaagcaga atgccactaa gctgtcagct ctgctcttca agcacaaaga
7921  gcagctcaga gccgagatcc tgaagaagag agcactcctg gacaaggatc tgcaaattga
7981  agtgcaggaa gagctgaaga gagacctgaa aattaagaaa gaaaagacc tgatgcagtt
8041  ggctcaggcc acagcagtag ctgcaccctg ccccccagtg acaccagctc ctccagcccc
8101  tccagcccct ccaccttcac ctccccctcc acctgctgtg caacacacag gccttctgtc
8161  cacgcccacc ttacctgctg cttcccagaa gaggaagcgg gaagaggaaa aagactccag
8221  ctcaaagtcc aagaaaaaga aaatgatctc tactacctca aaggaaacta gaaggacac
8281  aaagctttac tgtatctgta aaacgcctta tgatgaatct aaatttata ttggctgtga
8341  tcggtgtcag aattggtacc atgggcgctc cgttggcatc ttgcaaagtg aggcagagct
8401  cattgatgag tatgtctgtc cacagtgcca gtcaacagag gatgccatga cagtgctcac
8461  gccactaaca gagaaggatt atgaggggtt gaagagggtg ctccgttcct acaggcccca
8521  taagatggcc tggccttttcc ttgaaccagt agaccctaat gatgcaccag attattatgg
8581  tgttattaag gaacctatgg accttgccac catggaagaa agagtacaaa gacgatatta
8641  tgaaaagctg acggaatttg tggcagatat gaccaaaatt tttgataact gtcgttacta
8701  caatccaagt gactccccat tttaccagtg tgcagaagtt ctcgaatcat tctttgtaca
8761  gaaattgaaa ggcttcaaag ctagcaggtc tcataacaac aaactgcagt ctacagcttc
8821  ttaaagttca gcgtgttaac ctaacataaa acacagcaag aatctggttg tctgaactat
8881  tttaaattaa ggagccagat gttttagtc aggctatcct gacaagactt gacctaaact
8941  tcgtttttat tggtcataac agtccaatta tattcttggc caattttgtc caacggacaa
9001  gaaaaagca aagtcaacga caccattatc ttgtcaagat cagatggttt tactattgtg
9061  gcagagcga aaaactttg tttattgaaa aaaaagaaa aagaaagcaa gaaaaaaaga
9121  tactatgggg tcaagtgtaa ctccatggaa atgccacgtc tgctcttcag tgaagaagct
9181  ggttagagt ctcacagaaa acttttgact gtatttattt attgttgcaa aaaagacgct
9241  tttttattgc tgccctcatt tgtcagctaa ttattttttc ttataaaatc cagccccggt
9301  tacatataat catctgtatc ttatcatgat tcctgtaggt aaaagtacaa gacgacctct
9361  agatgtcttt tctttctatg aaaggagctg ctatgtacac atgtgcacac acacacaact
9421  gggaatcaac aatgagttta ttgttcatgg tagattaaaa ttaagcttgc ataaaggttg
```

-continued

```
      9481 ggctaagtgg tcctggacta cagactctgt tgccttgaat ataacagtac aatttgtcaa
      9541 ttactctgca ccaggctaaa atgagtaaaa tctatttgaa ggtatcttgt ttgtaaacat
      9601 ttgtcagatt ctaattttt tattttgtat taaaattcaa ctatggatgt atatgaaaca
      9661 aaataaatgg agataatttt tctcccacag acagaggtgt ctttgaatgt gcgctaatga
      9721 ttatctgtaa gcctttgtgg ggagggaggc ctgcaaggtc atgaaaggca gaagagtcta
      9781 attgtgcctg gatttctcca ggacagcagt ggcccctcgt tttatcattc ccagtccatt
      9841 gtcatcacgt cagagaaaaa tcttcagggg tgctaatcct gttgcatcag ttgatcatac
      9901 taacgagaac ggtaatgcga caagatacac attgccttca tctgtacatt ctgtgatacc
      9961 aggcaaatta ccaattacac acagctactt atattttatg aagggcattt tttagatgac
     10021 ctcatcctct gtgttatttg ttgattgggt ttgttttctg tttgttggtt tgtttgtttc
     10081 ttccacgtaa ggaaaagtag tgtaaacagt agcgagaaaa tggaaaccac agaggaagat
     10141 gtattttgca tgttttttcct ttcagtgttc ttacacgttg tatcactgca ttgtggtaat
     10201 agcttctata aaatctgcca tagttggatt atgcagcttt gcaaaaattt ttactagatt
     10261 ttgcactaac tcatattagc tttgtcctac caacttctgg aatttatcta attattgttt
     10321 ttcaaagttt ctttcctttt aatgtttccc tgctatgcaa aacctttccc agacctcagt
     10381 ttcttaaaag aaagatgttg ctacagttcc cgattctttc ttattacagg ctcaggtgta
     10441 caggttattc tgggttaatt ttatctaatg aagcccattc cttttgtac ataaagatgt
     10501 cacttaaact tatgcttaca aactaaagac taatcgctca atatgaaaac atgaaaaaat
     10561 ttttgcttaa agtattaaga tggaagtagt taaatatggg ttattttgtc cttttacttt
     10621 tttaaaaaat gttacatatt gtatgcactg tgctgatgca agaattctac attttaatga
     10681 gttataaaat tattctgcat ctcatcacgt cacagtattt ctgtactatt tattcatata
     10741 tataaatata tatgggctta atcattaaa atttgttgca gcaagaactt tcctacctgt
     10801 aggcaataga ttgctatgtt tttaacaaat tgtggcaaat tctaaacagc aattcttttg
     10861 tacgtaatag gacatttcat cctagaaaaa taaagtaatg tttttgacat tgga
SMARCA1 (accession No. NM_001282874):
         1 ggcctgagcg aagggggttgg aagcggagtg attccccacc cctgctccat ctagctcttt
        61 ccagtgcagc cactgccgcc gcccaggagc cctcgtcccc tgccttgtcc ccctactcgt
       121 tcccgctccc acggcatgga gcaggacact gccgcagtgg cagccaccgt ggcagccgcg
       181 gatgcgaccg ccactatcgt ggtcatagag gacgagcagc ccgggccgtc cacctctcag
       241 gaggagggag cggccgccgc ggccaccgaa gccaccgcgg ccacggagaa gggcgagaag
       301 aagaaggaga aaaacgtttc ttcatttcaa ctcaaacttg ctgctaaagc gcctaaatct
       361 gaaaaggaaa tggacccaga atatgaagag aaaatgaaag ccgaccgagc aaagagattt
       421 gaattttac tgaagcagac agaactttttt gcacatttca ttcagccttc agcacagaaa
       481 tctccaacat ctccactgaa catgaaattg ggacgtcccc gaataaagaa agatgaaaag
       541 cagagcttaa tttctgctgg agactaccgc cataggcgca cagagcaaga agaagatgaa
       601 gagctactgt ctgagagtcg gaaaacatct aatgtgtgta ttagatttga ggtgtcacct
       661 tcatatgtga aagggggggcc actgagagat tatcagattc gaggactgaa ttggttgatc
       721 tctttatatg aaaatggagt caatggcatt ttggctgatg aaatgggcct tgggaaaact
       781 ttacaaacaa ttgctttgct tggttacctg aaacactacc gaaatattcc tggacctcac
       841 atggttttag ttccaaagtc tactttacac aactgatga atgaatttaa acgatgggtc
       901 ccatctctcc gtgtcatttg ttttgtcgga gacaaggatg ccagagctgc ttttattcgt
```

-continued

```
 961  gatgaaatga tgccaggaga gtgggatgtt tgcgttactt cttatgagat ggtaattaaa
1021  gaaaaatctg tattcaaaaa gtttcactgg cgatacctgg tcattgatga agctcacaga
1081  ataaagaatg aaaaatctaa gctttcagag attgttcgtg agttcaagtc gactaaccgc
1141  ttgctcctaa ctggaacacc tttgcagaat aacctgcatg aactgtgggc cttactcaac
1201  tttttattgc ctgatgtctt taattctgca gatgactttg attcttggtt tgacactaaa
1261  aattgtcttg gtgatcaaaa actcgtggaa agacttcatg cagttttaaa accattttg
1321  ttacgccgta taaaaactga tgtagagaag agtctgccac ctaaaaagga aataaagatt
1381  tacttggggc tgagtaagat gcaacgagaa tggtatacaa aaatcctgat gaaagatatt
1441  gatgttttaa actcttctgg caagatggac aagatgcgac tcttaaacat tctgatgcag
1501  cttcgaaagt gttgtaatca tccatatctg tttgatggtg ctgaacctgt tccaccttat
1561  accactgatg agcatattgt cagcaacagt ggtaaaatgg tagttctgga taaactattg
1621  gccaaactca agaacaggg ttcaagggtt ctcattttca gccagatgac tcgcttgctg
1681  gatattttgg aagattattg catgtggcgt ggttatgagt attgtcgact ggatggacaa
1741  accccgcatg aagaaagaga ggataaattc ctagaagtgg aatttctggg tcaaagggaa
1801  gcaatagagg cttttaatgc tcctaatagt agcaaattca tctttatgct aagtaccagg
1861  gctggaggtc tcggaattaa cctggcaagt gctgatgtgg ttatactata tgattcagac
1921  tggaacccac aggttgatct acaagctatg gatcgagcac atcgtattgg tcagaagaaa
1981  ccagtacgtg tattccgtct catcactgac aacactgttg aagagaggat tgtagaaaga
2041  gctgagataa aactgagact cgattcaatt gttatacaac aaggaagact cattgaccaa
2101  cagtctaaca agctggcaaa agaggaaatg ttacaaatga tacggcatga agccacccat
2161  gtttttgctt ctaaagagag tgagttgaca gatgaagaca ttacaactat tctggaaaga
2221  ggggaaaaga agactgcaga gatgaatgaa cgcctgcaaa aaatgggaga gtcttctcta
2281  agaaattta gaatggacat tgaacaaagt ttatacaaat ttgagggaga agattataga
2341  gaaaaacaga agcttggcat ggtggaatgg attgaacctc ctaaacgaga acgcaaagca
2401  aactacgcag tggatgccta ctttagagag gctttgcgtg tcagcgagcc aaagattcca
2461  aaggctccac ggcctccaaa acagccaaat gttcaggatt ttcaattttt cccaccacgc
2521  ttatttgagc tcctggaaaa ggaaattctt tattatcgga agacaatagg ctataaggtt
2581  ccaaggaatc ctgatatccc aaatccagct ctggctcaaa gagaagagca aaaaaagatt
2641  gatggagctg aacctcttac accagagag actgaagaaa aggaaaaact ctcacacaa
2701  ggtttcacaa actggactaa acgagatttt aaccagttta ttaaagctaa tgagaaatat
2761  ggaagagatg acattgataa catagctcga gaggtagagg gcaaatcccc tgaggaggtc
2821  atggagtatt cagctgtatt ttgggaacgt tgcaatgaat acaggacat tgagaaaatt
2881  atggctcaaa ttgaacgtgg agaagcaaga attcaacgaa ggatcagtat caagaaagcc
2941  ctggatgcca aaattgcaag atacaaggct ccatttcatc agttgcgcat tcagtatgga
3001  accagcaaag gaagaacta tactgaggaa gaagatagat tcttgatttg tatgttacac
3061  aaaatgggct tgatagaga aaatgtatat gaagaattaa gacagtgtgt acgaaatgct
3121  ccccagttta gatttgactg gtttatcaag tctaggactg ccatggaatt ccagagacgc
3181  tgtaacactc tgatttcatt gattgagaaa gaaaatatgg aaattgagga aagagagaga
3241  gcagaaaaga gaaacgggc aactaaaact ccaatgtcac agaaaagaaa agcagagtca
3301  gctactgaga gctctggaaa gaaggatgtc aagaaggtga atcctaaag cctagaaata
```

```
-continued
3361    aagttttaaa tgggaaactg ctattttctt gttcccatct tcaaatgcta attgccagtt 3421    ccagtgtatt catggtactc taagaaaaat ctctttggtt ttgatttctt gcatatttta 3481    tatattttac aatgctttct acctgaaatg tgtagcttta tattttatgg cattctagta 3541    tttttgtgta ctgtattttg tgcatttcat gtcttcatca aaatcctctc agtccttgtt 3601    cttttgaagc ttgtgctgag gttttagctt ttctatgttt tatatgccgc tgctttgaaa 3661    gagaacctag attctatagt tgtattattg ttgtttcata ctttaaattt atatggctgt 3721    ggaaaaacga attaaaatgt tttgaggaga aagacttttt cacttctttg ttgctttctt 3781    ttctattgag tctgggcttg tttgtgttac tgcatactgt gattagcata ataattgttt 3841    ctttgaggtc atctaaatat tttttccta aaggaataaa gggtgaggaa agaaaaatat 3901    taaaaaagct aatatttgat actgtgcttg ctgtcagtat gcattacatt taaattattc 3961    tctattcaag tgggaaaata taataaagaa atgtctataa gaaatttaaa aaaaaaaaaa 4021    aaaaa
```

IV. Cancer Treatment

Bacteria such as *Salmonella, Clostridium* and *Bifidobacterium* have a natural tropism for cancers, such as solid tumors. Types of cancer that can be treated using the methods of the invention include, but are not limited to, solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

V. Administration

The invention includes administration of the attenuated *Salmonella* strains described herein and methods for preparing pharmaceutical compositions and administering such as well. Such methods comprise formulating a pharmaceutically acceptable carrier with one or more of the attenuated *Salmonella* strains described herein.

A pharmaceutical composition of the invention is formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

For intravenous administration, suitable carriers include physiological saline, bacteriostatic water, Cremophor EL™ (BASF; Parsippany, N.J.) or phosphate buffered saline (PBS). It must be stable under the conditions of manufacture and storage and must be preserved against the contaminating action of other (undesired) microorganisms. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Injectable solutions can be prepared by incorporating the active compound in the required amount in an appropriate solvent with one or a combination of ingredients discussed above. Generally, dispersions are prepared by incorporating the active compound into a vehicle which contains a basic dispersion medium and various other ingredients discussed above. In the case of powders for the preparation of injectable solutions, the preferred methods of preparation are vacuum drying and freeze-drying which yields a powder of the active ingredient plus any additional desired ingredient from a previously.

Oral compositions generally include an inert diluent or an edible carrier. For example, they can be enclosed in gelatin capsules. For the purpose of oral therapeutic administration, the active compound can be incorporated with excipients and used in the form of tablets, troches, or capsules.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the bacteria are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the bacteria are formulated into ointments, salves, gels, or creams as generally known in the art.

It is especially advantageous to formulate compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

When administered to a patient the attenuated *Salmonella* can be used alone or may be combined with any physiological carrier. In general, the dosage ranges from about 1.0 c.f.u./kg to about $1\times10^{12}$ c.f.u./kg; optionally from about 1.0 c.f.u./kg to about $1\times10^{10}$ c.f.u./kg; optionally from about 1.0 c.f.u./kg to about $1\times10^{8}$ c.f.u./kg; optionally from about $1\times10^{2}$ c.f.u./kg to about $1\times10^{8}$ c.f.u./kg; optionally from about $1\times10^{4}$ c.f.u./kg to about $1\times10^{8}$ c.f.u./kg; optionally from about $1\times10^{5}$ c.f.u./kg to about $1\times10^{12}$ c.f.u./kg; optionally from about $1\times10^{5}$ c.f.u./kg to about $1\times10^{10}$ c.f.u./kg; optionally from about $1\times10^{5}$ c.f.u./kg to about $1\times10^{8}$ c.f.u./kg.

EXAMPLES

The following examples are provided in order to demonstrate and further illustrate certain embodiments and aspects of the present invention and are not to be construed as limiting the scope thereof.

Example I

A Bacterial Macromolecule Delivery System— a bacterial strain that localizes to the cytosol of cancer cells and lyses to deposit molecular cargo.

The natural capabilities of *Salmonella* for cell invasion render it a suitable vector for intracellular gene and protein delivery—a bacterial delivery system (BDS). *Salmonella* is a facultative intracellular pathogen that utilizes two type III secretion systems (T3SS) to manipulate host cell functions. *Salmonella* pathogenicity island 1 (SPI1)-T3SS is responsible for delivering effector proteins across the plasma membrane of the host, which promotes invasion. The second pathogenicity island SPI2-T3SS is for intracellular survival and is activated after host cell invasion (76). To effectively deliver macromolecules into the mammalian cytosol, a bacterial lysis system was created that is triggered upon intracellular invasion. The strategy is to couple an intracellularly induced *Salmonella* promoter to a phage lysis gene to induce bacterial lysis upon its entry into the mammalian cytosol (FIG. 4). In this example, the sseJ promoter, which is part of the SPI2-T3SS that is only activated intracellularly, was used to trigger lysis (76).

The bacteria also need to localize in the mammalian cytosol. Upon invasion, *Salmonella* forms an intracellular vacuole, the *Salmonella*-containing vacuole (SCV). A sifA deletion has been shown to enable a bacterial escape into the cytosol (*Salmonella enterica* supbsp *enterica* serovar *Typhimurium* strain 14028s containing SifA: CP001363). A bacterial sifA knockout which will increase the level of bacteria in the mammalian cytosol (77, 78) was created. This deletion is introduced into *Salmonella* and combined with the intracellular lysis system.

Methods

Construction of a Bacterial Delivery System

The Bacterial Delivery System (BDS) will be designed to deliver DNA and proteins (FIG. 4). It will be based on non-toxic *Salmonella* (VNP20009, ΔmsbB, ΔpurI), have a sifA deletion, and contain the intracellular lysis system (sseJ-iEPS5 lysis cassette). The lysis system and the sifA deletion will be built into the bacterial genome with λ red homologous recombination. Both modifications will be verified by PCR and sequencing.

Quantifying Protein and Gene Delivery

Gene and protein delivery will be tested on a monolayer of MCF-7 cells. For peptide delivery, $1\times10^{7}$ CFU/ml of the BDS and the control strain, both expressing EGFP, will be co-incubated with MCF7 cells for 2 hours. Cells will be washed and incubated with gentamycin to remove all extracellular bacteria. Cells will then be fixed and stained with EGFP antibodies to determine the amount of protein released. For plasmid delivery, BDS and control bacteria, both containing the eukaryotic EGFP plasmid, will be co-incubated with MCF-7, after which cells will be washed and incubated with gentamycin for 48 hours. The number of mammalian cells expressing EGFP will be measured by fluorescence imaging.

Gene Delivery in 3D Tissue

To measure the delivery of genes to 3D tissue, the BDS will be administered to a tumor-on-a-chip device (FIG. 9). It is believed that gene delivery will be greater in tissue because of bacterial colonization patterns. Bacteria reach densities of $10^{10}$ CFU/ml in tissue and are in closer proximity to cells than in monolayers (79). BDS containing the eukaryotic EGFP plasmid and a prokaryotic RFP plasmid will be administered for one hour to six chambers. RFP will be constitutively expressed and used to measure bacterial density. EGFP production will indicate the extent of gene delivery. Fluorescence will be quantified from microscopy images acquired every 30 minutes for 72 hours. A control strain containing the eukaryotic EGFP plasmid and the prokaryotic RFP plasmid will be tested in a similar setup. This experiment will determine the extent of 3D tumor tissue affected by gene delivery.

Mice Models

Two tumor models will be used: spontaneous metastases formed in MMTV-PyVT mice and 4T1 subcutaneous tumors. Spontaneous tumors and metastases will be formed in mice carrying the MMTV-PyMT transgene. In these mice, mammary-gland-specific expression of the polyoma middle T antigen (PyMT) is driven by the mouse-mammary-tumor-virus (MMTV) promoter (80). Female carriers develop mammary tumors that involve the entire mammary fat pad by 5 weeks of age [81]. Pulmonary metastases typically form in 80-94% of female mice within 14 weeks (80, 82, 83). A subcutaneous model will be used as well. In this model, tumors will be formed by injecting 4T1 mammary carcinoma cells under the dorsal skin of 3 week old, female, BALB/c mice. Immunocompetent mice (BALB/c) and syngeneic cell lines will be used because tumor targeting is not robust in immunodeficient mice [84], and immunocompetent mice would reject a human line. In all animal experiments, groups of ten mice will be used, and statistical significance will be determined at a P-value of 0.05. Comparisons will be performed using Student's t-test.

Gene and Protein Delivery in Tumors and Metastasis

To quantify the percentage of the tumor cells and metastasis treated by bacterial gene or protein delivery, the metastatic MMTV-PyMT mouse model will be used.

1) Protein Delivery:

Two groups of ten mice will be treated with the BDS or control bacteria expressing prokaryotic EGFP. Bacteria will be administered by tail vein (100,000 CFU/g). After 48 hours, mice will be sacrificed and tumors and lungs will be excised and fixed. All tissues will be stained with H&E, Salmonella-specific and EGFP antibodies. The Salmonella-specific antibodies will determine if the tumors and metastasis were colonized. These images will be merged to determine the localization of free EGFP protein in the mammalian cytosol. The spleen and liver tissue will be harvested, fixed and stained for EGFP to test the specificity of the BDS strain for tumor tissue.

2) Plasmid Delivery:

Two groups of ten mice will be treated with BDS and the control strain, both containing the eukaryotic EGFP plasmid. Bacteria will be administered by tail vein (100,000 CFU/g). After 72 hours, mice will be sacrificed and the tumors and lungs will be excised and fixed. The bacterial tissue localization will be determined as described above. The cancer cells that are expressing EGFP will be counted in the primary tumor and the metastases. Spleen and liver tissue will be harvested, fixed and stained for EGFP to test the specificity of the BDS strain.

These experiments will determine the treatment efficiency of both gene and protein delivery in primary and metastatic tumors by determining 1) how many tumors and metastasis are affected and 2) the percentage of tumor tissue that is treated with BDS.

Results sseJ is a Specific Intracellularly Induced Promoter

Figure 5A:
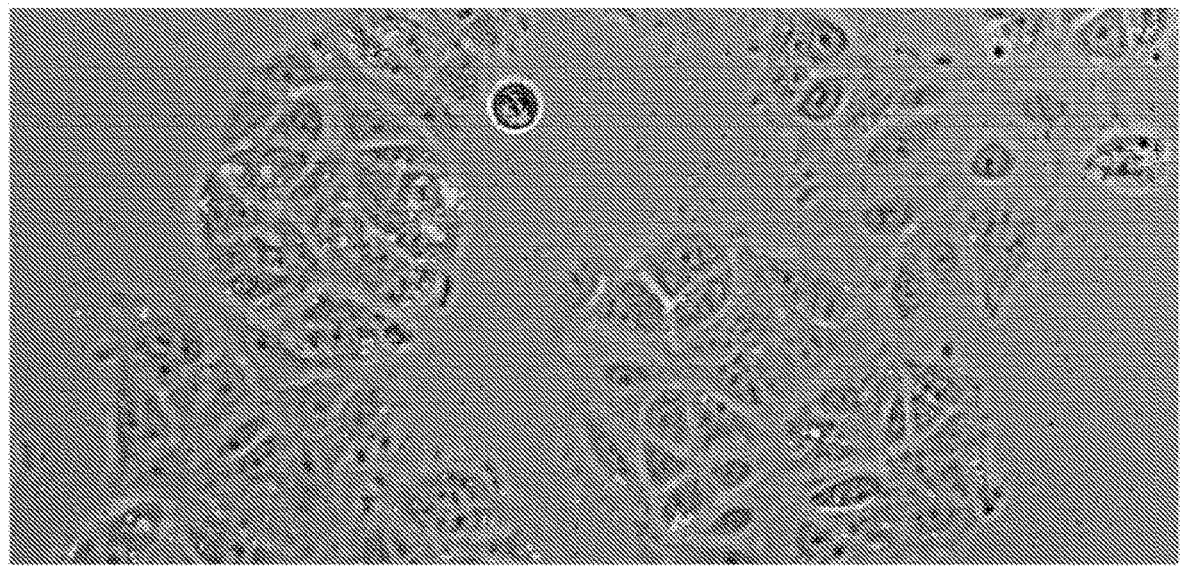
FIGS. 5A-B. The sseJ promoter is a specific intracellular promoter. A) *Salmonella* carrying a plasmid expressing prokaryotic EGFP under the lac promoter was added to MCF-7 breast cancer cells. The cells were incubated with $1 \times 10^7$ CFU/ml for two hours and then washed and incubated with gentamycin for one hour to kill extracellular bacteria. B) MCF-7 cells were infected with $1 \times 10^7$ CFU/ml of *Salmonella*, transformed with EGFP under the control of sseJ promoter, and incubated for two hours to allow for invasion. The mammalian cells were washed with PBS and gentamycin was added to remove external bacteria. Fluorescent and bright light microscopy images were taken before (extracellular) and after washing and gentamycin incubation (intracellular). Black arrows indicate bacteria.

For an intracellular delivery system, maximal invasion into the mammalian cell is desired. It was determined that after two hours of infection with 1×10$^7$ CFU/ml of attenuated Salmonella, the cells contained an average of 3-4 bacteria (FIG. 5A). To generate an intracellular release system, a strict intracellular activated promoter was necessary to prevent extracellular lysis. To test its specificity, the sseJ promoter (ACATGTCACATAAAACACTAGCACTTTAGCAATAATAGTCGGATGATAA

GTTTGTCTGTTTTTCCTGAGTATCAAGCCAGCTCATACTCACGCCAGCAC

ACTAAAATCAGGAGTGGCTTCTTTTTTAGATCTTTGCCTTAGCCAGGCGC

ACACTCAATAATGATAGCAGTCAGATAATATGTACCAGGCATTAACCTCA

CGTTGTTGATGATATATTTACTTCGTTGAAAAACAATAAACATTGTATGT

ATTTTATTGGCGACGAAAAACTGTTAAAGAAGCGTAATTCCATATACACC

ATTTACCTGATTACTTTTCTTGCTAATATTTGCTAATTAATTATTTGCTA

Figure 5B:
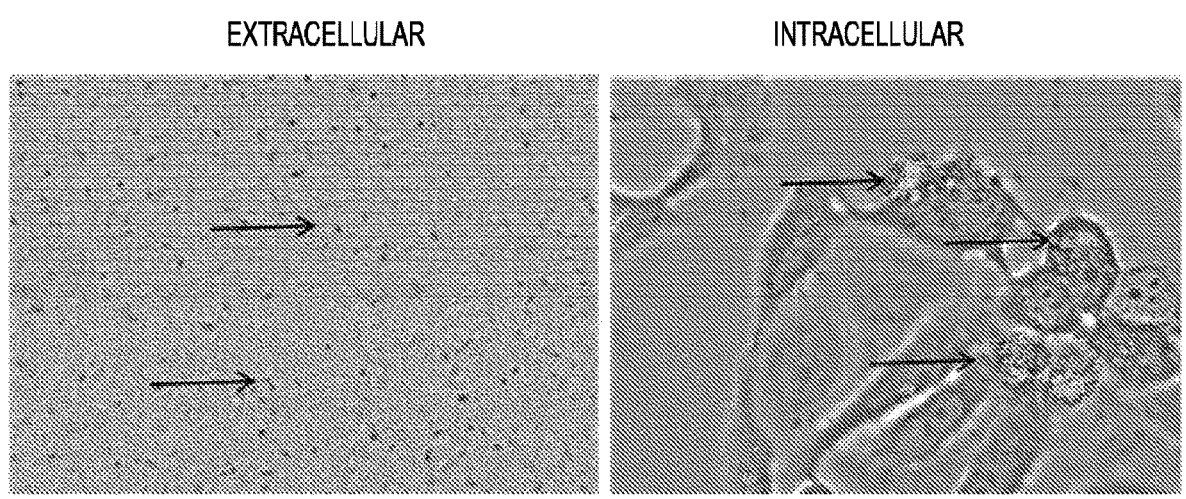

AAGCGTGTTTAATAAAGTAAGGAGGTCTAGA; SEQ ID NO: 1)

was coupled to an EGFP reporter gene and transformed into the therapeutic strain. The sseJ promoter showed specific intracellular activation two hours after incubation by expressing EGFP (FIG. 5B) and no fluorescence was observed in the extracellular pool of bacteria.

Figure 6A:
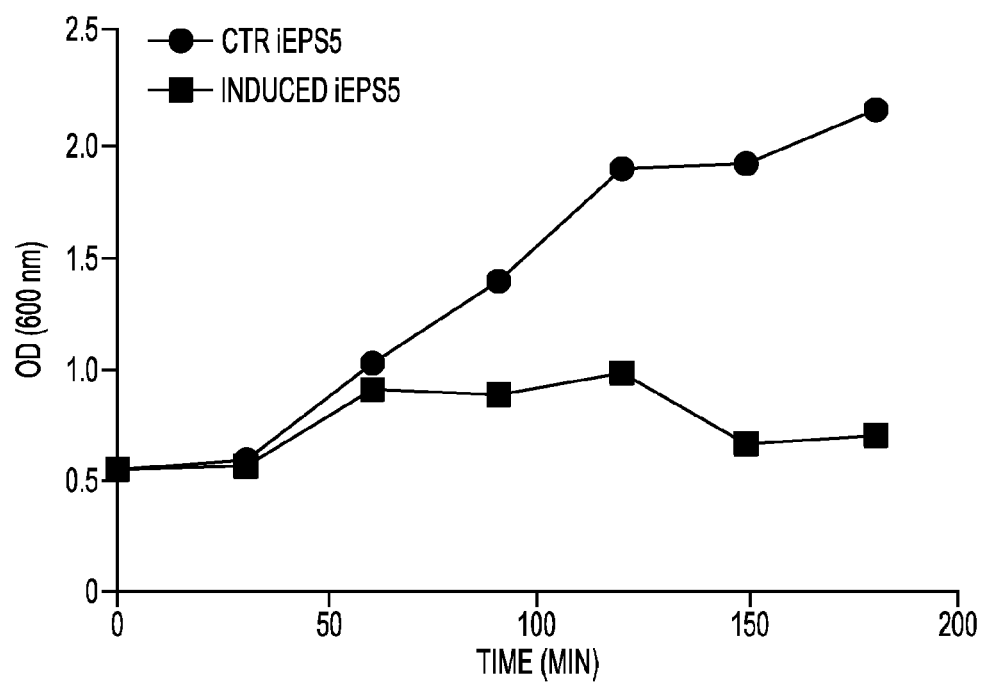
FIGS. 6A-B. Intracellularly induced lysis. A) Non-toxic *Salmonella* carrying the lysis cassette of phage iEPS5 under control of a pBAD promoter was grown in liquid culture and at an O.D. of 0.5. *Salmonella* were induced with 0.2% arabinose. O.D. was measured every 30 minutes for three hours. B) *Salmonella* containing the lysis cassette and a prokaryotic EGFP plasmid were incubated with for two hours with MCF-7 cells. After two hours, the cells were washed 10 times with PBS and incubated with gentamycin. Fluorescent and bright light microscopy images were taken every minute for two hours. The arrows indicate the lysing bacteria. The EGFP diffusion can be observed 30 minutes after gentamycin addition.

An Intracellularly Activated Lysis System Lyses Salmonella Upon Cancer Cell Invasion and Delivers Peptides To obtain intracellular lysis, the lysis gene or cassette (multiple genes) can be induced rapidly after intracellular invasion and the protein leakage should have minimal effects on bacterial growth. The multiple gene lysis system of phage iEPS5 (Jeong J H, et al. PLoS One 2014, 9(1): e80050), a Salmonella phage, was used. The lysis cassette of phage iEPS5 was brought under the control of an inducible pBAD promoter and transformed into the therapeutic strain. At an O.D. of 0.5, the bacteria were induced with arabinose. The lysis cassette of iEPS5 was active after 60 minutes. The control kept a steady growth rate, indicating that promoter leakage did not hinder the bacterial growth (FIG. 6A). Other lysis systems include, but are not limited to, the lysis cassette is Lysin E from phage phiX174, the lysis cassette of phage iEPS5, or the lysis cassette from lambda phage. There are many lysis systems, and most include a lysin and a holin. The cassette from phage iEPS5 has three genes. One is a lysin. The lysis cassette from lambda phage contains Endolysin R, Holin S, Spanin Rz and Spanin Rz1.

Figure 6B:
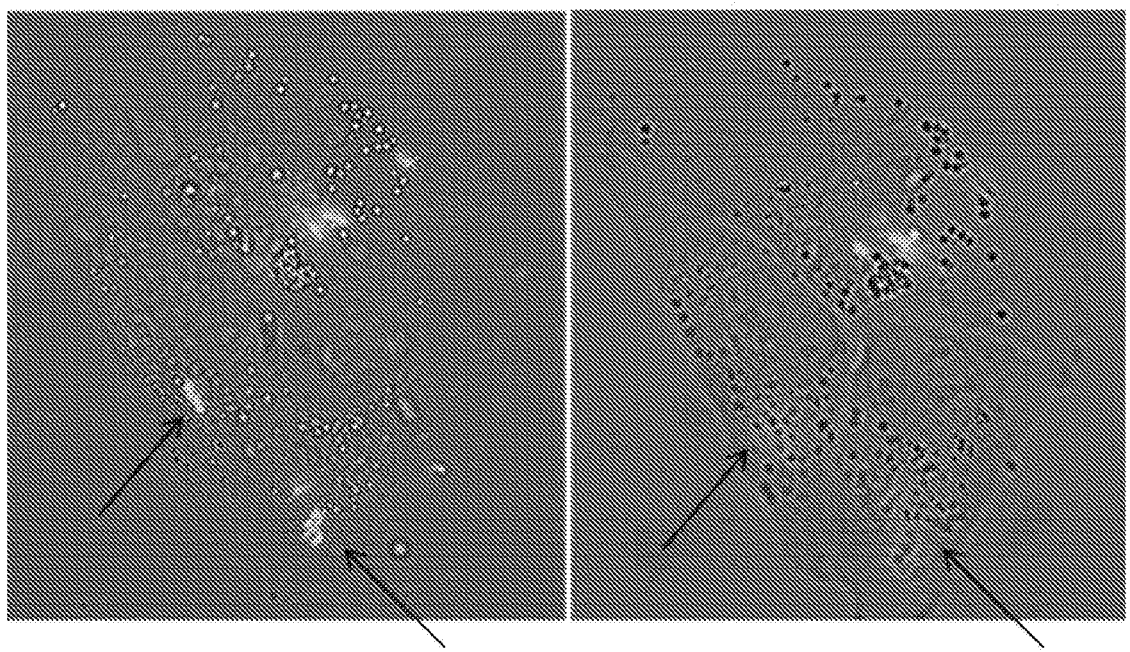

The intracellular lysis system was generated by fusing the sseJ promoter to the phage iESP5 lysis cassette. The plasmid, that also expressed EGFP constitutively, was transformed into therapeutic Salmonella. This system lyses bacteria and releases EGFP into the mammalian cytosol (FIG. 6). The resulting bacterial strain was incubated for two hours with MCF-7 cells, after which the cells were washed and incubated with gentamycin to remove extracellular bacteria. 30 Minutes after gentamycin incubation, the lysis of Salmonella was observed as the dilution of the EGFP into the cytosol. (FIG. 6B).

The Deletion of sifA Enables Bacterial Escape into the Cytosol

Figure 7:
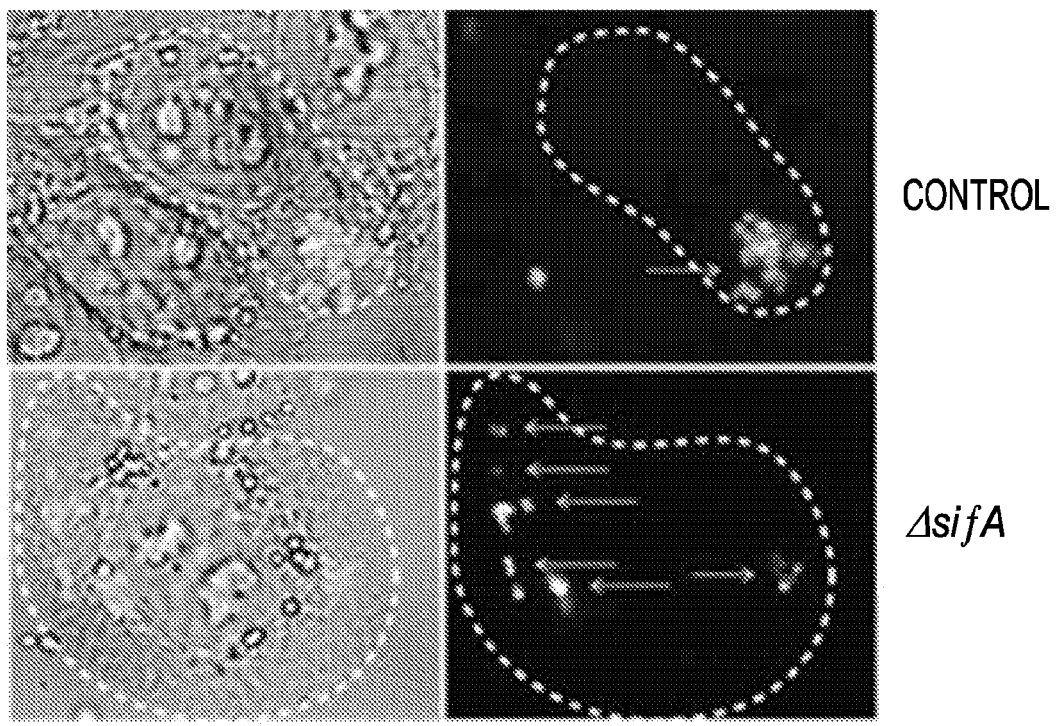
FIG. 7. The deletion of sifA enables bacterial escape into the cytosol. Control and ΔsifA *Salmonella* expressing EGFP under control of the sseJ promoter were incubated with for two hours with MCF-7 cells. After two hours, the cells were washed with PBS and incubated with gentamycin. Fluorescent and bright light microscopy images were taken three hours after gentamycin incubation. Arrows indicate intracellular bacteria. The invaded control bacteria are all localized in a *Salmonella*-containing vacuole (SCV) in the cell. Invaded ΔsifA bacteria are spread throughout the mammalian cell.

To eliminate the SCV and increase the number of bacteria in the host cell cytosol, the sifA gene was deleted in the non-toxic Salmonella strain using the λ red homologous recombination system. To validate the deletion, the mutated strain and the control were transformed with a plasmid to express GPF under the control of the sseJ promoter. Both strains were incubated with MCF-7 cells for two hours and consequently washed and incubated with gentamycin to remove extracellular bacteria. Due to the specificity of the sseJ promoter, only intracellular bacteria turn green. Control bacteria were all in localized in an SCV in contrast to the mutated strain that was scattered throughout the mammalian cell cytosol (FIG. 7).

Salmonella Delivers Plasmids to Cells

Figure 8:
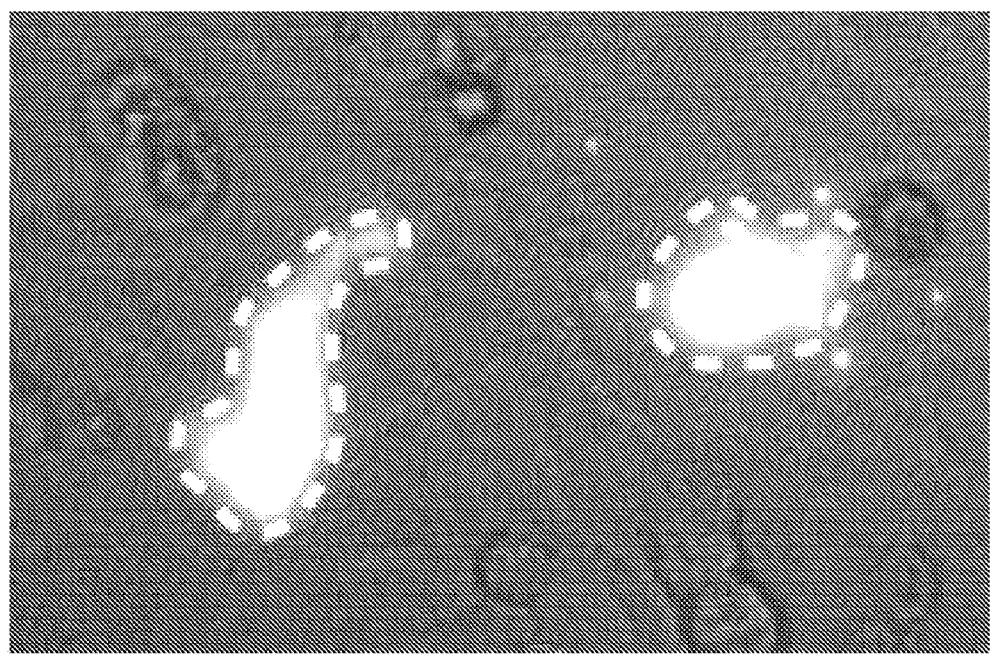
FIG. 8. *Salmonella* plasmid delivery. Bacteria containing the lysis cassette and a eukaryotic EGFP plasmid were incubated for two hours with MCF-7 cells. After two hours, the cells were washed with PBS and incubated with gentamycin for 48 hours. Fluorescent and bright light microscopy images were taken after 48 hours.

To demonstrate gene delivery, non-toxic bacteria were co-transformed with the lysis cassette and a eukaryotic EGFP expression vector. On this plasmid, EGFP is under the control of a mammalian promoter and can only be expressed by mammalian cells and not by bacteria. The resulting bacterial strain was incubated for two hours with MCF-7 cells, after which the cells were washed and incubated with gentamycin for 48 hours. A two day incubation was necessary for the mammalian cells to express EGFP. Bacteria containing the lysis system resulted in MCF-7 cells expressing EGFP, demonstrating that the gene delivery was successful. No green MCF-7 cells were detected after incubation with control *Salmonella* containing only the eukaryotic EGFP plasmid (FIG. 8).

This BDS yields intracellular release that enables effective macromolecule delivery.

Example II

A Bacterial shRNA Delivery System that Targets NIPP1 and EZH2:

silencing NIPP1 and EZH2 with bacterially delivered shRNA reduces tumor volume and eliminates metastasis.

Depletion of the transcriptional repressors NIPP1 and EZH2 stops cancer cell proliferation (5, 10). To date, no systemic therapies targeting these genes have been taken to clinical trials. The BDS described herein can deplete cancer cells of specific epigenetic regulators, e.g., NIPP1 and EZH2, and impair tumor growth. NIPP1 and EZH2 will be silenced/knocked down with bacterially delivered shRNA that will then reduce tumor volume and eliminate metastasis.

Cancer Stem Cells and Metastasis

Cancer stem cells (CSC) are a small side population purported to be present in cancers that is responsible for tumor recurrence and metastasis [86]. These cells acquire stem cell-like features and are able to reconstitute tumors upon serial transplantation (87). They are often refractory to therapy due to their stem cell properties, including relative quiescence, expression of ABC transporters, an active DNA repair system and resistance to apoptosis (88, 89). The cancer stem cells are highly dependent on EZH2 for their tumorigenic capabilities (74, 75). In prostate cancer, EZH2 inhibitors induce apoptosis in the cancer stem cell fraction, but cause a G0/G1 arrest in less aggressive, androgen-sensitive cancer cells (90). In the MMTV-PyMT metastatic model, the induced tumors have high EZH2 expression levels and have a cancer stem cell population that is dependent on PcG proteins (91, 92). Similarly, NIPP1 is highly expressed in stem cells and regulates the promoter binding of EZH2 on proliferation-related genes (7, 9). The dependence of cancer stem cells on EZH2 and NIPP1 suggests that targeting them would prevent both proliferation and metastatic invasion. Described herein is the use of shRNA plasmids that contain the H1 polymerase III promoter, which drives the endogenous expression of shRNAs.

Methods

Creation of a Bacterial shRNA Delivery System shRNAs targeting NIPP1, EZH2 as well as a control non-target shRNA will be cloned into a pSUPER shRNA expressing backbone. The generated plasmids will be transformed into the BDS (BDS-shNIPP1, BDS-shEZH2 and BDS-shCtr), containing the lysis system and a genomic sifA deletion. As discussed above, it was shown that this system can deliver eukaryotic plasmids.

Efficacy of Bacterial Delivery of shRNA Targeting NIPP1 or EZH2

To quantify the efficiency of BDS delivered shRNA plasmids, MCF-7 and 4T1 cells will be infected with BDS-shNIPP1, BDS-shEZH2 and BDS-shCtr to determine knockdown percentage of NIPP1 and EZH2. Cells will be washed five times with PBS to remove residual bacteria. Proliferation will be measured using BrdU staining, viability will be measured by the addition of ethidium homodimer. Cells will be lysed and the protein concentration will be evaluated by Western Blot to determine the level of NIPP1 and EZH2 depletion. The overall H3K27me3 level in the cells will be checked by Western Blot to quantify the level of its depletion. EZH2 and H3K27me3 chromatin immuno-precipitations (ChIP) will be performed on the HOXA-region, a known EZH2 and NIPP1 target [8]. This will determine the reduction of EZH2 association with its NIPP1-regulated target genes and the subsequent decrease in trimethylation of H3K27. This experiment will have three outcomes: it will determine the potency of NIPP1 and EZH2 knockdown by bacterial gene delivery on 1) the target protein concentration, 2) downstream targets of NIPP1 and EZH2 and 3) cell viability.

Cell Death in 3D Tissue after Bacterial shRNA Delivery

Figure 9:
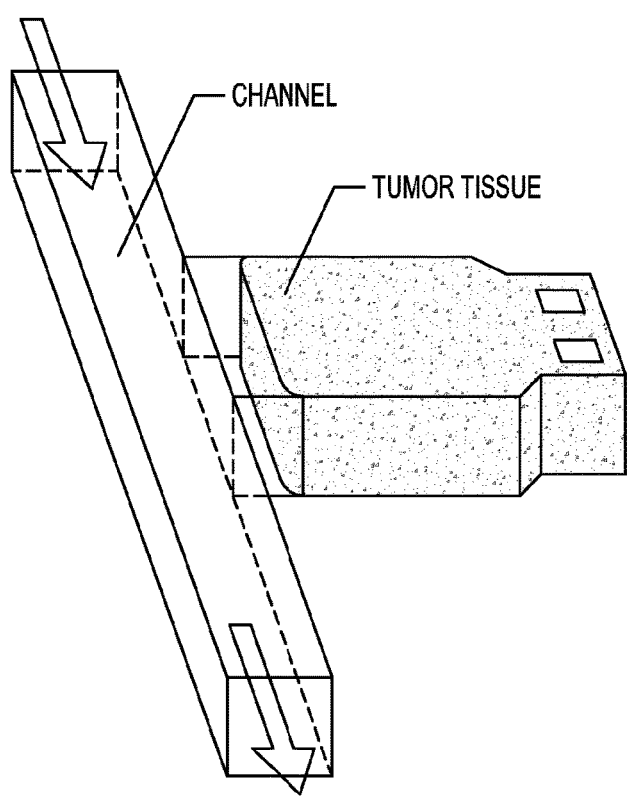
FIG. 9. Tumor-on-a-chip device. The device has similar geometry to in vivo tumors. It exposes a chamber of tumor tissue to flowing medium on one side to mimic the interaction between cells and blood vessels in tumors. This geometry enables direct, real-time visualization of bacteria and tumor tissue. Devices are formed by imprinting designs on PDMS. Oxygen plasma treatment is used to bond the PDMS to glass slides. Tumor tissue is introduced into the 1000× 300×150 µm chamber as spheroids that grow and equilibrate for 24 hours. Syringe pumps are used to supply medium at 3 ml·min$^{-1}$. The device enables quantification of eukaryotic EGFP expression (green) and cell death (red fluorescent ethidium homodimer).
Figure 9:
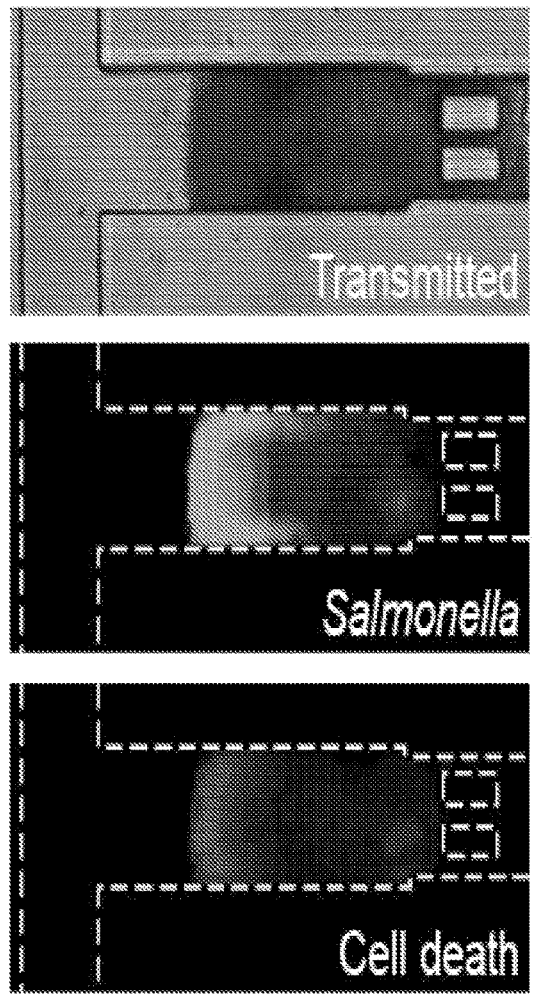

The microfluidic tumor-on-a-chip device will be used to demonstrate that the depletion of NIPP1 or EZH2 induces cell death in 3D tumor tissue. BDS-shNIPP1 or BDS-shEZH2 will be administered for one hour to six chambers each. BDS-shCtr will be used as a control. Dead cells will be stained with ethidium homodimer. Time-lapse fluorescence images will be acquired every 30 minutes for 72 hours. Temporal viability profiles will be generated from the resultant image series (FIG. 9). This will determine if there is an increase in cancer cell death in three-dimensional tissue due to the bacterial delivery of NIPP1 or EZH2 shRNA.

Bacterial Delivery of shRNA Targeting NIPP1 and EZH2 in an In Vivo Xenograft Mouse Model Three experiments will be used to determine that the depletion of NIPP1 or EZH2 reduces tumor volume and decreases the cancer stem cell population. Three distinct experiments are used to investigate the mechanisms that occur at different time scales. NIPP1 and EZH2 depletion will be measured five days after bacterial injection to allow for bacterial tumor colonization, plasmid release and gene silencing. The cancer stem cell population will be measured after ten days to allow for differentiation and death. Tumor volume will be measured until maximal tumor burden is reached. For all three experiments, size-matched, subcutaneous 4T1 tumors will be grown to 200 mm$^3$. Then treatment will start with BDS-shNIPP1, BDS-shEZH2 or BDS-shCtr.

1) Level of NIPP1 Depletion.

Five days after bacterial administration, mice will be sacrificed and tumors excised. Half of each tumor will be fixed and immunostained with NIPP1 and EZH2 antibodies to determine the number of cells that show NIPP1 or EZH2 depletion. Adjacent sections will be stained with H3K27me3 antibody to localize the effects of gene knockdown. Half of each tumor will be lysed. The percentage of NIPP1 and EZH2 knockdown and the overall H3K27me3 levels of the tumor tissue will be determined by Western Blot. Spleen and liver tissue will be harvested and the levels of NIPP1 and EZH2 will be determined by Western Blot.

2) Size of Cancer Stem Cell Population.

Ten days after bacterial administration, mice will be sacrificed and the tumors excised. Half of each tumor will be lysed and the percentage of knockdown will be determined by Western Blot. Half of the tumor will be minced for FACS sorting to determine the percentage of cancer stem cells in the total tumor cell population. For the 4T1 model, the CSC markers CD44$^+$/CD24$^+$/ALDH$^+$ will be used to discern this stem cell population (93).

3) Effect on Tumor Volume.

Tumor volume will be measured until control mice reach the maximal tumor burden. At this end point, all tumors will be excised and the extent of knockdown and H3K27me3 depletion will be measured by immunohistochemistry and by Western Blot.

The outcome of this experiment will be the effect of bacterial shRNA delivery on NIPP1 and EZH2 protein levels. It will also determine concomitant effects on downstream targets. In addition, it will determine the effect on tumor volume after NIPP1 or EZH2 depletion. The determination of NIPP1 and EZH2 levels in other tissues will verify the specificity of the treatment to tumors. FACS analysis will determine if the knockdown of NIPP1 or EZH2 reduces the CSC population in tumors.

Bacterial Delivery of shRNA to Prevent Metastasis Formation

MMTV-PyMT mice will be used to demonstrate that depletion of NIPP1 or EZH2 in primary tumors eliminates and/or diminishes the formation of metastasis. These experiments will also test the hypothesis that depleting EZH2 and NIPP1 reduces metastasis formation by reducing the population of cancer stem cells. Three effects will be measured in each group of mice: tumor volume, extent of gene depletion and CSC population. In all mice, bacterial therapy will be administered via the tail vain after 5 weeks, when MMTV-PyMT mice have primary tumors, but before the formation of metastasis. After 16 weeks, all mice will be sacrificed and primary tumors and lungs will be excised.

Tumor volume will be measured at the beginning and end of each experiment with 18F-FDG small-animal PET. Primary tumor volume will be calculated by contouring on a visual basis (3-dimensional isocontour) and tumor glucose uptake will be determined. Metastatic burden will be measured by calculating the tumor glucose uptake across the lungs. The metastatic burden will also be determined by H&E staining of the lungs and counting metastases. EZH2 and NIPP1 depletion will be determined by immunohistochemistry. Half of each tumor and one lung will be fixed and immunostained for NIPP1 and EZH2 to determine the extent of depletion. The size of the cancer stem cell population will be determined in the other tumor half and the second lung by FACS analysis with $CD90^+/CD24^+$ markers (92, 94).

This experiment will determine the effect of bacterial delivery of shRNA targeting NIPP1 and EZH2 on metastasis formation and the CSC population.

Bacterial Delivery of shRNA to Treat Established Metastases

A second experiment with MMTV-PyMT mice will demonstrate that depletion of NIPP1 or EZH2 in metastasis reduces total metastatic volume. BDS-shNIPP1, BDS-shEZH2 and BDS-shCtr will be administered via tail vein after 15 weeks, once substantial metastases have formed. Mice will be sacrificed after 10 weeks. Tumor volume and metastatic burden will be determined at the start and end of the experiment (after 10 weeks) using the PET and histology techniques as described above. The extent of EZH2 and NIPP1 depletion will be determined by immunostaining. This experiment will show the effect on NIPP1 or EZH2 depletion on metastatic tumor volume.

Example III

A Bacterial Peptide Delivery System Disrupts NIPP1:PP1 Complexes:

intracellular delivery of NIPP1:PP1 dissociative peptides by bacteria will disrupt NIPP1:PP1 complexes and reduce tumor burden.

To date, a targeted, direct delivery mechanism of short peptides into the cytosol of cancer cells does not exist. Described herein is a bacterial peptide delivery system. Intracellular delivery of NIPP1:PP1 dissociative peptides by bacteria will disrupt NIPP1:PP1 complexes and reduce tumor burden.

The NIPP1:PP1 Complex

The NIPP1-interactor Ser/Thr phosphatase PP1 catalyzes at least one third of all eukaryotic dephosphorylation events [95]. NIPP1 is a potent and specific nuclear inhibitor of PP1 and contains three PP1 interaction sites. While PP1 binds the RVXF motif of NIPP1, its inhibition depends on the interaction of the N-terminally flanking basic stretch of this motif as well as the C-terminus with PP1 (96, 97). The NIPP1:PP1 complex regulates the association of EZH2 specifically to proliferation-related target genes: PP1 is an EZH2 phosphatase and the phosphorylation-regulated association of EZH2 to these target genes is controlled by NIPP1 (9) (FIG. 1). The dissociation of the NIPP1:PP1 complex reduces the binding of EZH2 to these targets (8).

NIPP1:PP1 Dissociative Peptide

A peptide, containing the RVXF motif and its N-terminally flanking basic stretch (AA 191-210 of NIPP1), competes for the NIPP1:PP1 binding in vitro (96). Low concentrations of the modified, cell-permeable version of this dissociative peptide disturb several PP1-holoenzymes in cancer cells, but show only minor dissociation of the NIPP1:PP1 complex (98). Increasing concentrations of this peptide lead to NIPP1:PP1 dissociation and are toxic to cancer cells (98). This peptide can be expressed in bacteria without inducing toxic effects to the bacteria.

Methods

Creation of Bacterial Peptide Delivery System

The peptide sequence (AA 191-210 of NIPP1) will be cloned under control of the lac promoter. To allow easy visualization of the peptide in the experiments described below, a Flag-tag will be fused to the peptide. BDS will be transformed with a prokaryotic vector expressing the Flag-tagged dissociative peptide. Untransformed BDS will be used as a control.

Bacterial Delivery of NIPP1:PP1 Dissociative Peptide in Cancer Cells

The efficacy of intracellular peptide delivery with the BDS will be tested in culture. MCF-7 and 4T1 cells will be infected with $1 \times 10^7$ CFU/ml of peptide-expressing and control BDS. After two hours, residual external bacteria will be removed by washing and incubation with gentamycin. Half of the mammalian cells will be harvested after four hours and lysed. Both PP1 and NIPP1 immunoprecipitations (IP) will be performed and the co-IP levels of NIPP1 and PP1, respectively, will be quantified. Comparison to control cells will determine the degree of NIPP1:PP1 complex disruption. The flag-tagged peptide will also be immunoprecipitated and a phosphatase phosphorylase assay will be performed to determine the amount of PP1 associated with the peptide. This assay measures the activity of peptide-associated PP1 after trypsin treatment, which maximally activates the phosphatase. The other half of the cells will be fixed and immunostained with a Flag-antibody to determine the concentration of these peptides in cells, compared to controls. This experiment will determine if the lysis-based bacterial release of NIPP1:PP1 dissociative peptides blocks NIPP1:PP1 complexes.

Effect of Bacterial Delivery of NIPP1:PP1 Dissociative Peptide on Cancer Cell Death The effect of bacterially delivered dissociative peptides on tumor cell death will be tested in a tumor-on-a-chip device, similar to that discussed above with BDS carrying the NIPP1:PP1 dissociative peptides and untransformed BDS as a control. This will determine if there is an increase in cancer cell death due to bacterial delivery of dissociative based peptide.

Efficacy of Bacterial Delivery of NIPP1:PP1 Dissociative Peptide in an In Vivo Mouse Model Mice with 4T1 subcutaneous tumors will be used to determine that the inhibition of NIPP1:PP1 reduces tumor volume. Two distinct experiments will be used to investigate mechanisms at different time scales. NIPP1:PP1 disruption will be measured two days after bacterial injection. Tumor volume will be measured for as long as possible. For both time-scales, 20 mice will be used, 10 for peptide-delivering BDS and 10 for controls. When the grafted tumors reach 200 mm³, bacteria will be administered by tail vein (100,000 CFU/g).

1) Level of NIPP1:PP1 disruption five days after bacterial administration, mice will be sacrificed and the tumors excised. Part of the tumors will be fixed and immunostained with a Flag-antibody to determine cells positive for peptide release. The rest of each tumor will be lysed and the percentage of NIPP1:PP1 inhibition will be determined via NIPP1- and PP1-co-IP. The level of PP1 complexed to the peptide will be measured via phosphatase phosphorylase assay.

2) Effect on Tumor Volume:

After bacterial injection, tumor volume will be measured daily until maximal tumor burden is reached in the controls. At this point, all tumors will be excised, lysed and the percentage of NIPP1:PP1 complex dissociation will be determined by co-IP and by phosphatase phosphorylase assay.

The outcomes of these experiments will be 1) the ability of BDS to deliver dissociative peptide to tumors and 2) the ability of NIPP1:PP1 dissociative peptides to reduce tumor volume.

Results

Figure 10:
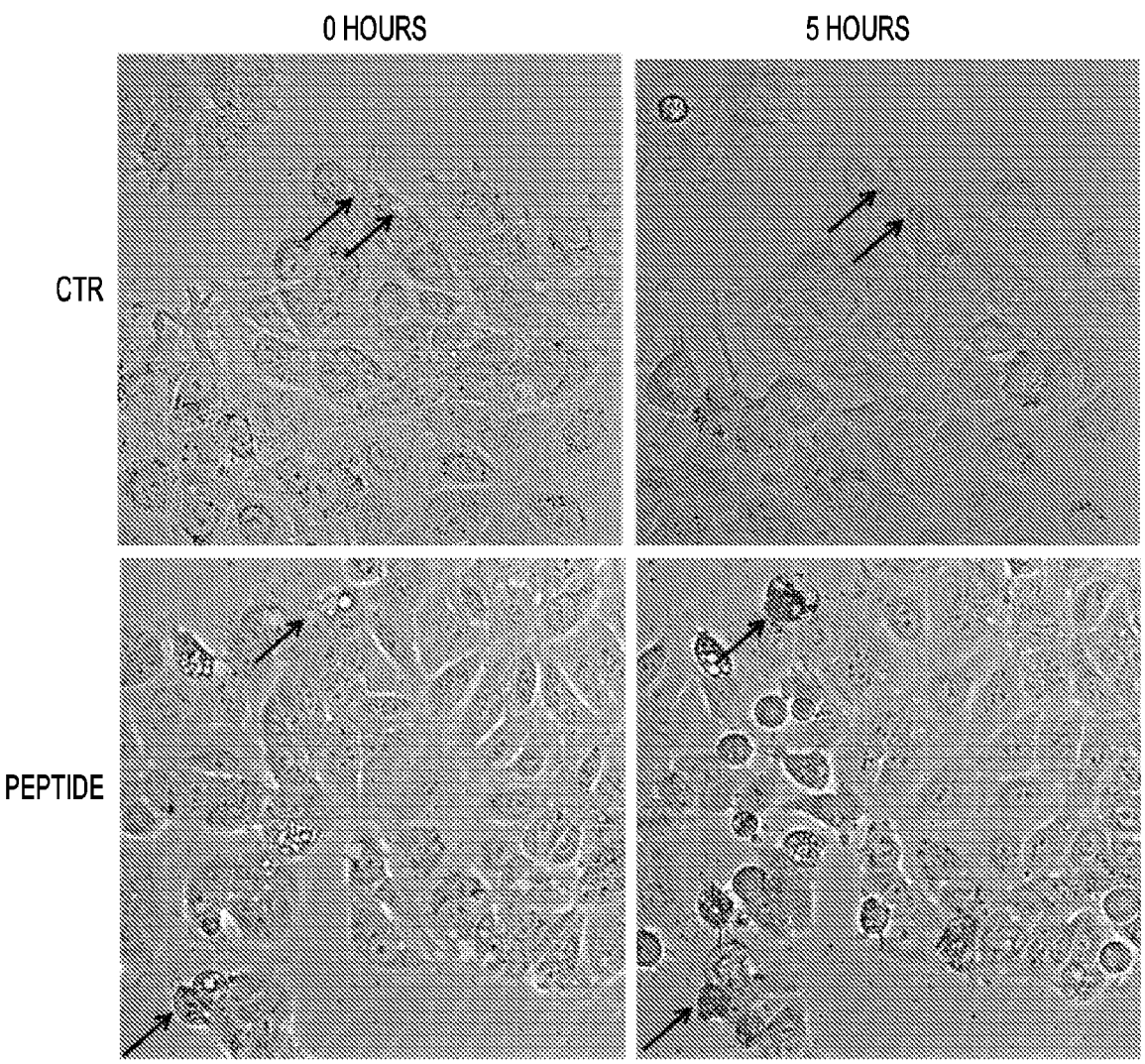
FIG. 10. Bacterial delivery of a NIPP1-based polypeptide induces cancer cell death. MCF-7 cells were treated for two hours with BDS containing NIPP1-based peptide expressing plasmid and untransformed BDS, washed and incubated with gentamycin for 1 hour. Dead cells were stained with ethidium homodimer. Both strains constitutively expressed EGFP. Time-lapse fluorescence images were acquired after gentamycin addition (0 hours) and after 5 hours. Intracellular control bacteria lysed after 5 hours, but did not induce cell death. Peptide-expressing bacteria induced cell death after lysis. Black arrows indicate invaded cells.

Bacterial Delivery of the NIPP1 Central Domain Induces Cancer Cell Death in Cells To test the effect of inhibiting the NIPP1:PP1 complex on cancer proliferation, the central domain of NIPP1 (AA 143-224, containing the basic stretch and the RVXF motif) was cloned and placed under the control of a Lac promoter. The plasmid was transformed into the BDS. MCF-7 cells were incubated for two hours with the BDS expressing the dissociative peptide and untransformed BDS (control). Both bacterial strains constitutively expressed EGFP. After two hours, the cells were washed and incubated with gentamycin for one hour. Dead cancer cells were stained with ethidium homodimer. At time 0 (after gentamycin incubation), bacterial invasion of the cancer cells was observed in both conditions. After 5 hours, the cells infected with untransformed BDS are viable and the bacteria had lysed. Infection with the peptide-expressing BDS resulted in cell death after bacterial lysis (FIG. 10).

Figure 11A:
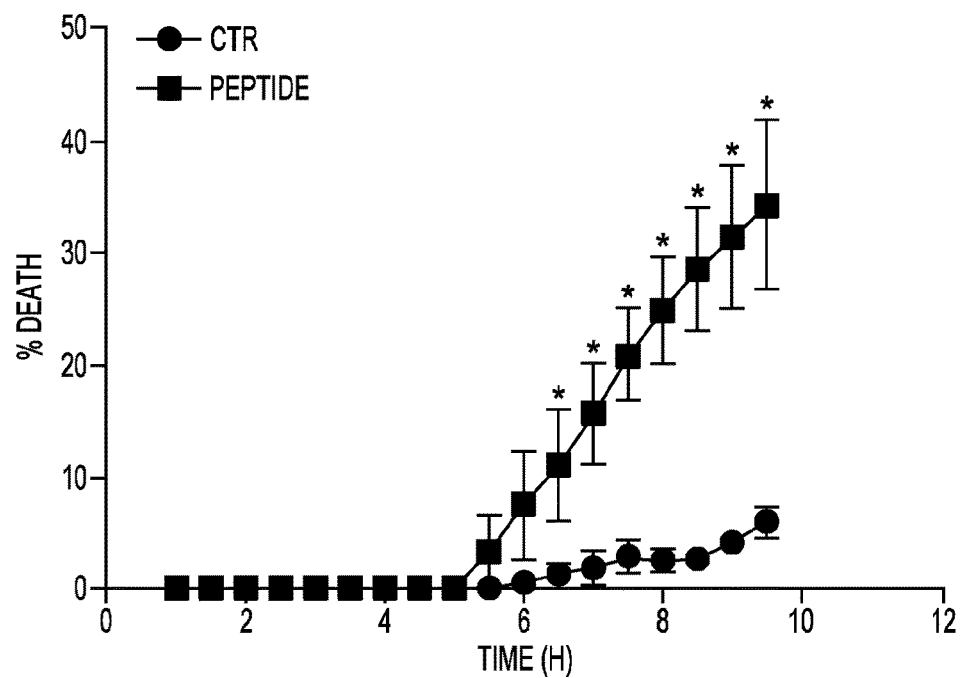
FIGS. 11A-B. Bacterial delivery of a NIPP1-based polypeptide induces cancer cell death. BDS containing the NIPP1-based peptide expressing plasmid and untransformed BDS were administered for two hours to two groups of chambers. Dead cells were stained with ethidium homodimer. Time-lapse fluorescence images were acquired every 30 minutes for 10 hours. The extent of cell death was determined from fluorescent images in regions at the interface between the tissue and the flow channel. After 6.5 hours there was significantly more cell death in tissue treated with peptide-expressing bacteria compared to controls (*, $P<0.05$). At 9.5 hours, BDS containing the peptide were 4 times more effective at killing cancer cells compared to controls (*, $P<0.05$). These data shows that bacterial delivery of NIPP1-based peptides kills cancer cells.
Figure 11B:
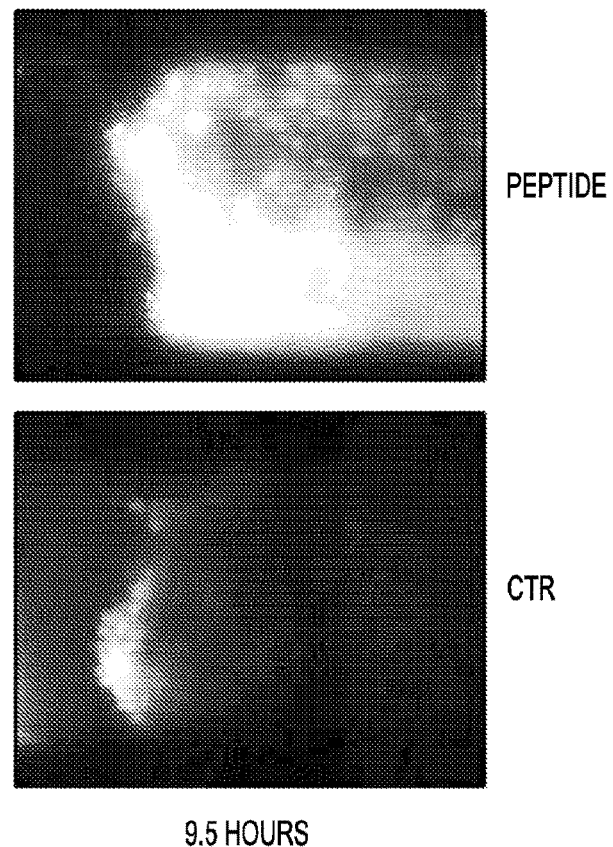
Figure 12:
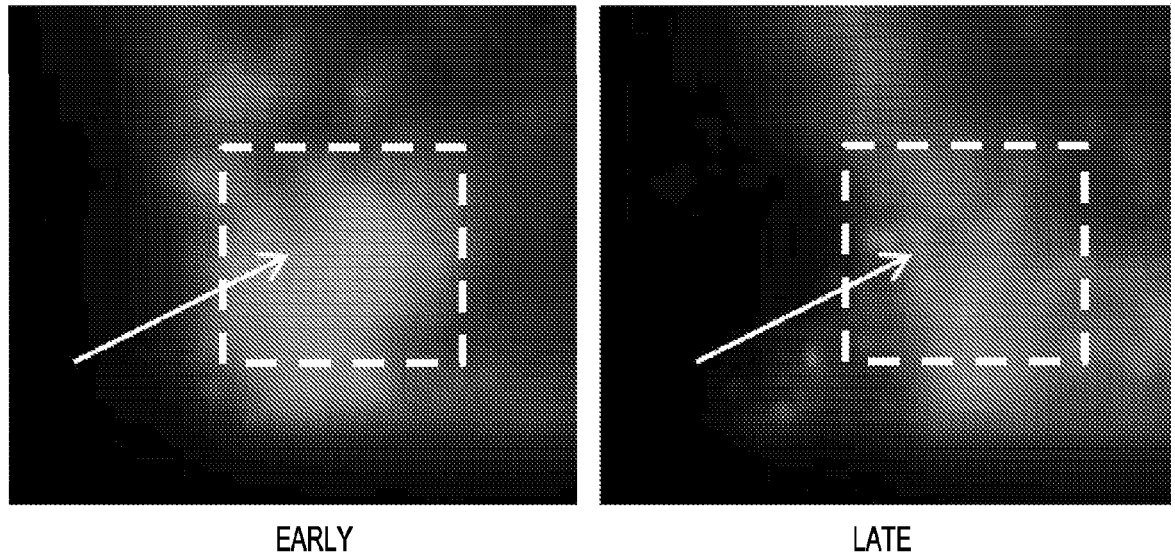
FIG. 12. Lysis of the delivery vector in tissue. BDS containing the NIPP1-based peptide expressing plasmid and untransformed BDS were administered to the tumor-on-a-chip device. This strains constitutively expressed EGFP. Green intensity decreased with time. This reduction indicated that the bacteria lysed once they had invaded into cancer cells.

Bacterial Delivery of the NIPP1 Central Domain Induces Cancer Cell Death in 3D Tissue A tumor-on-a-chip device was used to test the effect of inhibiting the NIPP1:PP1 complex on 3D tumor growth. BDS expressing the peptide and untransformed BDS (as a control) were administered to six chambers. Both strains were expressing EGFP constitutively. Time-lapse fluorescence images were acquired every 30 minutes for 10 hours. Dead cancer cells were stained with ethidium homodimer. The percent of dead cells was quantified in the first 225 µm of tissue as a function of time (FIG. 11). After 5 hours, cell death increased in the tissue treated with BDS expressing the peptide, while only minimal cell death was caused by untransformed BDS. After 9.5 hours, the peptide-expressing strain was 4 times more effective at killing cancer cells than the control strain (P<0.05) (FIG. 11). Loss of green fluorescence demonstrated the functionality of the lysis system (FIG. 12). In regions of bacterial colonization, for both sets of devices, green intensity decreased with time (FIG. 12). In bacteria without lysis, green florescence steadily increases as colonization progresses (99). This decrease in fluorescence indicates that the lysis system effectively killed intracellular bacteria. In these regions, increased cell death followed the decrease in green fluorescence. This experiment shows that bacterial delivery of a NIPP1-based polypeptides induces cancer cell death in tissue.

Example IV

Ultra-Safe *Salmonella* that are Cleared by Failsafe Circuitry:

a genetic circuit to clear bacteria after therapy has finished.

Figure 13:
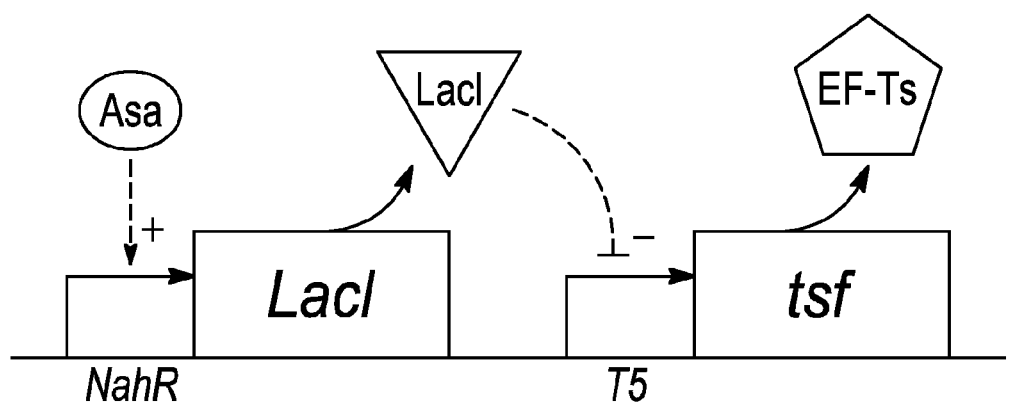
FIG. 13. Failsafe circuitry. The *Salmonella* gene tsf will be placed under the control of a T5 promoter. The repressor gene lad will be placed under the control of the salicylate-dependent promoter nahR. Upon addition of aspirin, nahR will be activated and lad transcribed. LacI will consequently silence T5 and block tsf transcription, inducing bacterial cell death.

A failsafe genetic circuit will enable bacterial clearance at the end of therapy and will prevent unwanted infection. The experiments will demonstrate that activation of failsafe circuitry clears bacteria from mouse organs. Thus, a system that can externally halt transcription of essential *Salmonella* genes is created—such genes are 1) essential for the survival of the *Salmonella* strain, single copy and expressed at high levels. One embodiment of such a system will utilizes tsf, the gene for Elongation Factor Ts (EF-Ts). This gene is essential and not part of an operon, which permits it to be independently controlled (100, 101). A circuit will be created that produces EF-Ts when a controlling molecule is not present (FIG. 13). When the controlling molecule is added to the system, EF-Ts production is stopped and bacterial transcription ceases. The circuit will use acetyl salicylic acid (ASA or aspirin) as the controlling molecule, because of its low molecular weight and established safety.

Methods

Design of a Genetic Circuit to Eliminate Bacteria after Treatment

The failsafe circuit will utilize a salicylate-dependent promoter (nahR) to control the LacI repressor (102) (FIG. 13). LacI will in turn repress a T5 promoter, containing three LacI binding sites, that regulates the expression of tsf. When ASA is not present, LacI is not expressed and tsf will be expressed. In the presence of ASA, the LacI repressor is expressed and binds the T5 promoter, thus blocking the transcription of tsf and lysing the bacteria. This circuit will be chromosomally incorporated to prevent negative selection. The upstream features (nahR, lad and T5) will be inserted into the location of the natural tsf promoter by λ red homologous recombination. To test the function of this circuit, bacteria will be grown in LB. After reaching an OD of 0.4, centrifuged organisms will be suspended with and without ASA and the OD will be measured over time.

Efficacy of Failsafe Gene Circuit

MMTV-PyMT mice with spontaneous metastases will be used to demonstrate that failsafe circuitry can eliminate unwanted bacteria. Two groups of mice will be housed for 15 weeks until metastases form. *Salmonella* containing the failsafe tsf circuit will be injected. After 48 hours, to permit bacterial colonization, ASA will be added liberally to the drinking water of one group. Mice will be sacrificed after 24 hours. Tumors, metastases, and organs will be excised, fixed, and sectioned. Bacterial density will be measured by plating and immunofluorescence. Comparison between groups will demonstrate the ability of the failsafe circuit to control bacterial density.

BIBLIOGRAPHY

1. Kerppola T K Trends Cell Biol 2009, 19(12):692-704.
2. Simon J A, Lange C A Mutat Res 2008, 647(1-2): 21-29.
3. Sauvageau M, Sauvageau G Cell Stem Cell 2010, 7(3): 299-313.
4. Bracken A P, et al. EMBO J 2003, 22(20):5323-5335.
5. Chen Y, et al. Hepatology 2007, 46(1):200-208.
6. Chiba T, et al. Int J Cancer 2012, 130(11):2557-2567.
7. Van Eynde A, et al. Mol Cell Biol 2004, 24(13):5863-5874.
8. Van Dessel N, et al. Nucleic Acids Res 2010, 38(21): 7500-7512.
9. Minnebo N, et al. Nucleic Acids Res 2013, 41(2):842-854.
10. Nuytten M, et al. Oncogene 2008, 27(10):1449-1460.
11. Ezhkova E, Pasolli et al. Cell 2009, 136(6):1122-1135.
12. Pawelek J M, et al. Cancer Res 1997, 57(20):4537-4544.
13. Low K B, et al. Nature biotechnology 1999, 17:37-41.
14. Zheng L M, et al. Oncology Research 2000, 12(3):127-135.
15. Platt J, Sodi S, et al. European Journal of Cancer 2000, 36(18):2397-2402.
16. Clairmont C, et al. The Journal of infectious diseases 2000, 181:1996-2002.
17. Luo X, et al. Oncol Res 2001, 12(11-12): 501-508.
18. Li Y H, et al. Acta Biochimica Et Biophysica Sinica 2001, 33(2):233-237.
19. Yuhua L, et al. Int J Cancer 2001, 94(3):438-443.
20. Toso J F, et al. Journal of clinical oncology: official journal of the American Society of Clinical Oncology 2002, 20:142-152.
21. Rosenberg S A, et al. Journal of Immunotherapy 2002, 25(3):218-225.
22. Pawelek J M, et al. Cancer Gene Therapy 2002, 9(10): 813-818.
23. Mei S, et al. Anticancer Res 2002, 22(6A): 3261-3266.
24. Feltis B A, et al. Journal of Surgical Research 2002, 107(1):101-107.
25. Dresselaers T, et al. Br J Cancer 2003, 89(9):1796-1801.
26. Lee C H, et al. Journal of Gene Medicine 2004, 6(12): 1382-1393.
27. Thamm D H, et al. Clinical cancer research: an official journal of the American Association for Cancer Research 2005, 11:4827-4834.
28. Lee C H, et al. Cancer Gene Therapy 2005, 12(2):175-184.
29. Lee C H, et al. Molecular Therapy 2005, 11(5):707-716.
30. Jia L J, et al. Cancer Biol Ther 2005, 4(8):840-845.
31. Gentschev I, et al. BMC Cancer 2005, 5:15.
32. Barnett S J, et al. Pediatr Surg 2005, 40(6):993-997; discussion 997-998.
33. Zhao M, et al. Cancer research 2006, 66:7647-7652.
34. Qi H, et al. Nan Fang Yi Ke Da Xue Xue Bao 2006, 26(12):1738-1741.
35. Chou C K, et al. Cancer Gene Therapy 2006, 13(8):746-752.
36. Zhao M, et al. PNAS USA 2007, 104:10170-10174.
37. Yoon W S, et al. Biotechnology Letters 2007, 29(4): 511-516.
38. Shilling D A, et al. Clin Exp Immunol 2007, 149(1): 109-116.
39. Loeffler M, et al. PNAS USA 2007, 104:12879-12883.
40. Jia L J, et al. Cancer Science 2007, 98(7):1107-1112.
41. Sorenson B S, et al. J Pediatr Surg 2008, 43(6):1153-1158.
42. Sorenson B S, et al. Clin Orthop Relat Res 2008, 466(6):1285-1291.
43. Loeffler M, et al. Journal of the National Cancer Institute 2008, 100(15):1113-1116.
44. Loeffler M, et al. Cancer Gene Therapy 2008, 15(12): 787-794.
45. Liu T, Konig et al. Microbial Pathogenesis 2008, 44(3): 224-237.
46. Lee C H, et al. International Journal of Cancer 2008, 122(4):930-935.
47. Fu W, et al. Journal of Gene Medicine 2008, 10(6):690-701.
48. Fu W, et al. Cancer Science 2008, 99(6):1172-1179.
49. Friedlos F, et al. Clinical Cancer Research 2008, 14(13): 4259-4266.
50. Fu W, et al. Cancer Gene Therapy 2008, 15(7):474-484.
51. Ryan R M, et al. Gene Ther 2009, 16(3):329-339.
52. Nagakura C, et al. Anticancer Res 2009, 29(6):1873-1878.
53. Loeffler M, et al. Cancer Immunology Immunotherapy 2009, 58(5):769-775.
54. Lee C H, et al. Journal of Immunotherapy 2009, 32(4): 376-388.
55. Ganai S, et al. Br J Cancer 2009, 101(10):1683-1691.
56. Chen G, et al. Cancer Science 2009, 100(12):2437-2443.
57. Al-Ramadi B K, et al. Clinical immunology (Orlando, Fla.) 2009, 130:89-97.
58. Kimura H, et al. Cell Prolif 2010, 43(1):41-48.
59. Ganai S, et al. Cancer Gene Ther 2011, 18(7):457-466.
60. Blache C A, et al. Cancer Res 2012, 72(24):6447-6456.
61. Zhang L, et al. Cancer Research 2007, 67(12):5859-5864.
62. Soto L J, 3rd, et al. J Pediatr Surg 2004, 39(6):937-940; discussion 937-940.
63. Bryant R J, et al. Prostate 2007, 67(5):547-556.
64. Varambally S, et al. Nature 2002, 419(6907):624-629.
65. Kleer C G, et al. PNAS USA 2003, 100(20):11606-11611.
66. Kasinskas R W, Forbes N S Biotechnology and Bioengineering 2006, 94(4):710-721.
67. Leschner S, et al. PloS one 2009, 4:e6692.
68. Forbes N S, et al. Cancer Res 2003, 63(17):5188-5193.
69. Kasinskas R W, et al. Cancer research 2007, 67:3201-3209.
70. Sznol M, et al. J Clin Invest 2000, 105(8):1027-1030.
71. Ganai S, et al. Annals of Surgical Oncology 2009, 16:18-19.
72. Clairmont C, et al. J Infect Dis 2000, 181(6):1996-2002.
73. Carswell E A, et al. PNAS USA 1975, 72(9):3666-3670.
74. van Vlerken L E, et al. Stem Cells Transl Med 2013, 2(1):43-52.
75. Li K, et al. Int J Mol Sci 2013, 14(6):11981-11993.
76. Galan J E Annu Rev Cell Dev Biol 2001, 17:53-86.
77. Salcedo S P, et al. Cell Microbiol 2001, 3(9):587-597.
78. Brumell J H, et al. Infect Immun 2002, 70(6):3264-3270.
79. Toley B J, Forbes N S Integr Biol 2012, 4(2):165-176.
80. Fantozzi A, Christofori G Breast Cancer Res 2006, 8(4):212.
81. Guy C T, et al. Mol Cell Biol 1992, 12(3):954-961.
82. Bugge T H, et al. Oncogene 1998, 16(24):3097-3104.
83. Kim I S, et al. Biochem Biophys Res Commun 2010, 394(3):443-447.
84. Forbes N S, et al. Cancer Research 2003, 63(17):5188-5193.
85. Kong W, PNAS USA 2012, 109(47):19414-19419.

86. Malanchi I, et al. Nature 2012, 481(7379):85-89.
87. Dick J E Blood 2008, 112(13):4793-4807.
88. Dean M Discov Med 2005, 5(27):278-282.
89. Li L, Bhatia R Clin Cancer Res 2011, 17(15):4936-4941.
90. Crea F, et al. Mol Cancer 2011, 10:40.
91. Hebbard L, et al. Oncogene 2011, 30(3):301-312.
92. Ma J, et al. Tumour Biol 2012, 33(6):1983-1996.
93. Kaur P, et al. BMC Cancer 2012, 12:120.
94. Cho R W, et al. Stem Cells 2008, 26(2):364-371.
95. Bollen M, et al. Trends Biochem Sci 2010, 35(8):450-458.
96. Beullens M, et al. J Biol Chem 1999, 274(20):14053-14061.
97. Beullens M, et al. Biochem J 2000, 352 Pt 3:651-658.
98. Chatterjee J, et al. Angewandte Chemie (International ed 2012, 51(40):10054-10059.
99. Toley B J, et al. J Vis Exp 2011, DOI: 10.3791/2425(57).
100. Meysman P, et al. Mol Biol Evol 2013, 30(6):1302-1314.
101. Knuth K, et al. Mol Microbiol 2004, 51(6):1729-1744.
102. Royo J L, et al. Nature Methods 2007, 4(11):937-942.

All publications, nucleotide and amino acid sequence identified by their accession nos., patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims. As used herein and in the appended claims, the singular forms "a," "an," and "the" include plural reference unless the context clearly dictates otherwise. Thus, for example, a reference to "a nucleic acid" or "a polypeptide" includes a plurality of such nucleic acids or polypeptides (for example, a solution of nucleic acids or polypeptides or a series of nucleic acid or polypeptide preparations), and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

What is claimed is:

1. An attenuated *Salmonella* strain comprising a lysis gene or cassette operably linked to an intracellularly induced *Salmonella* promoter, wherein the intracellularly induced *Salmonella* promoter induces lysis of the *Salmonella* strain when in mammalian cytosol without an extracellular inducer agent, wherein the promoter is selected from the group consisting of SseJ, SseK2, SifB, SopD2, SseL or SteC.

2. The *Salmonella* strain of claim 1, further comprising a sifA deletion or wherein expression of sifA has been reduced.

3. The *Salmonella* strain of claim 1, wherein the promoter is SseJ.

4. The *Salmonella* strain of claim 1, wherein an essential *Salmonella* gene is under the regulation of an inducible promoter, wherein the gene is selected from ftsW, ftsA, ftsZ, murE, mukF, imp, secF, eno, hemH, tmk, dxs, uppS, cdsA, accA, pssA, msbA, tsf, trmD, cca, infB, rpoA, rpoB, rpoC, holA, dnaC, or eng.

5. The *Salmonella* strain of claim 4, wherein the essential gene is tsf, eno, or cca.

6. The *Salmonella* strain of claim 1 further comprising a plasmid that expresses DNA, shRNA, non-coding RNA and/or a peptide.

7. The *Salmonella* strain of claim 6, wherein the shRNA molecule is complimentary to a gene that encodes a cytoplasmic protein that promotes survival of a cancer cell.

8. The *Salmonella* strain of claim 6, wherein the shRNA molecule or peptide inhibits, suppresses or blocks expression and/or activity of an epigenetic target.

9. The *Salmonella* strain of claim 8, wherein the peptide comprises amino acids 143-224 of NIPP1 (SEQ ID NO:93) or 191-210 of NIPP1 (SEQ ID NO:93).

10. An attenuated *Salmonella* strain, wherein the *Salmonella* strain is VNP20009 with a sifA deletion, an intracellularly induced lysis gene or cassette, a plasmid that expresses at least one DNA, shRNA or peptide and wherein the tsf gene of the *Salmonella* strain is under the regulation of an inducible promoter.

11. A composition comprising the attenuated *Salmonella* strain claim 1 and pharmaceutically acceptable carrier.

12. A method to treat cancer comprising administering to subject in need thereof an effective amount of the attenuated *Salmonella* strain of claim 1 so as to treat said cancer, wherein said cancer is a solid tumor.

13. A method of inhibiting solid tumor growth/proliferation or reducing the volume/size of the tumor comprising administering to subject in need thereof an effective amount of the attenuated *Salmonella* strain of claim 1 so as to suppress the tumor growth or reduce the volume of the tumor.

14. A method to treat, reduce formation/number or inhibit spread of metastases from a solid tumor comprising administering to subject in need thereof an effective amount of the attenuated *Salmonella* strain of claim 1 so as to treat, reduce formation/number or inhibit spread of metastases from a solid tumor.

15. The method of claim 12, wherein the cancer is selected from the group consisting of lung cancer, liver cancer, kidney cancer, breast cancer, prostate cancer, pancreatic cancer, colon cancer, head and neck cancer, ovarian cancer and gastroenterological cancer.

16. The *Salmonella* strain of claim 1, wherein the lysis cassette is Lysin E from phage phiX174, the lysis cassette of phage iEPS5, or the lysis cassette from lambda phage.

17. The *Salmonella* strain of claim 8, wherein the epigenetic target is at least one of EZH2, NIPP1, or PP1.

18. The *Salmonella* strain of claim 4, wherein the inducible promoter is tightly regulated and induced by a small molecule that is safe to inject into humans.

19. The *Salmonella* strain of claim 18, wherein the inducible promoter includes pBAD (L-arabinose), LacI (IPTG) or nahR (acetyl salicylic acid (ASA)).

20. The *Salmonella* strain of claim 8, wherein the epigenetic target is at least one of EZH2, NIPP1, PP1, Suz12, EED, EZH1, RbAp48, Jarid2, YY1, CBX2, CBX4, CBX6, CBX7, PHC1, PHC2, PHC3, BMI1, PCGF2, ZNF134, RING1, RNF2, PHF1, MTF2, PHF19, SETD1A, SETD1B, CXXC1, ASH2L, DPY30, RBBP5, WDR5, KMT2A, KMT2B, KMT2C, KATE, KDM6A, NCOA6, PAGR1, PAXIP1, ASH1L, SMARCA2, SMARCA4, BPTF, or SMARCA1.

* * * * *

UNITED STATES PATENT AND TRADEMARK OFFICE
CERTIFICATE OF CORRECTION

| | | |
|---|---|---|
| PATENT NO. | : 11,103,538 B2 | Page 1 of 1 |
| APPLICATION NO. | : 15/503380 | |
| DATED | : August 31, 2021 | |
| INVENTOR(S) | : Forbes et al. | |

It is certified that error appears in the above-identified patent and that said Letters Patent is hereby corrected as shown below:

In the Claims

In Column 600, Line 30, in Claim 19, delete "Lad" and insert --LacI-- therefor

In Column 600, Line 38, in Claim 20, delete "KATE," and insert --KAT8,-- therefor Signed and Sealed this
Fourth Day of January, 2022

Drew Hirshfeld
*Performing the Functions and Duties of the*
*Under Secretary of Commerce for Intellectual Property and*
*Director of the United States Patent and Trademark Office*